US007125589B1

(12) United States Patent
Kimura et al.

(10) Patent No.: US 7,125,589 B1
(45) Date of Patent: Oct. 24, 2006

(54) LIQUID CRYSTAL COMPOUND HAVING HYDROGEN AS A TERMINAL GROUP, COMPOSITION COMPRISING THE COMPOUND, AND LIQUID CRYSTAL DISPLAY ELEMENT COMPRISING THE COMPOSITION

(75) Inventors: Keiji Kimura, Ichihara (JP); Shuichi Matsui, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 354 days.

(21) Appl. No.: 10/409,104

(22) Filed: Apr. 9, 2003

(30) Foreign Application Priority Data

Apr. 9, 2002 (JP) ............................ 2002-106624

(51) Int. Cl.
*C09K 19/12* (2006.01)
*C09K 19/32* (2006.01)
*C09K 19/30* (2006.01)
*C09K 19/34* (2006.01)
*C07C 25/13* (2006.01)

(52) U.S. Cl. ............ 428/1.1; 252/299.61; 252/299.62; 252/299.63; 252/299.66; 252/299.67; 570/127; 570/129; 570/183

(58) Field of Classification Search ................ 428/1.1; 252/299.61, 299.62, 299.64, 299.66, 299.67; 570/128, 129, 183
See application file for complete search history.

(56) References Cited

U.S. PATENT DOCUMENTS 4,329,057 A 5/1982 Zampiello
4,594,465 A 6/1986 Chan et al.
4,696,549 A 9/1987 Chan et al.
4,808,333 A 2/1989 Huynh-ba et al.
4,820,443 A 4/1989 Goto et al.
4,855,076 A * 8/1989 Goto et al. ............ 252/299.63
5,279,764 A 1/1994 Reiffenrath et al.
5,358,663 A 10/1994 Gray et al.
5,523,127 A 6/1996 Ohnishi et al.
5,525,258 A 6/1996 Wingen et al.
5,545,747 A * 8/1996 Kawaguchi et al. ........ 560/123
5,849,216 A 12/1998 Illian et al.
6,180,026 B1 1/2001 Rieger et al.
6,579,577 B1 * 6/2003 Kondo et al. ............... 428/1.1
6,723,866 B1 * 4/2004 Kirsch et al. ................ 558/17
2002/0066888 A1 6/2002 Shibata et al.

FOREIGN PATENT DOCUMENTS

| | | | |
|---|---|---|---|
| DE | 3839213 | | 5/1990 |
| DE | 4338267 | | 5/1995 |
| GB | 2310669 | | 9/1997 |
| JP | 57-173134 | * | 11/1982 |
| JP | 5-310618 | | 11/1993 |
| JP | 6-298685 | | 10/1994 |
| JP | 7-278546 | | 10/1995 |
| JP | 2001-316346 | | 11/2001 |
| WO | 95/13257 | | 5/1995 |
| WO | 95/13999 | | 5/1995 |

OTHER PUBLICATIONS

English abstract for JP 57-179134.*
CAPLUS 1970: 121606.*
CAPLUS 1983: 160433.*
English translation by omputer for JP 5-310618, http://www4.ipdl.ncipi.go.jp/Tokujitu/PAJdetail.ipdl?N0000=60&N0120=01&N2001=2&N3001=H05-310618.*
English translation bu computer for JP 6-298685, http://www4.ipdl.ncipi.go.jp/Tokujitu/PAJdetail.ipdl?N0000=60&N0120=01&N2001=2&N3001=H06-298685.*

* cited by examiner

*Primary Examiner*—Shean C. Wu
(74) *Attorney, Agent, or Firm*—Wenderoth, Lind & Ponack, L.L.P.

(57) ABSTRACT

A compound represented by the following formula (1), a composition comprising the composition and an element comprising the composition:

(1)

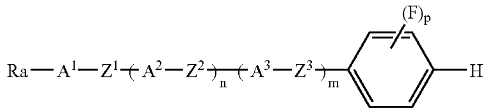

Ra is alkyl having 1 to 15 carbons and so forth; $A^1$, $A^2$ and $A^3$ are 1,4-cyclohexylene and so forth; $Z^1$, $Z^2$ and $Z^3$ are a single bond and so forth; n and m are 0 or 1; and phenyl having $(F)_p$ is phenyl, 2-fluorophenyl and so forth.

27 Claims, No Drawings

LIQUID CRYSTAL COMPOUND HAVING HYDROGEN AS A TERMINAL GROUP, COMPOSITION COMPRISING THE COMPOUND, AND LIQUID CRYSTAL DISPLAY ELEMENT COMPRISING THE COMPOSITION

BACK GROUND OF THE INVENTION

1. Field of the Invention

This invention mainly relates to a liquid crystal compound, a liquid crystal composition and a liquid crystal display element. More particularly, it relates to a liquid crystal compound having hydrogen as a terminal group, a liquid crystal composition comprising the compound, and a liquid crystal display element comprising the composition.

The term "a liquid crystal compound" used herein is a generic term for a compound having a liquid crystal phase and a compound having no liquid crystal phase but useful as a component of a liquid crystal composition. A liquid crystal compound(s), a liquid crystal composition(s) and a liquid crystal display element(s) may be expressed herein simply as a compound(s), a composition(s) and an element(s), respectively. Compounds represented by formulas (1) to (12) are optionally expressed as compounds (1) to (12), respectively. In formulas (2) to (12), structural units such as B, D, E, and so forth surrounded by a hexagon represent ring B, ring D, ring E, and so forth.

2. Related Art

In liquid crystal display elements, operating modes are classified into PC (phase change), TN (twisted nematic), IPS (in-plain switching), STN (super twisted nematic), OCB (optically compensated bend), ECB (electrically controlled birefringence), VA (vertical alignment), and so forth, while driving methods are classified into PM (passive matrix) and AM (active matrix). PM (passive matrix) is classified into static, multiplex, and so forth and AM is classified into TFT (thin film transistor), MIM (metal insulator metal), and so forth.

These elements comprise a liquid crystal composition having proper characteristics. The composition requires the following general characteristics in order to improve general characteristics of the elements.

| No. | General Characteristics Required for a Composition | General Characteristics Required for an Element |
|---|---|---|
| 1. | stable against heat | long-lived |
| 2. | stable against ultraviolet[1)] | long-lived |
| 3. | wide nematic phase range | usable in a wide temperature range |
| 4. | small in viscosity[2)] | short in response time |
| 5. | low in threshold voltage | low in electric power consumption |
| 6. | high in specific resistance | high in voltage holding ratio |

[1)]Ultraviolet is usable in the process of production.
[2)]Time for pouring a composition into a liquid crystal cell is short.

The characteristics of Nos. 1 to 6 are important for a composition used in an AM element. The characteristics of Nos. 1 to 5 are important for a composition used in a PM element. In addition to these characteristics, optical anisotropy (Δn), dielectric anisotropy (Δϵ), an elastic constant, and so forth are also important.

Recent advanced techniques for preparing plates used in an element tend to make a cell gap of the palates smaller. In an AM element of TN mode, OCB mode and so forth, there is a trend to make the cell gap especially small. The cell gap is a distance between two plates, which is the same with the thickness of a layer of a liquid crystal composition. In an element of the TN mode, smaller cell gap results in shorter response time and reversed domain is not easily formed. In an element of the OCB mode, smaller cell gap results in shorter time for transiting from splay orientation to bend orientation (shorter transition time) and shorter time for changing an orientation of liquid crystal molecules caused by the change of impressed voltage (shorter response time).

Product (Δn×d) of optical anisotropy (Δn) and a cell gap (d) is constant in these modes. In this case, the optical anisotropy is larger when the cell gap is smaller. Thus, a composition with a large optical anisotropy is needed. A compound having a large optical anisotropy may advantageously be added for preparing such a composition. It is preferred to add the compound in a larger amount. However, crystals may deposit during storage when a large amount of a single compound is added to the composition. This does not enable the element to display. Therefore, a compound having a large optical anisotropy and also an excellent miscibility with other liquid crystal compounds was demanded.

Patent specifications that relate to the compound of this invention are as follows; JP 60-051,135 A (U.S. Pat. No. 4,594,465), JP 2-004,725 A (U.S. Pat. No. 5,279,764), JP 5-286,905 A (U.S. Pat. No. 5,849,216), DE 4,338,266 A, DE 4,338,267 A, DE 4,338,540 A, JP 2001-316,346 A, JP 58-121,225 A, (U.S. Pat. No. 4,808,333), JP 5-339,573A (U.S. Pat. No. 5,523,127), JP 5-500,679 A (U.S. Pat. No. 6,180,026), JP 5-502,433 A (U.S. Pat. No. 5,358,663), JP 6-263,662 A (U.S. Pat. No. 5,525,258), JP 7-278,546 A JP 9-249,881 A (GB 2,310,669 A), and DE 3,839,213 A.

SUMMARY OF THE INVENTION

Summary of this invention includes a compound represented by the following formula (1), a composition comprising the compound (1) and a liquid crystal display element comprising the composition:

(1)

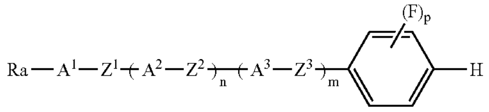

wherein Ra is alkyl having 1 to 15 carbons and any —$CH_2$— in the alkyl may be replaced by —O—, —S—, —CH═CH—, or —C≡C—; $A^1$, $A^2$ and $A^3$ independently are 1,4-cyclohexylene, 1,3-dioxane-2,5-diyl, decahydronaphthalene-2,6-diyl, 1,4-phenylene in which any hydrogen may be replaced by fluorine, naphthalene-2,6-diyl in which any hydrogen may be replaced by fluorine, or 1,2,3,4-tetrahydronaphthalene-2,6-diyl in which any —CH═ may be replaced by —CF═; $Z^1$, $Z^2$ and $Z^3$ independently are a single bond, —$(CH_2)_2$—, —$(CF_2)_2$—, —COO—, —OCO—, —$CH_2O$—, —$OCH_2$—, —$CF_2O$—, —$OCF_2$—, —CH═CH—, —CF═CF—, —C≡C—, —$(CH_2)_4$—, —$(CH_2)_3O$—, or —$O(CH_2)_3$—; n and m independently are 0 or 1; phenyl having $(F)_p$ is phenyl, 2-fluorophenyl, 2,5-difluorophenyl, 2,3,5-trifluorophenyl, 2,3,6-trifluorophenyl, or 2,3,5,6-tetrafluorophenyl; with the proviso that when $A^1$, $A^2$ and $A^3$ are 1,4-phenylene in which any hydrogen may be replaced by fluorine and $Z^1$, $Z^2$ and $Z^3$ are a single bond, the total number of fluorine in formula (1) is at least two.

DETAILED DESCRIPTION OF THE INVENTION

The first subject of the invention is to provide a compound having a large optical anisotropy and an excellent miscibility with other liquid crystal compounds, and being superior as a component of the composition. The second subject is to provide a composition comprising the compound and having the general characteristics required for the composition and a large optical anisotropy, and a liquid crystal display element comprising the composition. The general characteristics mean the six items already described.

The present inventors found that the compound (1) whose terminal group is hydrogen has the following characteristics: The compound has a good stability against heat and ultraviolet, a large optical anisotropy, a small dielectric anisotropy, and an excellent miscibility with other liquid crystal compounds. A composition comprising the compound has the general characteristics required for a composition, a large optical anisotropy and good miscibility with other compounds at low temperature. The composition is useful especially for a liquid crystal display element having a small cell gap. The compound (1) whose terminal group is hydrogen has a good stability against heat and ultraviolet, a high clearing point, a small viscosity, and a good miscibility with other liquid crystal compounds at low temperature.

Embodiments to solve the subjects of this invention are illustrated as follows. In the embodiments, preferable examples of terminal groups, rings, and bonding groups in compound (1) are also described.

1. A compound represented by the following formula (1):

(1)

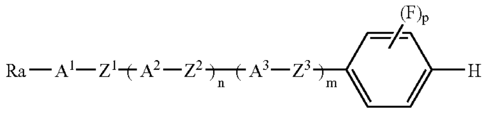

in formula (1), Ra is alkyl having 1 to 15 carbons and any $—CH_2—$ in the alkyl may be replaced by —O—, —S—, —CH═CH—, or —C≡C—.

An example is given for the meaning of "any $—CH_2—$ in the alkyl may be replaced by —O—, —CH═CH—, and so forth". A part of the groups, when any $—CH_2—$ in $C_4H_9—$ is replaced by —O— or —CH═CH—, is $C_3H_7O—$, $CH_3—O—(CH_2)_2—$, $CH_3—O—CH_2—O—$, $H_2C═CH—(CH_2)_3—$, $CH_3—CH═CH—(CH_2)_2—$, and $CH_3—CH═CH—CH_2—O—$. As seen above, the term of "any" means "at least one selected indiscriminatingly". In consideration of stability of a compound, $CH_3—O—CH_2—O—$ in which oxygen and oxygen are not adjacent is preferable to $CH_3—O—O—CH_2—$ in which oxygen and oxygen are adjacent.

Preferable Ra is alkyl, alkoxy, alkoxyalkyl, alkoxyalkoxy, alkylthio, alkylthioalkyl, alkylthioalkoxy, alkenyl, alkenyloxy, alkenyloxyalkyl, alkoxyalkenyl, alkynyl, and alkynyloxy. In these groups, a straight chain is preferable to a branched chain. Branched Ra is preferable when the compound (1) is optically active. Especially preferable Ra is alkyl, alkoxy, alkenyl, and alkenyloxy.

Preferable configuration of —CH═CH— in the alkenyl depends on the position of a double bond. trans-Configuration is preferable in the alkenyl such as 1-propenyl, 1-butenyl, 1-pentenyl, 1-hexenyl, 3-pentenyl, 3-hexenyl. cis-Configuration is preferable in the alkenyl such as 2-butenyl, 2-pentenyl, 2-hexenyl. Alkenyl having a preferable configuration has a high clearing point or a wide temperature range of a liquid crystal phase. See Mol. Cryst. Liq. Cryst., 1985, 131, 109.

Concrete examples of Ra are methyl, ethyl, propyl, butyl, pentyl, hexyl, heptyl, octyl, nonyl, decyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymenthyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl, and 1-pentynyl. Especially preferable Ra is ethyl, propyl and pentyl.

$A^1$, $A^2$ and $A^3$ independently are 1,4-cyclohexylene, 1,3-dioxane-2,5-diyl, decahydronaphthalene-2,6-diyl, 1,4-phenylene in which any hydrogen may be replaced by fluorine, naphthalene-2,6-diyl in which any hydrogen may be replaced by fluorine, or 1,2,3,4-tetrahydronaphthalene-2,6-diyl in which any —CH═ may be replaced by —CF═.

1,4-Phenylene in which any hydrogen may be replaced by fluorine is 1,4-phenylene and fluorine-substituted 1,4-phenylene. Positions of fluorine are at 2-position, 2,3-position, 2,5-position, 2,6-position, 2,3,5-position, or 2,3,5,6-position. These are shown below.

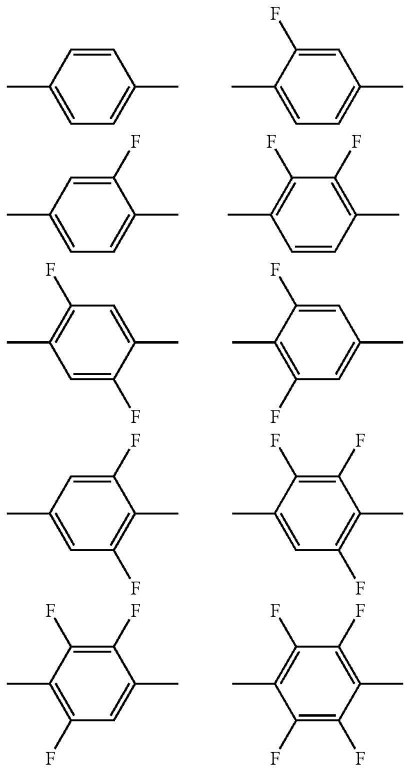

Naphthalene-2,6-diyl in which any hydrogen may be replaced by fluorine is naphthalene-2,6-diyl and fluorine-substituted naphthalene-2,6-diyl. Positions of fluorine are at 1-position, 3-position, 4-position, 1,3-position, 1,5-position, 1,7-position, 1,8-position, 3,4-position, 3,8-position, 1,3,4-position, 1,3,5-position, 1,3,7-position, 1,3,8-position, 1,4,5-position, 1,4,7-position, 1,4,8-position, 1,3,4,5-position, 1,3,4,7-position, 1,3,4,8-position, 1,3,4,5,7-position, 1,3,4,5,8-position, or 1,3,4,5,7,8-position.

1,2,3,4-Tetrahydronaphthalene-2,6-diyl in which any —CH= may be replaced by —CF= is 1,2,3,4-tetrahydronaphthalene-2,6-diyl and fluorine-substituted 1,2,3,4-tetrahydronaphthalene-2,6-diyl. Positions of fluorine are at 5-position, 7-position, 8-position, 5,7-position, 5,8-position, 7,8-position, or 5,7,8-position.

Preferable $A^1$, $A^2$ or $A^3$ is 1,4-cyclohexylene, 1,3-dioxane-2,5-diyl, decahydronaphthalene-2,6-diyl, 1,4-phenylene, 2-fluoro-1,4-phenylene, difluoro-1,4-phenylene, naphthalene-2,6-diyl, fluoronaphthalene-2,6-diyl, difluoronaphthalene-2,6-diyl, and 1,2,3,4-tetrahydronaphthalene-2,6-diyl. trans is preferable to cis in the configurations of 1,4-cyclohexylene and 1,3-dioxane-2,5-diyl.

$Z^1$, $Z^2$ and $Z^3$ independently are a single bond, $—(CH_2)_2—$, $—(CF_2)_2—$, —COO—, —OCO—, $—CH_2O—$, $—OCH_2—$, $—CF_2O—$, $—OCF_2—$, —CH=CH—, —CF=CF—, —C≡C—, $—(CH_2)_4—$, $—(CH_2)_3O—$, or $—O(CH_2)_3—$. Preferable $Z^1$, $Z^2$ or $Z^3$ are a single bond, $—(CH_2)_2—$, —COO—, —OCO—, $—CH_2O—$, $—OCH_2—$, $—CF_2O—$, $—OCF_2—$, —CH=CH—, —C≡C—, and $—(CH_2)_4—$. More preferable $Z^1$, $Z^2$ or $Z^3$ are a single bond, $—(CH_2)_2—$, —COO—, —OCO—, $—CH_2O—$, $—OCH_2—$, $—CF_2O—$, $—OCF_2—$, and $—(CH_2)_4—$. Especially preferable $Z^1$, $Z^2$ or $Z^3$ are a single bond, $—(CH_2)_2—$, $—CH_2O—$, and $—OCH_2—$. Especially preferable $Z^1$, $Z^2$ or $Z^3$ are also a single bond and $—(CH_2)_2—$.

n and m independently are 0 or 1. Here, divalent groups of naphthalene-2,6-diyl and its analogues are counted as one ring. The compound wherein m and n are 0 has two rings. The compound wherein m is 1 and n is 0, or m is 0 and n is 1 has three rings. The compound wherein m and n are 1 has four rings. The compound (1) may comprise an isotope such as $^2H$ (deuterium) and $^{13}C$ in an amount more than its natural abundance, because no large difference is found in the physical properties of the compound.

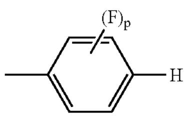

Phenyl having $(F)_p$ described above is phenyl, 2-fluorophenyl, 2,5-difluorophenyl, 2,3,5-trifluorophenyl, 2,3,6-trifluorophenyl, or 2,3,5,6-tetrafluorophenyl. These are shown below.

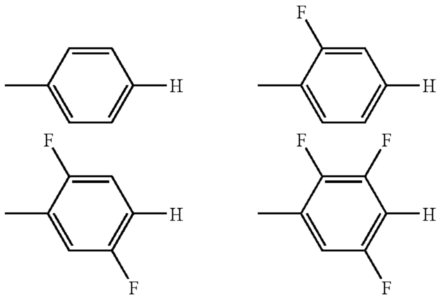

-continued

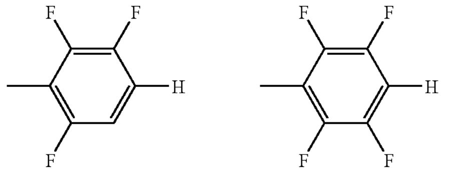

Preferable phenyl having $(F)_p$ is phenyl, 2-fluorophenyl and 2,5-difluorophenyl.

In the above, it should be noted that, when $A^1$, $A^2$ and $A^3$ are 1,4-phenylene in which any hydrogen may be replaced by fluorine and $Z^1$, $Z^2$ and $Z^3$ are a single bond, the total number of fluorine in formula (1) is at least two.

2. A compound represented by the following formula (1):

(1)

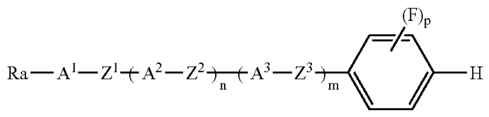

wherein Ra is alkyl having 1 to 15 carbons and any $—CH_2—$ in the alkyl may be replaced by —O— or —CH=CH—; $A^1$, $A^2$ and $A^3$ independently are 1,4-cyclohexylene, 1,3-dioxane-2,5-diyl, 1,4-phenylene in which any hydrogen may be replaced by fluorine, or naphthalene-2,6-diyl in which any hydrogen may be replaced by fluorine; $Z^1$, $Z^2$ and $Z^3$ independently are a single bond, $—(CH_2)_2—$, —COO—, —OCO—, $—CH_2O—$, $—OCH_2—$, $—CF_2O—$, $—OCF_2—$, —CH=CH—, —C≡C—, or $—(CH_2)_4—$; n and m independently are 0 or 1; phenyl having $(F)_p$ is phenyl, 2-fluorophenyl, 2,5-difluorophenyl, 2,3,5-trifluorophenyl, 2,3,6-trifluorophenyl, or 2,3,5,6-tetrafluorophenyl; with the proviso that when $A^1$, $A^2$ and $A^3$ are 1,4-phenylene in which any hydrogen may be replaced by fluorine and $Z^1$, $Z^2$ and $Z^3$ are a single bond, the total number of fluorine in formula (1) is at least two.

3. The compound according to the item 1 or 2, wherein phenyl having $(F)_p$ in formula (1) is phenyl.

4. The compound according to the item 1 or 2, wherein phenyl having $(F)_p$ in formula (1) is 2-fluorophenyl.

5. The compound according to the item 1 or 2, wherein phenyl having $(F)_p$ in formula (1) is 2,5-difluorophenyl.

6. The compound according to the item 1 or 2, wherein phenyl having $(F)_p$ in formula (1) is 2,3,5-trifluorophenyl.

7. The compound according to the item 1 or 2, wherein phenyl having $(F)_p$ in formula (1) is 2,3,6-trifluorophenyl.

8. The compound according to the item 1 or 2, wherein phenyl having $(F)_p$ in formula (1) is 2,3,5,6-tetrafluorophenyl.

9. The compound according to the item 1 or 2, wherein $Z^1$, $Z^2$ and $Z^3$ in formula (1) independently are a single bond, $—(CH_2)_2—$, —COO—, —OCO—, $—CH_2O—$, $—OCH_2—$, $—CF_2O—$, $—OCF_2—$, or $—(CH_2)_4—$.

10. The compound according to the item 1 or 2, wherein in formula (1), $A^1$, $A^2$ and $A^3$ independently are 1,4-phenylene in which any hydrogen may be replaced by fluorine or naphthalene-2,6-diyl in which any hydrogen may be replaced by fluorine; and $Z^1$, $Z^2$ and $Z^3$ independently are a single bond, $—(CH_2)_2—$, $—CH_2O—$, or $—OCH_2—$.

11. The compound according to the item 1 or 2, wherein in formula (1), at least one of $A^1$ and $A^2$ is 1,4-phenylene, 2-fluoro-1,4-phenylene, 3-fluoro-1,4-phenylene, or 2,5-difluoro-1,4-phenylene; $Z^1$, $Z^2$ and $Z^3$ independently are a single bond, $—(CH_2)_2—$, $—CH_2O—$, or $—OCH_2—$; n is 1 and m is 0; and phenyl having $(F)_p$ is phenyl, 2-fluorophenyl or 2,5-difluorophenyl.

12. The compound according to the item 1 or 2, wherein in formula (1), at least two of $A^1$, $A^2$ and $A^3$ are 1,4-phenylene, 2-fluoro-1,4-phenylene, 3-fluoro-1,4-phenylene, or 2,5-difluoro-1,4-phenylene; $Z^1$, $Z^2$ and $Z^3$ independently are a single bond, $—(CH_2)_2—$ or $—OCH_2—$; n is 1 and m is 1; and phenyl having $(F)_p$ is phenyl, 2-fluorophenyl or 2,5-difluorophenyl.

13. The compound according to the item 1 or 2, wherein in formula (1), $A^1$, $A^2$ and $A^3$ independently are 1,4-phenylene, 2-fluoro-1,4-phenylene, 3-fluoro-1,4-phenylene, or 2,5-difluoro-1,4-phenylene; and phenyl having $(F)_p$ is phenyl, 2-fluorophenyl or 2,5-difluorophenyl.

14. The compound according to the item 13, wherein $Z^1$, $Z^2$ and $Z^3$ in formula (1) are a single bond or $—(CH_2)_2—$.

15. The compound according to the item 14, wherein phenyl having $(F)_p$ in formula (1) is phenyl.

16. The compound according to the item 14, wherein phenyl having $(F)_p$ in formula (1) is 2-fluorophenyl.

17. The compound according to the item 14, wherein phenyl having $(F)_p$ in formula (1) is 2,5-difluorophenyl.

18. A compound represented by any one of the following formulas:

(1-1)

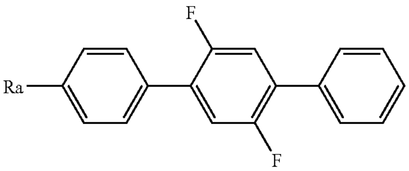

(1-2)

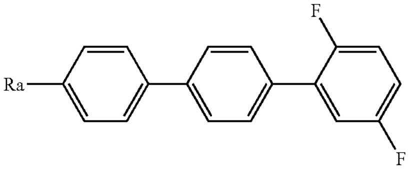

(1-3)

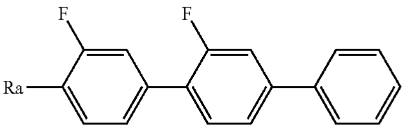

(1-4)

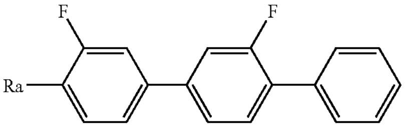

(1-5)

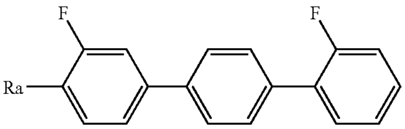

-continued (1-6)

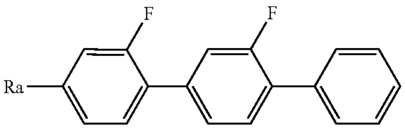

(1-7)

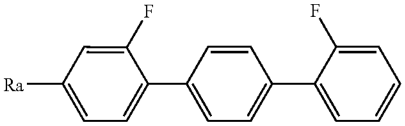

(1-8)

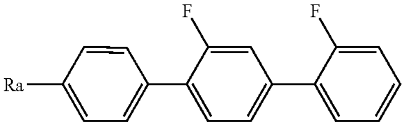

(1-9)

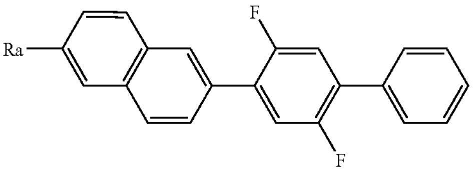

(1-10)

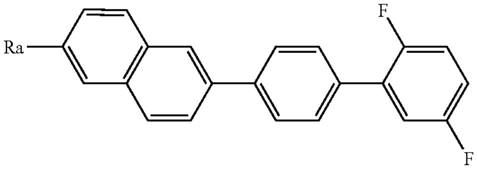

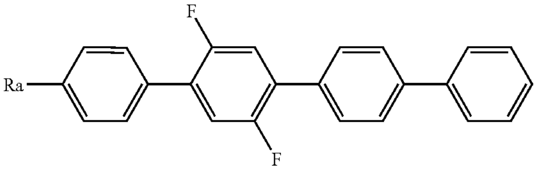

(1-11)

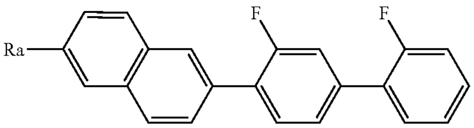

(1-12)

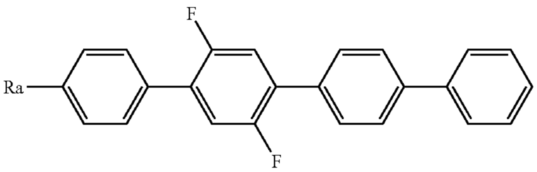

(1-13)

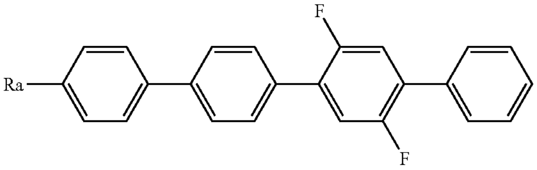

-continued
(1-14)
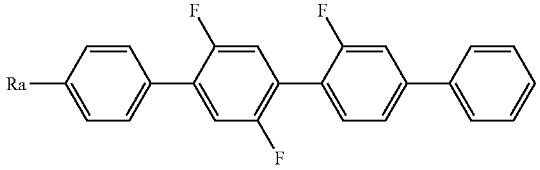
(1-15)
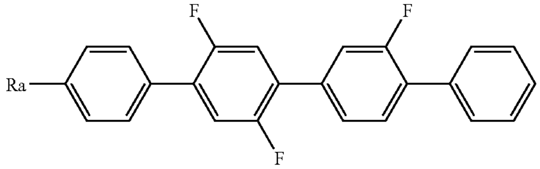
(1-16)
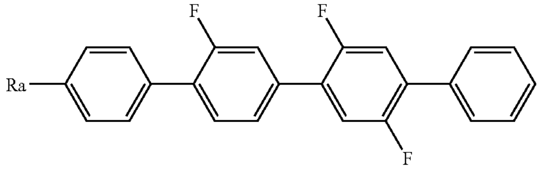
(1-17)
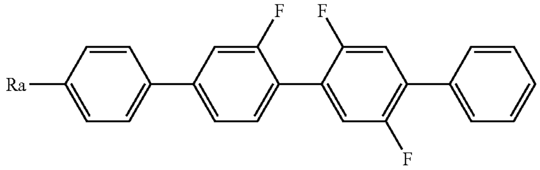
(1-18)
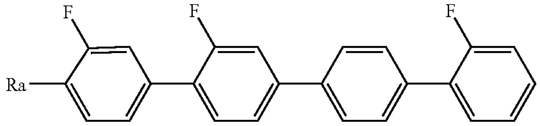
(1-19)
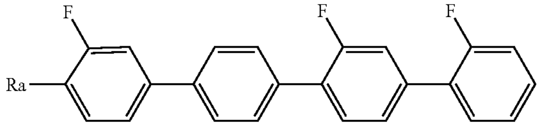
(1-20)
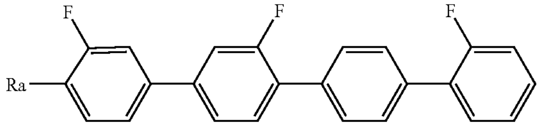
(1-21)
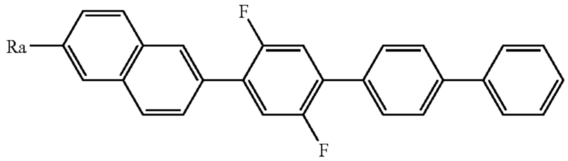
-continued
(1-22)
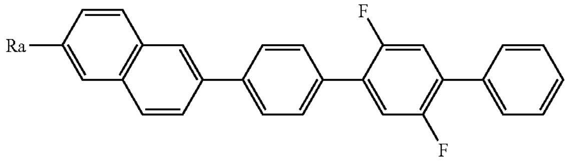
(1-23)
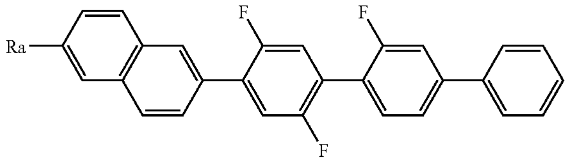
(1-24)
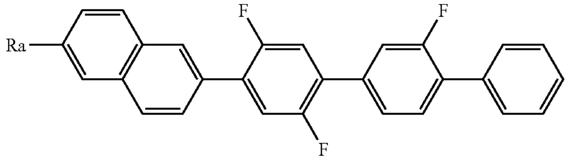
(1-25)
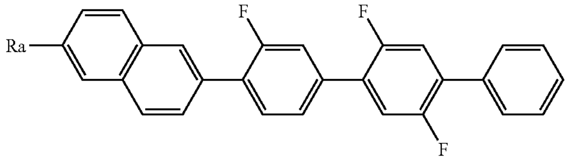
(1-26)
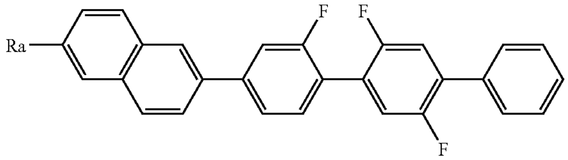
(1-27)
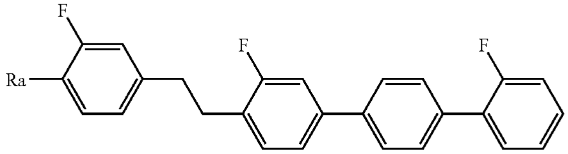
(1-30)
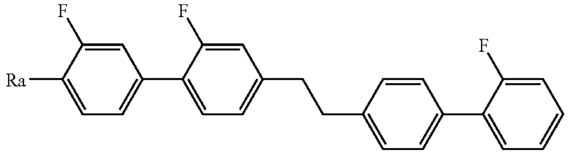
(1-28)
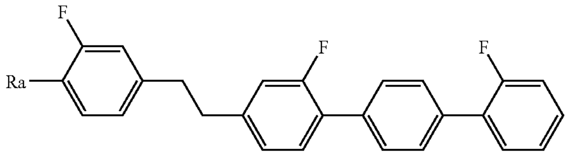

-continued (1-29)

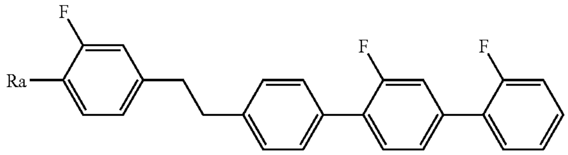

(1-30)

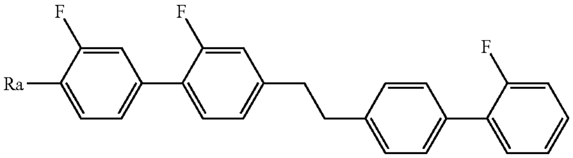

(1-31)

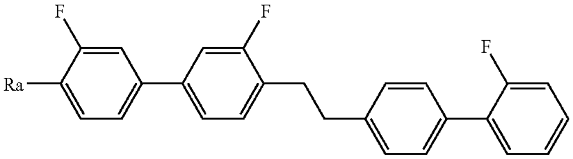

(1-32)

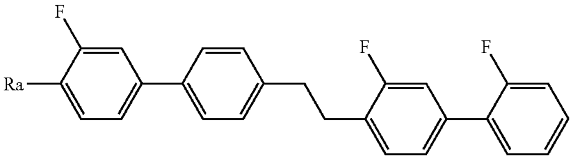

(1-33)

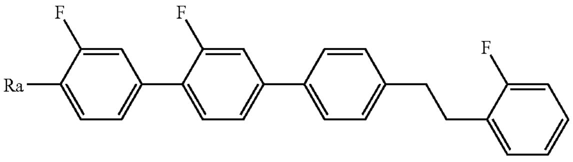

(1-34)

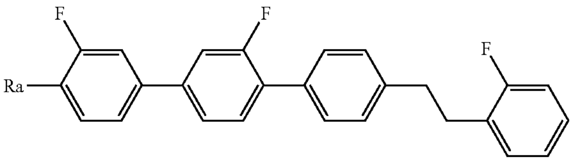

(1-35)

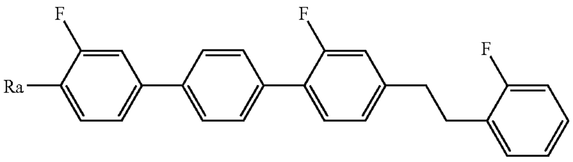

wherein Ra is alkyl having 1 to 15 carbons and any —$CH_2$— in the alkyl may be replaced by —O— or —CH═CH—. Preferable Ra is alkyl having 1 to 10 carbons, alkyl having 1 to 10 carbons in which one —$CH_2$— is replaced by —O—, and alkyl having 1 to 10 carbons in which one —$CH_2$— is replaced by —CH═CH—.

19. A liquid crystal composition comprising at least one compound described in any one of the items 1 to 18.

20. The composition according to the item 19, further comprising at least one compound selected from the group consisting of the compounds represented by formulas (2), (3) and (4):

(2)

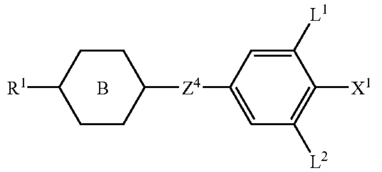

(3)

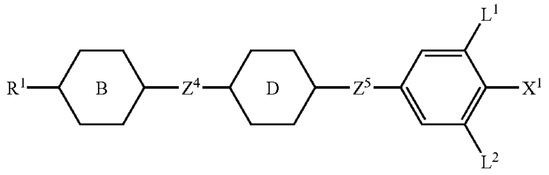

(4)

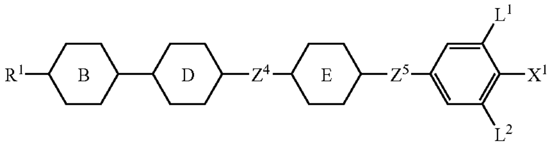

wherein $R^1$ is alkyl having 1 to 10 carbons, any —$CH_2$— in the alkyl may be replaced by —O— or —CH═CH— and any hydrogen in the alkyl may be replaced by fluorine; $X^1$ is fluorine, chlorine, —$OCF_3$, —$OCHF_2$, —$CF_3$, —$CHF_2$, —$CH_2F$, —$OCF_2CHF_2$, or —$OCF_2CHFCF_3$; ring B and ring D independently are 1,4-cyclohexylene, 1,3-dioxane-2,5-diyl or 1,4-phenylene in which any hydrogen may be replaced by fluorine; ring E is 1,4-cyclohexylene or 1,4-phenylene in which any hydrogen may be replaced by fluorine; $Z^4$ and $Z^5$ independently are —$(CH_2)_2$—, —$(CH_2)_4$—, —COO—, —$CF_2O$—, —$OCF_2$—, —CH═CH—, or a single bond; and $L^1$ and $L^2$ independently are hydrogen or fluorine.

21. The composition according to the item 19, further comprising at least one compound selected from the group consisting of the compounds represented by formulas (5) and (6):

(5)

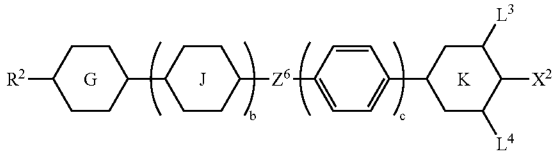

(6)

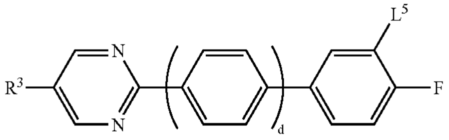

wherein $R^2$ and $R^3$ independently are alkyl having 1 to 10 carbons, any —$CH_2$— in the alkyl may be replaced by —O— or —CH═CH— and any hydrogen in the alkyl may be replaced by fluorine; $X^2$ is —CN or —C≡C—CN; ring G is 1,4-cyclohexylene, 1,4-phenylene, 1,3-dioxane-2,5-diyl, or pyrimidine-2,5-diyl; ring J is 1,4-cyclohexylene, pyrimidine-2,5-diyl or 1,4-phenylene in which any hydrogen may be replaced by fluorine; ring K is 1,4-cyclohexylene or 1,4-phenylene; $Z^6$ is —$(CH_2)_2$—, —COO—, —$CF_2O$—, —$OCF_2$—, or a single bond; $L^3$, $L^4$ and $L^5$ independently are hydrogen or fluorine; and b, c and d independently are 0 or 1.

22. The composition according to the item 19, further comprising at least one compound selected from the group consisting of the compounds represented by formulas (7), (8) and (9):

(7)

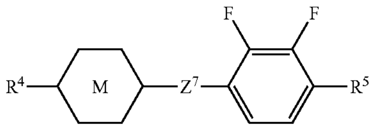

(8)

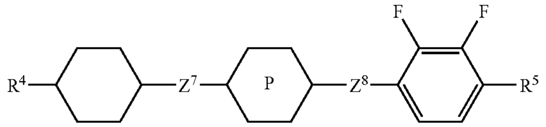

(9)

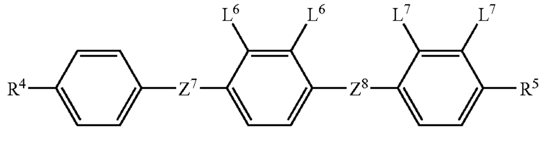

wherein $R^4$ and $R^5$ independently are alkyl having 1 to 10 carbons, any —$CH_2$— in the alkyl may be replaced by —O— or —CH═CH— and any hydrogen in the alkyl may be replaced by fluorine; ring M and ring P independently are 1,4-cyclohexylene or 1,4-phenylene; $Z^7$ and $Z^8$ independently are —$(CH_2)_2$—, —COO— or a single bond; $L^6$ and $L^7$ independently are hydrogen or fluorine, and at least one of $L^6$ and $L^7$ is fluorine.

23. The composition according to the item 20, further comprising at least one compound selected from the group consisting of the compounds represented by formulas (10), (11) and (12):

(10)

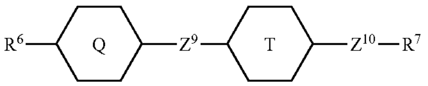

(11)

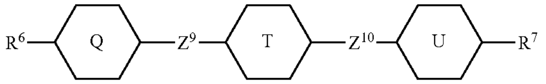

(12)

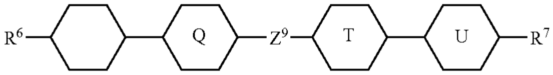

wherein $R^6$ and $R^7$ independently are alkyl having 1 to 10 carbons, any —$CH_2$— in the alkyl may be replaced by —O— or —CH═CH— and any hydrogen in the alkyl may be replaced by fluorine; ring Q, ring T and ring U independently are 1,4-cyclohexylene, pyrimidine-2,5-diyl, or 1,4-phenylene in which any hydrogen may be replaced by fluorine; $Z^9$ and $Z^{10}$ independently are —C≡C—, —COO—, —$(CH_2)_2$—, —CH═CH—, or a single bond.

24. The composition according to the item 21, further comprising at least one compound selected from the group consisting of the compounds represented by formulas (10), (11) and (12) described in the item 23.

25. The composition according to the item 22, further comprising at least one compound selected from the group consisting of the compounds represented by formulas (10), (11) and (12) described in the item 23.

26. The composition according to the item 23, further comprising at least one compound selected from the group consisting of the compounds represented by formulas (5) and (6) described in the item 21.

27. The composition according to any one of the items 19 to 26, further comprising at least one optically active compound.

28. A liquid crystal display element comprising the composition described in any one of the items 19 to 27.

In the compounds (2) to (12), preferable groups are as follows. Straight alkyl is preferable to branched alkyl. In 1,4-cyclohexylene and 1,3-dioxane-2,5-diyl, trans-configuration is preferable to cis-configuration. Meaning of the phrase "any —$CH_2$— in the alkyl may be replaced by —O— or —CH═CH—" was described in the item 1 of the embodiment in this invention. Symbols such as $R^1$, ring B, and so forth are used in plural compounds and these $R^1$ (or ring B and so forth) may be the same or different each other. These compounds may comprise an isotope such as $^2H$ (deuterium) and $^{13}C$ in an amount more than its natural abundance, because no large difference is found in the physical properties of the compound.

Firstly, the compound (1) of this invention is further explained. One of the terminal groups of the compound (1) is hydrogen. The compound is highly stable both physically and chemically under the conditions for normal use of the element, has a large optical anisotropy and a proper dielectric anisotropy, and is excellent in a miscibility with other liquid crystal compounds. The composition comprising the compound is stable under the conditions for normal use of the element. Keeping the composition even at low temperature does not allow the compound to be separated out as a solid. A composition comprising the compound (1) in which Ra is alkyl has good miscibility at low temperature compared with a composition comprising the compound in which both of terminal groups are alkyl.

Physical properties of the compound (1) can be controlled by proper selection of a terminal group, a ring and a bonding group in the compound (1). Effects to physical properties of the compound (1) depending on the kinds of a terminal group Ra, rings $A^1$, $A^2$, $A^3$, and bonding groups $Z^1$, $Z^2$, $Z^3$ will be explained below. The compound (1), when added to a composition, influences the physical properties of the composition.

When Ra in the compound (1) is straight, a temperature range of the liquid crystal phase is wide and a viscosity is small. When Ra is branched, the miscibility with other liquid crystal compounds is excellent. The compound in which Ra is an optically active group is useful as a chiral dopant. The addition of the compound to a composition prevents a reversed twisted domain that will be formed in an element. The compound in which Ra is not an optically active group is useful as a component of the composition.

When ring $A^1$, $A^2$ or $A^3$ in the compound (1) is 1,4-phenylene in which any hydrogen is replaced by fluorine, or 1,3-dioxane-2,5-diyl, a dielectric anisotropy is large. When the ring is 1,4-phenylene in which any hydrogen may be replaced by fluorine, the optical anisotropy is large. When the ring is 1,4-cyclohexylene or 1,3-dioxane-2,5-diyl, the optical anisotropy is small.

When at least two rings are 1,4-cyclohexylene, a clearing point is high, a optical anisotropy is small and a viscosity is small. When at least one ring is 1,4-phenylene, the optical anisotropy is relatively large, and the orientational order parameter is large. When at least two rings are 1,4-phenylene, the optical anisotropy is large, the temperature range of the liquid crystal phase is wide, and the clearing point is high.

When a bonding group, $Z^1$, $Z^2$ or $Z^3$ is a single bond, $-(CH_2)_2-$, $-CH_2O-$, $-OCH_2-$, $-CF_2O-$, $-OCF_2-$, $-CH{=}CH-$, $-CF{=}CF-$, or $-(CH_2)_4-$, a viscosity is small. When the bonding group is a single bond, $-(CH_2)_2-$, $-OCF_2-$, $-CF_2O-$, $-CH{=}CH-$, or $-(CH_2)_4-$, the viscosity is smaller. When the bonding group is $-CH{=}CH-$ or $-CF{=}CF-$, the temperature range of the liquid crystal phase is wide, and the ratio of the elastic constant is large. When the bonding group is $-C{\equiv}C-$, the optical anisotropy is large.

When the compound (1) has two or three rings, the viscosity is small, and when it has three or four rings, the clearing point is high. As described above, the compound having desired physical properties can be obtained by selecting properly a kind of a terminal group, a ring, a bonding group, and the number of the ring.

Preferable examples of the compound (1) are the compounds (a1) to (a26). More concrete compounds are the compounds (b1) to (b58). Meanings of the symbols Ra, $Z^1$, $Z^2$, $Z^3$, and phenyl having $(F)_p$ in these compounds are the same as those in the item 1. Preferable meanings of the symbols Ra, $Z^1$, $Z^2$, $Z^3$ and phenyl having $(F)_p$ in these compounds are the same as those in the item 2. Especially preferable meaning of the symbol Ra in these compounds is the same as that in the item 18. 1,4-Phenylene having (F) denotes 1,4-phenylene in which any hydrogen may be replaced by fluorine. Naphthalene-2,6-diyl having (F) denotes naphthalene-2,6-diyl in which any hydrogen may be replaced by fluorine. 1,2,3,4-Tetrahydronaphthalene-2,6-diyl having (F) denotes 1,2,3,4-tetrahydronaphthalene-2,6-diyl in which any hydrogen may be replaced by fluorine.

(a1)

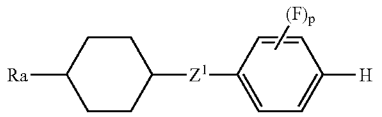

(a2)

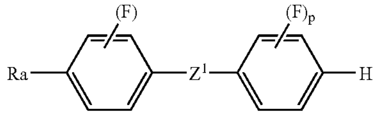

(a3)

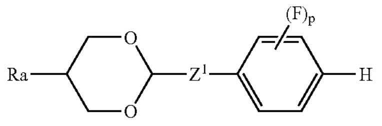

(a4)

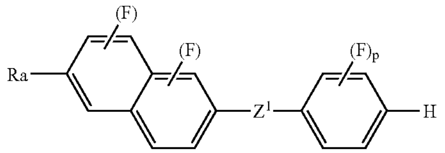

(a5)

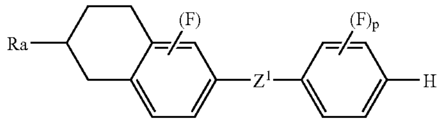

(a6)

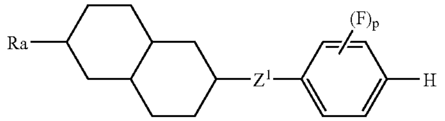

(a7)

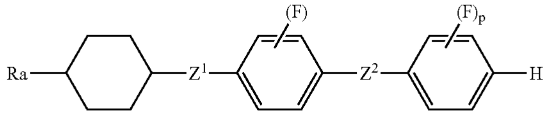

(a8)

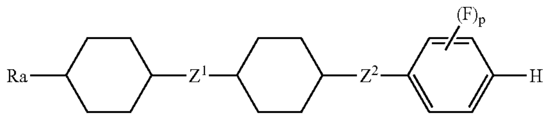

(a9)

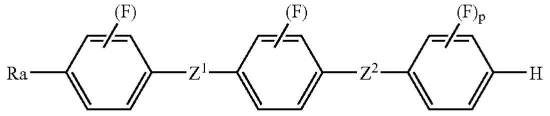

(a10)

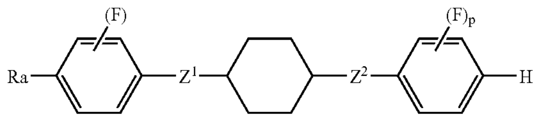

-continued
(a11)
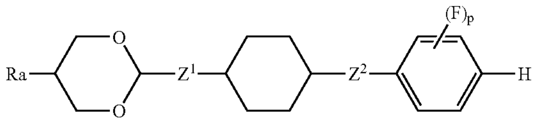
(a12)
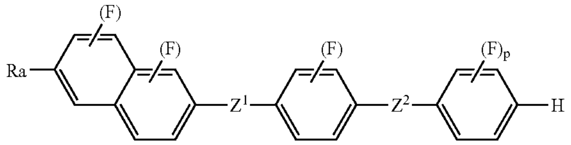
(a13)
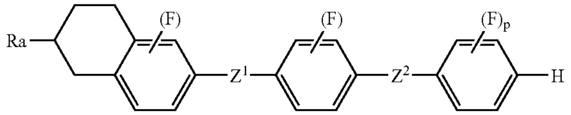
(a14)
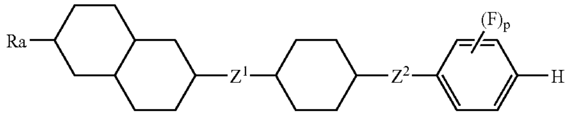
(a15)
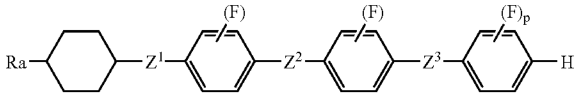
(a16)
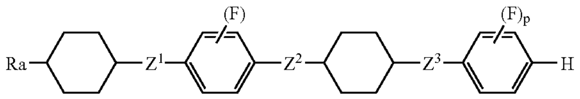
(a17)
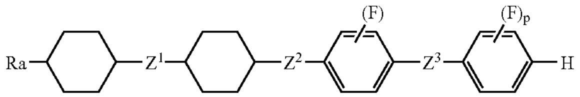
(a18)
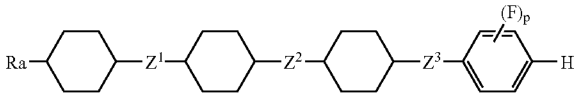
(a19)
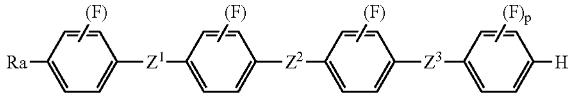
(a20)
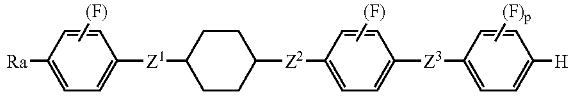
(a21)
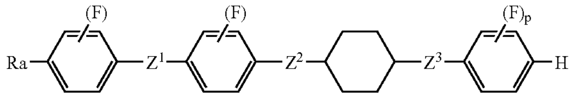
-continued
(a22)
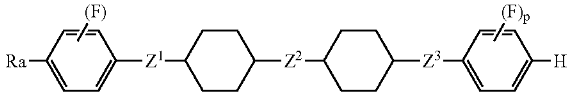
(a23)
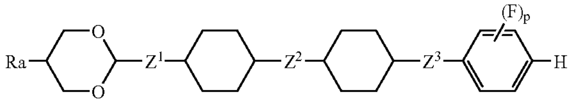
(a24)
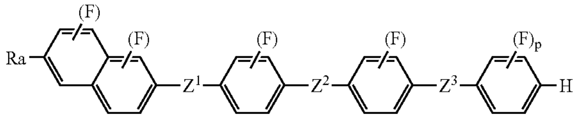
(a25)
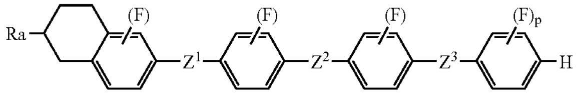
(a26)
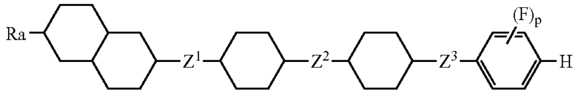
(b1)
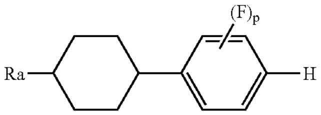
(b2)
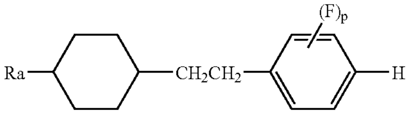
(b3)
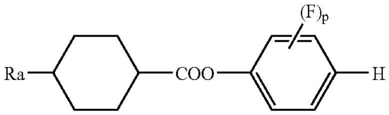
(b4)
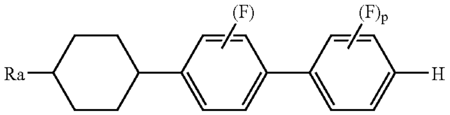
(b5)
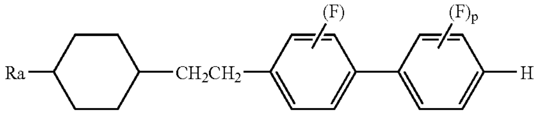
(b6)
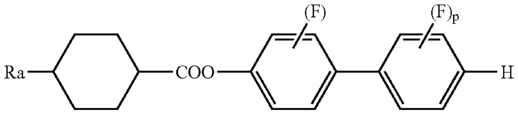
(b7)
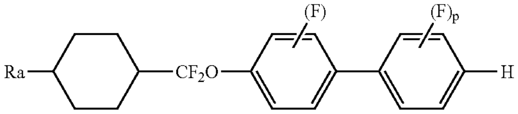

-continued
(b8)
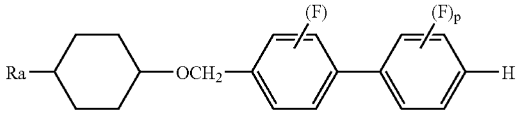
(b9)
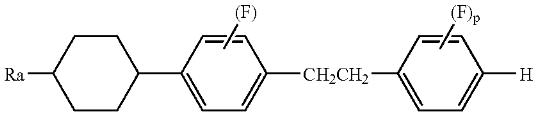
(b10)
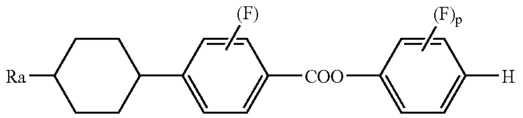
(b11)
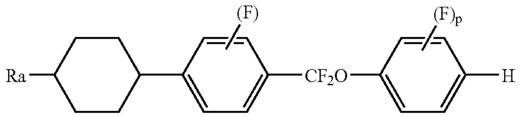
(b12)
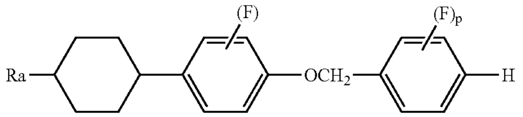
(b13)
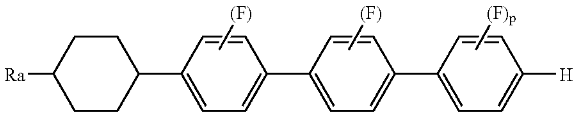
(b14)
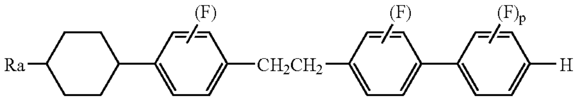
(b15)
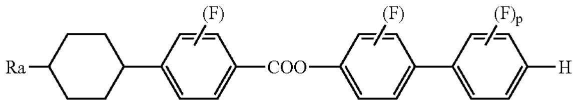
(b16)
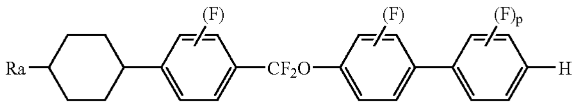
(b17)
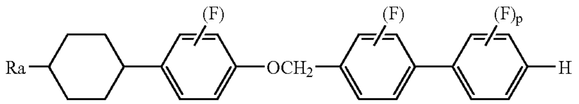
(b18)
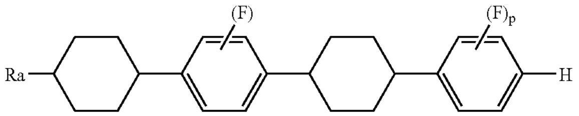
-continued
(b19)
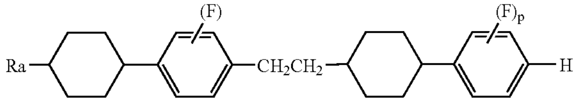
(b20)
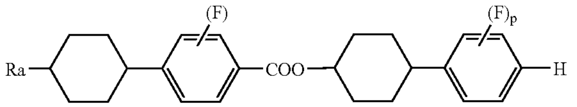
(b21)
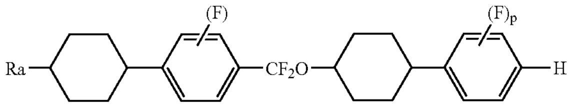
(b22)
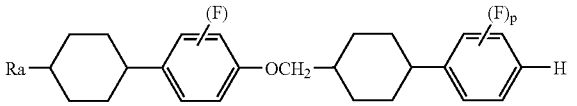
(b23)
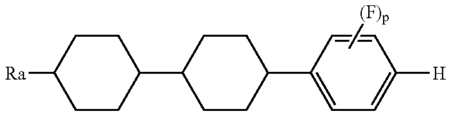
(b24)
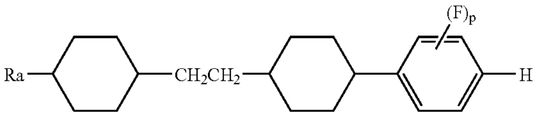
(b25)
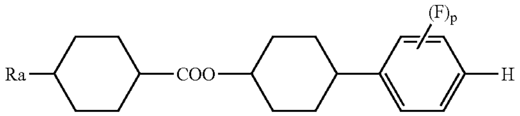
(b26)
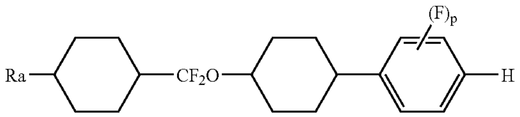
(b27)
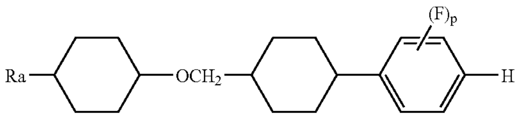
(b28)
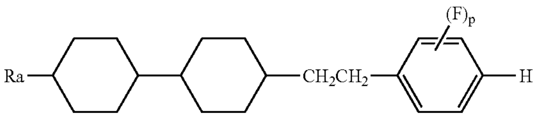
(b29)
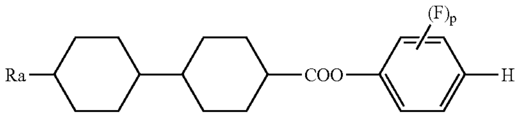

-continued
(b30)
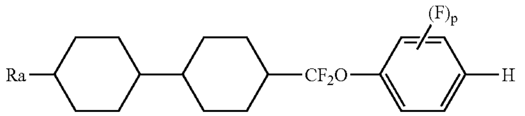
(b31)
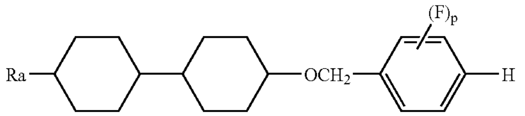
(b32)
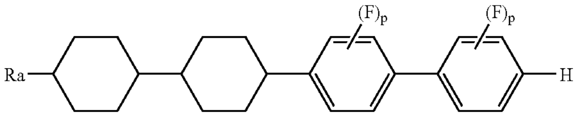
(b33)
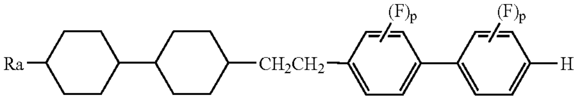
(b34)
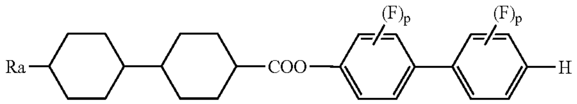
(b35)
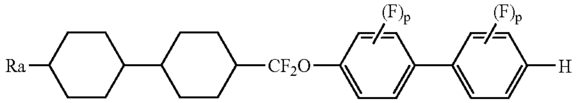
(b36)
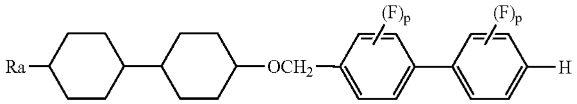
(b37)
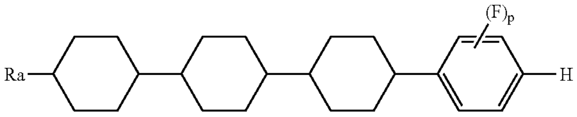
(b38)
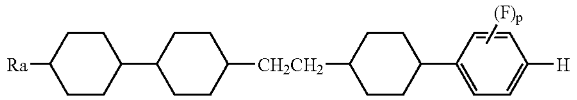
(b39)
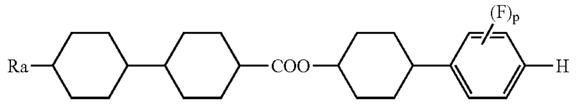
(b40)
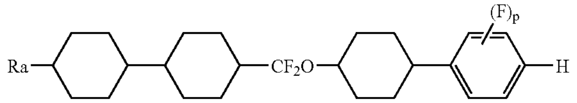
-continued
(b41)
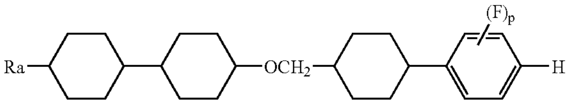
(b42)
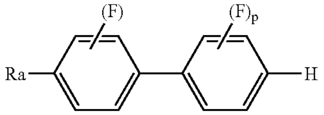
(b43)
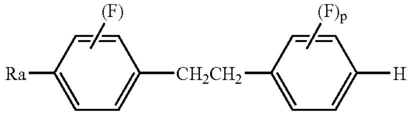
(b44)
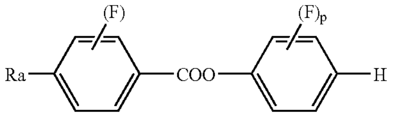
(b45)
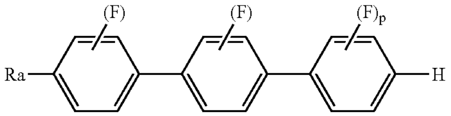
(b46)
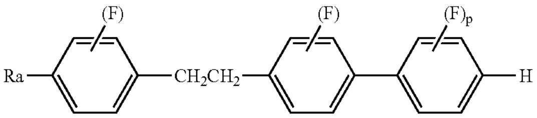
(b47)
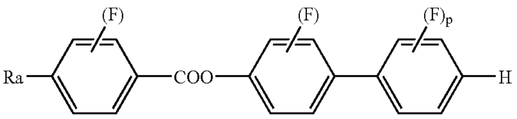
(b48)
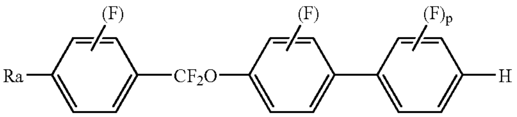
(b49)
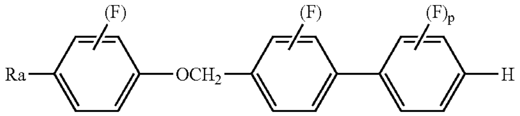
(b50)
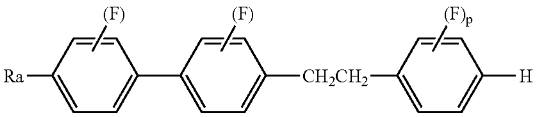
(b51)
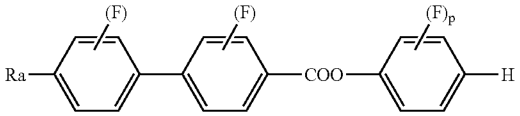

-continued (b52)

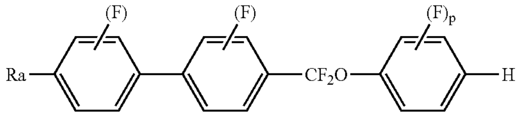

(b53)

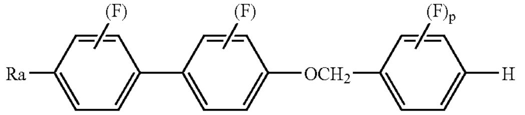

(b54)

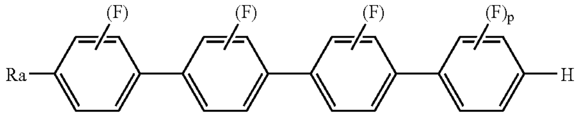

(b55)

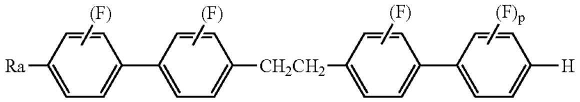

(b56)

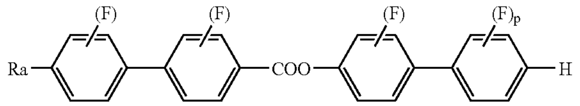

(b57)

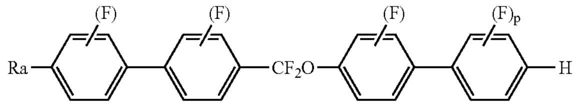

(b58)

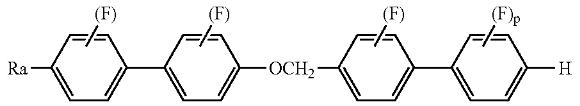

-continued (b59)

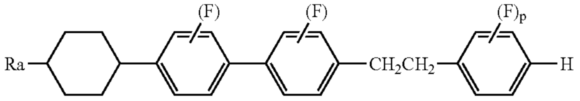

(b60)

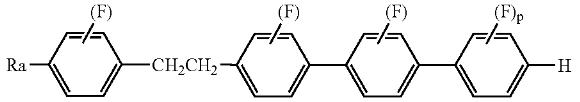

(b61)

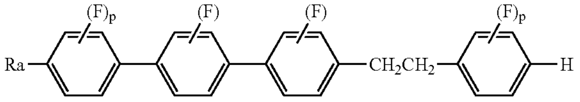

The compound (1) can be prepared by appropriately combining methods known in synthetic organic chemistry. Methods of introducing objective terminal groups, rings and bonding groups to a starting material are described, for example, in Organic Syntheses, John Wiley & Sons, Inc., Organic Reactions, John Wiley & Sons, Inc., Comprehensive Organic Synthesis, Pergamon Press, Shin-Jikken Kakagu Koza (Maruzen).

One example of the method for the formation of a bonding group, $Z_1$, $Z_2$ or $Z_3$, is firstly shown in a scheme, which is explained in the items (I) to (XI). In the scheme, $MSG^1$ or $MSG^2$ is a mono-valent organic group having at least one ring, and plural $MSG^1$ (or $MSG^2$) may be the same or different each other. The compounds (1A) to (1K) correspond to the compound (1).

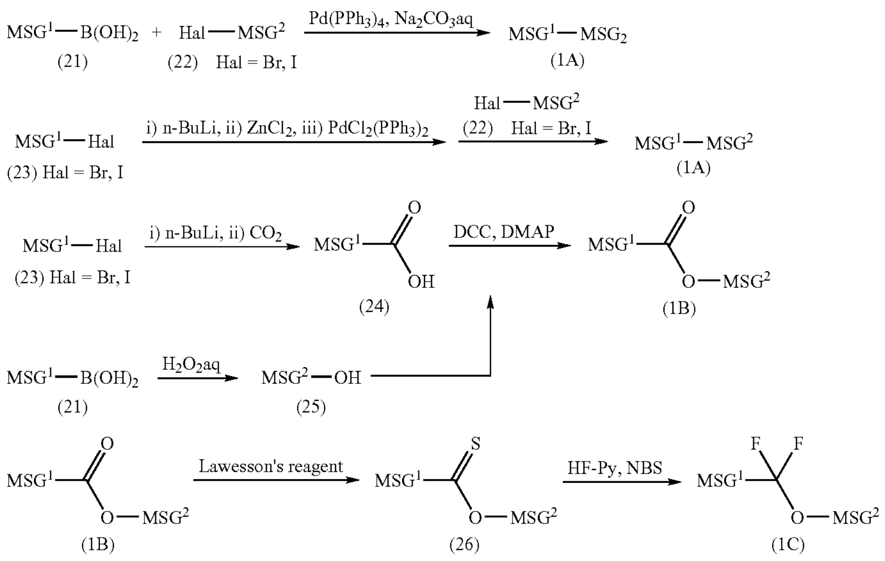

-continued

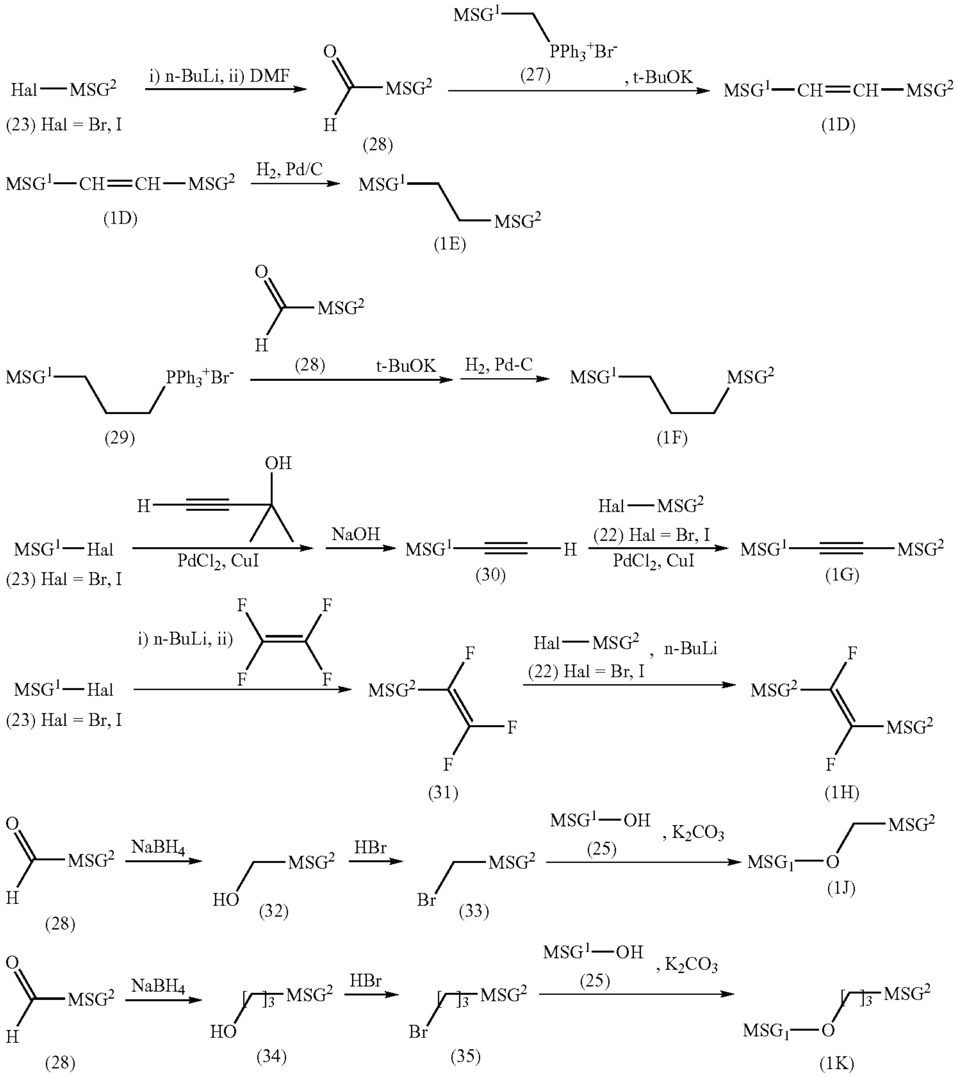

(I) Formation of a Single Bond

The compound (1A) is prepared by the reaction of arylboric acid (21) with the compound (22) prepared by a known method, in the presence of catalysts such as an aqueous solution of carbonate and tetrakis(triphenylphosphine)palladium. The compound (1A) is also prepared by the reaction of the compound (23) prepared by a known method with n-butyl lithium and zinc chloride, and then with the compound (22) in the presence of a catalyst such as dichlorobis(triphenylphosphine)palladium.

(II) Formation of —COO— and —OCO—

The carboxylic acid (24) is obtained by the reaction of the compound (23) with n-butyl lithium followed by carbon dioxide. The compound (1B) having —COO— is prepared by dehydration of the compound (24) and phenol (25) prepared by a known method in the presence of DDC (1,3-dicyclohexylcarbodiimide) and DMAP (4-dimethylaminopyridine).

The compound having —OCO— is also prepared by this method.

(III) Formation of —$CF_2O$— and —$OCF_2$—

The compound (26) is obtained by treating the compound (1B) with a sulfurating agent such as Lawesson's reagent. The compound (1C) having —$CF_2O$— is prepared by fluorination of the compound (26) with hydrogen fluoride-pyridine complex and NBS (N-bromosuccinimide). See M. Kuroboshi et al., Chem. Lett., 1992, 827. The compound (1C) is also prepared by fluorination of the compound (26) with (diethylamino)sulfur trifluoride. See William. H. Bunnelle et al., J. Org. Chem., 1990, 55, 768. The compound having —OCF2— is also prepared by this method.

(IV) Formation of —CH=CH—

The compound (23) is treated with n-butyl lithium and then formamide such as N,N-dimethylformamide to give aldehyde (28). The compound (1D) is prepared by the reaction of the aldehyde (28) with phoshine ylide which is generated by the treatment of phosphonium salt (27) prepared by a known method with a base such as potassium t-butoxide. cis-Isomer, which may be formed depending on the reaction conditions, is isomerized to trans-isomer by a known method if needed.

(V) Formation of —$(CH_2)_2$—

The compound (1E) is prepared by hydrogenation of the compound (1D) in the presence of a catalyst such as palladium carbon.

(VI) Formation of $—(CH_2)_4—$

The compound having $—(CH_2)_2—CH{=}CH—$ is obtained using phosphonium salt (29) instead of the phosphonium salt (27) according to the method described in the item (IV). The resulting compound is subjected to a catalytic hydrogenation to prepare the compound (1F).

(VII) Formation of $—C{\equiv}C—$

The compound (23) is reacted with 2-methyl-3-butyn-2-ol in the presence of palladium dichloride and copper halide as catalysts, followed by deprotection under the basic conditions to give the compound (30). The compound (1G) is prepared by the reaction of the compound (30) with the compound (22) in the presence of palladium dichloride and copper halide as catalysts.

(VIII) Formation of $—CF{=}CF—$

The compound (31) is obtained by the reaction of the compound (23) with n-butyl lithium and then tetrafluoroethylene. The compound (1H) is prepared by the reaction of the compound (22) with n-butyl lithium and then the compound (31).

(IX) Formation of $—CH_2O—$ and $—OCH_2—$

The compound (32) is obtained by the reduction of the compound (28) with a reducing agent such as sodium borohydride. The compound (33) is obtained by halogenation of the compound (32) with hydrobromic acid. The compound (1J) is prepared by the reaction of the compound (33) with the compound (25) in the presence of potassium carbonate.

(X) Formation of $—(CH_2)_3O—$ and $—O(CH_2)_3—$

The compound (1K) is prepared using the compound (34) instead of the compound (32) according to the method in the item (IX).

(XI) Formation of $—(CF_2)_2—$

The compound having $—(CF_2)_2—$ is obtained by fluorination of diketone (—COCO—) with sulfur tetrafluoride in the presence of hydrogen fluoride as a catalyst according to the method described in J. Am. Chem. Soc., 2001, 123, 5414.

Secondly, the composition of this invention is further explained. Amount of the compound (percentage) described below is percent by weight based on the total weight of the composition. The composition may comprise plural compounds selected only from the compound (1) as a substantial component. Preferably, the composition comprises at least one compound selected from the compound (1) in the ratio of 1 to 99%. The composition may further comprise at least one compound selected from the group consisting of the compounds (2), (3) and (4), at least one compound selected from the group consisting of the compounds (5) and (6), or at least one compound selected from the group consisting of the compounds (7), (8) and (9). The composition may further comprise at least one compound selected from the group consisting of the compounds (10), (11) and (12) for the purpose of controlling a temperature range of the liquid crystal phase, viscosity, optical anisotropy, dielectric anisotropy, threshold voltage, and so forth. The composition may further comprise other compounds for the purpose of controlling the physical properties.

The compounds (2), (3) and (4) are used mainly for the composition for a TN-TFT mode, because their dielectric anisotropy is positive and large, and the thermal and chemical stabilities are excellent. In the composition, the amount of these compounds is 1 to 99%, preferably 10 to 97%, and more preferably 40 to 95%. The compounds (10), (11) or (12) may be further added to the composition for the purpose of controlling a temperature range of the liquid crystal phase, viscosity, optical anisotropy, dielectric anisotropy, or threshold voltage.

The compounds (5) and (6) are used mainly for the composition for STN and TN modes, because their dielectric anisotropy is positive and very large. These compounds are used for the purpose of widening a temperature range of the liquid crystal phase, controlling the viscosity and the optical anisotropy, decreasing the threshold voltage, improving the sharpness of the threshold voltage, and so forth. In the composition for the STN or TFT mode, the amount of the compound (5) or (6) is 1 to 99%, preferably 10 to 97%, and more preferably 40 to 95%. The compounds (10), (11) or (12) may be further added to the composition for the purpose of controlling a temperature range of the liquid crystal phase, viscosity, optical anisotropy, dielectric anisotropy, or threshold voltage.

The compounds (7), (8) and (9) are used mainly for the composition for a VA mode, because their dielectric anisotropy is negative. The compound (7) is used for the purpose of controlling viscosity, optical anisotropy and threshold voltage. The compound (8) is used for the purpose of increasing a clearing point, increasing optical anisotropy and decreasing threshold voltage, and so forth. An increased amount of these compounds decreases the threshold voltage but increases the viscosity of the composition. Therefore, these compounds are used preferably in a smaller amount as long as the required value of the threshold voltage is satisfied. As these compounds have a negative dielectric anisotropy with the absolute value of 5 or less, they are used in the amount of preferably 40% or more, more preferably 40 to 80%. These compounds may be added to a composition having a positive dielectric anisotropy in order to control an elastic constant and a voltage-transmittance curve, preferably in an amount of 30% or less.

The dielectric anisotropy of the compounds (10), (11) and (12) is small in terms of absolute value. The compound (10) is used mainly for the purpose of controlling viscosity or optical anisotropy. The compounds (11) and (12) are used for the purpose of increasing a clearing point to widen a temperature range of a liquid crystal phase or controlling optical anisotropy. An increased amount of the compounds (10), (11) and (12) increases the threshold voltage and decreases the viscosity of the composition. Thus, these compounds may be used in a larger amount as long as the required value of the threshold voltage is satisfied. In the composition for the TN-TFT mode, these compounds are used preferably in an amount of 40% or less, more preferably 35% or less. In the composition for the STN or TN mode, these compounds are used preferably in an amount of 70% or less, more preferably 60% or less.

Preferable compounds (2) to (12) are the compounds (2-1) to (2-9), the compounds (3-1) to (3-97), the compounds (4-1) to (4-33), the compounds (5-1) to (5-58), the compounds (6-1) to (6-3), the compounds (7-1) to (7-3), the compounds (8-1) to (8-5), the compounds (9-1) to (9-3), the compounds (10-1) to (10-11), the compounds (11-1) to (11-12), and the compounds (12-1) to (12-6), respectively. In these compounds, the symbols $R^1$, $R^2$, $R^3$, $R^4$, $R^5$, $R^6$, $R^7$, $X^1$, and $X^2$ have the same meanings as those in the compounds (2) to (12).

(2-1)
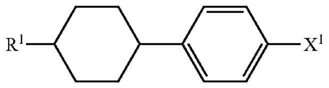
(2-2)
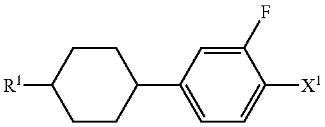
(2-3)
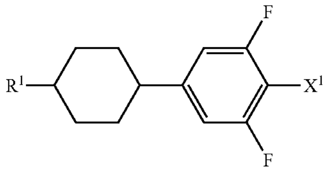
(2-4)
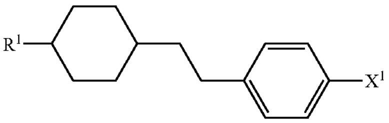
(2-5)
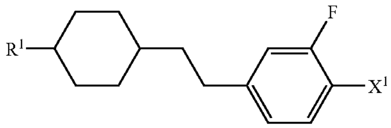
(2-6)
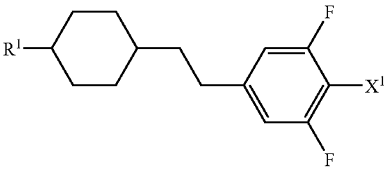
(2-7)
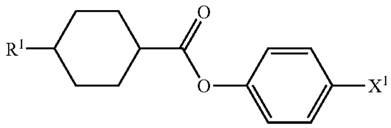
(2-8)
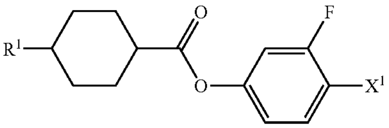
(2-9)
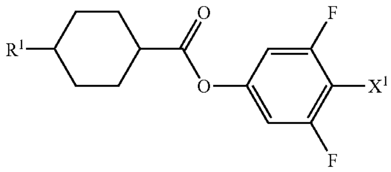
(3-1)
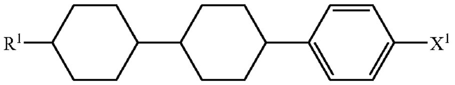
(3-2)
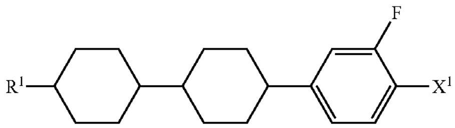
(3-3)
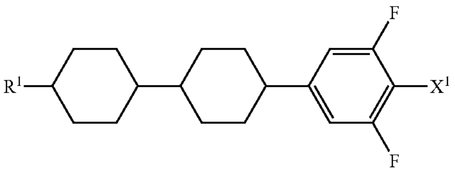
(3-4)
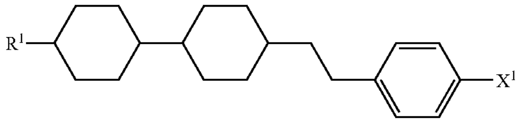
(3-5)
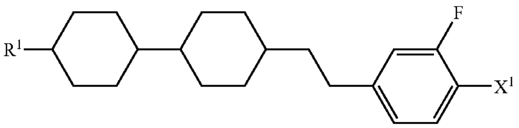
(3-6)
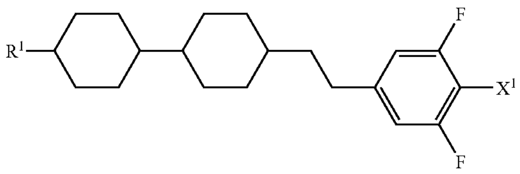
(3-7)
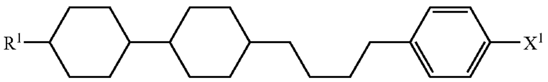
(3-8)
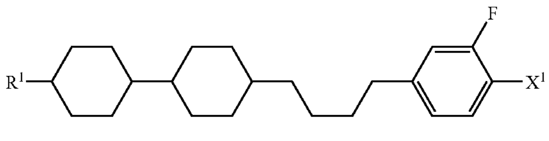
(3-9)
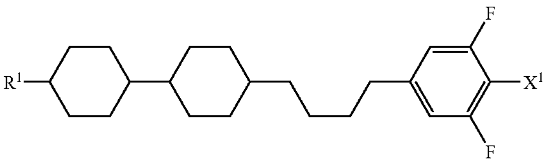

-continued
(3-10)
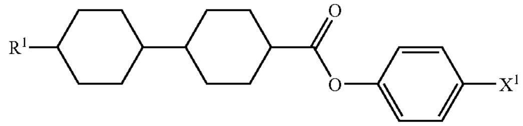
(3-11)
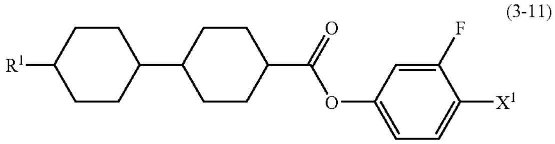
(3-12)
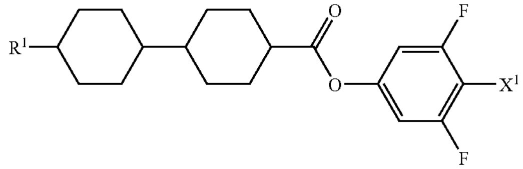
(3-13)
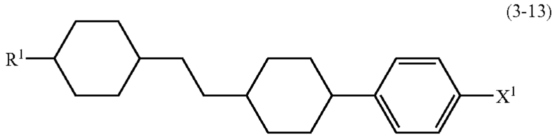
(3-14)
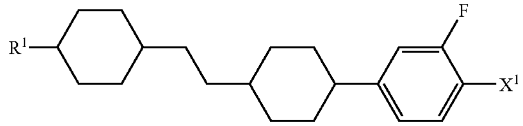
(3-15)
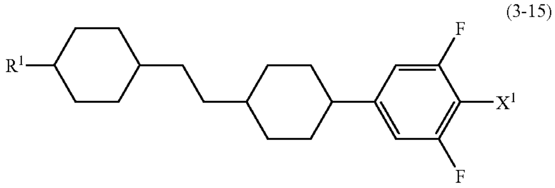
(3-16)
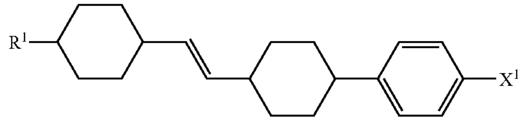
(3-17)
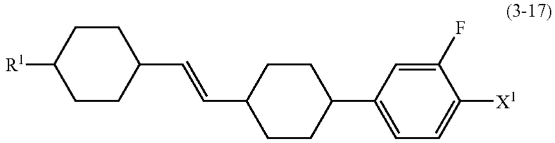
(3-18)
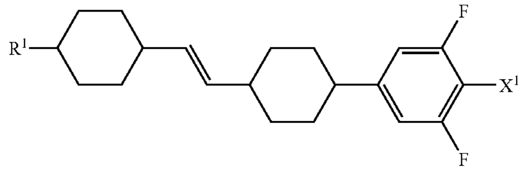
(3-19)
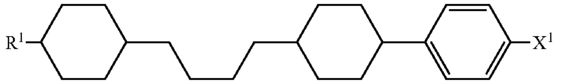
(3-20)
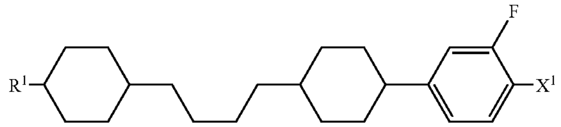
(3-21)
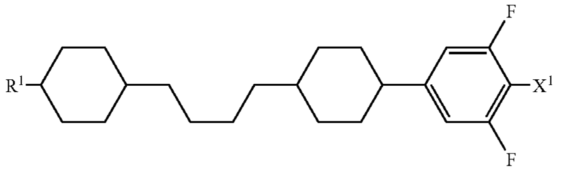
(3-22)
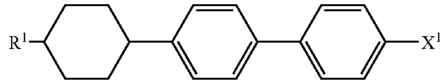
(3-23)
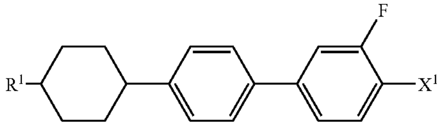
(3-24)
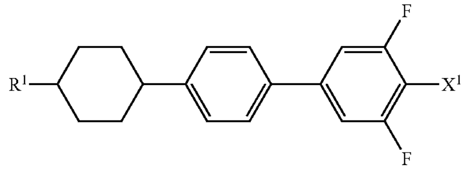
(3-25)
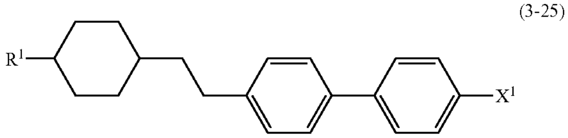
(3-26)
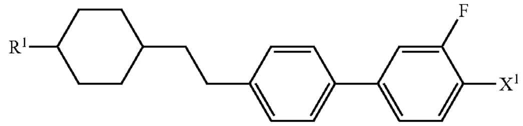
(3-27)
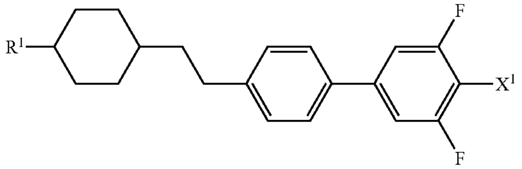

-continued
(3-28)
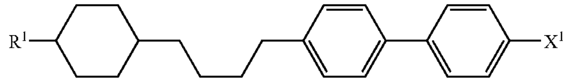
(3-29)
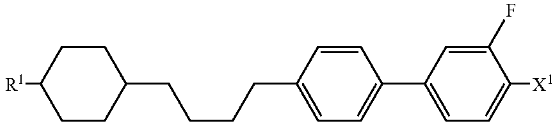
(3-30)
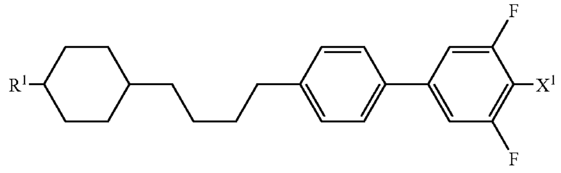
(3-31)
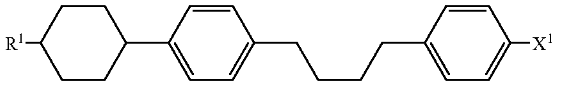
(3-32)
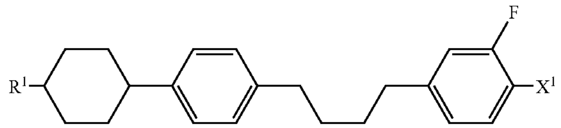
(3-33)
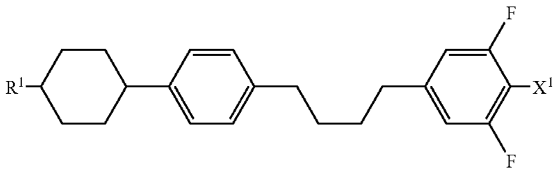
(3-34)
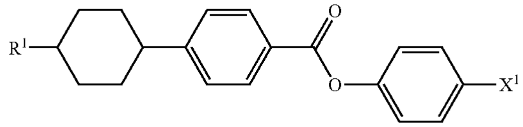
(3-35)
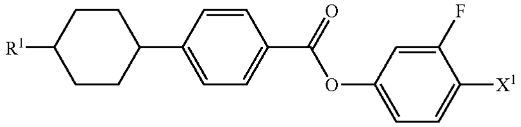
(3-36)
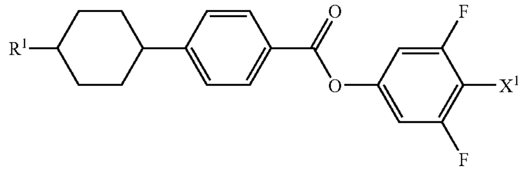
(3-37)
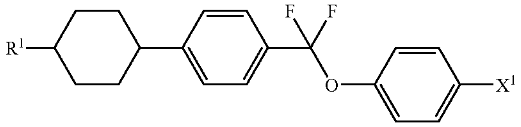
(3-38)
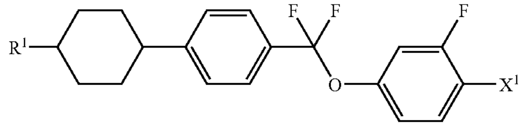
(3-39)
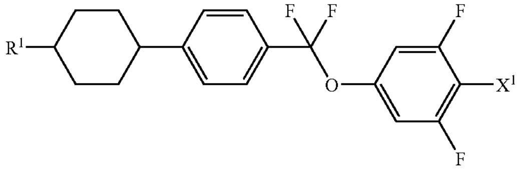
(3-40)
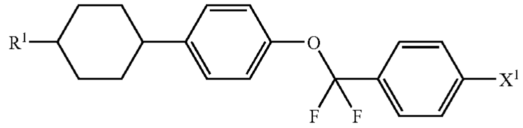
(3-41)
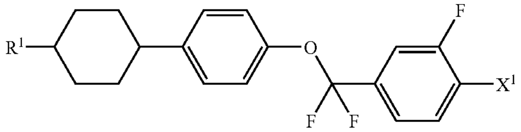
(3-42)
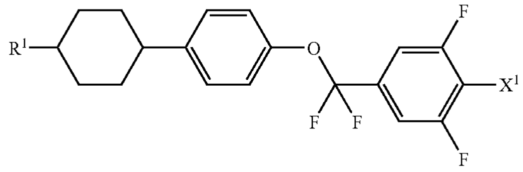
(3-43)
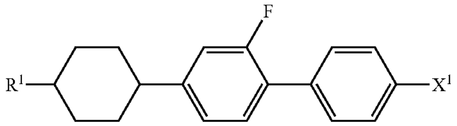
(3-44)
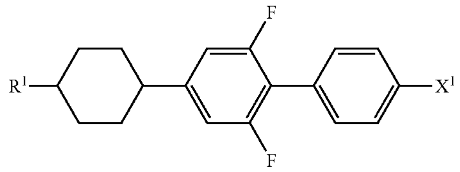
(3-45)
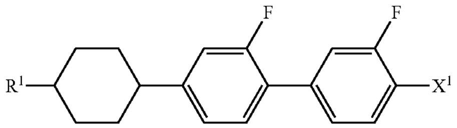

-continued
(3-46)
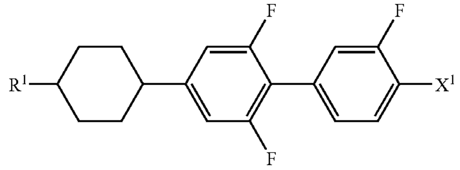
(3-47)
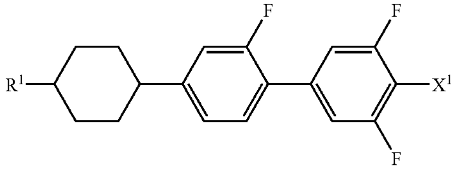
(3-48)
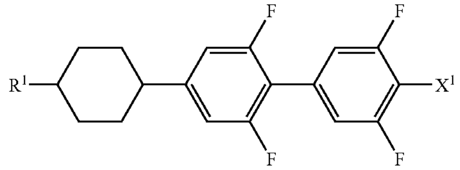
(3-49)
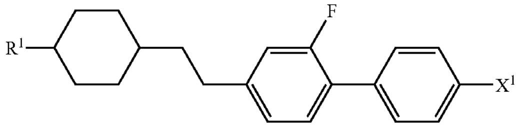
(3-50)
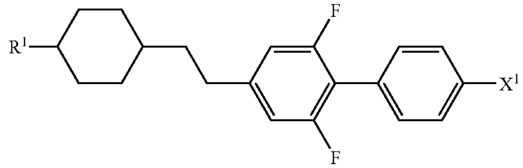
(3-51)
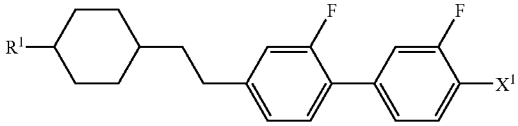
(3-52)
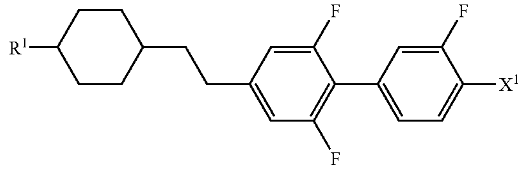
(3-53)
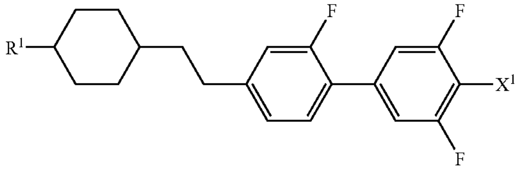
(3-54)
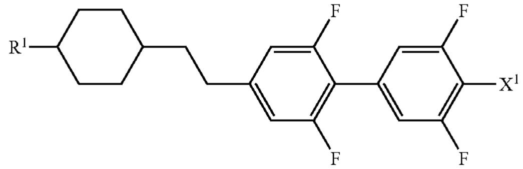
(3-55)
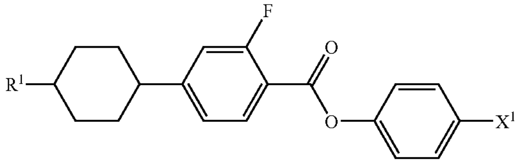
(3-56)
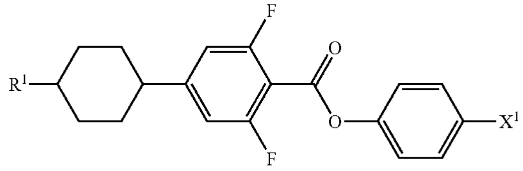
(3-57)
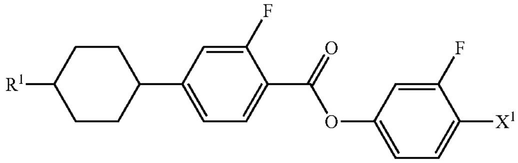
(3-58)
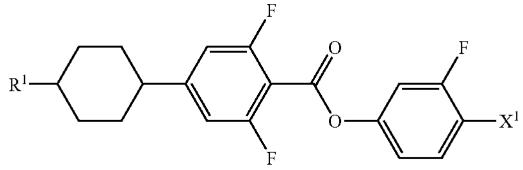
(3-59)
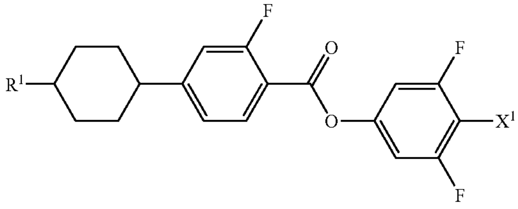
(3-60)
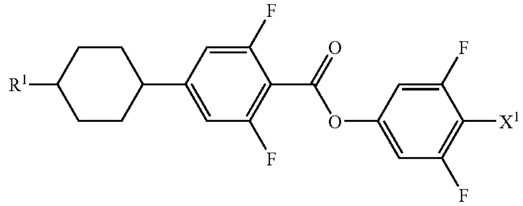
(3-61)
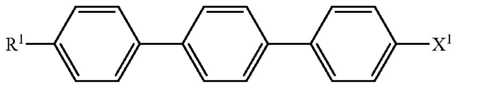

-continued
(3-62)
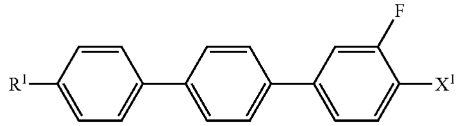
(3-63)
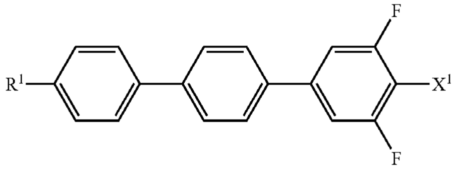
(3-64)
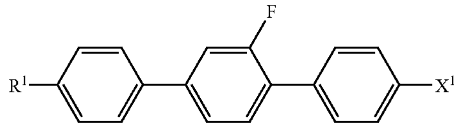
(3-65)
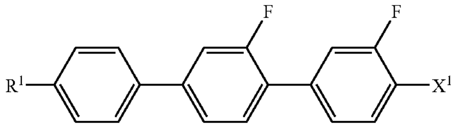
(3-66)
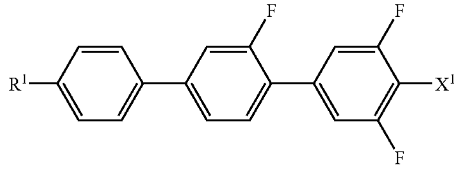
(3-67)
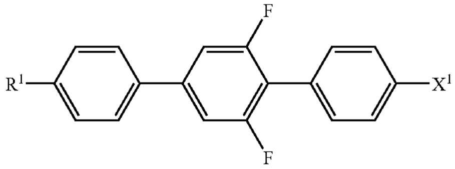
(3-68)
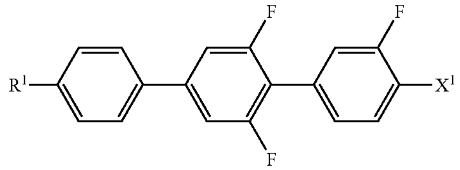
(3-69)
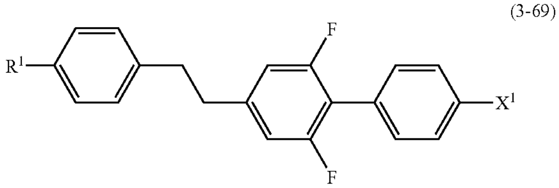
(3-70)
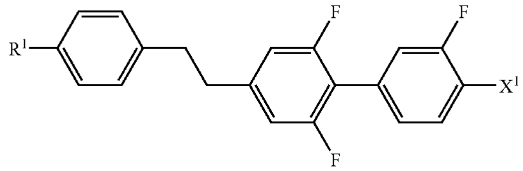
(3-71)
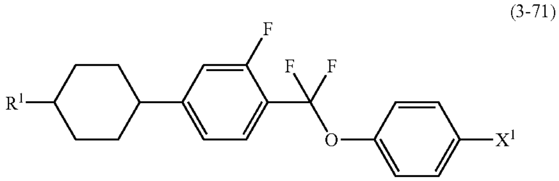
(3-72)
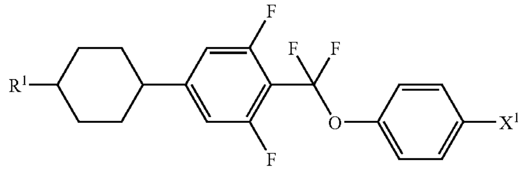
(3-73)
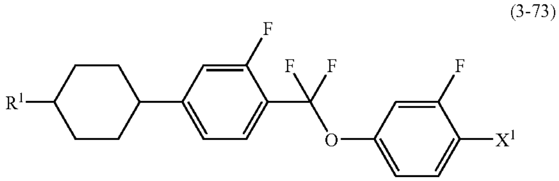
(3-74)
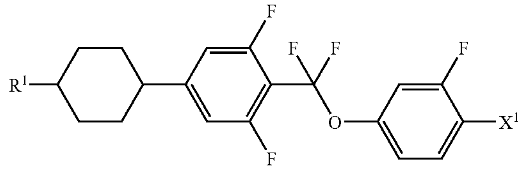
(3-75)
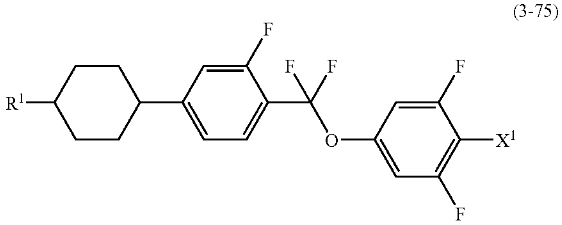
(3-76)
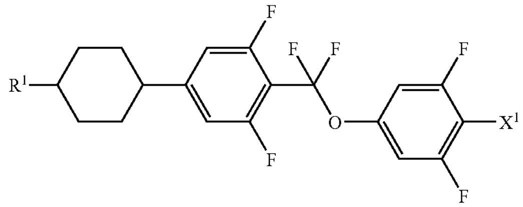
(3-77)
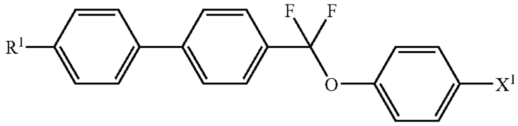

-continued
(3-78)
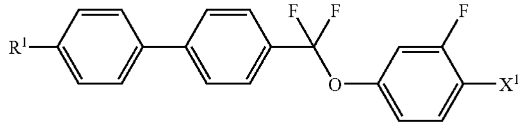
(3-79)
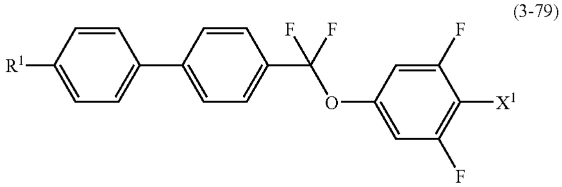
(3-80)
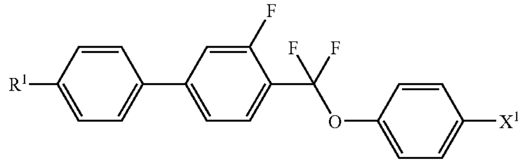
(3-81)
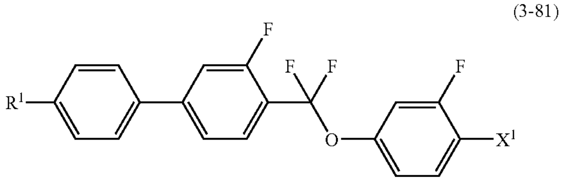
(3-82)
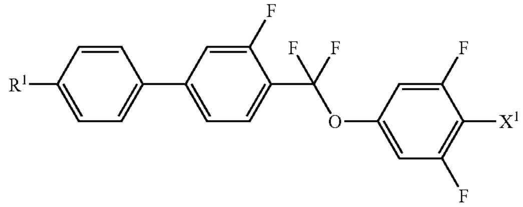
(3-83)
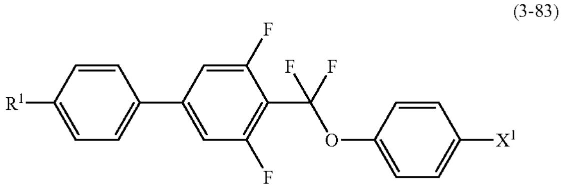
(3-84)
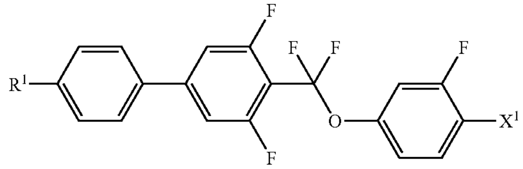
(3-85)
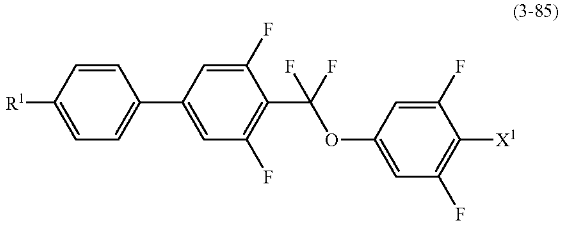
(3-86)
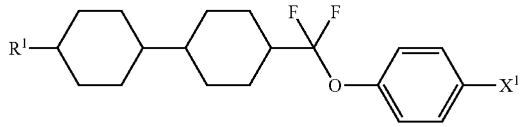
(3-87)
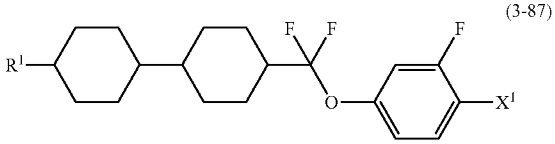
(3-88)
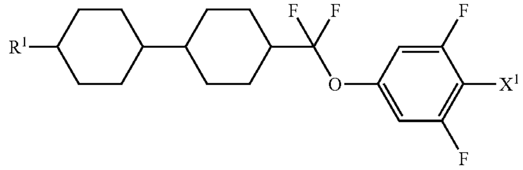
(3-89)
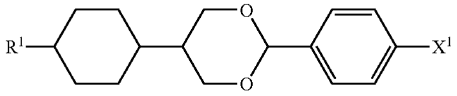
(3-90)
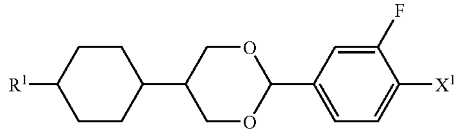
(3-91)
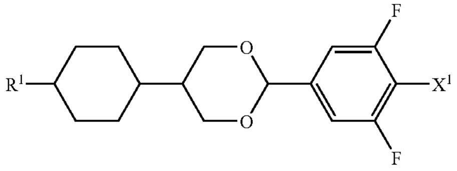
(3-92)
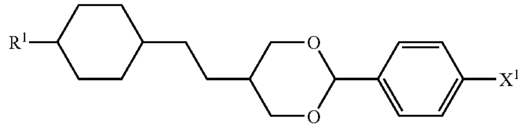
(3-93)
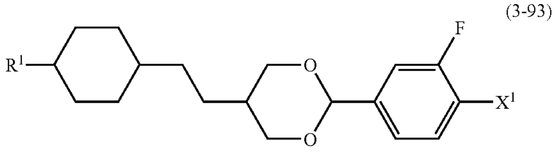
(3-94)
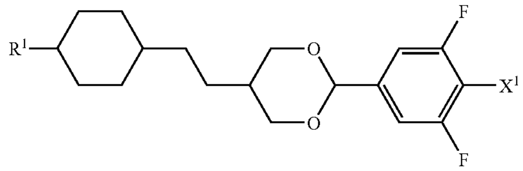
(3-95)
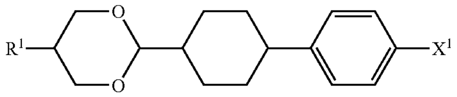

-continued
(3-96)
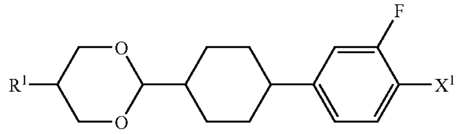
(3-97)
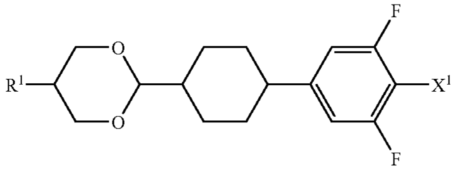
(4-1)
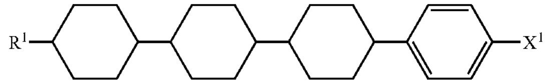
(4-2)
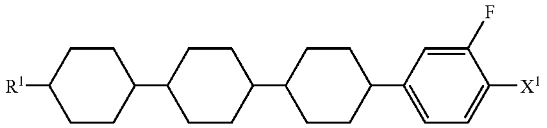
(4-3)
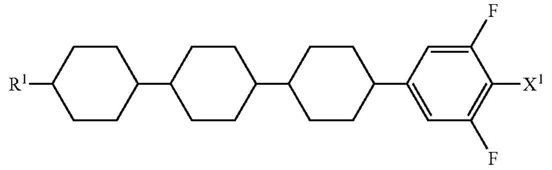
(4-4)
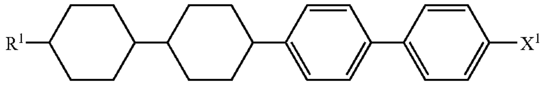
(4-5)
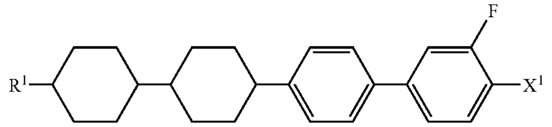
(4-6)
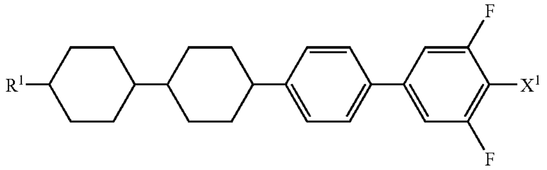
(4-7)
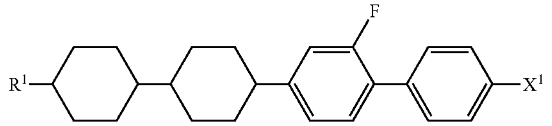
(4-8)
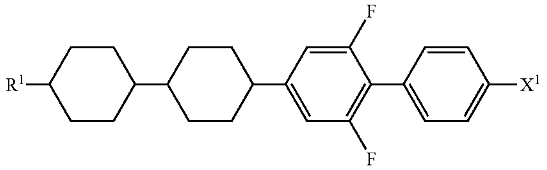
(4-9)
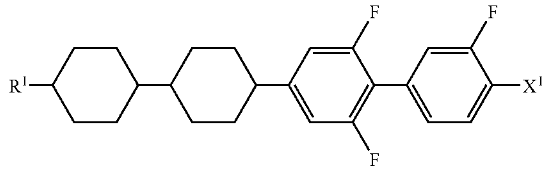
(4-10)
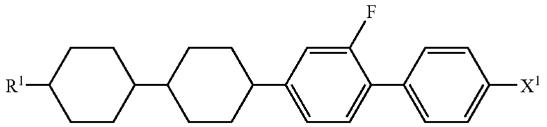
(4-11)
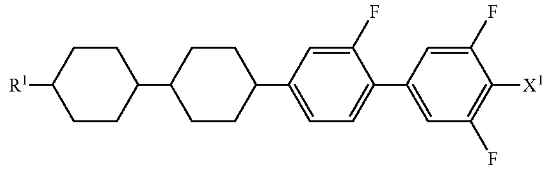
(4-12)
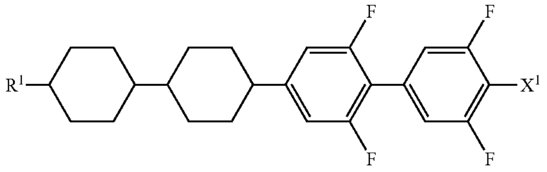
(4-13)
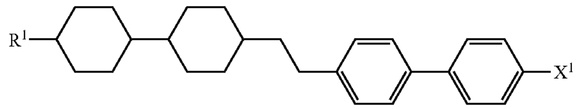
(4-14)
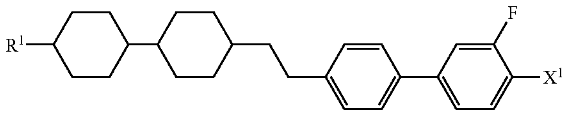

-continued
(4-15)
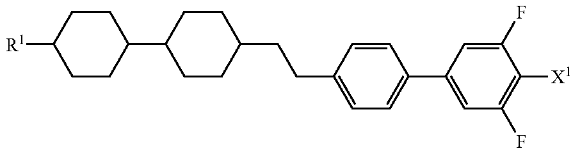
(4-16)
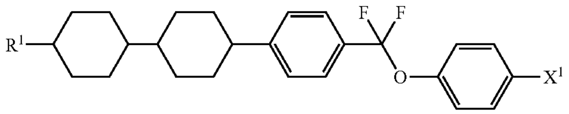
(4-17)
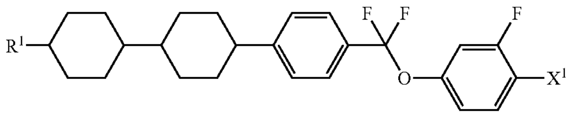
(4-18)
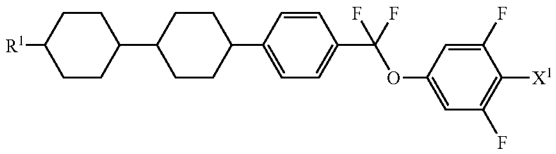
(4-19)
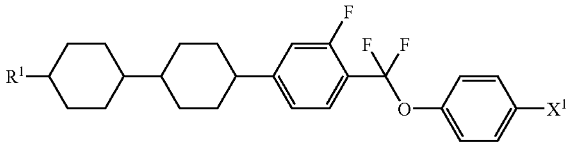
(4-20)
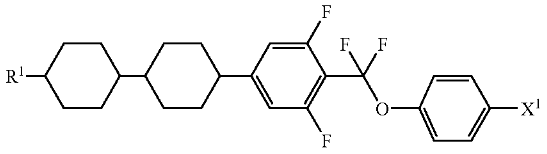
(4-21)
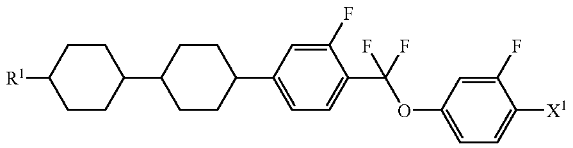
(4-22)
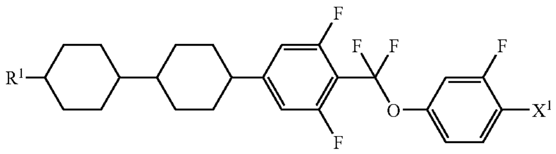
(4-23)
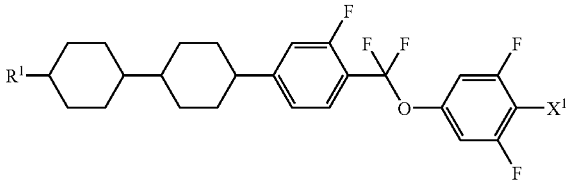
(4-24)
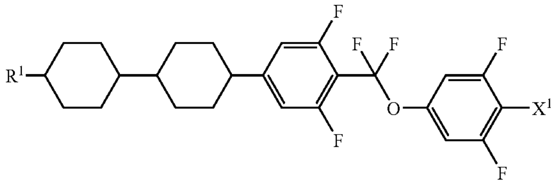
(4-25)
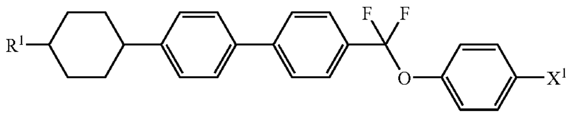
(4-26)
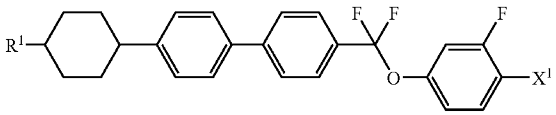
(4-27)
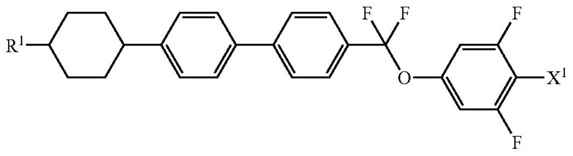
(4-28)
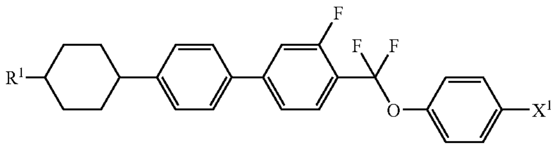
(4-29)
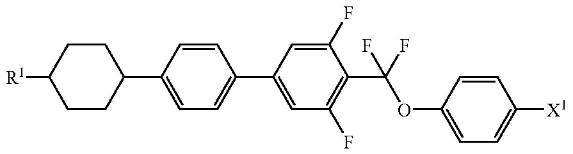
(4-30)
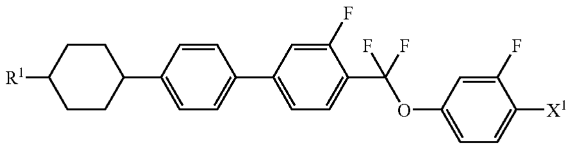

-continued
(4-31)
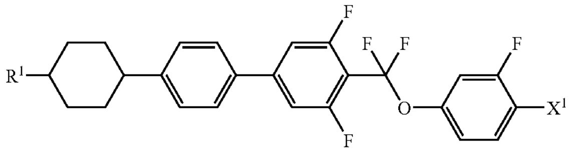
(4-33)
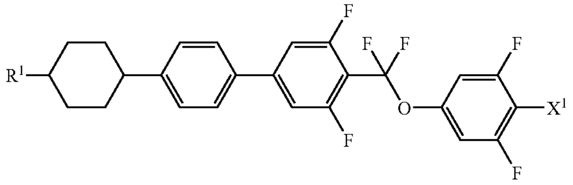
(5-2)
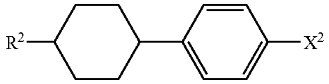
(5-4)
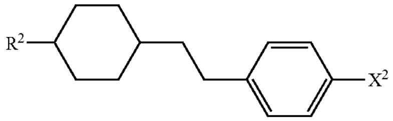
(5-6)
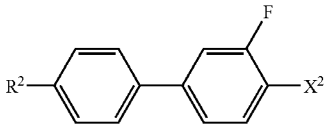
(5-8)
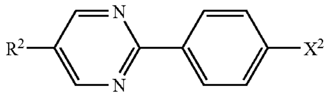
(5-10)
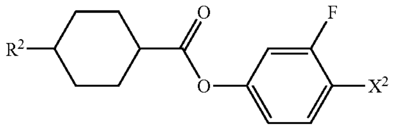
(5-12)
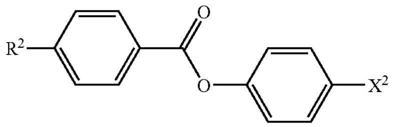
(5-14)
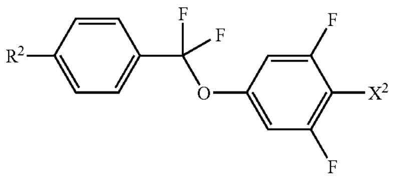
(4-32)
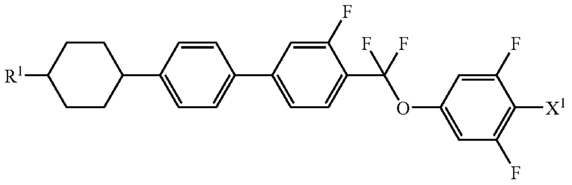
(5-1)
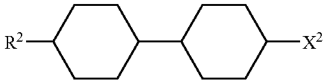
(5-3)
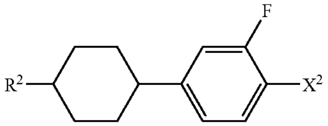
(5-5)
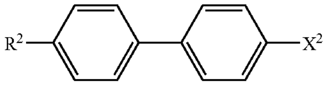
(5-7)
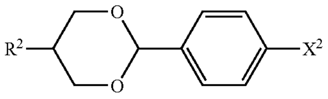
(5-9)
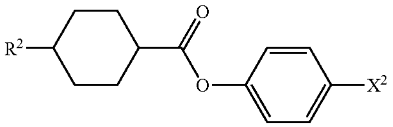
(5-11)
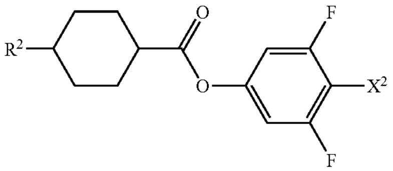
(5-13)
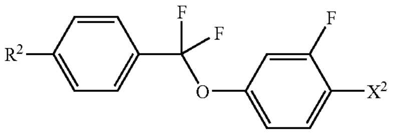
(5-15)
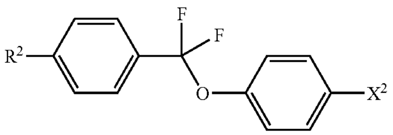

-continued
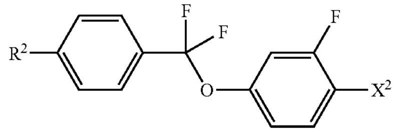
(5-16)
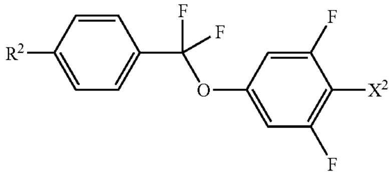
(5-17)
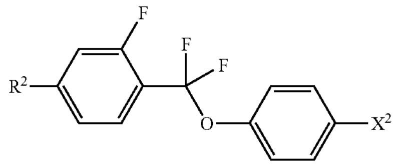
(5-18)
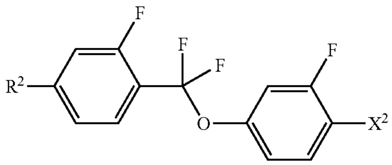
(5-19)
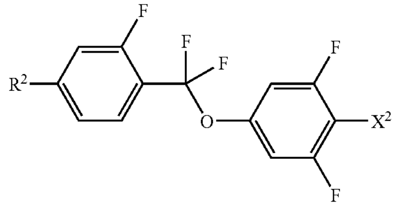
(5-20)
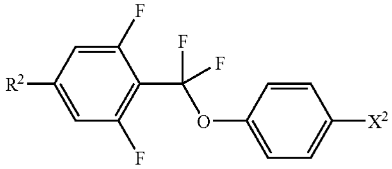
(5-21)
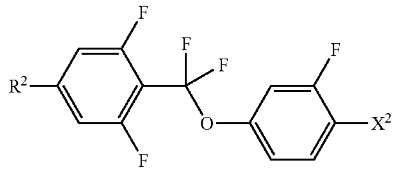
(5-22)
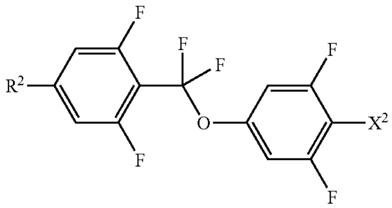
(5-23)
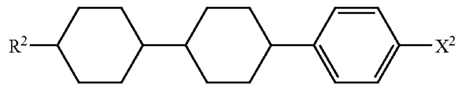
(5-24)
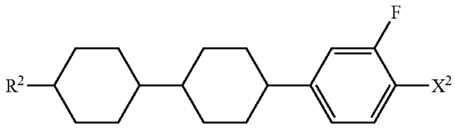
(5-25)
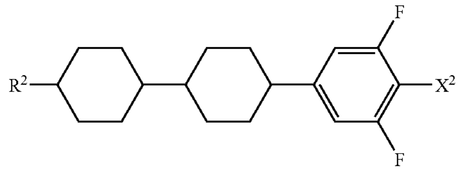
(5-26)
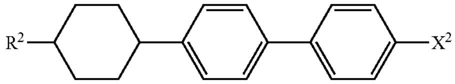
(5-27)
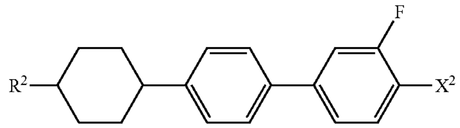
(5-28)
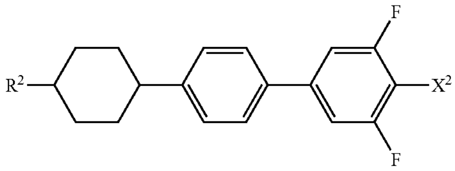
(5-29)
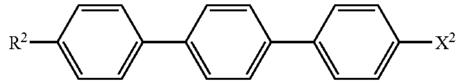
(5-30)
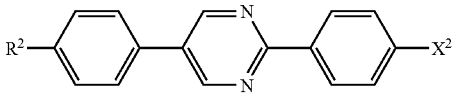
(5-31)
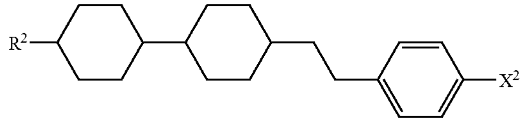
(5-32)
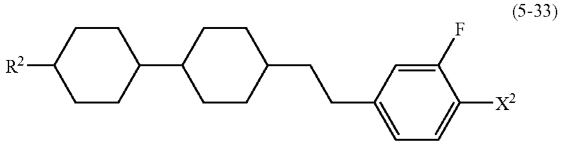
(5-33)

-continued
(5-34)
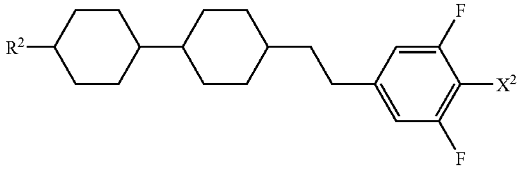
(5-35)
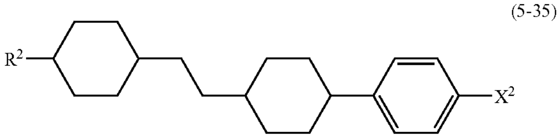
(5-36)
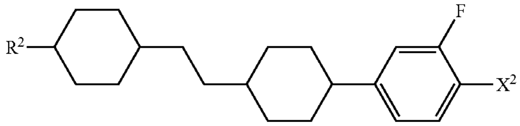
(5-37)
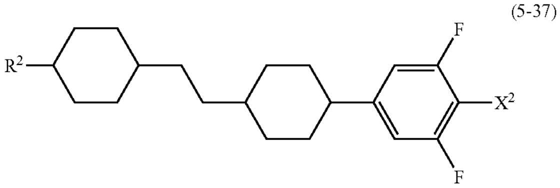
(5-38)
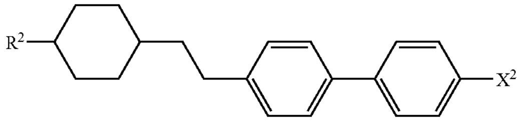
(5-39)
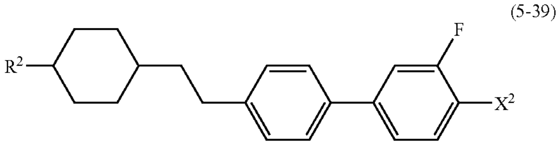
(5-40)
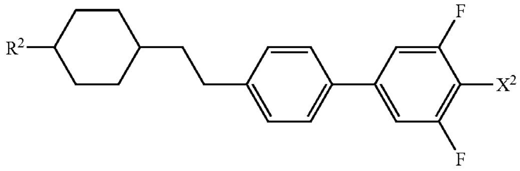
(5-41)
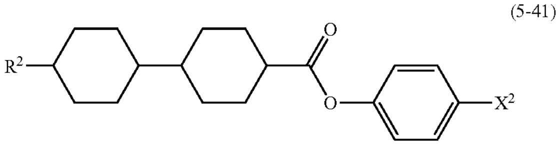
(5-42)
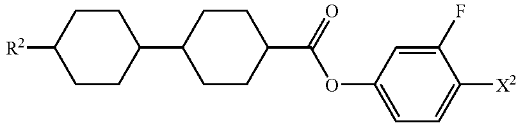
(5-43)
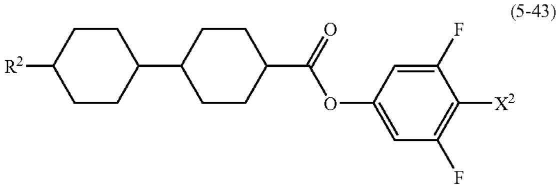
(5-44)
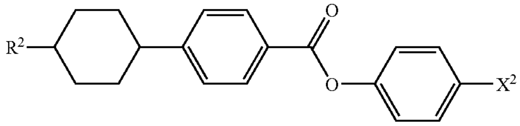
(5-45)
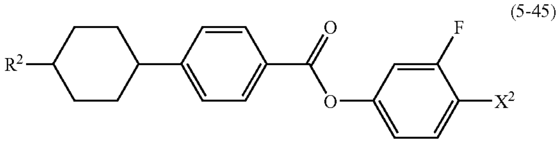
(5-46)
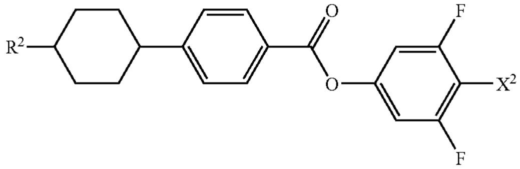
(5-47)
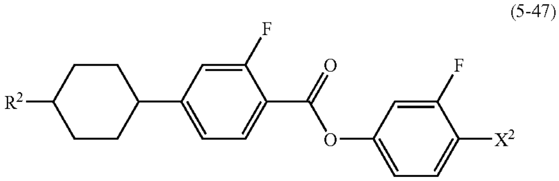
(5-48)
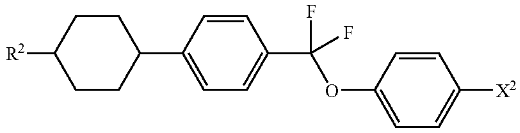
(5-49)
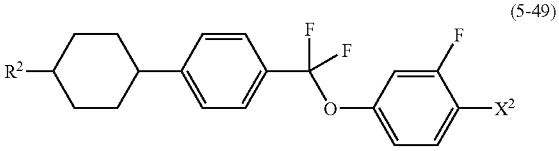
(5-50)
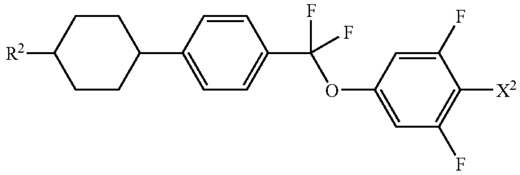
(5-51)
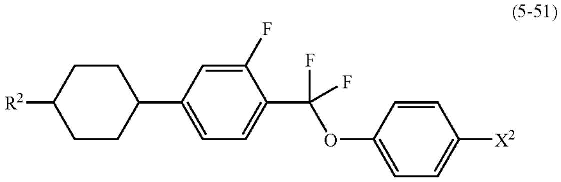

-continued
(5-52)
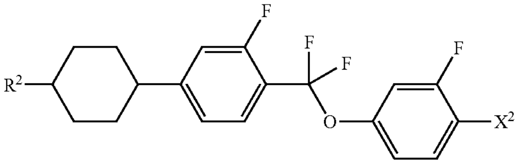
(5-53)
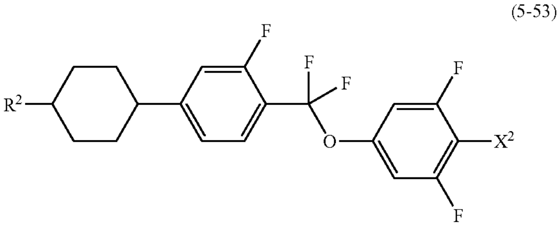
(5-54)
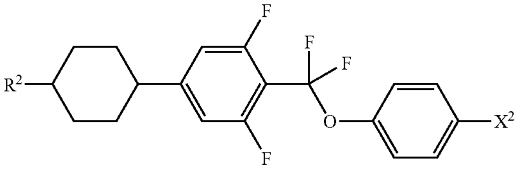
(5-55)
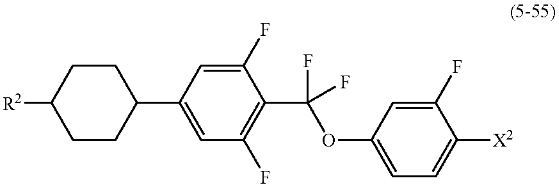
(5-56)
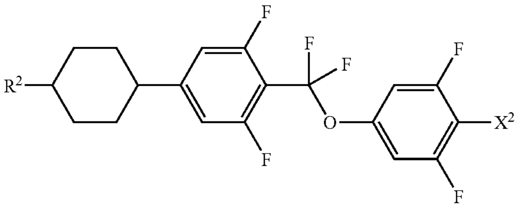
(5-57)
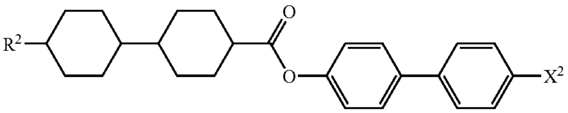
(5-58)
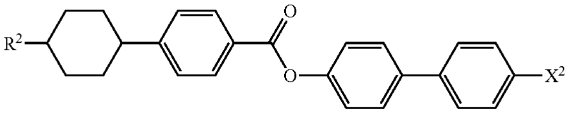
(6-1)
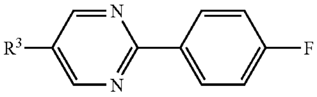
(6-2)
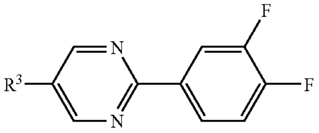
(6-3)
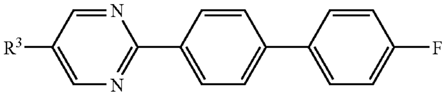
(7-1)
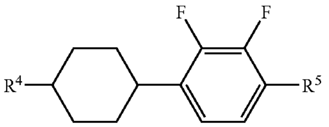
(7-2)
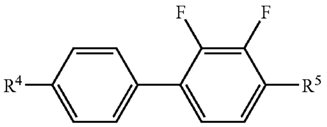
(7-3)
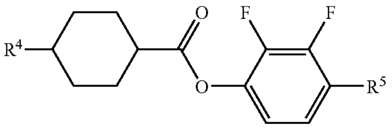
(8-1)
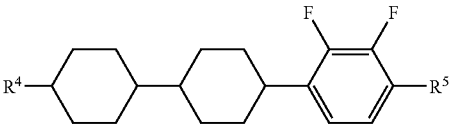
(8-2)
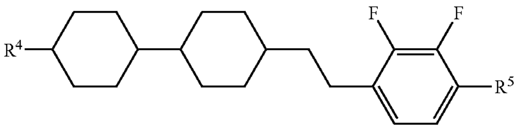
(8-3)
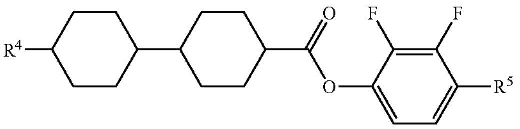
(8-4)
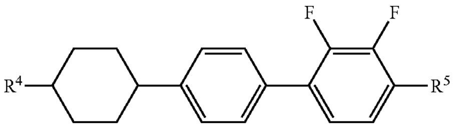
(8-5)
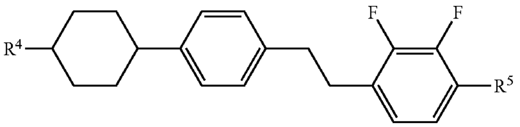
(9-1)
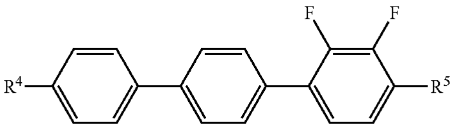
(9-2)
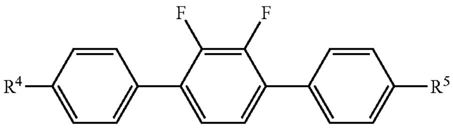

-continued
(9-3)
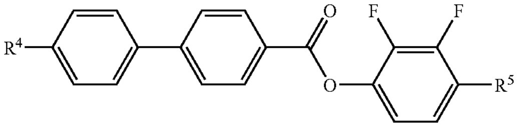
(10-1)
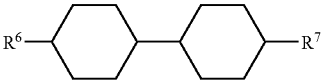
(10-2)
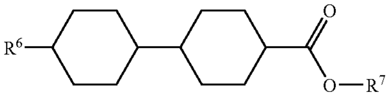
(10-3)
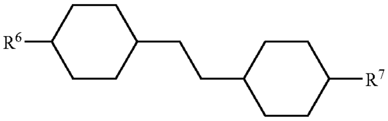
(10-4)
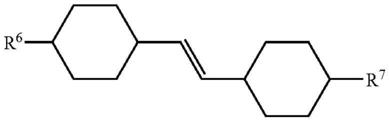
(10-5)
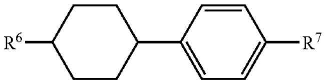
(10-6)
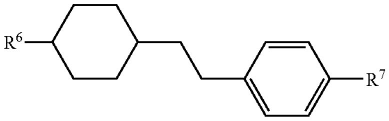
(10-7)
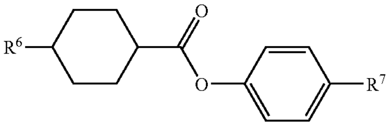
(10-8)
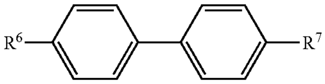
(10-9)
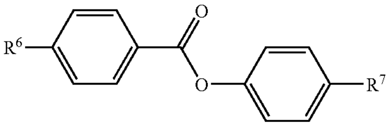
(10-10)
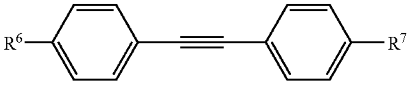
(10-11)
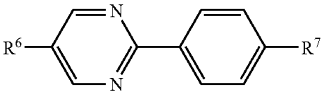
(11-1)
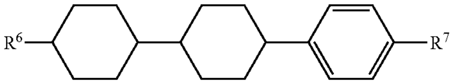
(11-2)
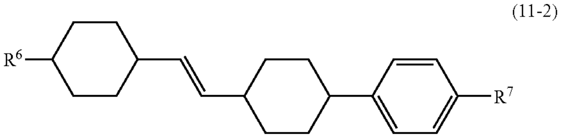
(11-3)
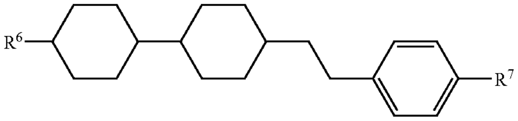
(11-4)
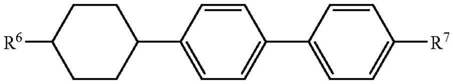
(11-5)
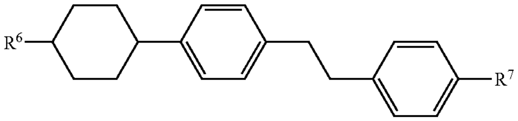
(11-6)
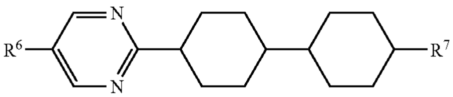
(11-7)
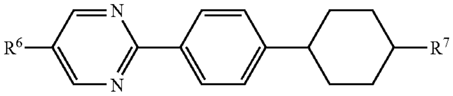
(11-8)
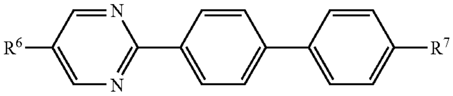
(11-9)
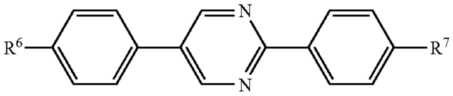
(11-10)
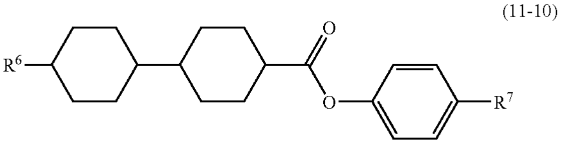
(11-11)
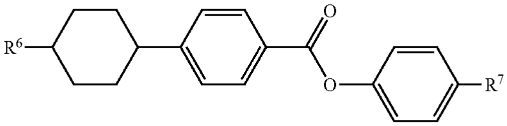
(11-12)
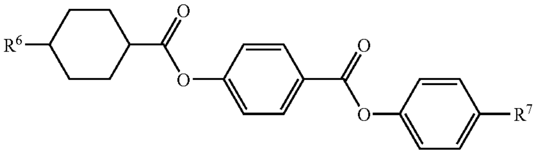

-continued
(12-1)
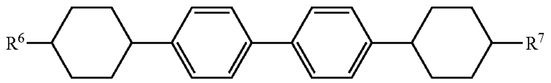
(12-2)
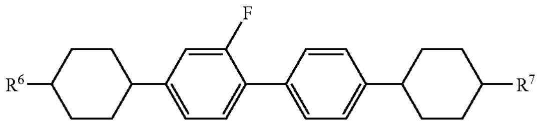
(12-3)
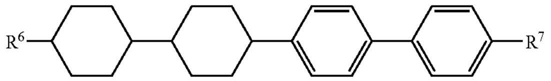
(12-4)
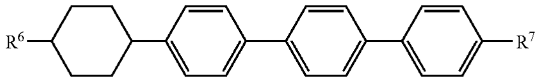
(12-5)
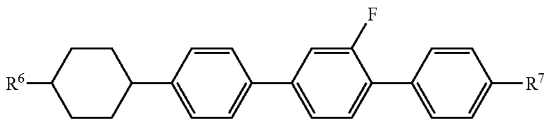
(12-6)
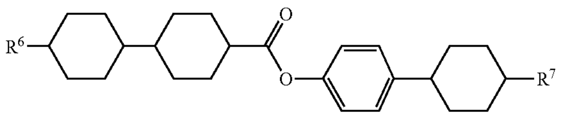
(Op-1)
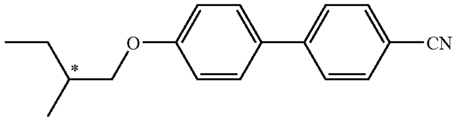
(Op-2)
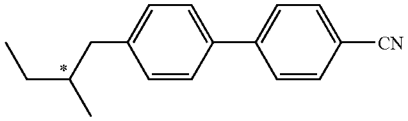
(Op-3)
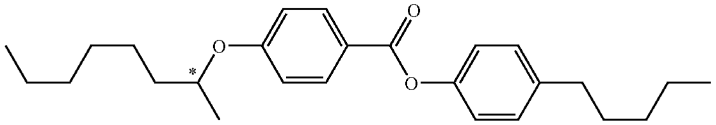
(Op-4)
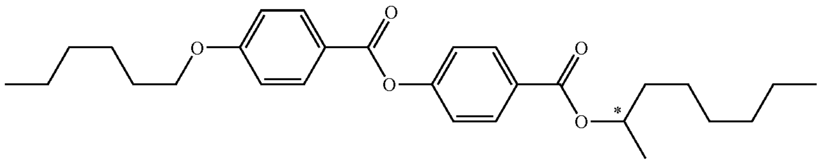
(Op-5)
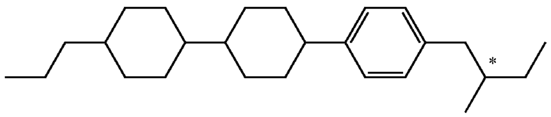
(Op-6)
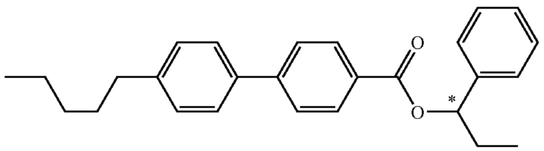
(Op-7)
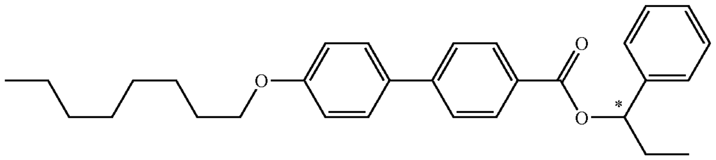
(Op-8)
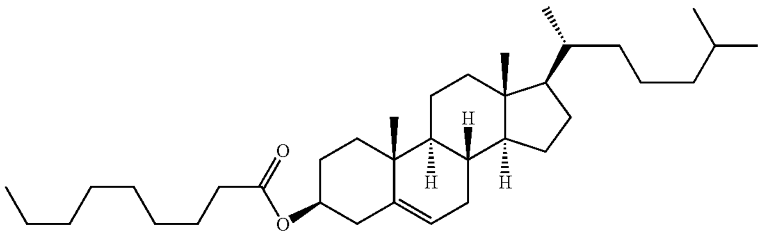
(Op-9)
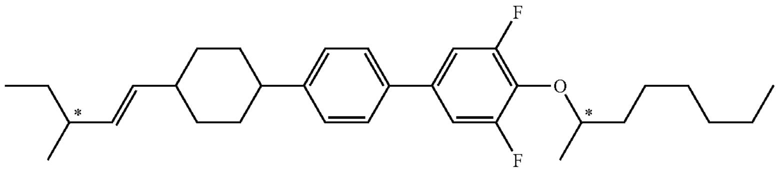

-continued (Op-10)

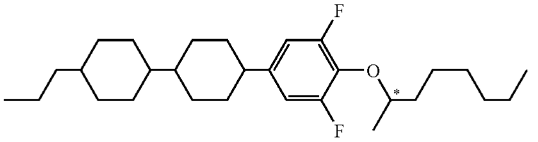

(Op-11)

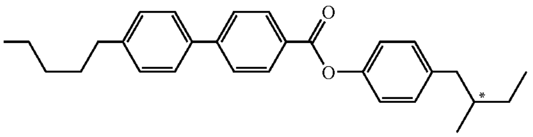

(Op-12)

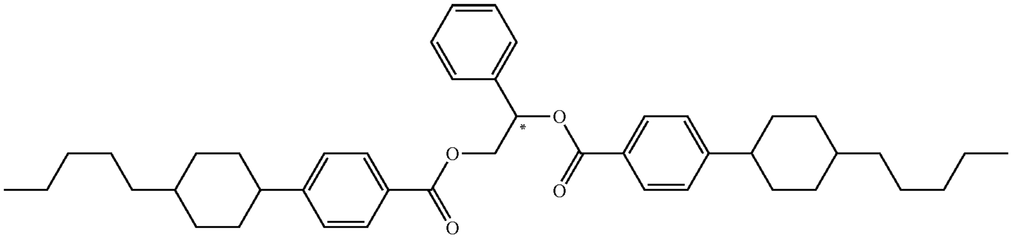

The composition of this invention is prepared by known methods. For example, component compounds are mixed and dissolved each other by heating. Physical properties of the composition may be controlled by the addition of appropriate additives. Such additives are well known by those skilled in the art. A chiral dopant is added for the purpose of inducing a helical structure of liquid crystals to give a twist angle desired. Examples of the chiral dopant are optically active compounds (Op-1) to (Op-12) given above.

Helical pitch is controlled by the addition of the chiral dopant to the composition. The pitch suitable for TN and TFT modes ranges between 40 and 200 micrometers. The pitch suitable for STN mode ranges between 6 and 20 micrometers. The pitch suitable for BTN mode ranges between 1.5 and 4 micrometers. A relatively large amount of a chiral dopant is added to the composition for PC mode. At least two chiral dopants may be added for the purpose of controlling temperature dependence of the pitch.

The composition of this invention can be used for modes of TN, TN-TFT, STN, GH, DS, ECB, and so forth. A composition for GH mode is prepared by the addition of a dichroic dye such as compounds of merocyanine, styryl, azo, azomethine, azoxy, quinophthalone, anthraquinone, tetrazine, and so forth. The composition of this invention can also be used for NCAP which is prepared by microcapsulating nematic liquid crystals, and for a polymer-dispersed liquid crystal display element (PDLCD) which is prepared by forming a three-dimensional polymer network in liquid crystals, for example, a polymer network liquid crystal display element (PNLCD) and so forth.

EXAMPLES

Thirdly, this invention is further explained by the examples. The invention is not limited by these examples. Examples 1 to 8 describe the preparation of the compound (1). The reaction was carried out under an atmosphere of nitrogen. The compound obtained was identified based on the data of NMR spectra, mass-spectra, and so forth. THF stands for tetrahydrofuran. C, Sm, 5 mA, SmB, N, and I denote crystals, a smectic phase, a smectic A phase, a smectic B phase, a nematic phase and an isotropic phase, at a phase transition temperature of the compounds, respectively. Parenthesised phase transition means monotropic one. The temperature is by centigrade scale (° C.).

TABLE 1

Method for Description of Compounds Using Symbols
R—(A1)—Z1— . . . —Zn—(An)—X

| 1)Left Terminal Group R— | Symbol |
|---|---|
| $C_nH_{2n+1}$— | n— |
| $C_nH_{2n+1}O$— | nO— |
| $C_nH_{2n+1}OC_mH_{2m+1}$— | nOm— |
| $CH_2$═CH— | V— |
| $CH_2$═$CHC_nH_{2n}$— | Vn— |
| $C_nH_{2n+1}CH$═$CHC_mH_{2m}$— | nVm— |
| $C_nH_{2n+1}CH$═$CHC_mH_{2m}CH$═$CHC_kH_{2k}$— | nVmVk— |
| $CF_2$═CH— | VFF— |
| $CF_2$═$CHC_nH_{2n}$— | VFFn— |
| **2)Ring Structure —An—** | **Symbol** |
| 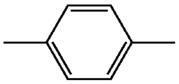 | B |
| 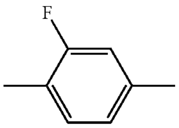 | B(2F) |
| 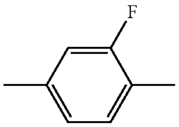 | B(F) |
| 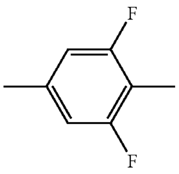 | B(F, F) |
| 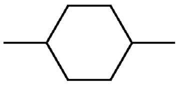 | H |

TABLE 1-continued

| Method for Description of Compounds Using Symbols R—(A1)—Z1— . . . —Zn—(An)—X | |
|---|---|
| 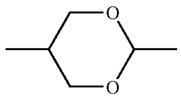 | G |
| 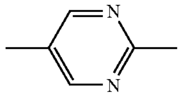 | Py |
| 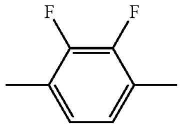 | B(2F, 3F) |
| 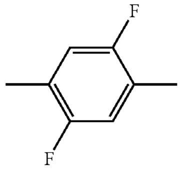 | B(2F, 5F) |

| 3)Bonding Group —Zn— | Symbol |
|---|---|
| $—C_2H_4—$ | 2 |
| $—C_4H_8—$ | 4 |
| —COO— | E |
| —C≡C— | T |
| —CH=CH— | V |
| $—CF_2O—$ | CF2O |
| $—OCF_2—$ | OCF2 |

| 4)Right Terminal Group —X | Symbol |
|---|---|
| —F | —F |
| —Cl | —CL |
| —CN | —C |
| $—CF_3$ | —CF3 |
| $—OCF_3$ | —OCF3 |
| $—OCF_2H$ | —OCF2H |
| $—C_nH_{2n+1}$ | —n |
| $—OC_nH_{2n+1}$ | —On |
| $—COOCH_3$ | —EMe |
| $—CH=CH_2$ | —V |
| $—C_nH_{2n}CH=CH_2$ | —nV |
| $—C_mH_{2m}CH=CHC_nH_{2n+1}$ | —mVn |
| $—CH=CF_2$ | —VFF |
| $—C_nH_{2n}CH=CF_2$ | —nVFF |
| —C≡C— | —T |

5)Example of Description

Example 1 3-H2B(F, F)B(F)-F

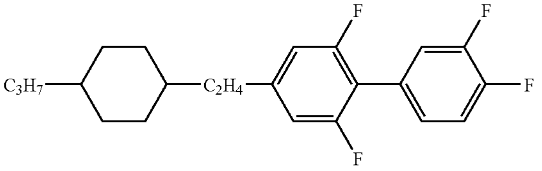

Example 2 5-HHEB-F

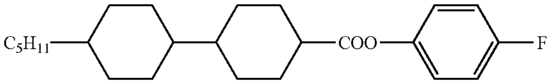

TABLE 1-continued

Method for Description of Compounds Using Symbols
R—(A1)—Z1— . . . —Zn—(An)—X

Example 3 5-BB(2F, 5F)B

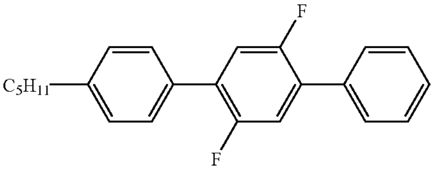

Representative compositions of this invention are summarized in Examples 10 to 48. Comparative Example 1 is given last. In these Examples, first shown are the component compounds of the composition with their respective amounts. The amount is percent by weight. The compounds are represented by the symbols of a left terminal group, a bonding group, a ring structure, and a right terminal group, according to the rules in Table 1 described above. Configuration of 1,4-cyclohexylene and 1,3-dioxane-2,5-diyl is trans. No symbol for a terminal group means that the terminal group is hydrogen. Physical properties of the composition are shown next. The physical properties were measured according to the method described in the Standard of Electric Industries Association of Japan, EIAJ ED-2521A or a modified method.

Phase transition temperature of a nematic phase-isotropic phase (NI; ° C.): A sample was placed on a hot plate in a melting point apparatus equipped with a polarization microscope and was heated at the rate of 1° C. per minute. The temperature was measured when a part of the sample began to change from a nematic phase to an isotropic phase. The transition temperature is also named a clearing point.

Viscosity (η; measured at 20° C.; mPa·s): E-type rotary viscometer was used for the measurement of viscosity.

Optical anisotropy (Refractive index anisotropy; Δn; measured at 25° C.): Optical anisotropy was measured using Abbe refractometer by the aid of light having the wavelength of 589 nanometers.

Dielectric Anisotropy (Δε; measured at 25° C.)

1) Composition having a positive value of dielectric anisotropy: A sample was poured into a liquid crystal cell in which the gap between two glass plates is 9 micrometers and a twist angle is 80 degrees. A dielectric constant (ε||) that is parallel to a liquid crystal molecule was measured by applying 20 volt to the cell. A dielectric constant (ε⊥) that is perpendicular to a liquid crystal molecule was measured by applying 0.5 volt. A value of dielectric anisotropy was calculated from the formula: $\Delta\epsilon=\epsilon\|-\epsilon\perp$.

2) Composition having a negative value of dielectric anisotropy: A sample was poured into a liquid crystal cell having homeotropic alignment and a dielectric constant (ε||) was measured by applying 0.5 volt. A sample was poured into a liquid crystal cell having homogeneous alignment and a dielectric constant (ε⊥) was measured by applying 0.5 volt. A value of dielectric anisotropy was calculated from the formula:

$$\Delta\epsilon=\epsilon\|-\epsilon\perp.$$

Threshold voltage (Vth; measured at 25° C.; volt): A sample was poured into a liquid crystal display element with a normally white mode, in which the gap between two glass plates was (0.5/Δn) micrometer and a twist angle was 80 degrees. Δn is a value of optical anisotropy measured by the method described above. Rectangle waves with a frequency of 32 Hz were applied to the element. Voltage of the rectangle waves was increased and the value of the voltage was measured when the transmission of a light passing through the element became 90%.

Example 1

Preparation of 2',5'-difluoro-4-pentylterphenyl (No. 275)

First Step: Preparation of 4'-Bromo-2',5'-difluoro-4-pentylbiphenyl

A mixture of 1-bromo-2,5-difluoro-4-iodbenzene (5.00 g, 15.68 mmol), 4-pentylphenylboronic acid (3.01 g, 15.67 mmol), potassium carbonate (3.25 g, 23.51 mmol), tetrabutylammonium bromide (1.26 g, 3.91 mmol), dichlorobis (triphenylphosphine)palladium (II) (0.55 g, 0.79 mmol), triphenylphosphine (0.41 g, 1.56 mmol), and a mixed solvent (toluene/water/ethanol=1/1/1, 100 ml) was refluxed for 32 hrs with stirring. The reaction mixture obtained was extracted with toluene (200 ml). The extract was washed with water (100 ml) twice and dried over anhydrous magnesium sulfate. Evaporation of the solvent under reduced pressure gave a brown oil (5.72 g). The oil was distilled under reduced pressure and was purified by silica-gel chromatography (eluent; heptane, Rf=0.58) to give a colorless oil (2.31 g).

Second Step: Preparation of 2',5'-difluoro-4-pentylterphenyl

A mixture of 4'-bromo-2',5'-difluoro-4-pentylbiphenyl (2.00 g, 5.90 mmol), phenylboric acid (1.01 g, 8.28 mmol), potassium carbonate (1.22 g, 8.83 mmol), tetrabutylammonium bromide (0.48 g, 1.49 mmol), tetrakis(triphenylphosphine)palladium (0) (0.21 g, 0.18 mmol), and a mixed solvent (toluene/water/ethanol=1/1/1, 90 ml) was refluxed for 4 hrs with stirring. The reaction mixture obtained was extracted with toluene (200 ml). The extract was washed with water (100 ml) twice and dried over anhydrous magnesium sulfate. Evaporation of the solvent under reduced pressure gave a dark brown solid (2.50 g). The solid was purified by silica-gel chromatography (eluent; heptane, Rf=0.25) and recrystallized from a mixed solvent (solmix/heptane=½) to give 2',5'-difluoro-4-pentylterphenyl (1.53 g, colorless crystals). C 65.5 I.

Example 2

Preparation of 2,5-difluoro-(trans-4-(trans-4-propylcyclohexyl)cyclohexyl)benzene (No. 1488)

First Step: Preparation of 2,5-difluoro(4-(trans-4-propylcyclohexyl)-1-hydroxycyclohexyl)benzene A solution of 2,5-difluorobromobenzene (1.33 mmol) in THF (10 ml) is added dropwise to magnesium (1.44 mmol). After the addition is completed, the reaction mixture is stirred at 50° C. for 2 hrs. To the reaction mixture, a solution of 4-(trans-4-propylcyclohexyl)cyclohexanone (1.03 mmol) in THF (10 ml) is added dropwise. After the addition is completed, the reaction mixture is stirred for 2 hrs at 50° C. A saturated aqueous solution of ammonium chloride (10 ml) is added in small portions and the aqueous layer is extracted with ethyl acetate (100 ml) twice. The extract is washed with water, and then dried over anhydrous magnesium sulfate. The titled compound is obtained by evaporation of the solvent under reduced pressure.

Second Step: Preparation of 2,5-difluoro-(4-(trans-4-propylcyclohexyl)cyclohexenyl)benzene A three-necked flask equipped with the Dean-Stark apparatus is used. A mixture of 2,5-difluoro-(4-(trans-4-propylcyclohexenyl)-1-hydroxycyclohexyl)benzene (1.06 mmol), p-toluenesulfonic acid (0.106 mmol), and toluene (50 ml) is refluxed for 7 hrs with stirring. The reaction mixture obtained is washed with an aqueous solution of sodium hydrogen carbonate (50 ml) three times, and dried over anhydrous magnesium sulfate. After concentrating the toluene solution under reduced pressure, purification with silica-gel column gives the titled compound.

Third Step: Preparation of 2,5-difluoro-(4-(trans-4-propylcyclohexyl)cyclohexyl)benzene (No. 1488)

A mixture of 2,5-difluoro(4-(trans-4-propylcyclohexyl) cyclohexenyl)benzene (0.84 mmol), ethyl acetate (30 ml), and 5% palladium carbon (0.013 g) is stirred under an atmosphere of hydrogen. After ceasing the absorption of hydrogen, 5% palladium carbon is filtered off from the reaction mixture. The filtrate is concentrated under reduced pressure and purified by silica-gel chromatography, and further recrystallized to give the titled compound.

Example 3

Preparation of 2,5-difluoro-4-ethoxyphenyl biphenyl-4-ylmethylether (No. 1101)

A mixture of 2,5-difluoro-4-ethoxyphenol (4.70 mmol), potassium carbonate (5.60 mmol), and N,N-dimethylformamide (300 ml) is heated under reflux. During refluxing, a solution of 4-iodomethylbiphenyl (9.4 mmol) in DMF (50 ml) is added dropwise. After the addition is completed, the reaction mixture is refluxed for 5 hrs. The reaction mixture obtained is poured into water and extracted with toluene (200 ml) twice. The extract is washed with in the order of 5% aqueous solution of sodium thiosulfate, water (two times), a saturated aqueous solution of sodium hydrogen carbonate (two times), water (two times), and a saturated aqueous sodium chloride, and then dried over anhydrous magnesium sulfate. The solution is concentrated under reduced pressure, purified by silica-gel chromatography, and further recrystallized to give the titled compound.

Example 4

Preparation of 1-(ethylphenyl)-2-(2,2',5'-trifluorobiphenyl-4-yl)ethane (No. 1140)

To a suspension of 1-ethyl-4-iodomethylbenzene (51.82 mmol) and copper iodide (10 mmol) in THF (100 ml) chilled on an ice bath, a solution of 2',5'-trifluorobiphenyl-4-ylmethyllithium (72.53 mmol) in THF (100 ml) is added dropwise, and the reaction mixture is stirred for additional 1 hr. After stirring for 3 hrs at room temperature, the reaction is ceased by adding a diluted hydrochloric acid. The reaction mixture obtained is extracted with toluene (500 ml), washed with water (300 ml) two times, and dried over anhydrous magnesium sulfate. The toluene solution is concentrated under reduced pressure, purified by silica-gel chromatography, and recrystallized to give the titled compound.

Example 5

Preparation of 3-fluoro-4-(trans-4-heptylcyclohexyl)-α, α-difluorobenzyl 2-fluorophenylether (No. 1716)

To a solution of 2-fluorophenyl 3-fluoro-4-(trans-4-heptylcyclohexyl)benzenethioate (30.60 mmol) in dichloromethane (100 ml), DAST (76.50 mmol) is added dropwise. After the addition is completed, the mixture is stirred for 20 hrs at room temperature. The reaction mixture obtained is poured into a saturated aqueous solution of sodium carbonate and extracted with dichloromethane (200 ml). The extract is washed with water (150 ml) three times and dried over anhydrous magnesium sulfate. The dichloromethane solution is concentrated under reduced pressure, purified with silica-gel chromatography, and further recrystallized to give the titled compound.

Example 6

Preparation of 2-fluoro-4-(2-fluorophenyl)phenyl 2,5-difluoro-4-(4-pentylphenyl)benzoate (No. 1382)

To a mixture of 2,5-difluoro-4-(4-pentylphenyl)benzoic acid (28.40 mmol), 2-fluoro-4-(2-fluorophenyl)phenol (28.40 mmol), and dichloromethane (100 ml), 4-dimetylaminopyridine (34.10 mmol) is added dropwise. Then, a solution of 1,3-dicyclohexylcarbodiimide (34.10 mmol) in dichloromethane (100 ml) is added dropwise. After the addition is completed, the reaction mixture is stirred for 17 hrs at room temperature. Solid formed is filtered off, and a saturated aqueous solution of sodium chloride is added dropwise to the reaction mixture. The organic layer is washed with in the order of 3N-hydrochloric acid (300 ml), water, a saturated aqueous solution of sodium hydrogen carbonate (300 ml), and dried over anhydrous magnesium sulfate. The dichloromethane solution is concentrated under reduced pressure, purified by silica-gel chromatography, and further recrystallized to give the titled compound.

Example 7

Preparation of 1-(2,5,3'-fluoro-4'-butoxybiphenyl-4-yl)-2-phenylethene (No. 1728)

To a solution of benzyltriphenylphosphoniumchloride (102.1 mmol) in THF (150 ml) chilled on a dry ice-acetone bath, potassium tert-butoxide (120.8 mmol) is added dropwise little by little. Then, a solution of 2,5-difluoro-4-(3-fluoro-4-butoxyphenyl)benzaldehyde in THF (25 ml) is added dropwise. After the addition is completed, the reaction mixture is stirred for 20 hrs at room temperature. The reaction mixture obtained is poured into ice water, and extracted with toluene (200 ml) twice. The extract is washed with water (150 ml) three times and dried over anhydrous magnesium sulfate. The toluene solution is concentrated under reduced pressure. A mixture of the reaction mixture obtained, sodium sulfinate (153.2 mmol), 6N-hydrochloric acid (50 ml), and ethanol (200 ml) is refluxed for 3 hrs with stirring. The reaction mixture obtained is extracted with toluene (200 ml) twice. The extract is washed with water (150 ml) three times and tried over anhydrous magnesium sulfate. The toluene solution is concentrated under reduced pressure, purified by silica-gel chromatography, and further recrystallized to give the titled compound.

Example 8

Preparation of 1-(2',3-difluorobiphenyl-4-yl)-2-(trans-4-heptylcyclohexyl)acetylene (No. 1090)

A mixture of 1-(trans-4-heptylcyclohexyl)acetylene (28.40 mmol), 2',3-difluoro-4-iodobiphenyl (28.40 mmol), tetrakis(triphenylphosphine)palladium(0)dichloromethane (0.85 mmol), copper iodide (1.43 mmol), and diethylamine (200 ml) is stirred for 4 hrs at room temperature. The reaction mixture obtained is extracted with toluene (200 ml) twice. The extract is washed with water (150 ml) three times and dried over anhydrous magnesium sulfate. The toluene solution is concentrated under reduced pressure, purified by silica-gel chromatography, and further recrystallized to give the titled compound.

Example 9

The following compounds No. 1 to No. 1949 are prepared cording to the synthetic method described in Examples 1 to and by further combination with known reactions.

| No. | 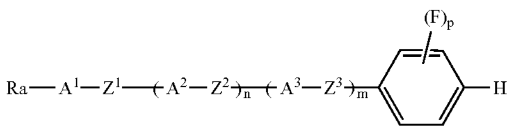 | |
|---|---|---|
| 1 | 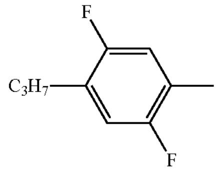 | 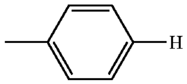 |
| 2 | 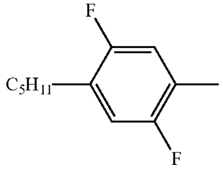 | 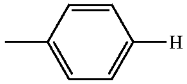 |
| 3 | 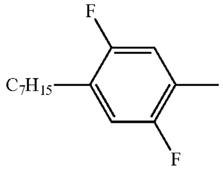 | 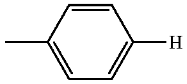 |
| 4 | 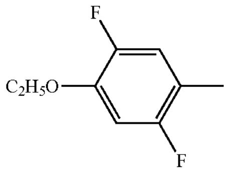 | 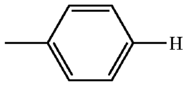 |
| 5 | 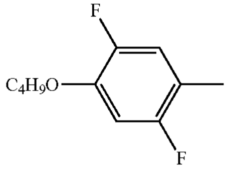 | 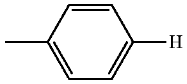 |

-continued
| No. | 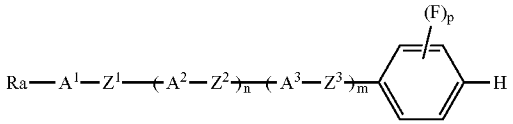 | |
|---|---|---|
| 6 | 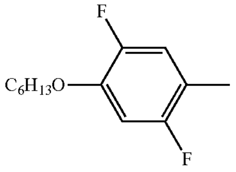 | 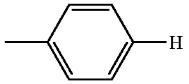 |
| 7 | 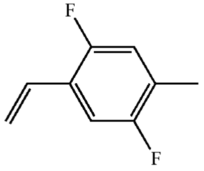 | 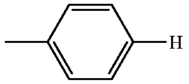 |
| 8 | 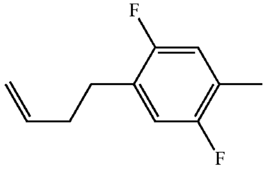 | 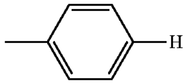 |
| 9 | 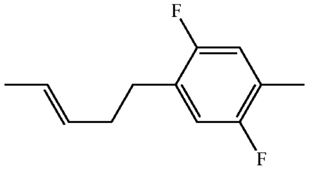 | 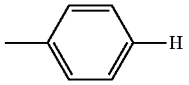 |
| 10 | 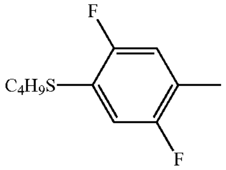 | 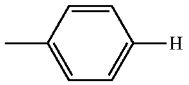 |

-continued
| No. | 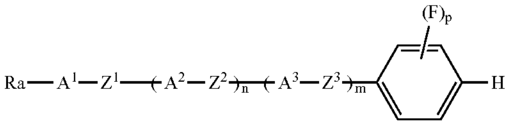 | |
|---|---|---|
| 11 | 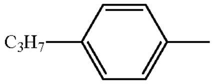 | 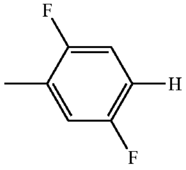 |
| 12 | 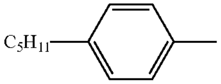 | 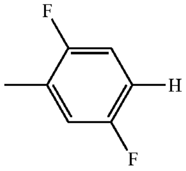 |
| 13 | 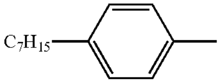 | 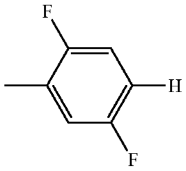 |
| 14 | 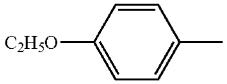 | 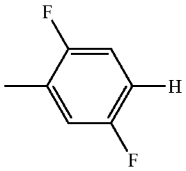 |
| 15 | 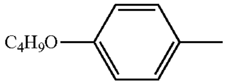 | 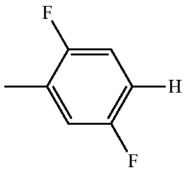 |

-continued
| No. | 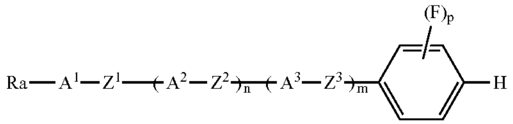 | |
|---|---|---|
| 16 | 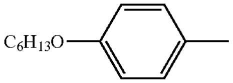 | 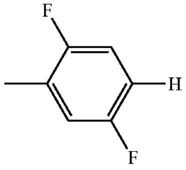 |
| 17 | 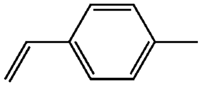 | 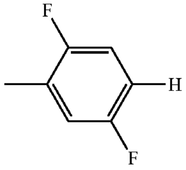 |
| 18 | 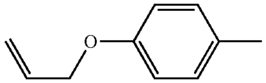 | 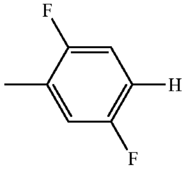 |
| 19 | 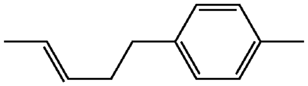 | 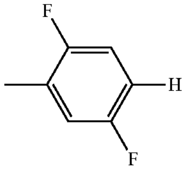 |
| 20 | 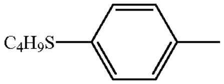 | 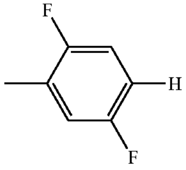 |

-continued
| No. | 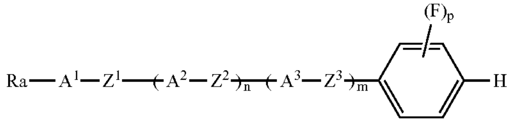 | |
|---|---|---|
| 21 | 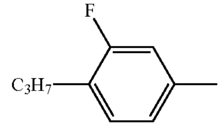 | 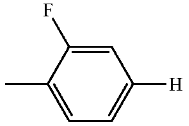 |
| 22 | 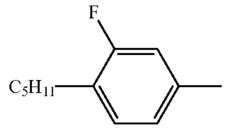 | 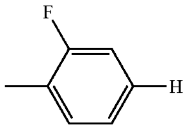 |
| 23 | 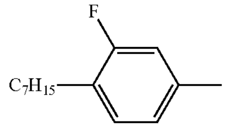 | 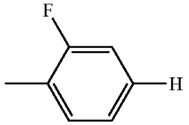 |
| 24 | 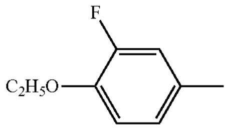 | 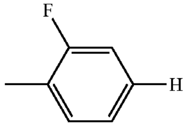 |
| 25 | 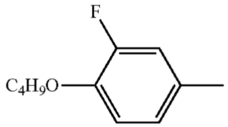 | 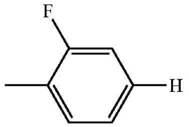 |
| 26 | 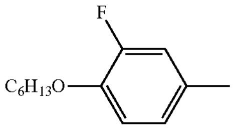 | 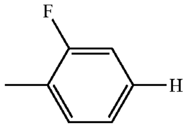 |

-continued
| No. | 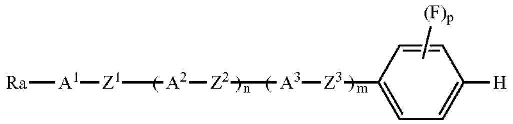 | |
|---|---|---|
| 27 | 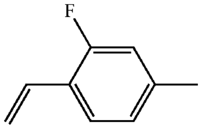 | 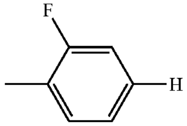 |
| 28 | 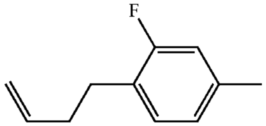 | 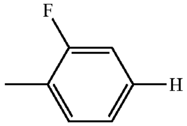 |
| 29 | 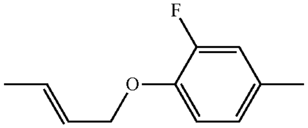 | 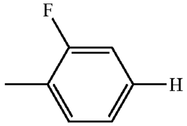 |
| 30 | 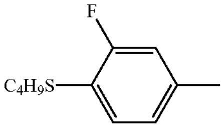 | 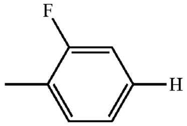 |
| 31 | 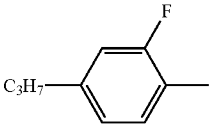 | 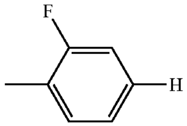 |
| 32 | 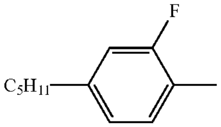 | 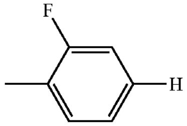 |

-continued
| No. | 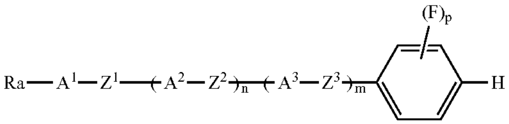 | |
|---|---|---|
| 33 | 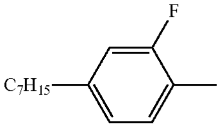 | 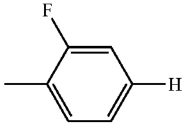 |
| 34 | 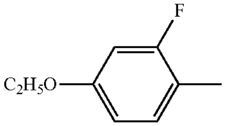 | 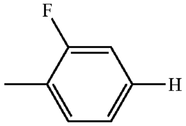 |
| 35 | 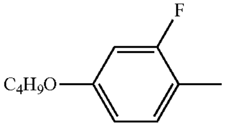 | 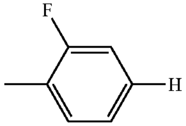 |
| 36 | 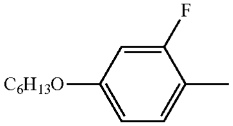 | 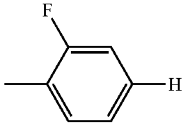 |
| 37 | 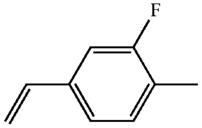 | 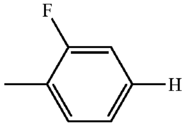 |
| 38 | 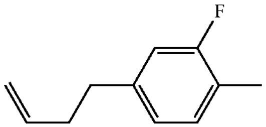 | 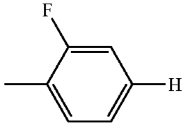 |

-continued
| No. | 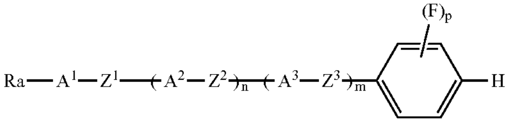 | |
|---|---|---|
| 39 | 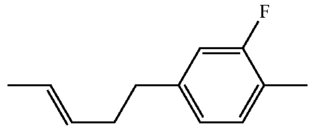 | 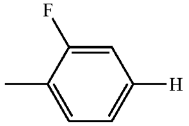 |
| 40 | 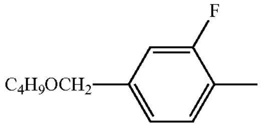 | 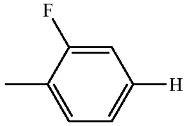 |
| 41 | 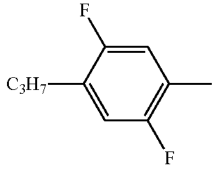 | 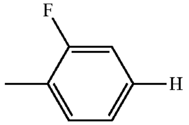 |
| 42 | 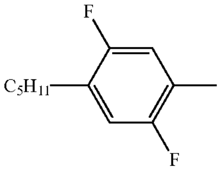 | 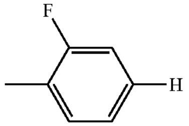 |
| 43 | 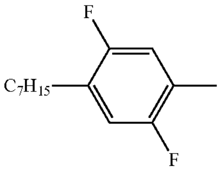 | 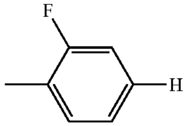 |

-continued
| No. | 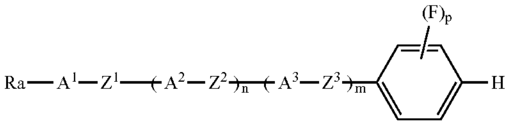 | |
|---|---|---|
| 44 | 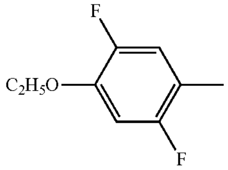 | 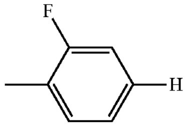 |
| 45 | 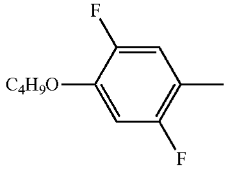 | 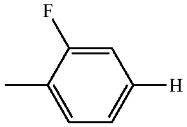 |
| 46 | 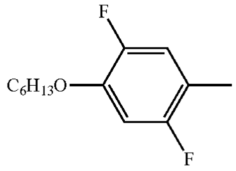 | 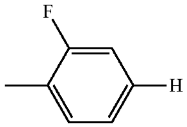 |
| 47 | 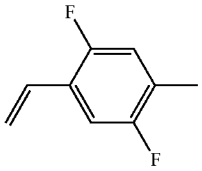 | 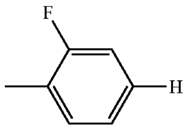 |
| 48 | 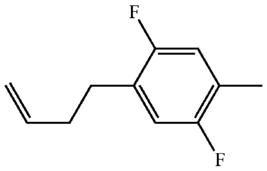 | 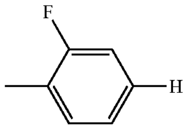 |

-continued
| No. | 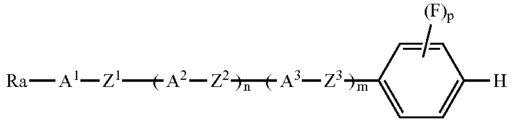 | |
|---|---|---|
| 49 | 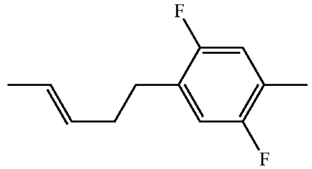 | 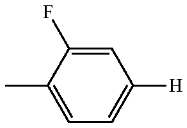 |
| 50 | 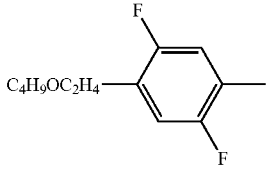 | 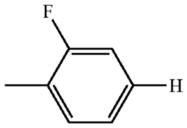 |
| 51 | 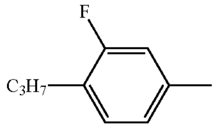 | 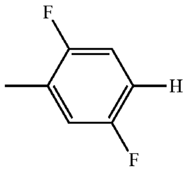 |
| 52 | 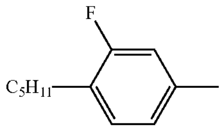 | 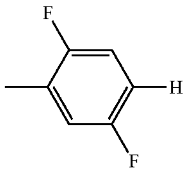 |
| 53 | 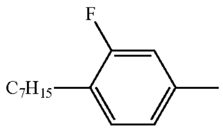 | 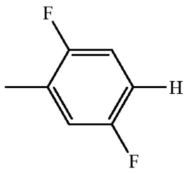 |

-continued
| No. | 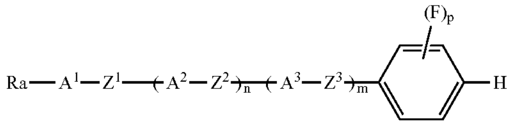 | |
|---|---|---|
| 54 | 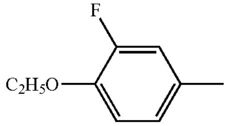 | 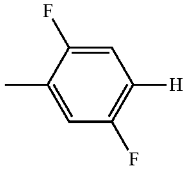 |
| 55 | 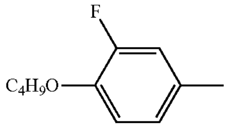 | 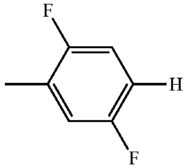 |
| 56 | 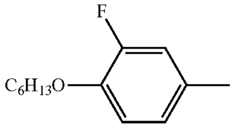 | 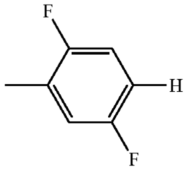 |
| 57 | 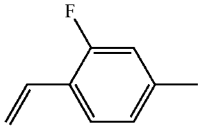 | 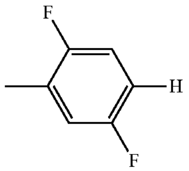 |
| 58 | 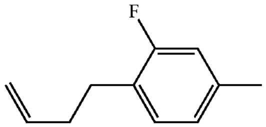 | 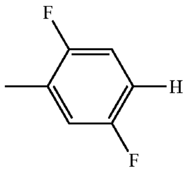 |

-continued
| No. | 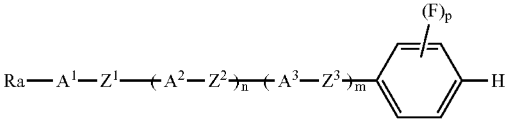 | |
|---|---|---|
| 59 | 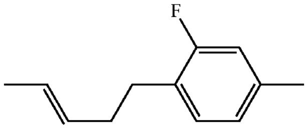 | 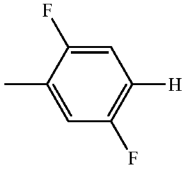 |
| 60 | 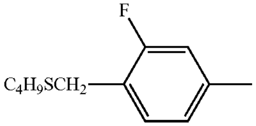 | 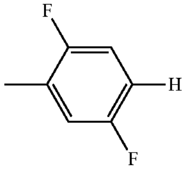 |
| 61 | 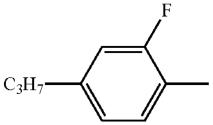 | 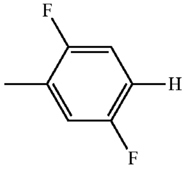 |
| 62 | 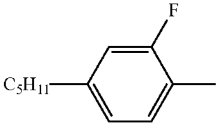 | 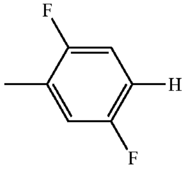 |
| 63 | 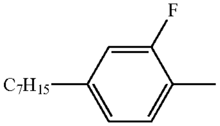 | 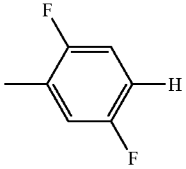 |

-continued
| No. | 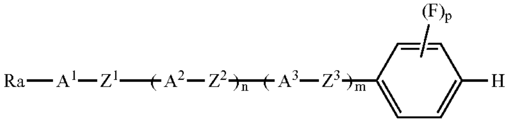 | |
|---|---|---|
| 64 | 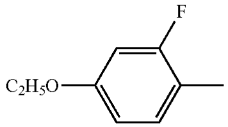 | 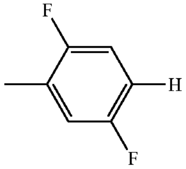 |
| 65 | 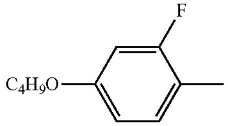 | 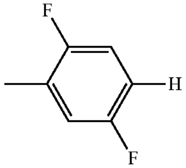 |
| 66 | 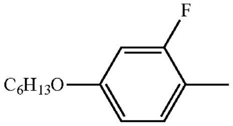 | 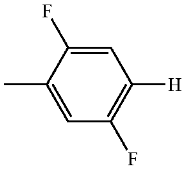 |
| 67 | 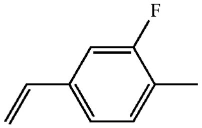 | 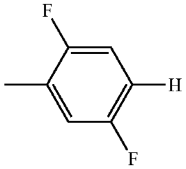 |
| 68 | 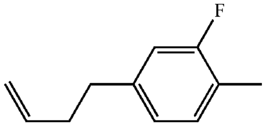 | 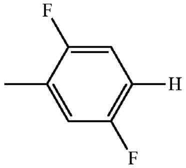 |

-continued
| No. | 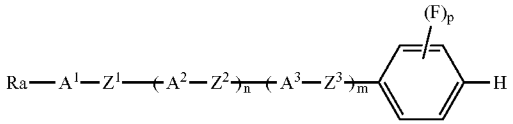 | |
|---|---|---|
| 69 | 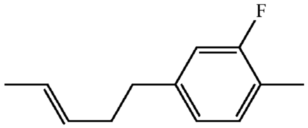 | 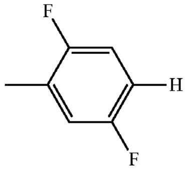 |
| 70 | 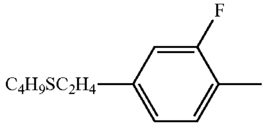 | 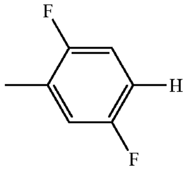 |
| 71 | 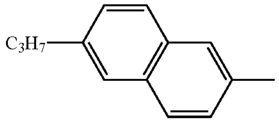 | 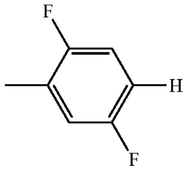 |
| 72 | 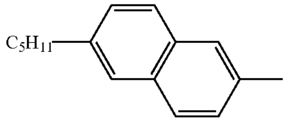 | 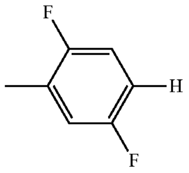 |

-continued
| No. | 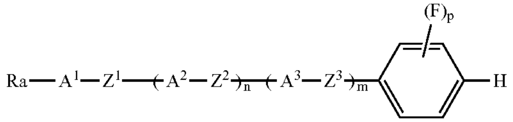 | |
|---|---|---|
| 73 | 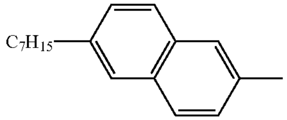 | 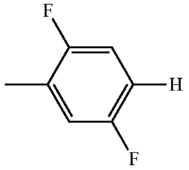 |
| 74 | 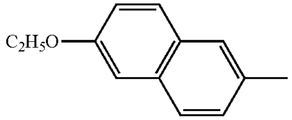 | 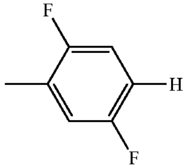 |
| 75 | 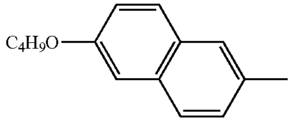 | 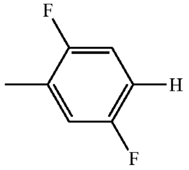 |
| 76 | 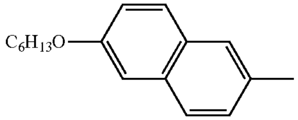 | 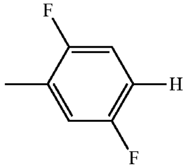 |

-continued
| No. | 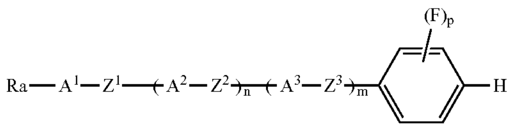 | |
|---|---|---|
| 77 | 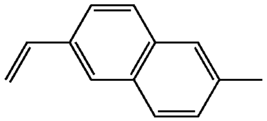 | 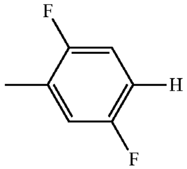 |
| 78 | 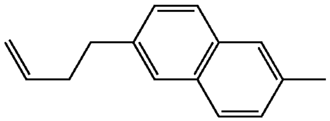 | 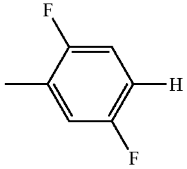 |
| 79 | 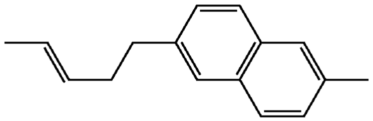 | 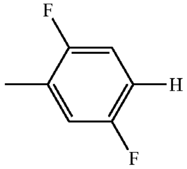 |
| 80 | 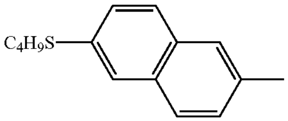 | 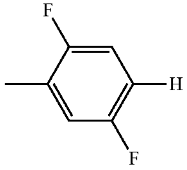 |

81
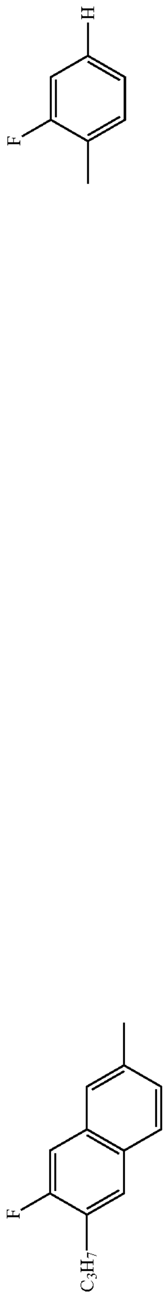
82
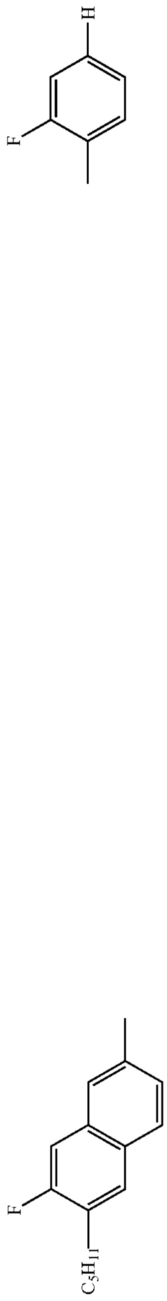
83
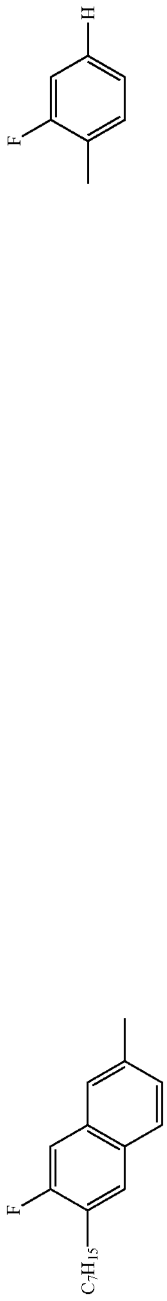
84
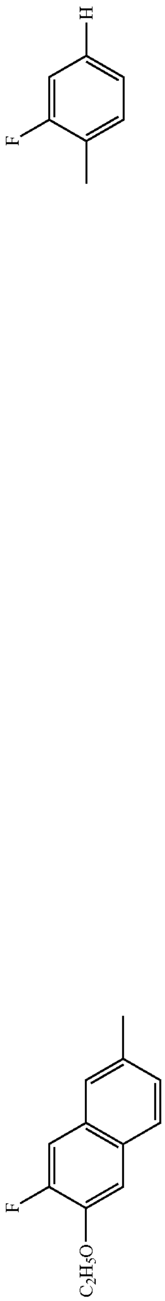
85
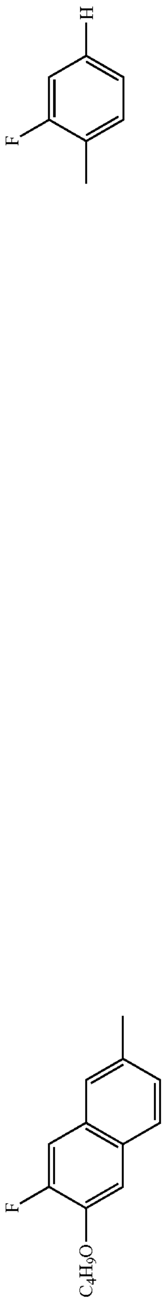
86
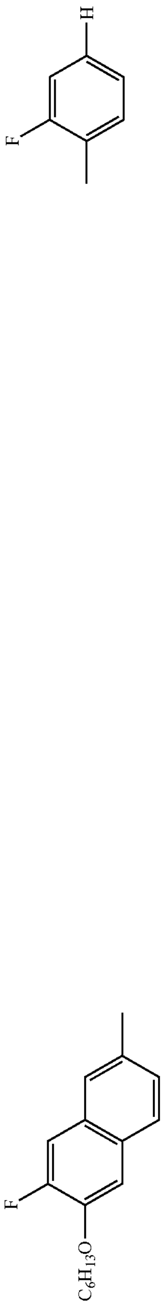

-continued
| | | |
|---|---|---|
| 87 | 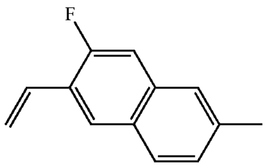 | 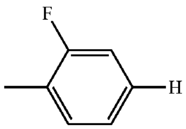 |
| 88 | 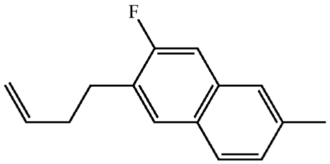 | 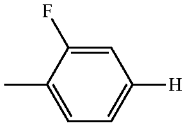 |
| 89 | 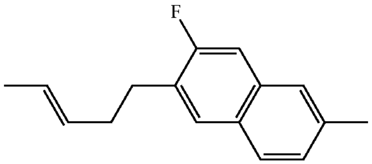 | 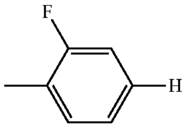 |
| 90 | 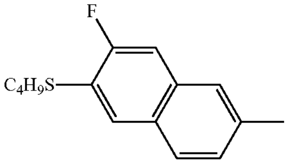 | 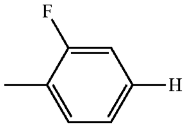 |
| 91 | 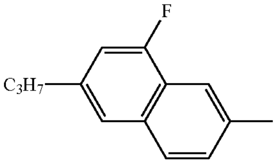 | 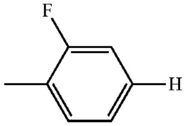 |

-continued
| | | |
|---|---|---|
| 92 | 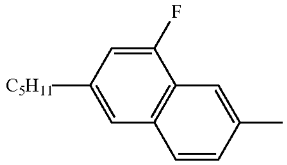 | 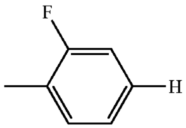 |
| 93 | 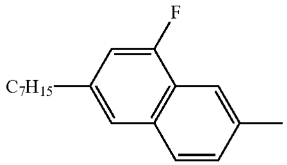 | 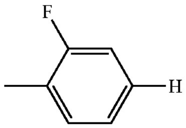 |
| 94 | 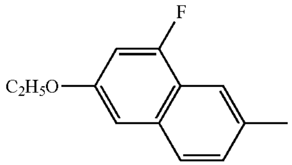 | 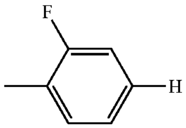 |
| 95 | 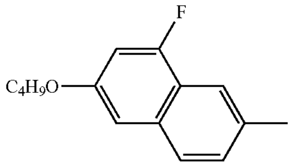 | 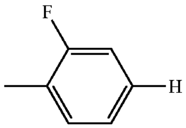 |

-continued
| | | |
|---|---|---|
| 96 | 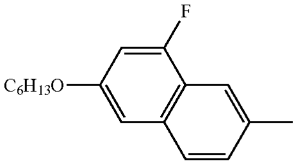 | 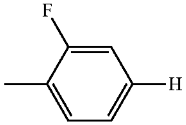 |
| 97 | 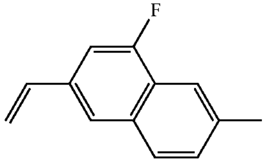 | 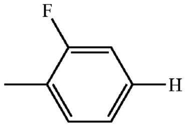 |
| 98 | 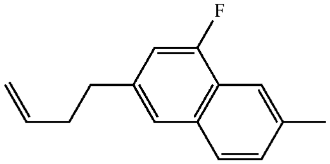 | 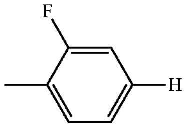 |
| 99 | 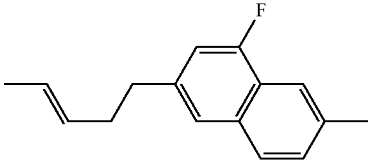 | 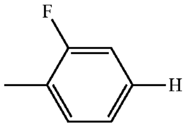 |
| 100 | 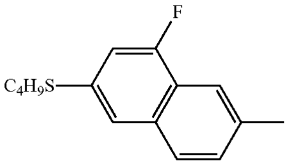 | 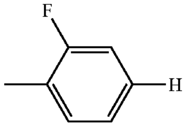 |

| | | |
|---|---|---|
| 101 | 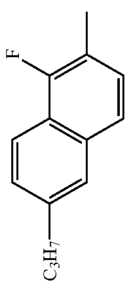 | 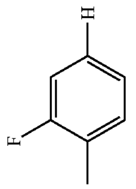 |
| 102 | 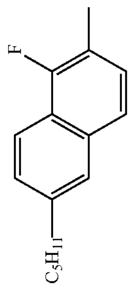 | 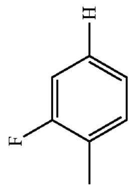 |
| 103 | 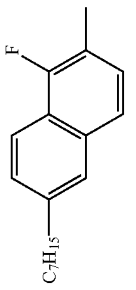 | 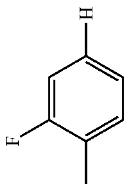 |
| 104 | 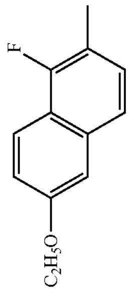 | 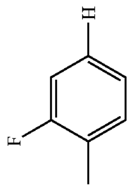 |
| 105 | 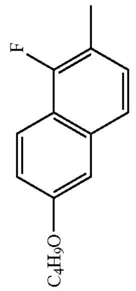 | 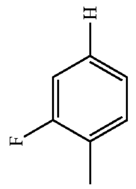 |

-continued
| | | |
|---|---|---|
| 106 | 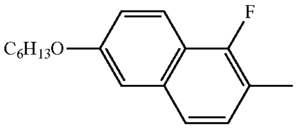 | 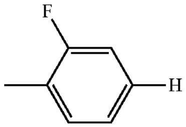 |
| 107 | 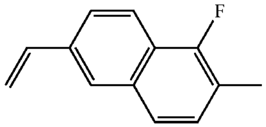 | 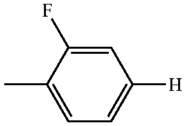 |
| 108 | 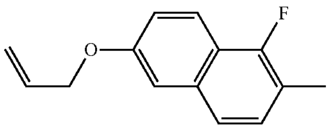 | 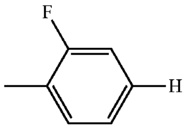 |
| 109 | 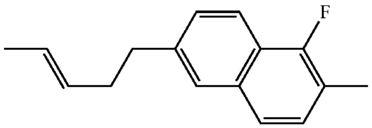 | 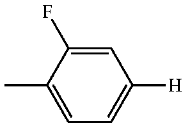 |
| 110 | 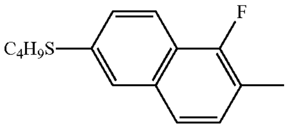 | 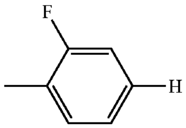 |

| | | |
|---|---|---|
| 111 | 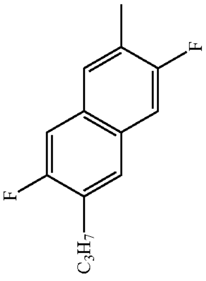 | 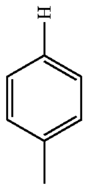 |
| 112 | 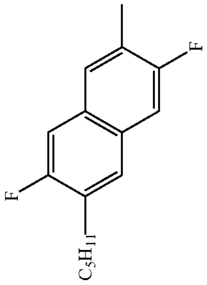 | 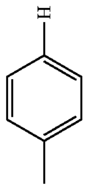 |
| 113 | 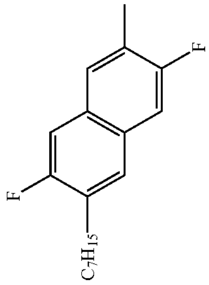 | 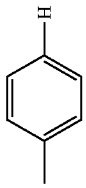 |
| 114 | 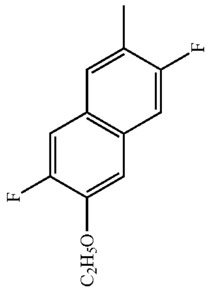 | 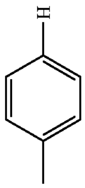 |

-continued
| | | |
|---|---|---|
| 115 | 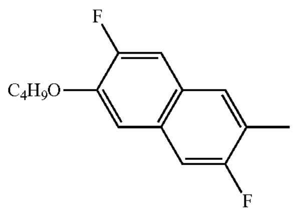 | 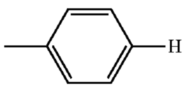 |
| 116 | 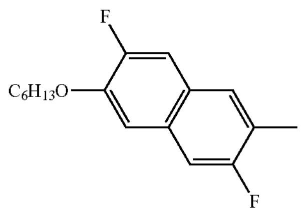 | 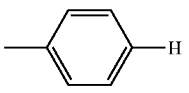 |
| 117 | 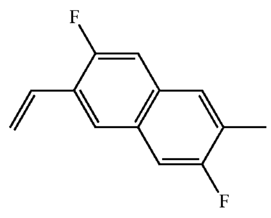 | 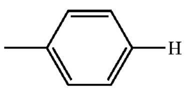 |

-continued
| | | |
|---|---|---|
| 118 | 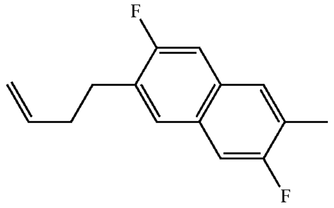 | 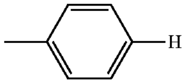 |
| 119 | 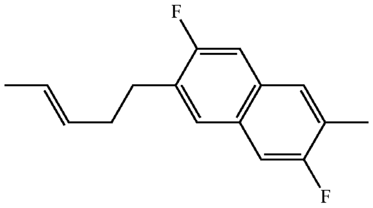 | 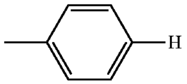 |
| 120 | 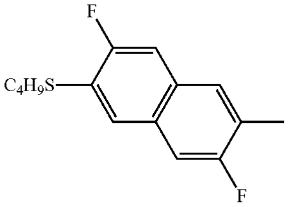 | 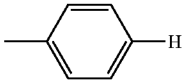 |

| | | |
|---|---|---|
| 121 | 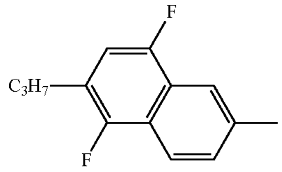 | 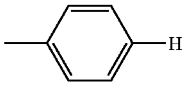 |
| 122 | 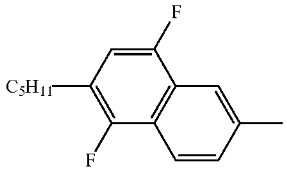 | 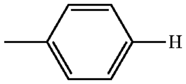 |
| 123 | 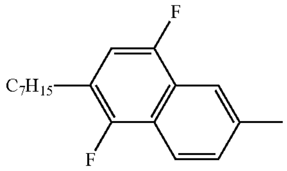 | 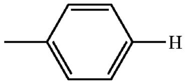 |
| 124 | 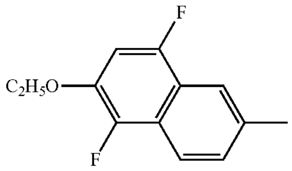 | 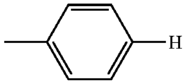 |
| 125 | 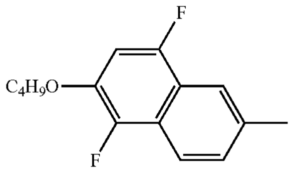 | 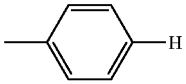 |

-continued
| | |
|---|---|
| 126 | 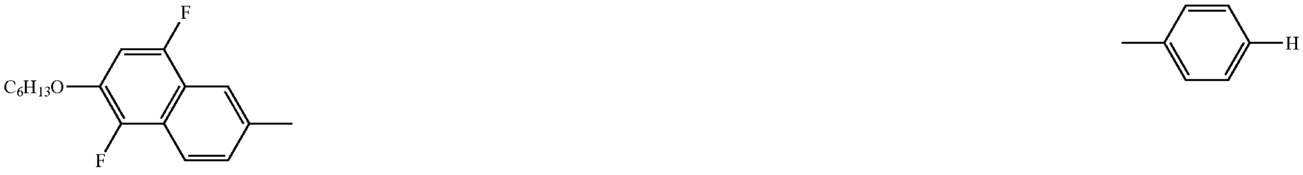 |
| 127 | 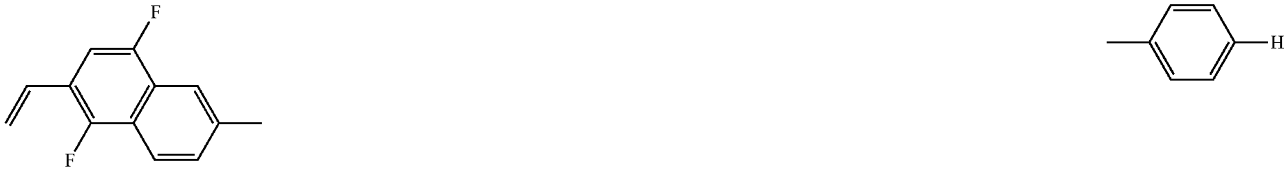 |
| 128 | 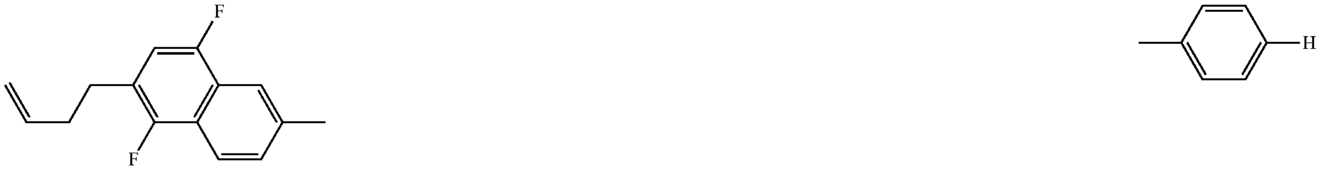 |
| 129 | 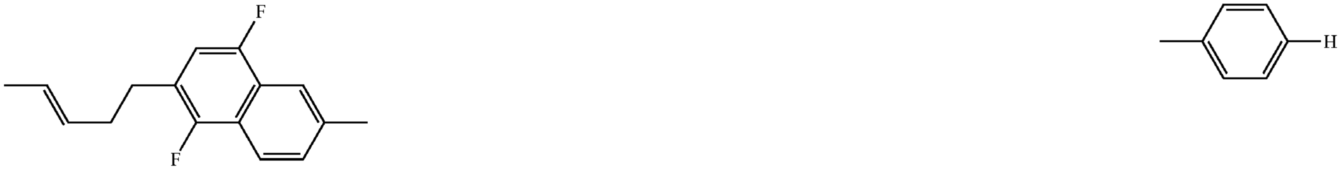 |
| 130 | 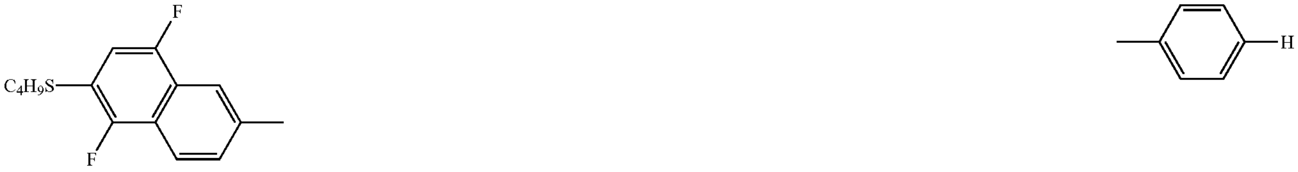 |

| | | |
|---|---|---|
| 131 | 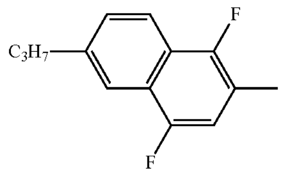 | 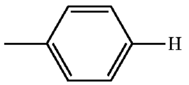 |
| 132 | 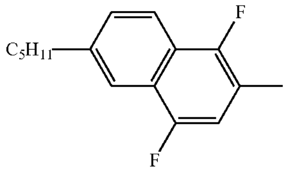 | 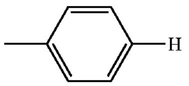 |
| 133 | 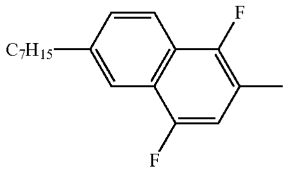 | 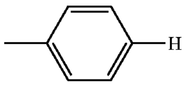 |
| 134 | 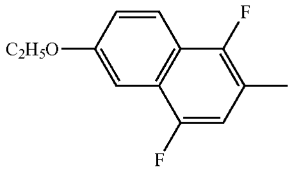 | 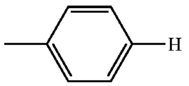 |
| 135 | 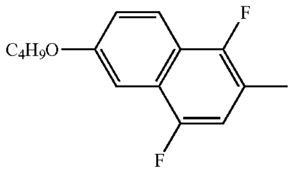 | 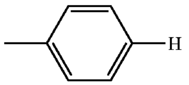 |

-continued
| | | |
|---|---|---|
| 136 | 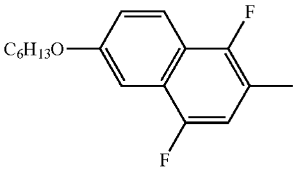 | 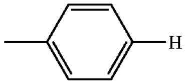 |
| 137 | 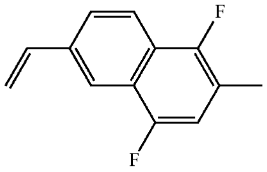 | 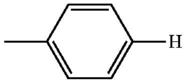 |
| 138 | 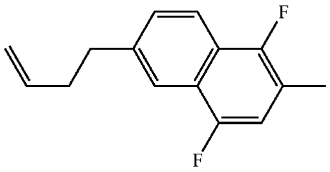 | 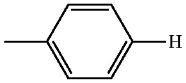 |
| 139 | 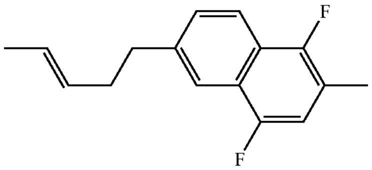 | 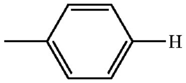 |
| 140 | 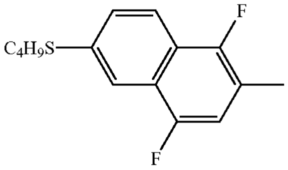 | 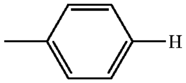 |

| | | |
|---|---|---|
| 141 | 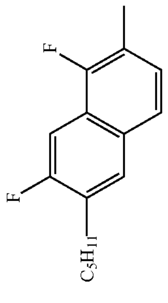 | 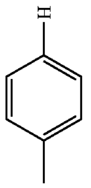 |
| 142 | 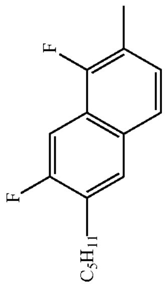 | 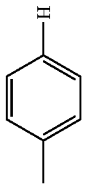 |
| 143 | 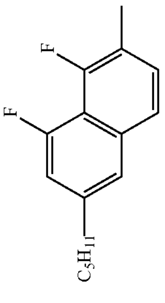 | 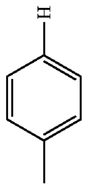 |
| 144 | 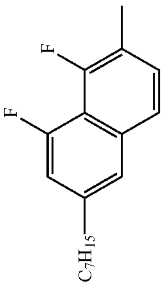 | 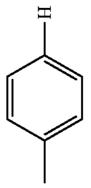 |
| 145 | 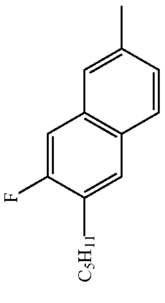 | 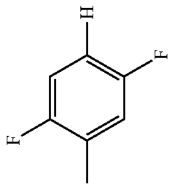 |

-continued
| | | |
|---|---|---|
| 146 | 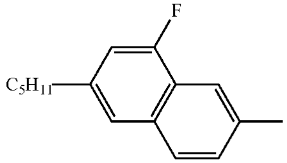 | 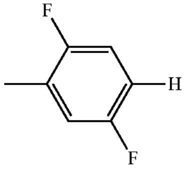 |
| 147 | 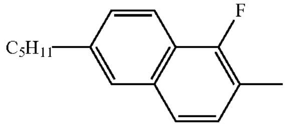 | 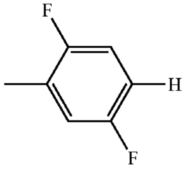 |
| 148 | 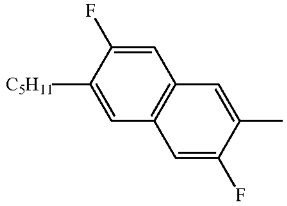 | 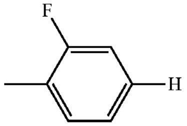 |
| 149 | 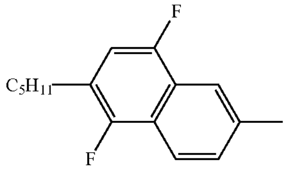 | 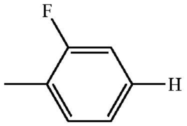 |
| 150 | 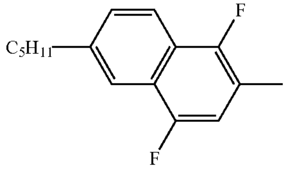 | 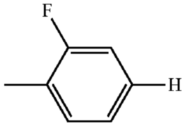 |

| | | |
|---|---|---|
| 151 | 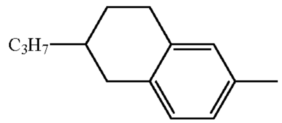 | 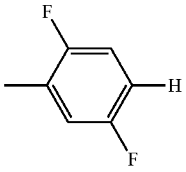 |
| 152 | 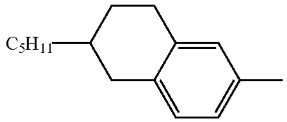 | 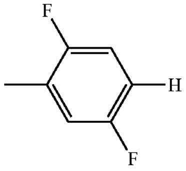 |
| 153 | 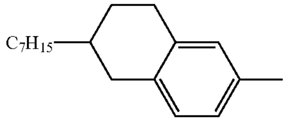 | 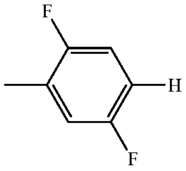 |
| 154 | 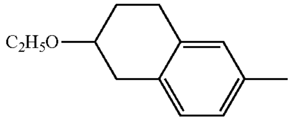 | 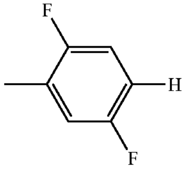 |
| 155 | 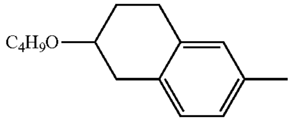 | 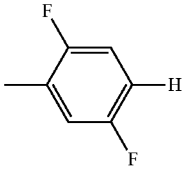 |

-continued
156 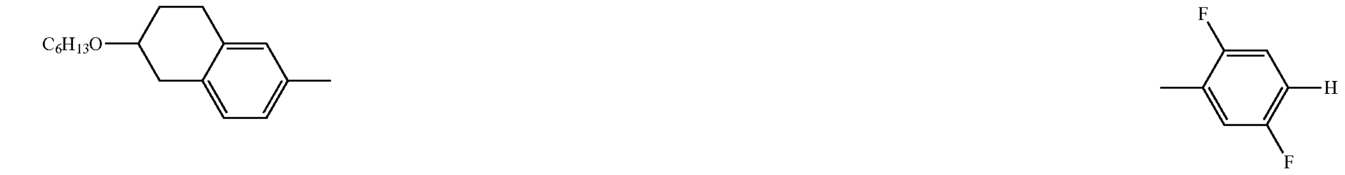
157 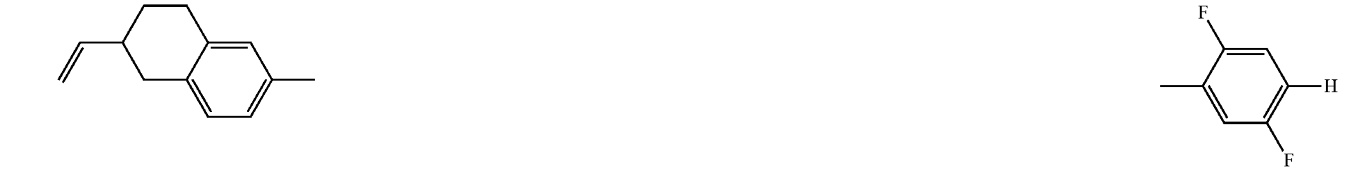
158 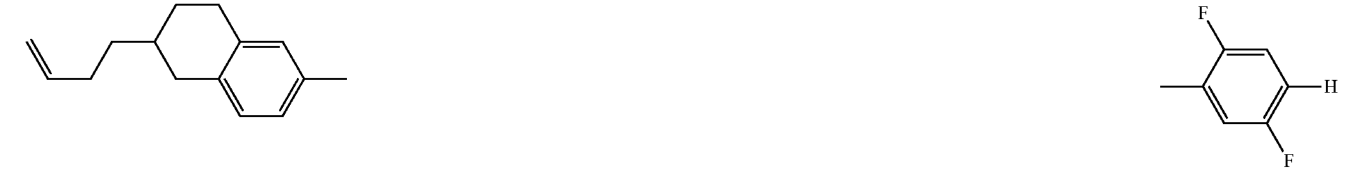
159 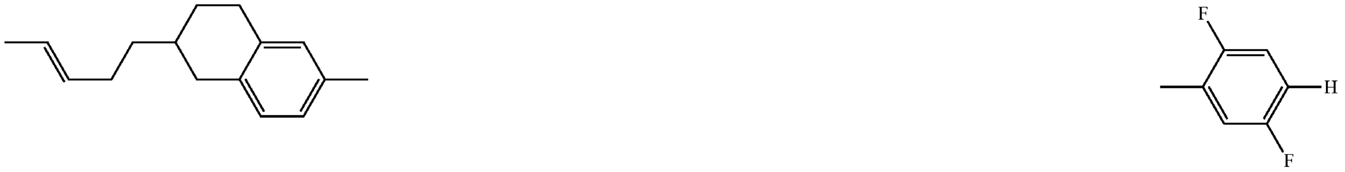
160 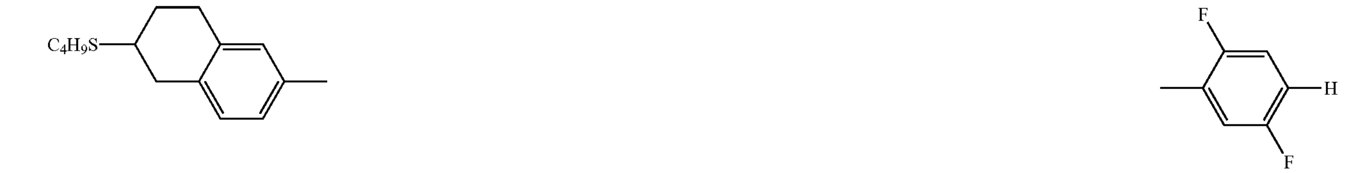
161 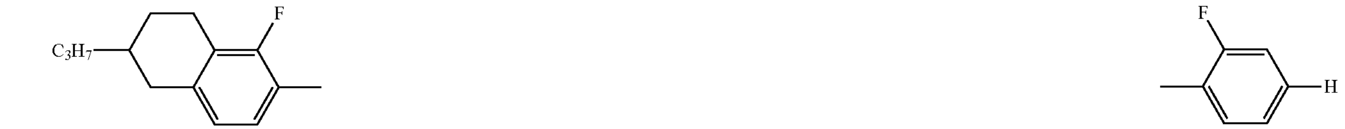

-continued
| | | |
|---|---|---|
| 162 | 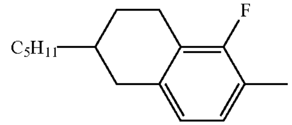 | 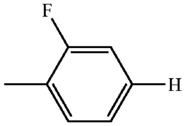 |
| 163 | 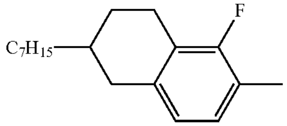 | 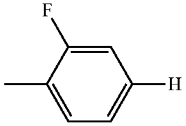 |
| 164 | 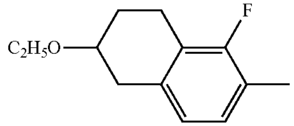 | 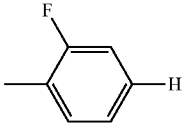 |
| 165 | 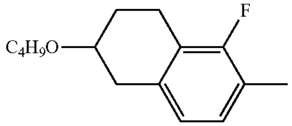 | 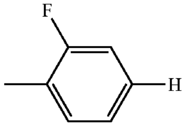 |
| 166 | 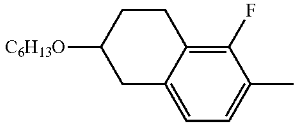 | 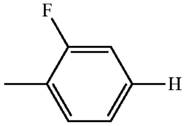 |
| 167 | 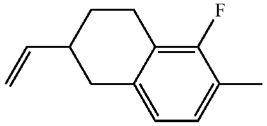 | 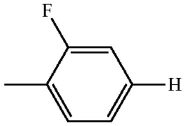 |
| 168 | 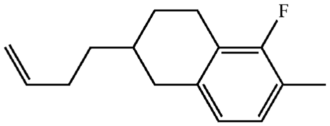 | 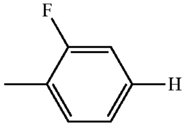 |

-continued
| | | |
|---|---|---|
| 169 | 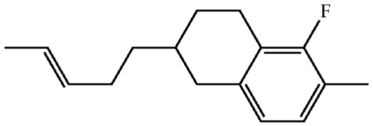 | 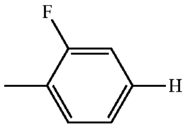 |
| 170 | 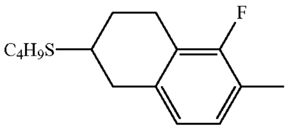 | 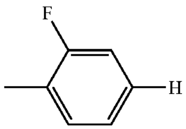 |
| 171 | 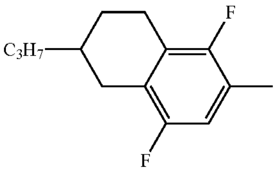 | 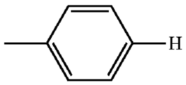 |
| 172 | 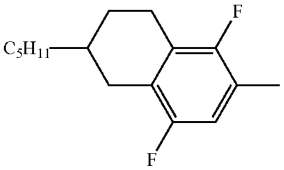 | 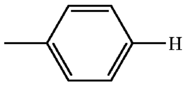 |
| 173 | 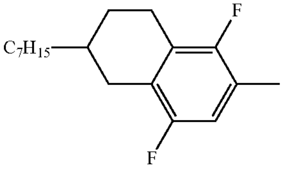 | 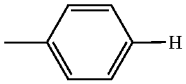 |

-continued
174 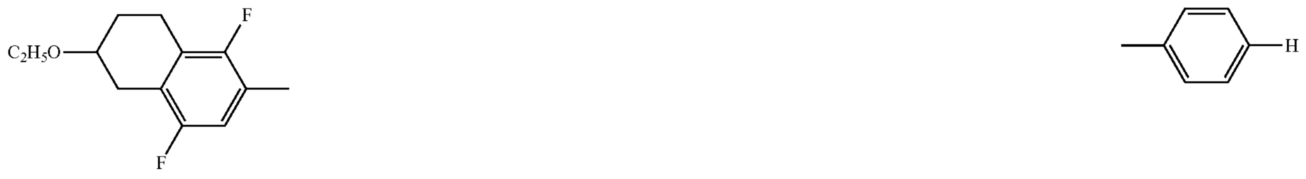
175 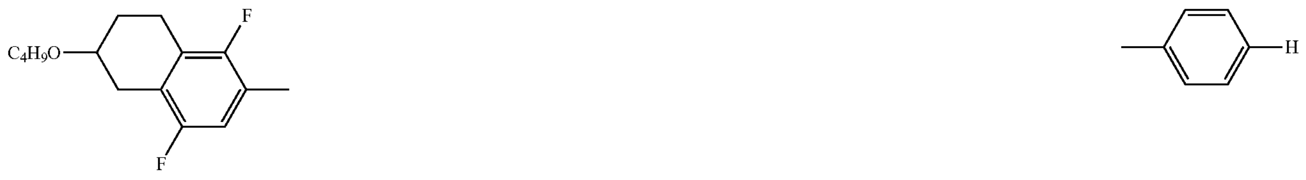
176 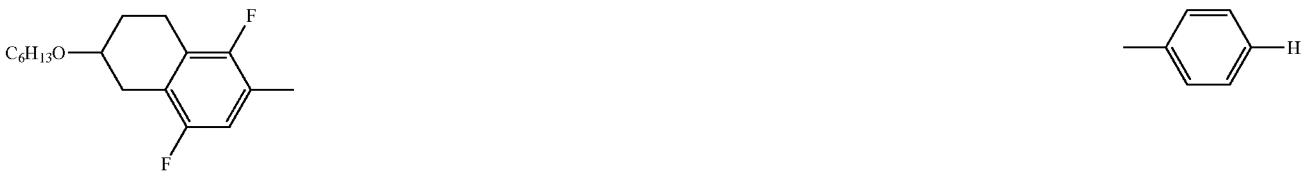
177 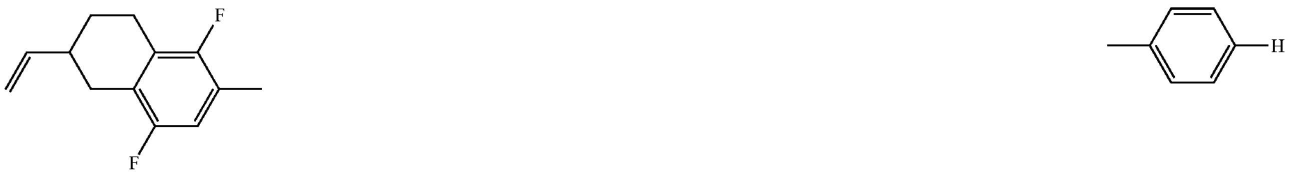

-continued
| | | |
|---|---|---|
| 178 | 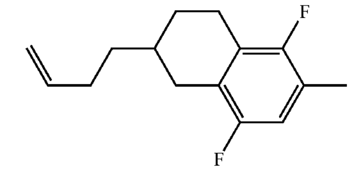 | 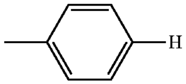 |
| 179 | 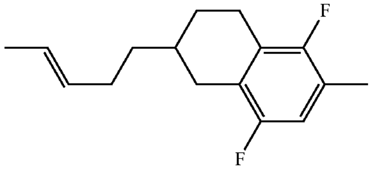 | 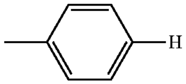 |
| 180 | 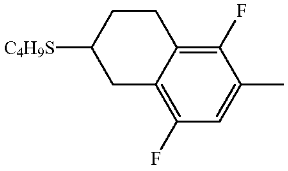 | 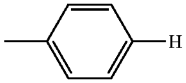 |

181 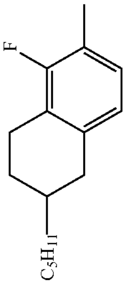 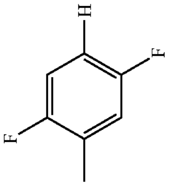
182 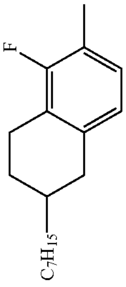 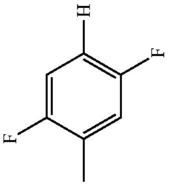
183 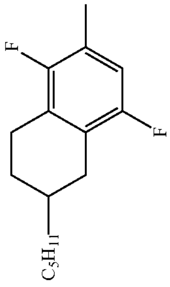 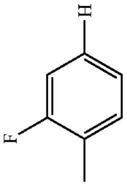
184 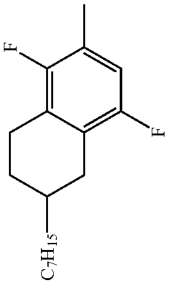 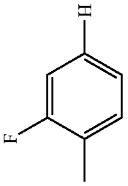
185 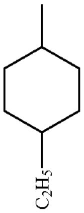 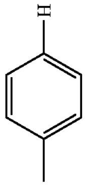 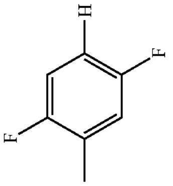

-continued
| | |
|---|---|
| 186 | 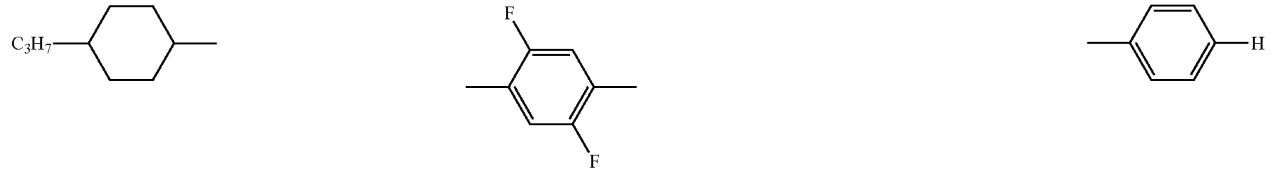 |
| 187 | 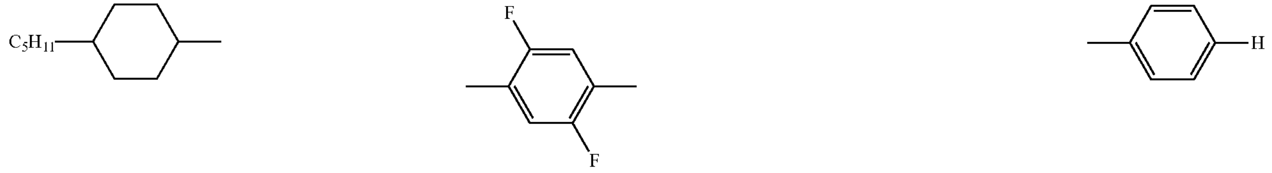 |
| 188 | 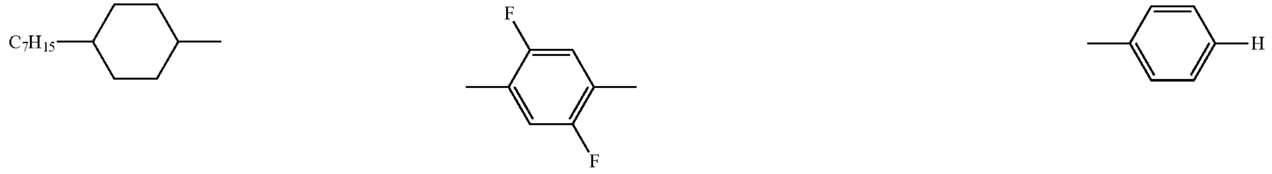 |
| 189 | 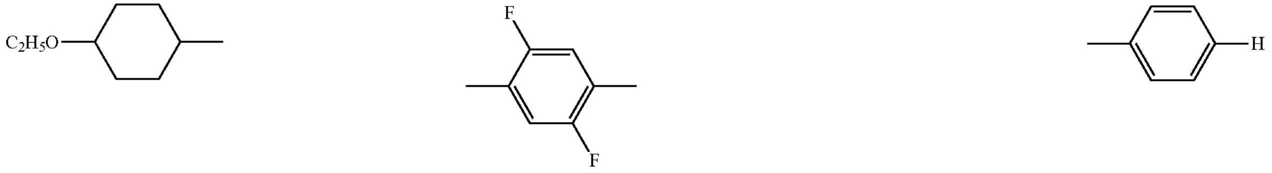 |
| 190 | 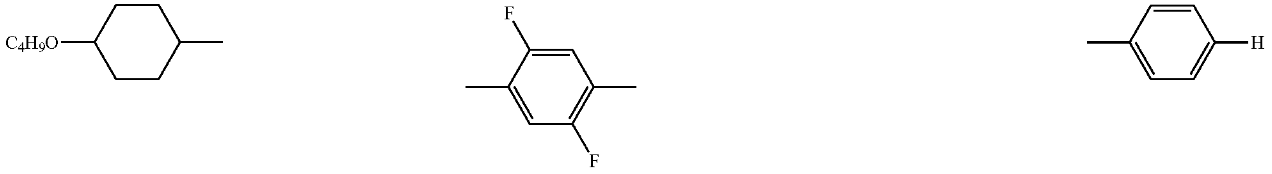 |

-continued
| | |
|---|---|
| 191 | 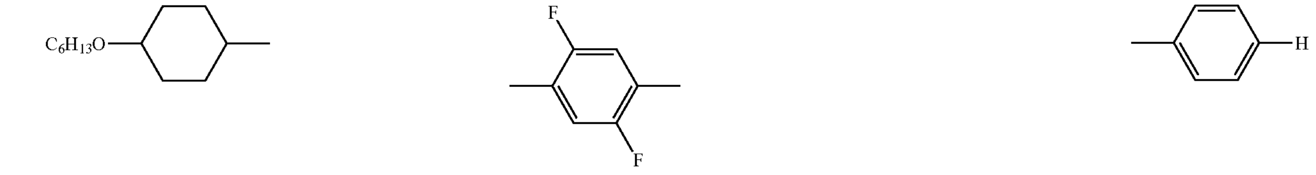 |
| 192 | 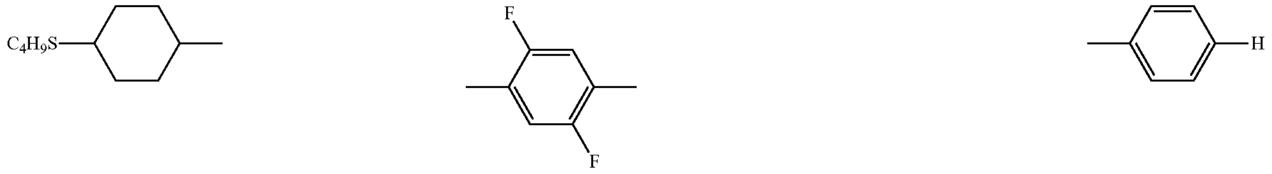 |
| 193 | 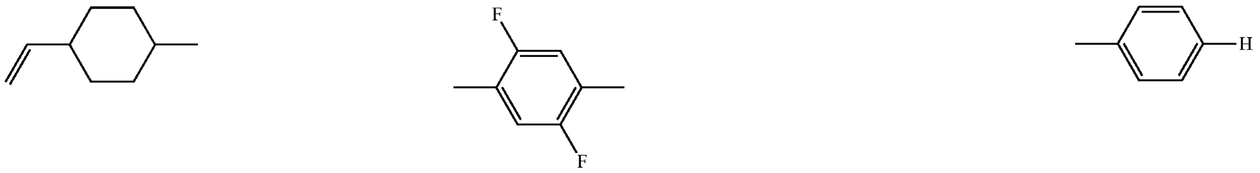 |
| 194 | 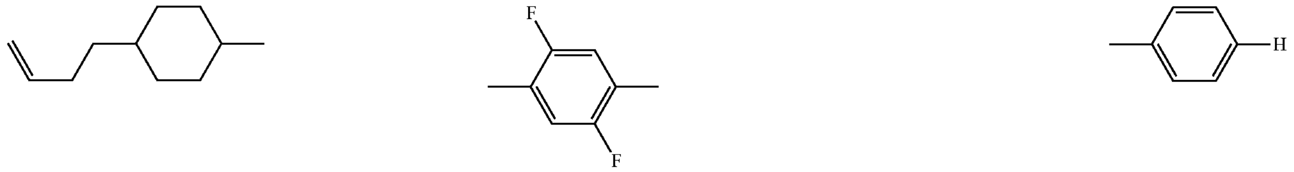 |
| 195 | 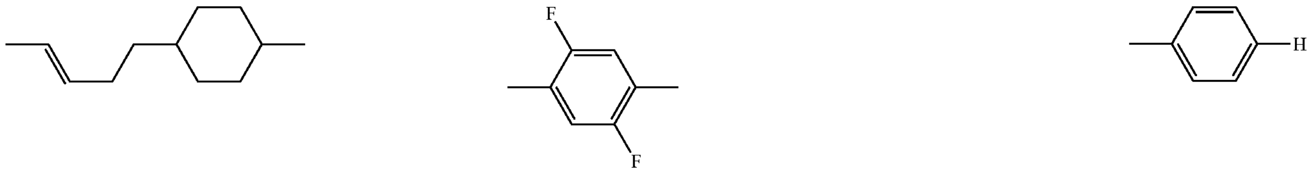 |

196 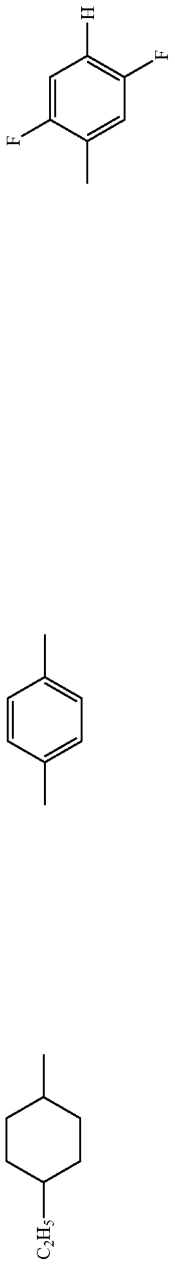
197 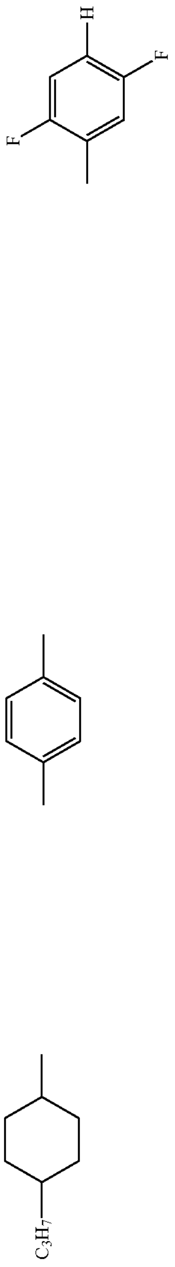
198 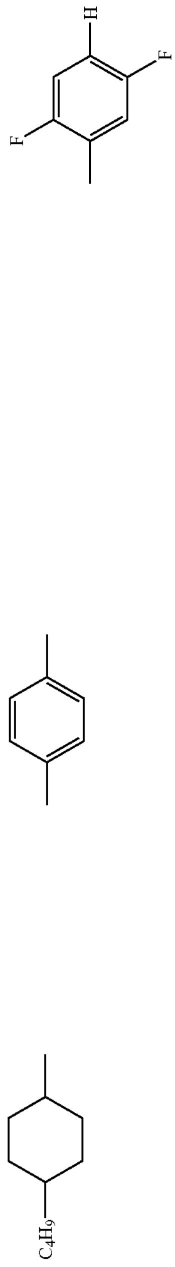
199 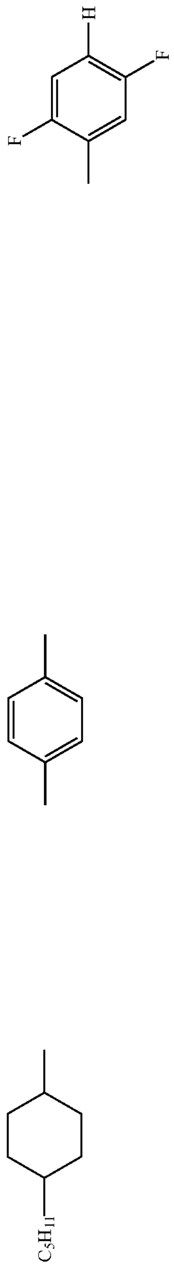
200 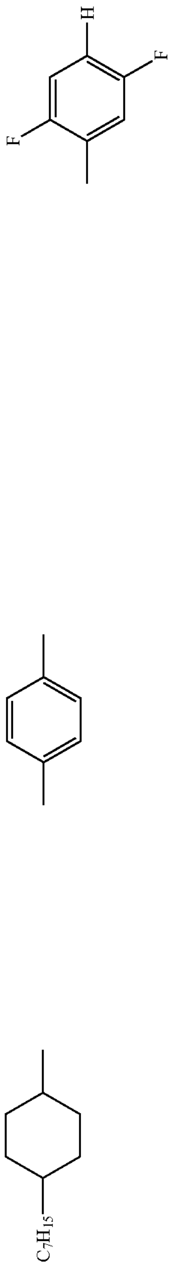

-continued
| | |
|---|---|
| 201 | 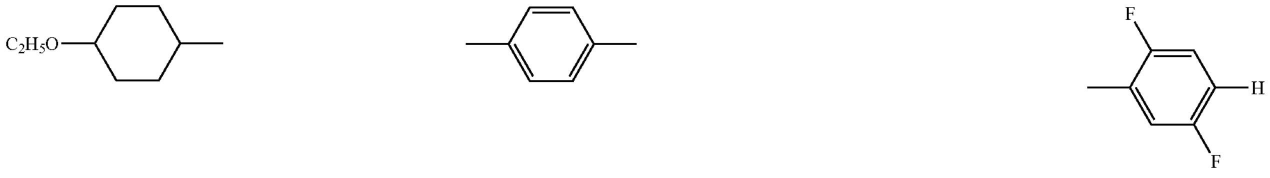 |
| 202 | 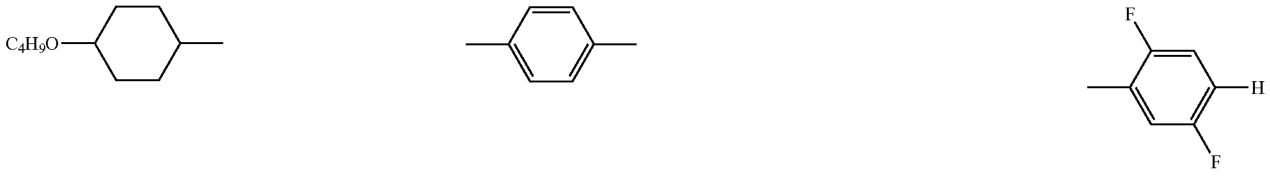 |
| 203 | 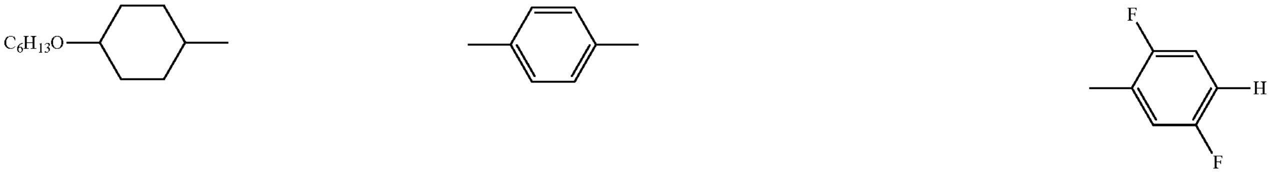 |
| 204 | 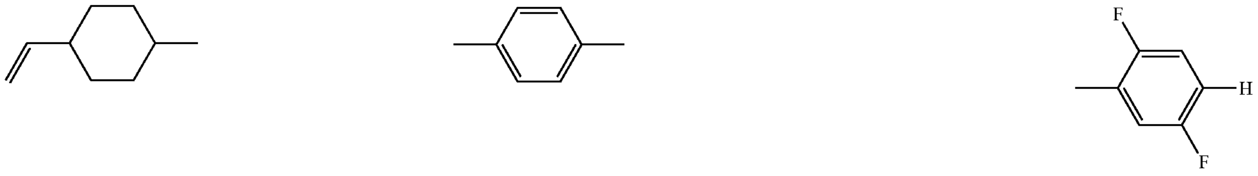 |

-continued
| | | | |
|---|---|---|---|
| 205 | 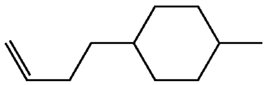 | 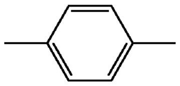 | 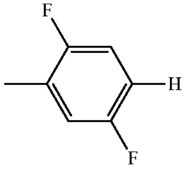 |
| 206 | 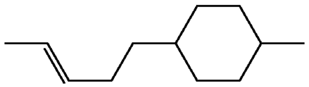 | 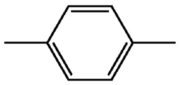 | 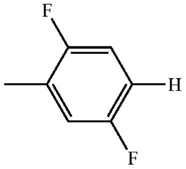 |

| | |
|---|---|
| 207 | 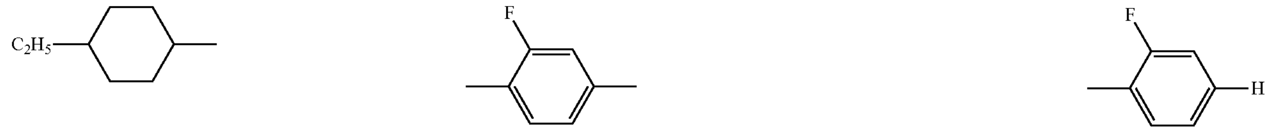 |
| 208 | 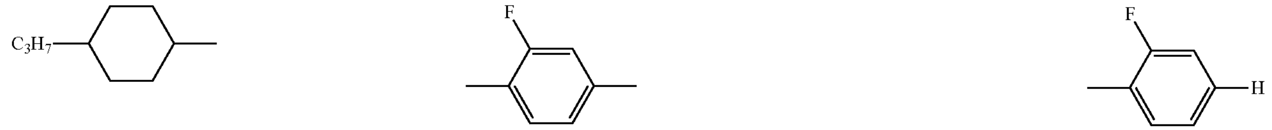 |
| 209 | 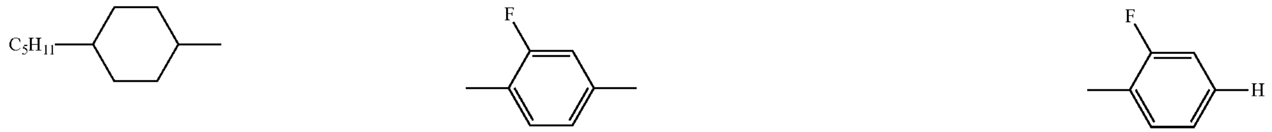 |
| 210 | 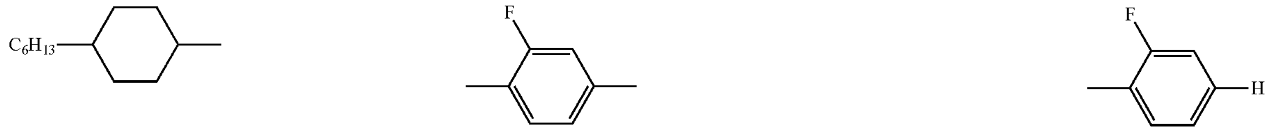 |
| 211 | 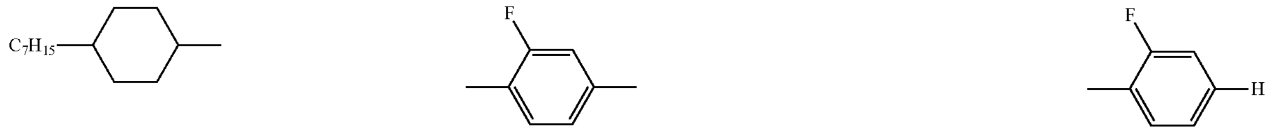 |
| 212 | 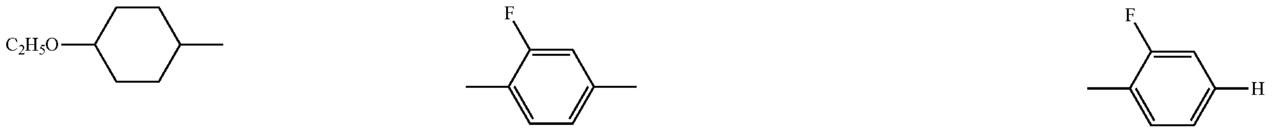 |
| 213 | 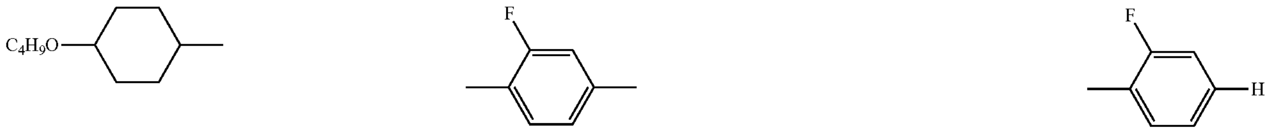 |

-continued
| | |
|---|---|
| 214 | 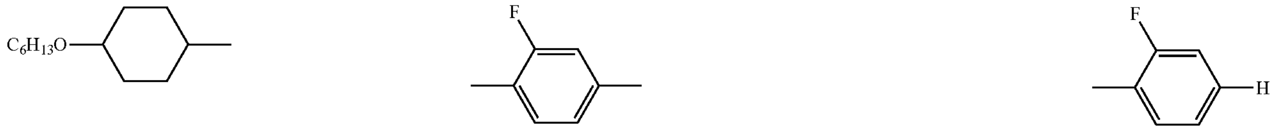 |
| 215 | 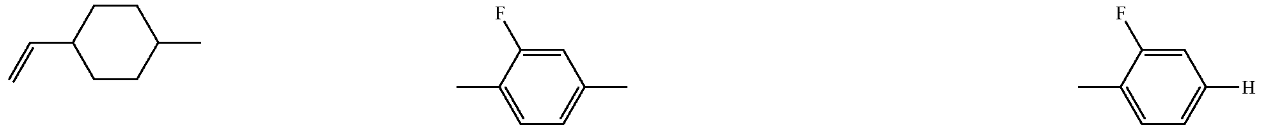 |
| 216 | 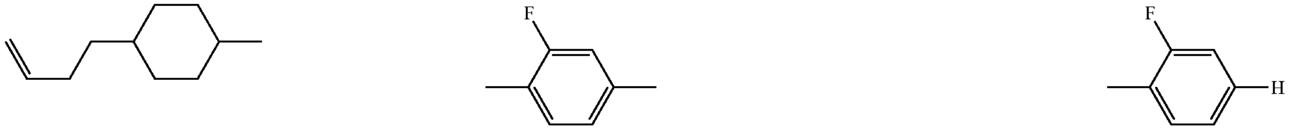 |
| 217 | 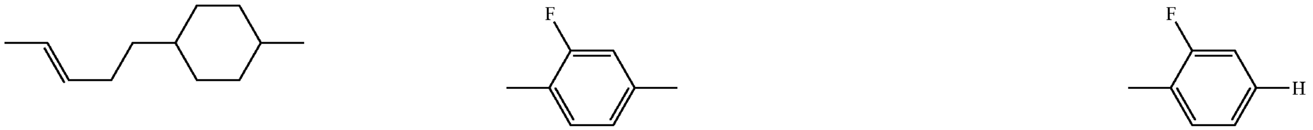 |
| 218 | 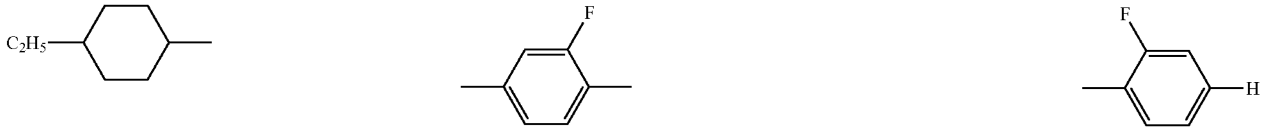 |
| 219 | 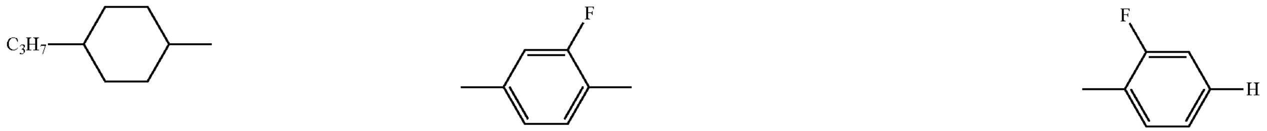 |
| 220 | 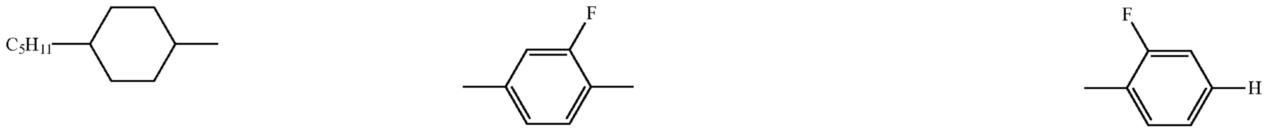 |

-continued
| | |
|---|---|
| 221 | 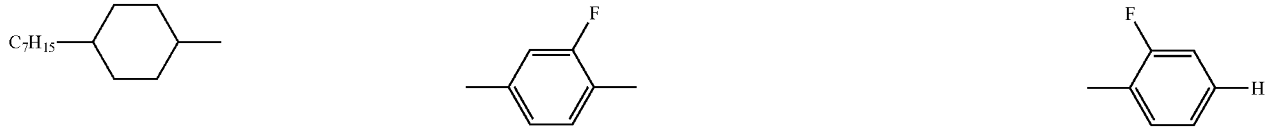 |
| 222 | 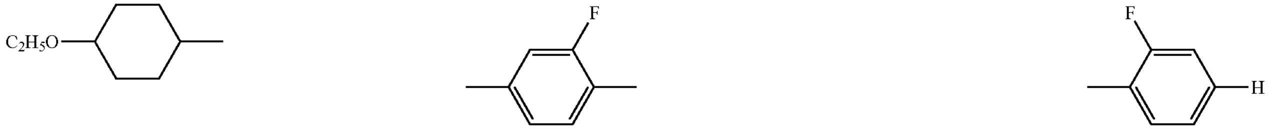 |
| 223 | 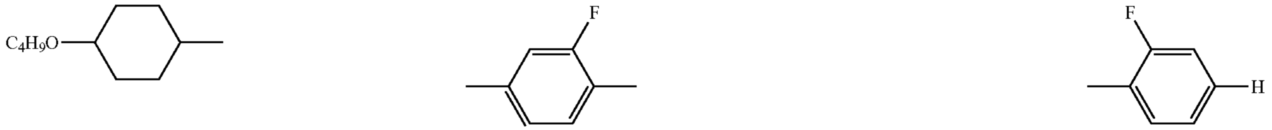 |
| 224 | 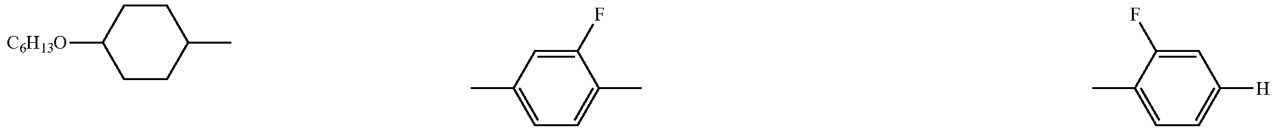 |
| 225 | 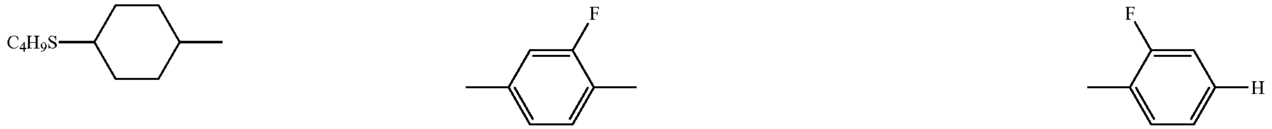 |
| 226 | 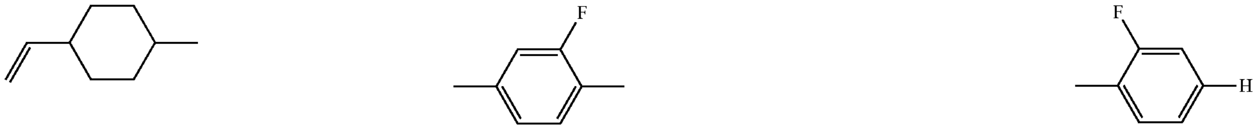 |
| 227 | 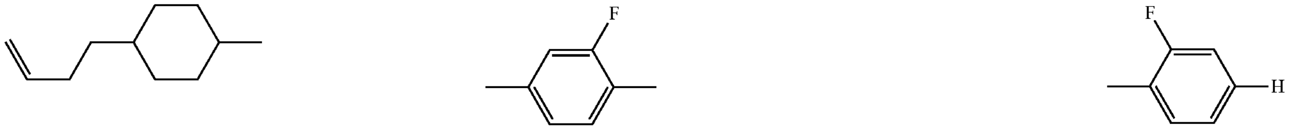 |

-continued
| | | | |
|---|---|---|---|
| 228 | 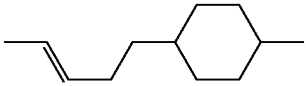 | 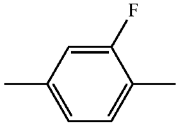 | 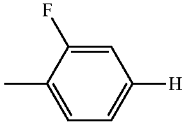 |
| 229 | 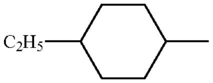 | 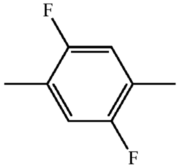 | 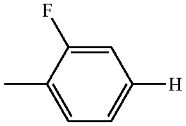 |
| 230 | 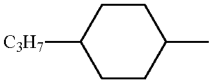 | 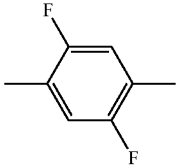 | 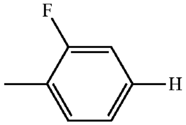 |
| 231 | 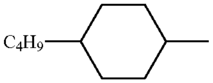 | 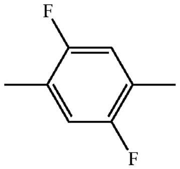 | 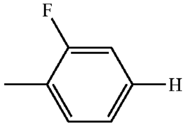 |
| 232 | 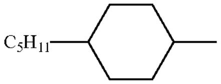 | 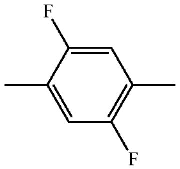 | 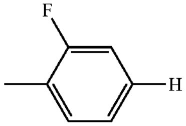 |
| 233 | 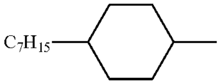 | 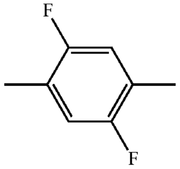 | 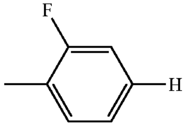 |

-continued
| | | | |
|---|---|---|---|
| 234 | 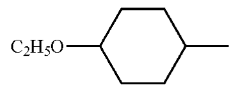 | 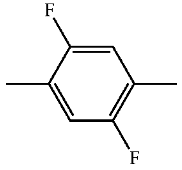 | 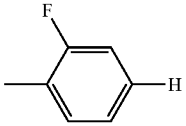 |
| 235 | 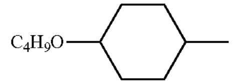 | 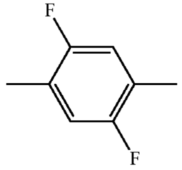 | 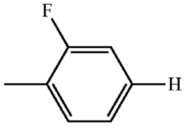 |
| 236 | 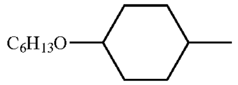 | 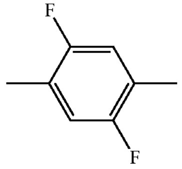 | 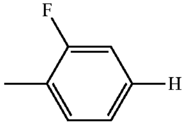 |
| 237 | 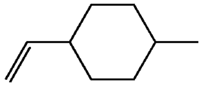 | 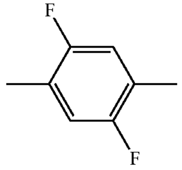 | 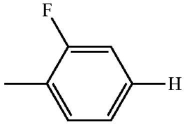 |
| 238 | 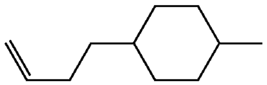 | 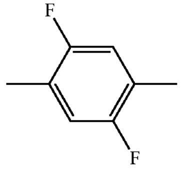 | 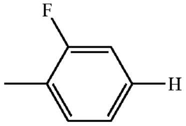 |

-continued
239 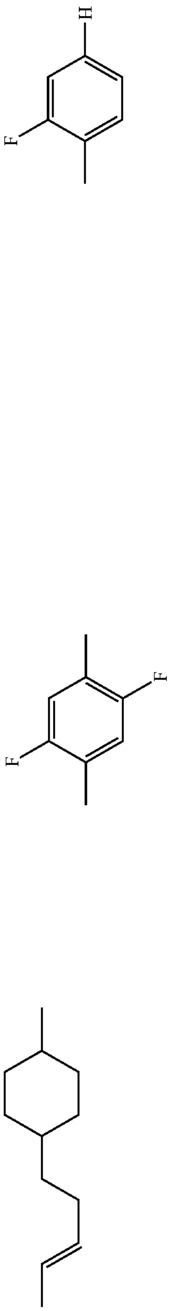
240 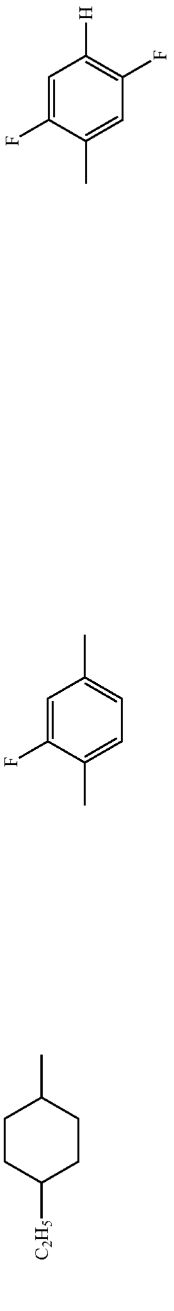
241 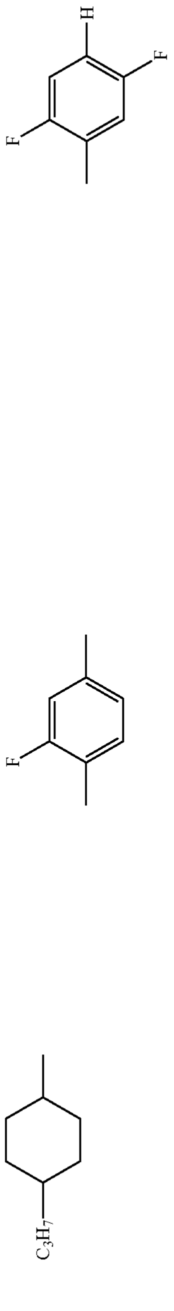
242 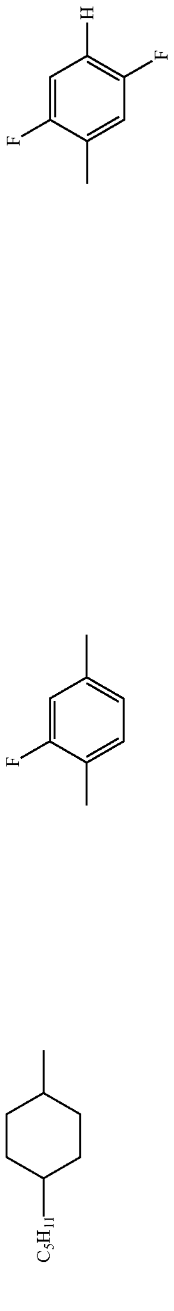
243 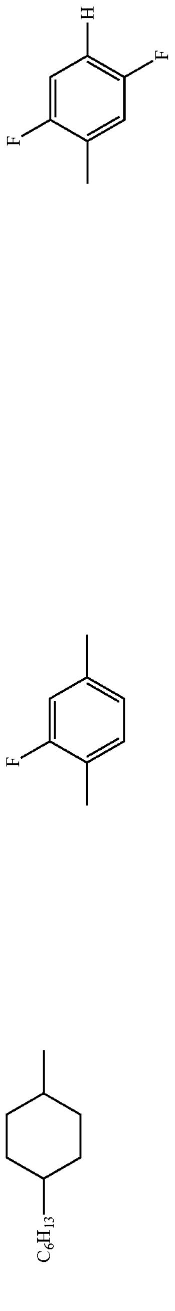

-continued
| | |
|---|---|
| 244 | 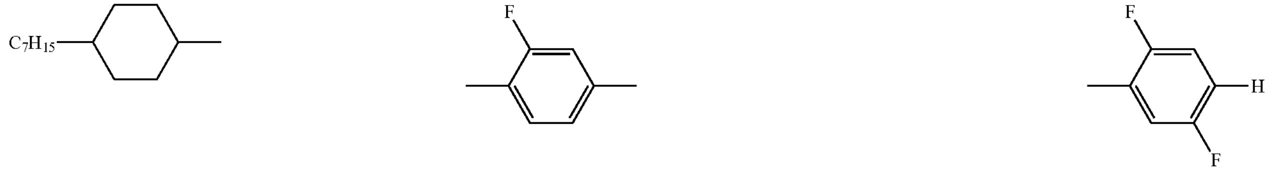 |
| 245 | 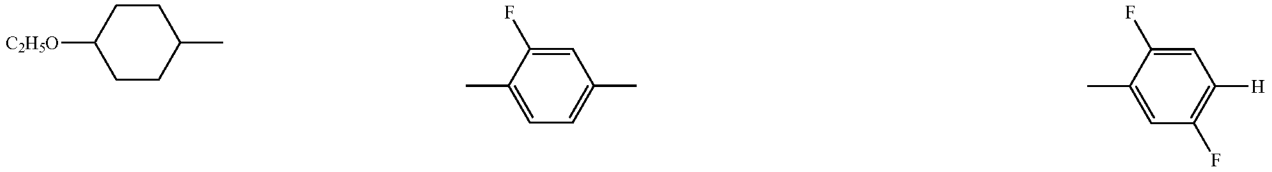 |
| 246 | 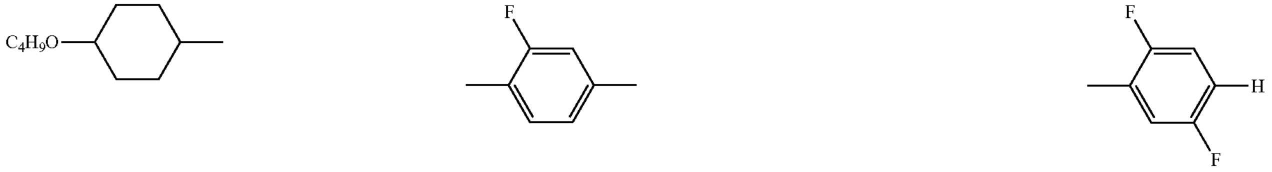 |
| 247 | 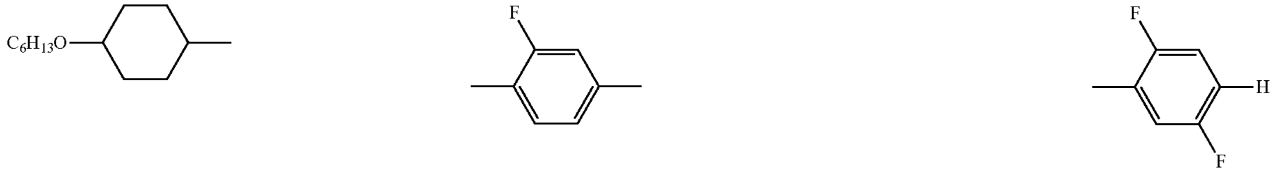 |
| 248 | 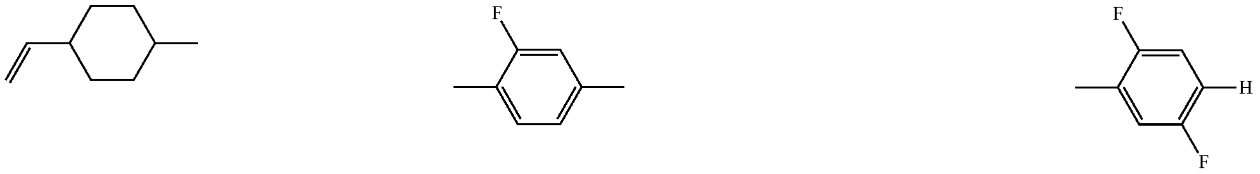 |

-continued
| | |
|---|---|
| 249 | 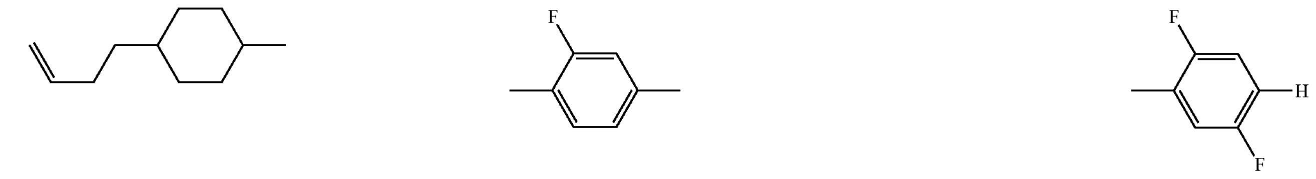 |
| 250 | 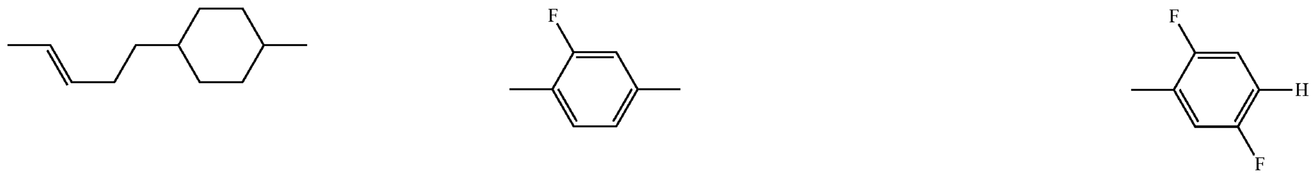 |
| 251 | 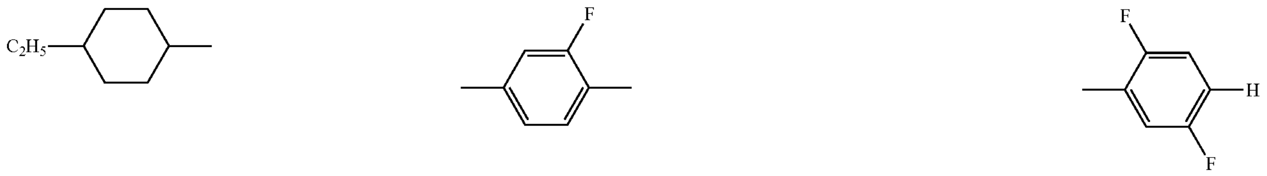 |
| 252 | 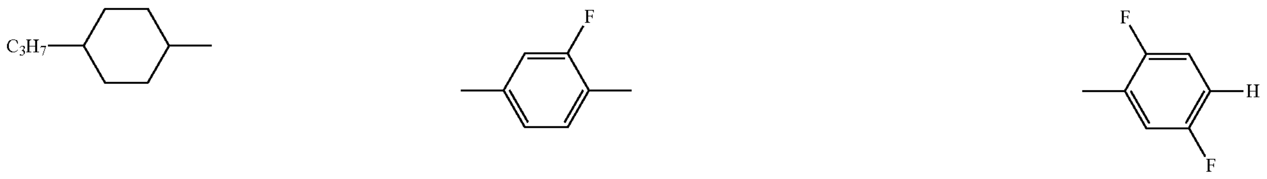 |

-continued
253 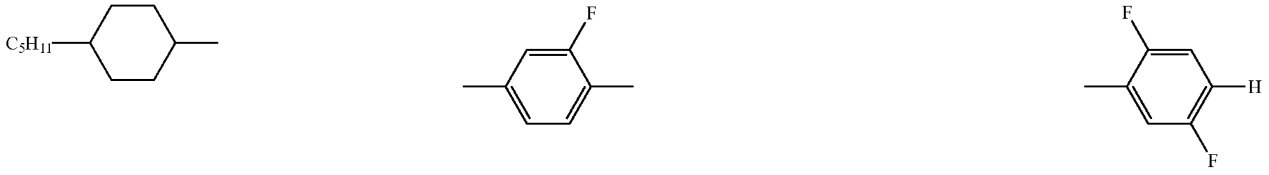
254 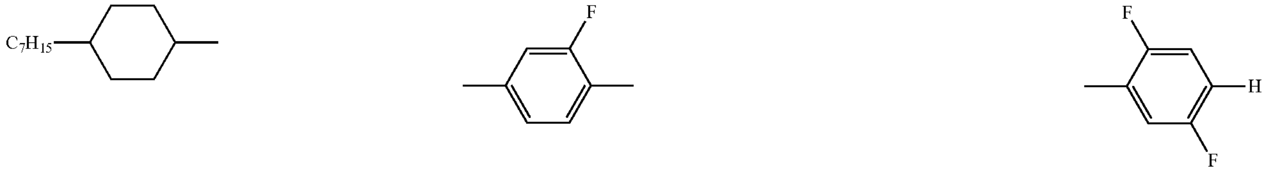
255 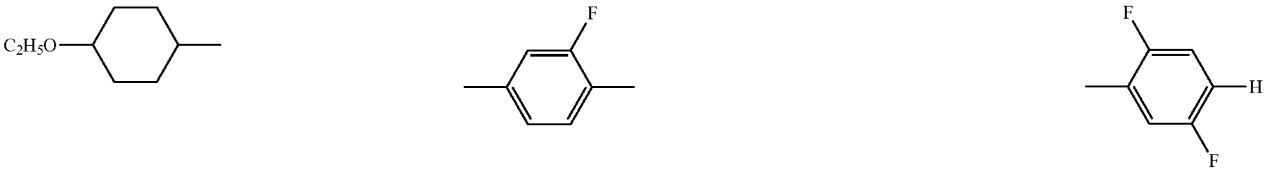
256 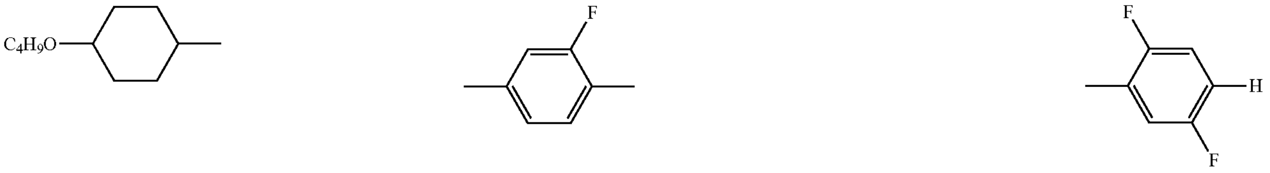

-continued
| | | | |
|---|---|---|---|
| 257 | 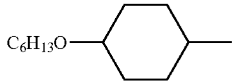 | 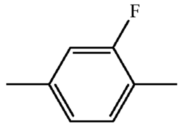 | 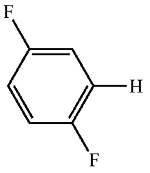 |
| 258 | 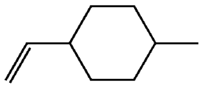 | 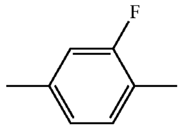 | 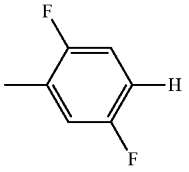 |
| 259 | 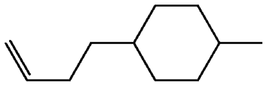 | 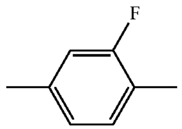 | 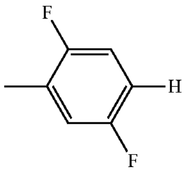 |
| 260 | 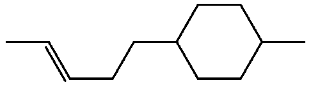 | 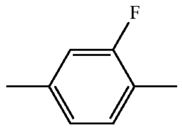 | 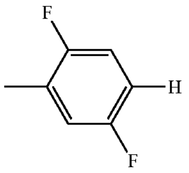 |

| | | | |
|---|---|---|---|
| 261 | 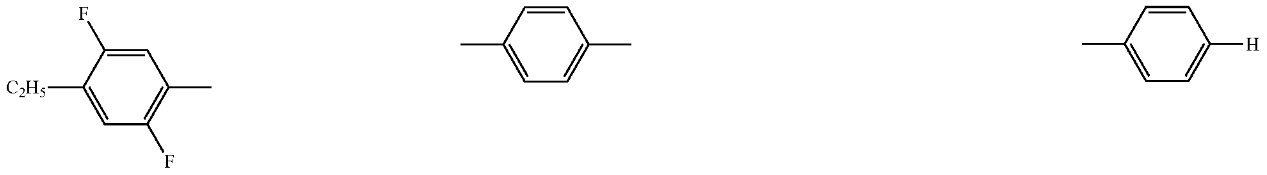 | | |
| 262 | 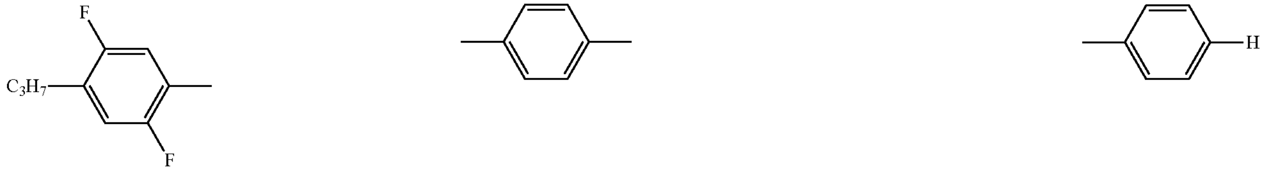 | | |
| 263 | 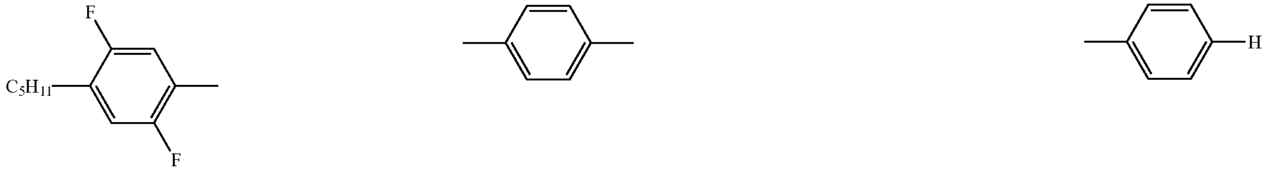 | | |
| 264 | 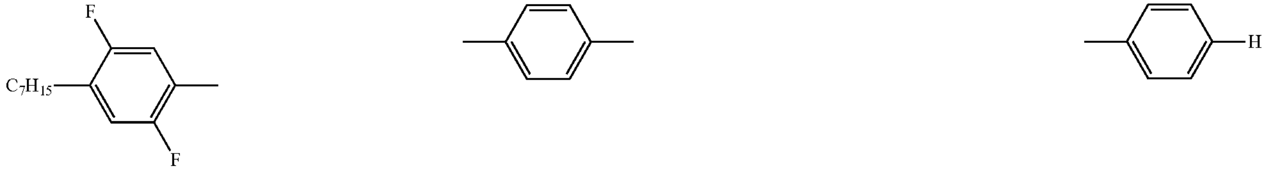 | | |

-continued
| | | | |
|---|---|---|---|
| 265 | 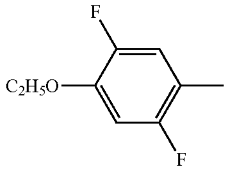 | 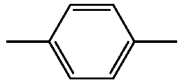 | 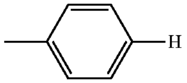 |
| 266 | 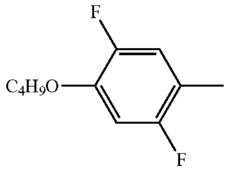 | 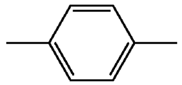 | 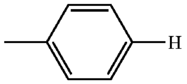 |
| 267 | 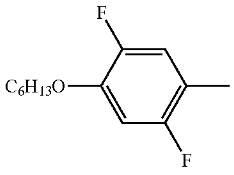 | 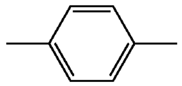 | 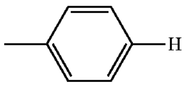 |
| 268 | 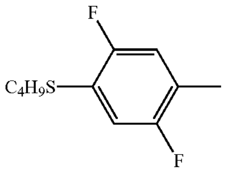 | 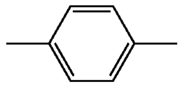 | 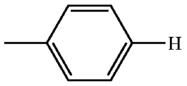 |

-continued
| | | | |
|---|---|---|---|
| 269 | 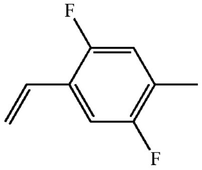 | 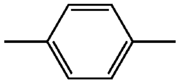 | 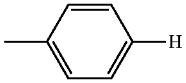 |
| 270 | 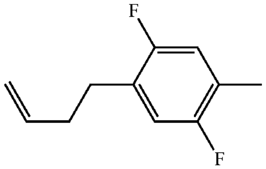 | 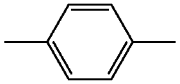 | 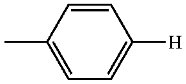 |
| 271 | 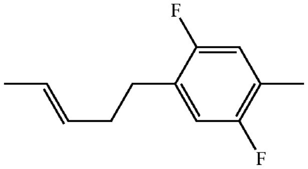 | 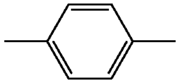 | 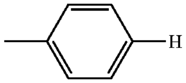 |

| | | |
|---|---|---|
| 272 | 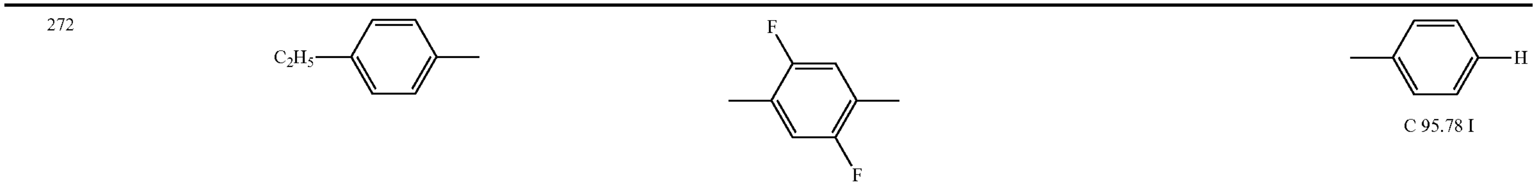 | C 95.78 I |
| 273 | 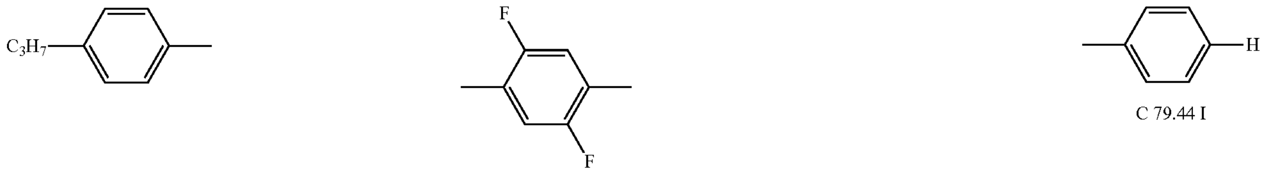 | C 79.44 I |
| 274 | 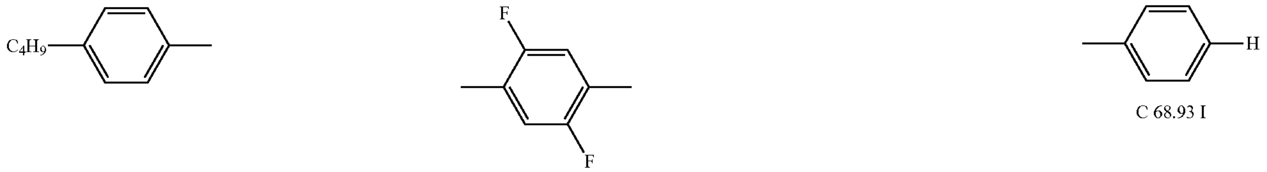 | C 68.93 I |
| 275 | 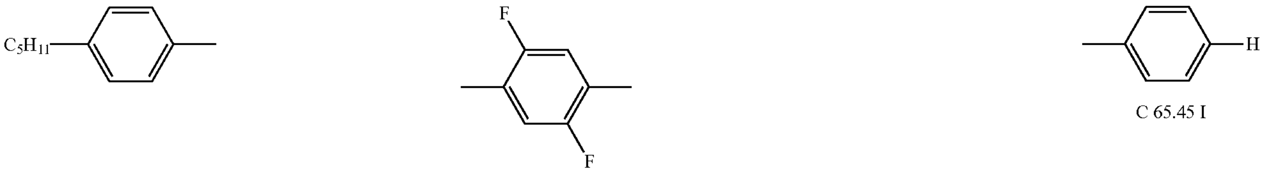 | C 65.45 I |
| 276 | 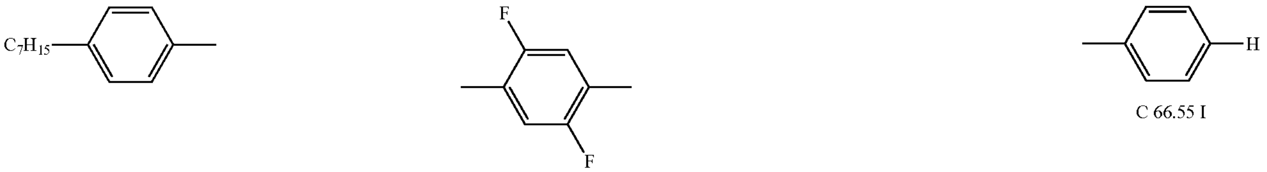 | C 66.55 I |

-continued
277 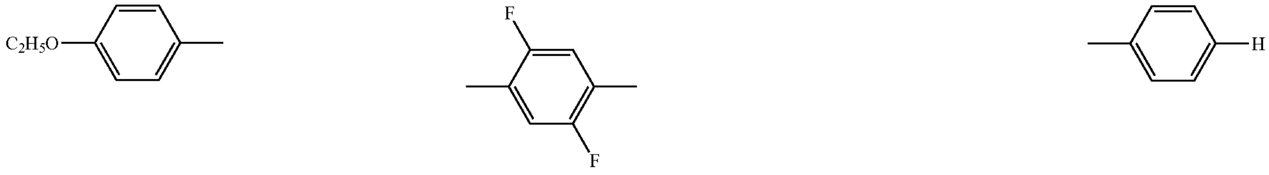
278 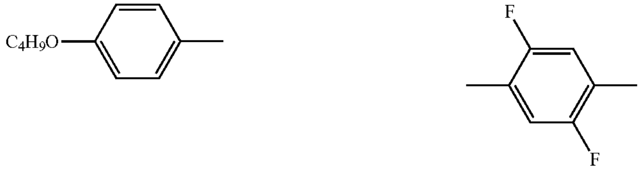 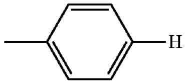
C 117.35 I
279 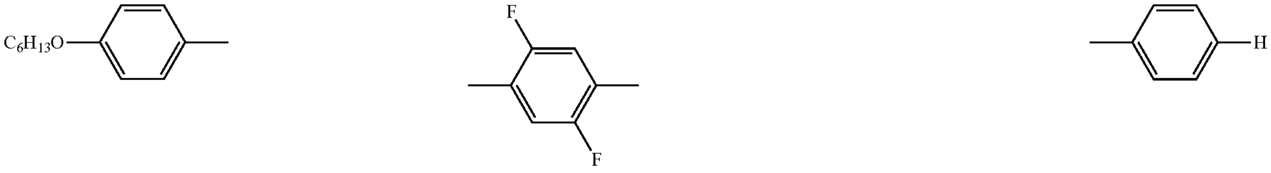
280 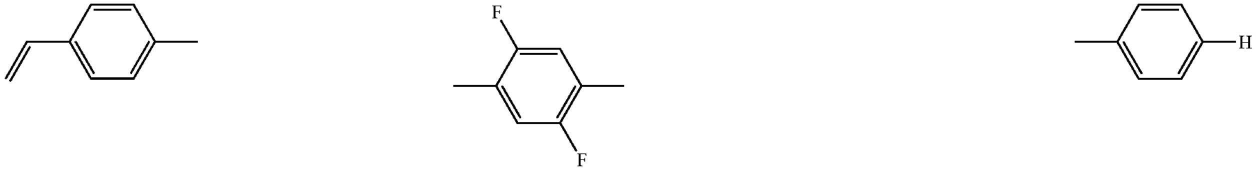
281 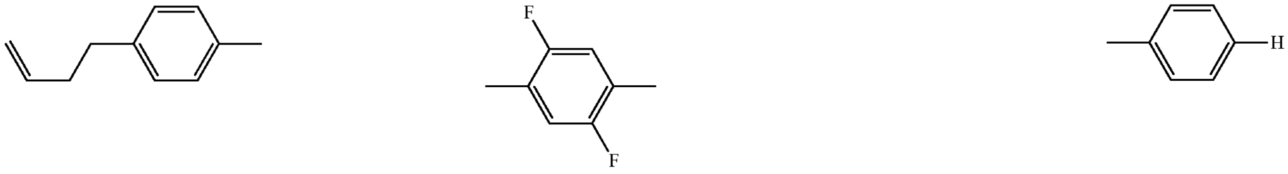

-continued
282 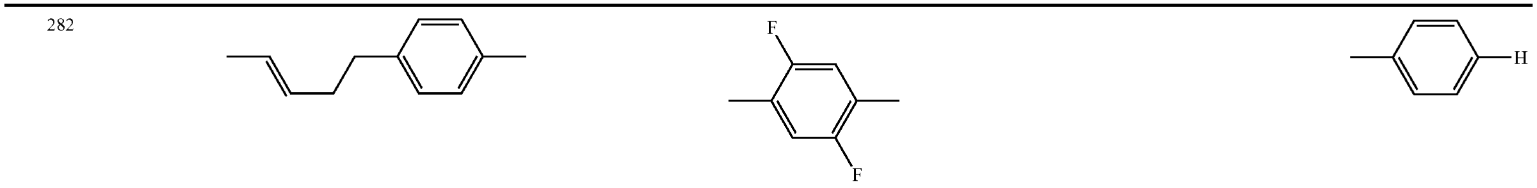
283 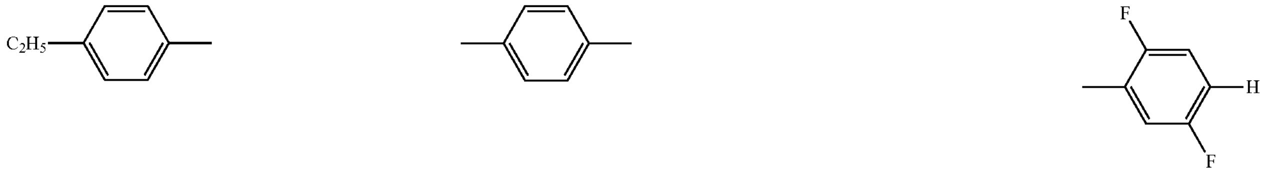
284 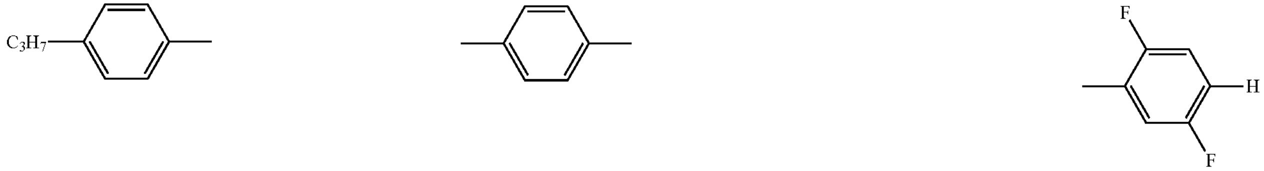
285 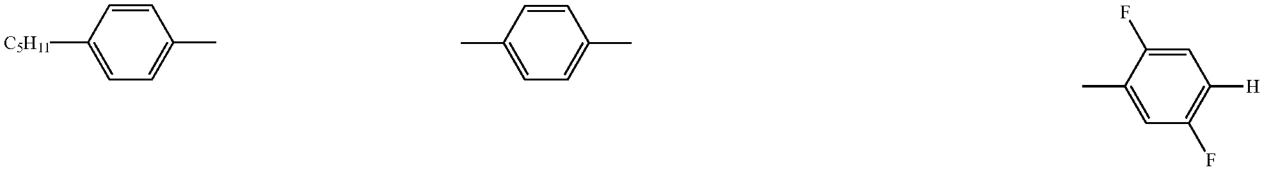
C 84.27 I
286 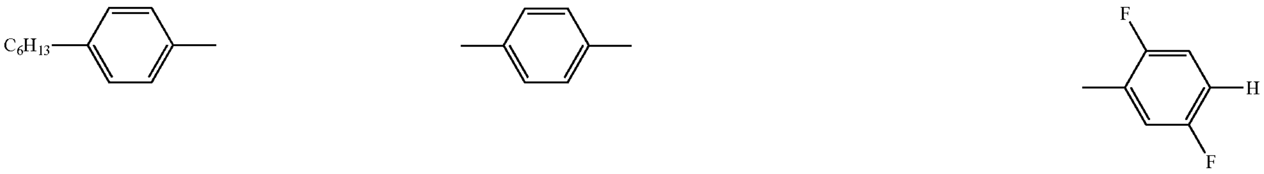

-continued
| | |
|---|---|
| 287 | 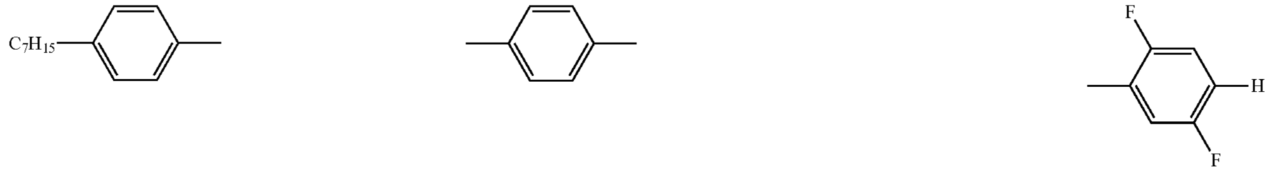 |
| 288 | 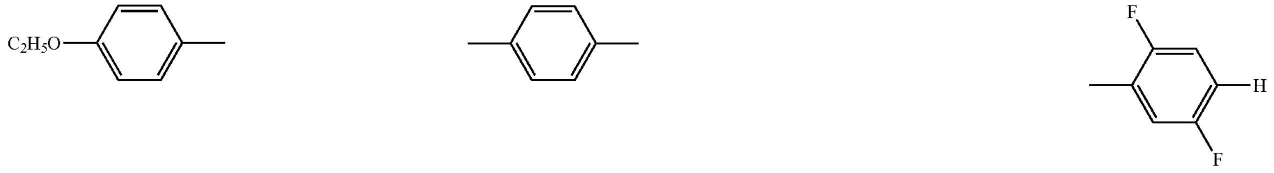 |
| 289 | 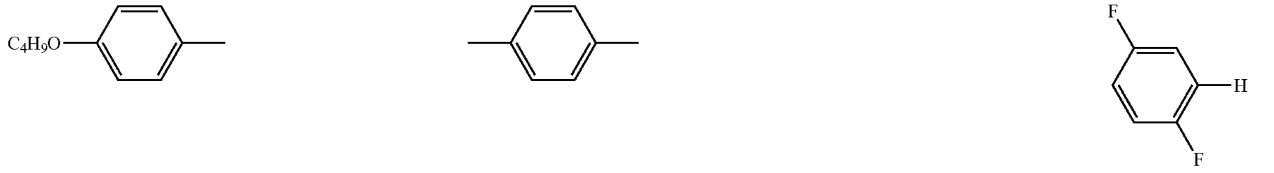 |
| 290 | 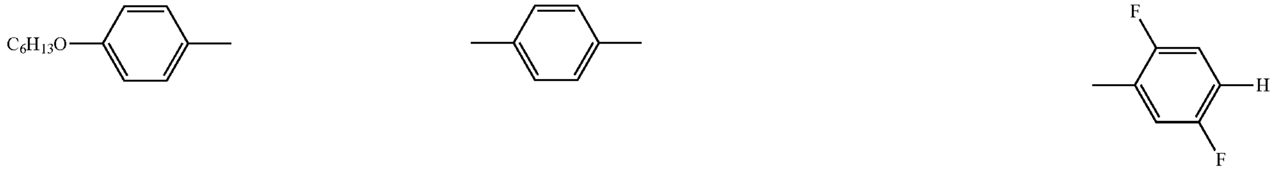 |
| 291 | 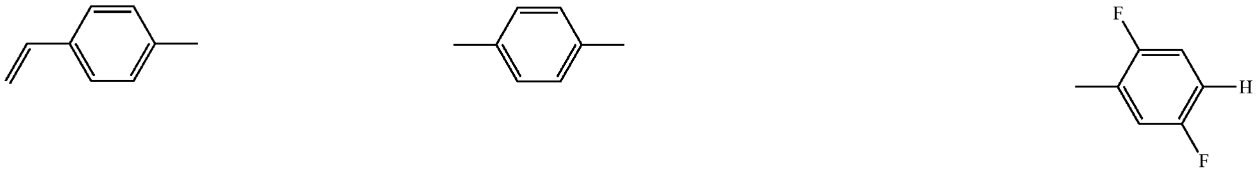 |
| 282 | 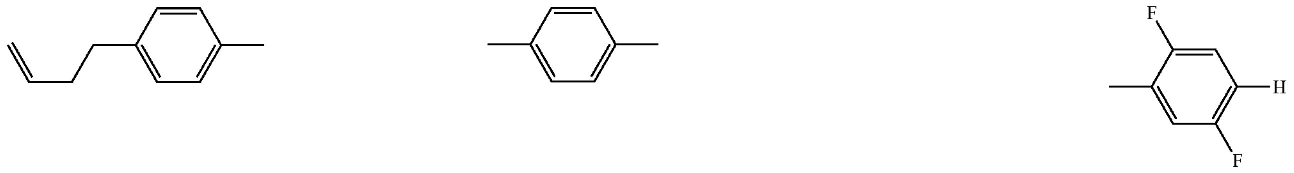 |

-continued
| | |
|---|---|
| 293 | 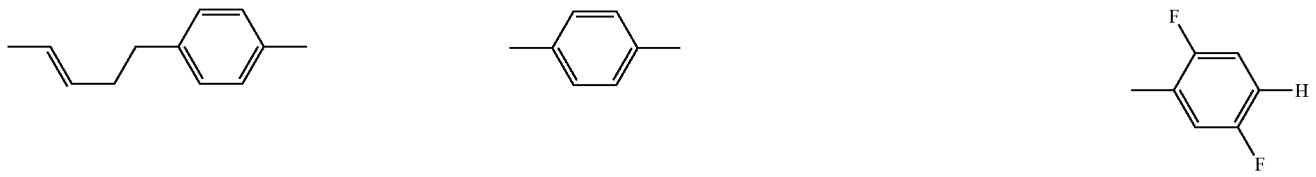 |
| 294 | 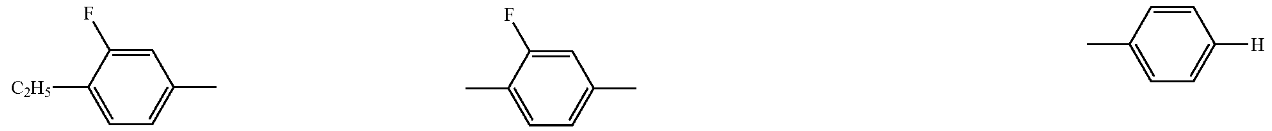 |
| 295 | 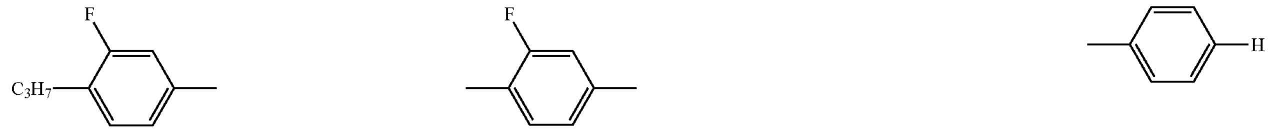 |
| 296 | 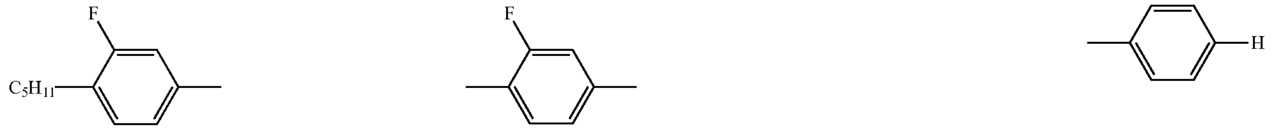 |
| 297 | 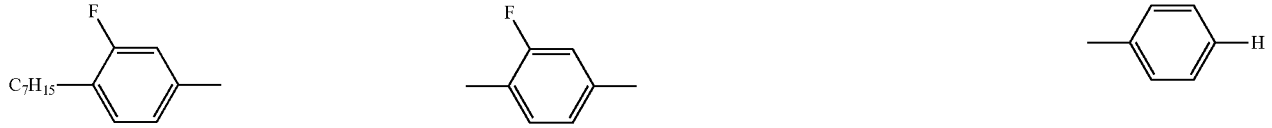 |
| 298 | 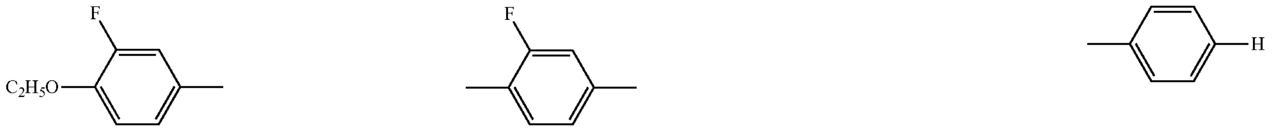 |
| 299 | 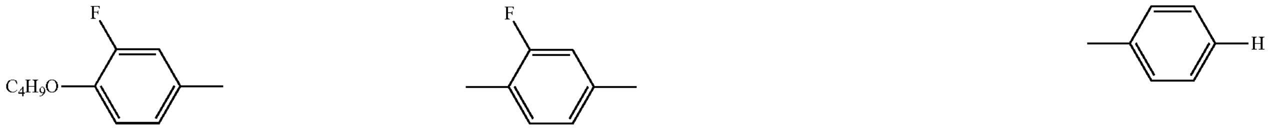 |

-continued
| | |
|---|---|
| 300 | 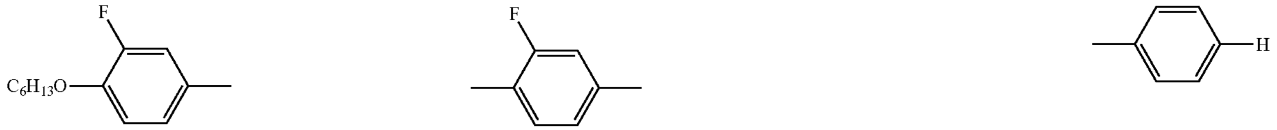 |
| 301 | 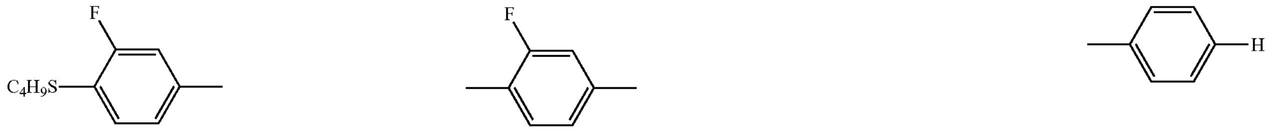 |
| 302 | 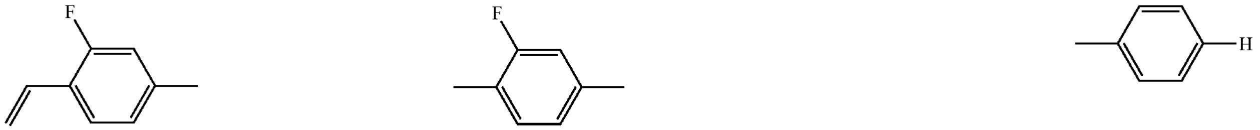 |
| 303 | 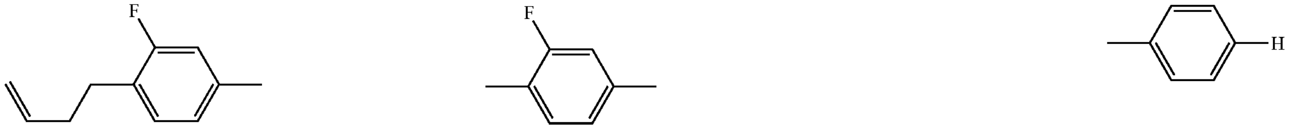 |
| 304 | 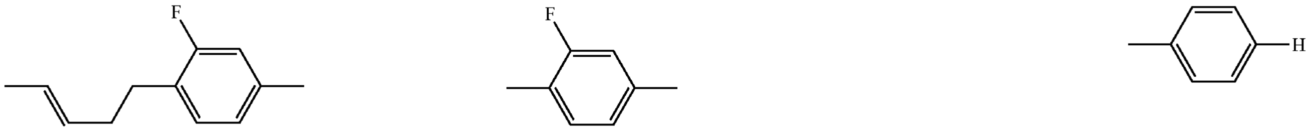 |
| 305 | 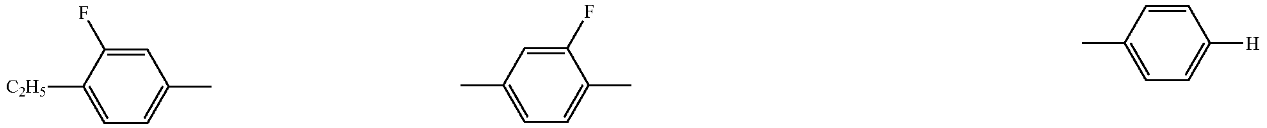 |
| 306 | 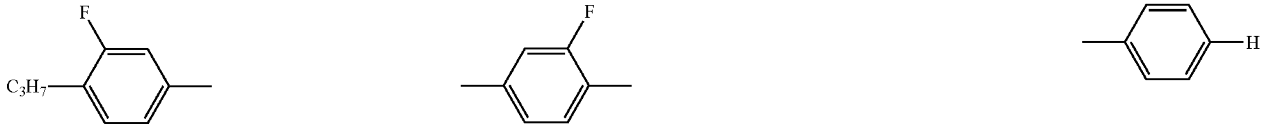 |

-continued
307 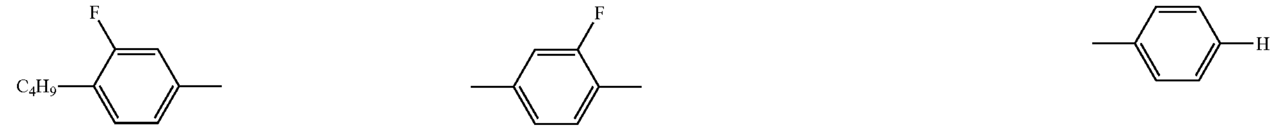
308 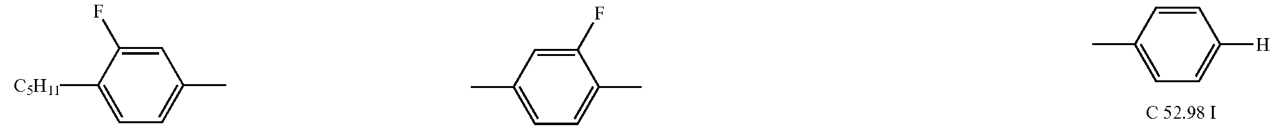
C 52.98 I
309 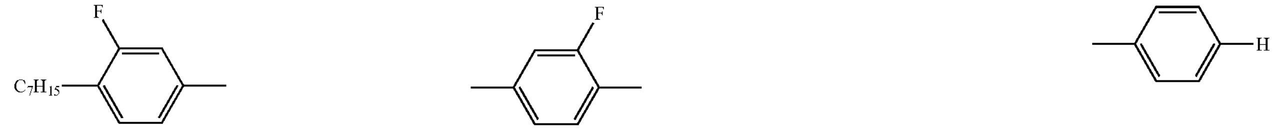
310 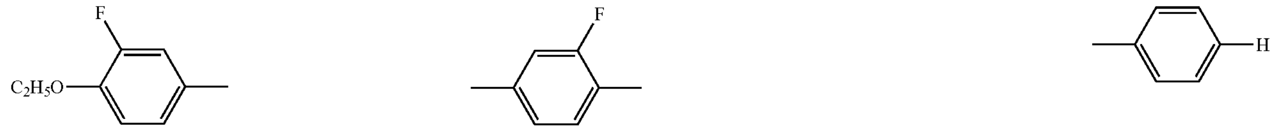
311 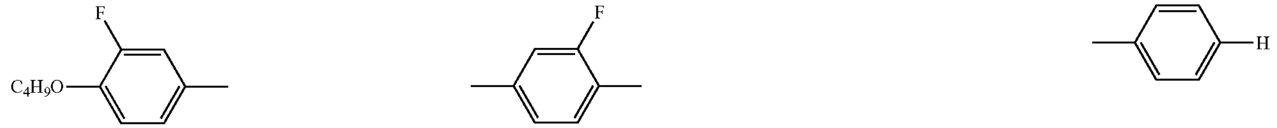
312 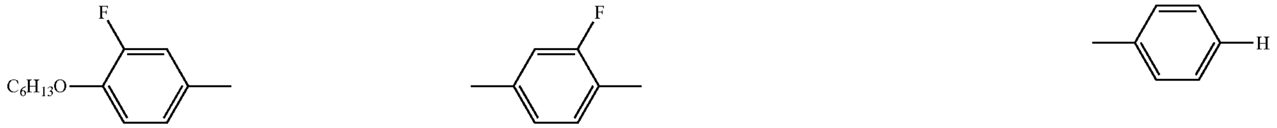
313 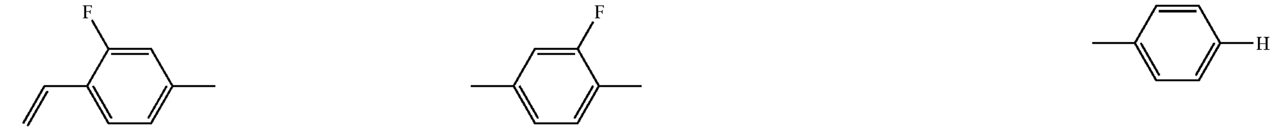

-continued
314 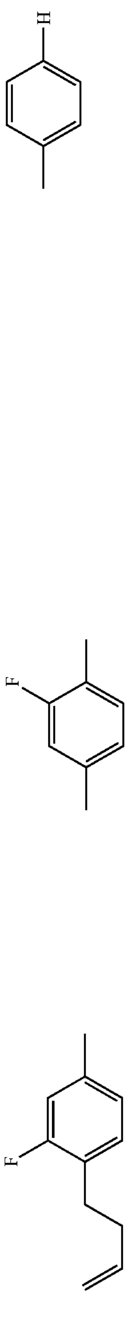
315 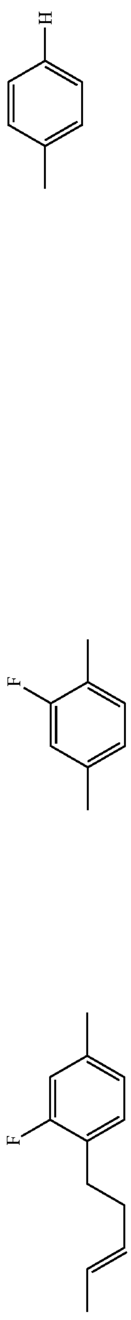
316 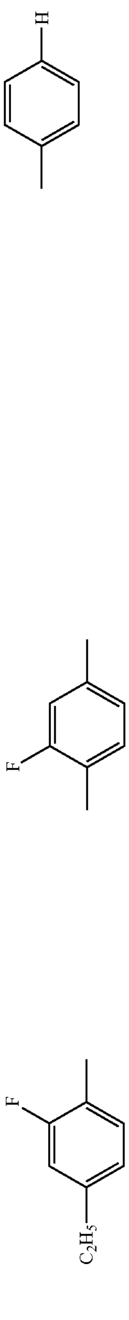
317 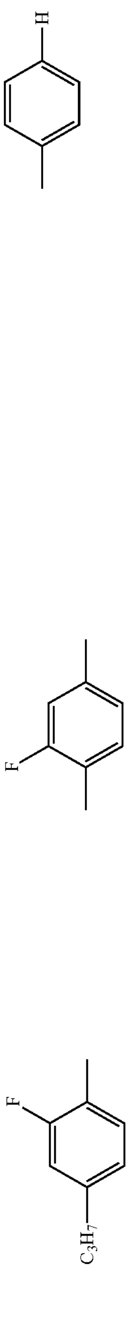
318 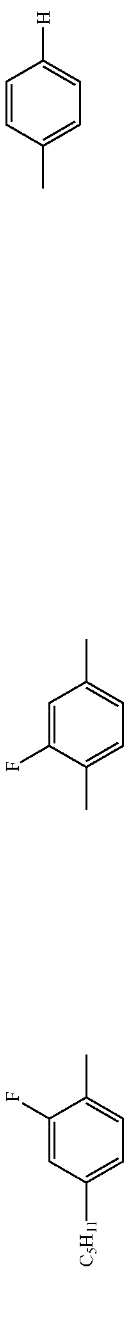
319 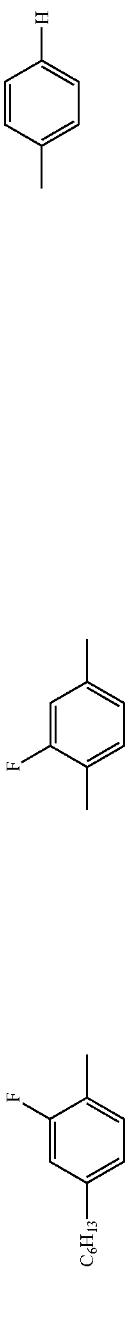
320 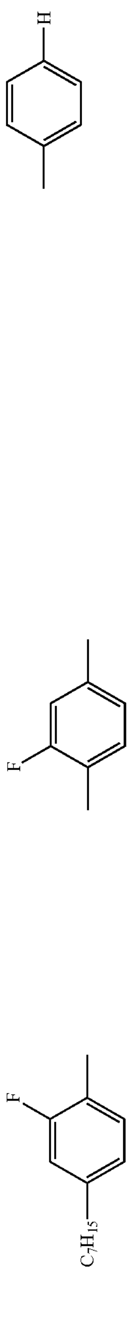

-continued
321 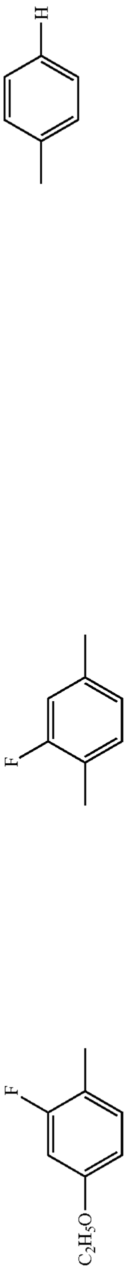
322 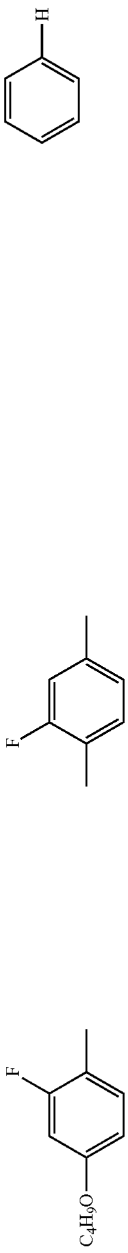
323 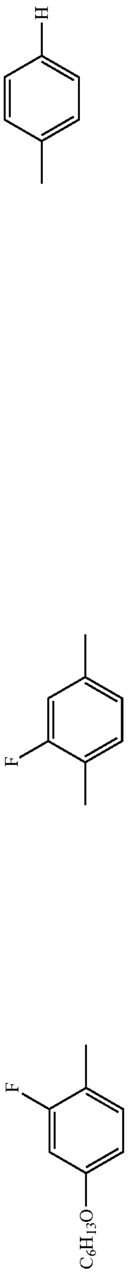
324 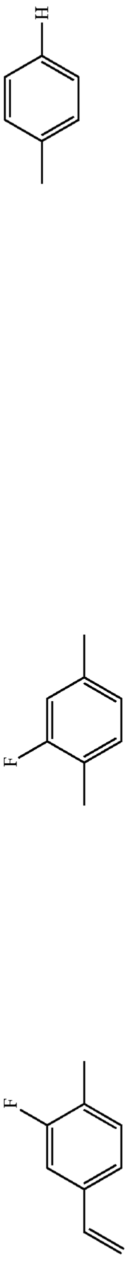
325 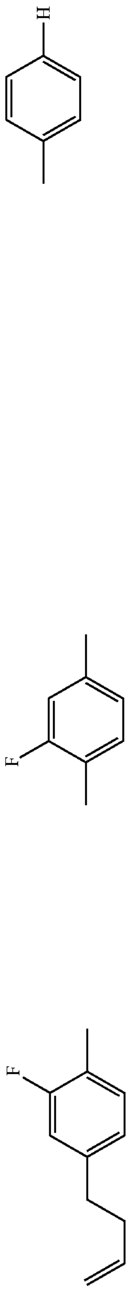
326 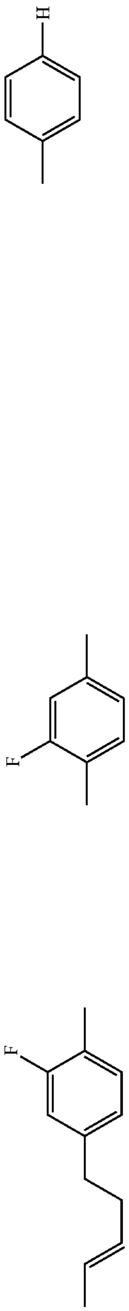
327 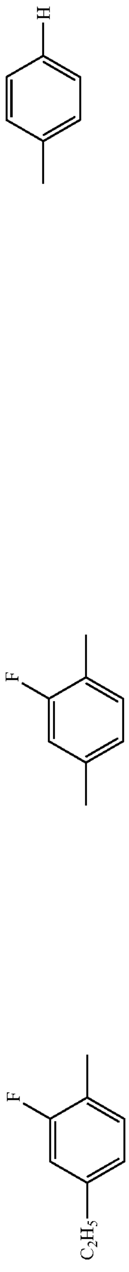

-continued
| | | | |
|---|---|---|---|
| 328 | 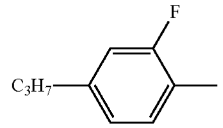 | 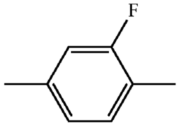 | 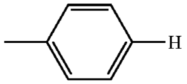 |
| 329 | 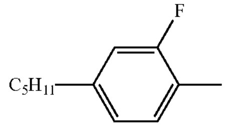 | 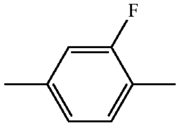 | 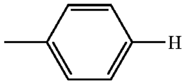 |
| 330 | 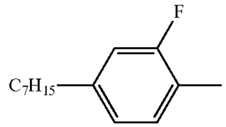 | 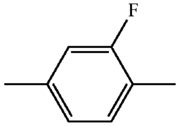 | 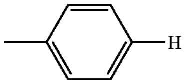 |
| 331 | 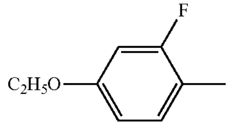 | 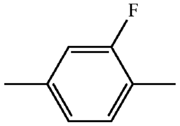 | 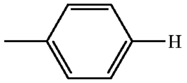 |
| 332 | 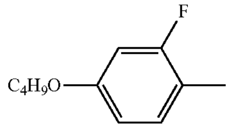 | 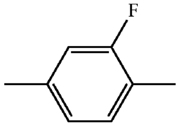 | 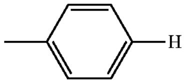 |
| 333 | 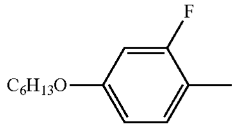 | 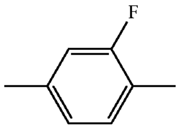 | 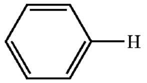 |
| 334 | 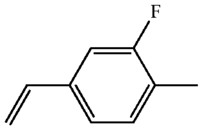 | 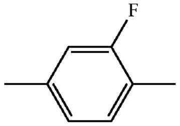 | 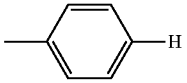 |

-continued
| | |
|---|---|
| 335 | 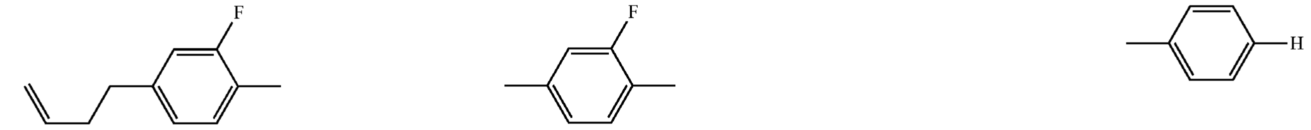 |
| 336 | 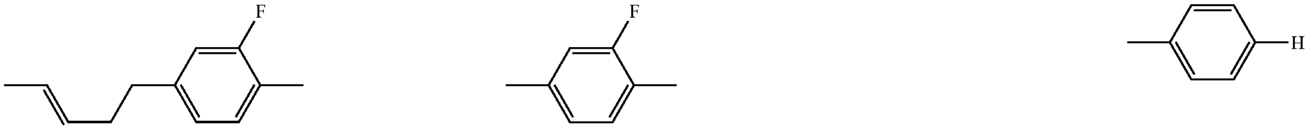 |
| 337 | 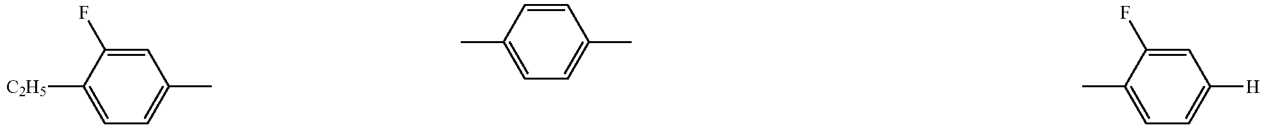 |
| 338 | 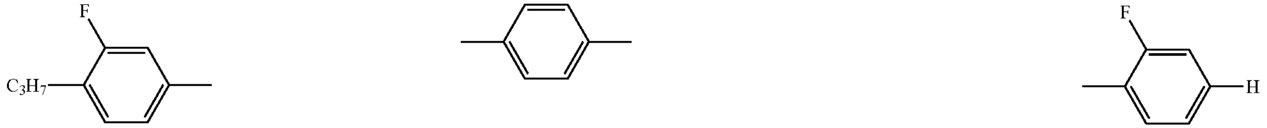 |
| 339 | 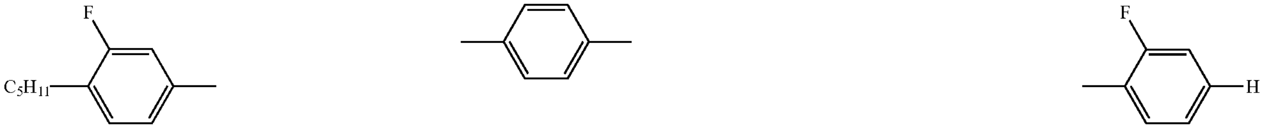 |
| 340 | 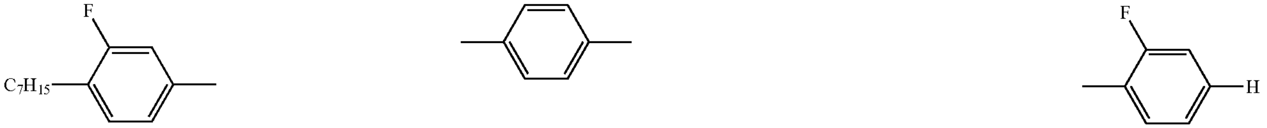 |
| 341 | 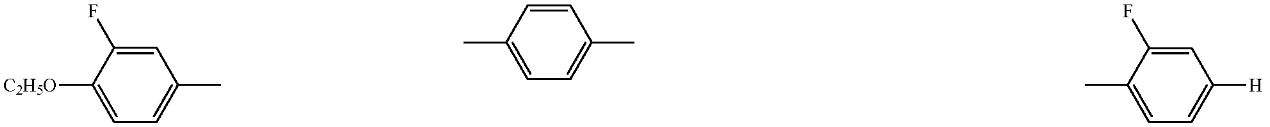 |

-continued
| | |
|---|---|
| 342 | 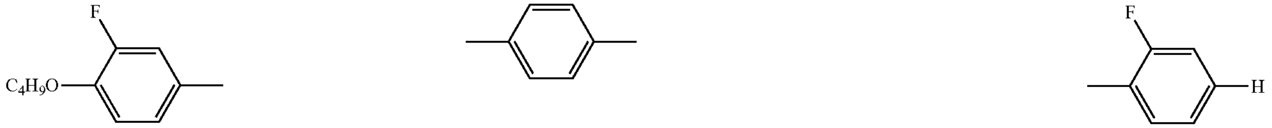 |
| 343 | 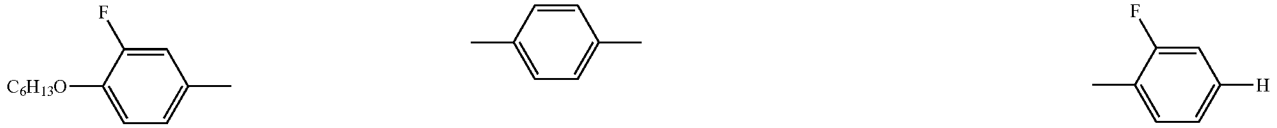 |
| 344 | 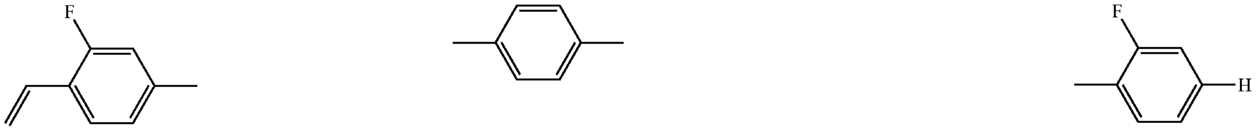 |
| 345 | 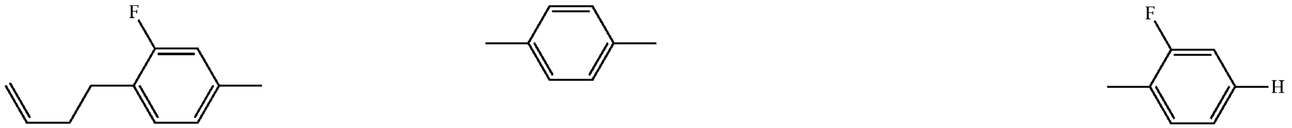 |
| 346 | 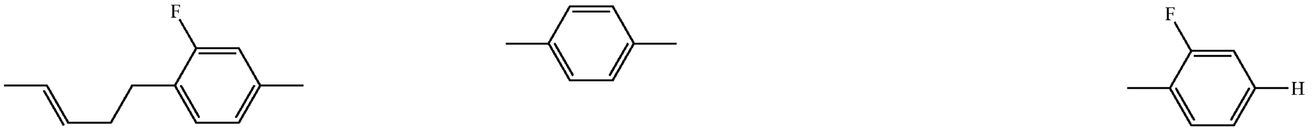 |
| 347 | 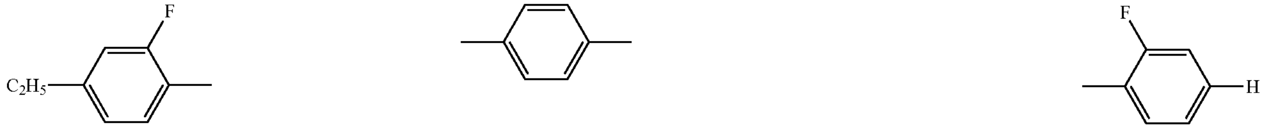 |
| 348 | 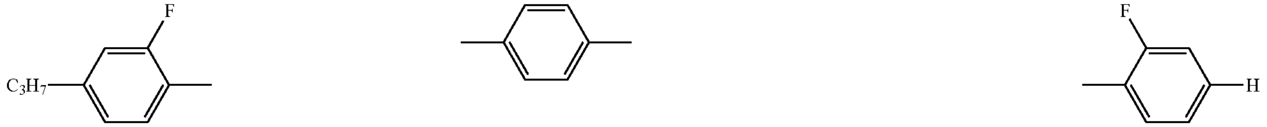 |

-continued
| | |
|---|---|
| 349 | 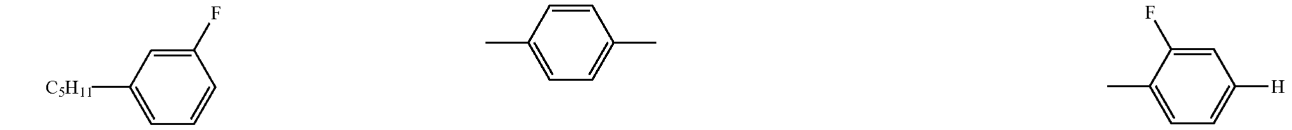 |
| 350 | 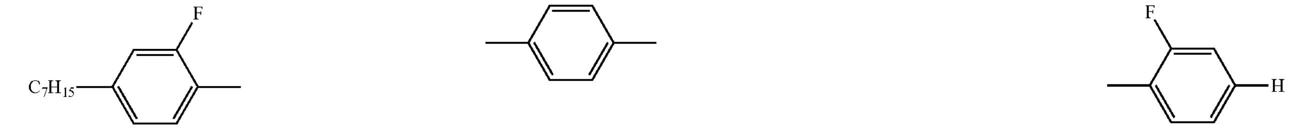 |
| 351 | 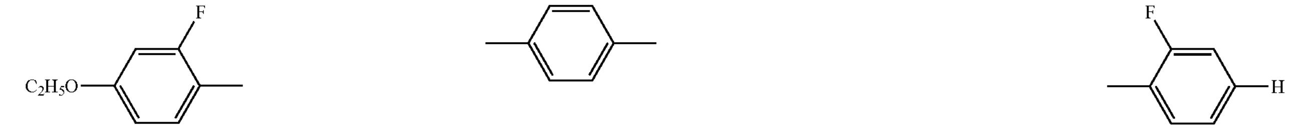 |
| 352 | 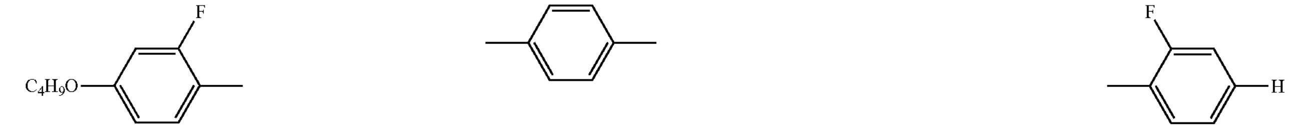 |
| 353 | 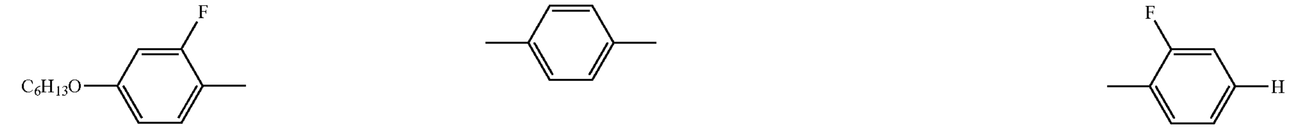 |
| 354 | 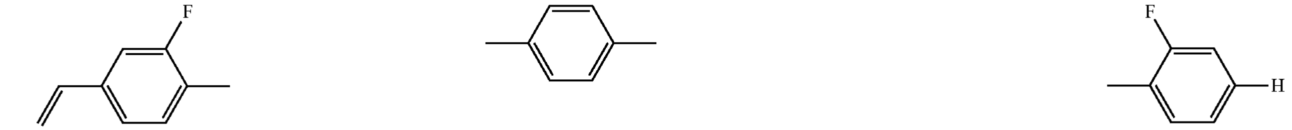 |
| 355 | 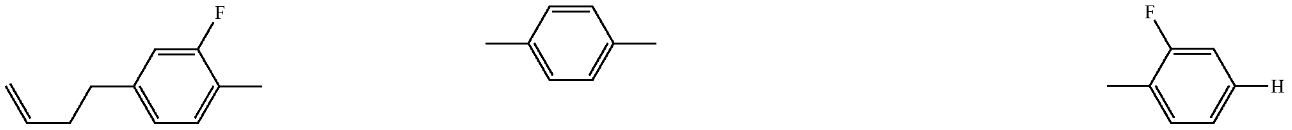 |

-continued
| | | | |
|---|---|---|---|
| 356 | 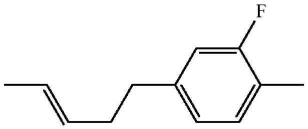 | 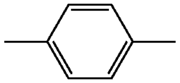 | 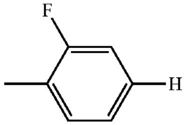 |
| 357 | 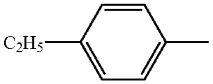 | 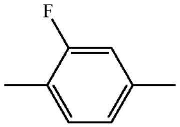 | 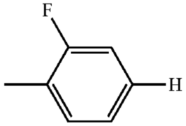 |
| 358 | 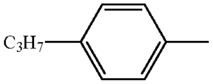 | 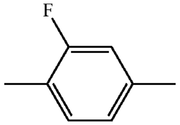 | 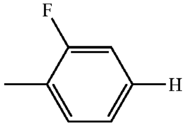 |
| 359 | 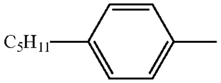 | 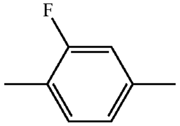 | 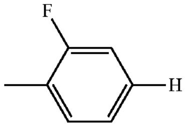 C 60.10 I |
| 360 | 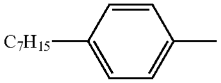 | 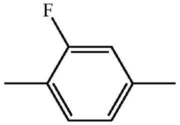 | 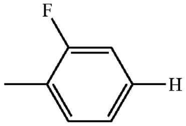 |
| 361 | 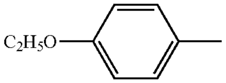 | 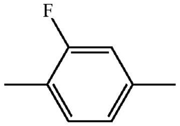 | 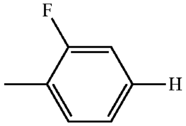 |
| 362 | 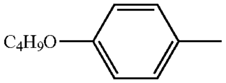 | 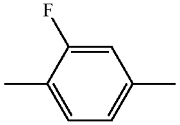 | 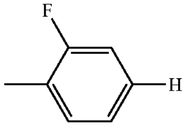 |

-continued
| | | | |
|---|---|---|---|
| 363 | 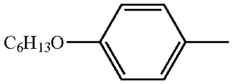 | 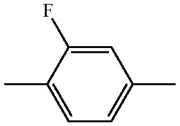 | 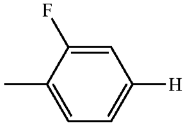 |
| 364 | 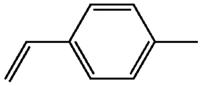 | 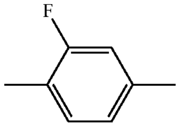 | 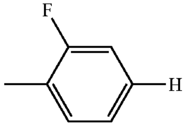 |
| 365 | 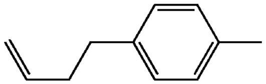 | 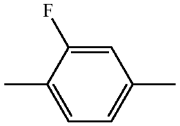 | 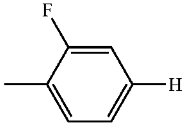 |
| 366 | 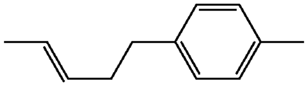 | 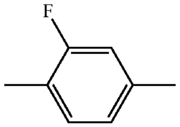 | 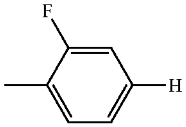 |
| 367 | 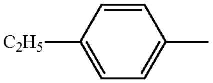 | 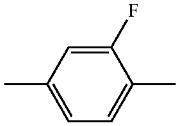 | 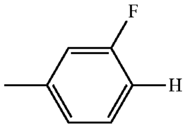 |
| 368 | 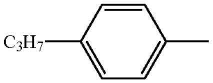 | 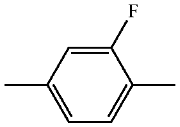 | 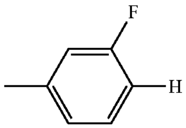 |
| 369 | 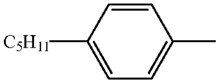 | 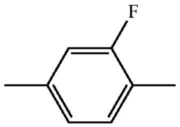 | 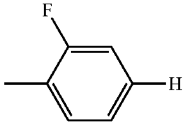 |

-continued
| | | | |
|---|---|---|---|
| 370 | 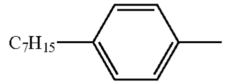 | 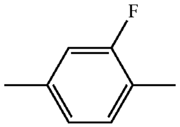 | 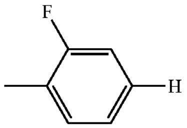 |
| 371 | 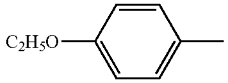 | 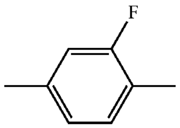 | 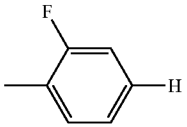 |
| 372 | 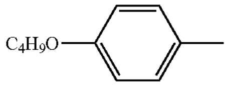 | 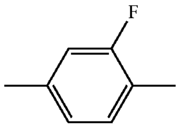 | 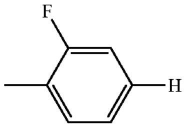 |
| 373 | 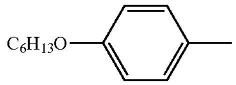 | 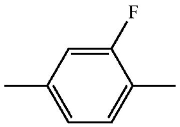 | 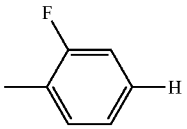 |
| 374 | 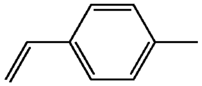 | 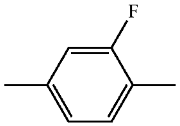 | 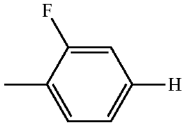 |
| 375 | 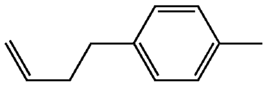 | 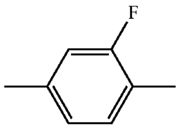 | 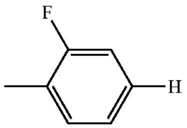 |
| 376 | 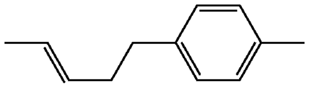 | 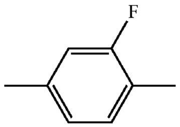 | 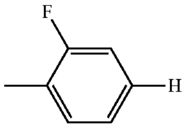 |

-continued
| | |
|---|---|
| 377 | 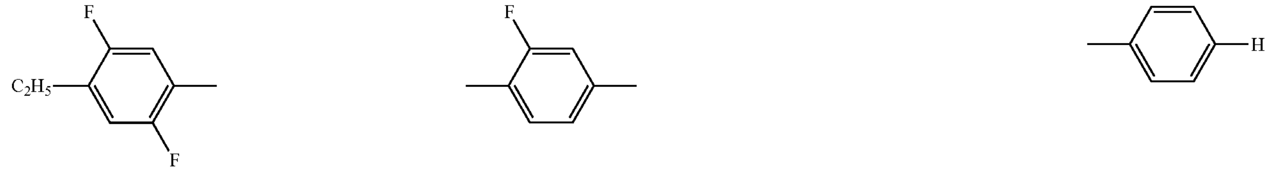 |
| 378 | 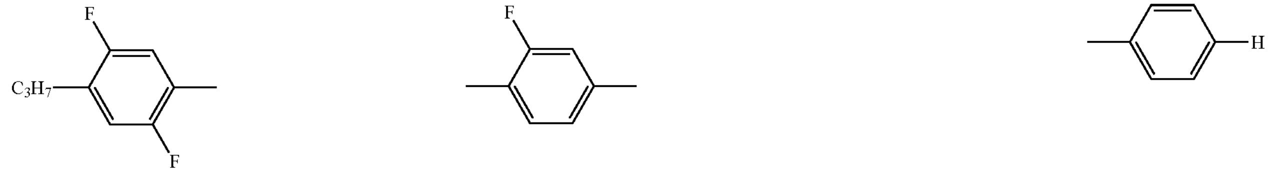 |
| 379 | 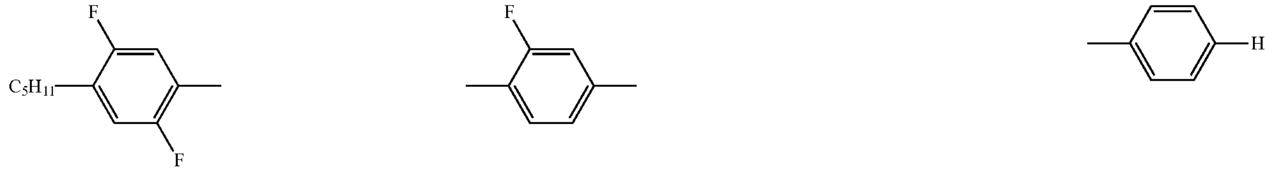 |
| 380 | 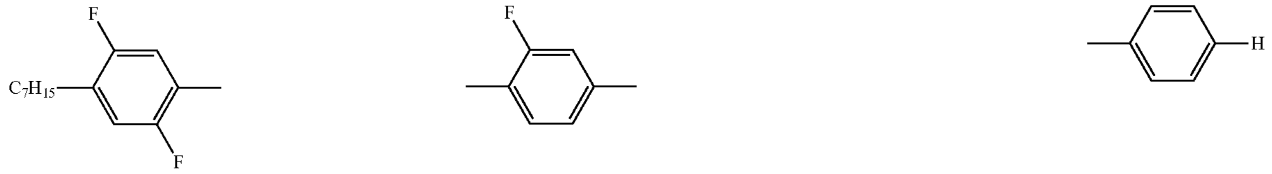 |
| 381 | 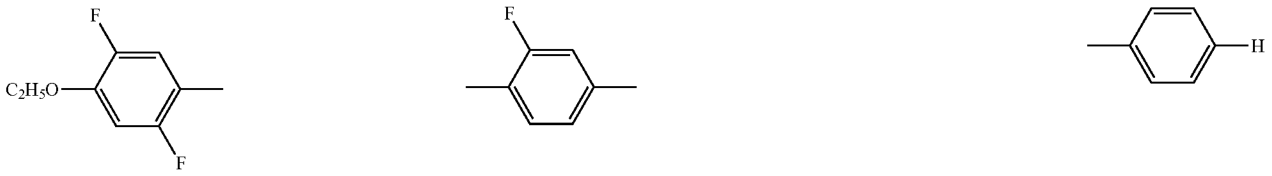 |

-continued
| | |
|---|---|
| 382 | 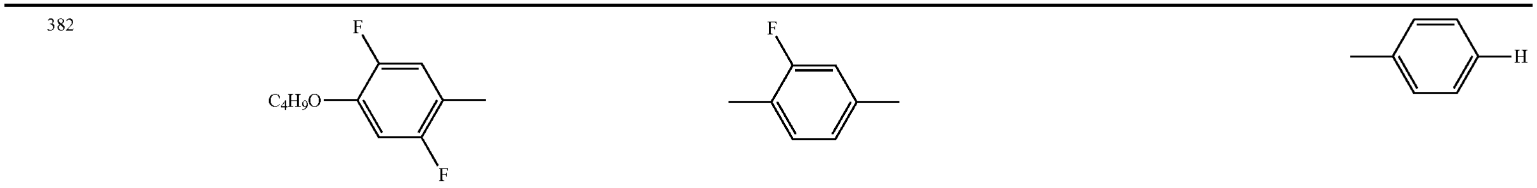 |
| 383 | 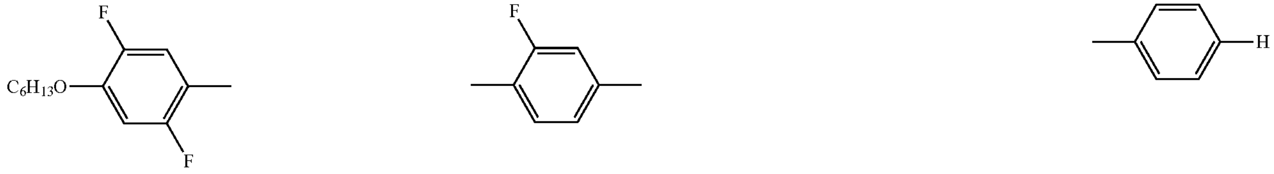 |
| 384 | 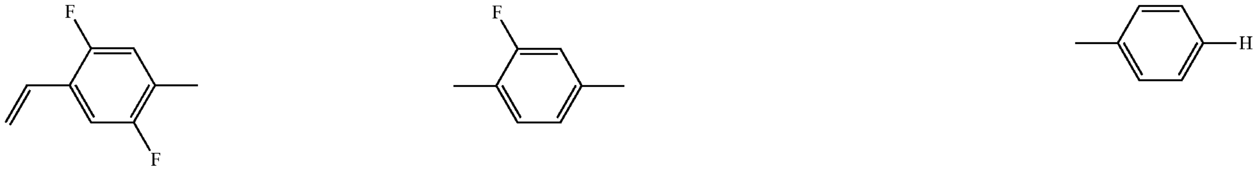 |
| 385 | 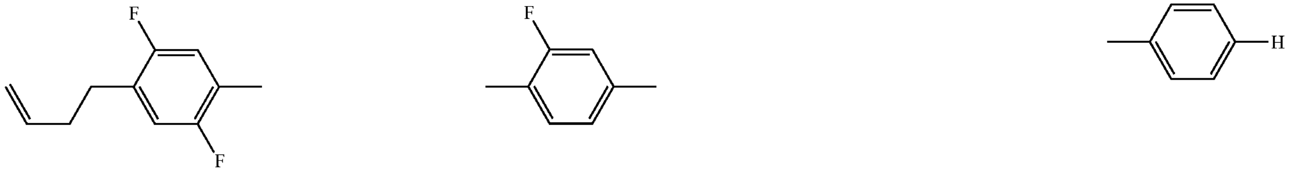 |
| 386 | 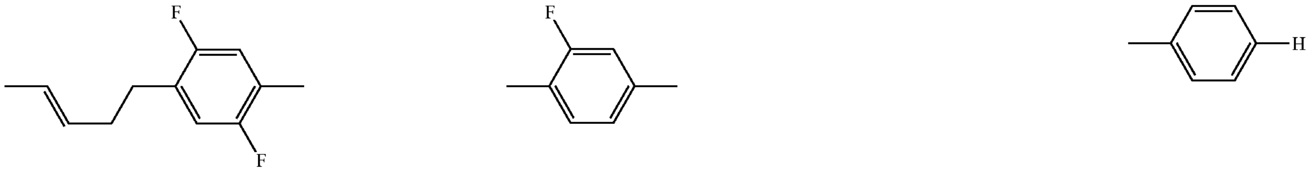 |

-continued
| | | | |
|---|---|---|---|
| 387 | 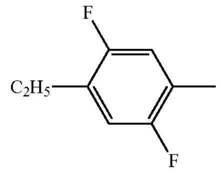 | 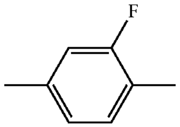 | 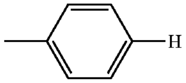 |
| 388 | 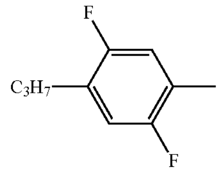 | 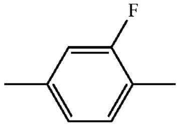 | 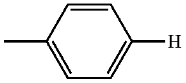 |
| 389 | 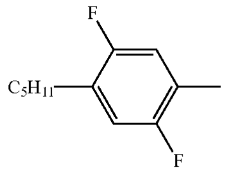 | 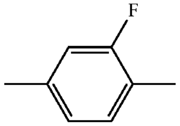 | 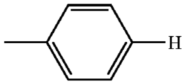 |
| 390 | 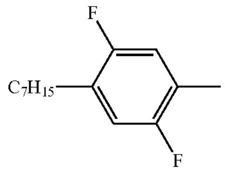 | 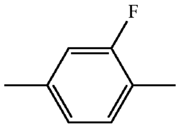 | 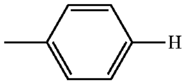 |
| 391 | 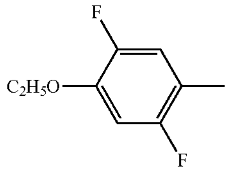 | 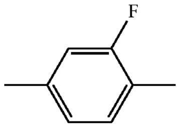 | 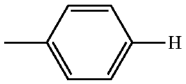 |

-continued
| | | | |
|---|---|---|---|
| 392 | 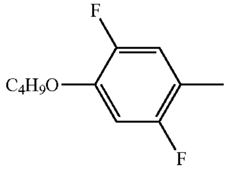 | 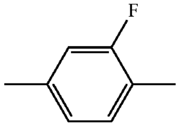 | 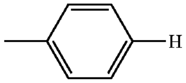 |
| 393 | 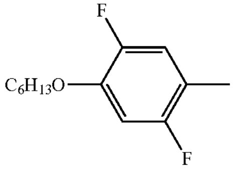 | 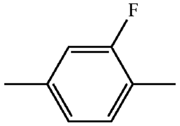 | 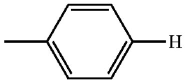 |
| 394 | 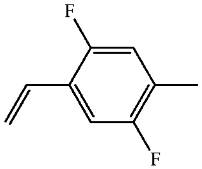 | 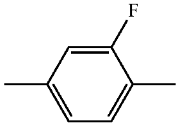 | 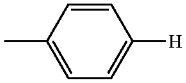 |
| 395 | 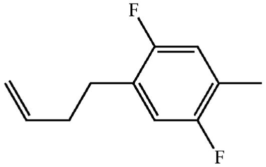 | 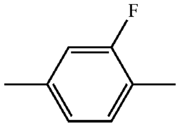 | 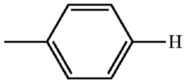 |
| 396 | 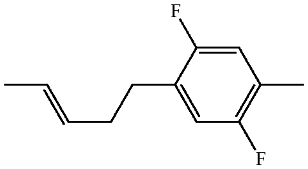 | 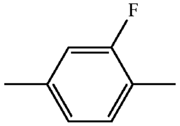 | 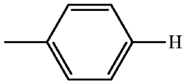 |

-continued
| | |
|---|---|
| 397 | 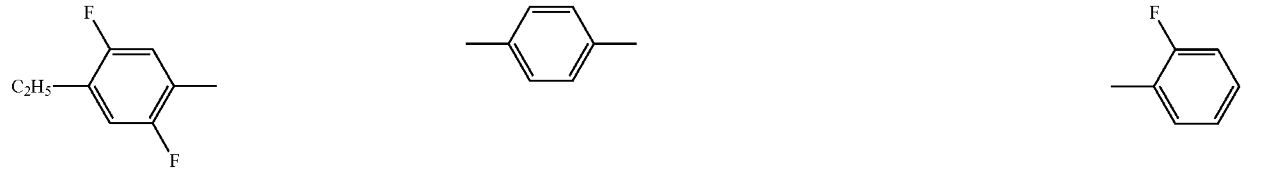 |
| 398 | 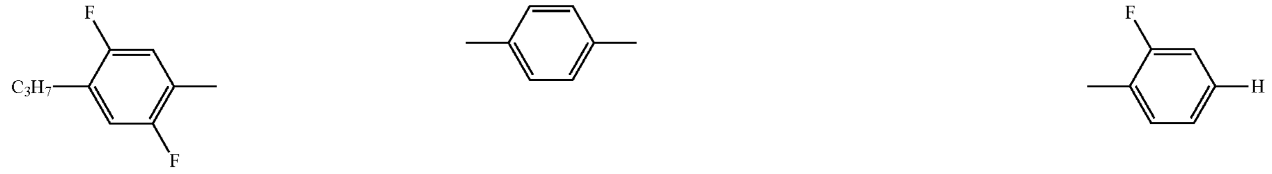 |
| 399 | 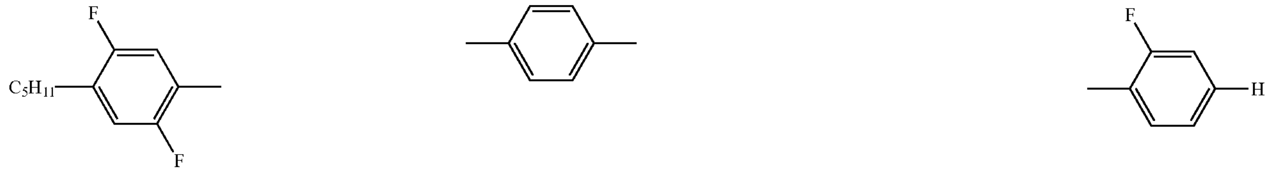 |
| 400 | 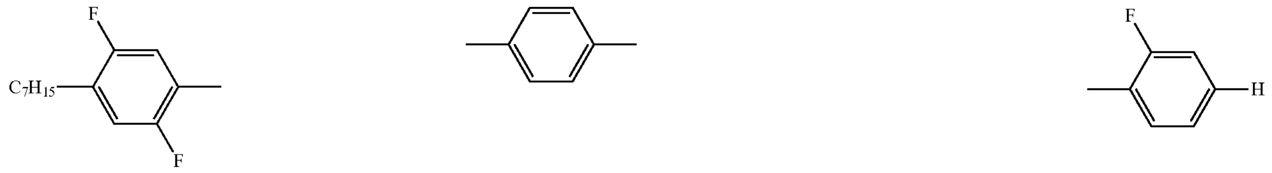 |
| 401 | 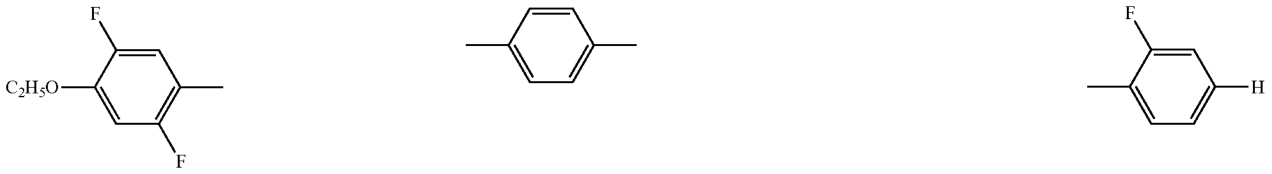 |

-continued
| | |
|---|---|
| 402 | 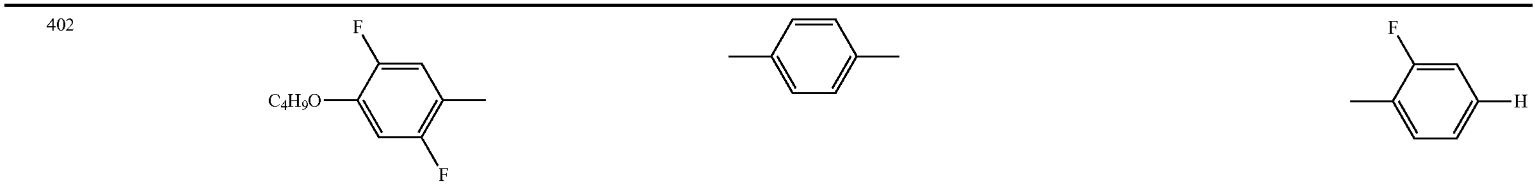 |
| 403 | 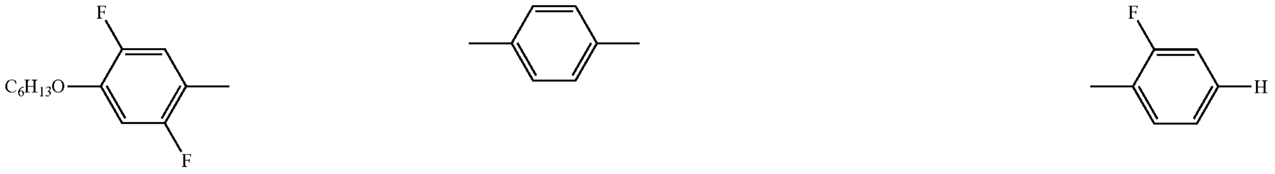 |
| 404 | 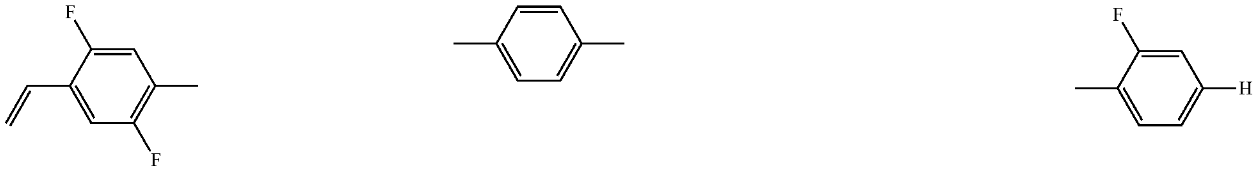 |
| 405 | 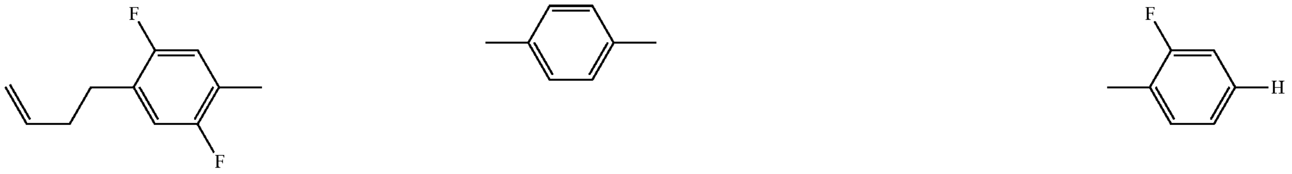 |
| 406 | 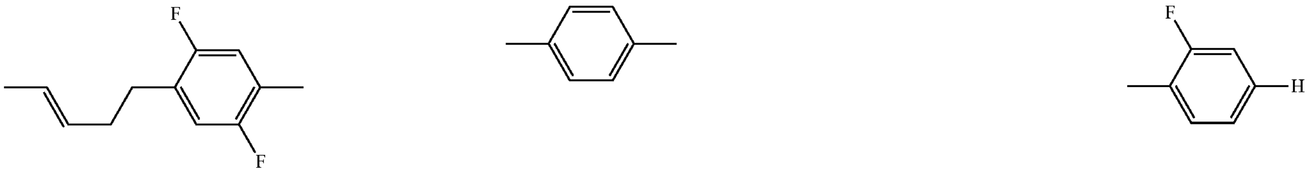 |

-continued
| | |
|---|---|
| 407 | 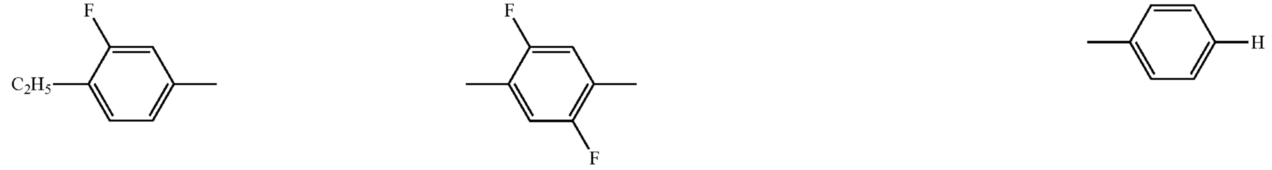 |
| 408 | 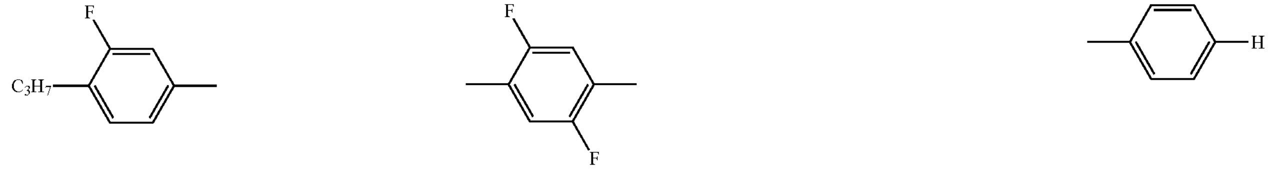 |
| 409 | 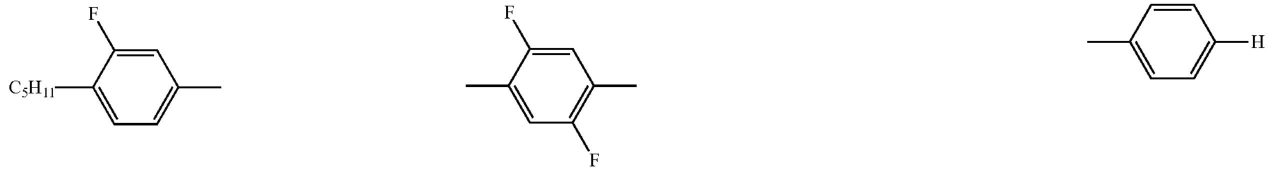 |
| 410 | 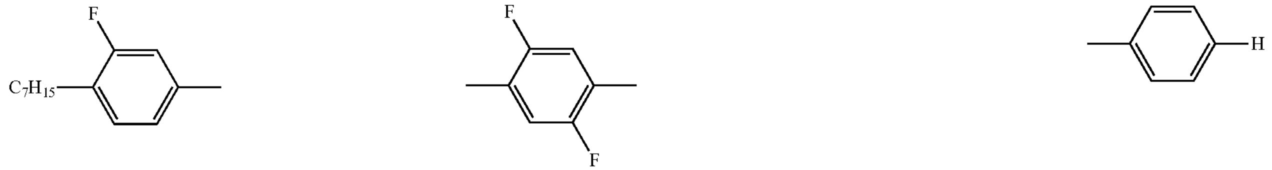 |
| 411 | 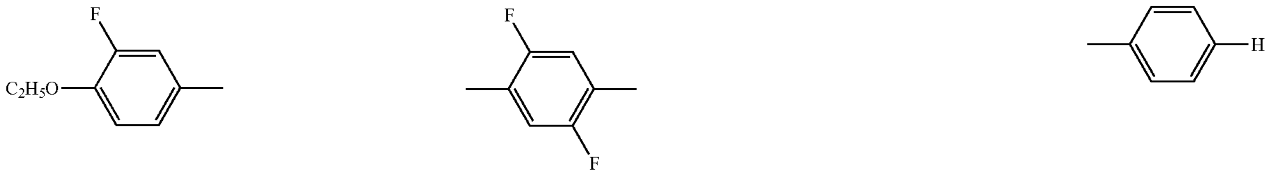 |

-continued
| | | | |
|---|---|---|---|
| 412 | 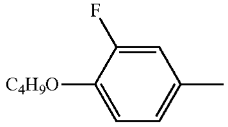 | 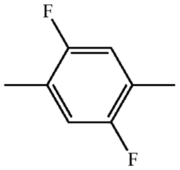 | 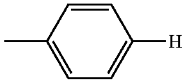 |
| 413 | 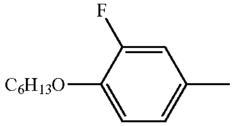 | 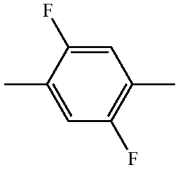 | 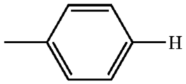 |
| 414 | 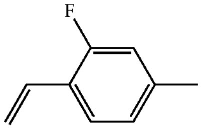 | 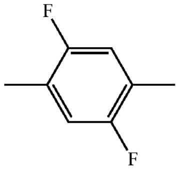 | 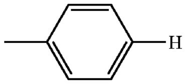 |
| 415 | 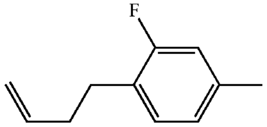 | 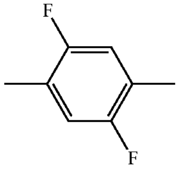 | 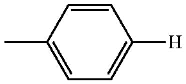 |
| 416 | 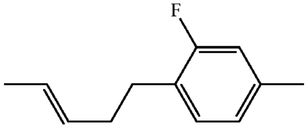 | 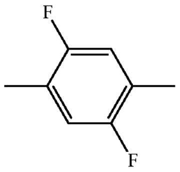 | 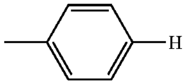 |

-continued
| | | | |
|---|---|---|---|
| 417 | 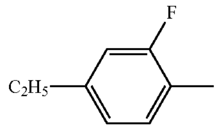 | 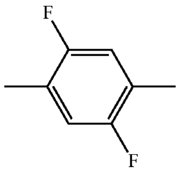 | 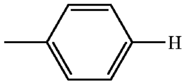 |
| 418 | 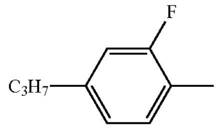 | 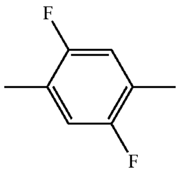 | 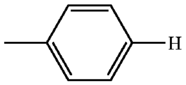 |
| 419 | 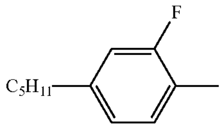 | 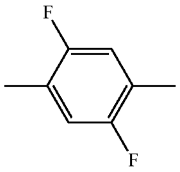 | 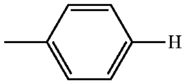 |
| 420 | 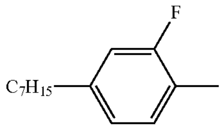 | 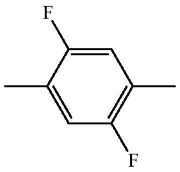 | 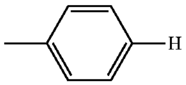 |
| 421 | 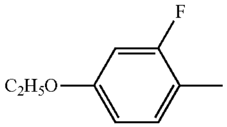 | 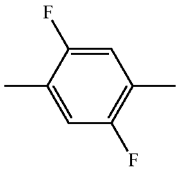 | 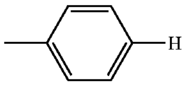 |

-continued
| | |
|---|---|
| 422 | 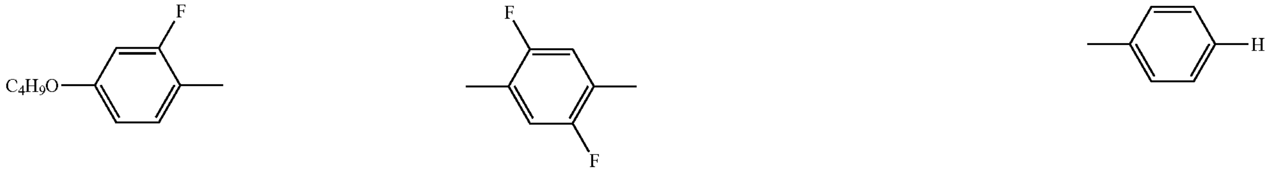 |
| 423 | 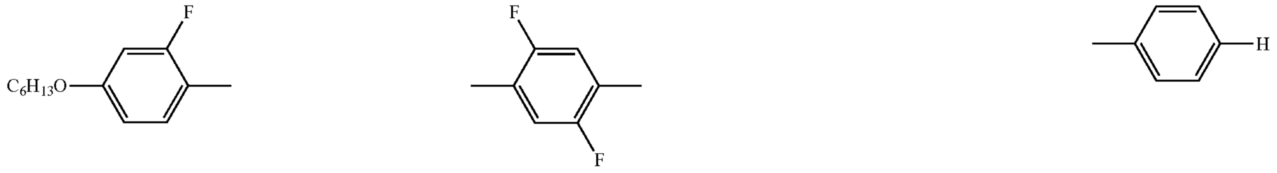 |
| 424 | 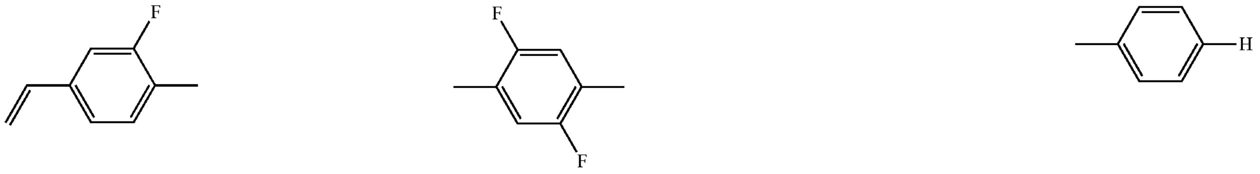 |
| 425 | 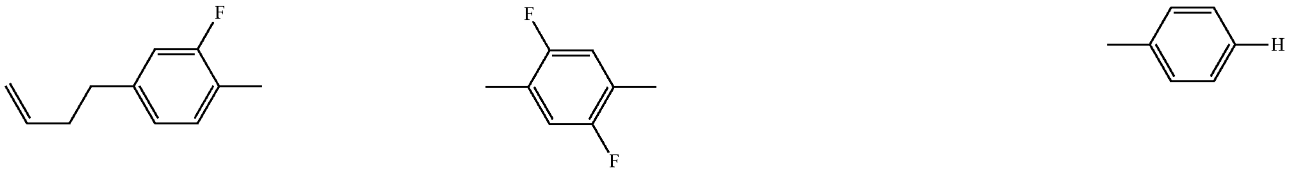 |
| 426 | 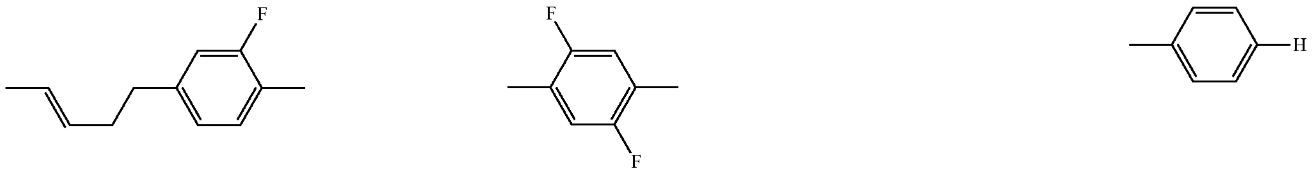 |

-continued
| | | |
|---|---|---|
| 427 | 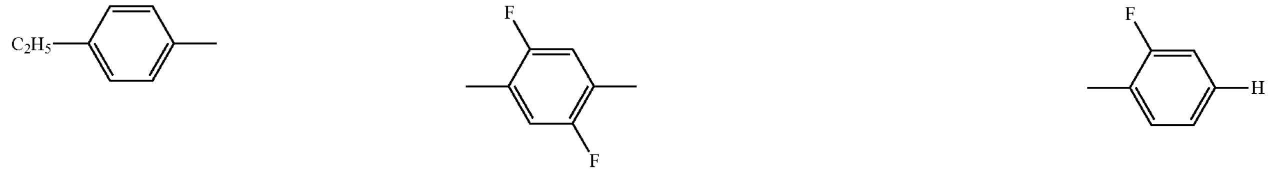 | |
| 428 | 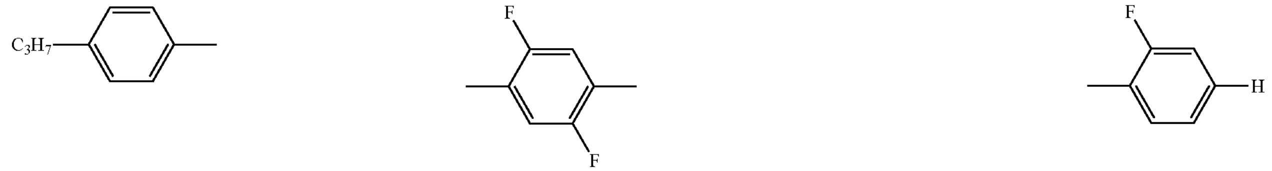 | |
| 429 | 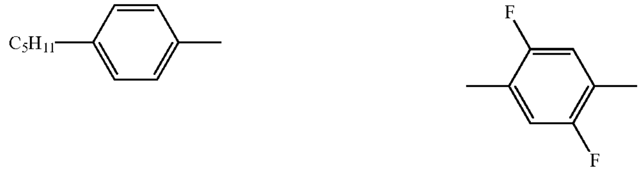 | 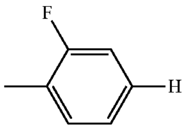 C 106.93 I |
| 430 | 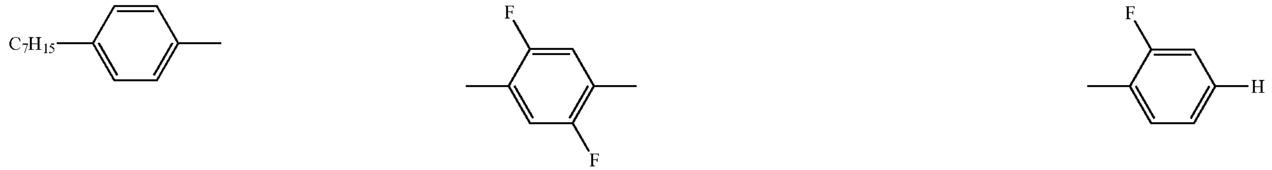 | |
| 431 | 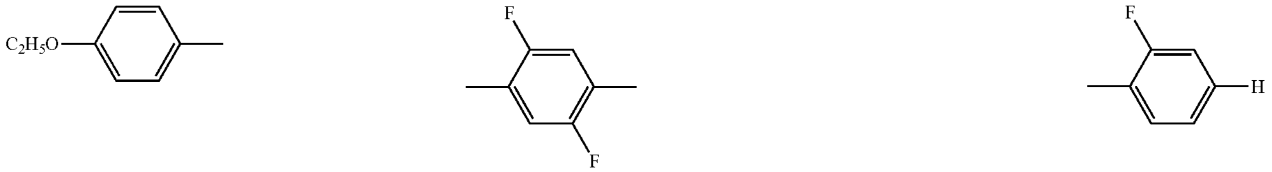 | |

-continued
432 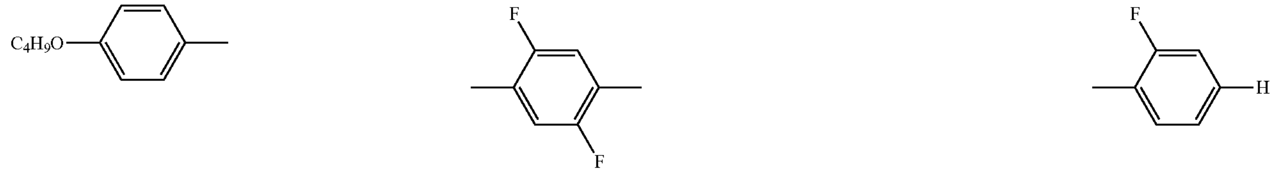
433 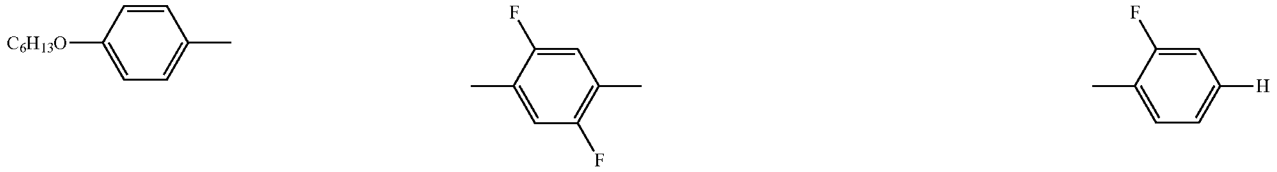
434 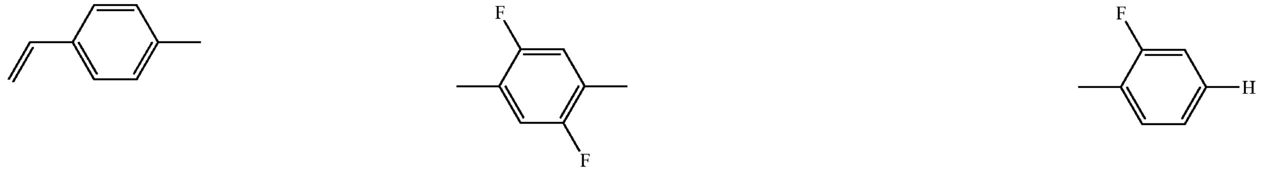
435 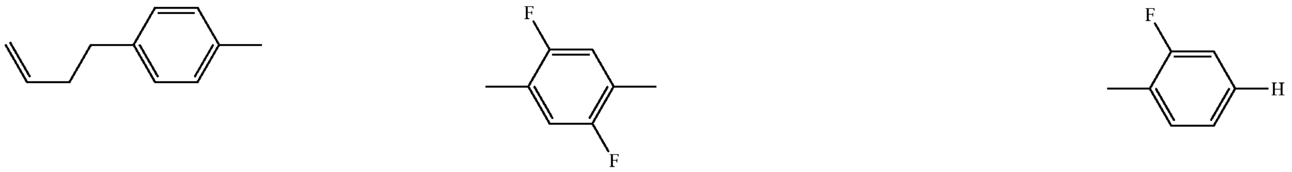
436 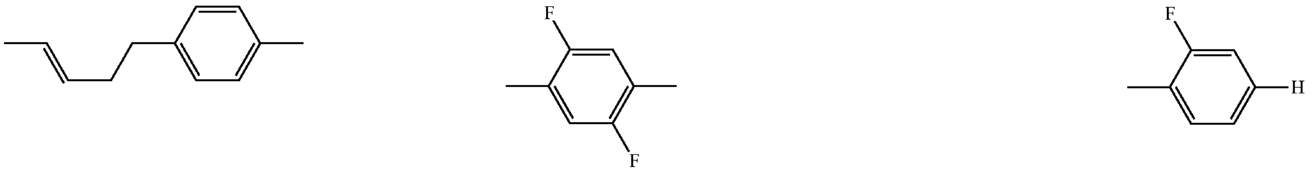

-continued
| | | | |
|---|---|---|---|
| 437 | 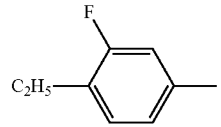 | 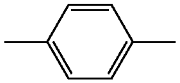 | 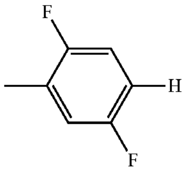 |
| 438 | 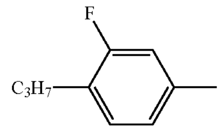 | 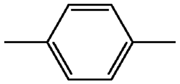 | 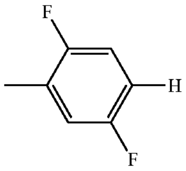 |
| 439 | 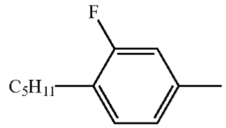 | 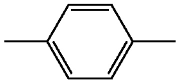 | 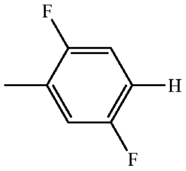 |
| 440 | 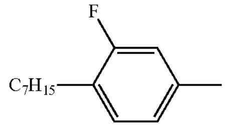 | 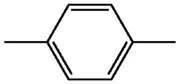 | 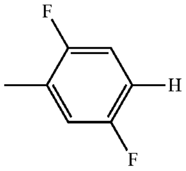 |
| 441 | 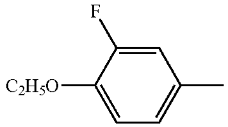 | 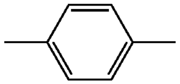 | 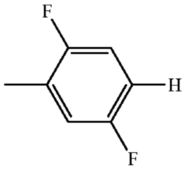 |
| 442 | 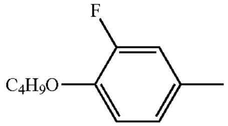 | 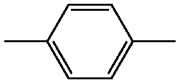 | 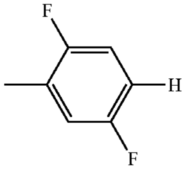 |

-continued
| | | | |
|---|---|---|---|
| 443 | 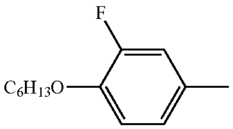 | 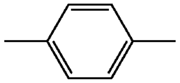 | 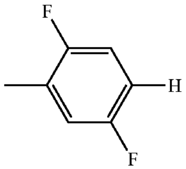 |
| 444 | 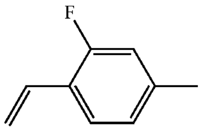 | 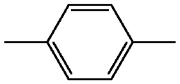 | 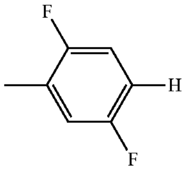 |
| 445 | 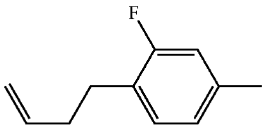 | 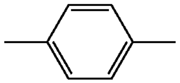 | 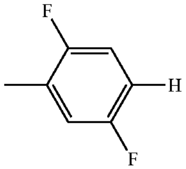 |
| 446 | 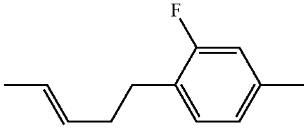 | 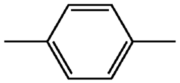 | 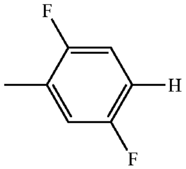 |
| 447 | 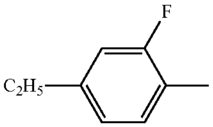 | 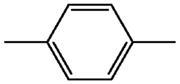 | 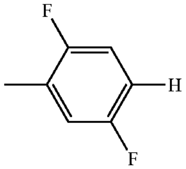 |

-continued
| | | | |
|---|---|---|---|
| 448 | 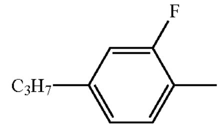 | 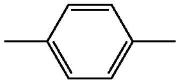 | 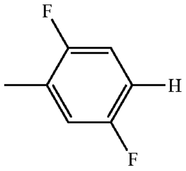 |
| 449 | 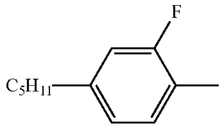 | 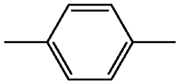 | 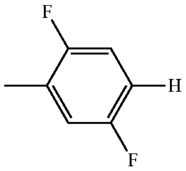 |
| 450 | 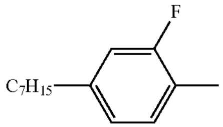 | 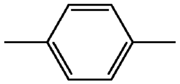 | 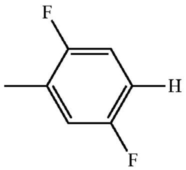 |
| 451 | 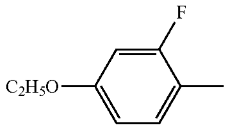 | 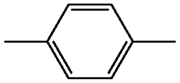 | 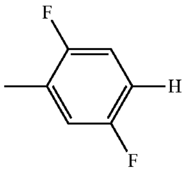 |
| 452 | 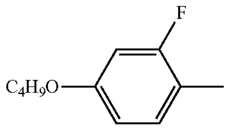 | 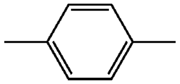 | 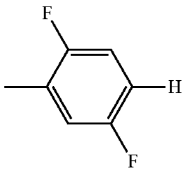 |

-continued
| | | | |
|---|---|---|---|
| 453 | 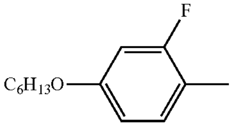 | 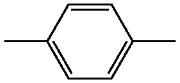 | 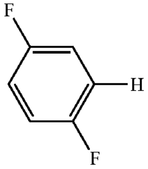 |
| 454 | 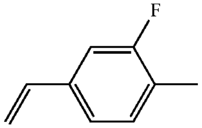 | 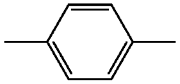 | 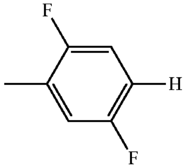 |
| 455 | 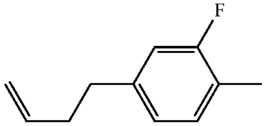 | 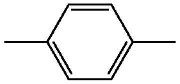 | 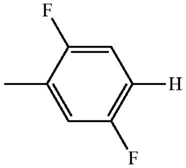 |
| 456 | 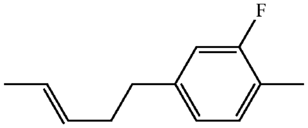 | 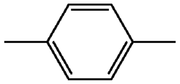 | 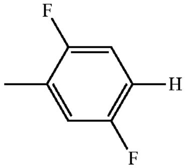 |
| 457 | 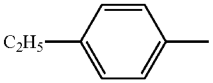 | 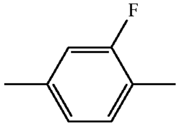 | 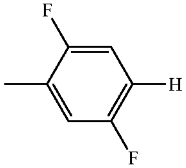 |

-continued
| | | | |
|---|---|---|---|
| 458 | 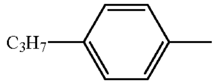 | 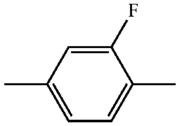 | 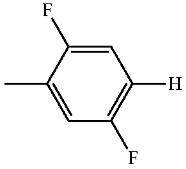 |
| 459 | 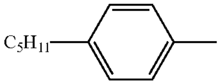 | 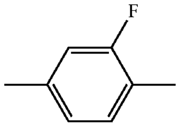 | 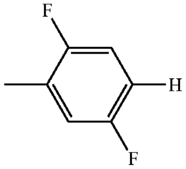 |
| 460 | 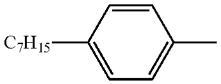 | 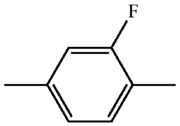 | 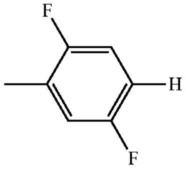 |
| 461 | 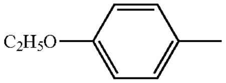 | 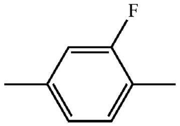 | 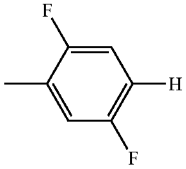 |
| 462 | 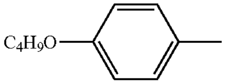 | 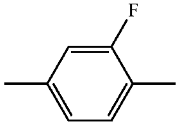 | 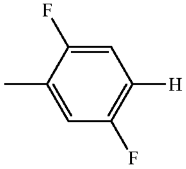 |

-continued
| | | | |
|---|---|---|---|
| 463 | 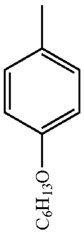 | 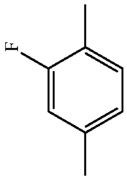 | 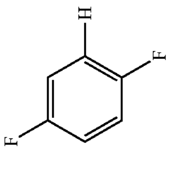 |
| 464 | 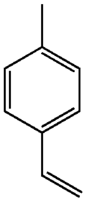 | 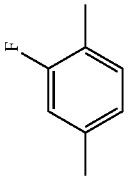 | 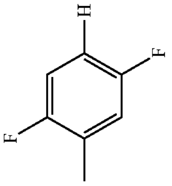 |
| 465 | 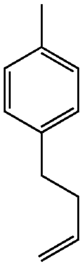 | 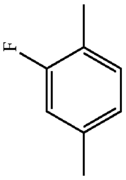 | 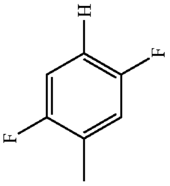 |
| 466 | 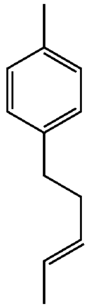 | 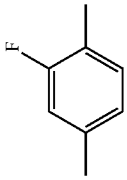 | 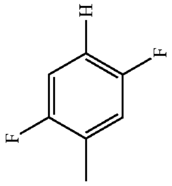 |
| 467 | 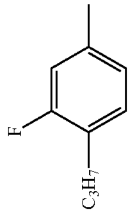 | 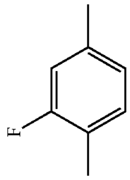 | 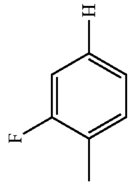 |
| 468 | 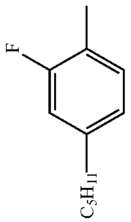 | 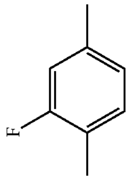 | 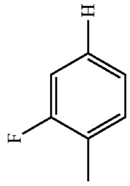 |

-continued
469 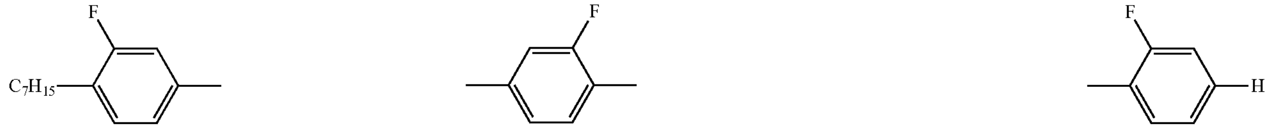
470 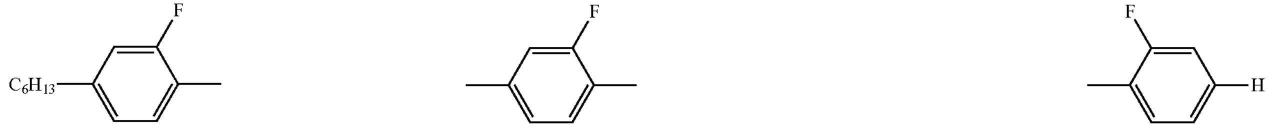
471 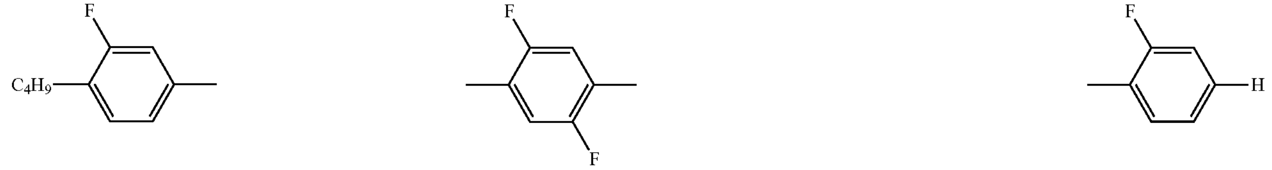
472 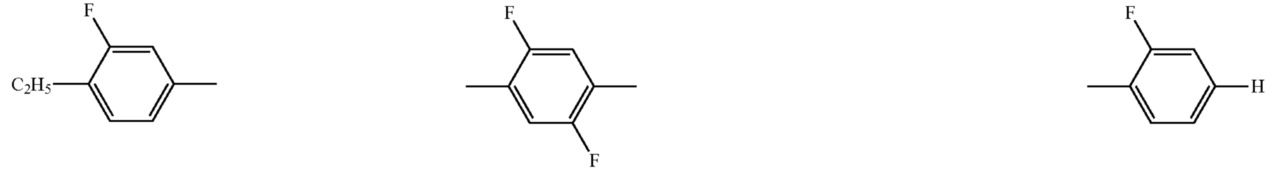
473 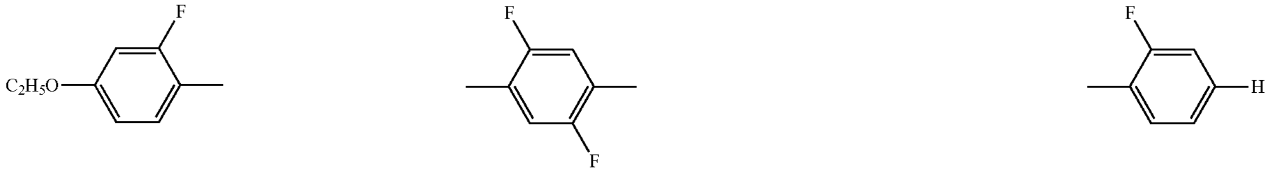
474 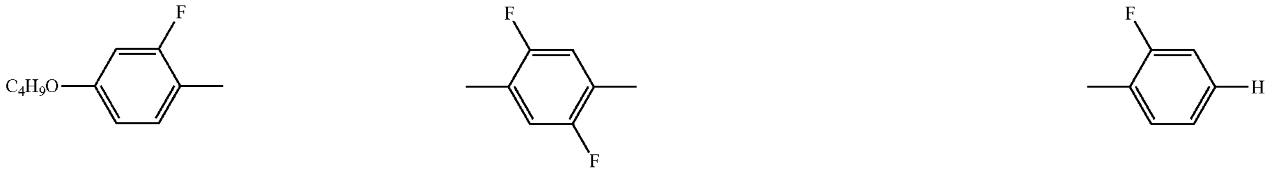

-continued
| | | | |
|---|---|---|---|
| 475 | 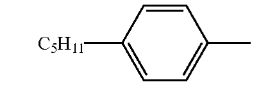 | 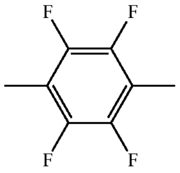 | 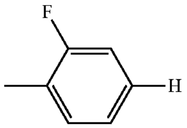 |
| 476 | 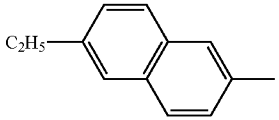 | 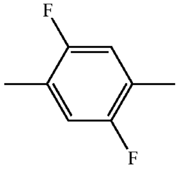 | 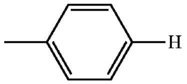 |
| 477 | 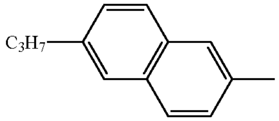 | 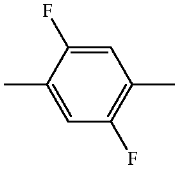 | 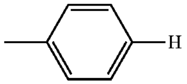 |
| 478 | 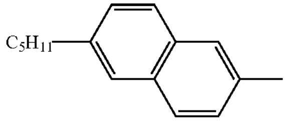 | 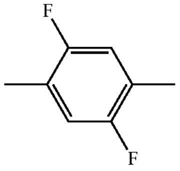 | 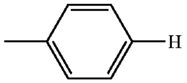 |
| 479 | 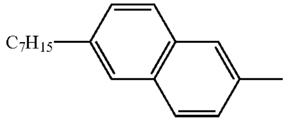 | 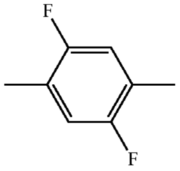 | 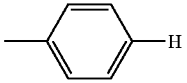 |

-continued
| | | | |
|---|---|---|---|
| 480 | 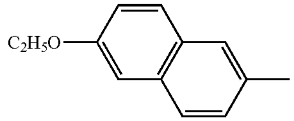 | 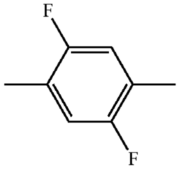 | 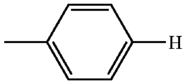 |
| 481 | 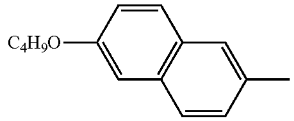 | 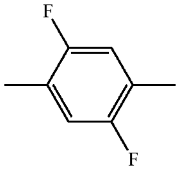 | 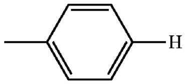 |
| 482 | 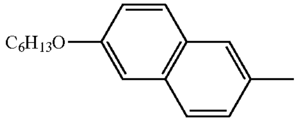 | 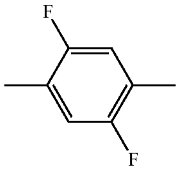 | 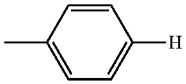 |
| 483 | 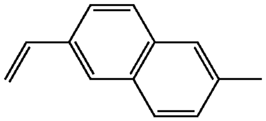 | 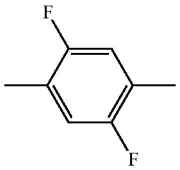 | 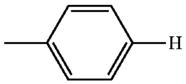 |
| 484 | 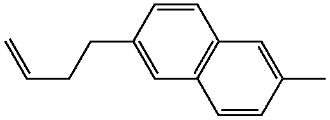 | 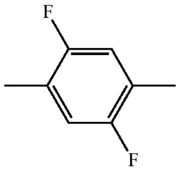 | 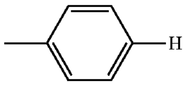 |

-continued
| | | | |
|---|---|---|---|
| 485 | 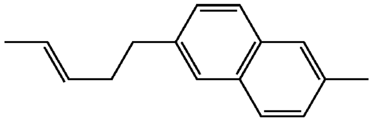 | 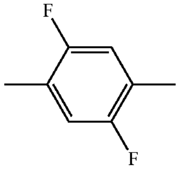 | 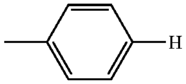 |
| 486 | 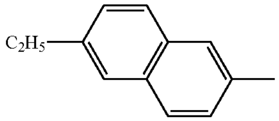 | 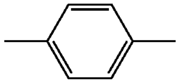 | 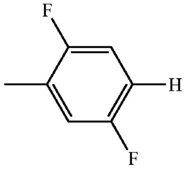 |
| 487 | 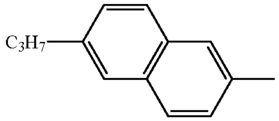 | 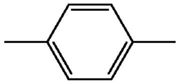 | 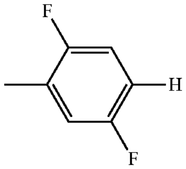 |
| 488 | 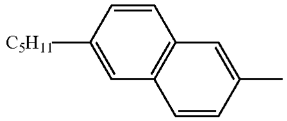 | 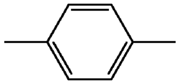 | 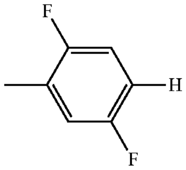 |
| 489 | 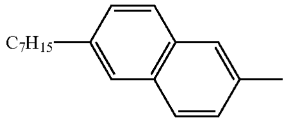 | 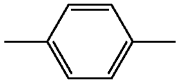 | 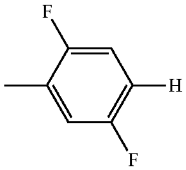 |

-continued
| | | | |
|---|---|---|---|
| 490 | 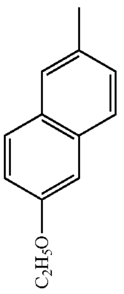 | 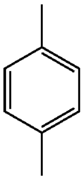 | 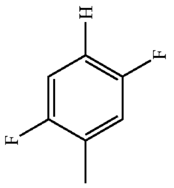 |
| 491 | 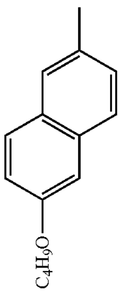 | 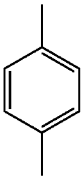 | 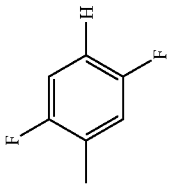 |
| 492 | 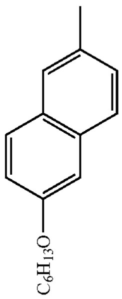 | 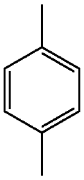 | 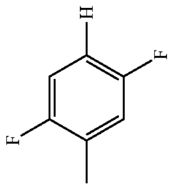 |
| 493 | 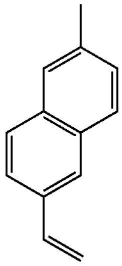 | 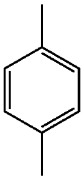 | 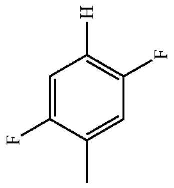 |
| 494 | 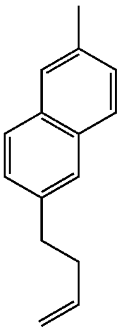 | 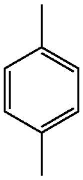 | 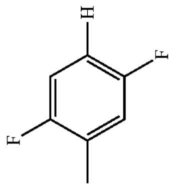 |

-continued
| | | | |
|---|---|---|---|
| 495 | 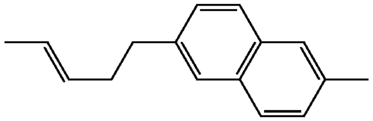 | 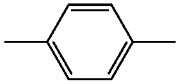 | 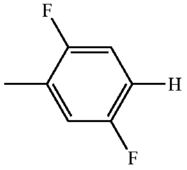 |
| 496 | 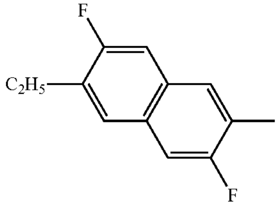 | 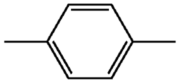 | 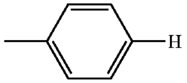 |
| 497 | 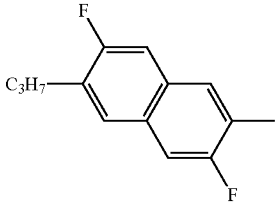 | 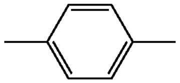 | 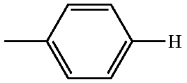 |
| 498 | 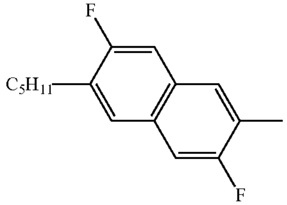 | 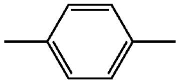 | 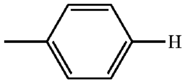 |
| 499 | 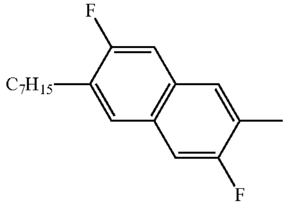 | 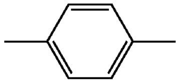 | 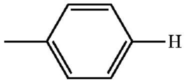 |

-continued
| | | | |
|---|---|---|---|
| 500 | 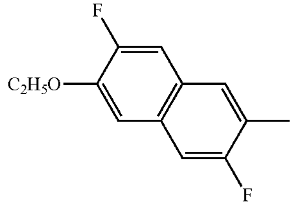 | 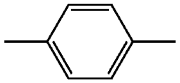 | 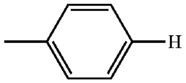 |
| 501 | 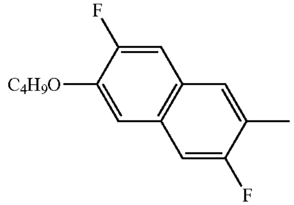 | 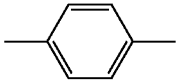 | 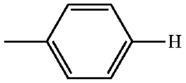 |
| 502 | 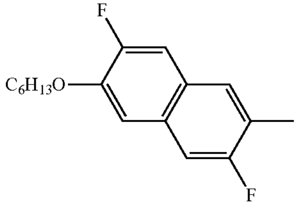 | 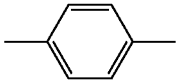 | 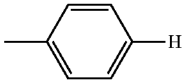 |
| 503 | 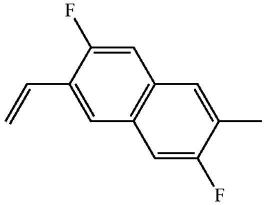 | 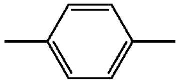 | 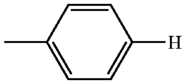 |
| 504 | 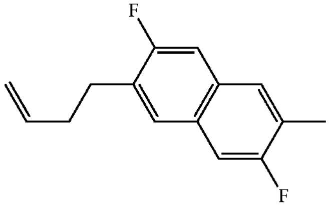 | 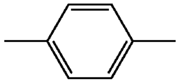 | 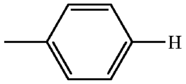 |

-continued
505 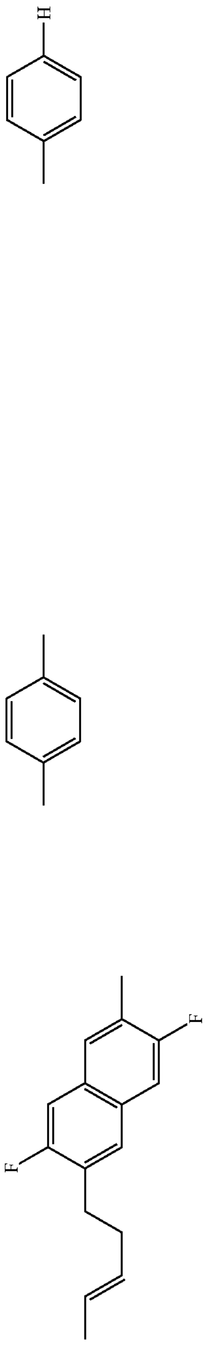
506 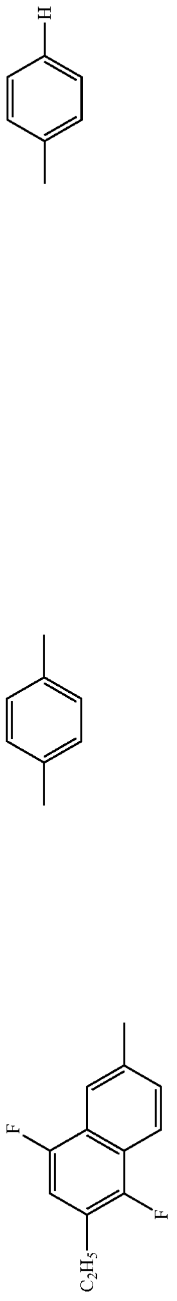
507 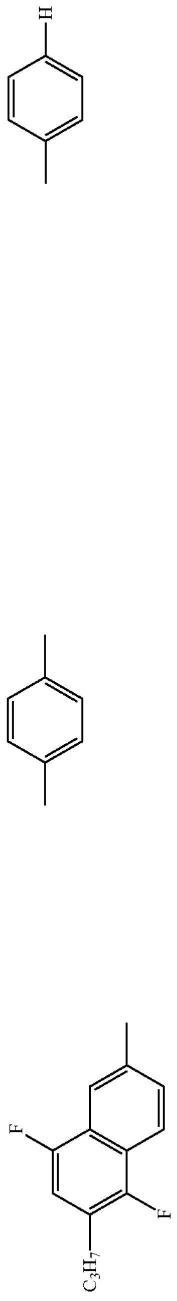
508 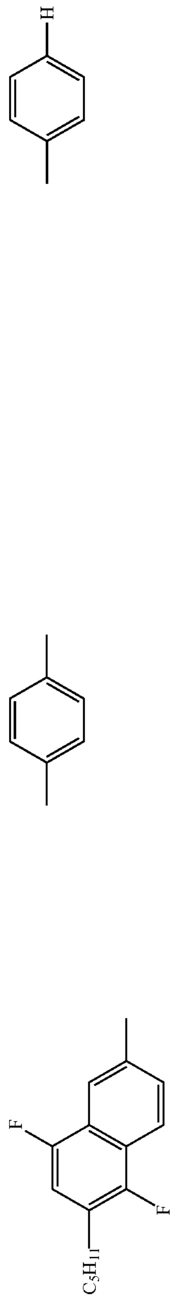
509 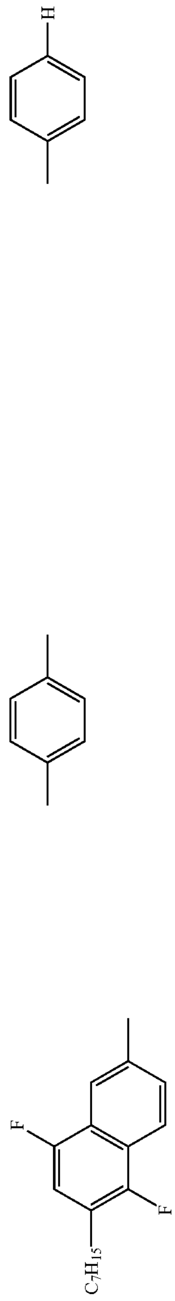

-continued
510 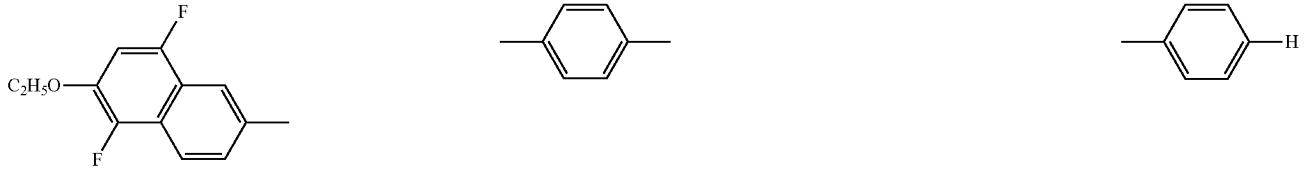
511 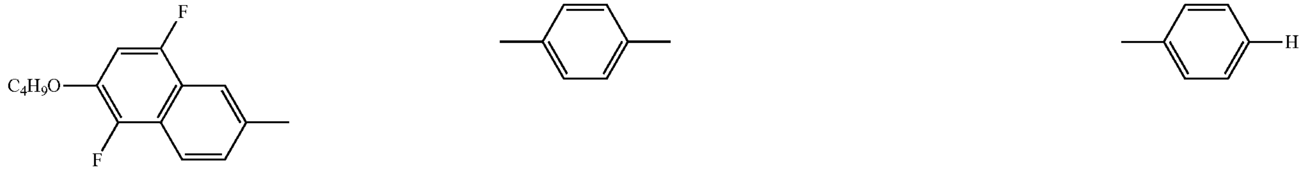
512 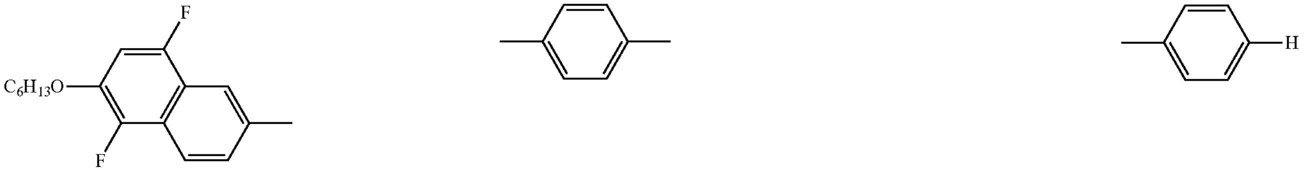
513 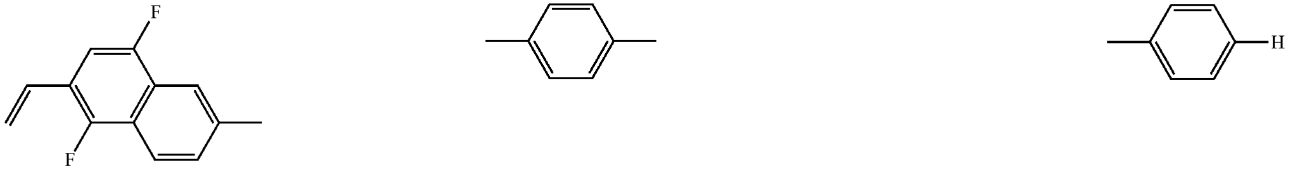
514 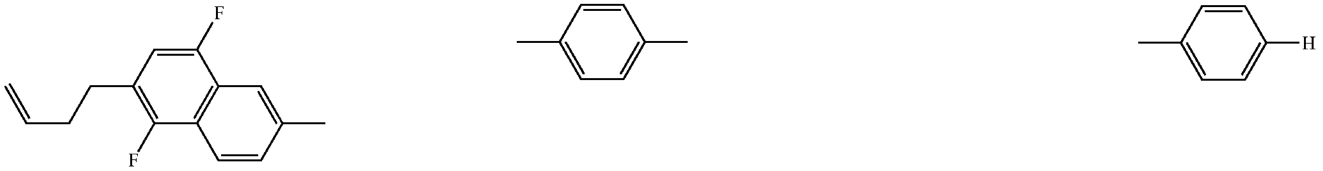

-continued
515 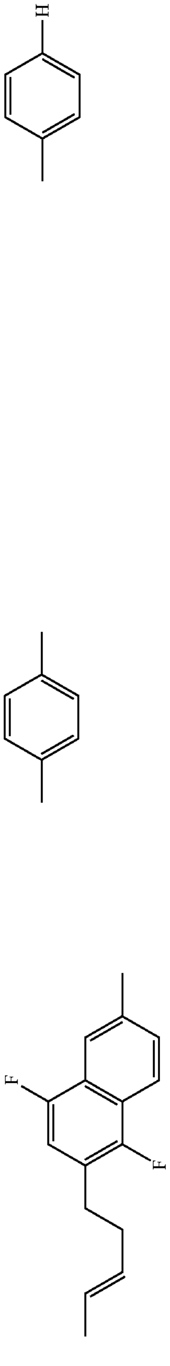
516 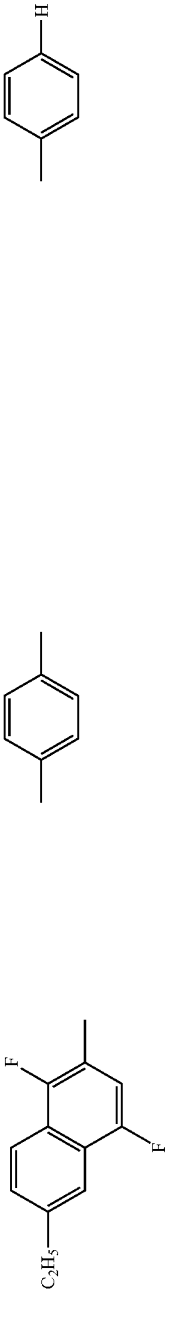
517 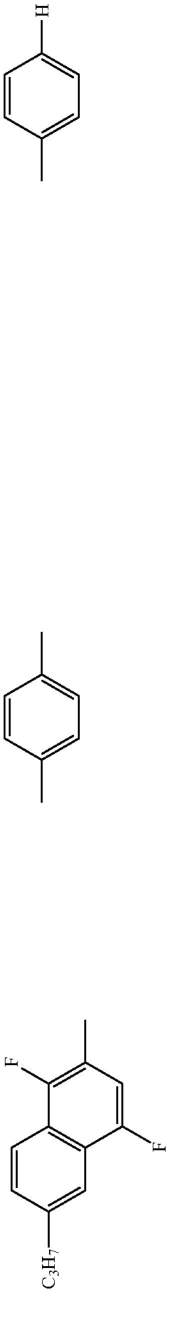
518 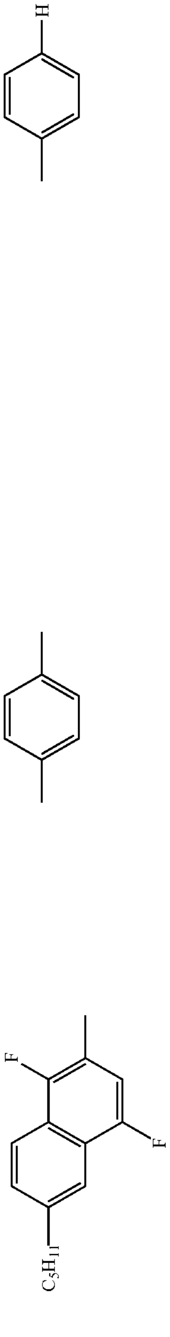
519 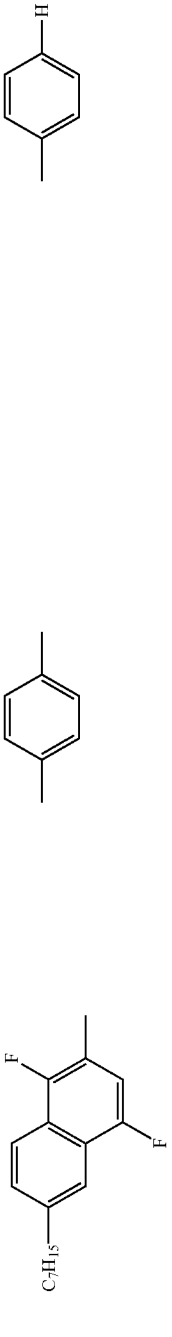

-continued
| | | | |
|---|---|---|---|
| 520 | 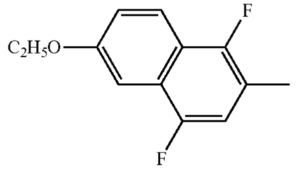 | 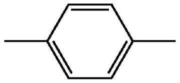 | 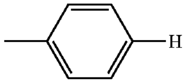 |
| 521 | 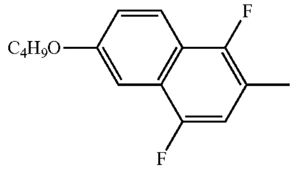 | 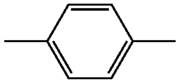 | 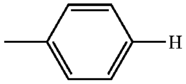 |
| 522 | 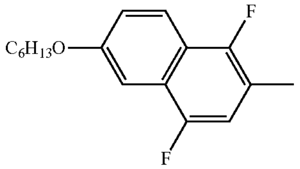 | 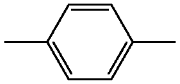 | 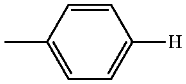 |
| 523 | 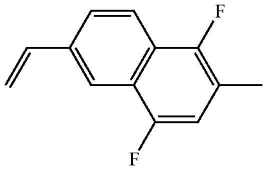 | 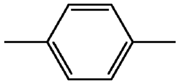 | 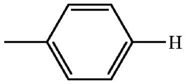 |
| 524 | 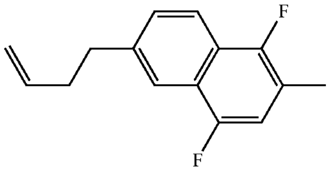 | 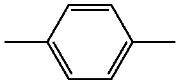 | 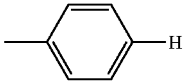 |

-continued
| | |
|---|---|
| 525 | 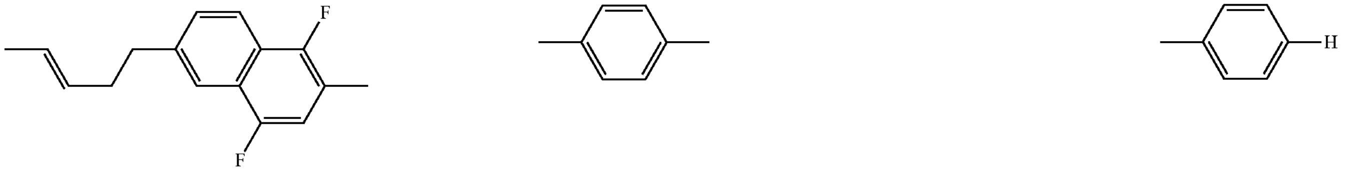 |
| 526 | 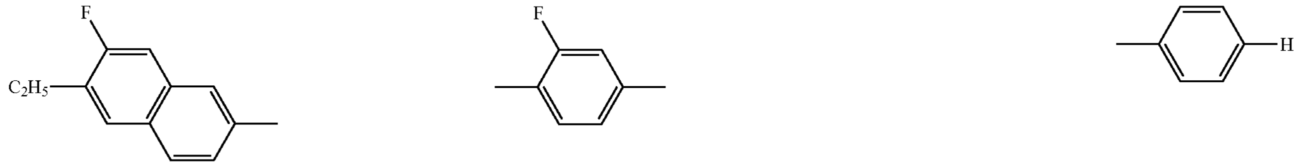 |
| 527 | 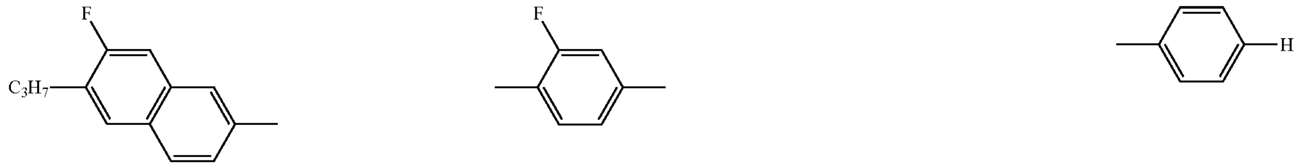 |
| 528 | 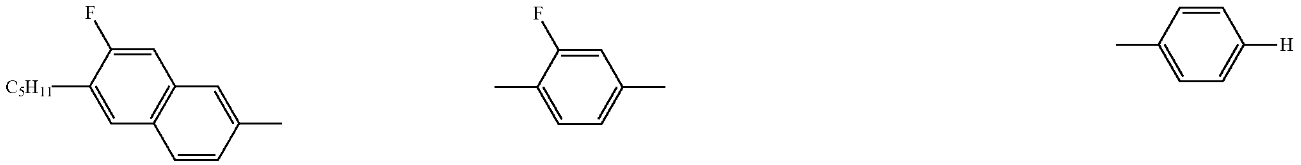 |
| 529 | 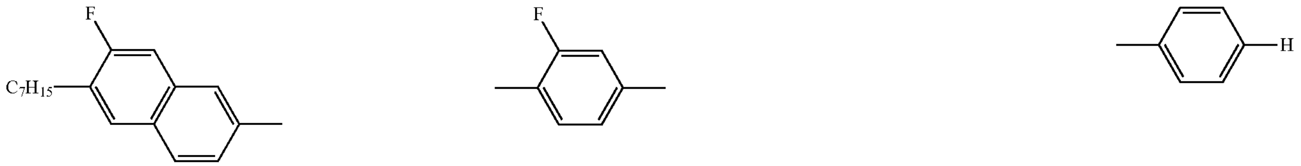 |
| 530 | 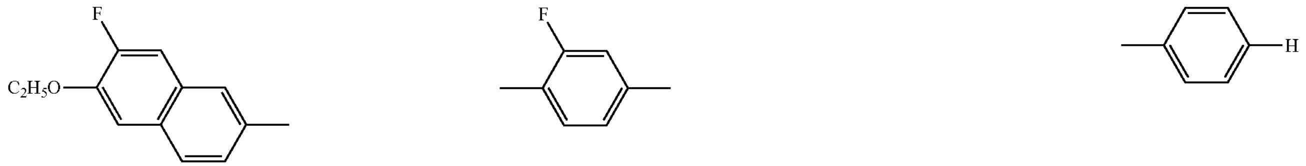 |

-continued
| | | | |
|---|---|---|---|
| 531 | 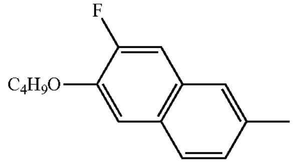 | 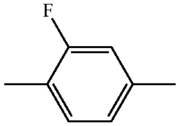 | 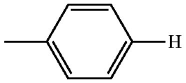 |
| 532 | 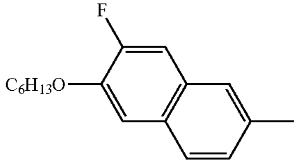 | 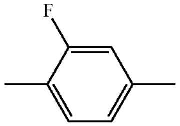 | 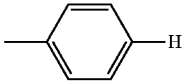 |
| 533 | 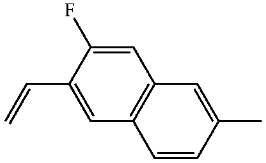 | 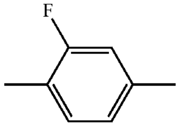 | 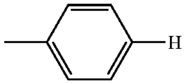 |
| 534 | 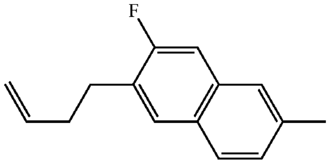 | 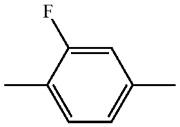 | 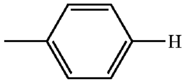 |
| 535 | 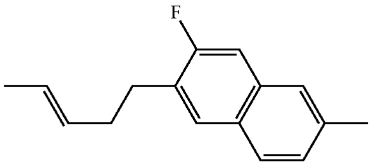 | 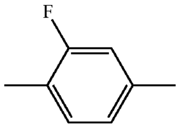 | 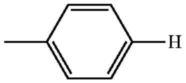 |
| 536 | 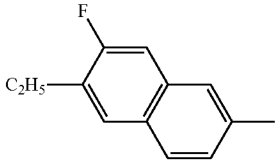 | 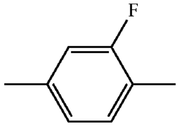 | 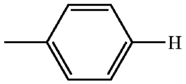 |

-continued
| | | | |
|---|---|---|---|
| 537 | 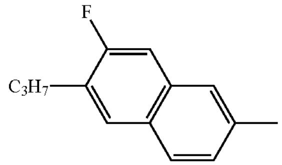 | 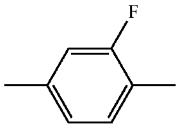 | 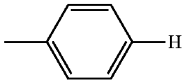 |
| 538 | 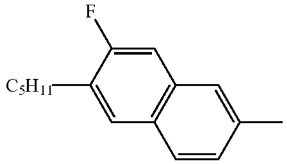 | 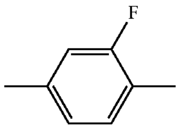 | 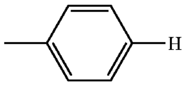 |
| 539 | 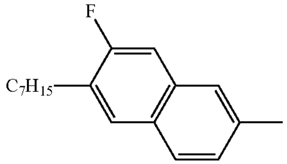 | 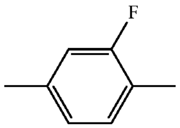 | 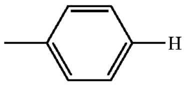 |
| 540 | 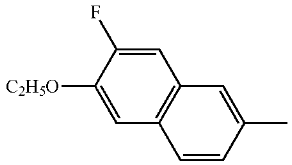 | 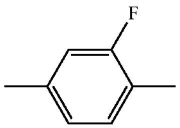 | 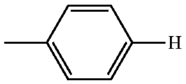 |
| 541 | 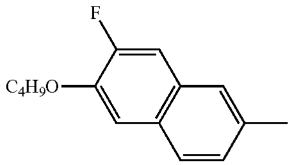 | 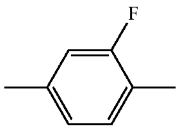 | 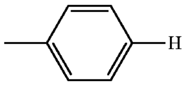 |
| 542 | 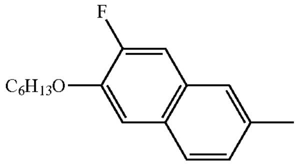 | 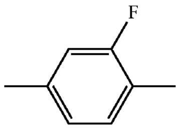 | 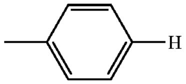 |

-continued
| | | | |
|---|---|---|---|
| 543 | 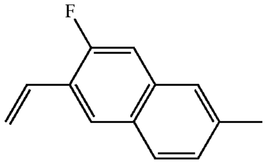 | 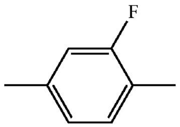 | 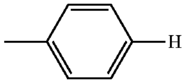 |
| 544 | 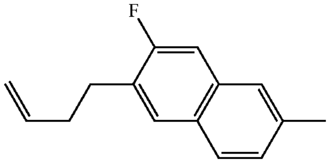 | 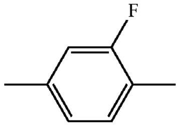 | 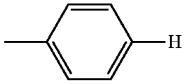 |
| 545 | 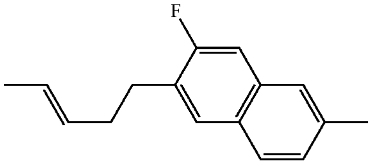 | 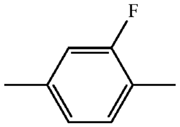 | 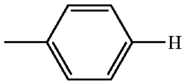 |
| 546 | 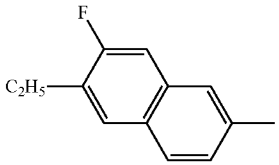 | 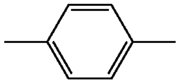 | 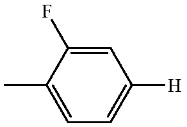 |
| 547 | 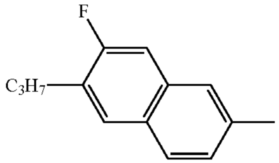 | 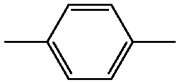 | 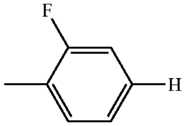 |
| 548 | 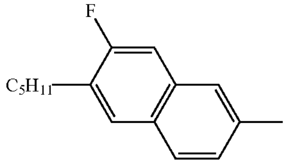 | 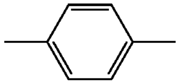 | 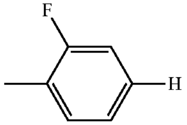 |

-continued
| | | | |
|---|---|---|---|
| 549 | 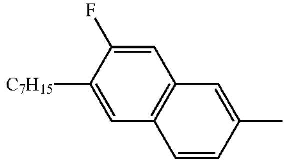 | 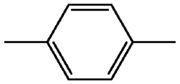 | 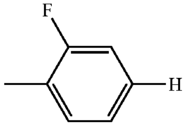 |
| 550 | 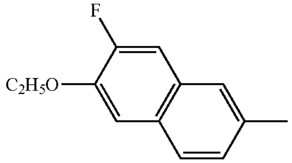 | 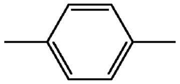 | 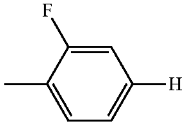 |
| 551 | 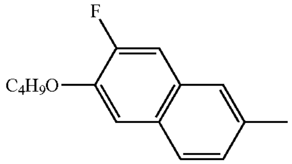 | 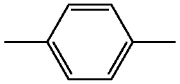 | 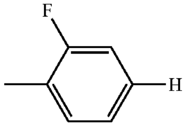 |
| 552 | 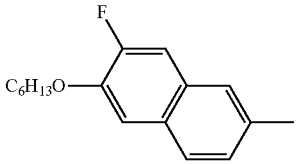 | 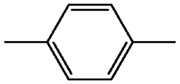 | 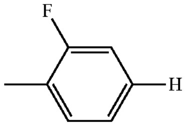 |
| 553 | 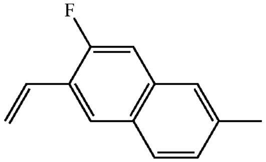 | 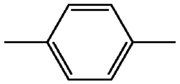 | 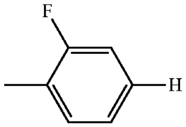 |
| 554 | 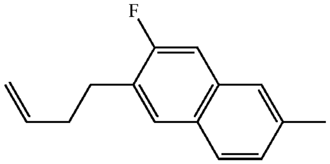 | 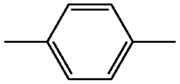 | 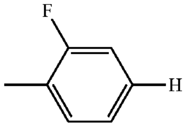 |

-continued
555 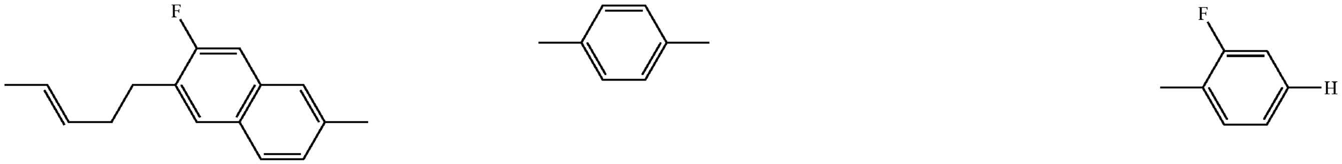
556 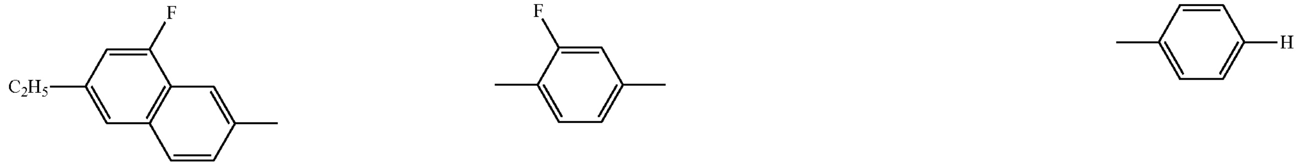
557 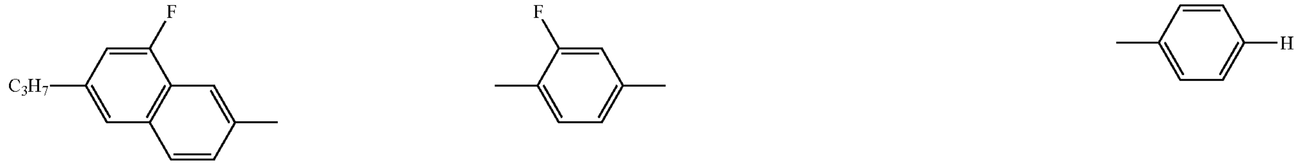
558 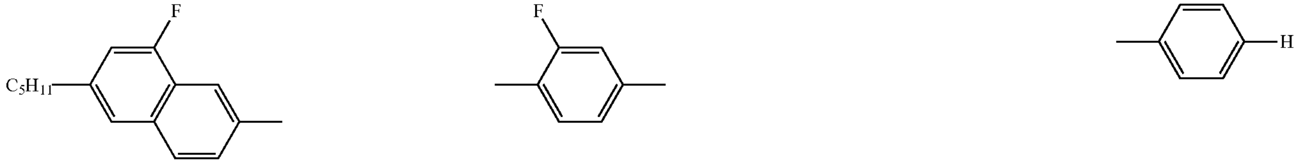
559 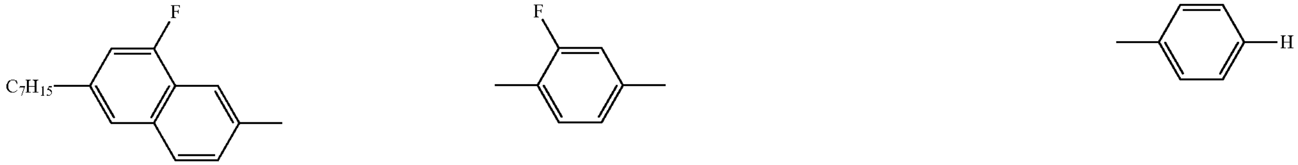
560 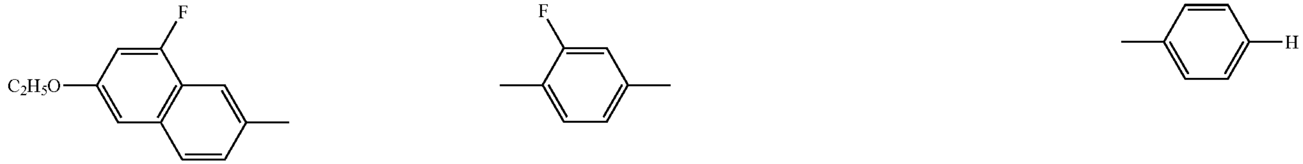

-continued
561 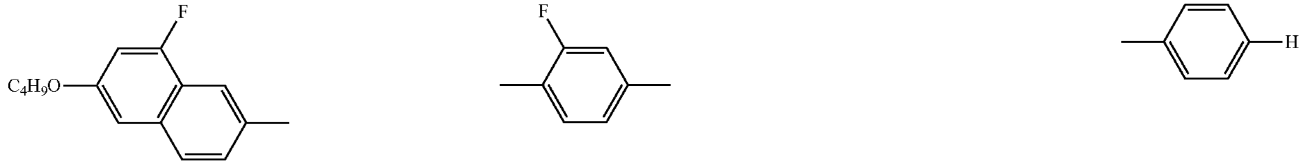
562 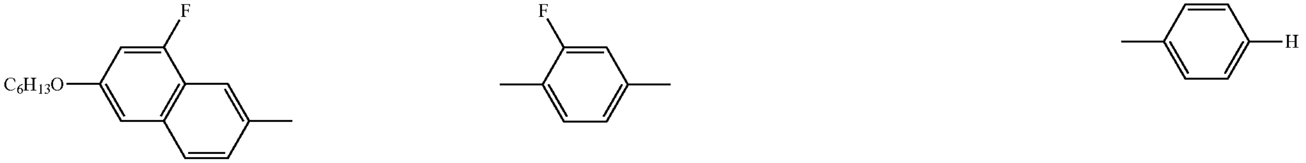
563 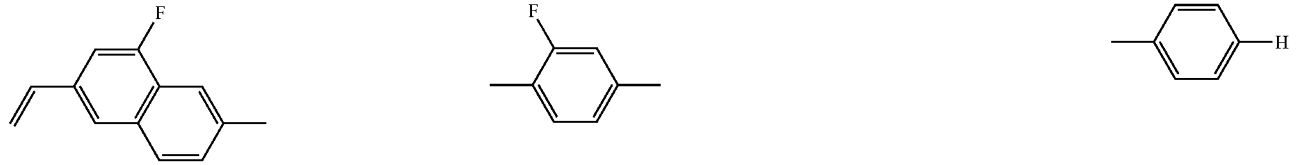
564 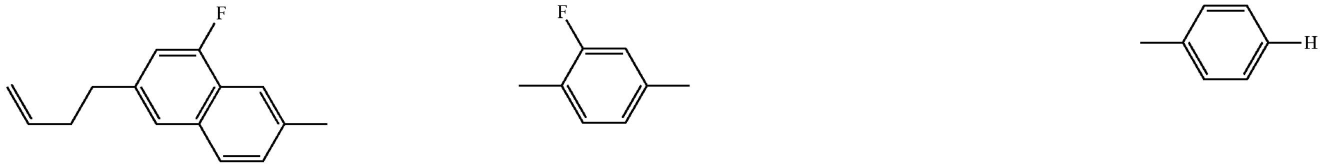
565 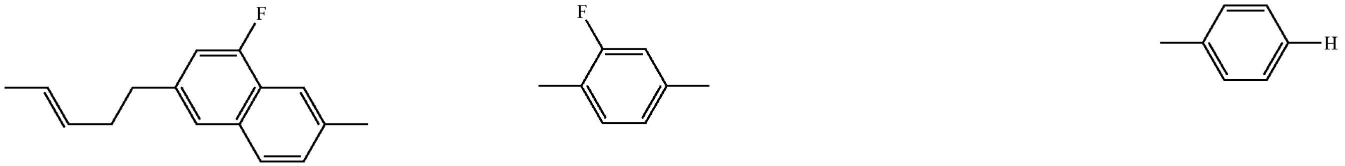
566 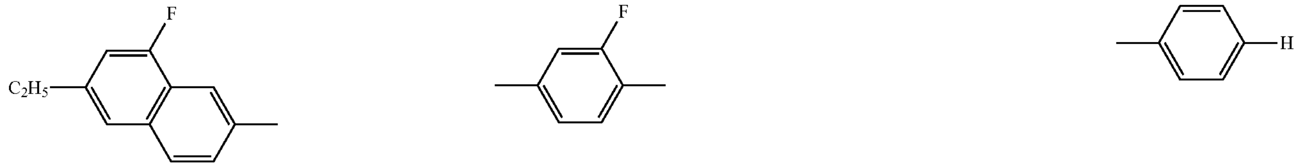

-continued
567 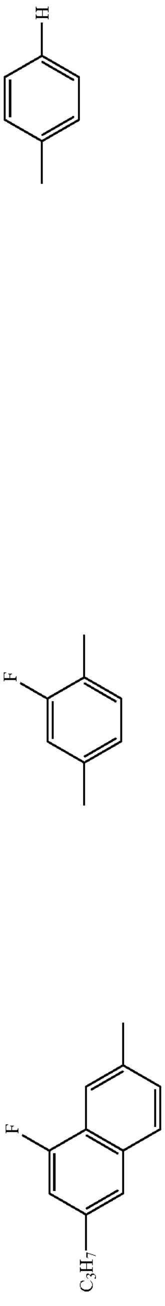
568 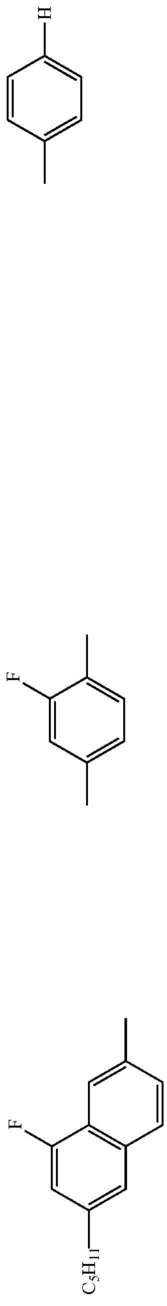
569 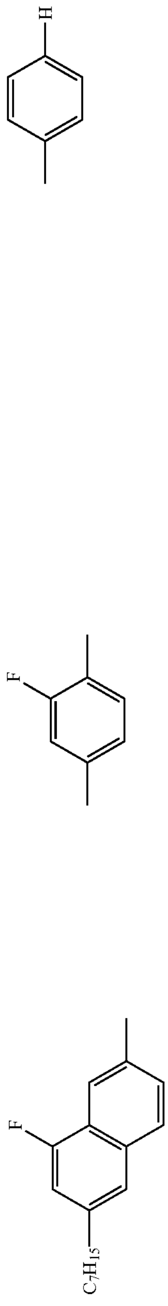
570 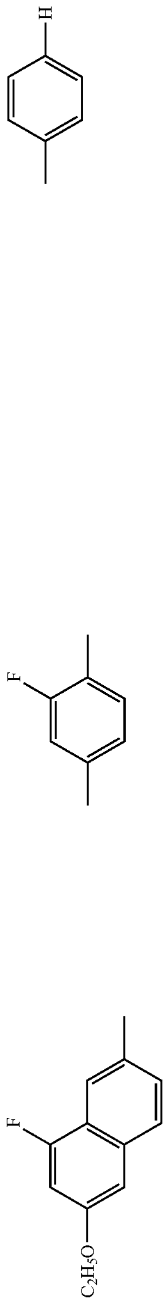
571 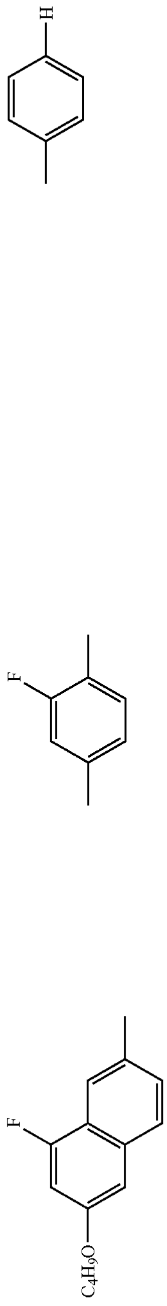
572 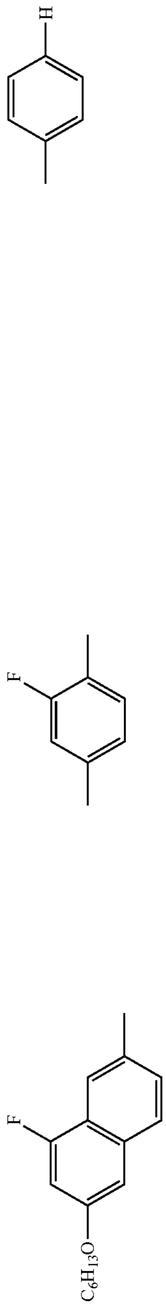

-continued
| | |
|---|---|
| 573 | 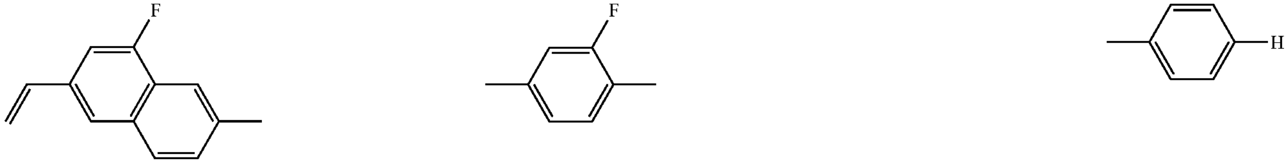 |
| 574 | 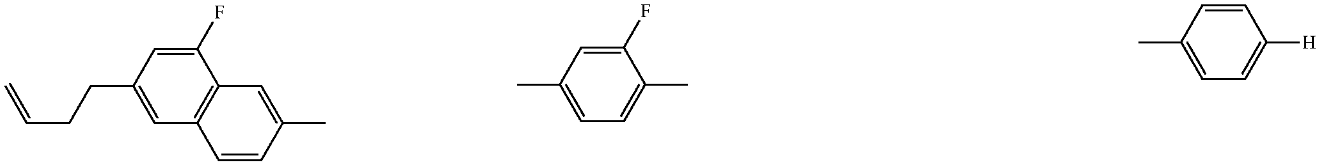 |
| 575 | 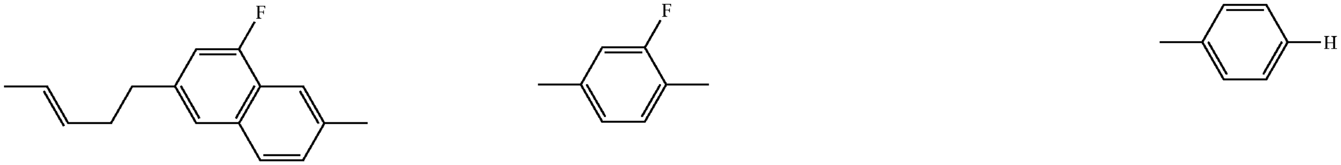 |
| 576 | 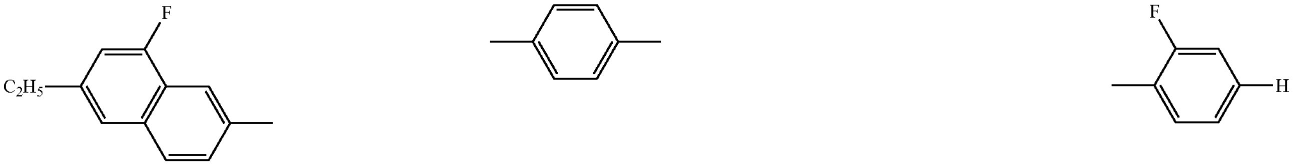 |
| 577 | 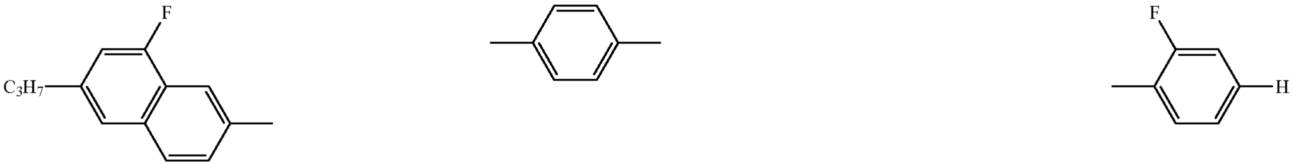 |
| 578 | 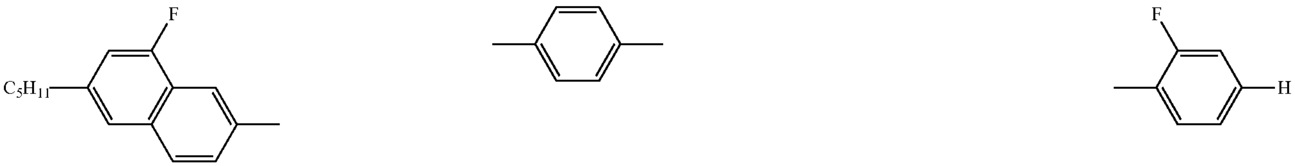 |

-continued
| | | | |
|---|---|---|---|
| 579 | 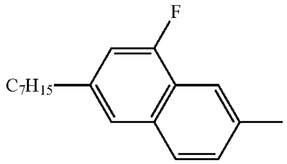 | 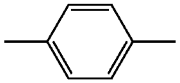 | 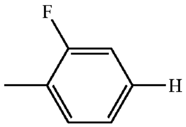 |
| 580 | 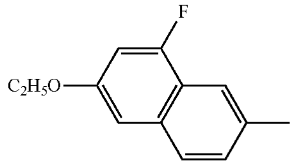 | 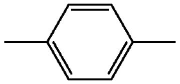 | 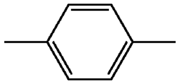 |
| 581 | 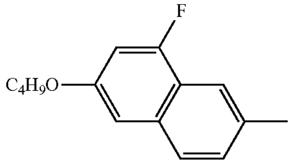 | 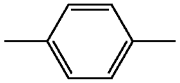 | 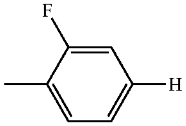 |
| 582 | 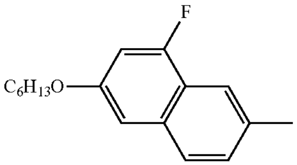 | 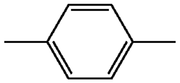 | 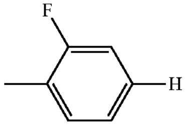 |
| 583 | 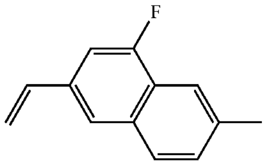 | 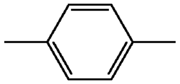 | 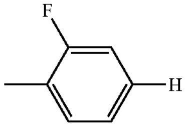 |
| 584 | 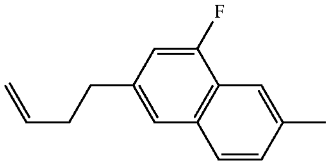 | 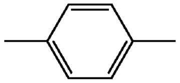 | 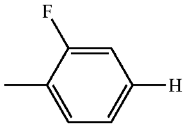 |

-continued
585 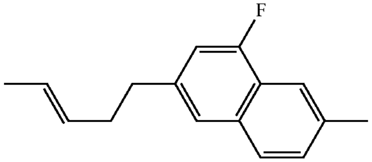 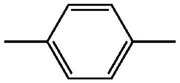 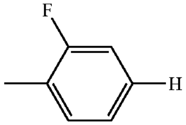
586 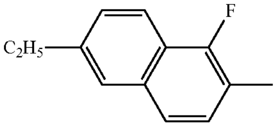 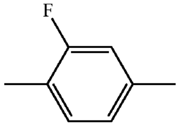 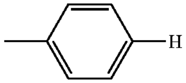
587 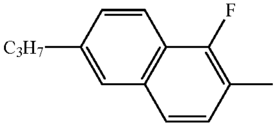 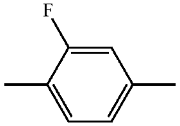 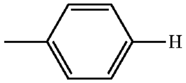
588 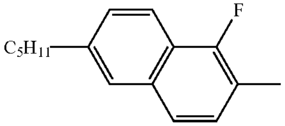 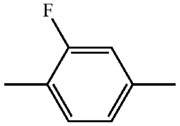 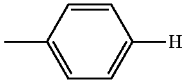
589 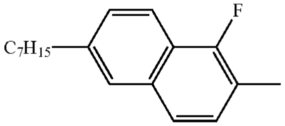 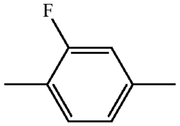 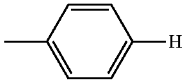
590 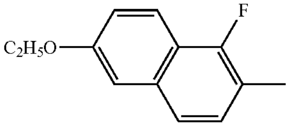 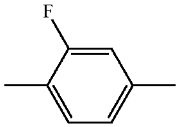 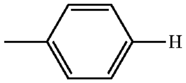
591 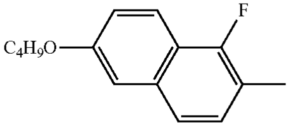 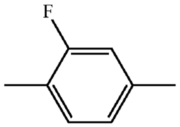 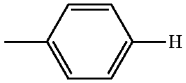

-continued
| | |
|---|---|
| 592 | 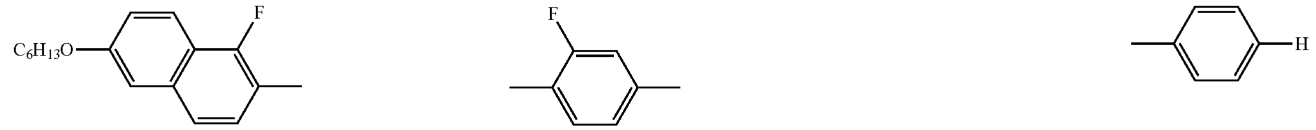 |
| 593 | 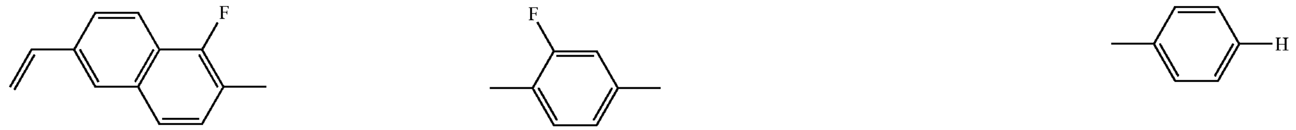 |
| 594 | 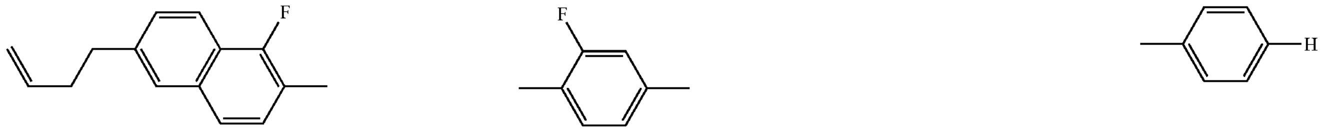 |
| 595 | 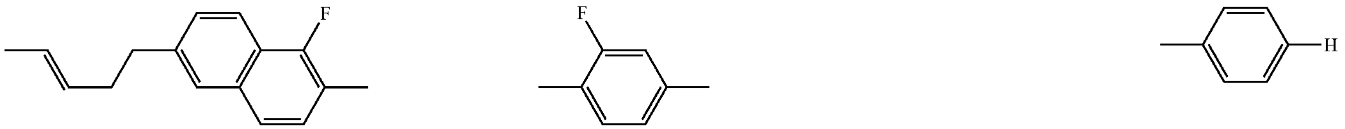 |
| 596 | 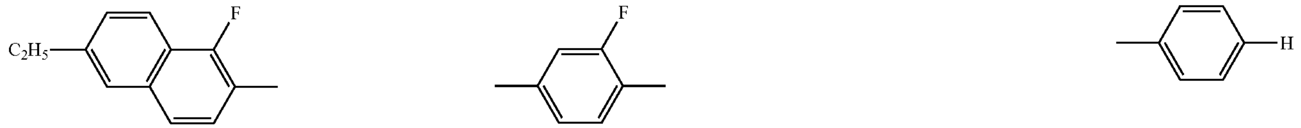 |
| 597 | 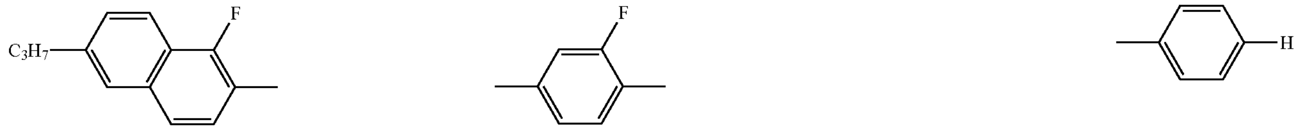 |
| 598 | 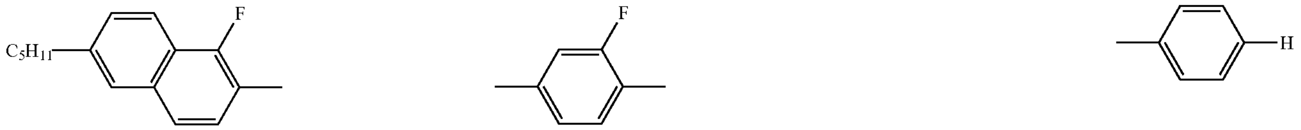 |

-continued
| | |
|---|---|
| 599 | 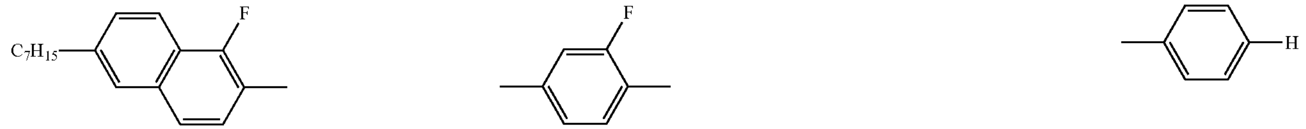 |
| 600 | 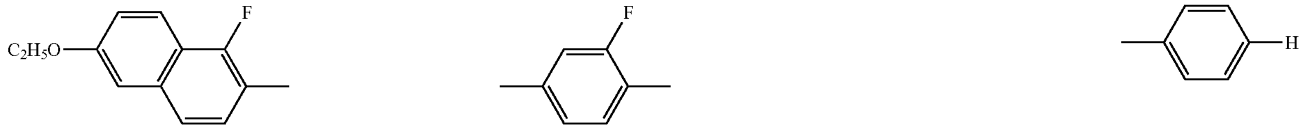 |
| 601 | 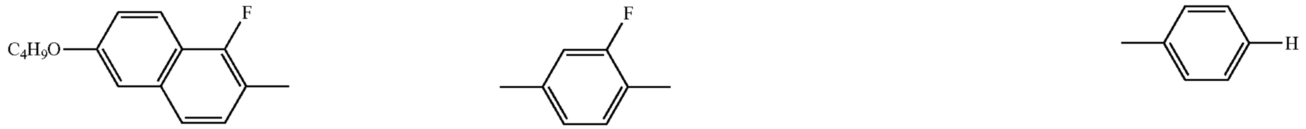 |
| 602 | 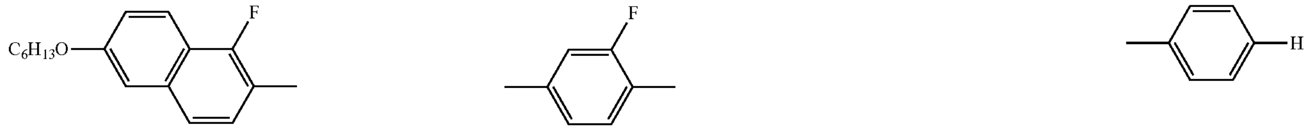 |
| 603 | 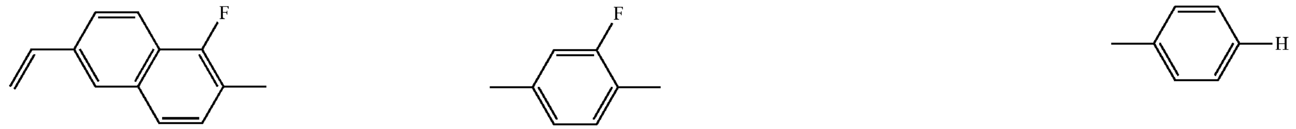 |
| 604 | 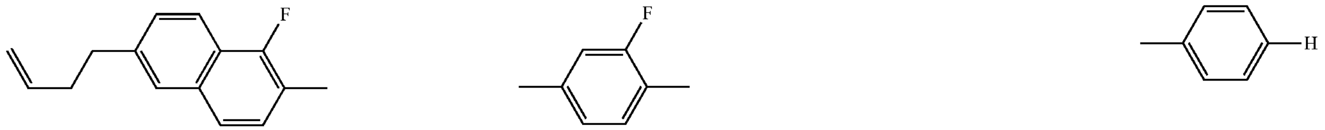 |
| 605 | 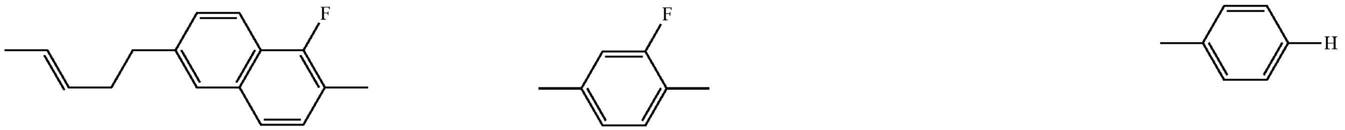 |

-continued
| | |
|---|---|
| 606 | 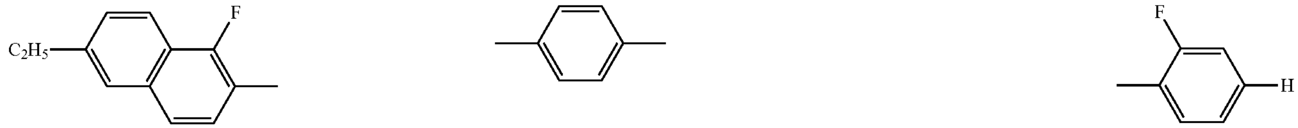 |
| 607 | 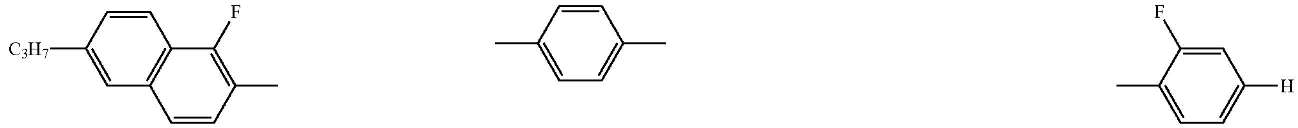 |
| 608 | 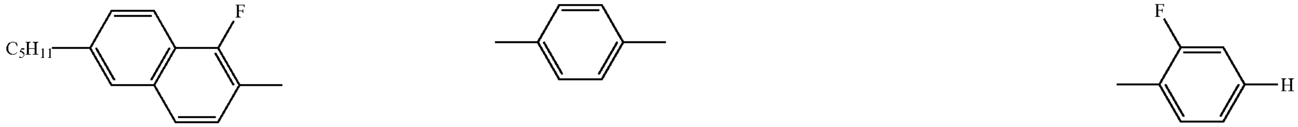 |
| 609 | 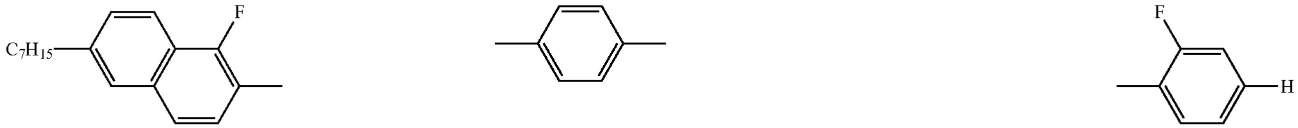 |
| 610 | 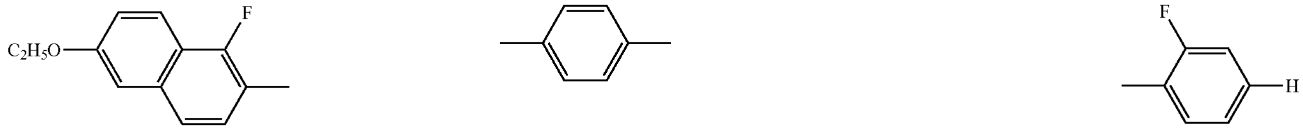 |
| 611 | 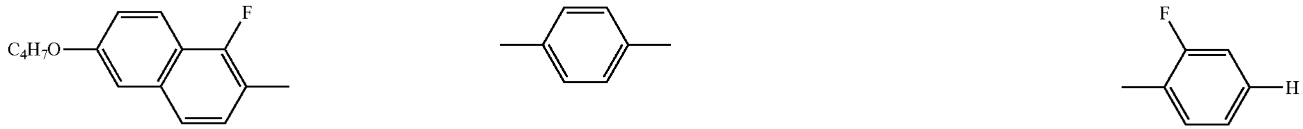 |
| 612 | 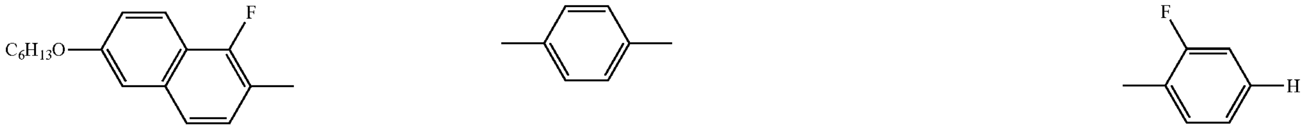 |

-continued
| | |
|---|---|
| 613 | 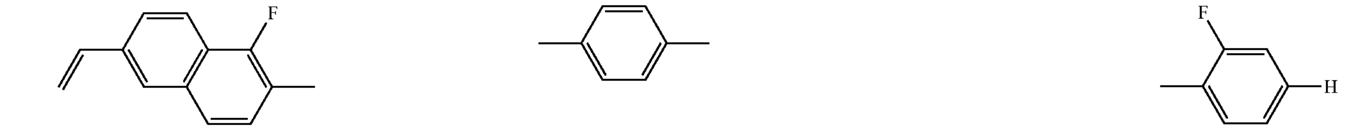 |
| 614 | 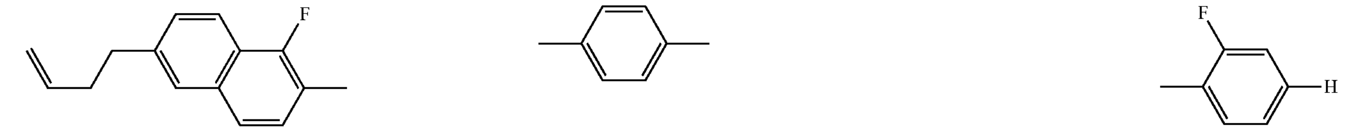 |
| 615 | 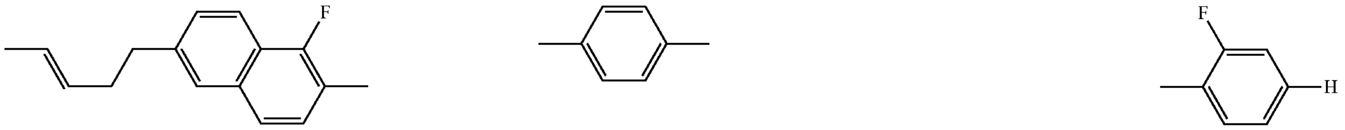 |
| 616 | 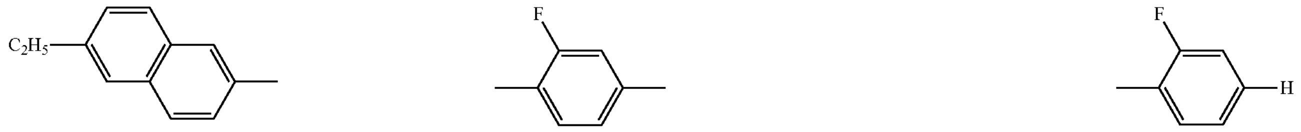 |
| 617 | 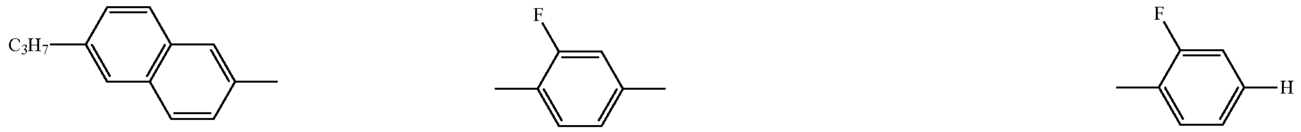 |
| 618 | 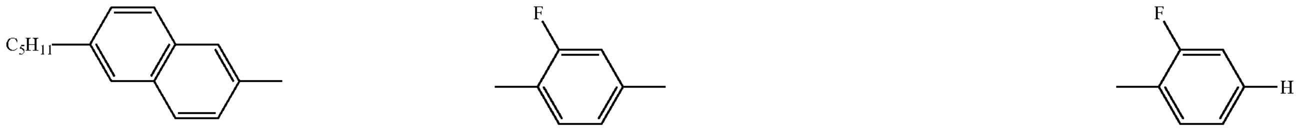 |
| 619 | 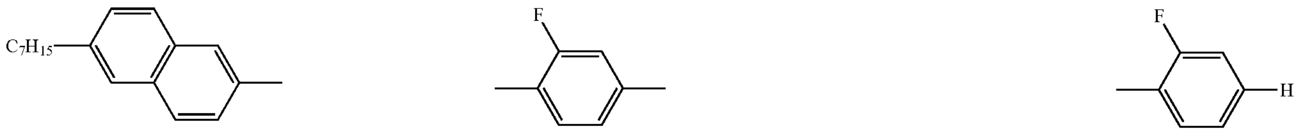 |

-continued
| | | | |
|---|---|---|---|
| 620 | 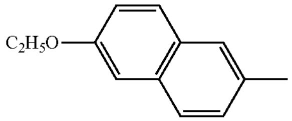 | 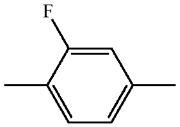 | 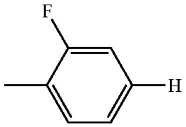 |
| 621 | 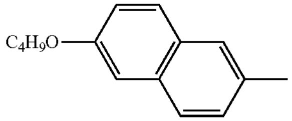 | 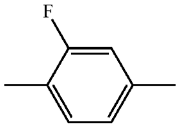 | 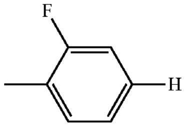 |
| 622 | 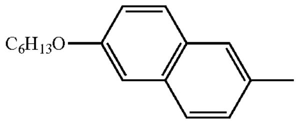 | 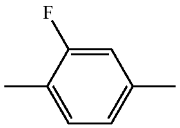 | 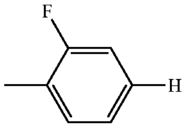 |
| 623 | 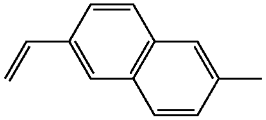 | 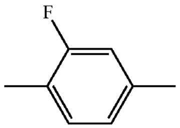 | 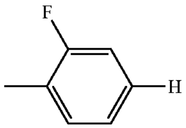 |
| 624 | 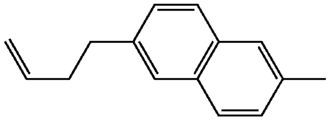 | 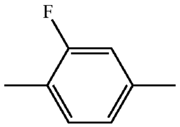 | 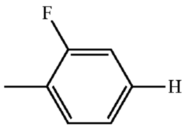 |
| 625 | 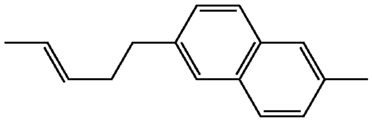 | 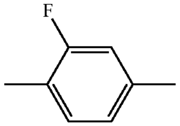 | 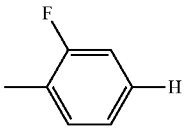 |
| 626 | 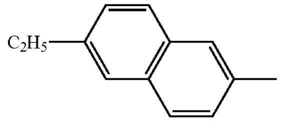 | 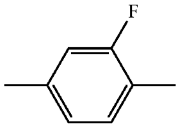 | 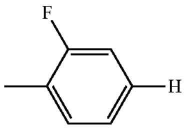 |

-continued
627 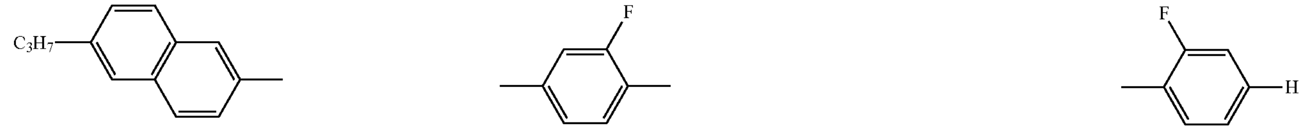
628 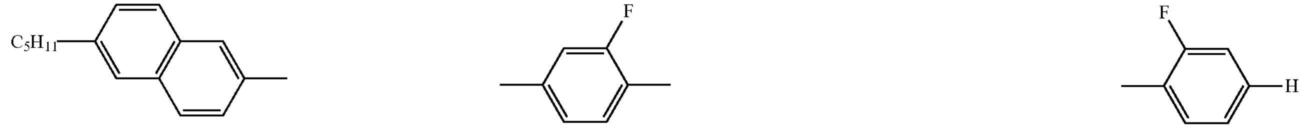
629 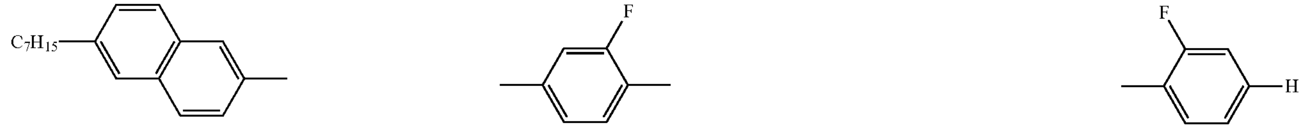
630 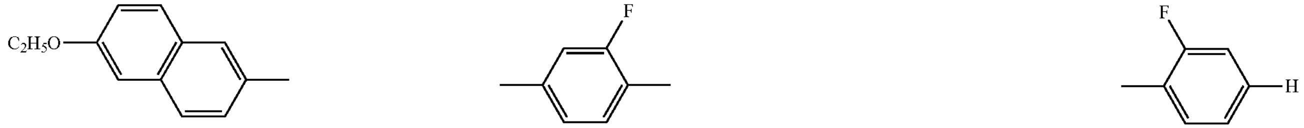
631 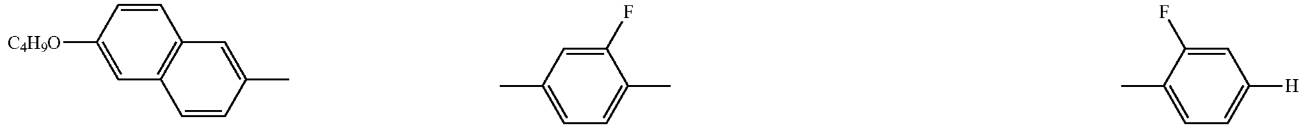
632 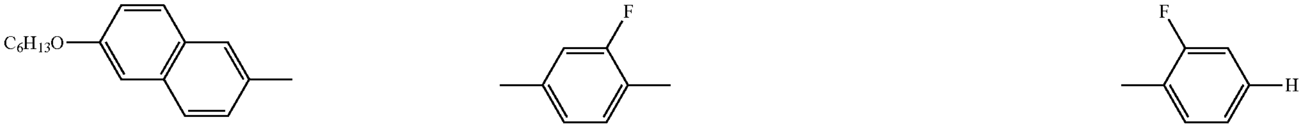
633 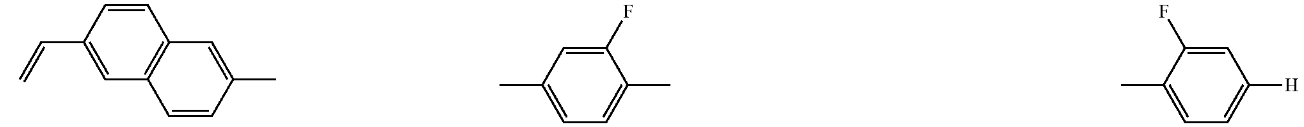

-continued
| | | | |
|---|---|---|---|
| 634 | 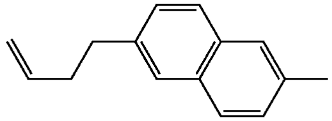 | 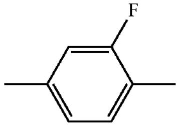 | 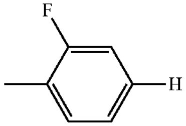 |
| 635 | 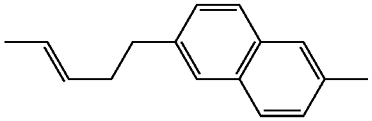 | 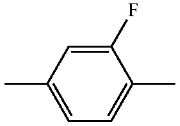 | 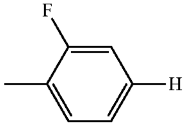 |
| 636 | 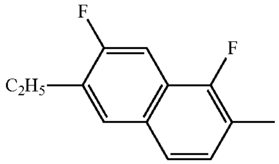 | 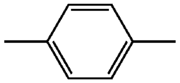 | 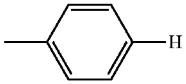 |
| 637 | 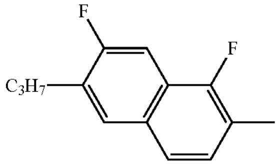 | 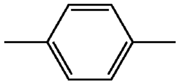 | 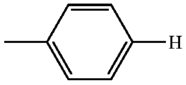 |
| 638 | 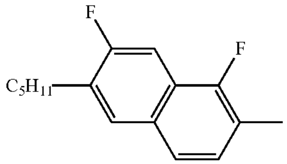 | 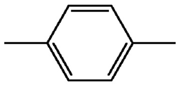 | 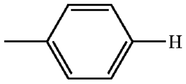 |
| 639 | 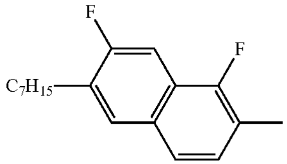 | 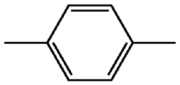 | 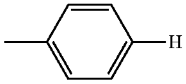 |

-continued
| | |
|---|---|
| 640 | 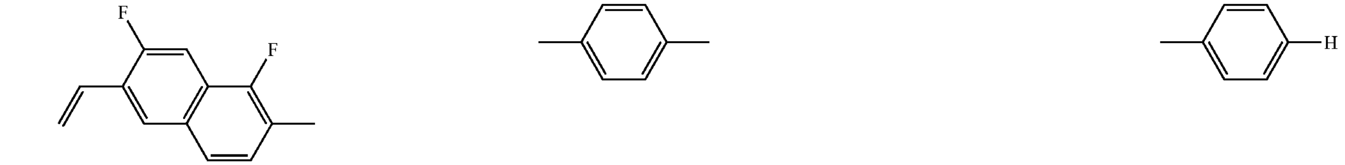 |
| 641 | 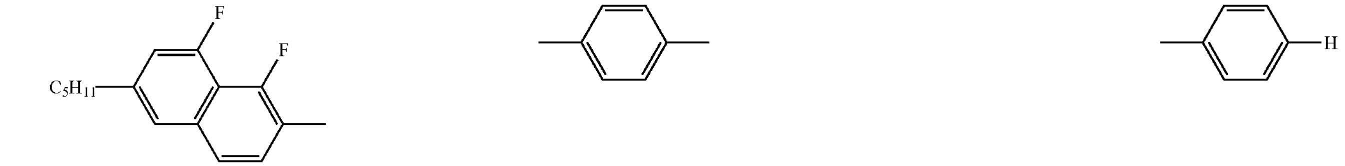 |
| 642 | 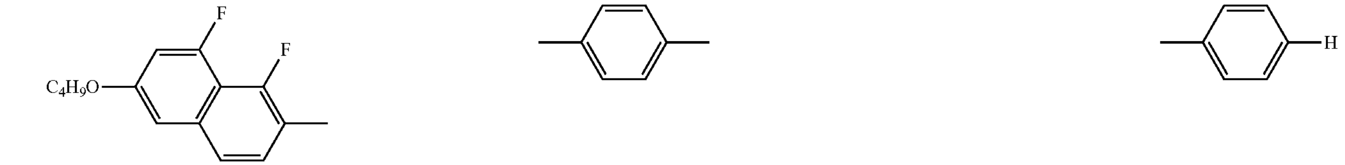 |
| 643 | 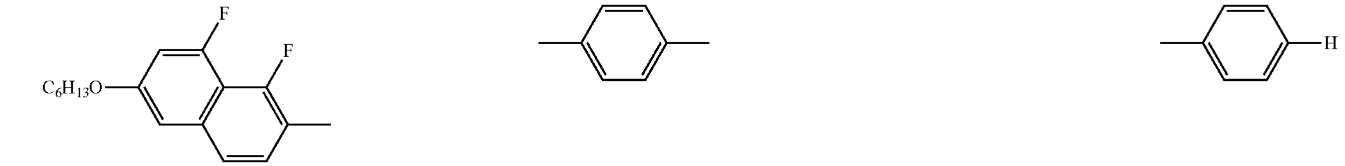 |
| 644 | 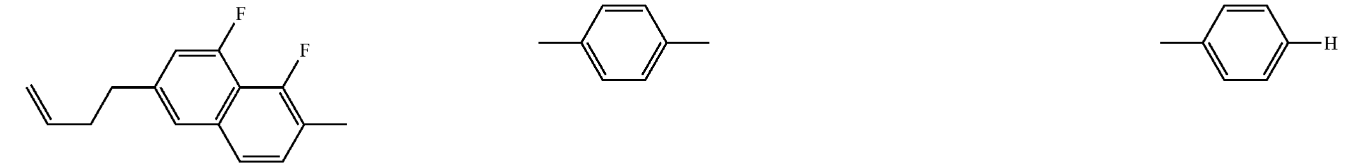 |
| 645 | 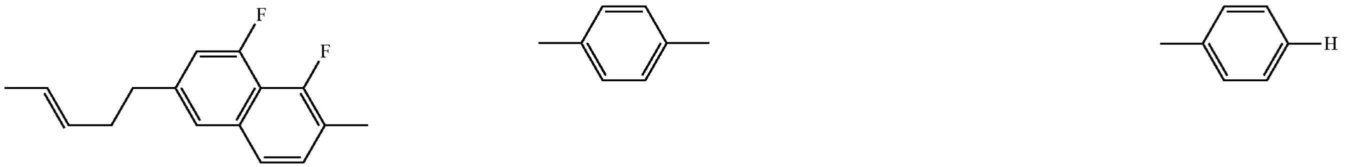 |

-continued
| | | | |
|---|---|---|---|
| 646 | 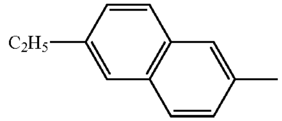 | 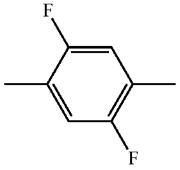 | 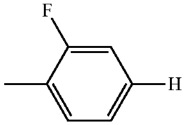 |
| 647 | 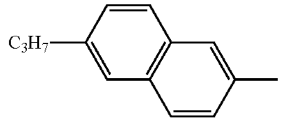 | 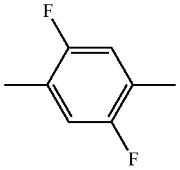 | 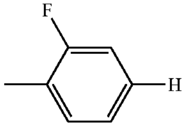 |
| 648 | 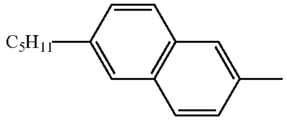 | 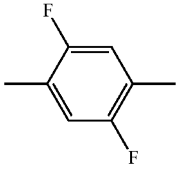 | 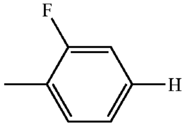 |
| 649 | 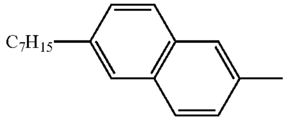 | 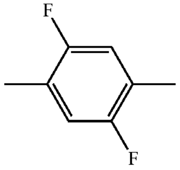 | 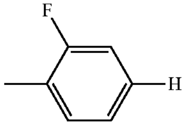 |
| 650 | 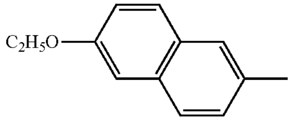 | 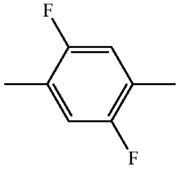 | 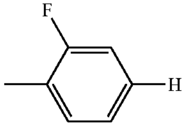 |
| 651 | 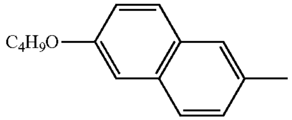 | 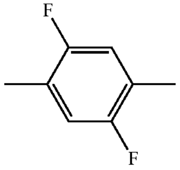 | 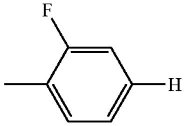 |

-continued
| | |
|---|---|
| 652 | 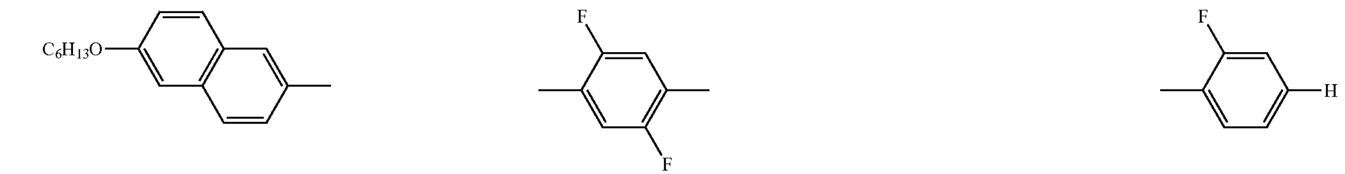 |
| 653 | 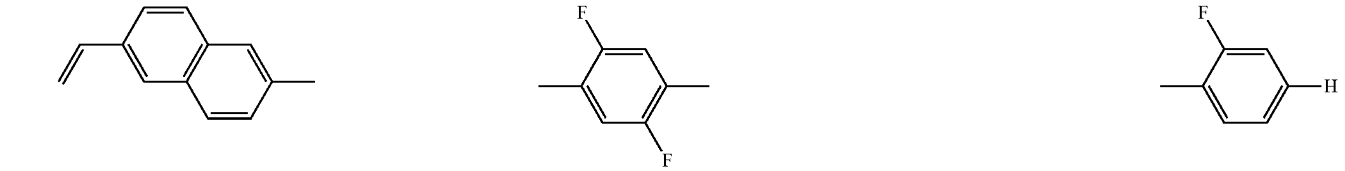 |
| 654 | 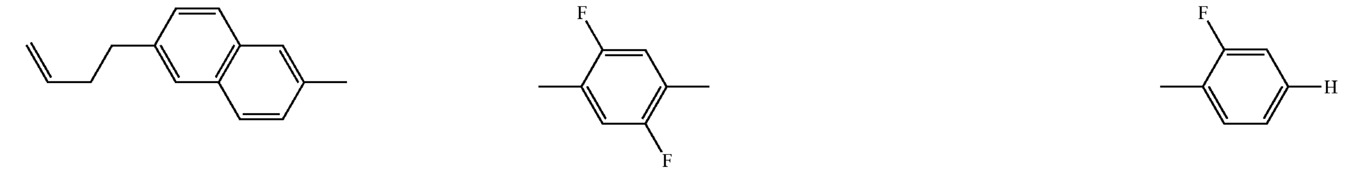 |
| 655 | 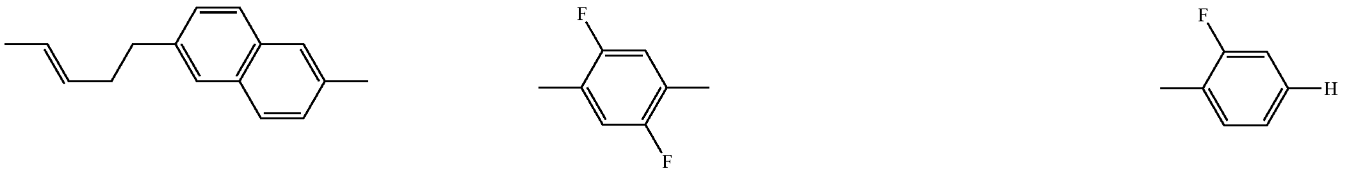 |
| 656 | 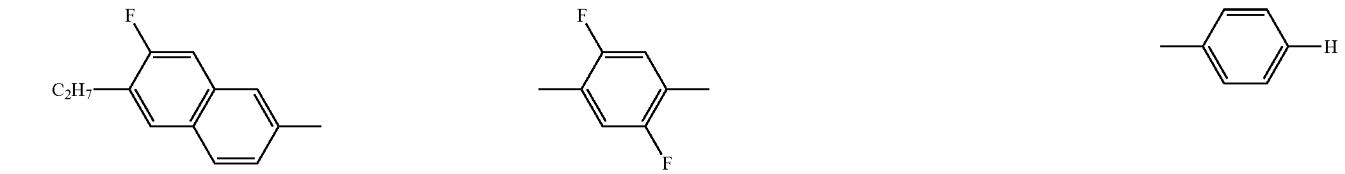 |

-continued
| | |
|---|---|
| 657 | 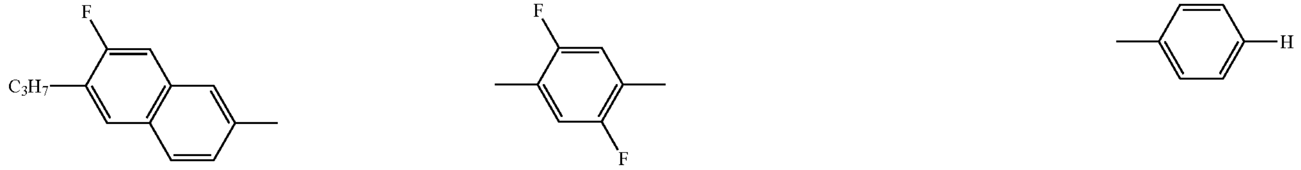 |
| 656 | 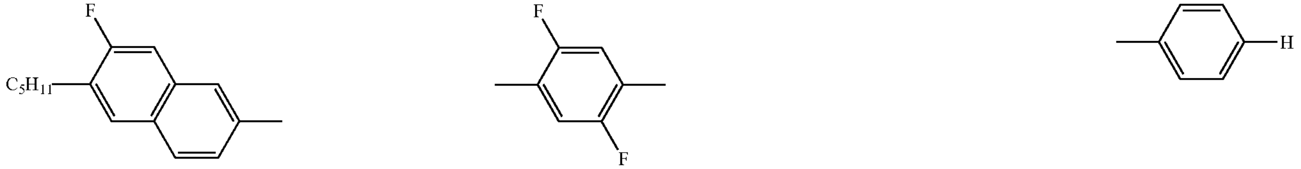 |
| 659 | 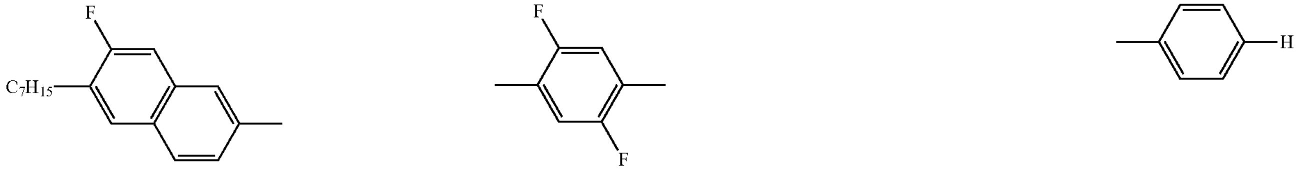 |
| 660 | 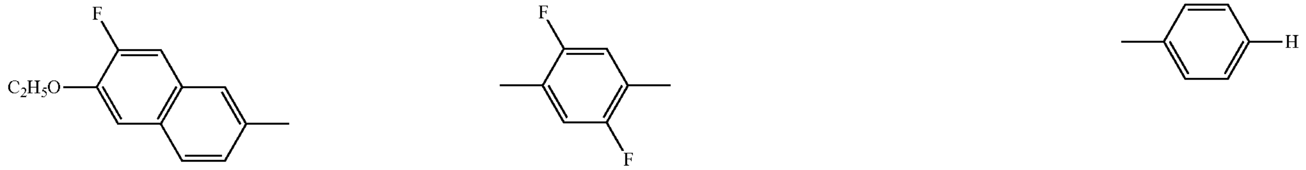 |
| 661 | 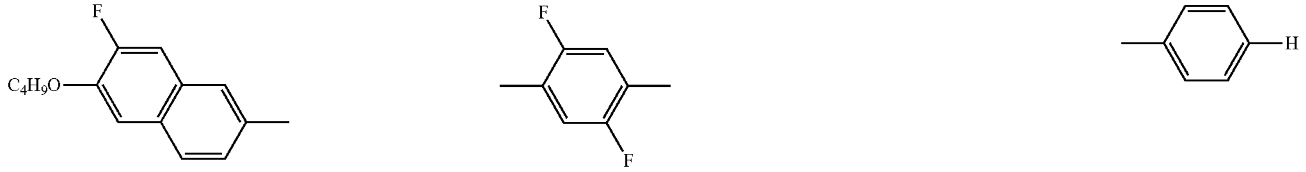 |

-continued
| | |
|---|---|
| 662 | 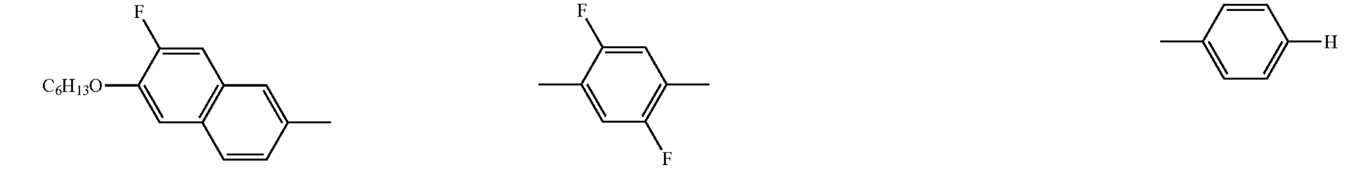 |
| 663 | 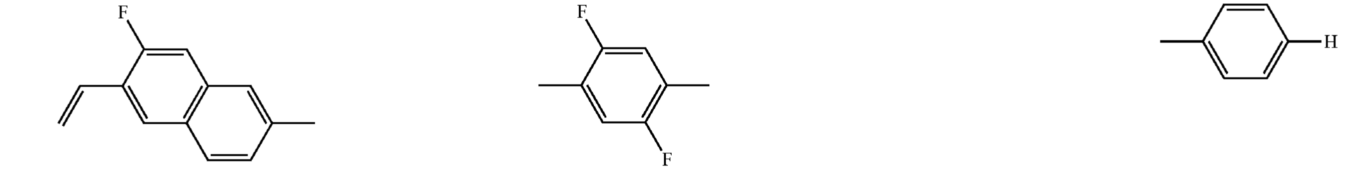 |
| 664 | 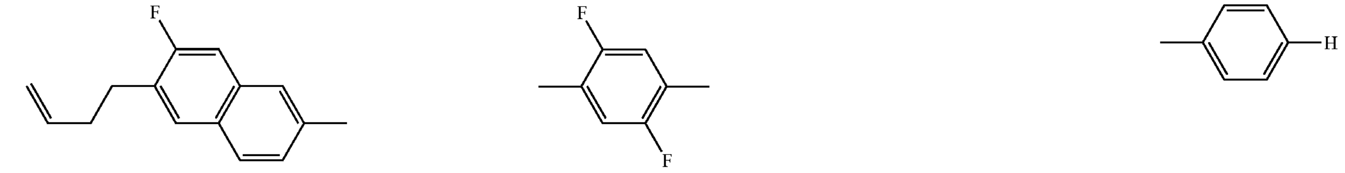 |
| 665 | 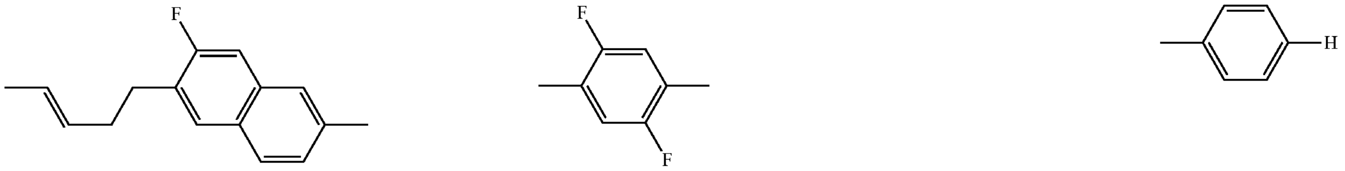 |
| 666 | 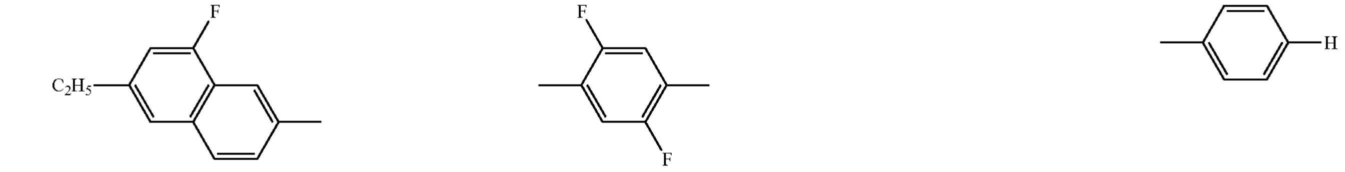 |

-continued
| | |
|---|---|
| 667 | 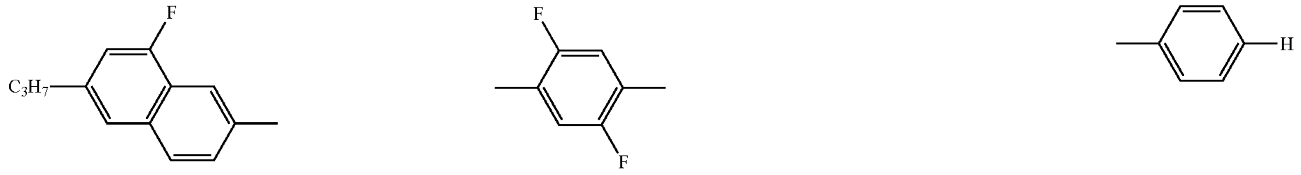 |
| 668 | 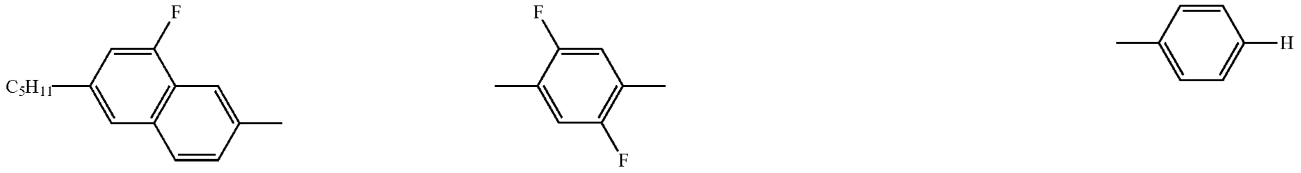 |
| 669 | 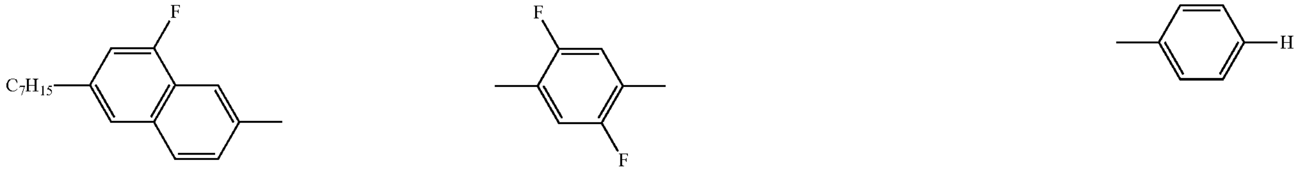 |
| 670 | 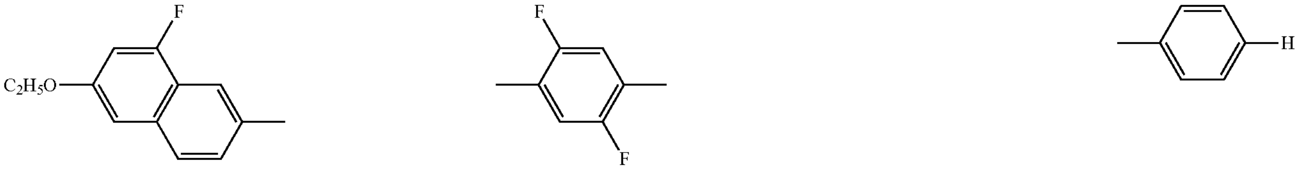 |
| 671 | 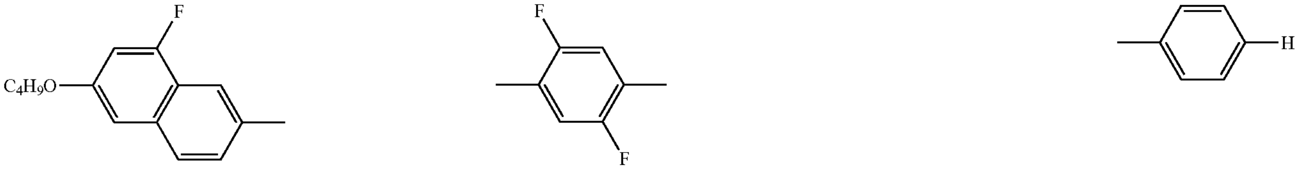 |

-continued
672 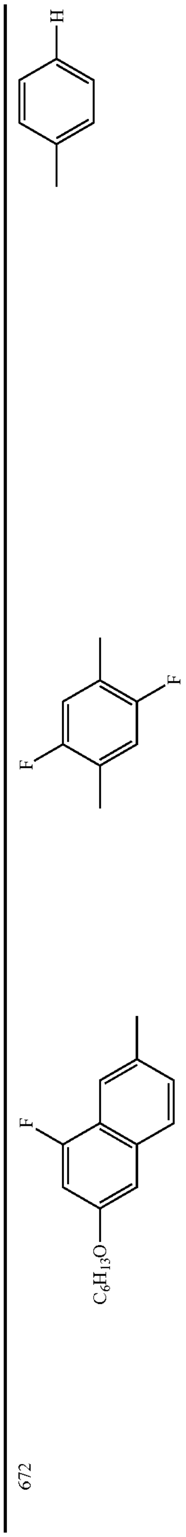
673 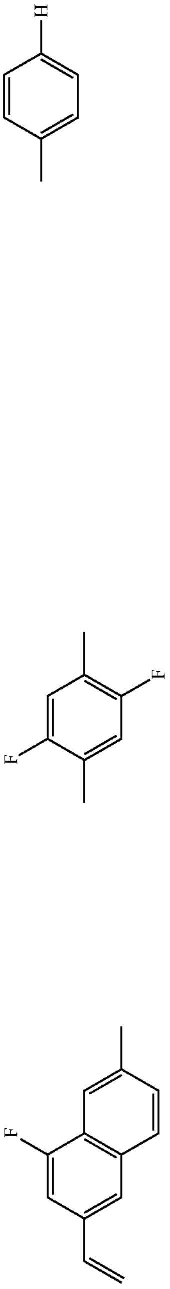
674 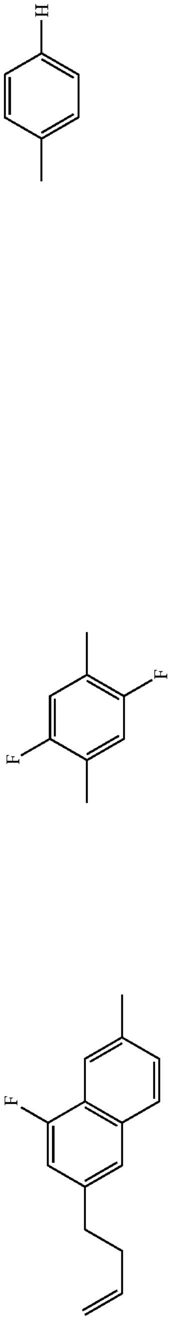
675 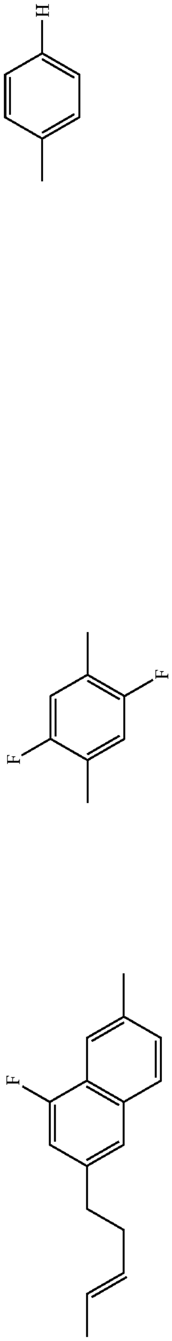
676 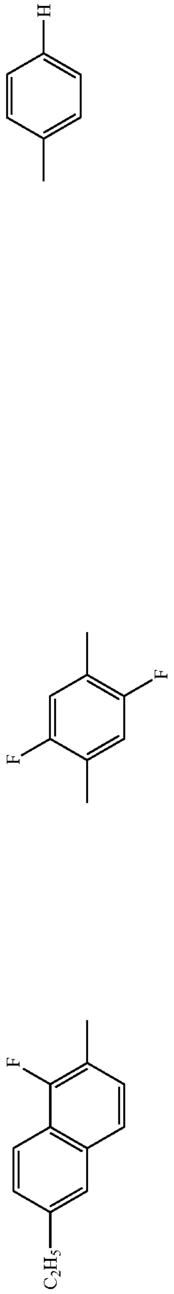

-continued
| | |
|---|---|
| 677 | 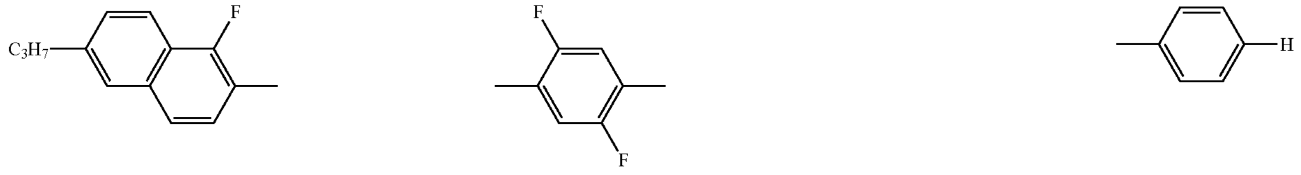 |
| 678 | 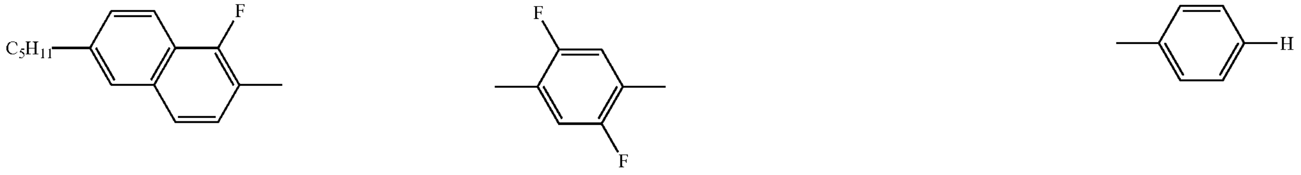 |
| 679 | 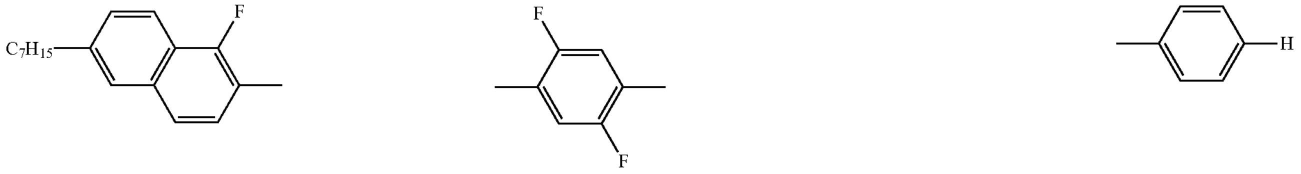 |
| 680 | 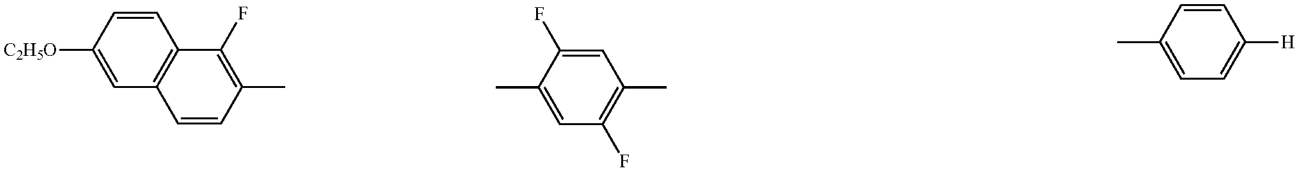 |
| 681 | 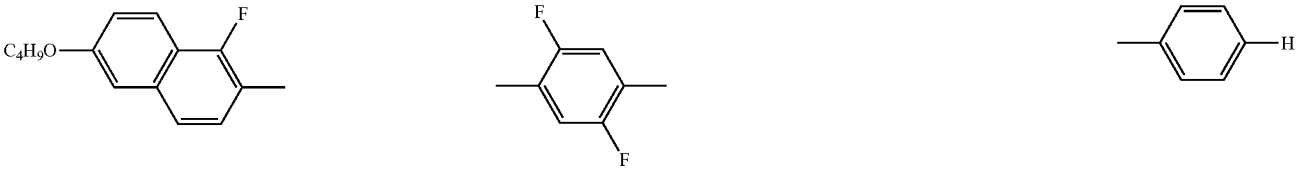 |

-continued
| | | | |
|---|---|---|---|
| 682 | 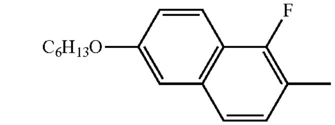 | 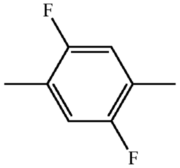 | 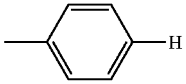 |
| 683 | 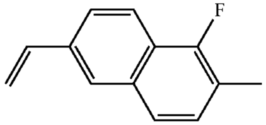 | 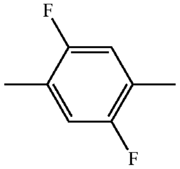 | 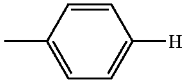 |
| 684 | 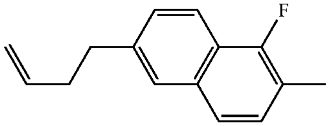 | 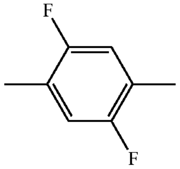 | 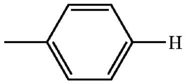 |
| 685 | 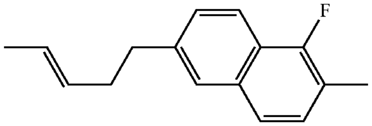 | 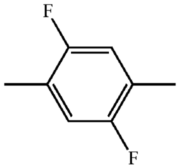 | 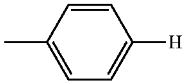 |
| 686 | 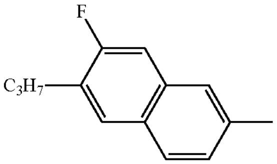 | 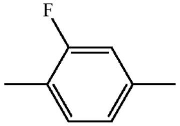 | 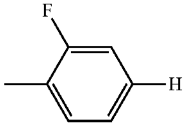 |
| 687 | 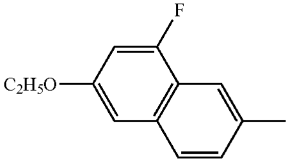 | 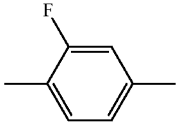 | 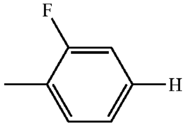 |

-continued
688 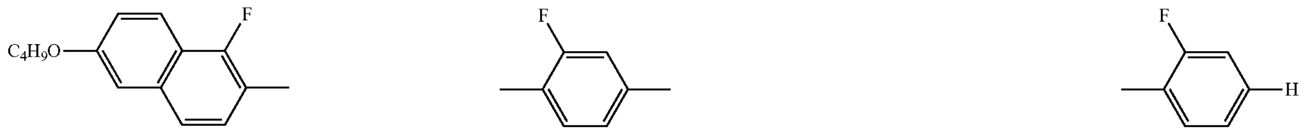
689 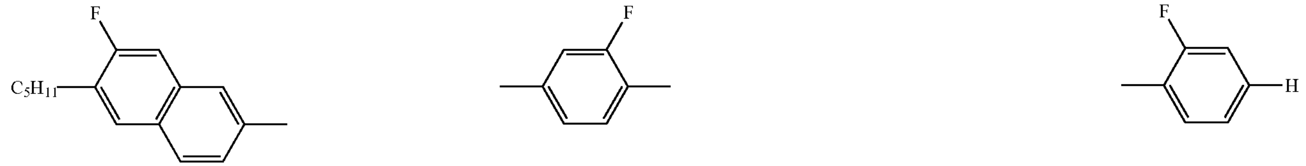
690 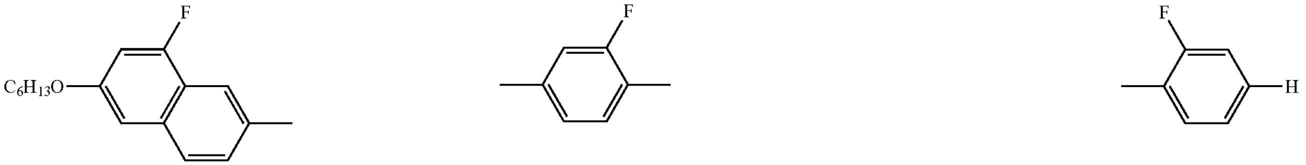
691 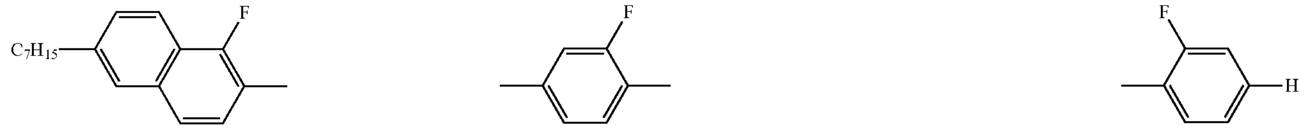
692 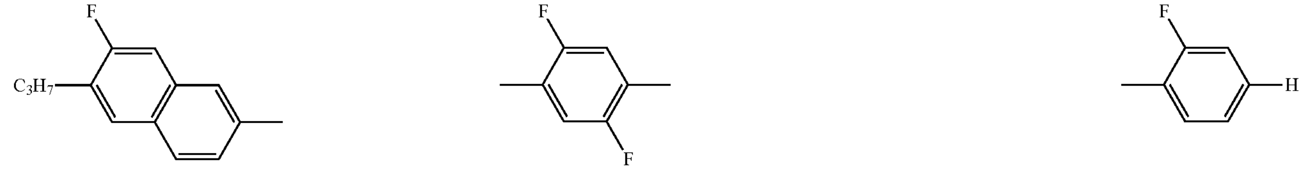
693 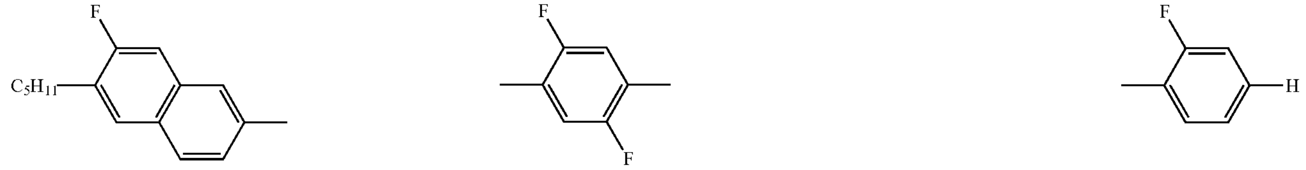

-continued
| | | | |
|---|---|---|---|
| 694 | 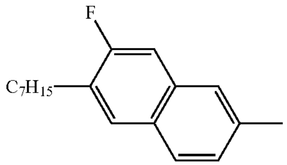 | 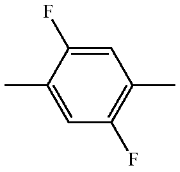 | 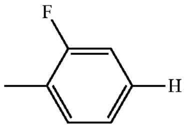 |
| 695 | 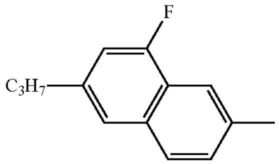 | 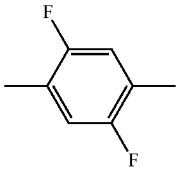 | 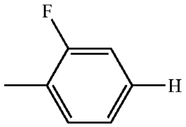 |
| 696 | 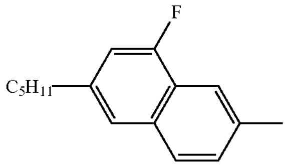 | 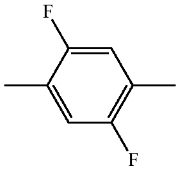 | 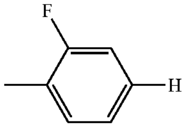 |
| 697 | 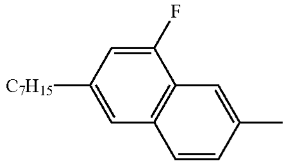 | 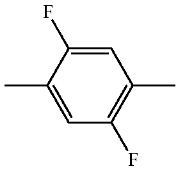 | 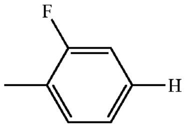 |
| 698 | 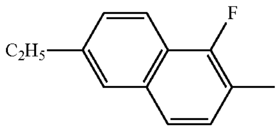 | 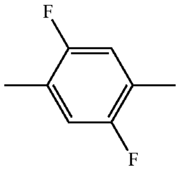 | 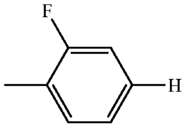 |

-continued
| | |
|---|---|
| 699 | 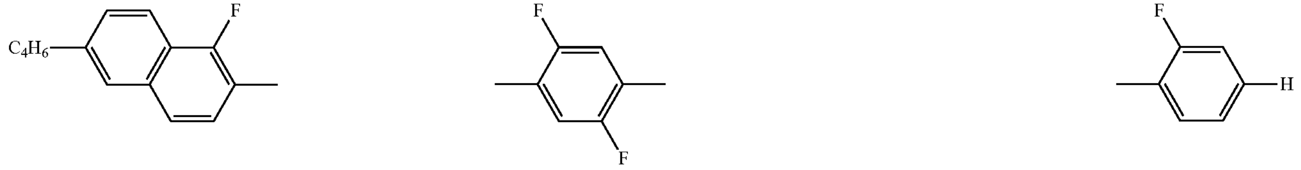 |
| 700 | 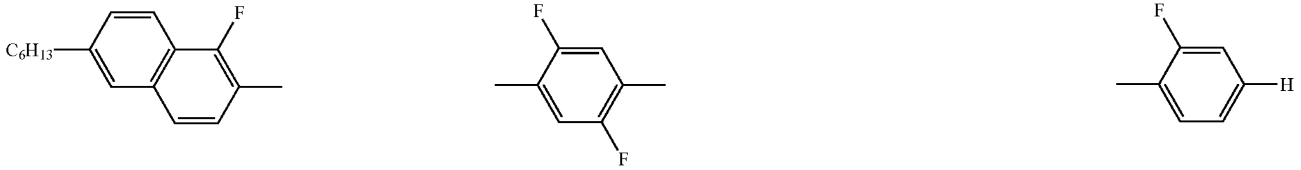 |
| 701 | 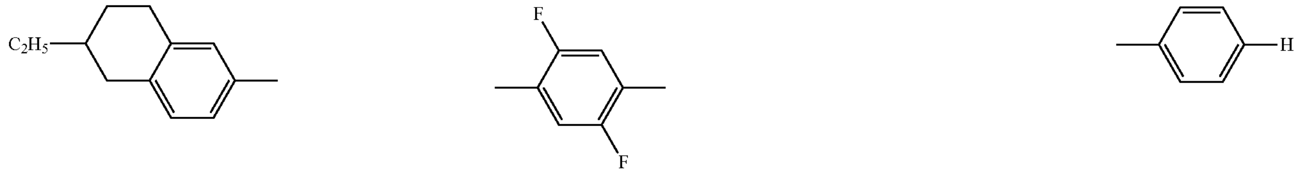 |
| 702 | 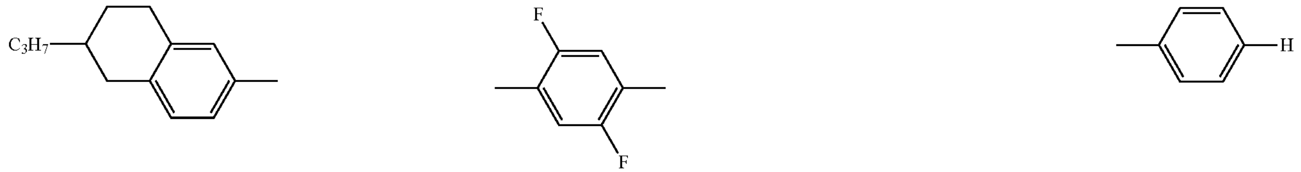 |
| 703 | 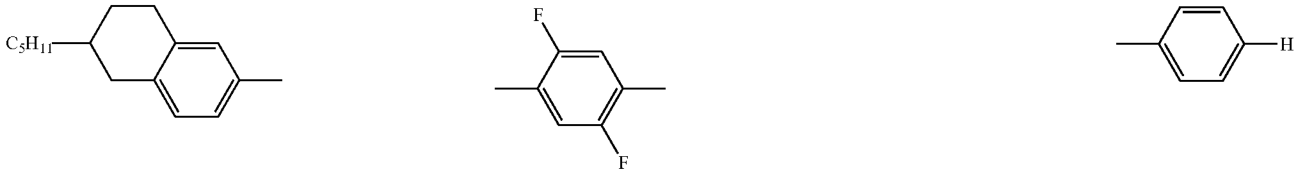 |

-continued
| | |
|---|---|
| 704 | 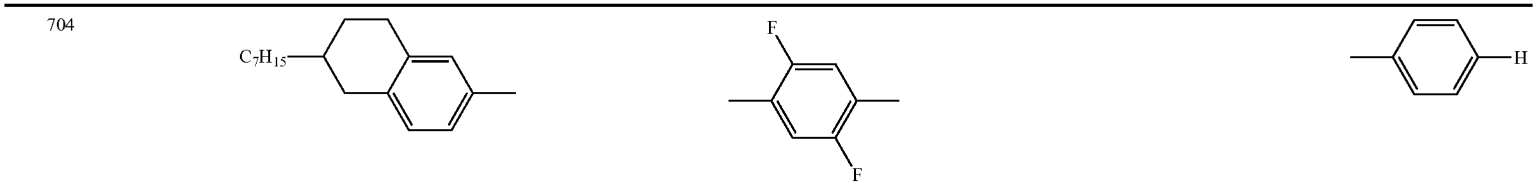 |
| 705 | 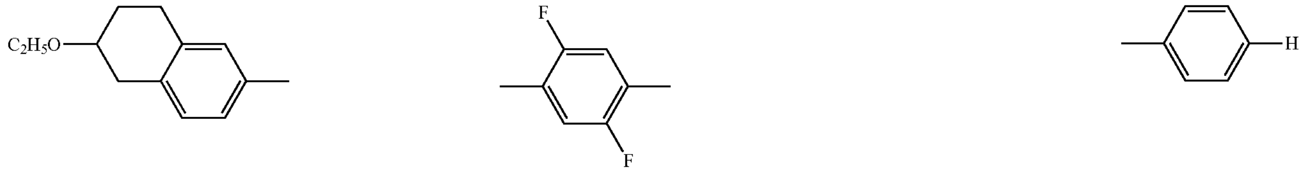 |
| 706 | 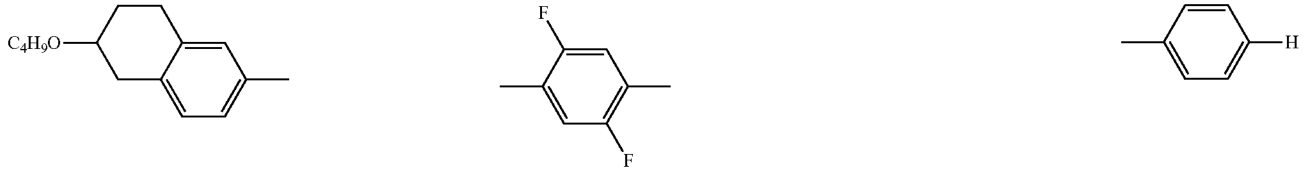 |
| 707 | 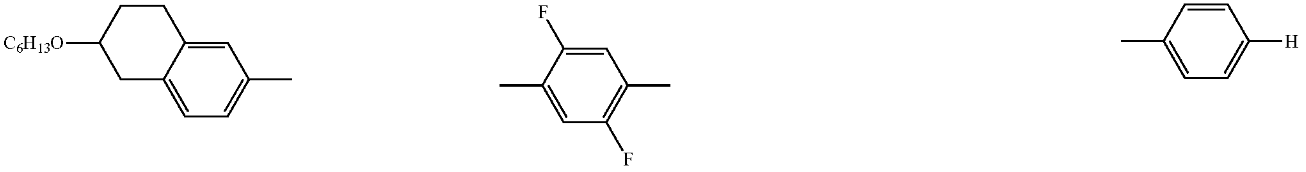 |
| 708 | 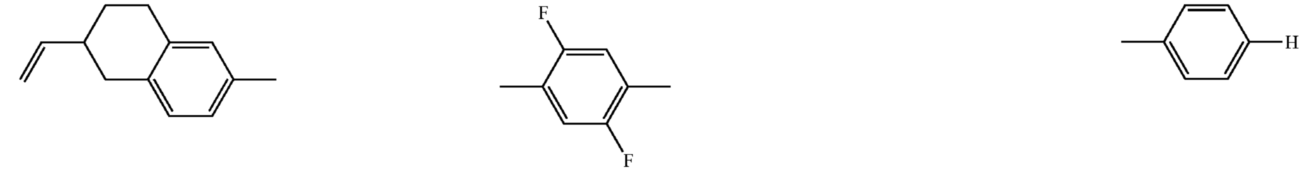 |

-continued
| | |
|---|---|
| 709 | 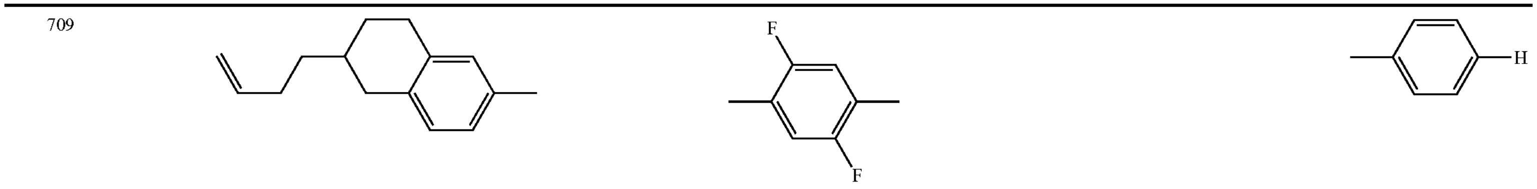 |
| 710 | 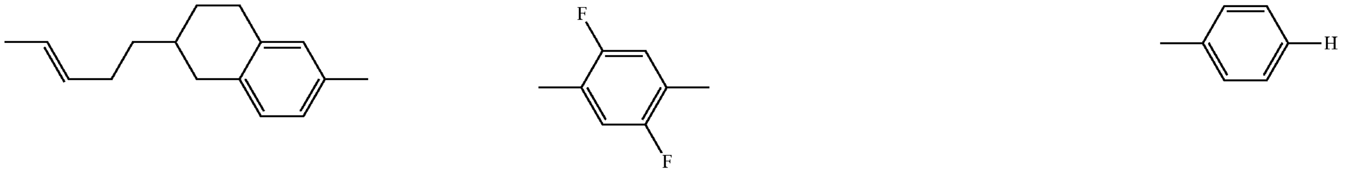 |
| 711 | 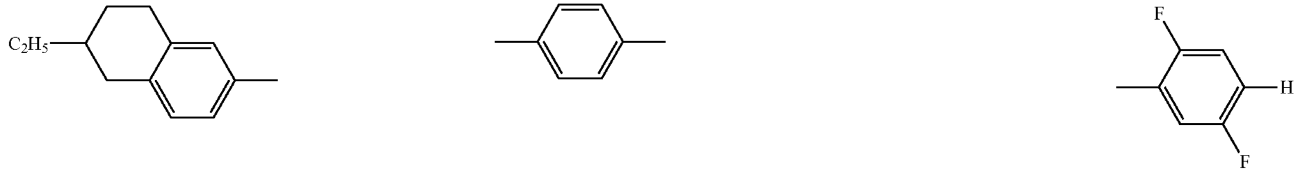 |
| 712 | 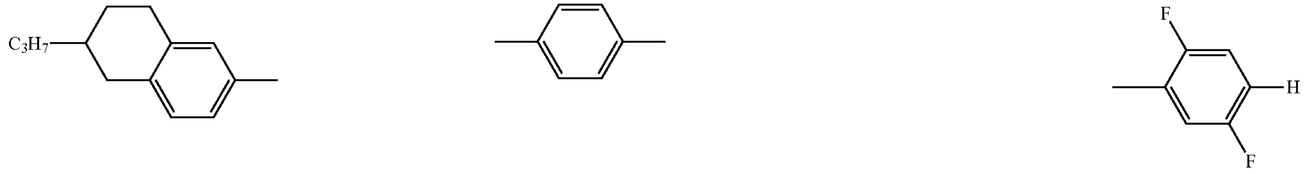 |
| 713 | 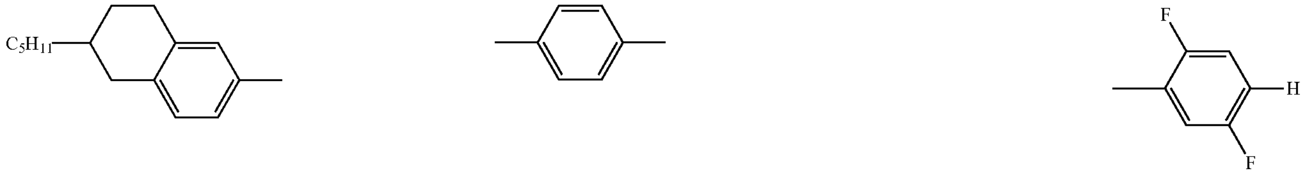 |

-continued
| | | | |
|---|---|---|---|
| 714 | 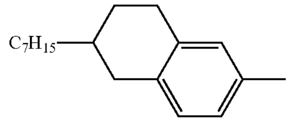 | 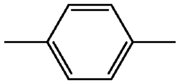 | 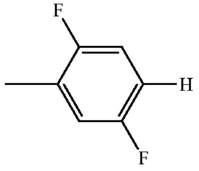 |
| 715 | 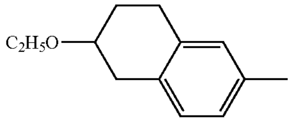 | 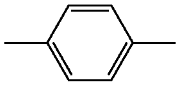 | 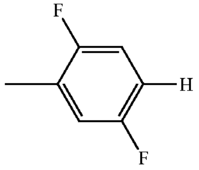 |
| 716 | 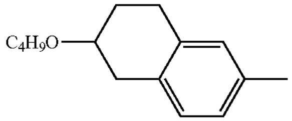 | 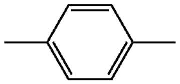 | 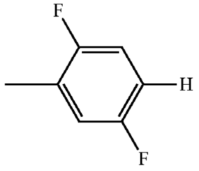 |
| 717 | 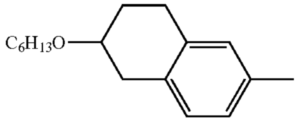 | 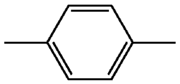 | 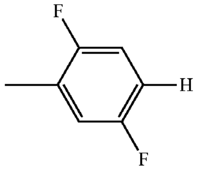 |
| 718 | 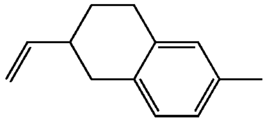 | 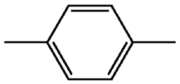 | 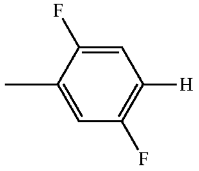 |

-continued
| | | | |
|---|---|---|---|
| 719 | 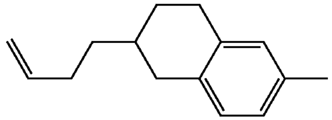 | 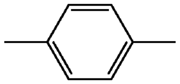 | 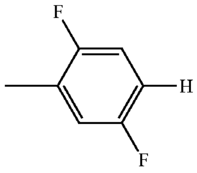 |
| 720 | 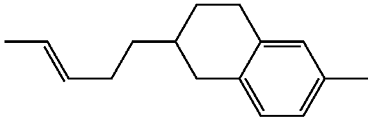 | 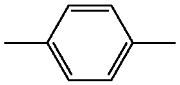 | 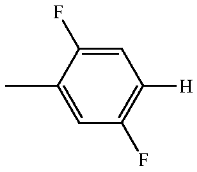 |
| 721 | 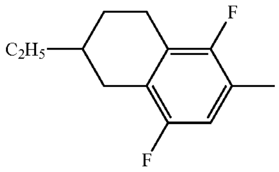 | 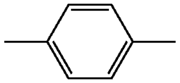 | 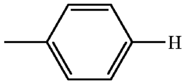 |
| 722 | 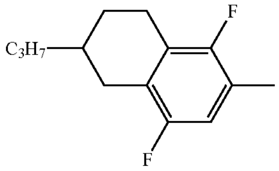 | 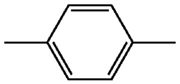 | 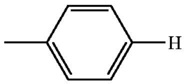 |
| 723 | 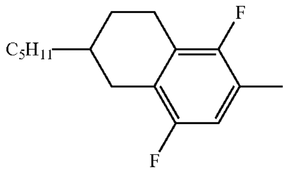 | 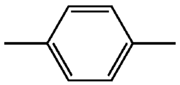 | 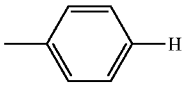 |

-continued
724 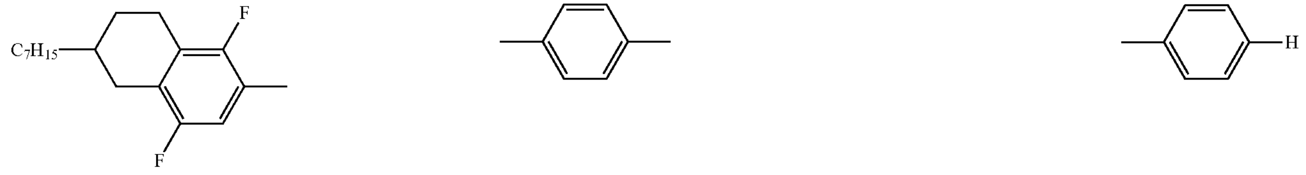
725 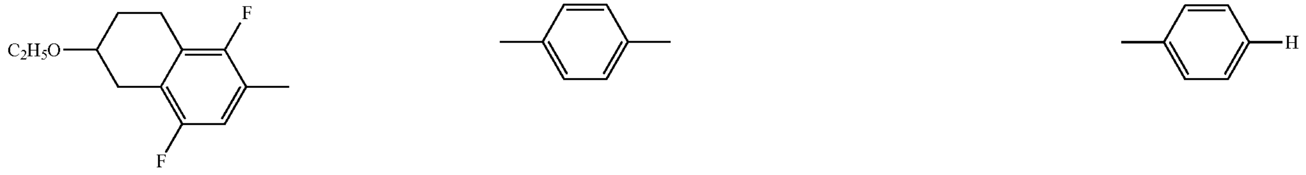
726 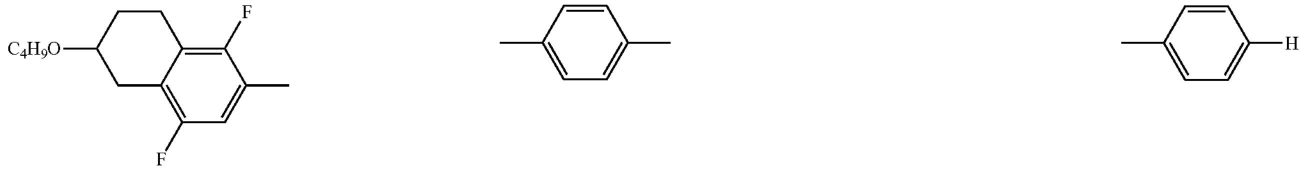
727 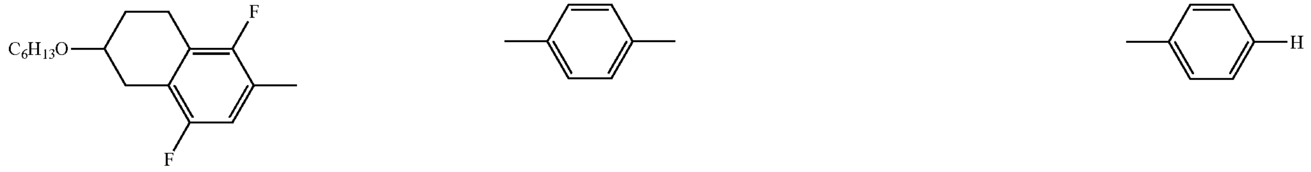
728 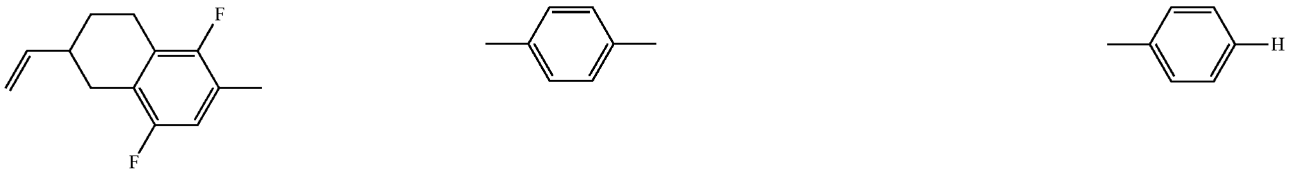

-continued
729 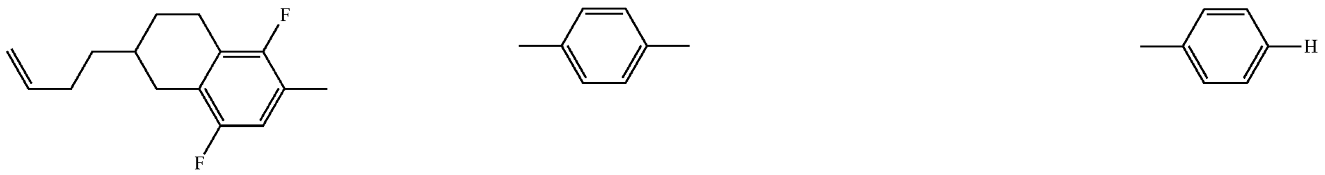
730 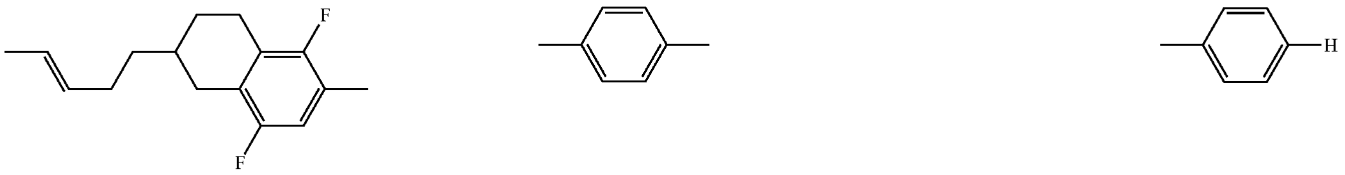
731 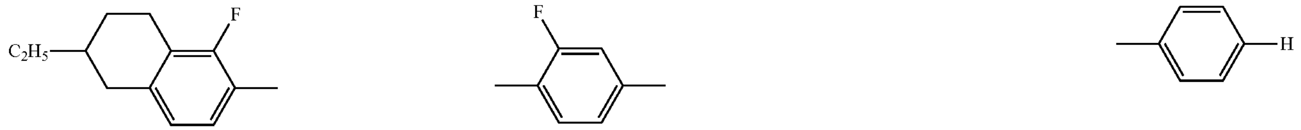
732 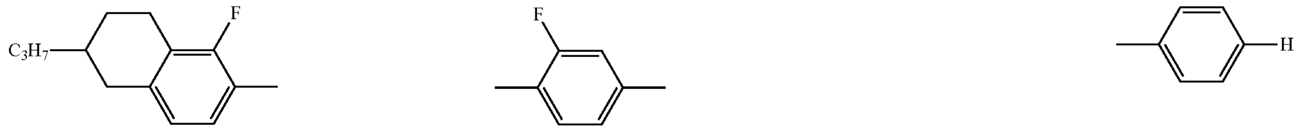
733 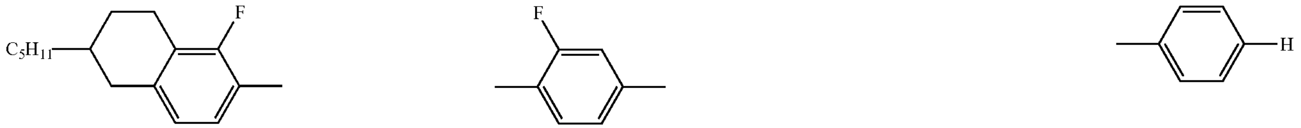
734 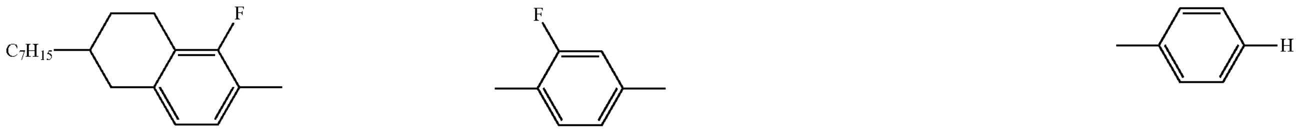
735 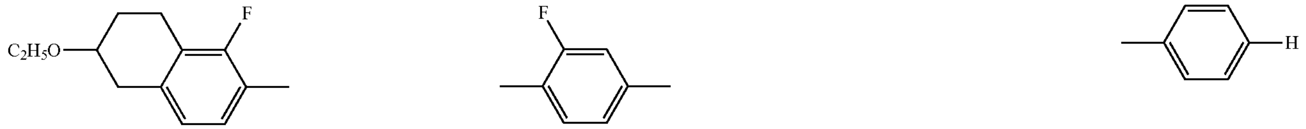

-continued
736 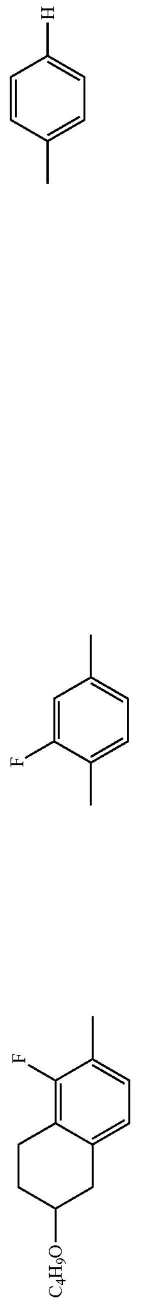
737 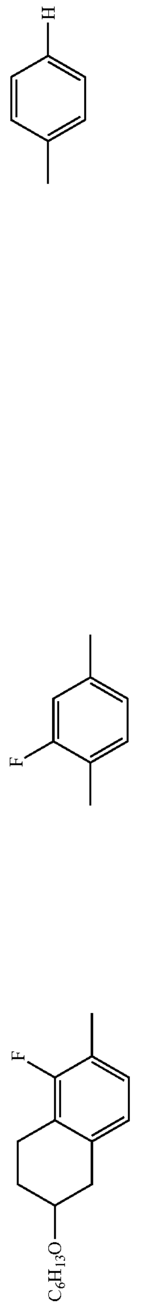
738 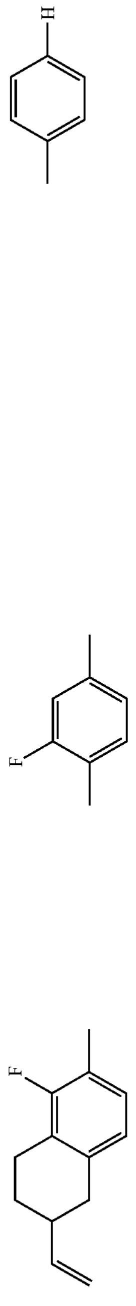
739 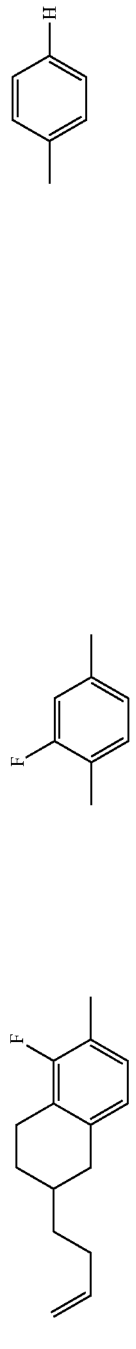
740 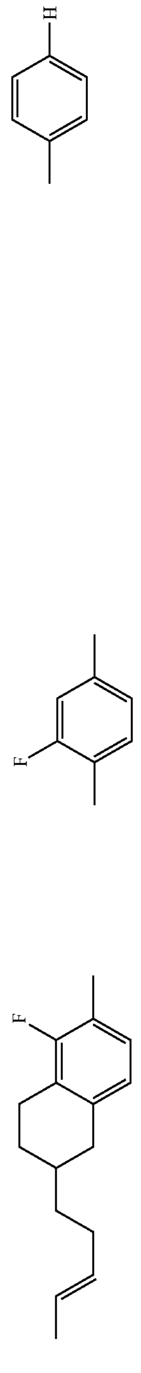
741 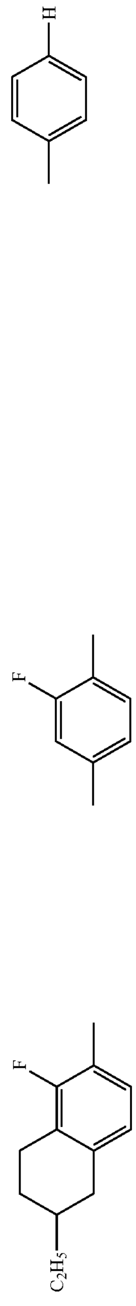
742 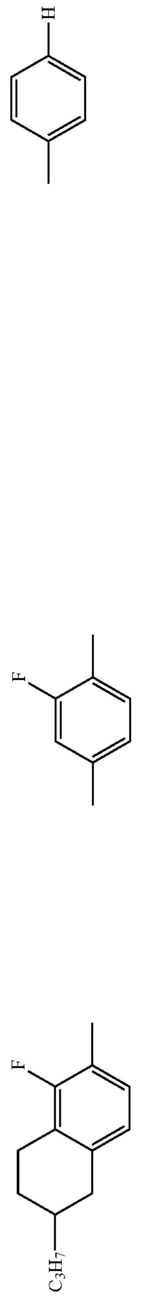

-continued
743 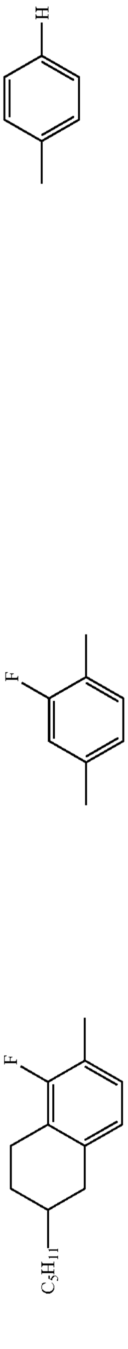
744 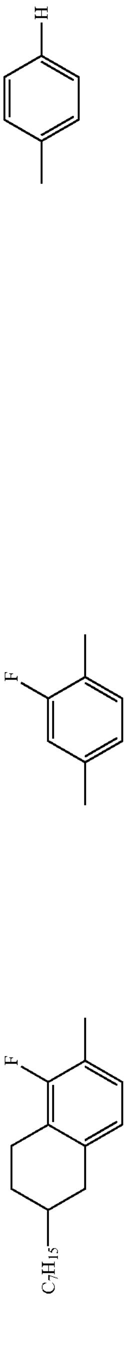
745 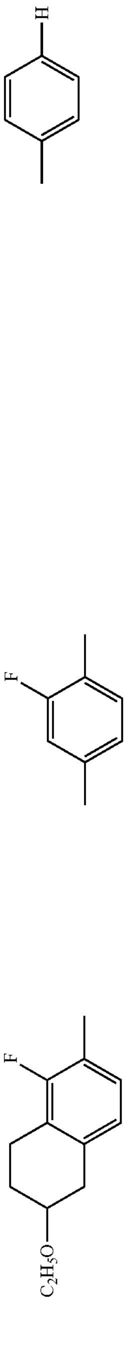
746 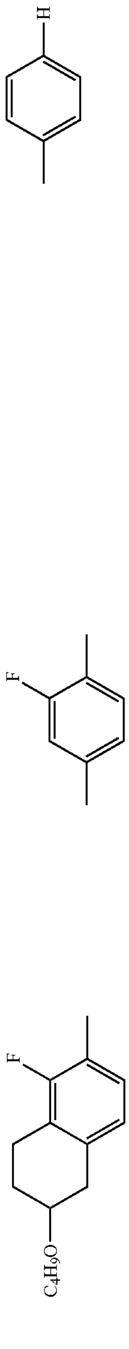
747 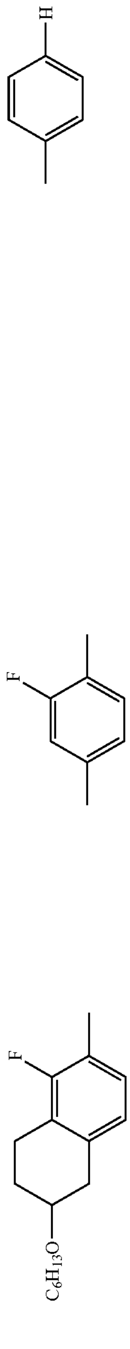
748 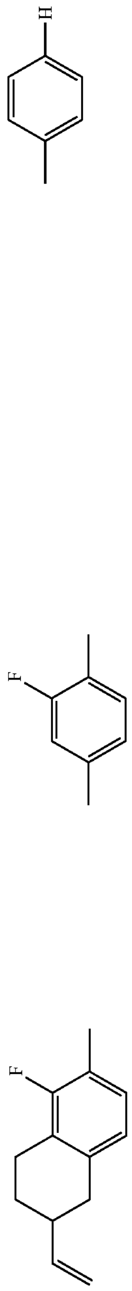
749 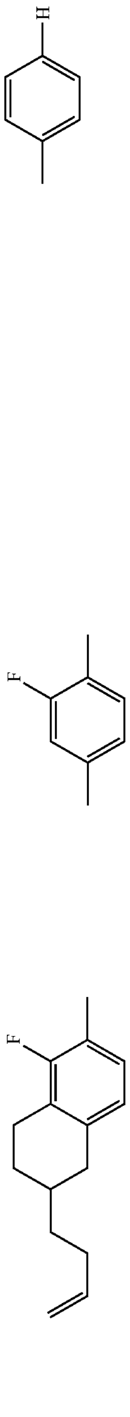

-continued
| | |
|---|---|
| 750 | 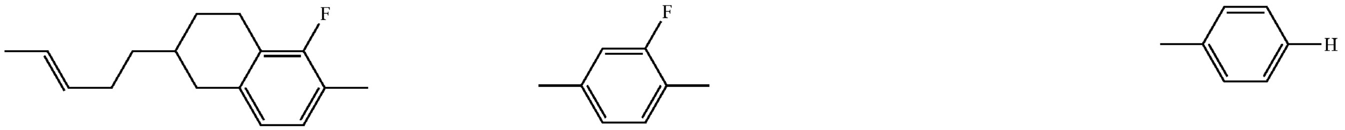 |
| 751 | 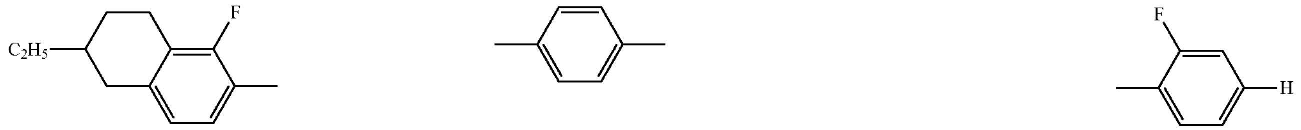 |
| 752 | 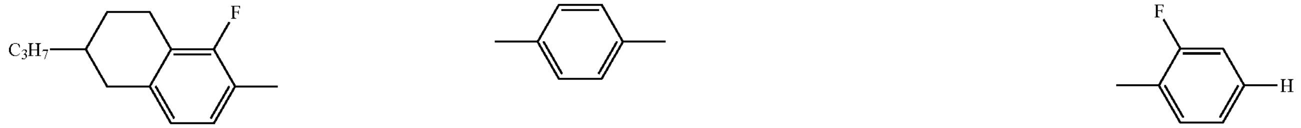 |
| 753 | 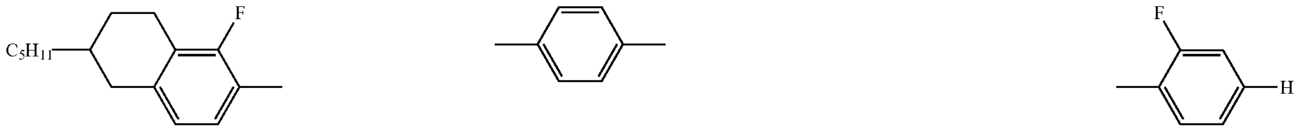 |
| 754 | 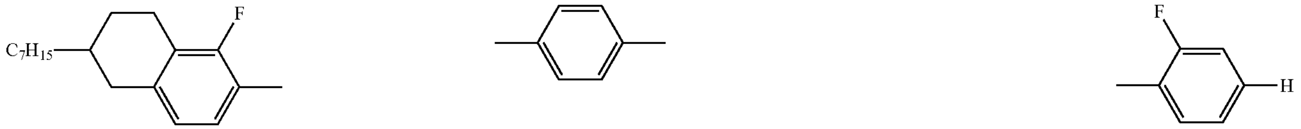 |
| 755 | 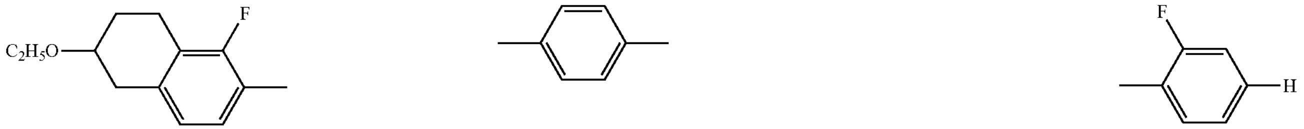 |
| 756 | 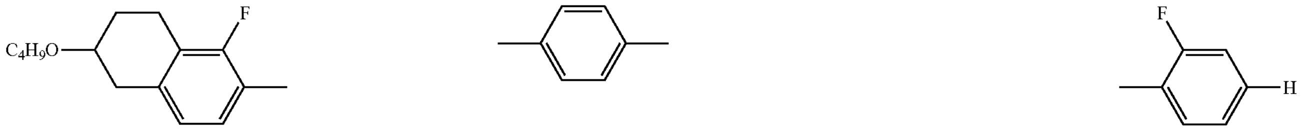 |

-continued
757 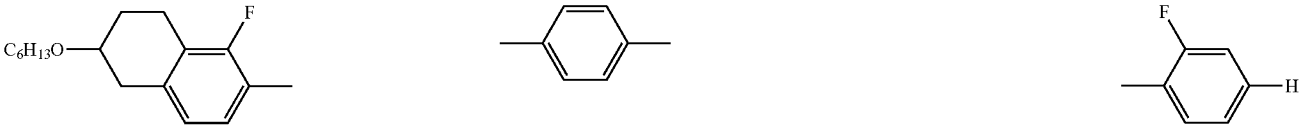
758 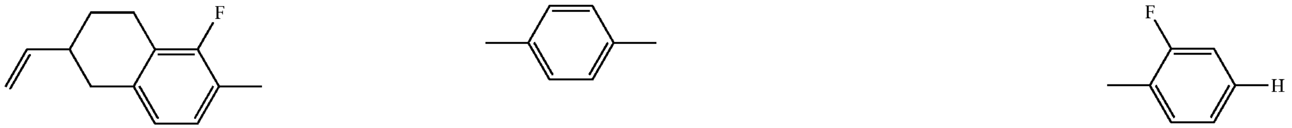
759 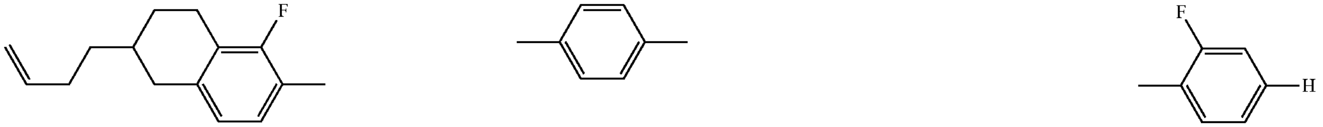
760 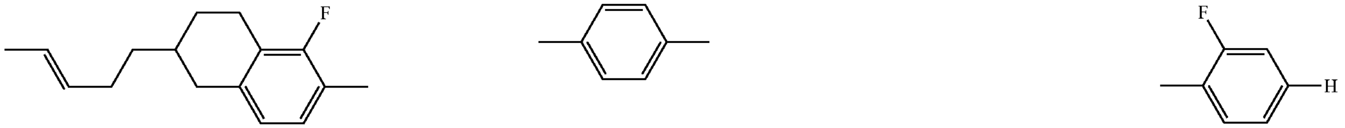
761 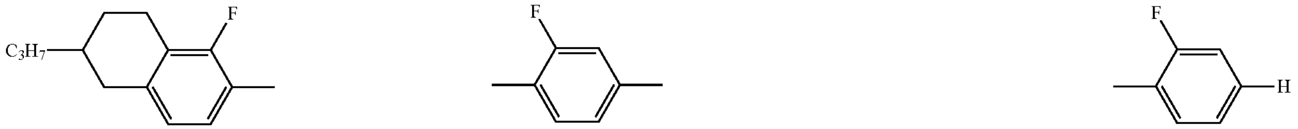
762 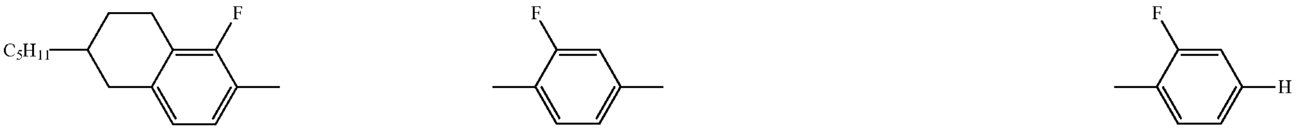
763 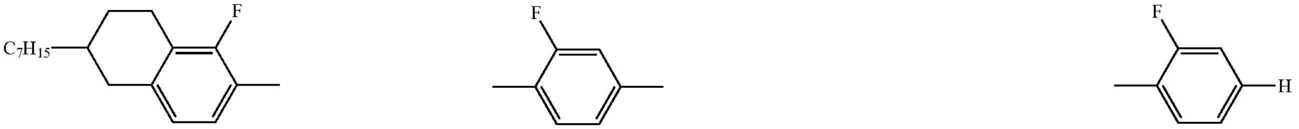

-continued
764 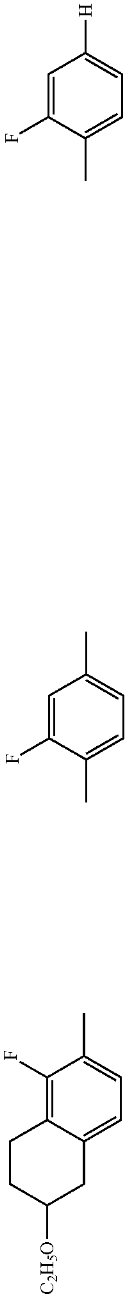
765 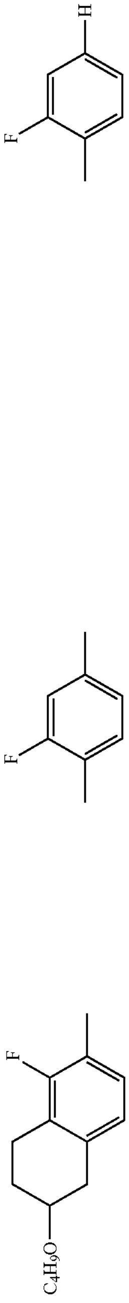
766 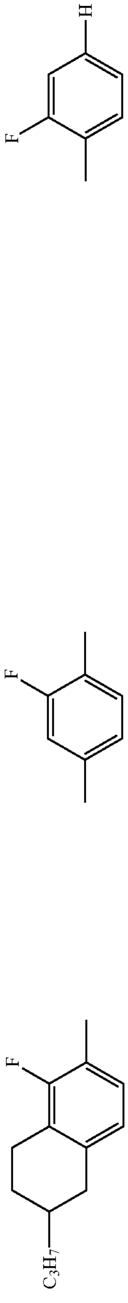
767 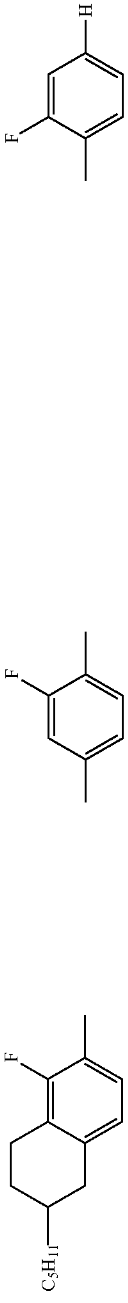
768 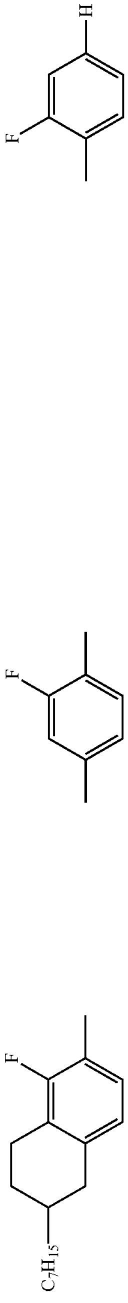
769 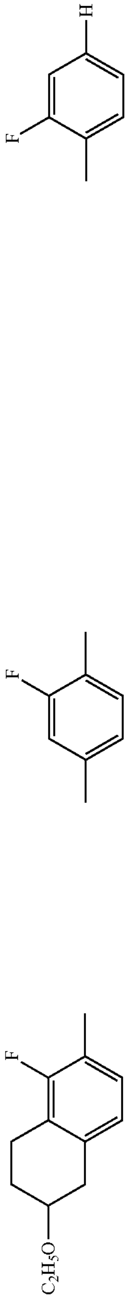
770 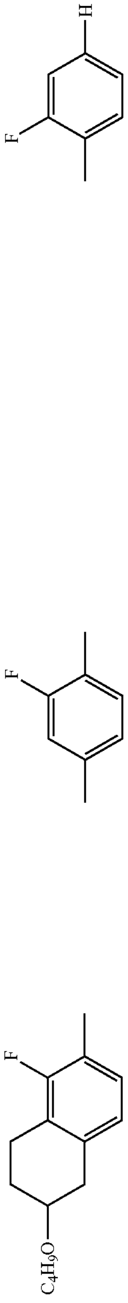

771 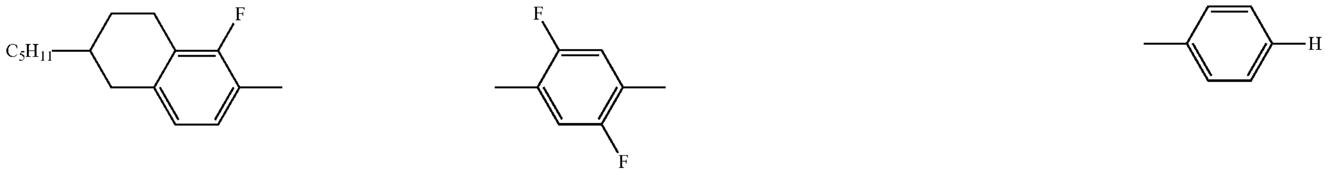
772 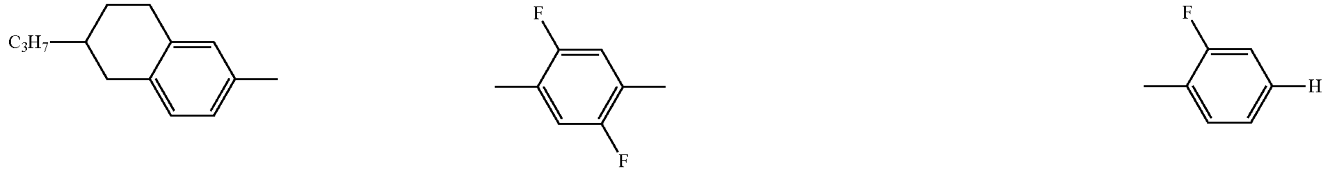
773 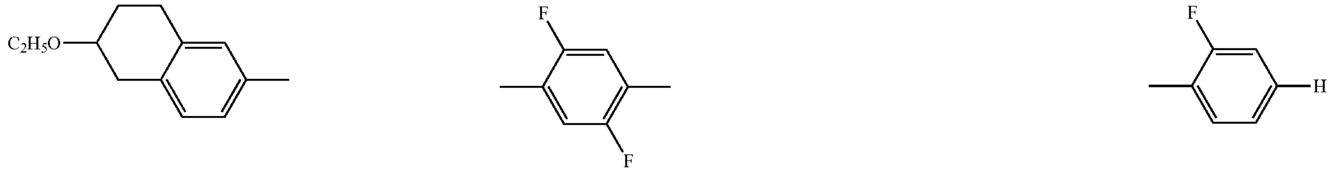
774 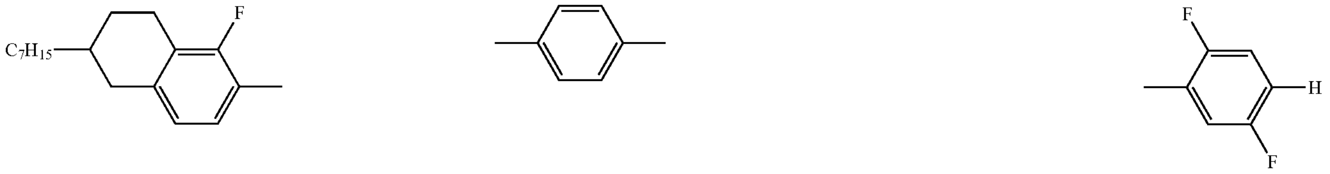
775 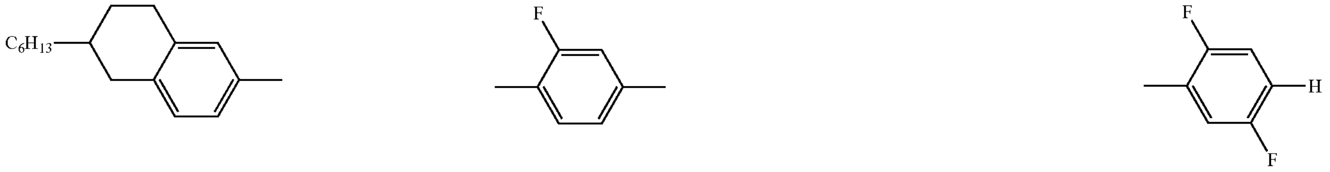

-continued
776 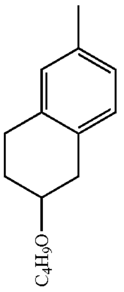 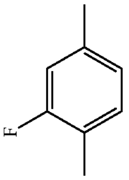 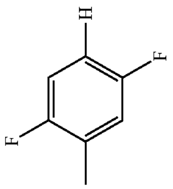
777 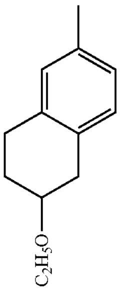 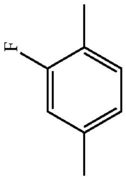 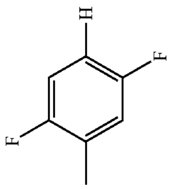
778 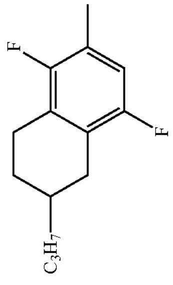 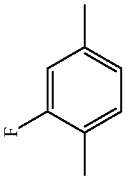 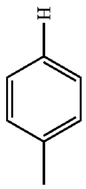
779 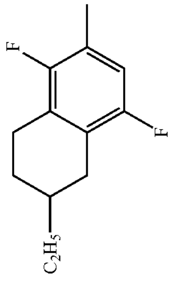 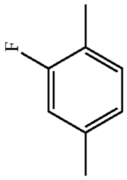 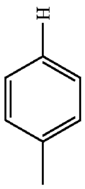
780 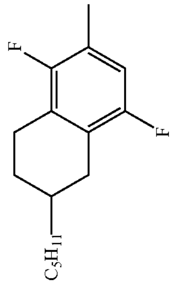 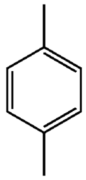 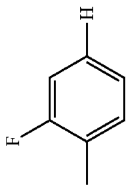

| | | | |
|---|---|---|---|
| 781 | 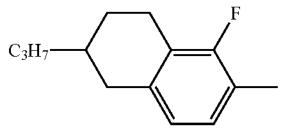 | 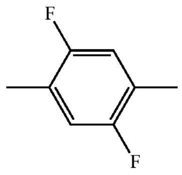 | 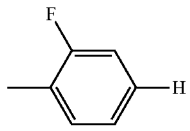 |
| 782 | 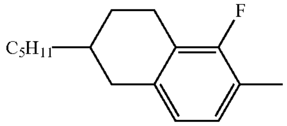 | 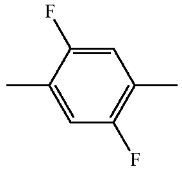 | 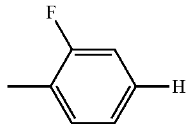 |
| 783 | 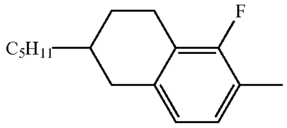 | 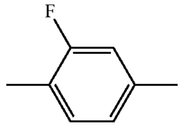 | 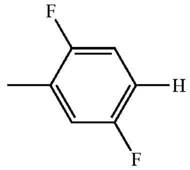 |
| 784 | 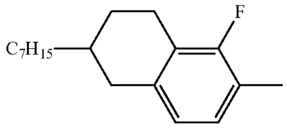 | 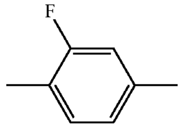 | 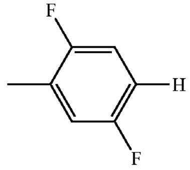 |
| 785 | 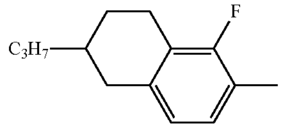 | 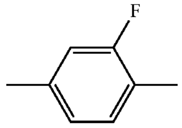 | 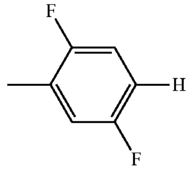 |

-continued
786 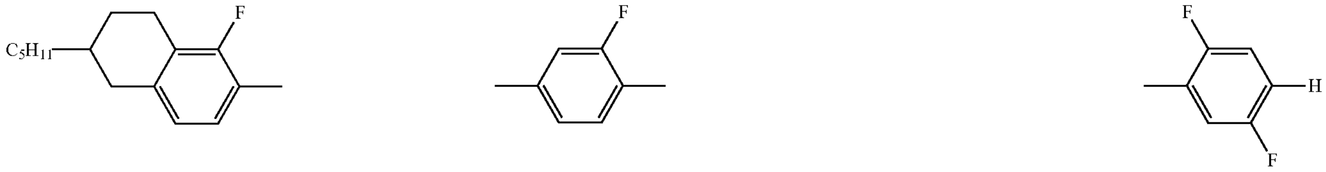
787 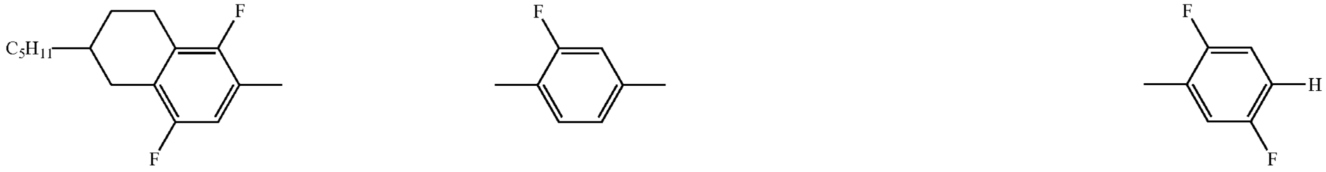
788 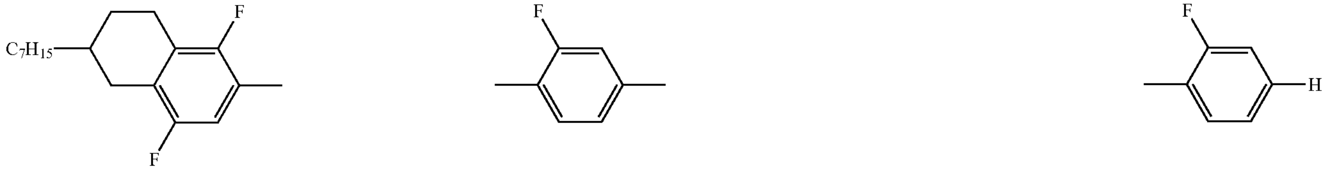
789 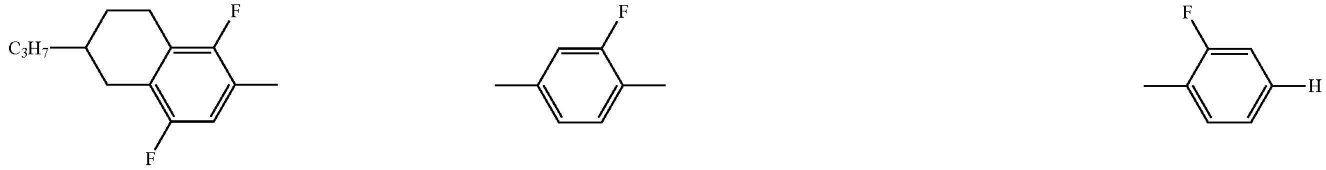
790 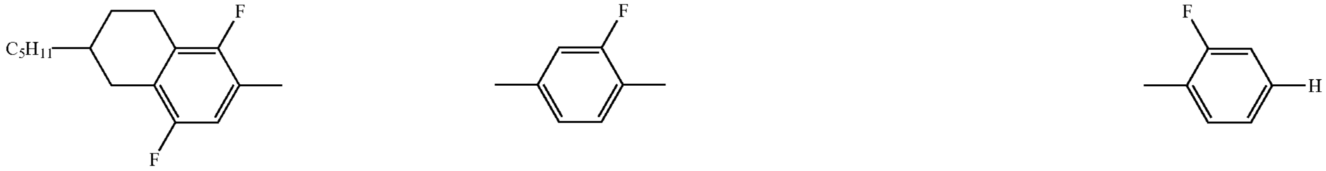

-continued
| | |
|---|---|
| 791 | 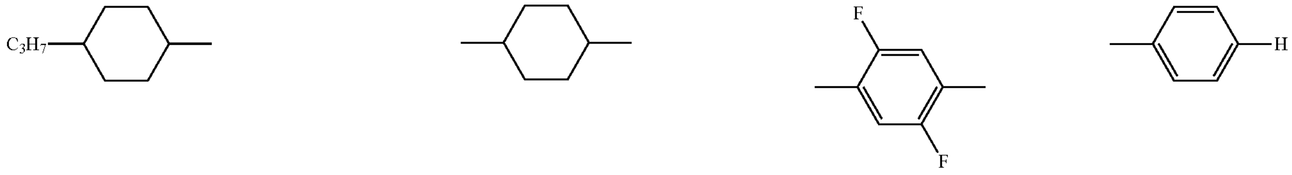 |
| 792 | 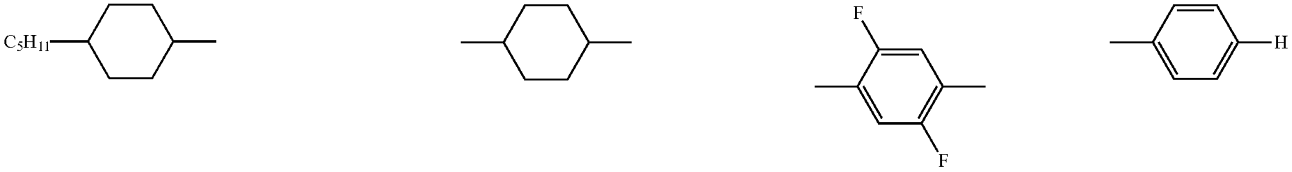 |
| 793 | 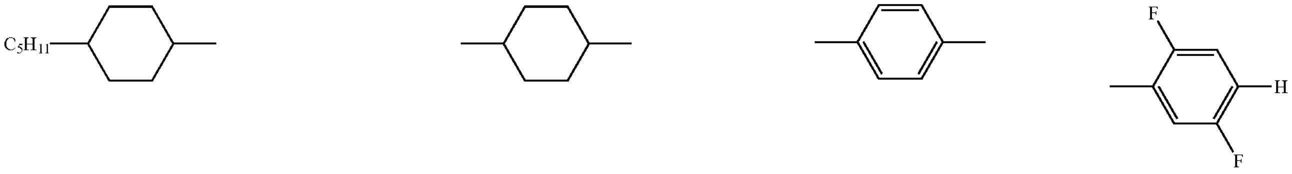 |
| 794 | 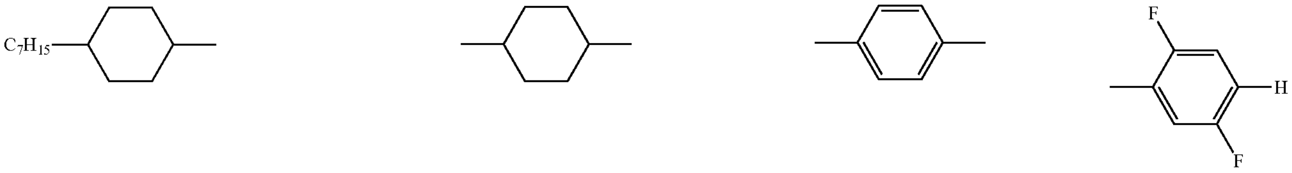 |
| 795 | 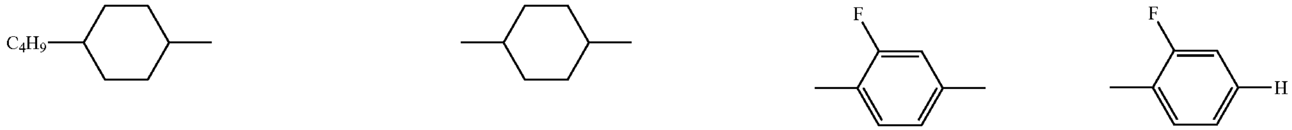 |
| 796 | 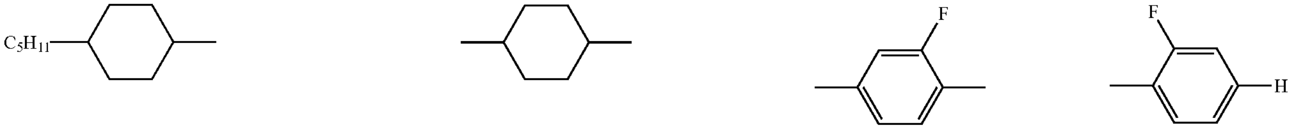 |

-continued
| | |
|---|---|
| 797 | 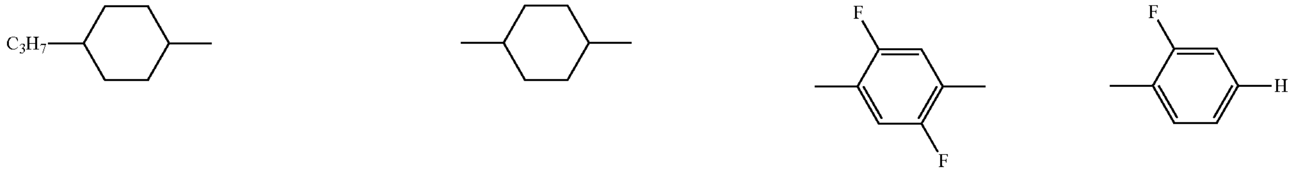 |
| 798 | 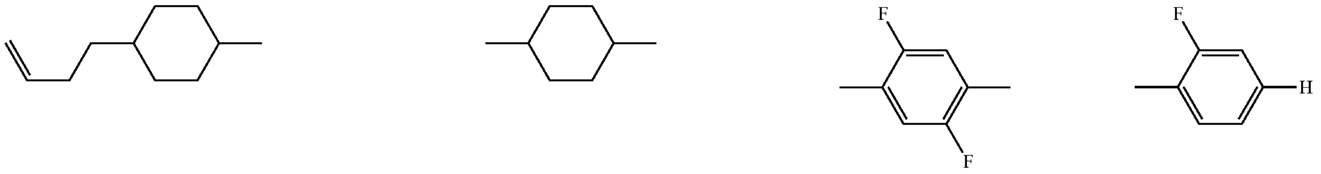 |
| 799 | 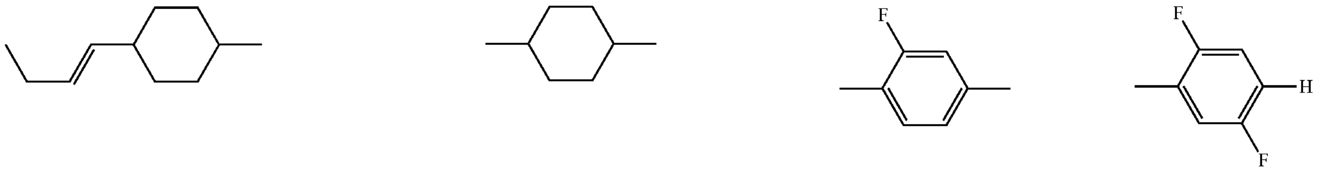 |
| 800 | 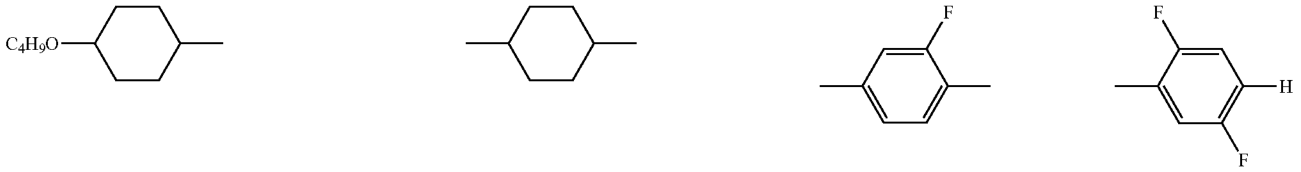 |
| 801 | 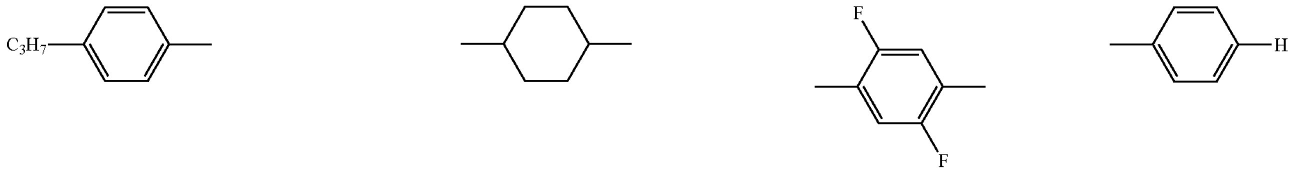 |

-continued
| | | | | |
|---|---|---|---|---|
| 802 | 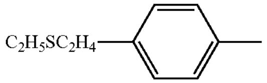 | 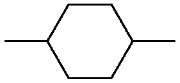 | 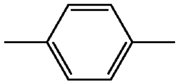 | 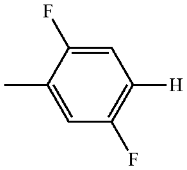 |
| 803 | 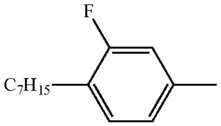 | 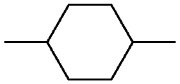 | 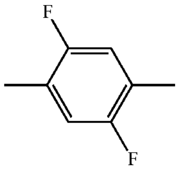 | 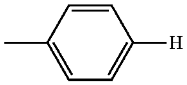 |
| 804 | 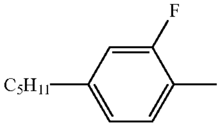 | 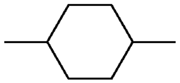 | 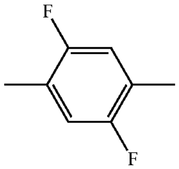 | 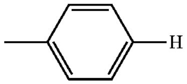 |
| 805 | 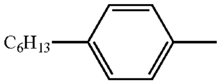 | 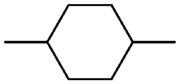 | 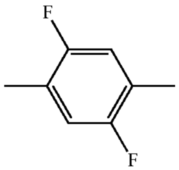 | 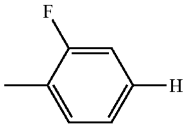 |
| 806 | 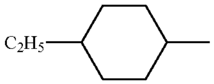 | 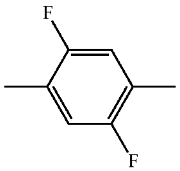 | 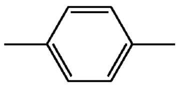 | 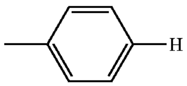 |

-continued
807 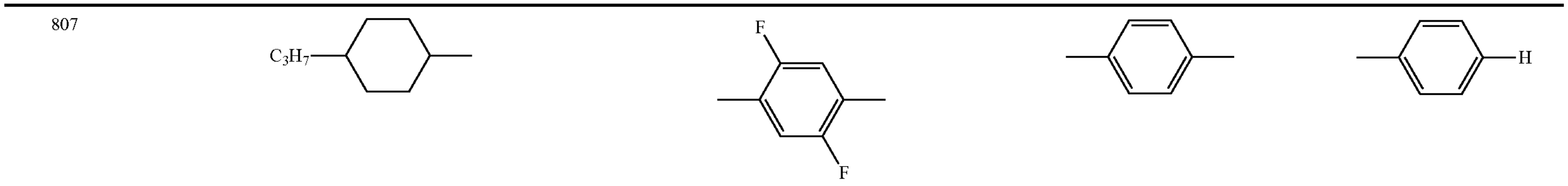
808 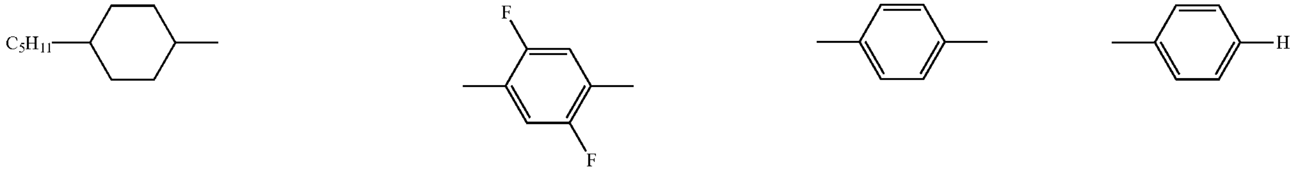
809 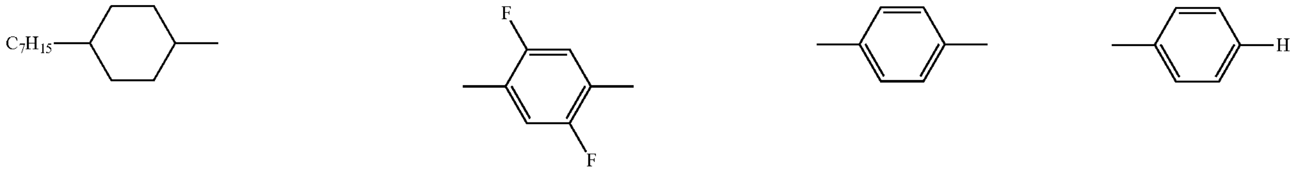
810 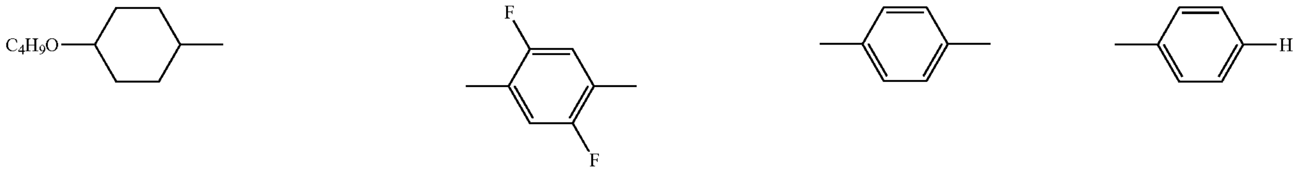
811 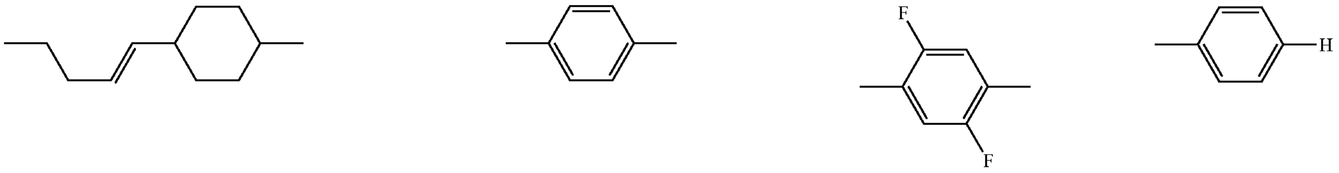

-continued
| | |
|---|---|
| 812 | 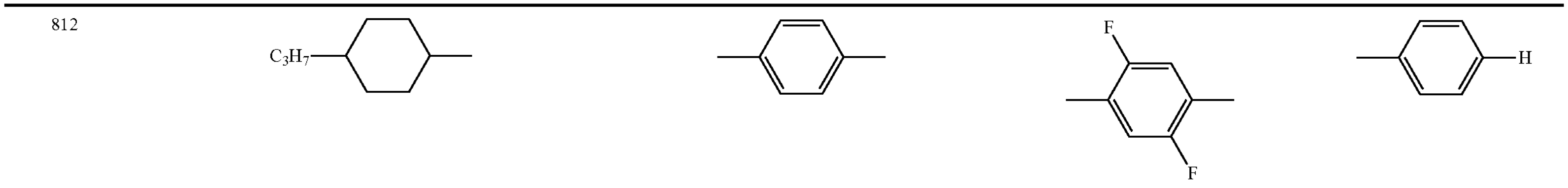 |
| 813 | 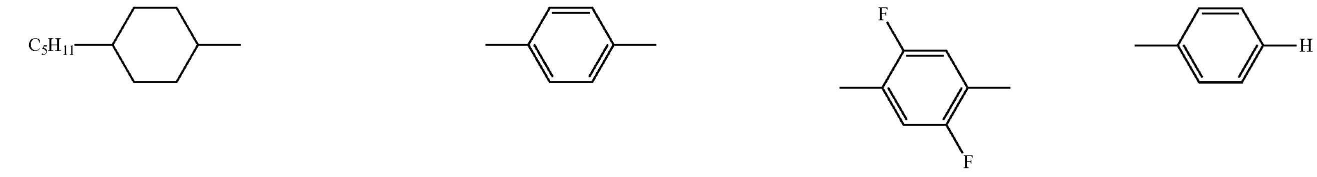 |
| 814 | 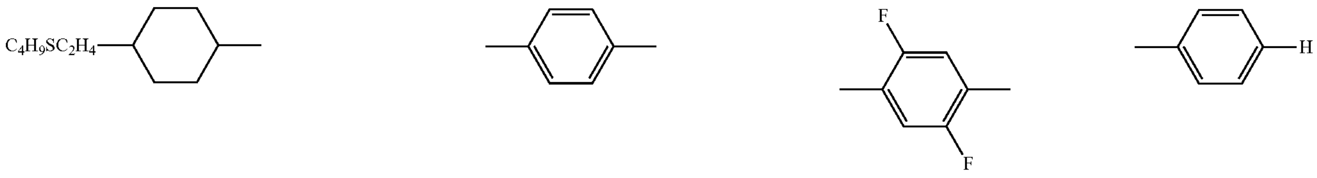 |
| 815 | 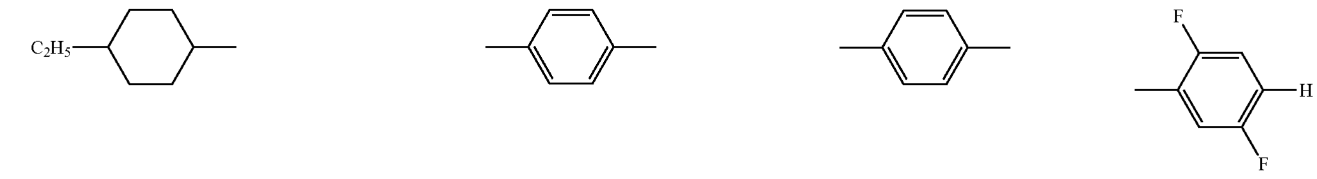 |
| 816 | 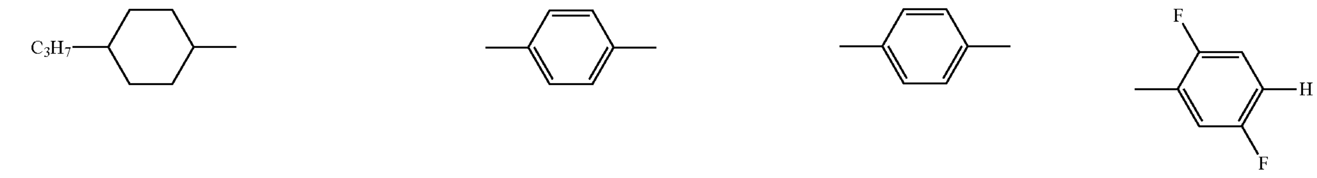 |

-continued
| | |
|---|---|
| 817 | 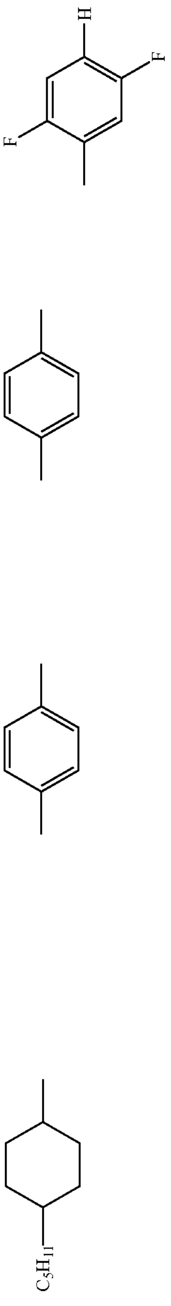 |
| 818 | 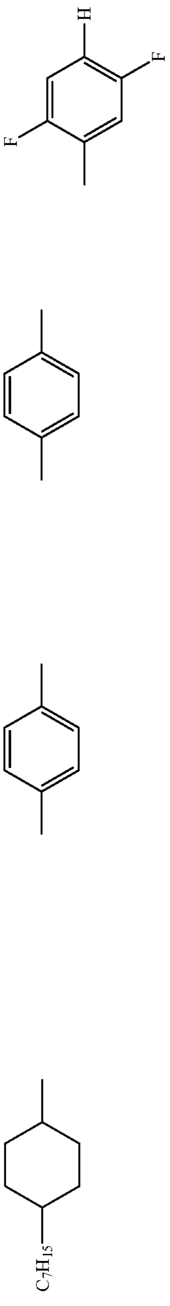 |
| 819 | 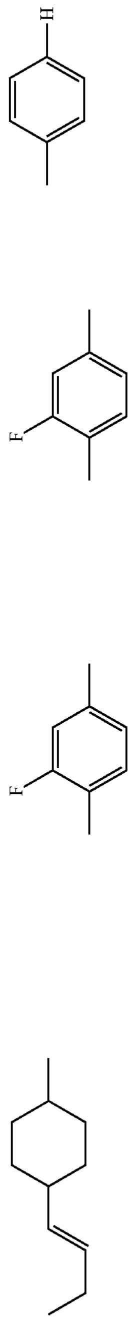 |
| 820 | 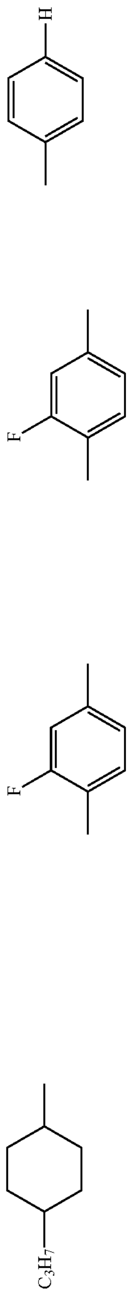 |
| 821 | 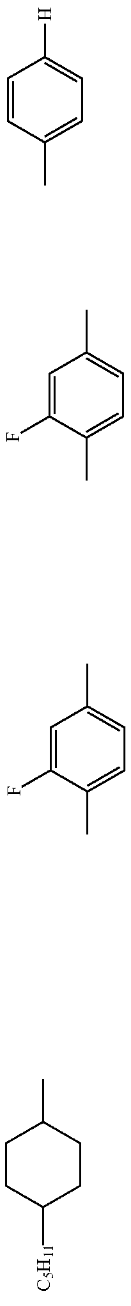 |
| 822 | 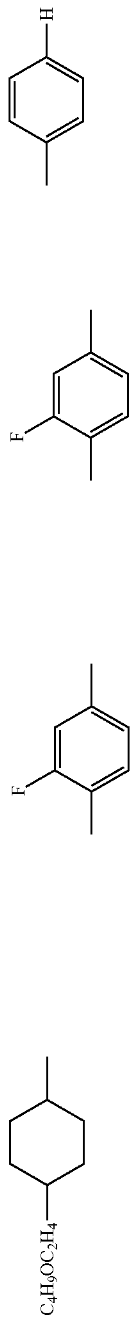 |
| 823 | 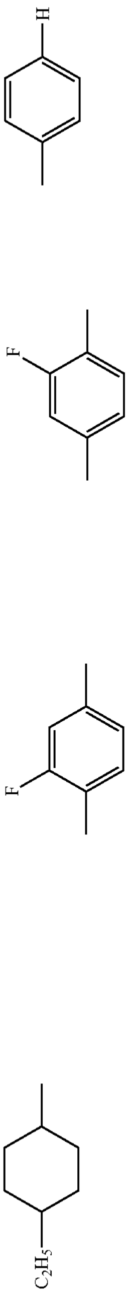 |

-continued
824 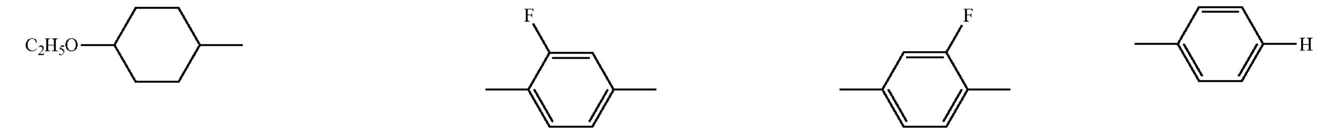
825 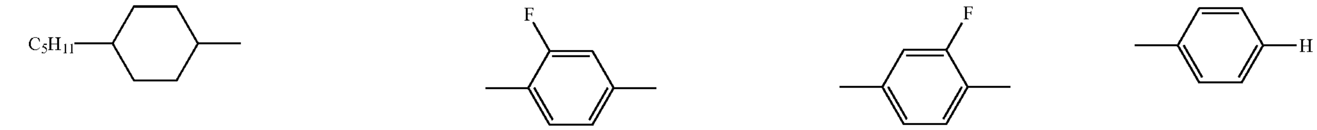
826 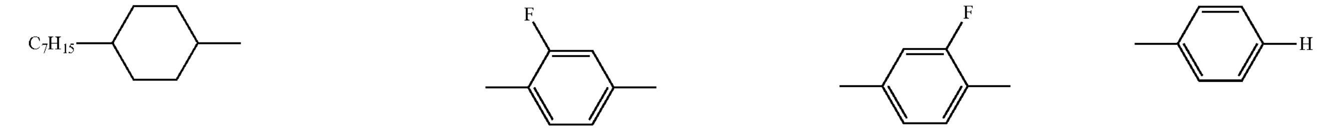
827 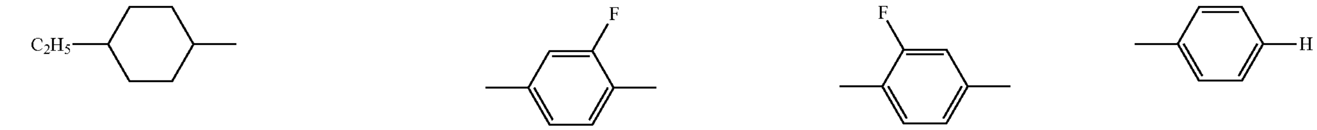
828 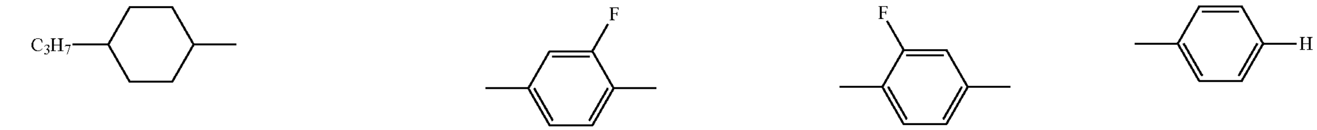
829 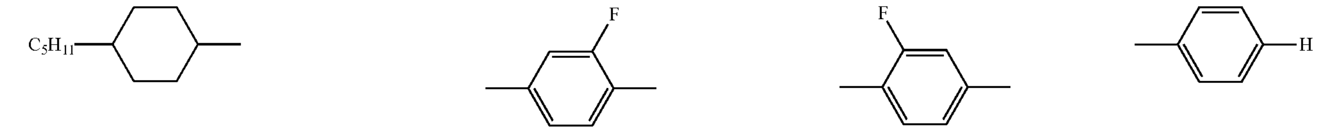
830 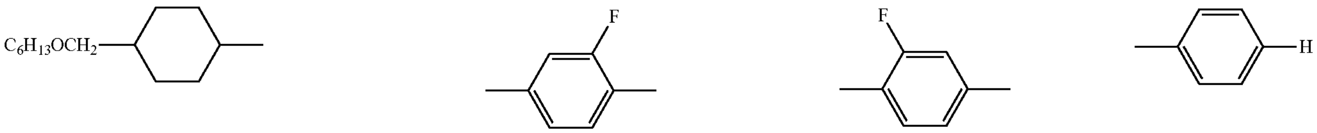

-continued
| | |
|---|---|
| 831 | 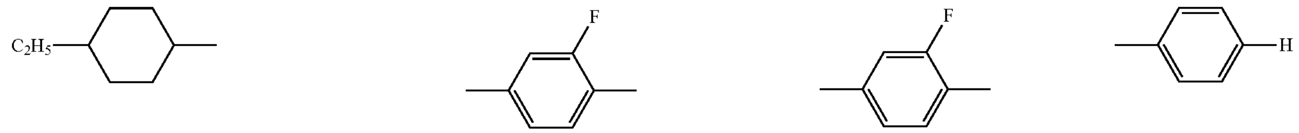 |
| 832 | 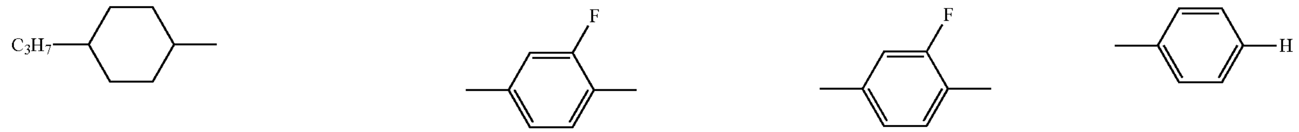 |
| 833 | 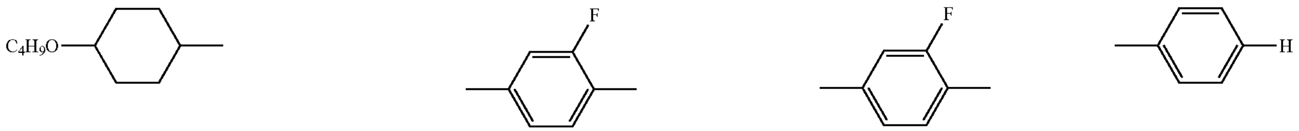 |
| 834 | 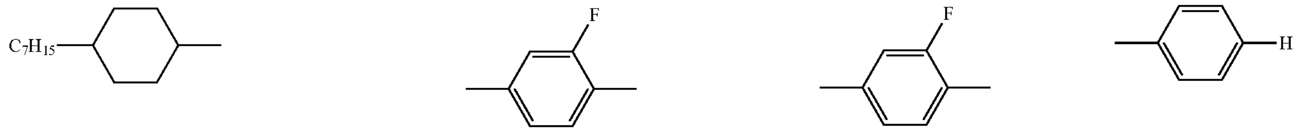 |
| 835 | 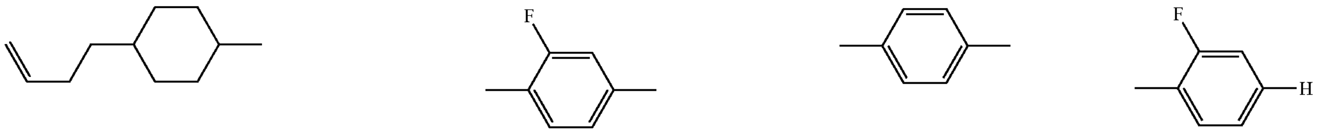 |
| 836 | 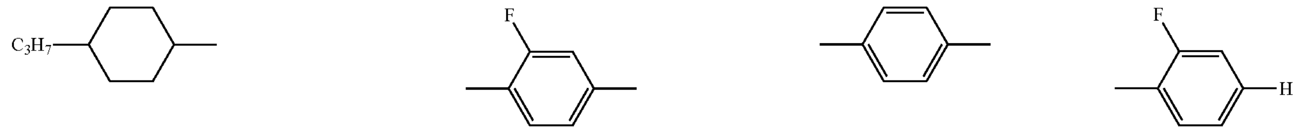 |
| 837 | 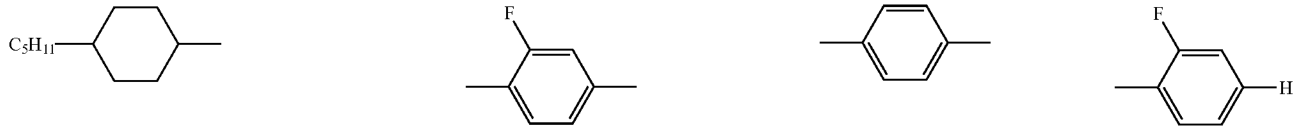 |

-continued
838 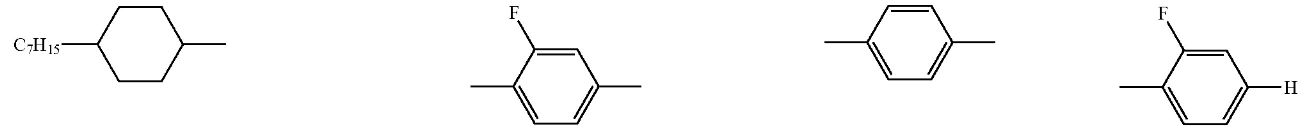
839 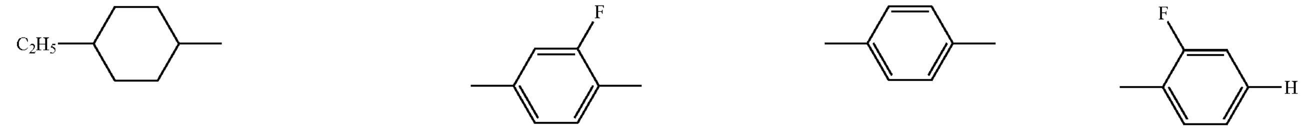
840 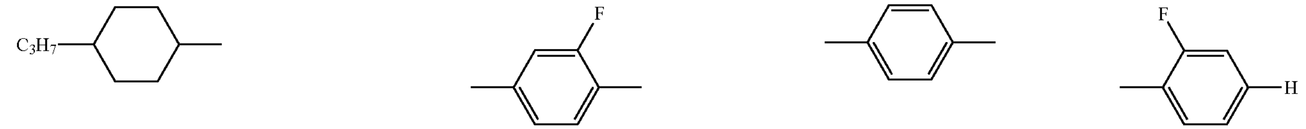
841 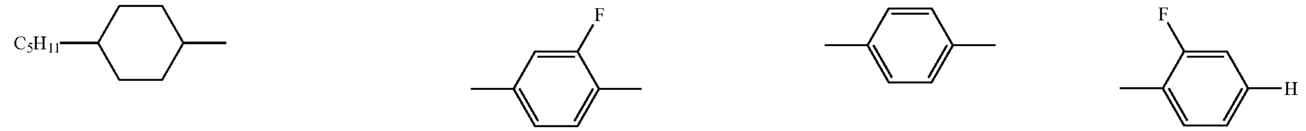
842 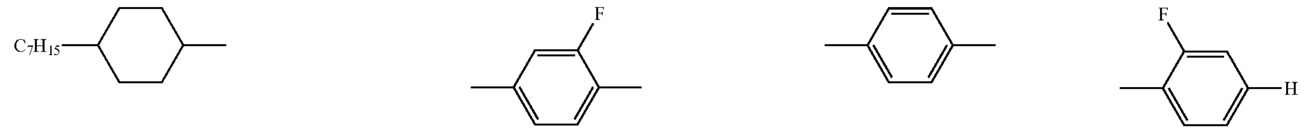
843 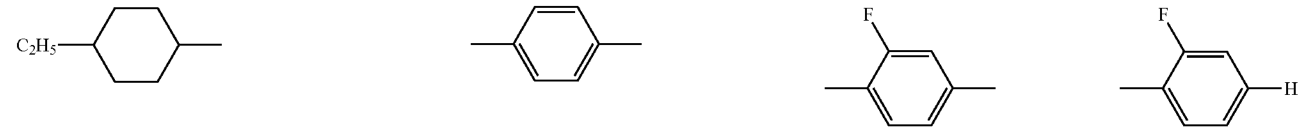
844 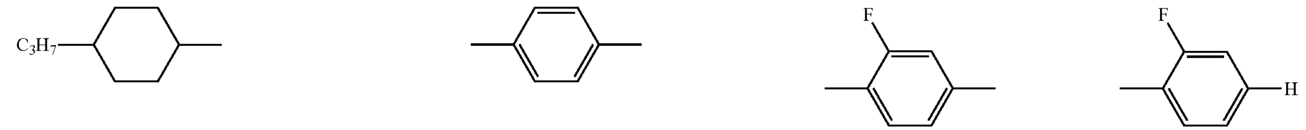

-continued
845 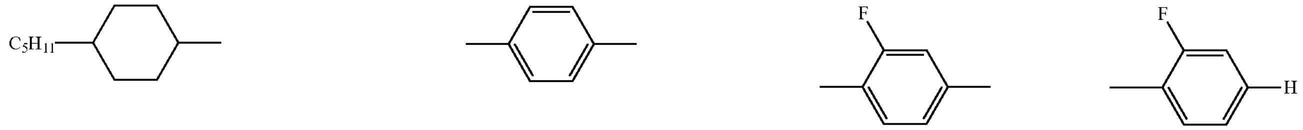
846 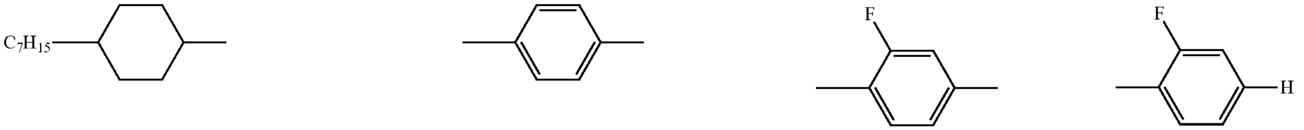
847 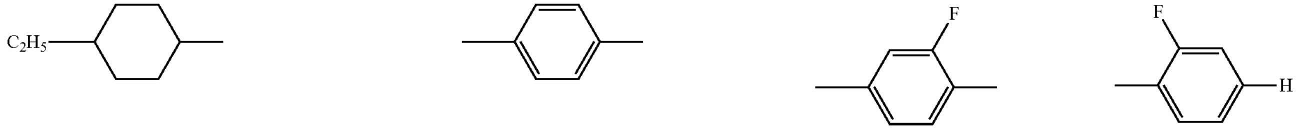
848 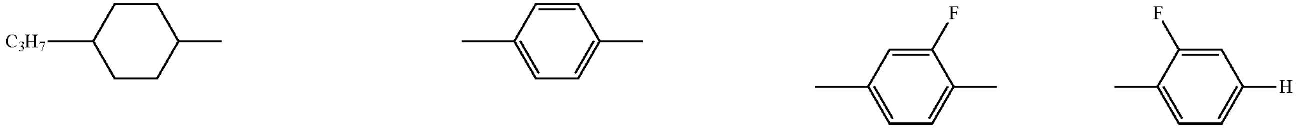
849 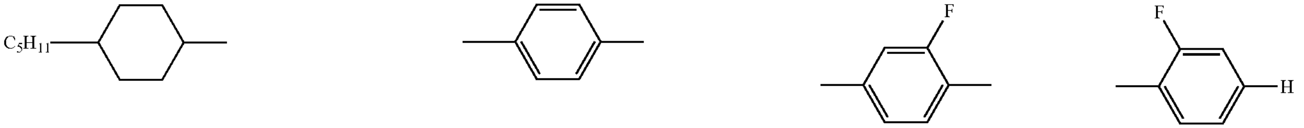
850 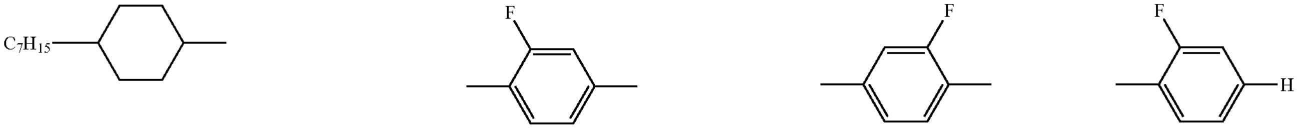
851 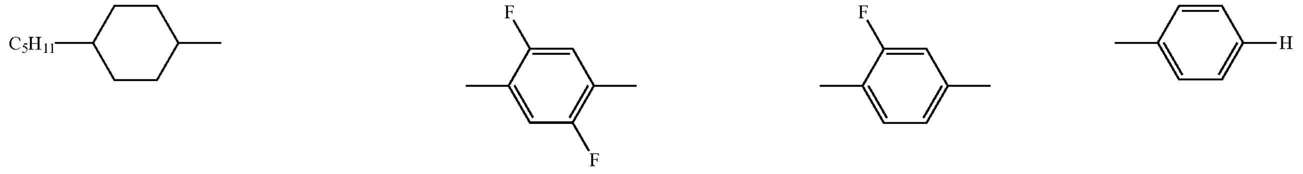

-continued
852 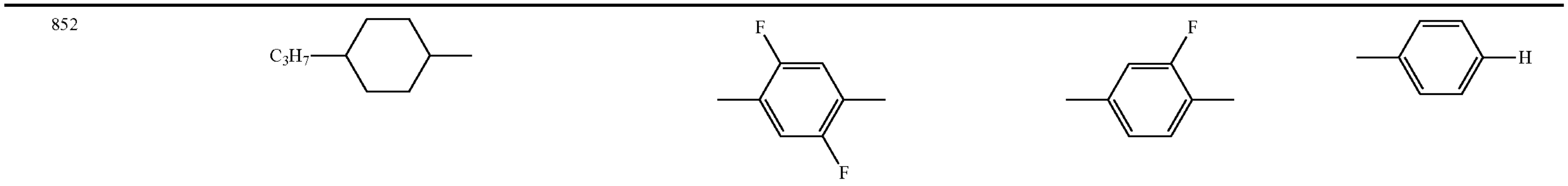
853 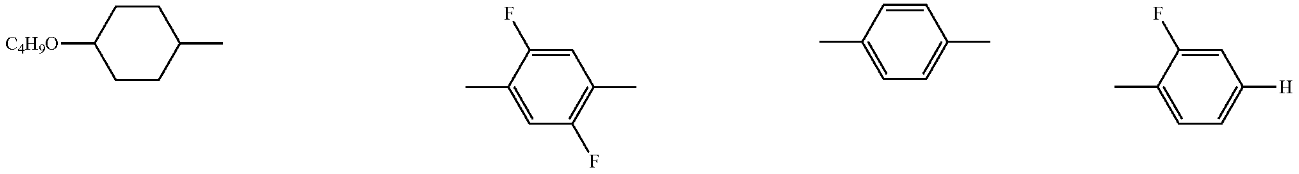
854 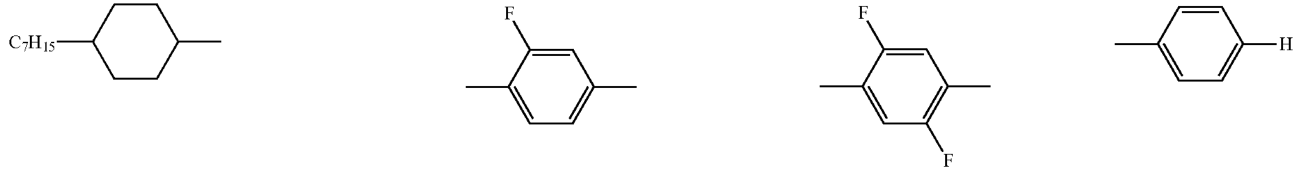
855 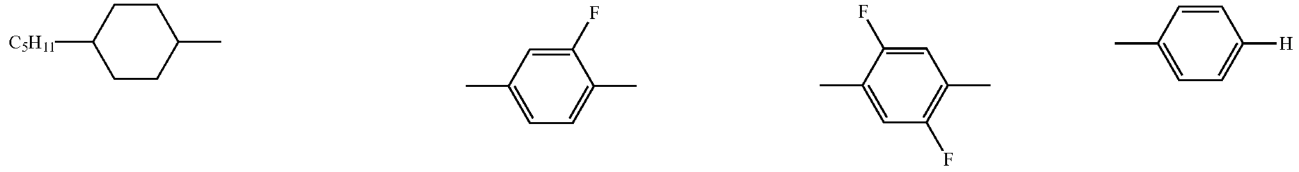
856 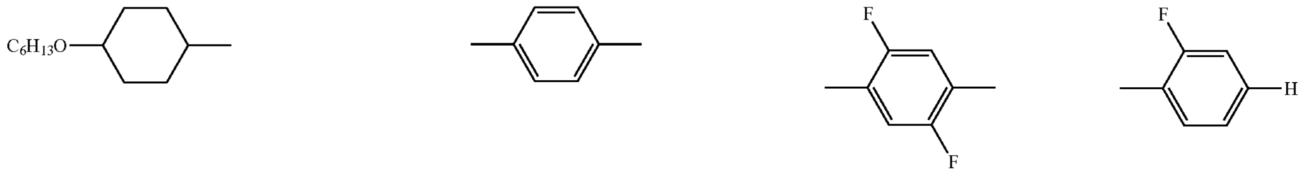

-continued
| | |
|---|---|
| 857 | 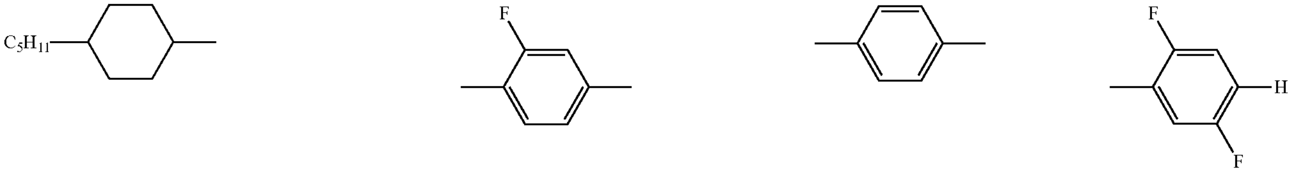 |
| 858 | 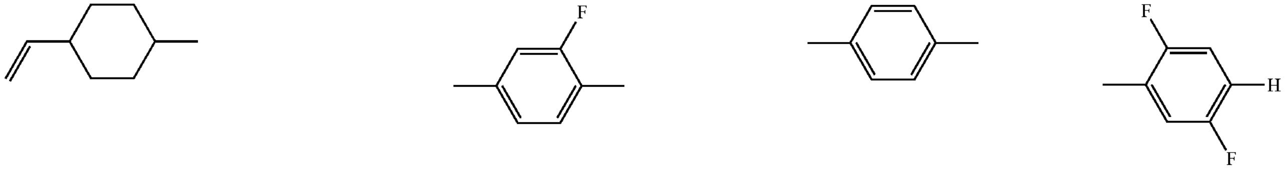 |
| 859 | 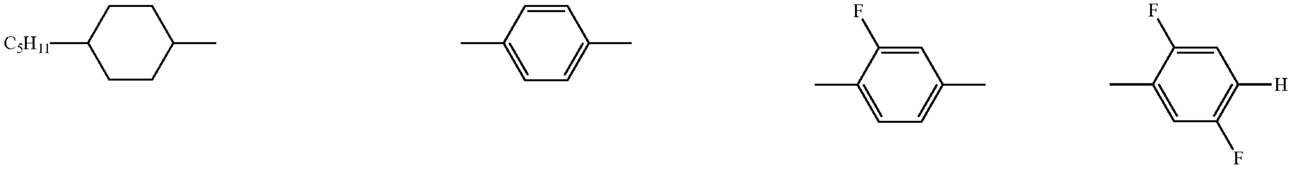 |
| 860 | 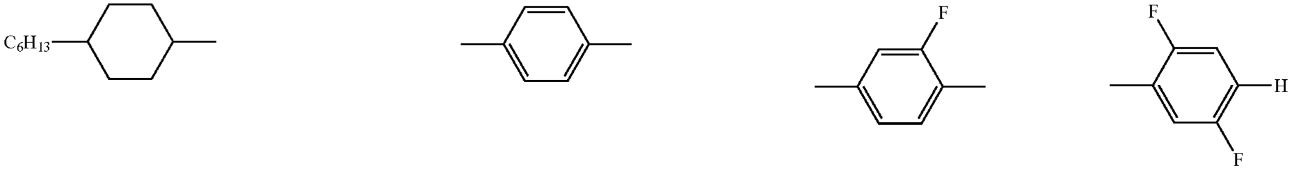 |
| 861 | 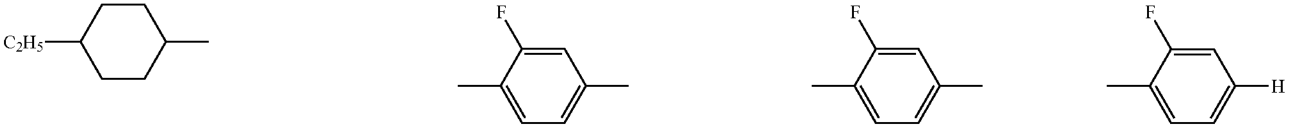 |
| 862 | 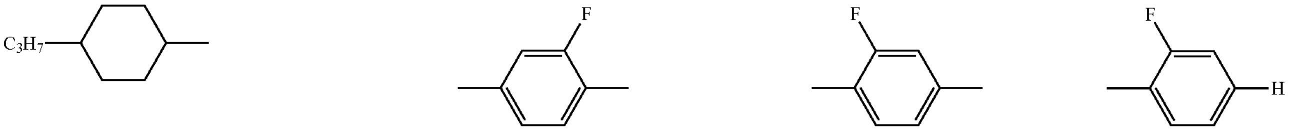 |

-continued
863 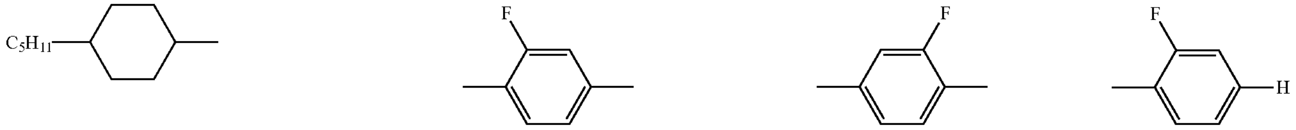
864 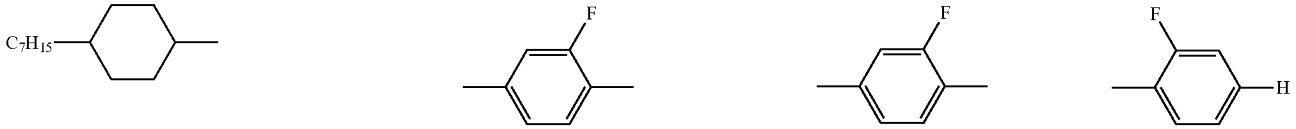
865 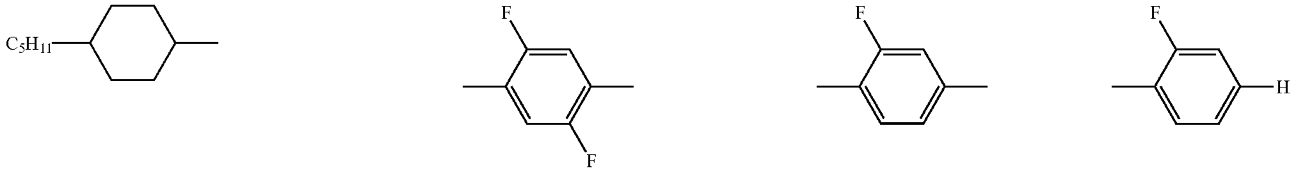
866 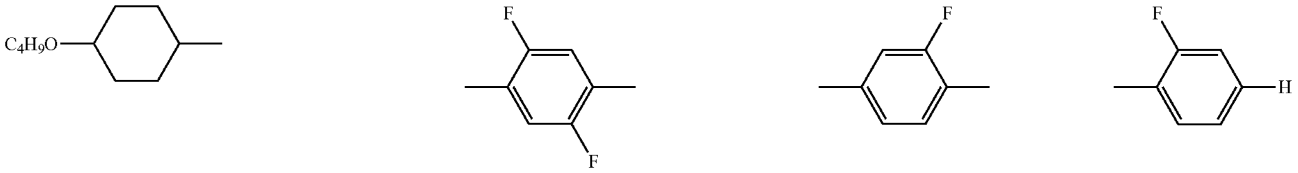
867 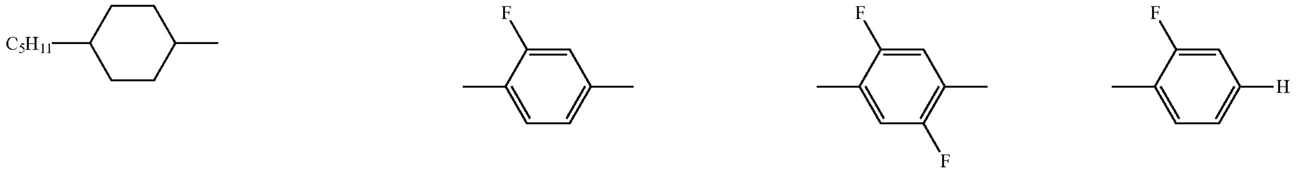
868 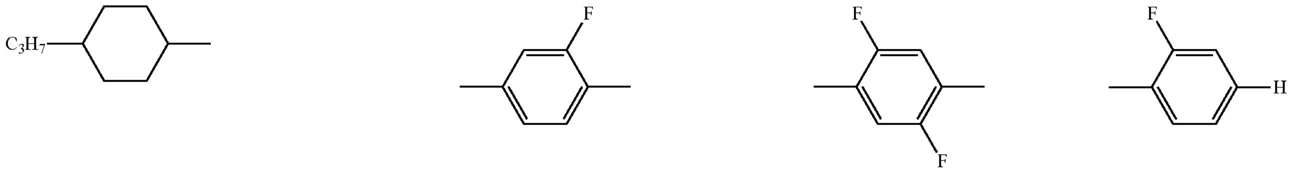

-continued
| | | | | |
|---|---|---|---|---|
| 869 | 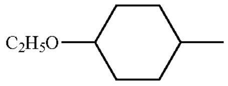 | 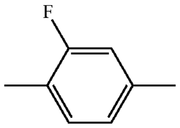 | 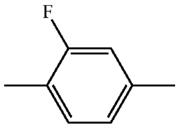 | 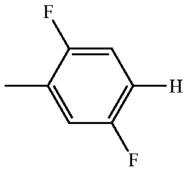 |
| 870 | 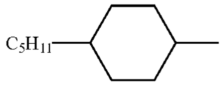 | 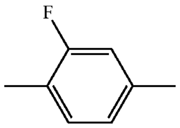 | 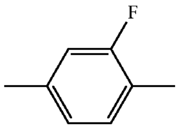 | 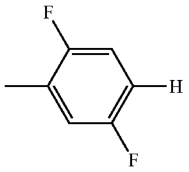 |
| 871 | 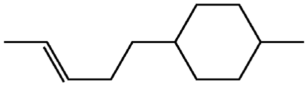 | 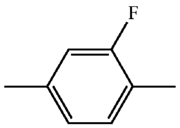 | 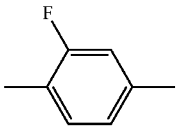 | 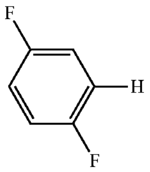 |
| 872 | 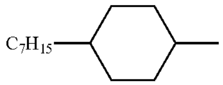 | 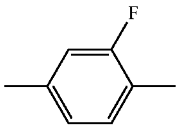 | 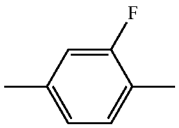 | 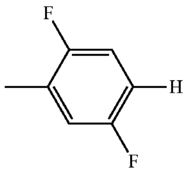 |
| 873 | 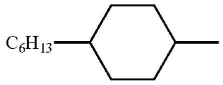 | 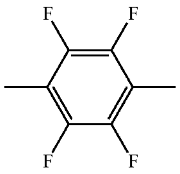 | 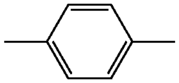 | 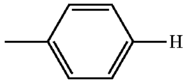 |

-continued
| | |
|---|---|
| 874 | 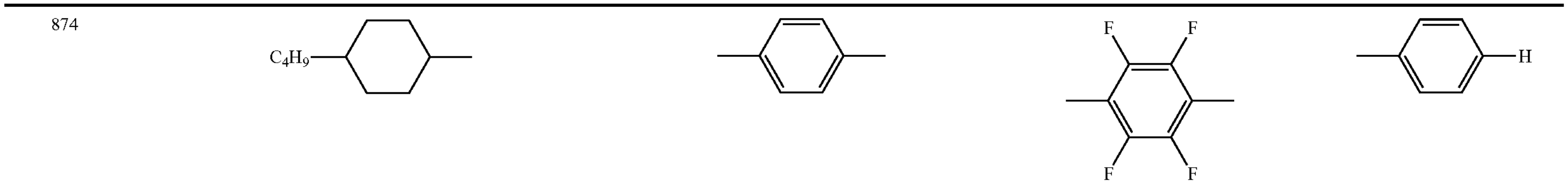 |
| 875 | 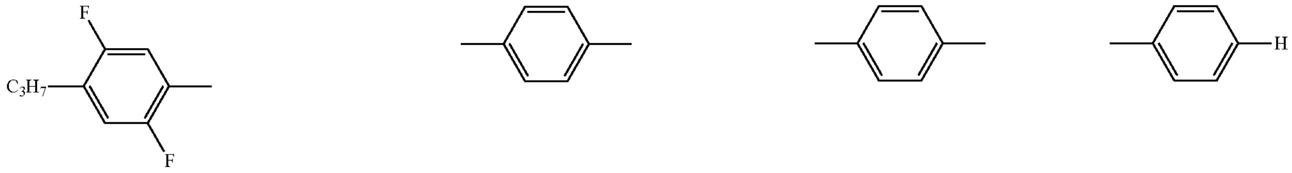 |
| 876 | 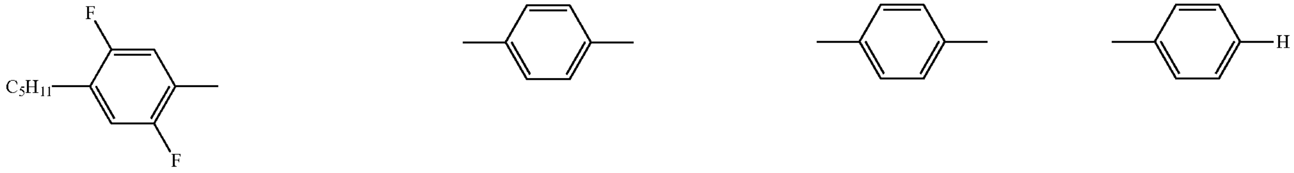 |
| 877 | 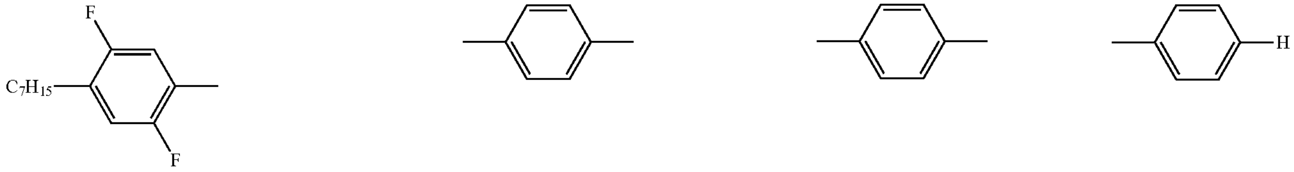 |
| 878 | 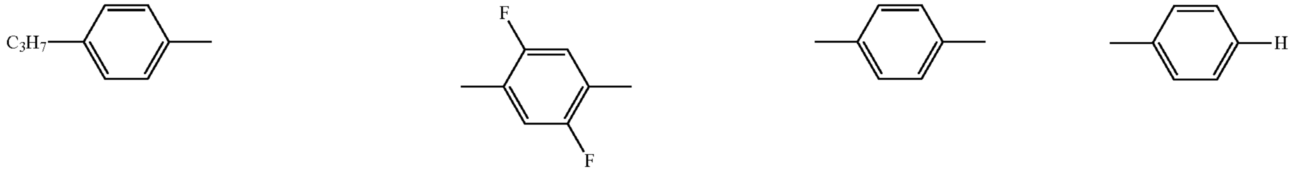 |

-continued
| | |
|---|---|
| 879 | 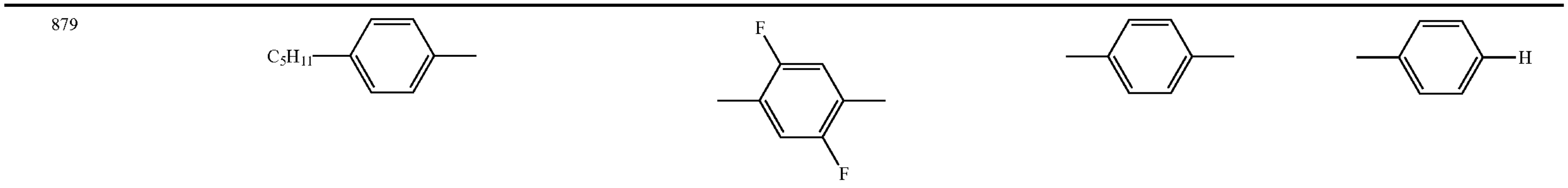 |
| 880 | 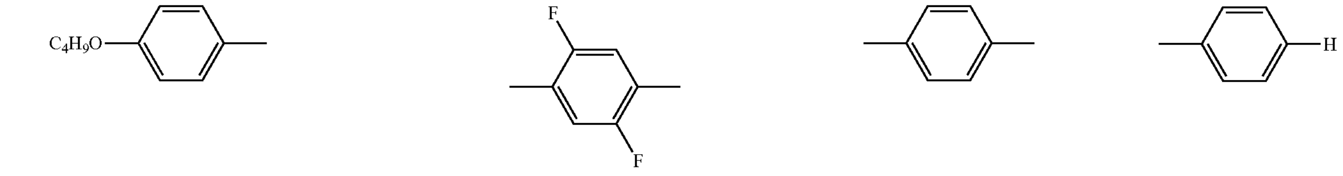 |
| 881 | 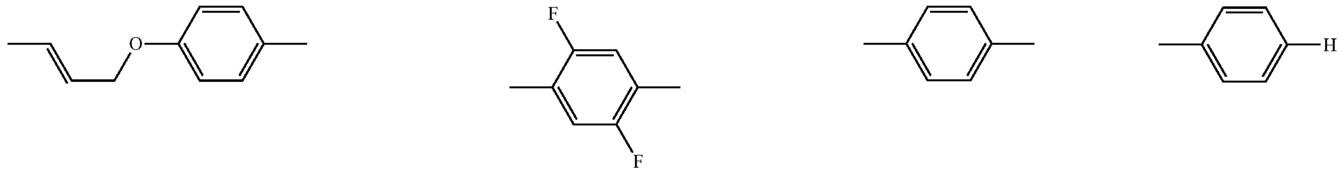 |
| 882 | 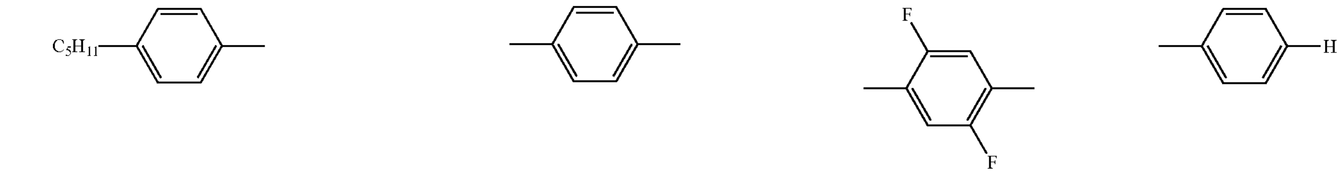 |
| 883 | 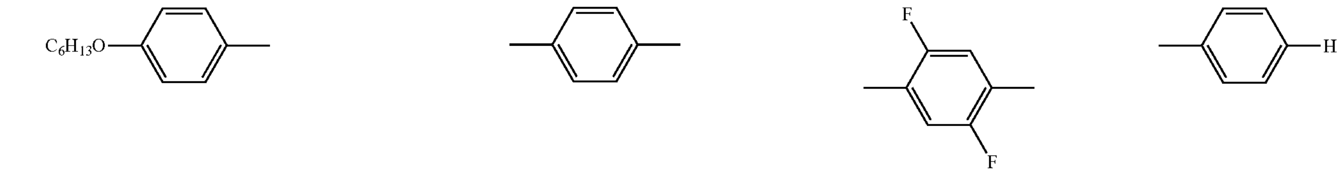 |

-continued
| | |
|---|---|
| 884 | 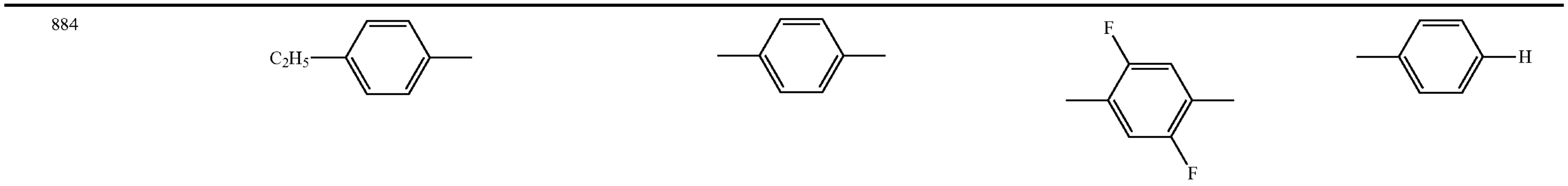 |
| 885 | 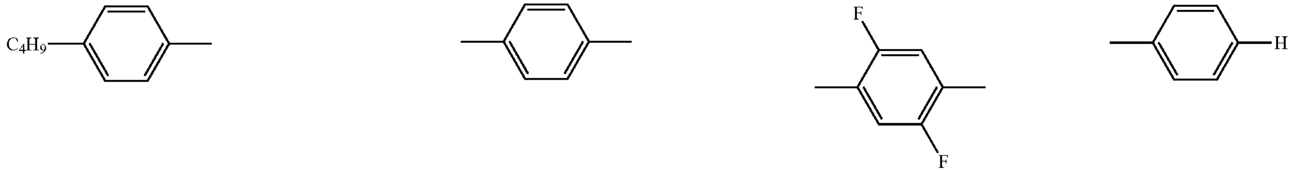 |
| 886 | 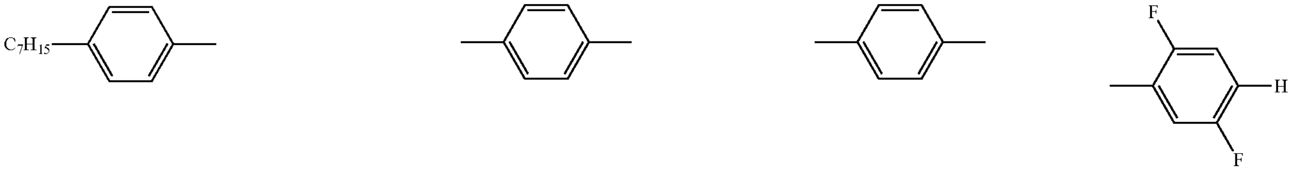 |
| 887 | 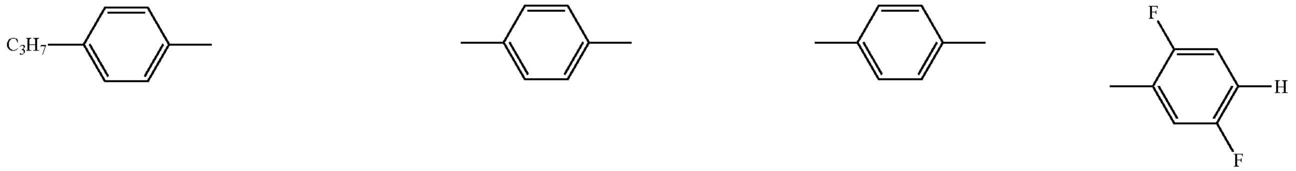 |
| 888 | 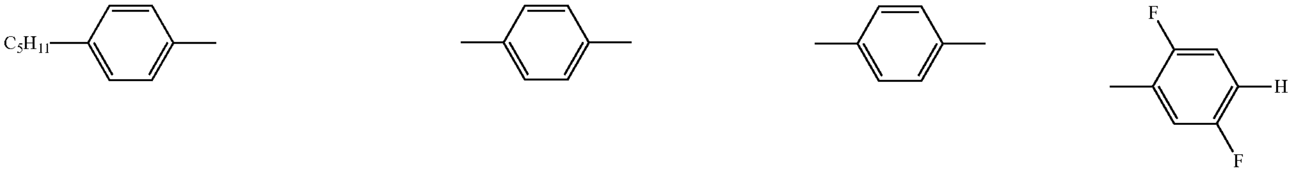 |

-continued
| | |
|---|---|
| 889 | 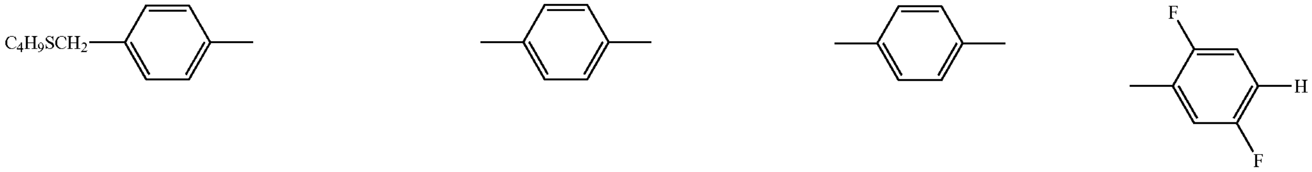 |
| 890 | 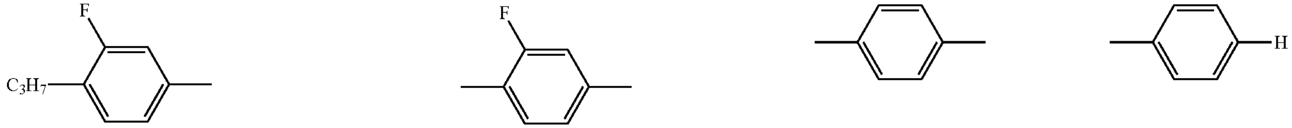 |
| 891 | 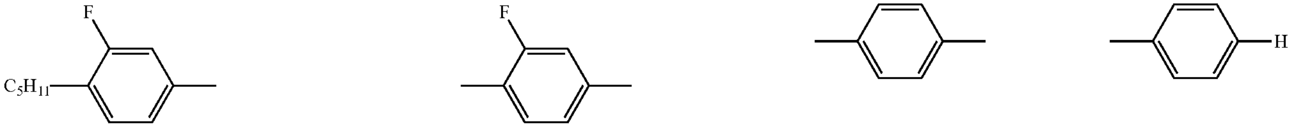 |
| 892 | 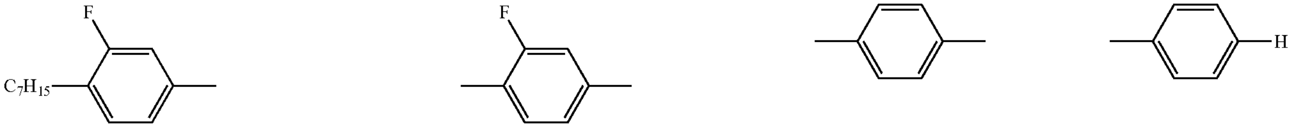 |
| 893 | 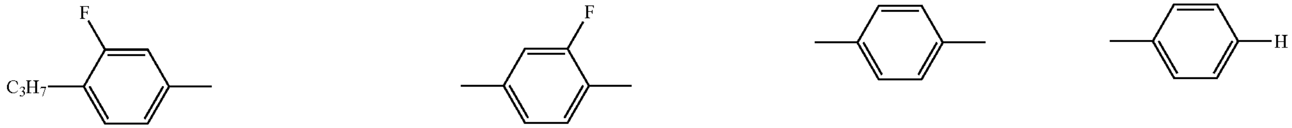 |
| 894 | 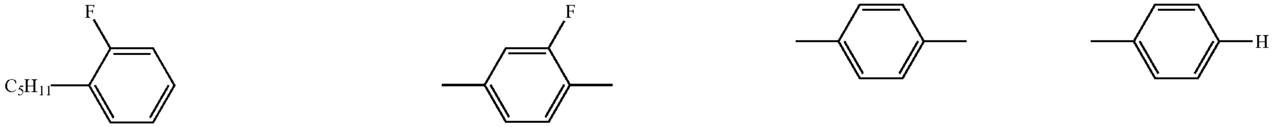 |
| 895 | 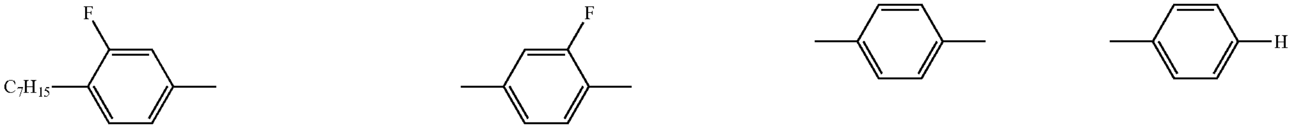 |

-continued
896 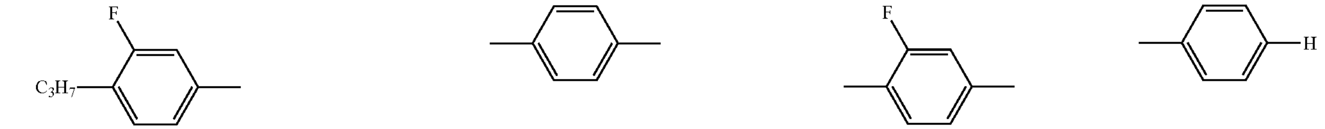
897 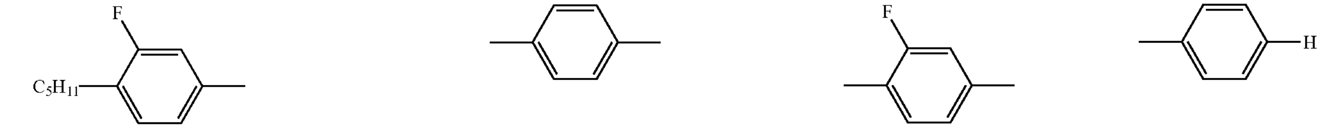
898 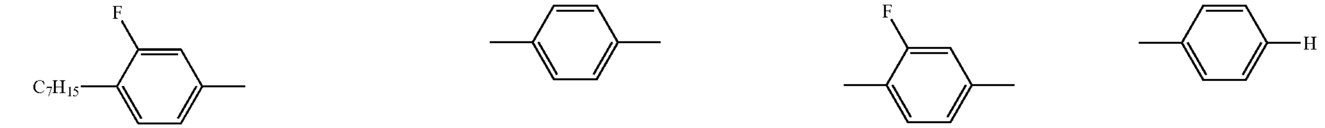
899 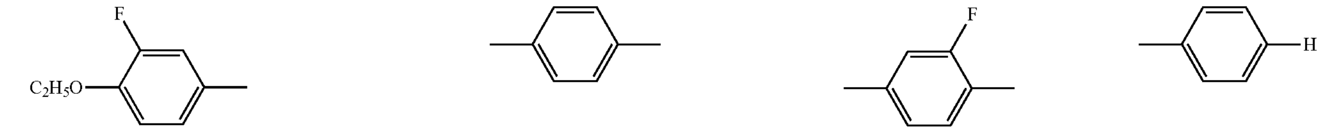
900 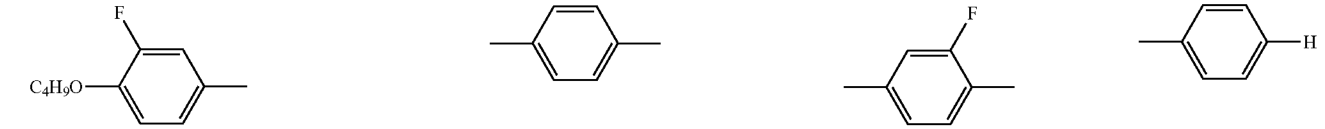
901 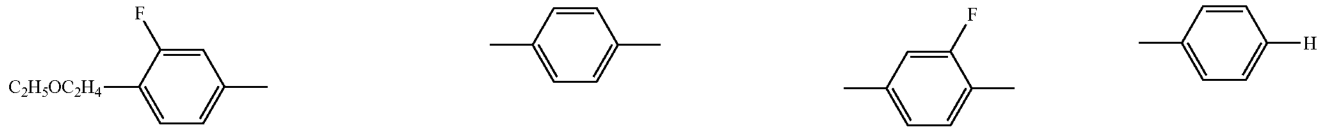
902 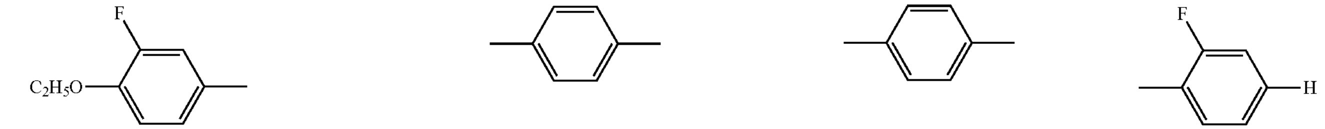

-continued
| | |
|---|---|
| 903 | 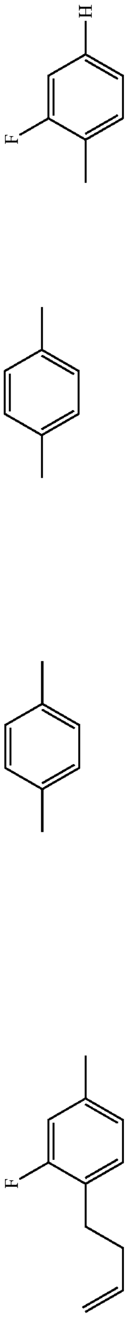 |
| 904 | 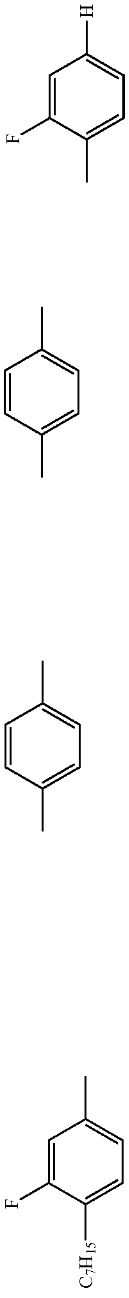 |
| 905 | 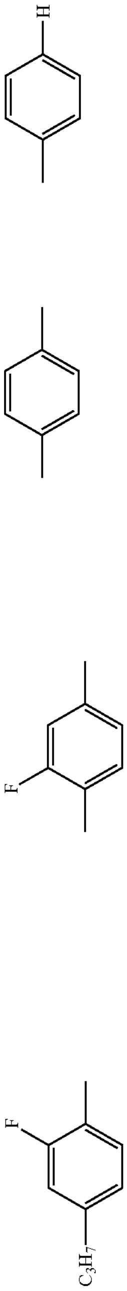 |
| 906 | 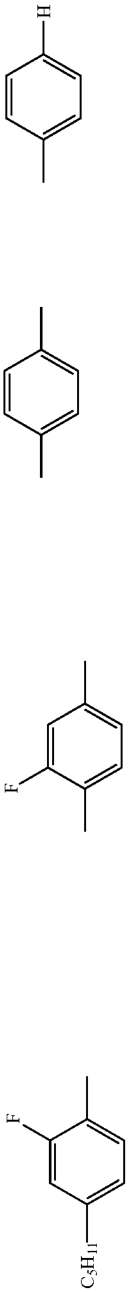 |
| 907 | 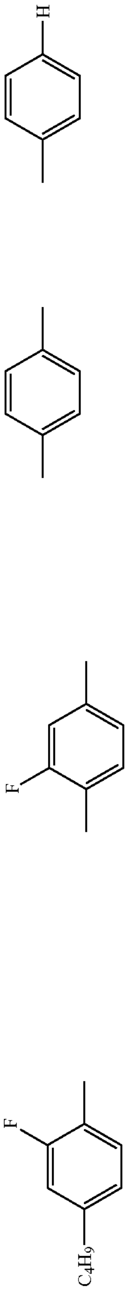 |
| 908 | 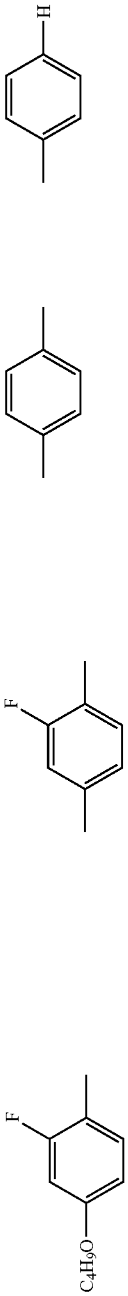 |
| 909 | 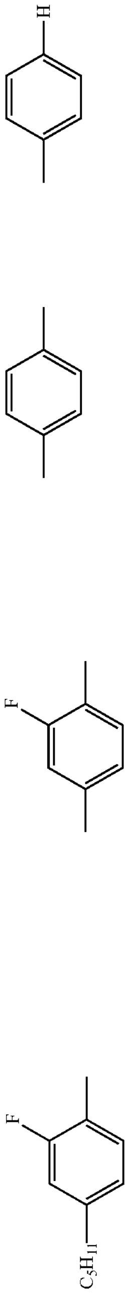 |

-continued
| | |
|---|---|
| 910 | 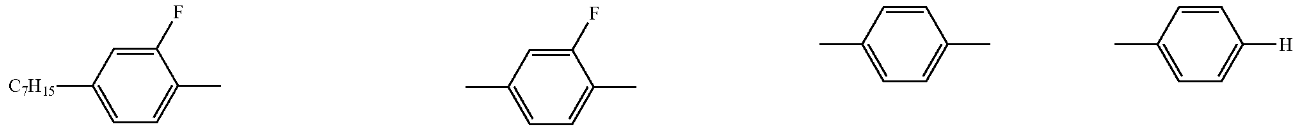 |
| 911 | 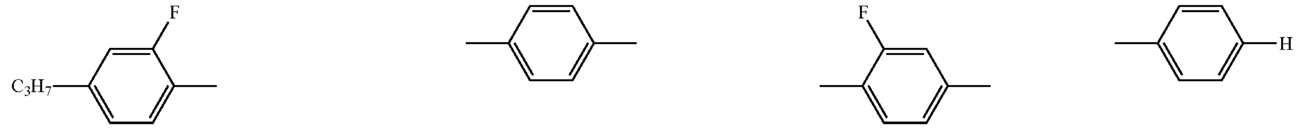 |
| 912 | 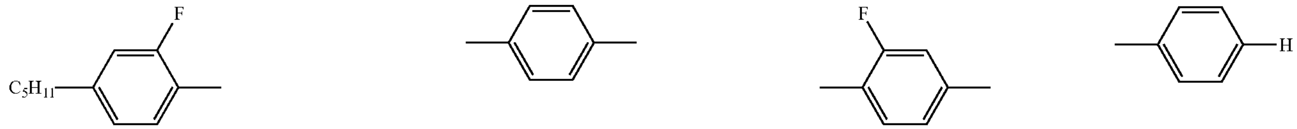 |
| 913 | 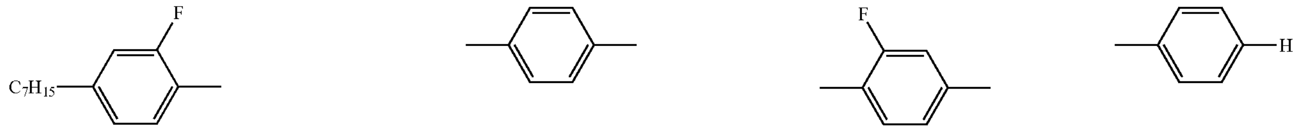 |
| 914 | 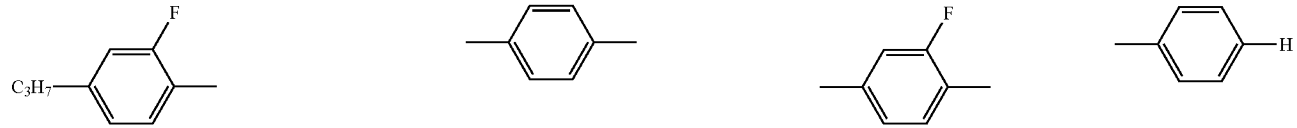 |
| 915 | 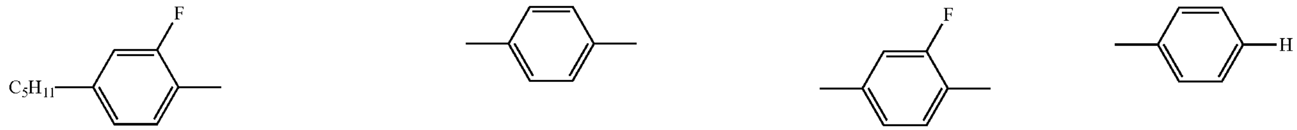 |
| 916 | 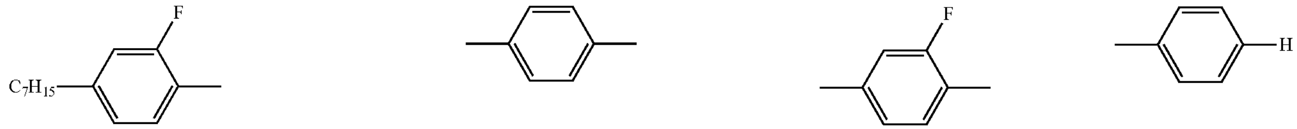 |

-continued
| | |
|---|---|
| 917 | 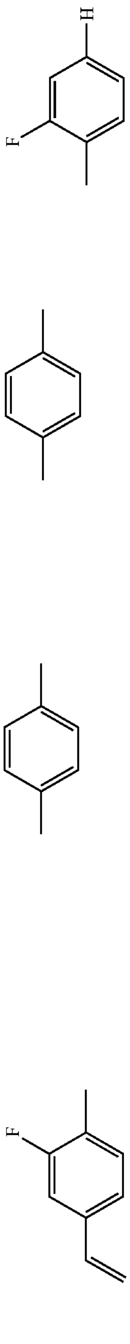 |
| 918 | 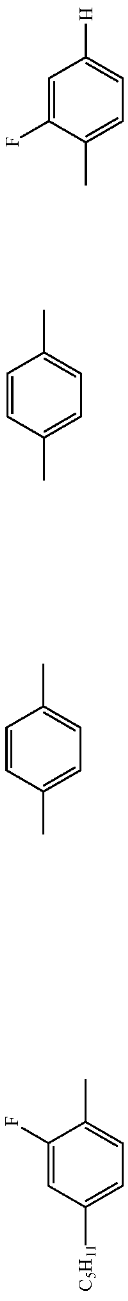 |
| 919 | 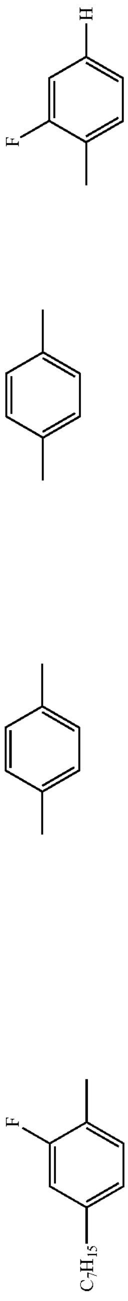 |
| 920 | 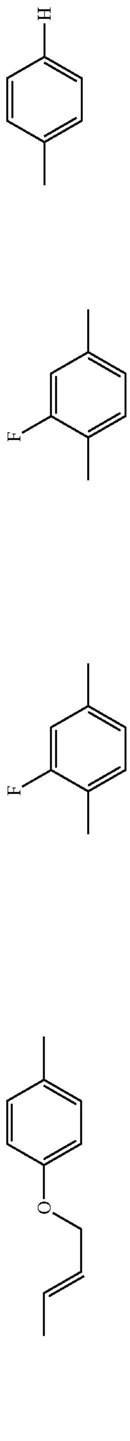 |
| 921 | 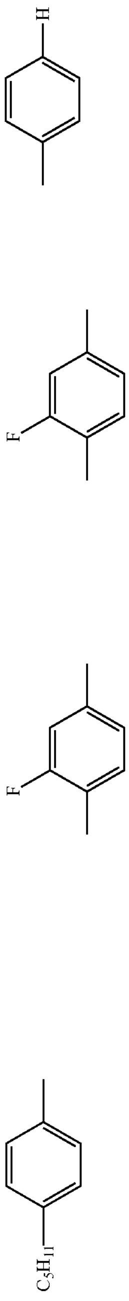 |
| 922 | 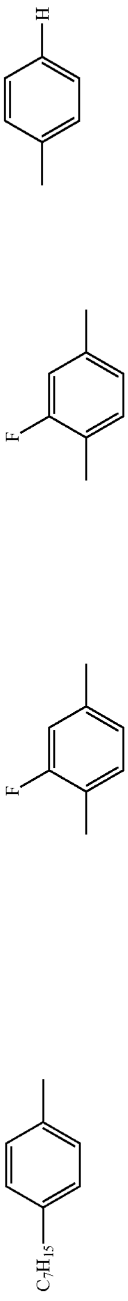 |
| 923 | 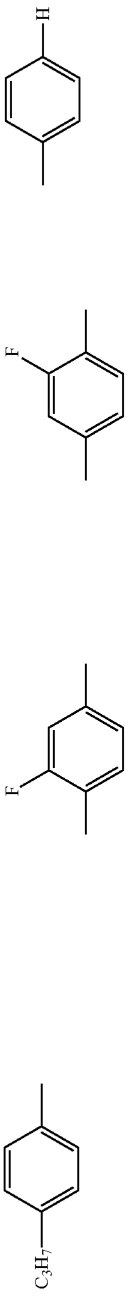 |

-continued
924 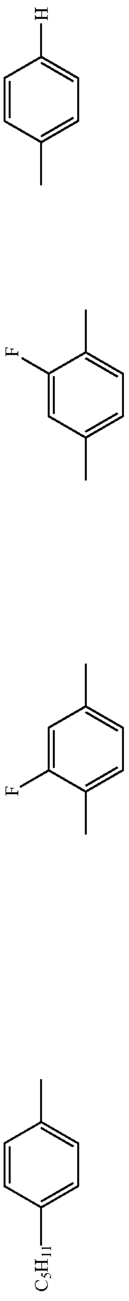
925 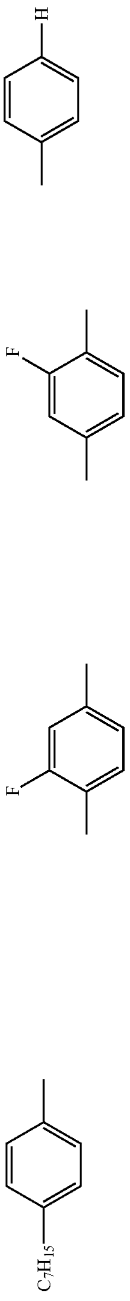
926 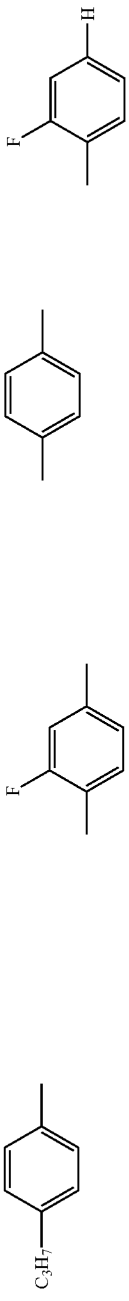
927 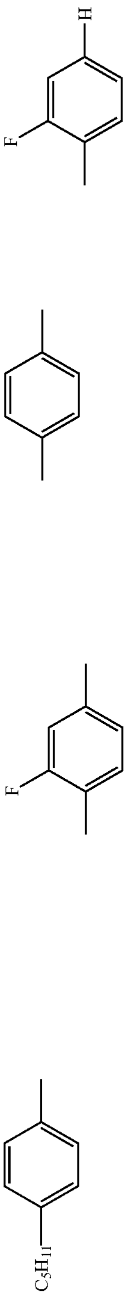
928 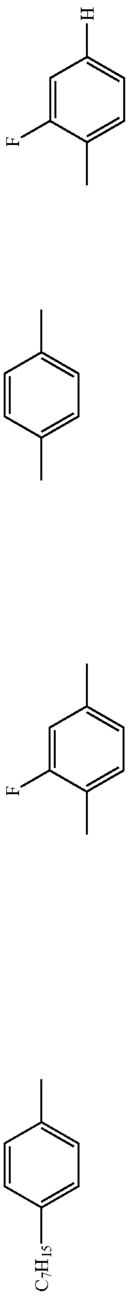
929 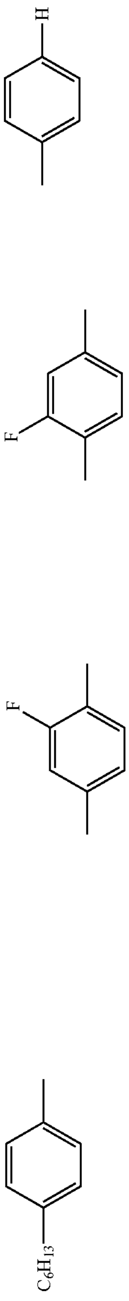
930 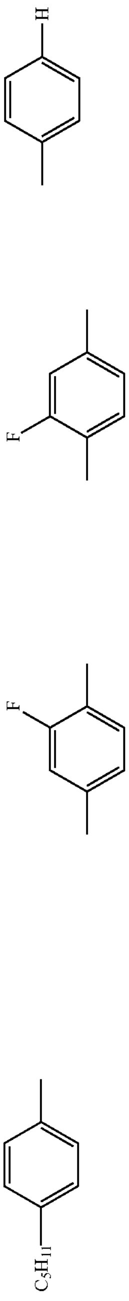

-continued
| | |
|---|---|
| 931 | 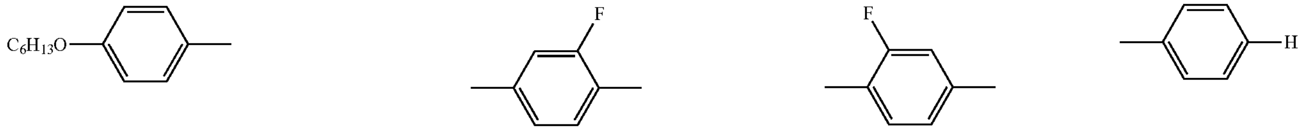 |
| 932 | 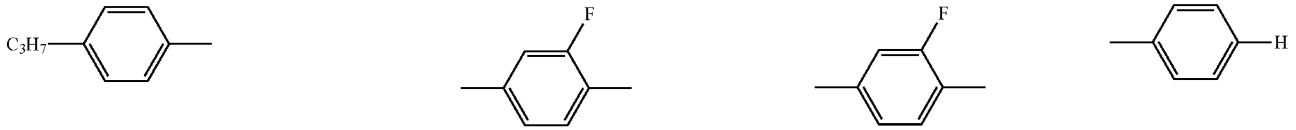 |
| 933 | 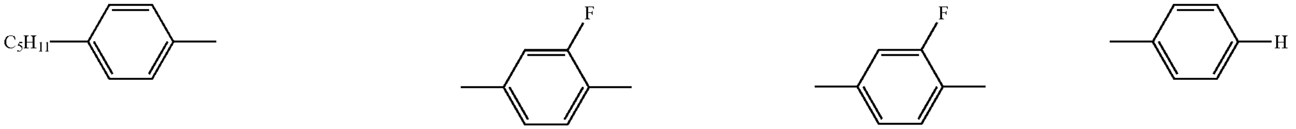 |
| 934 | 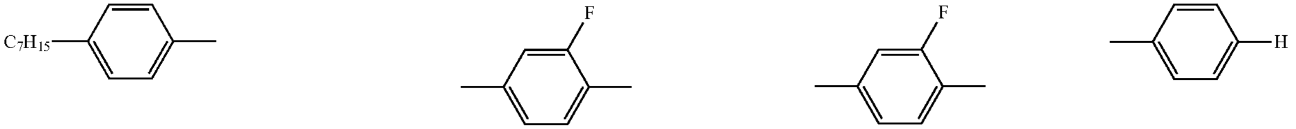 |
| 935 | 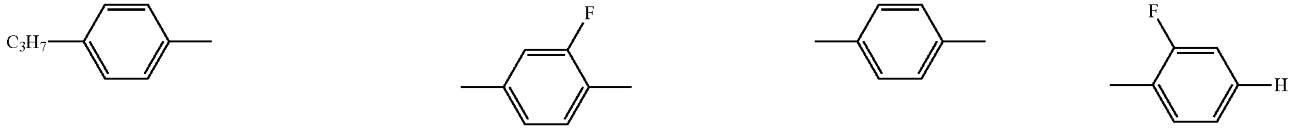 |
| 936 | 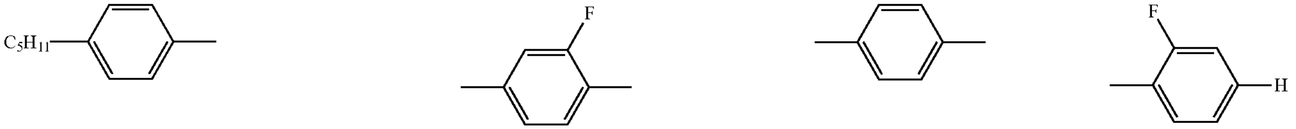 |
| 937 | 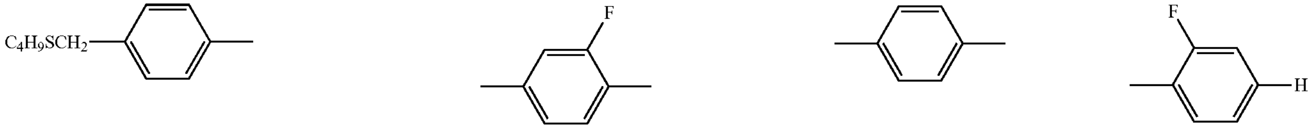 |

-continued
| | |
|---|---|
| 938 | 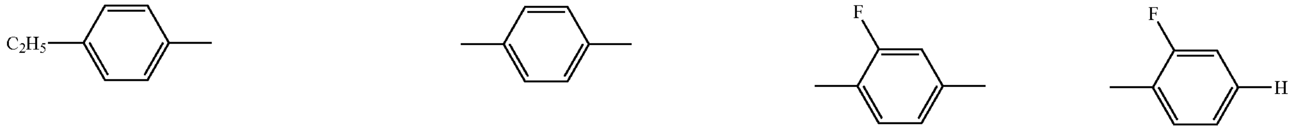 |
| 939 | 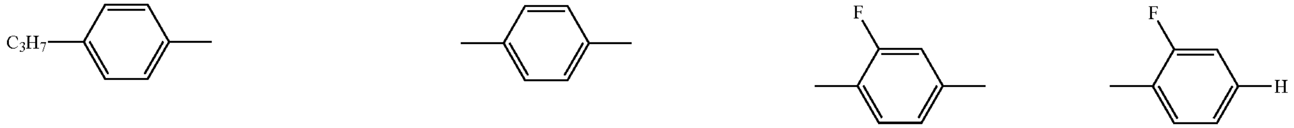 |
| 940 | 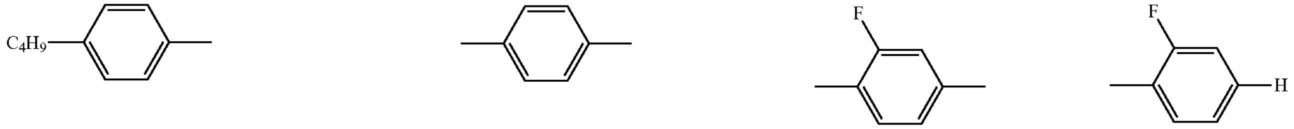 |
| 941 | 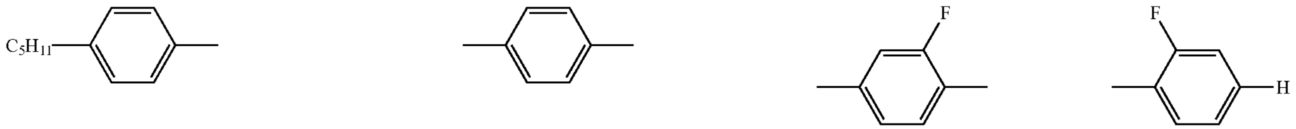 |
| 942 | 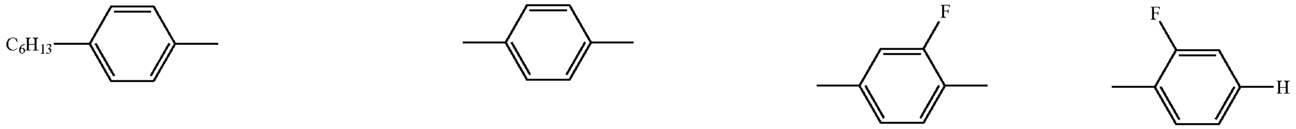 |
| 943 | 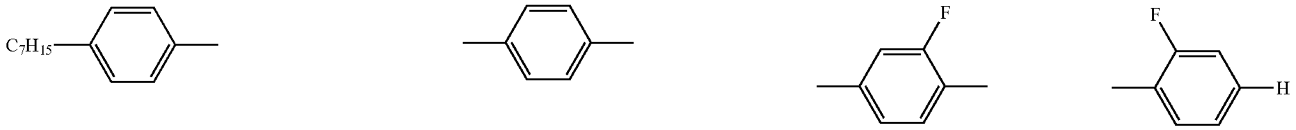 |
| 944 | 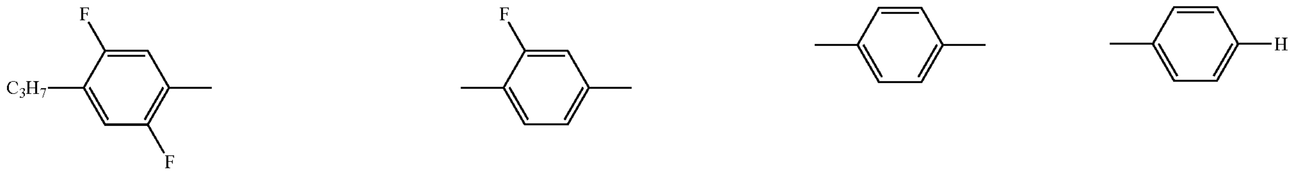 |

-continued
945 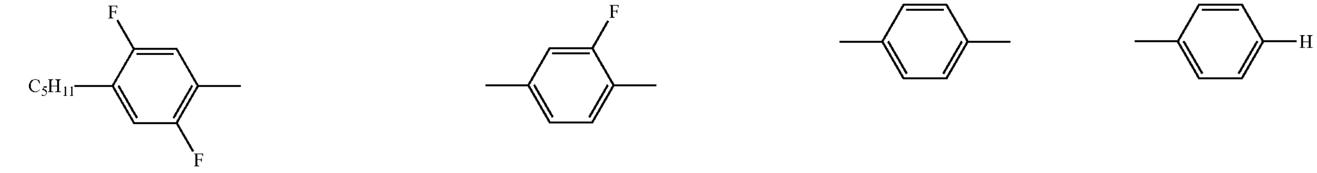
946 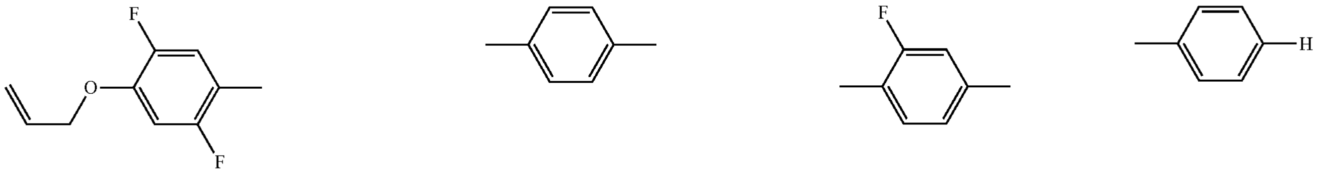
947 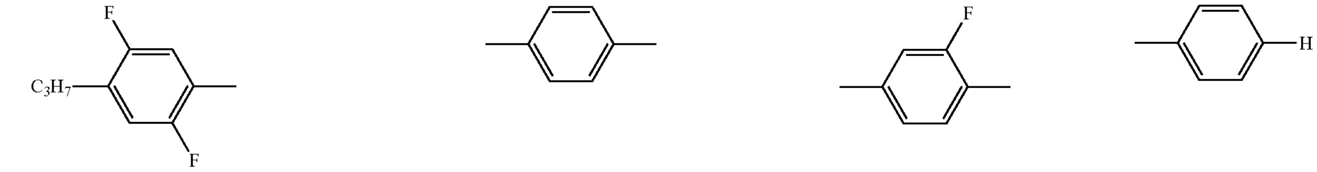
948 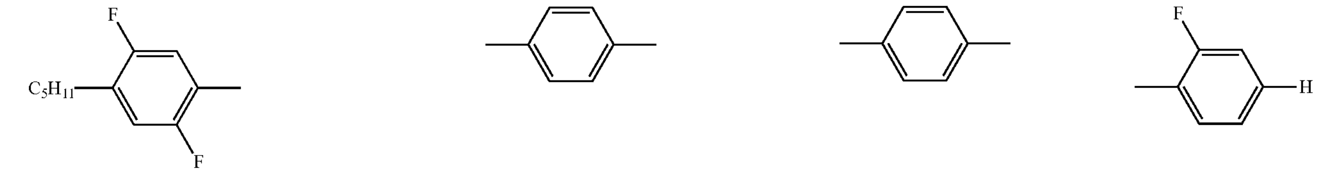
949 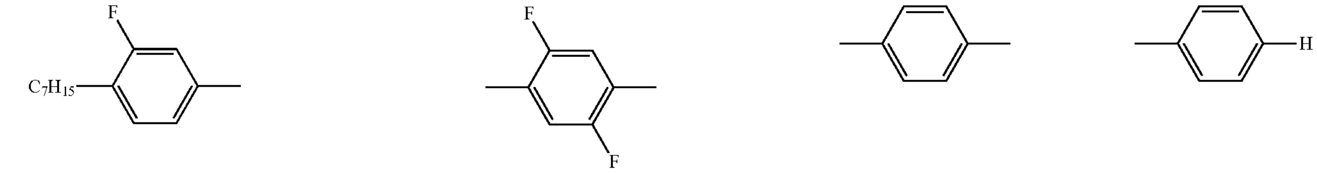

-continued
| | | |
|---|---|---|
| 950 | 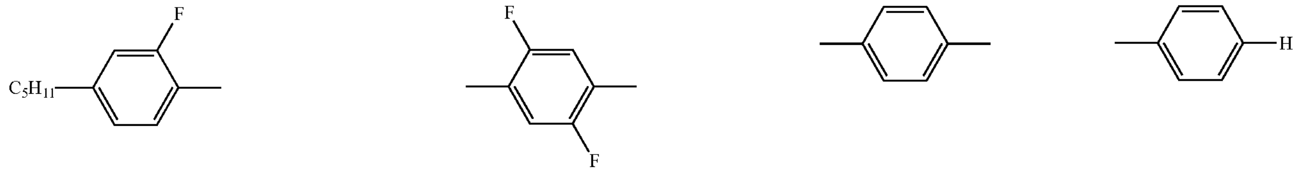 | |
| 951 | 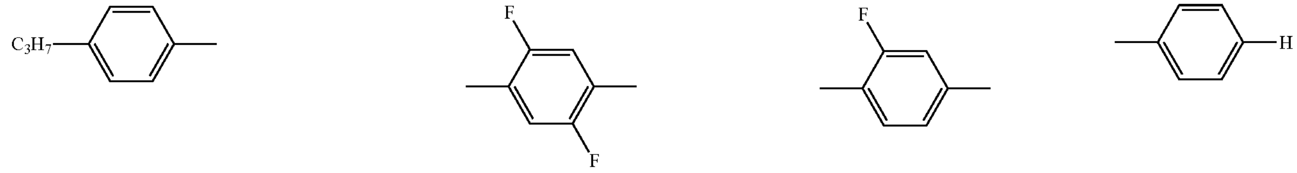 | |
| 952 | 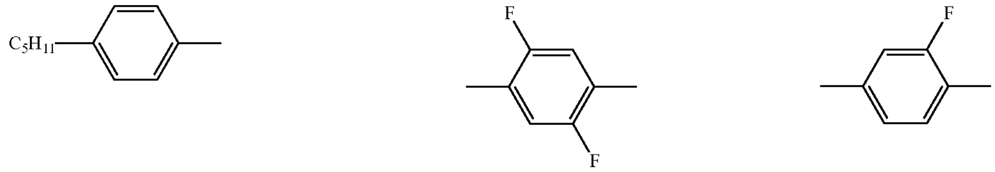 | 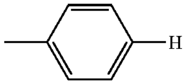<br>C 144.1 N 160.1 I |
| 953 | 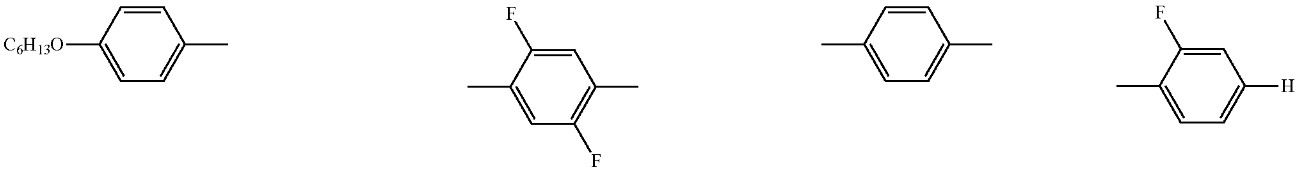 | |
| 954 | 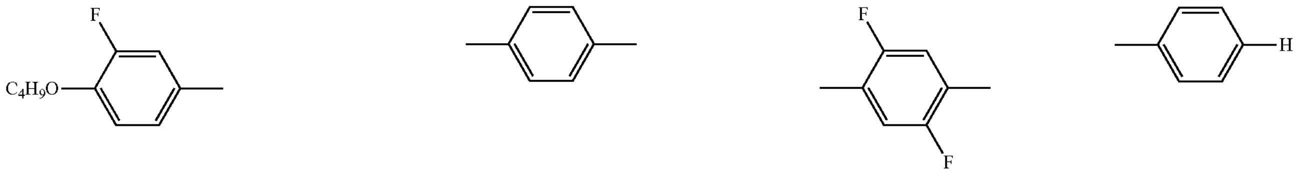 | |

-continued
955 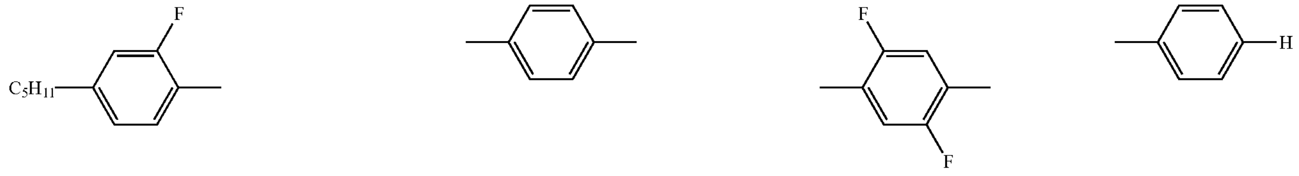
956 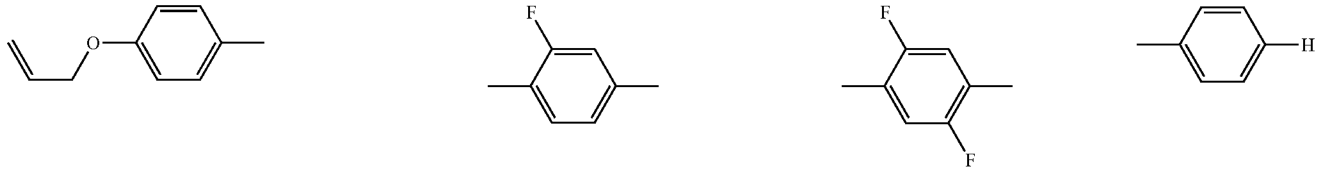
957 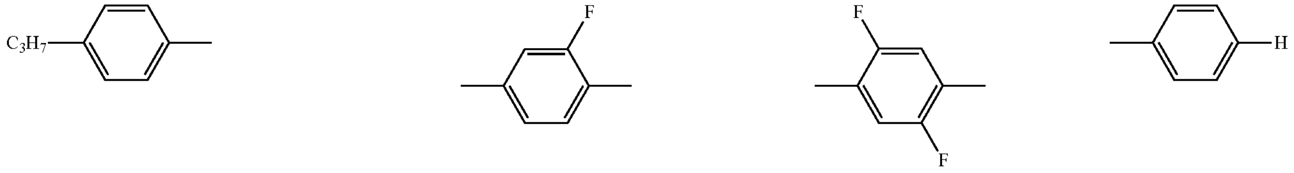
958 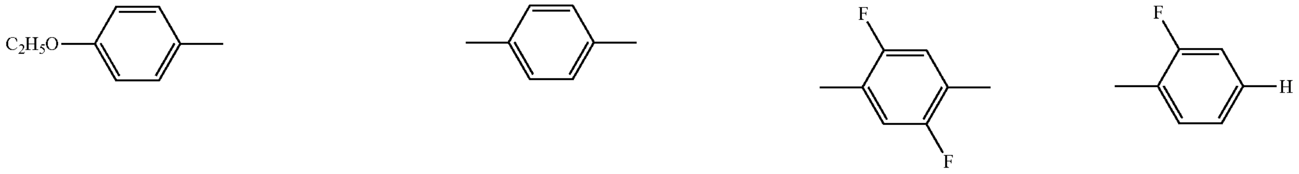
959 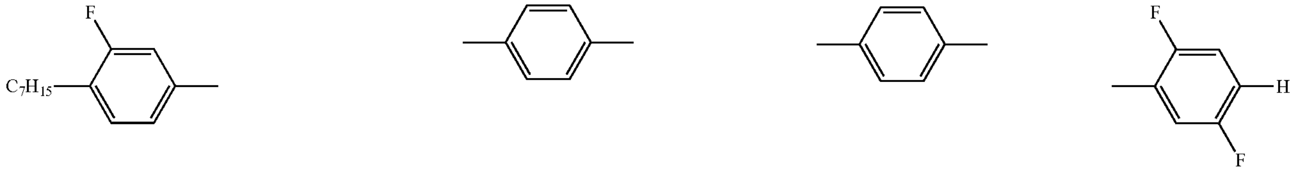

-continued
| | |
|---|---|
| 960 | 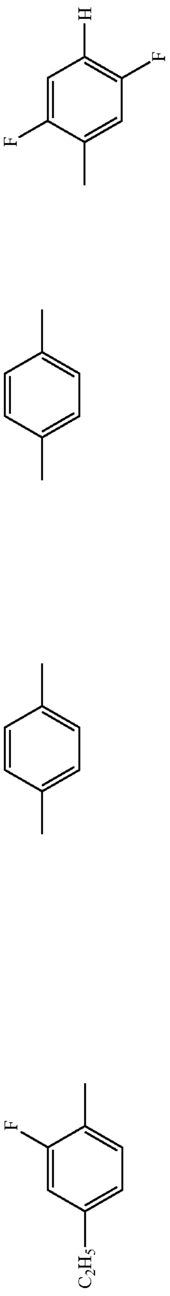 |
| 961 | 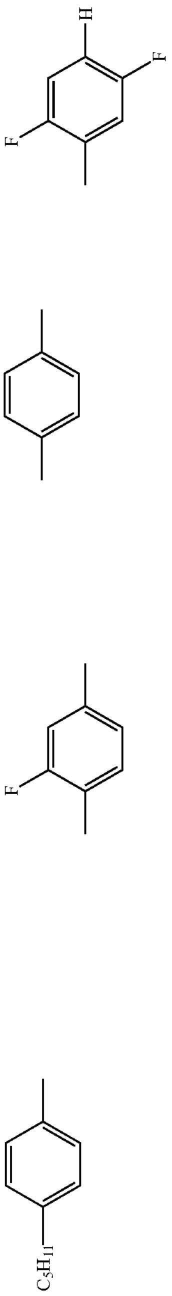 |
| 962 | 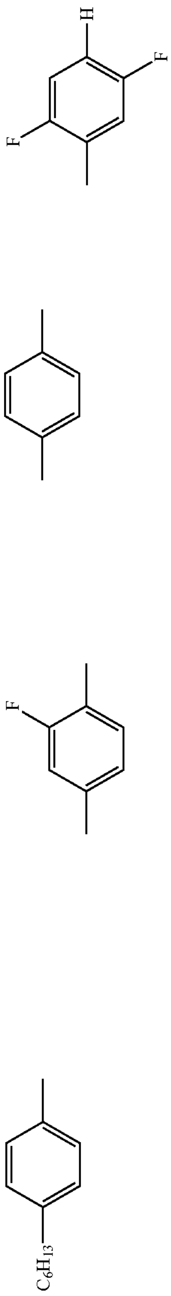 |
| 963 | 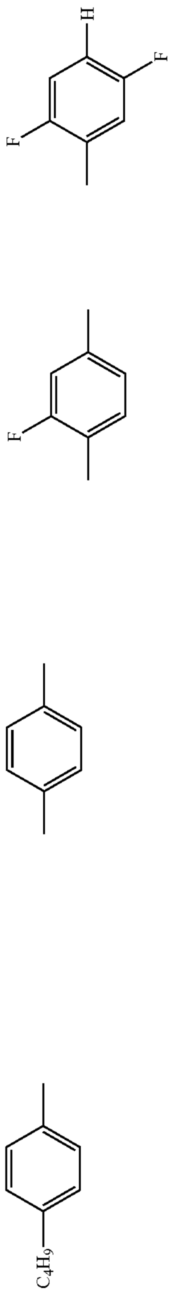 |
| 964 | 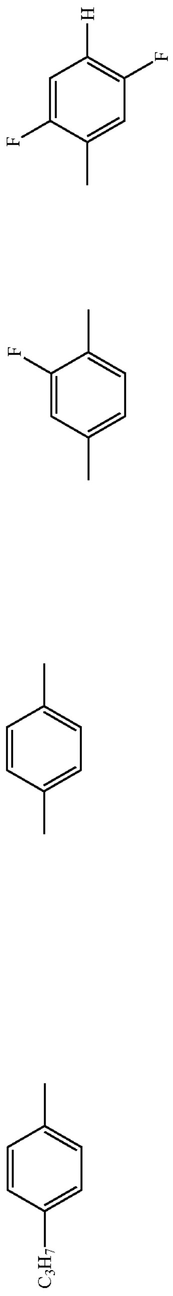 |
| 965 | 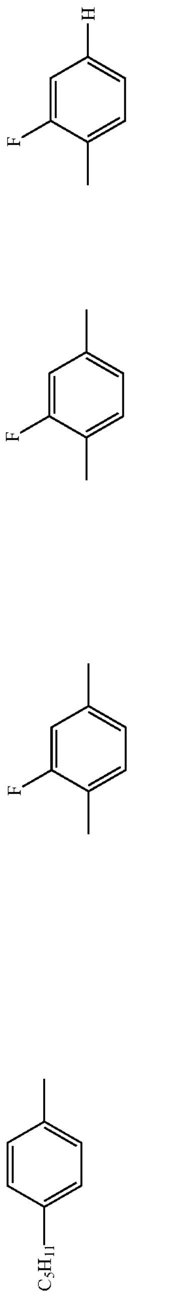 |

-continued
| | |
|---|---|
| 966 | 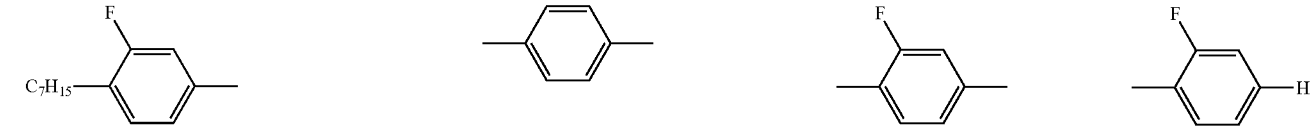 |
| 967 | 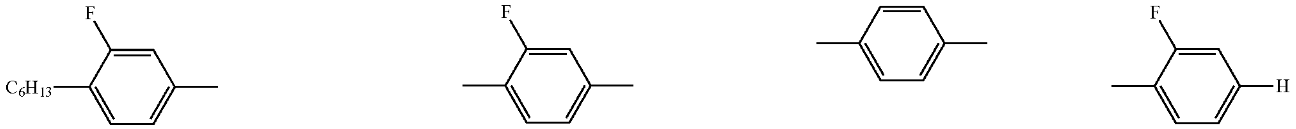 |
| 968 | 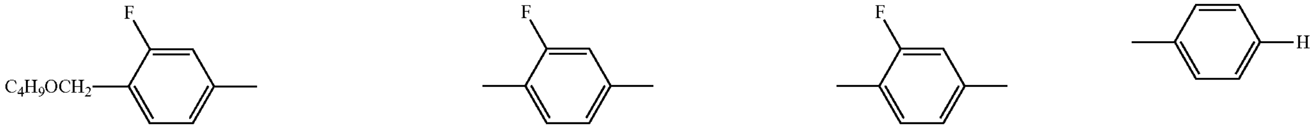 |
| 969 | 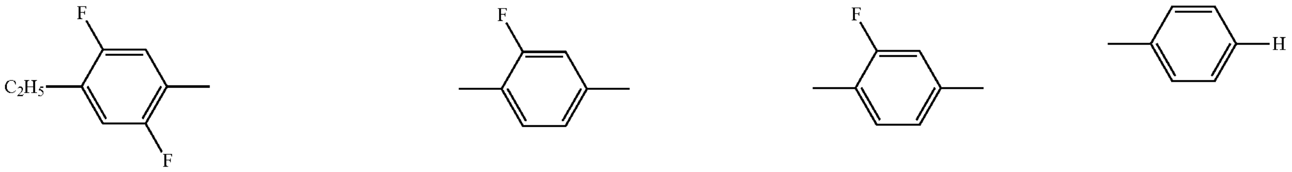 |
| 970 | 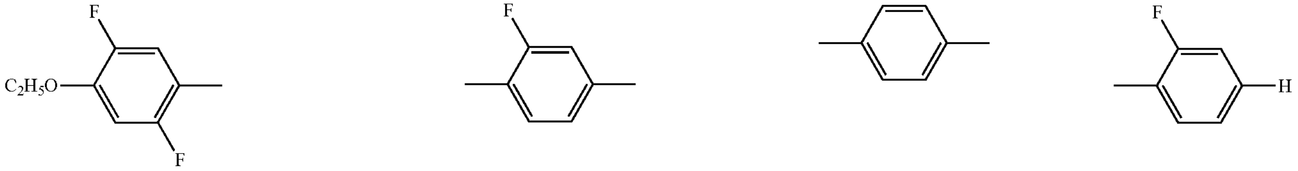 |
| 971 | 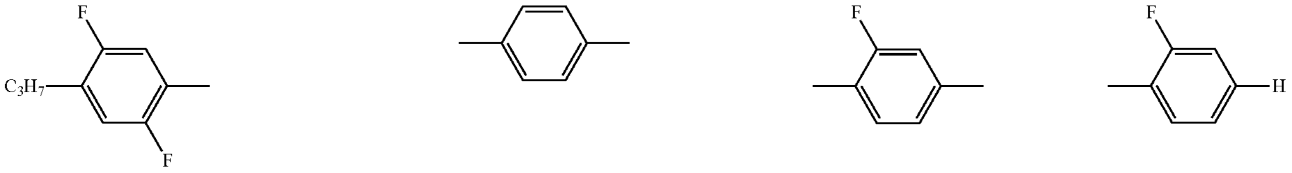 |

-continued
| | |
|---|---|
| 972 | 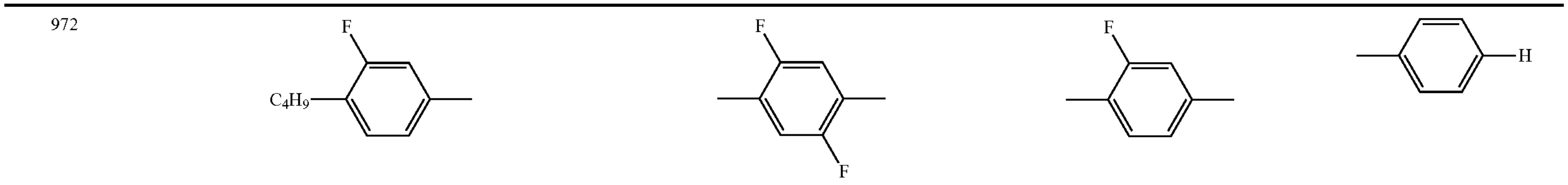 |
| 973 | 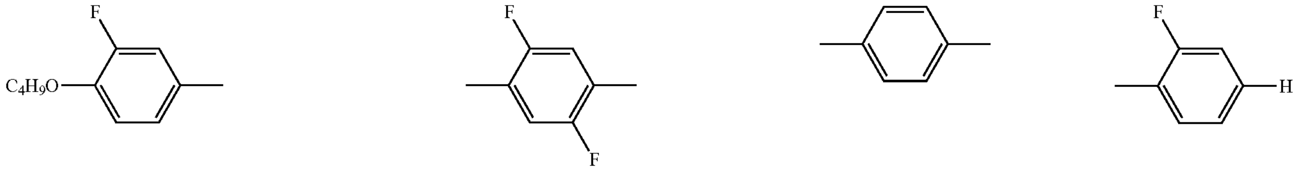 |
| 974 | 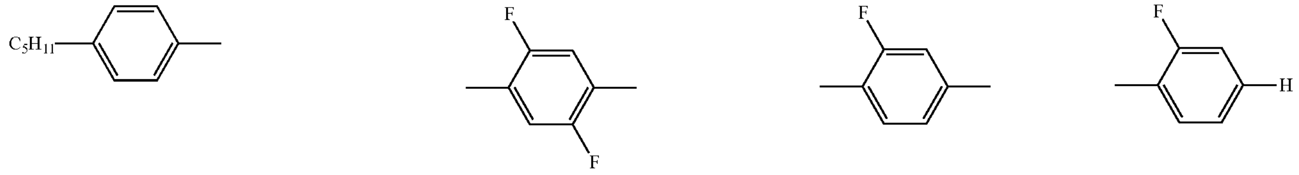 |
| 975 | 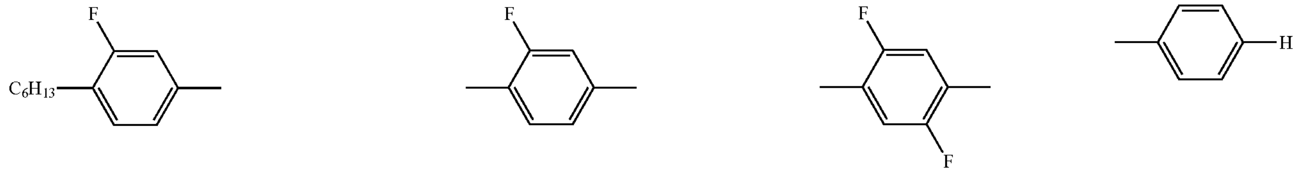 |
| 976 | 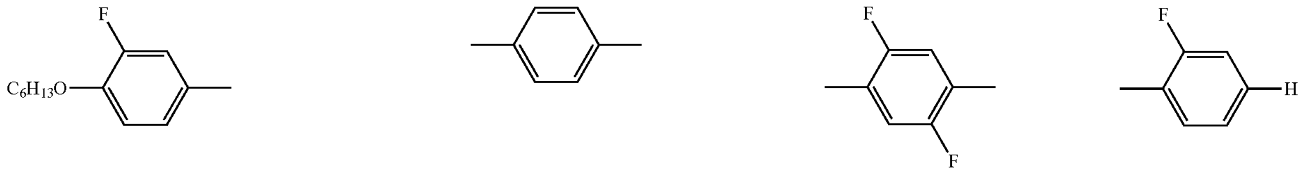 |

-continued
| | |
|---|---|
| 977 | 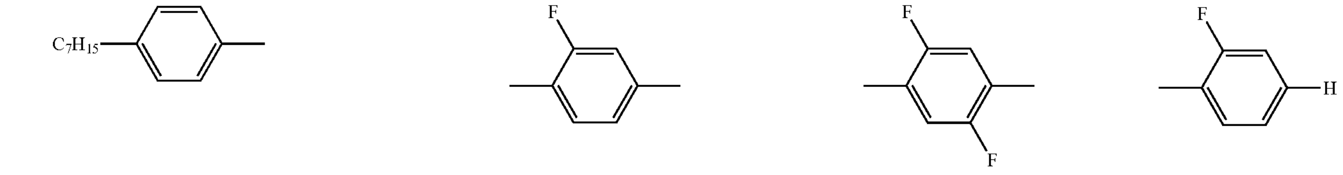 |
| 978 | 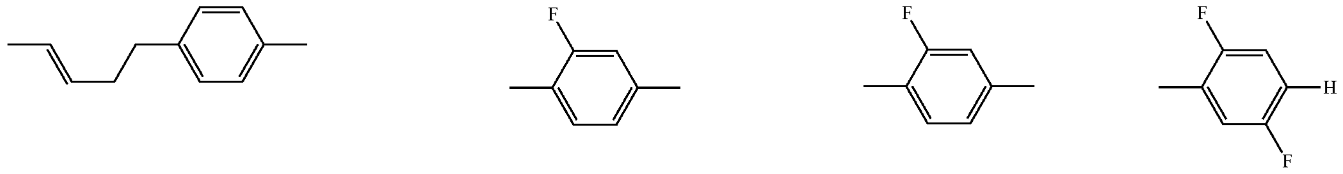 |
| 979 | 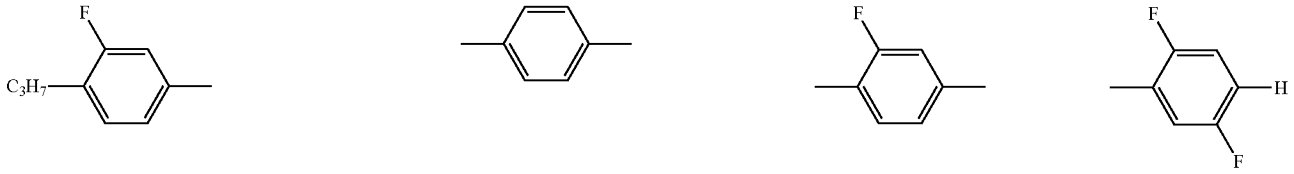 |
| 980 | 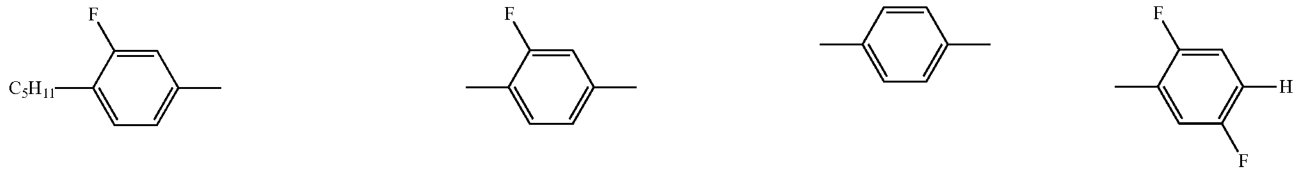 |
| 981 | 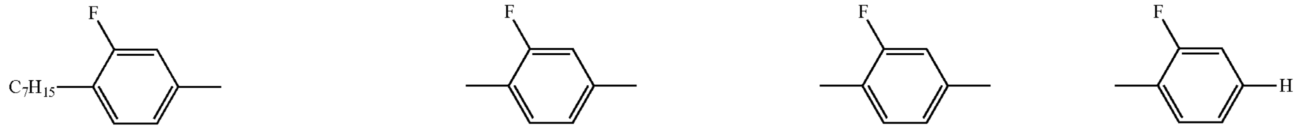 |
| 982 | 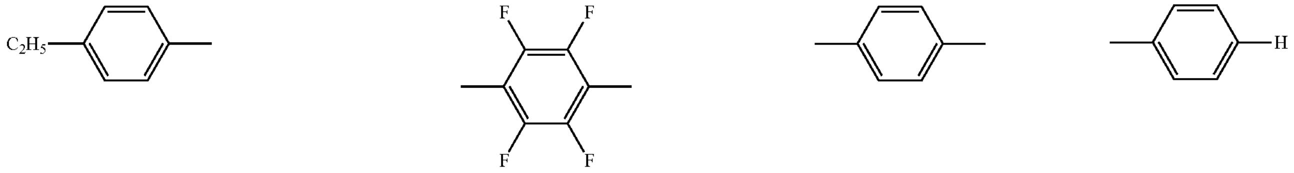 |

-continued
| | |
|---|---|
| 983 | 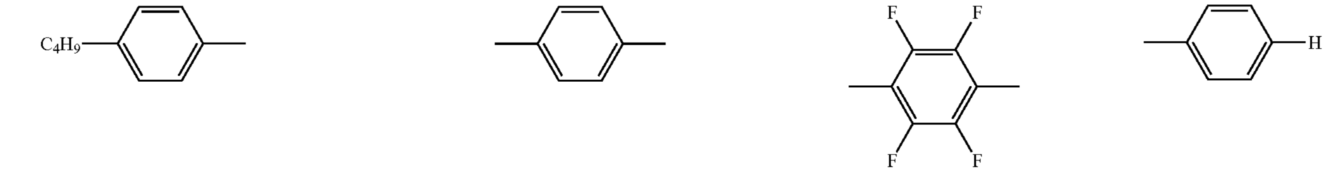 |
| 984 | 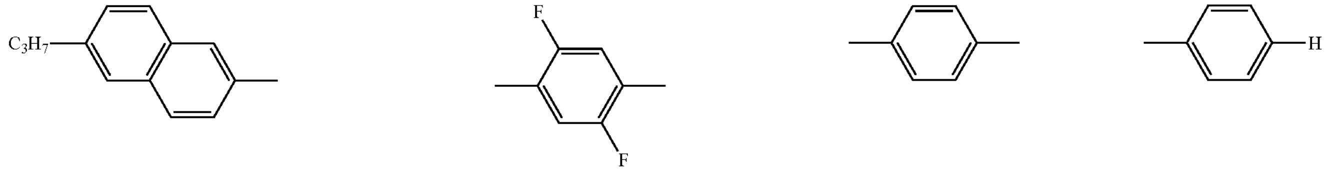 |
| 985 | 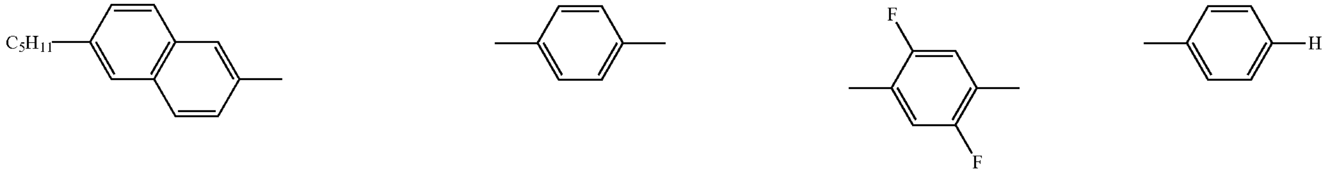 |
| 986 | 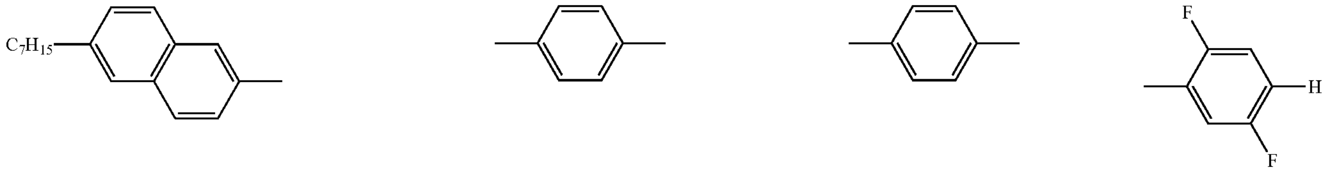 |
| 987 | 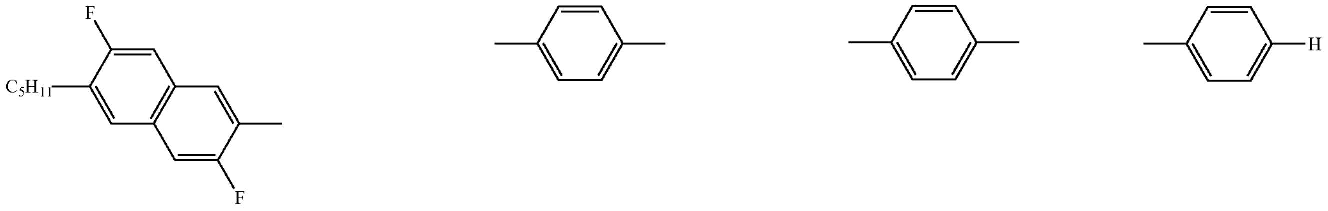 |

-continued
988 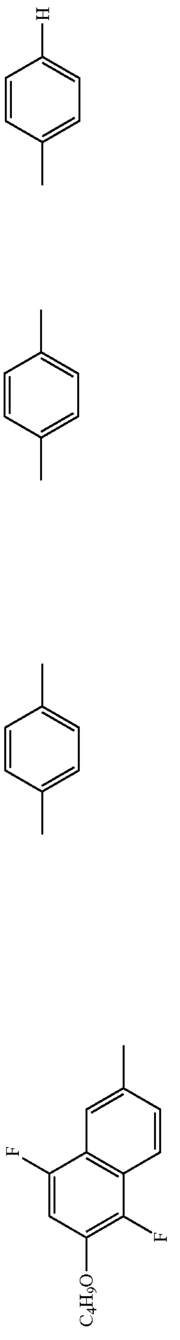
989 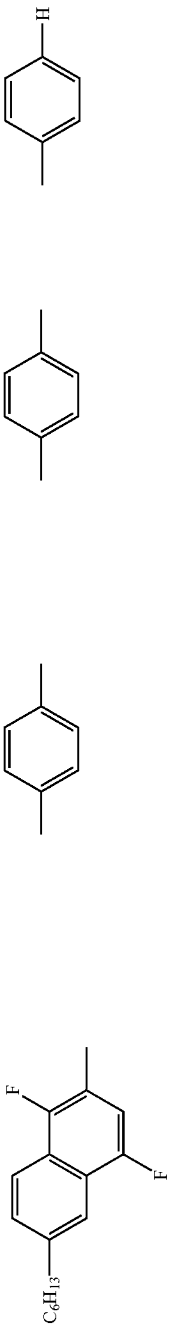
990 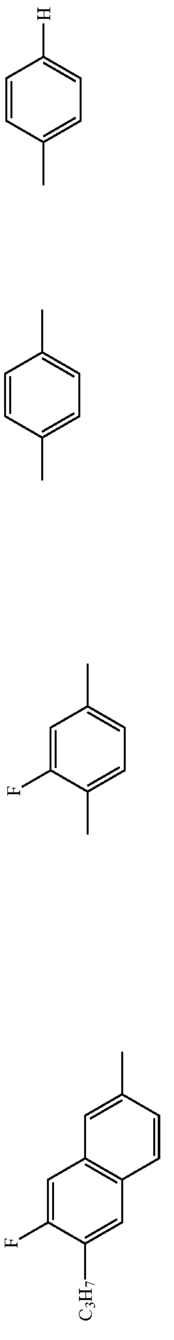
991 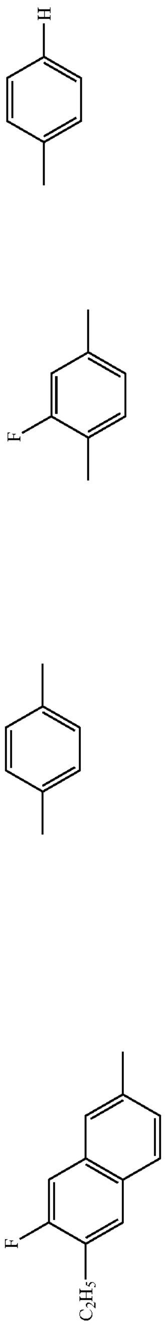
992 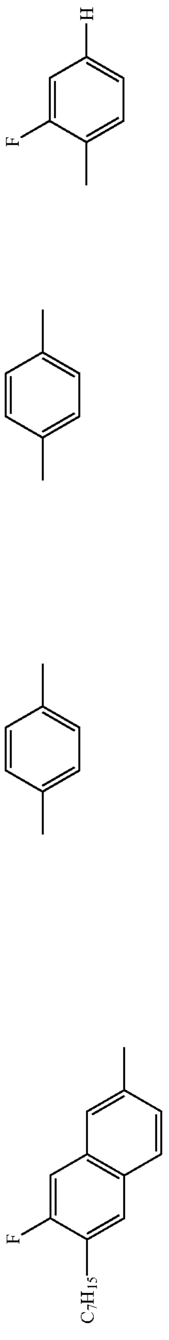
993 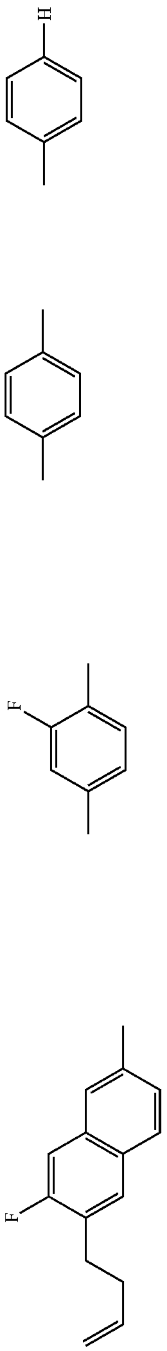

-continued
994 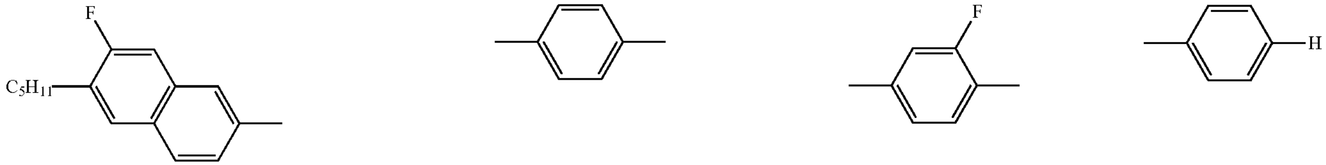
995 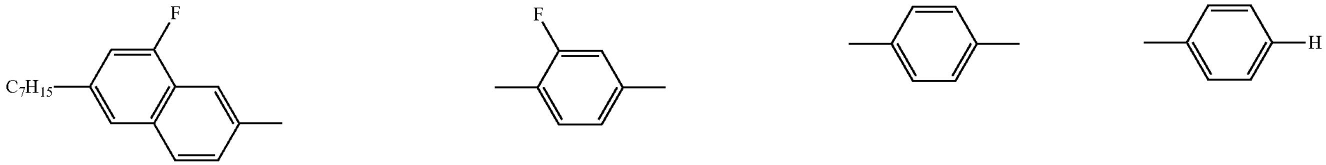
996 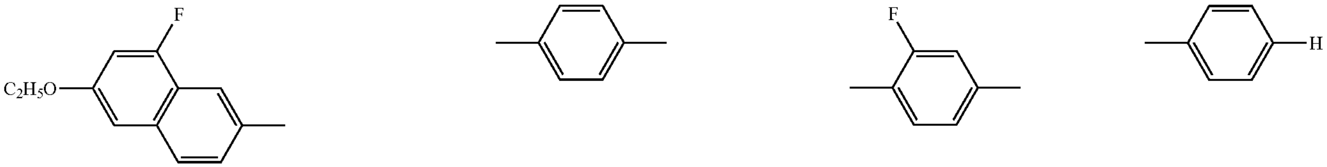
997 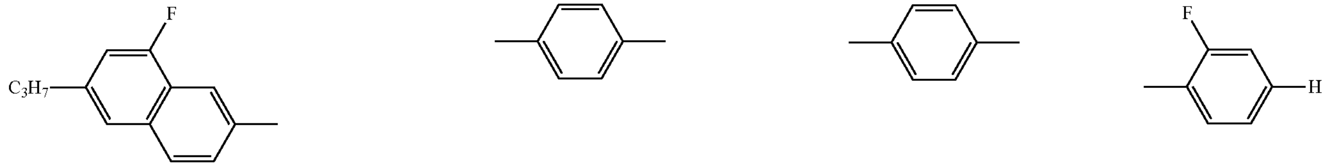
998 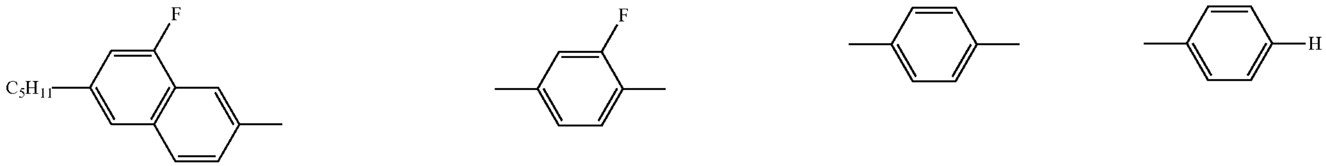
999 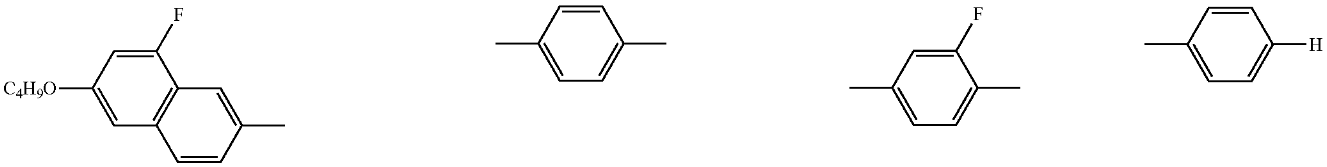

-continued
1000 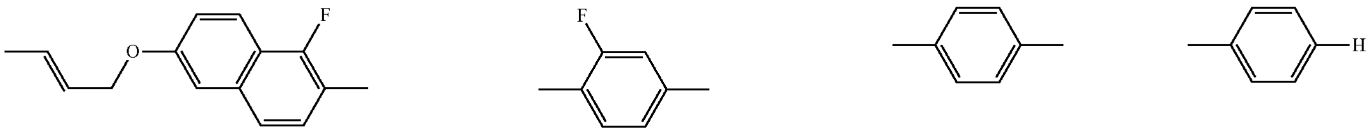
1001 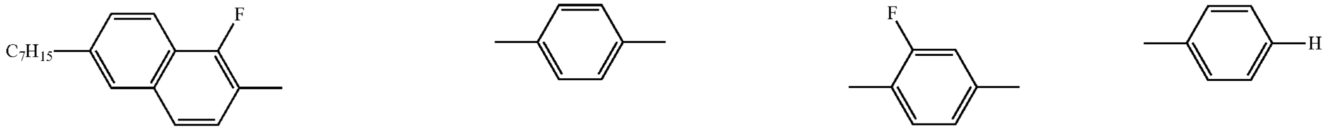
1002 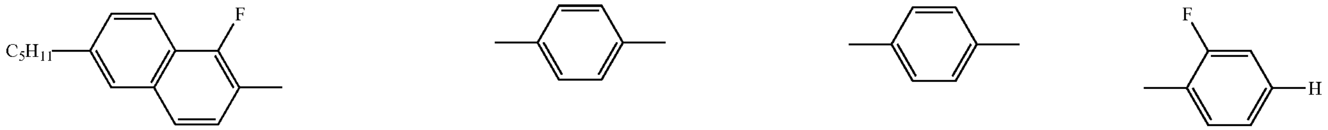
1003 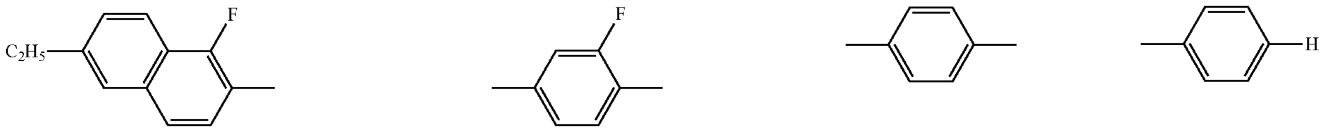
1004 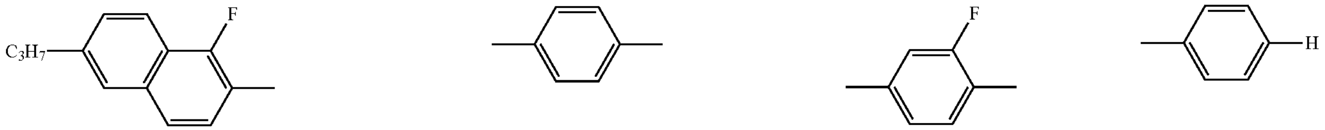
1005 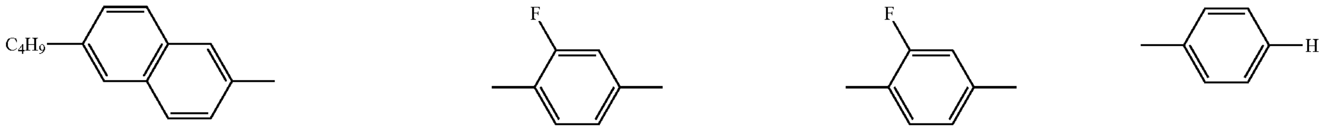
1006 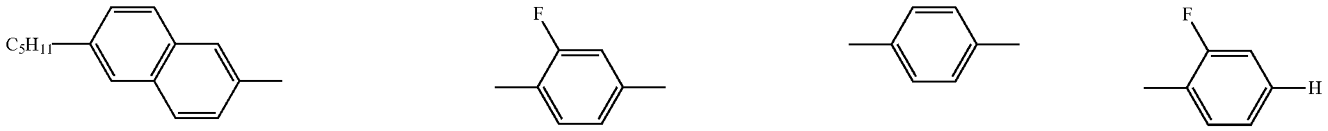

-continued
1007 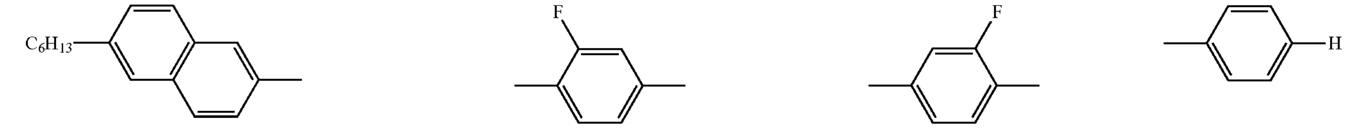
1008 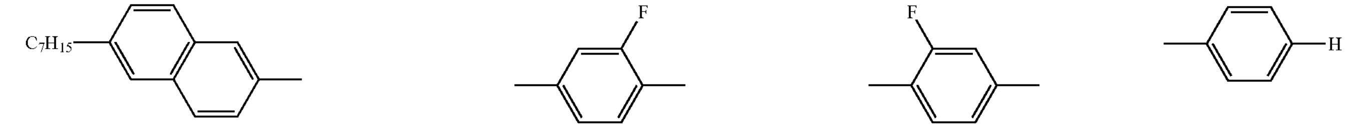
1009 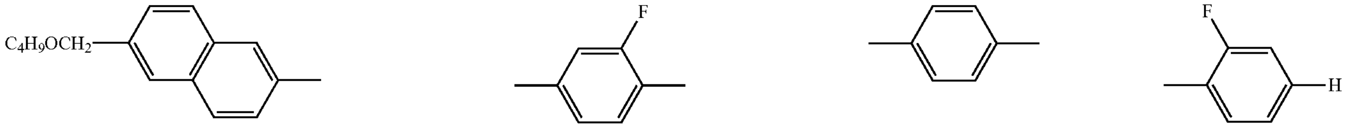
1010 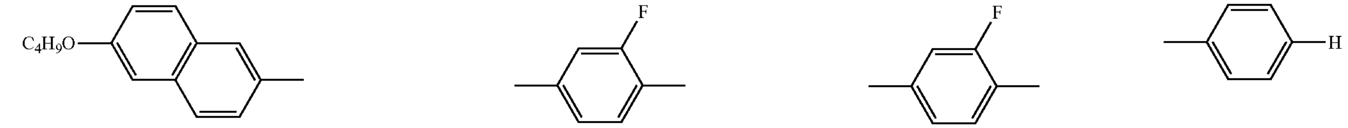
1011 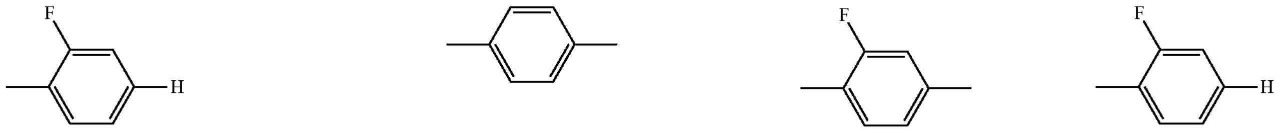
1012 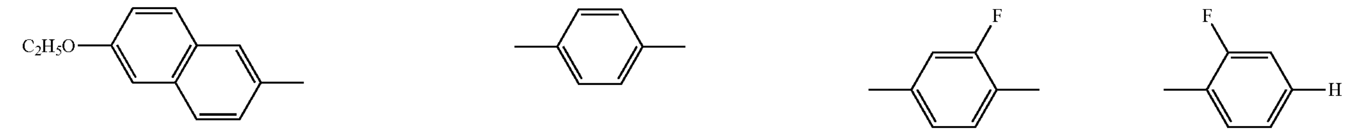
1013 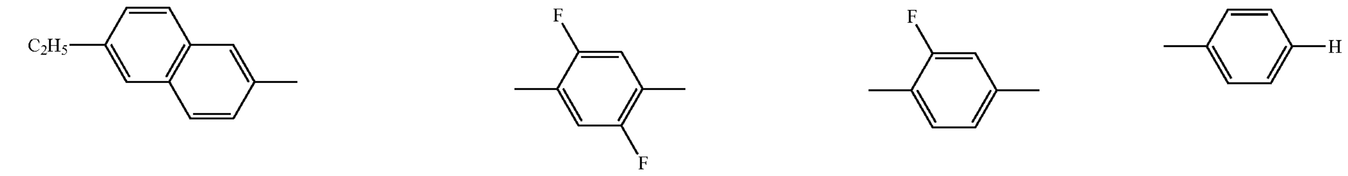

-continued
| | |
|---|---|
| 1014 | 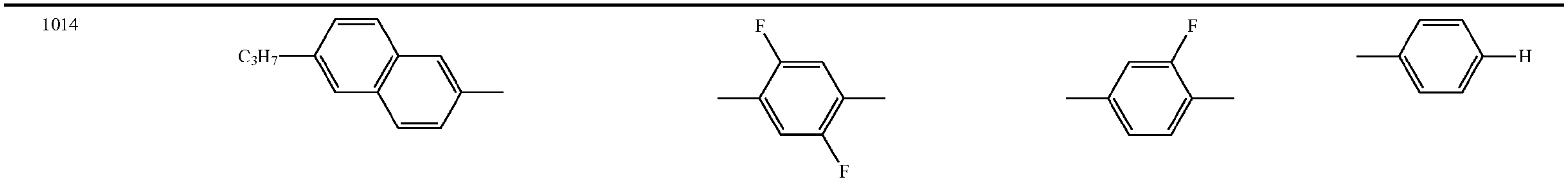 |
| 1015 | 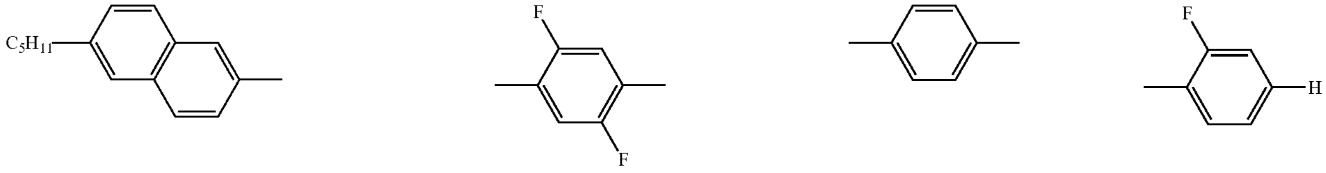 |
| 1016 | 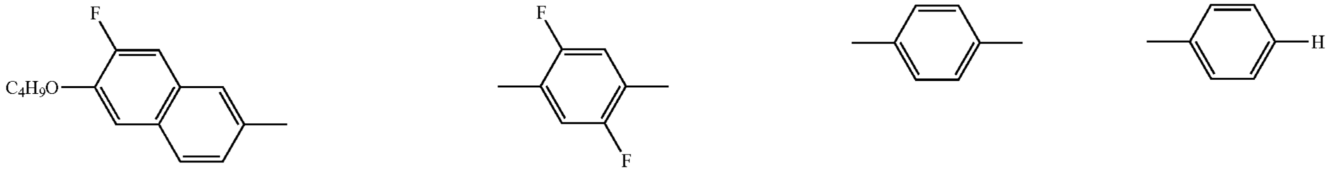 |
| 1017 | 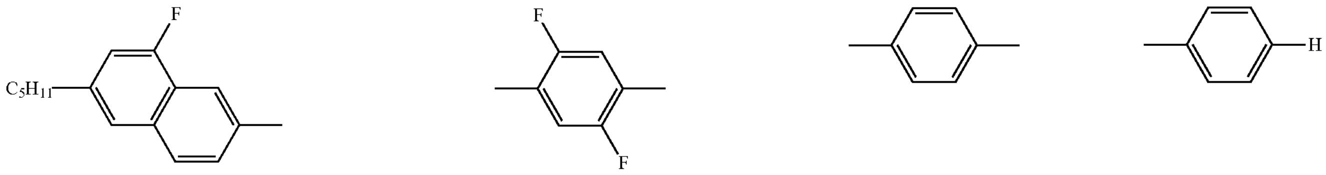 |
| 1018 | 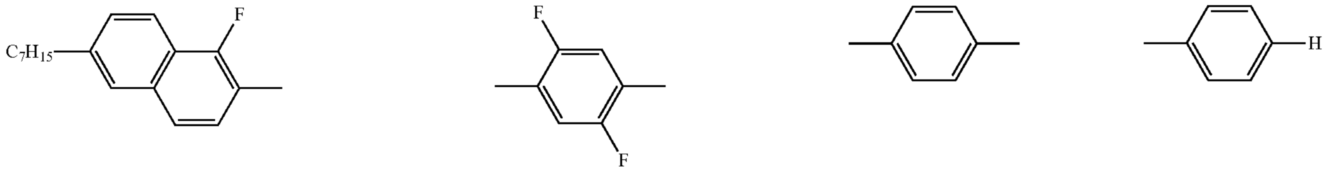 |

-continued
1019 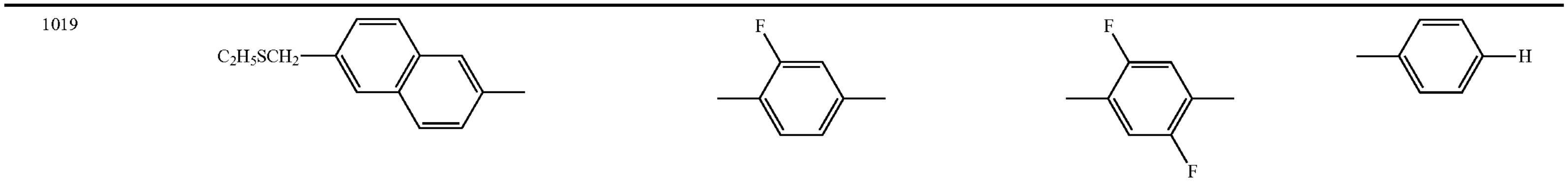
1020 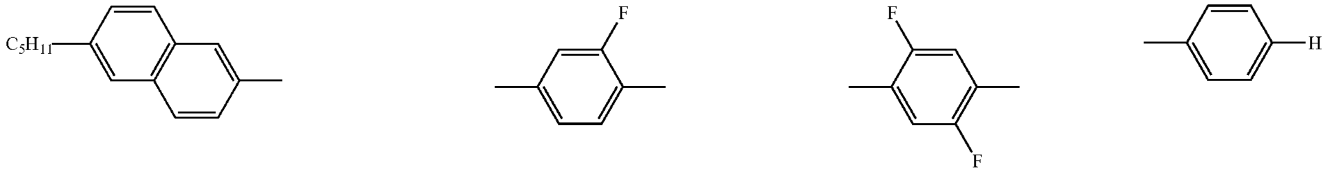
1021 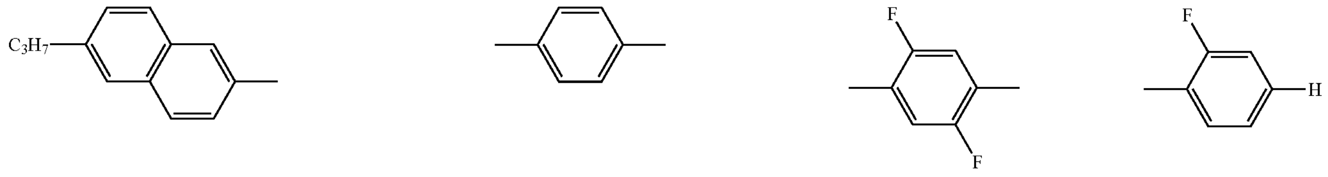
1022 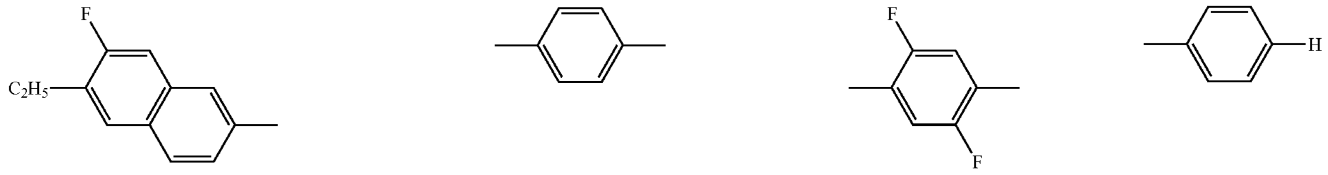
1023 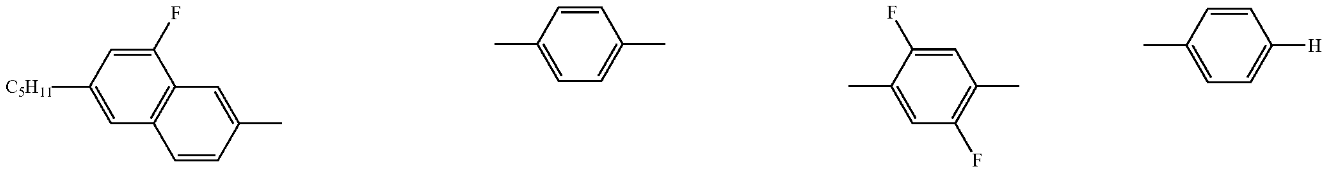

-continued
1024 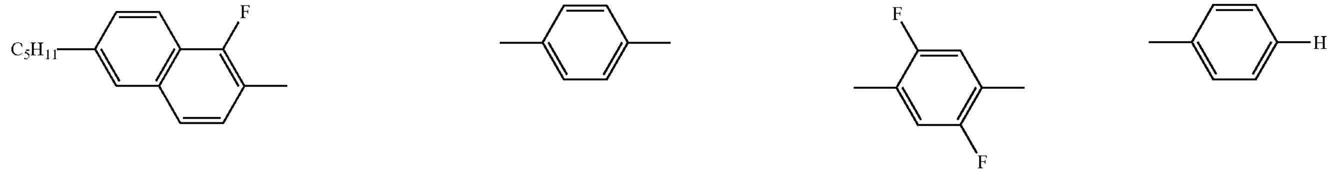
1025 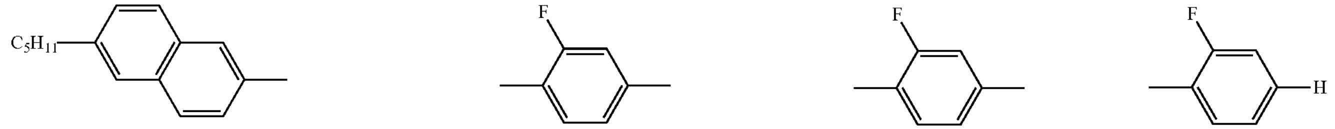
1026 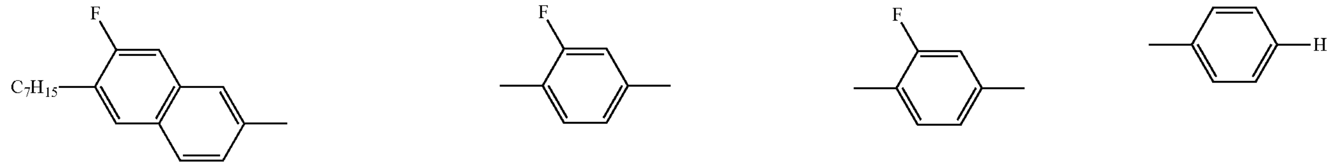
1027 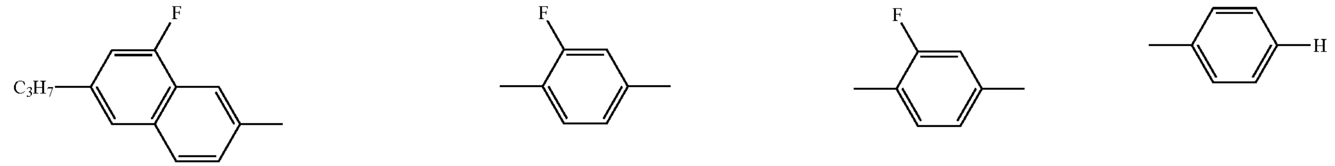
1028 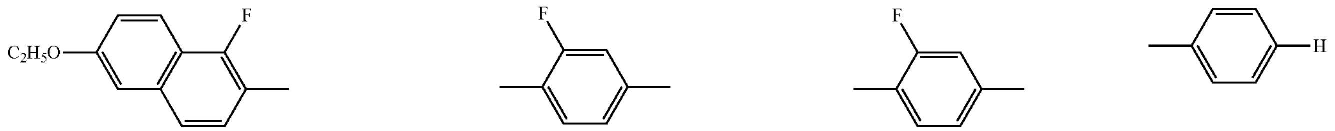
1029 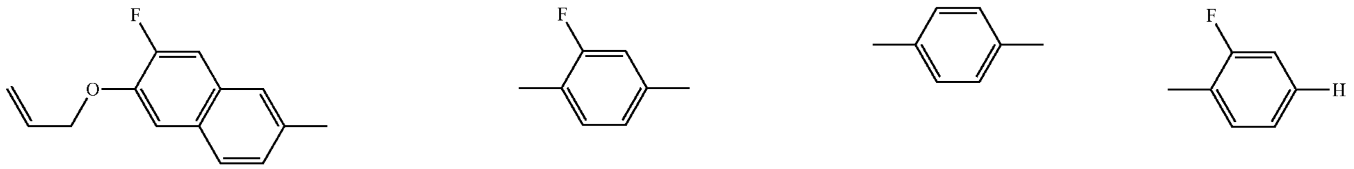

-continued
1030
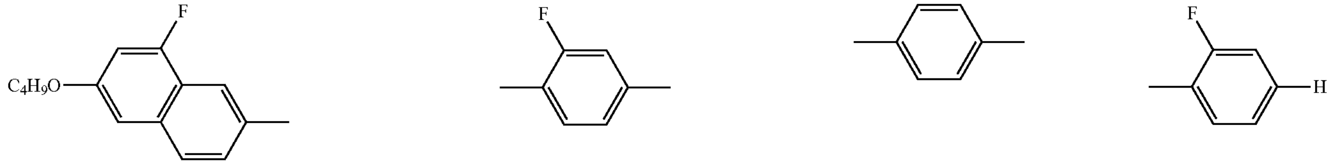
1031
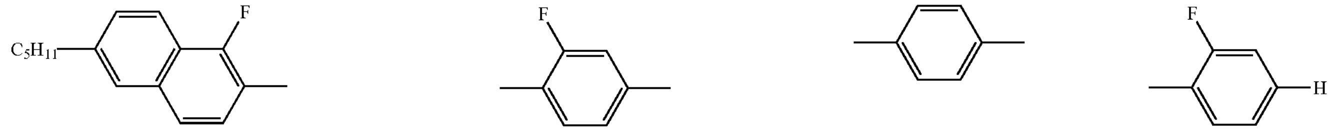
1032
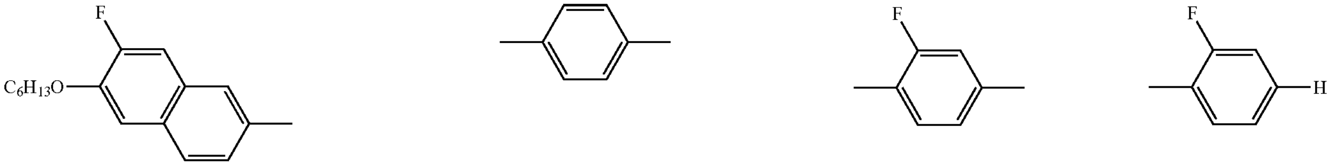
1033
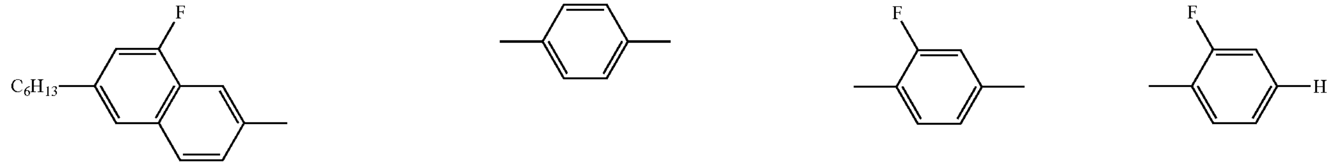
1034
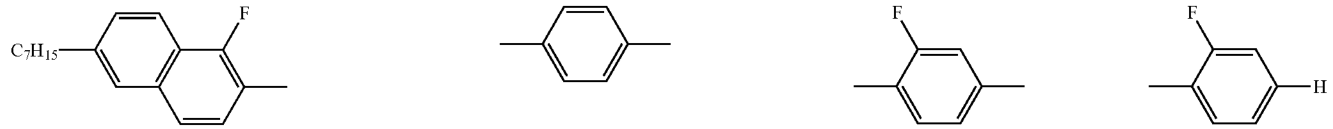
1035
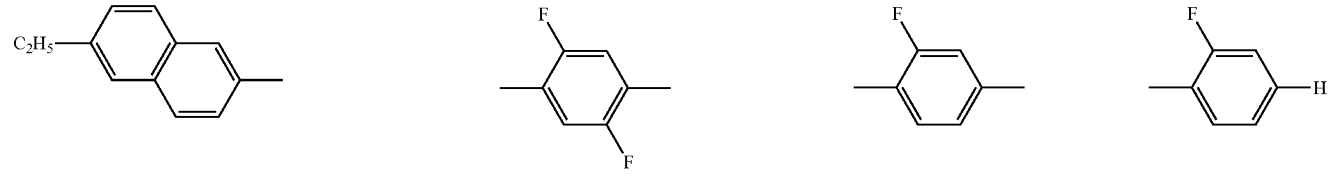

-continued
1036 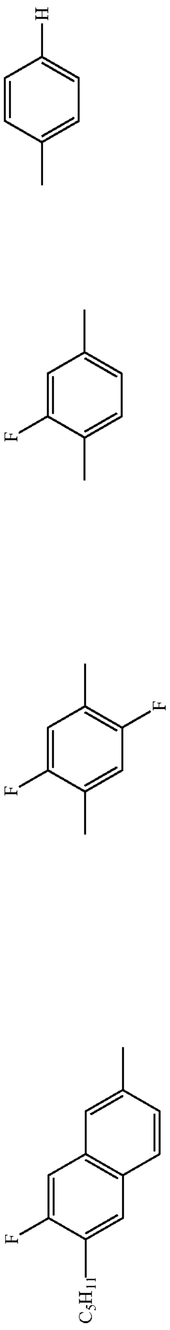
1037 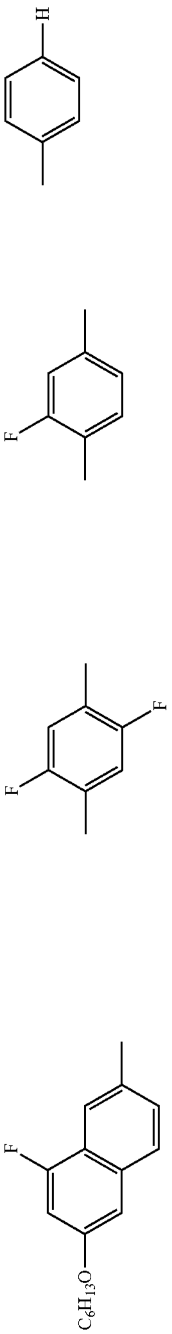
1038 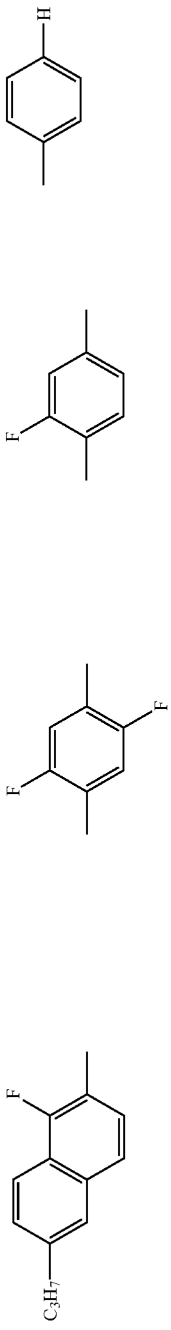
1039 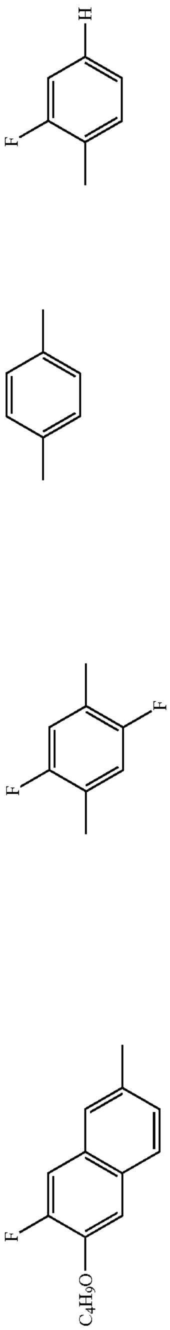
1040 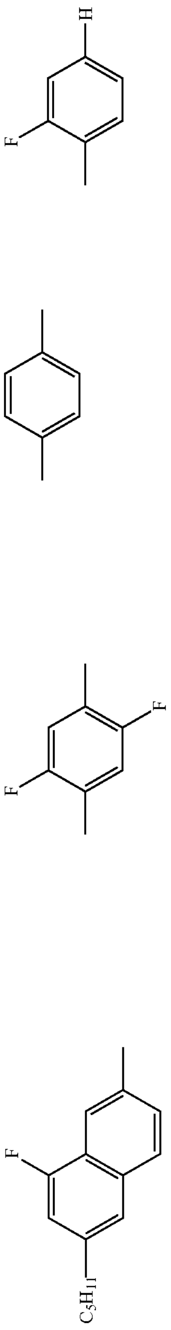

-continued
| | |
|---|---|
| 1041 | 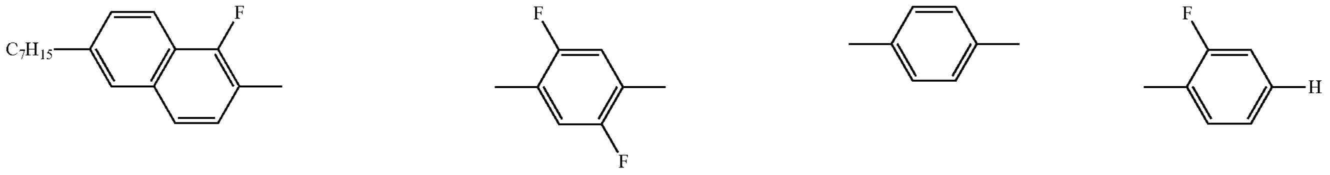 |
| 1042 | 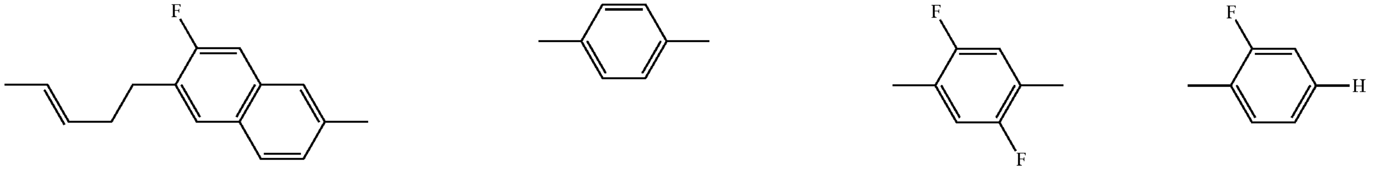 |
| 1043 | 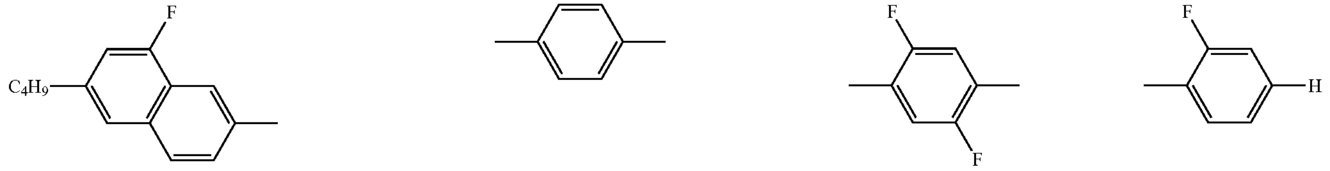 |
| 1044 | 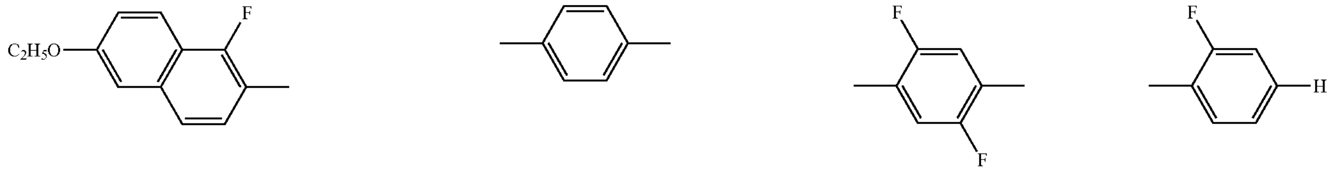 |
| 1045 | 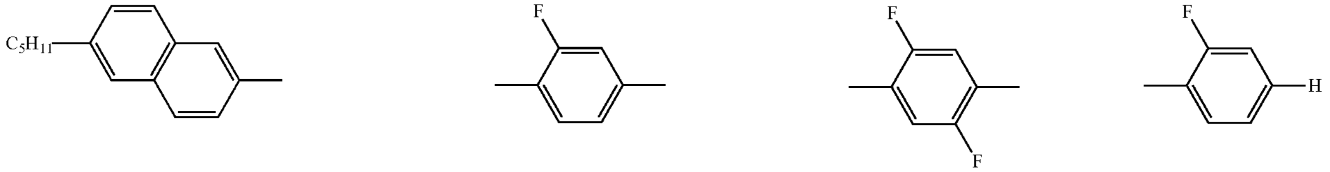 |

-continued
| | |
|---|---|
| 1046 | 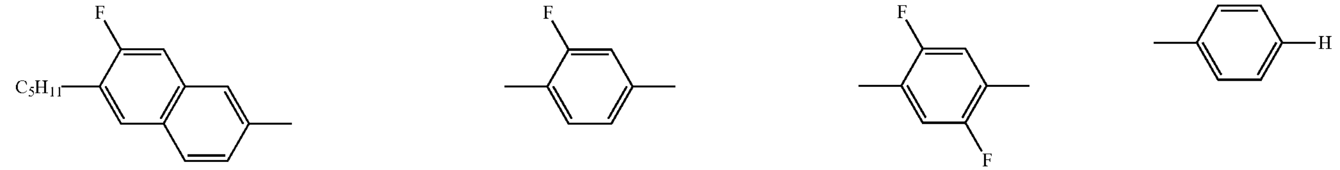 |
| 1047 | 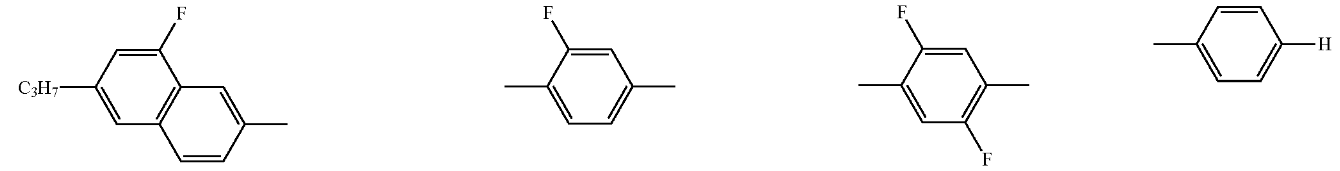 |
| 1048 | 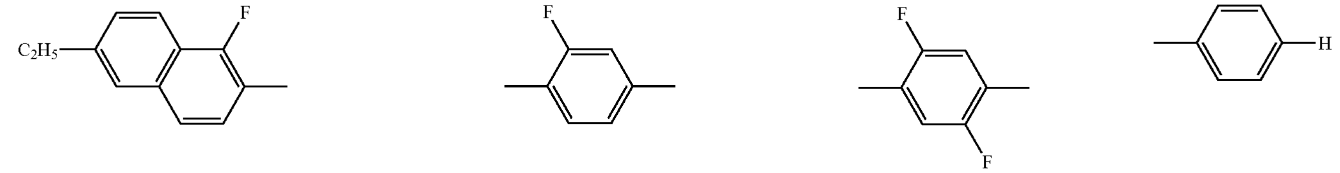 |
| 1049 | 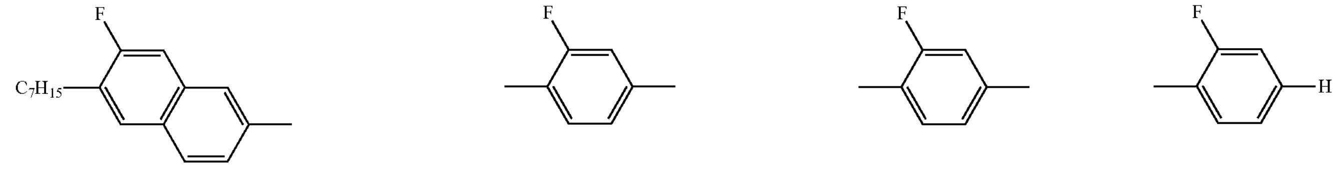 |
| 1050 | 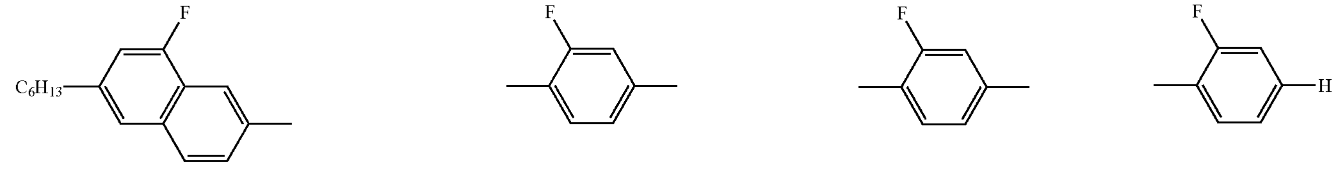 |
| 1051 | 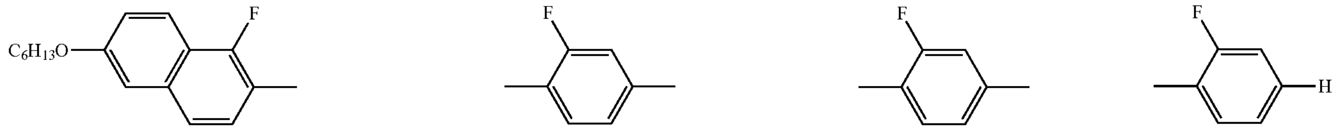 |

-continued
1052 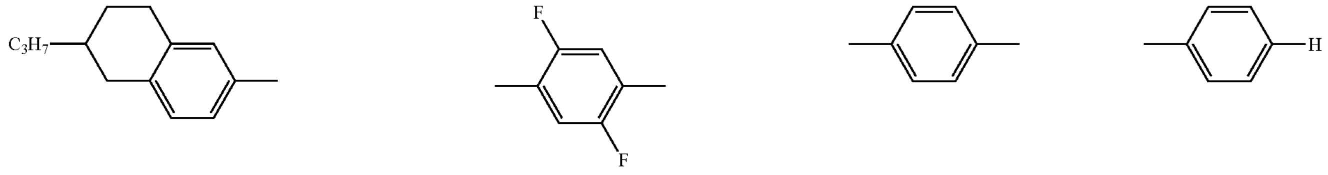
1053 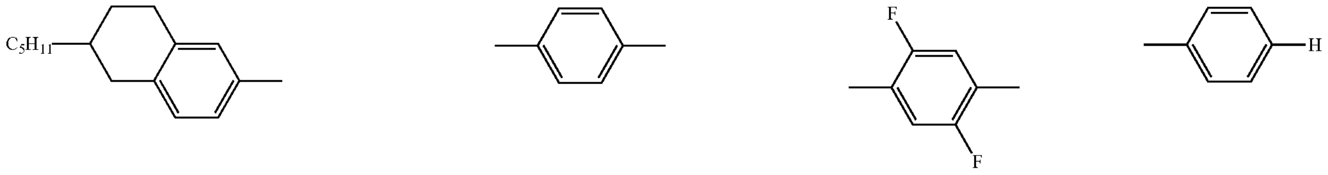
1054 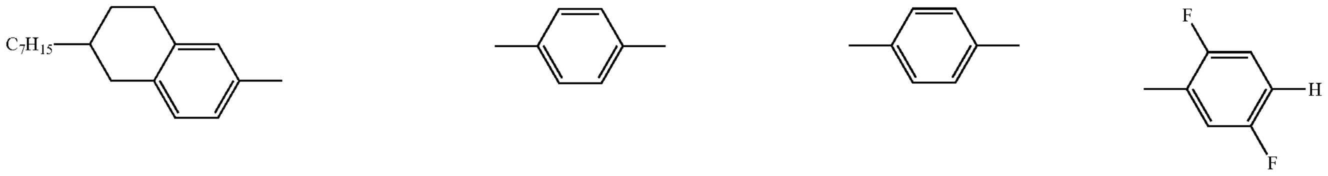
1055 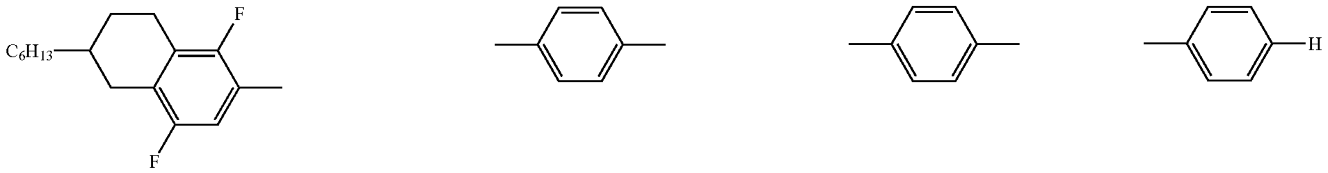
1056 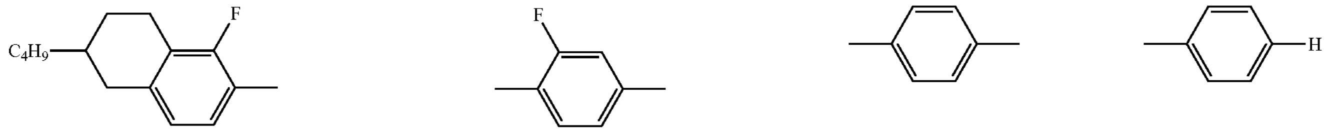
1057 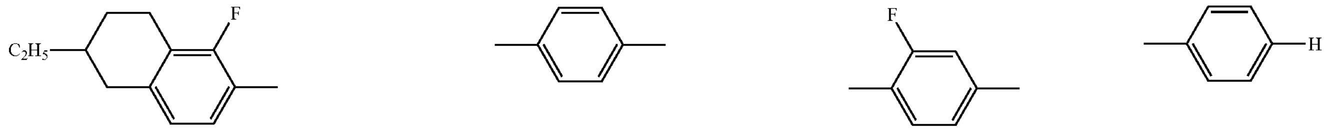

-continued
1058 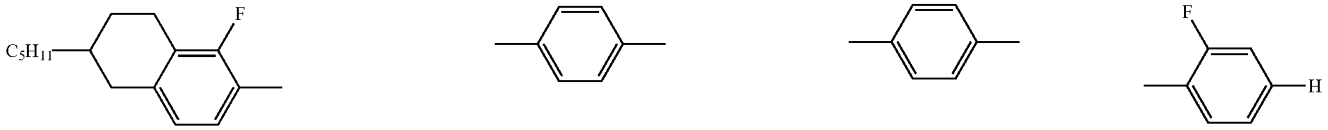
1059 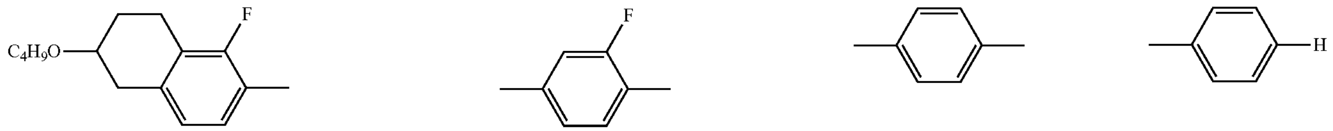
1060 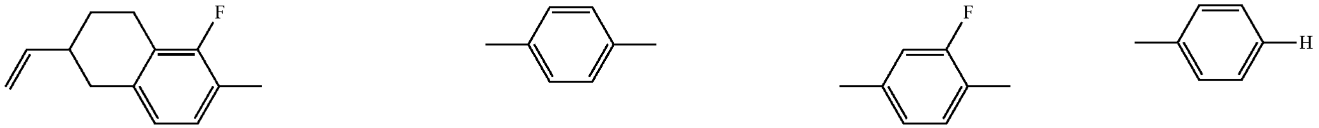
1061 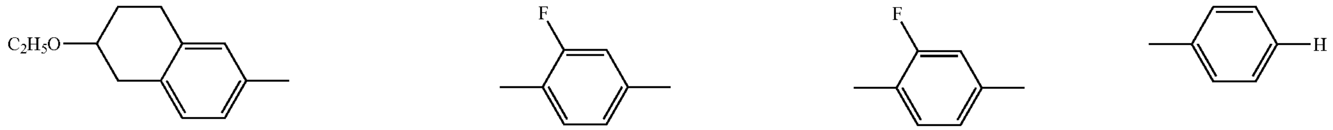
1062 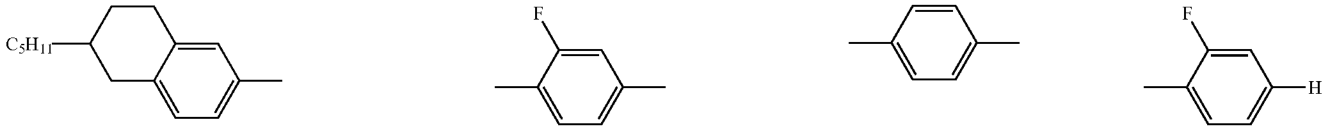
1063 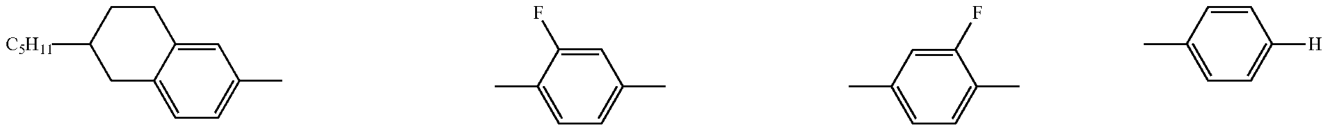
1064 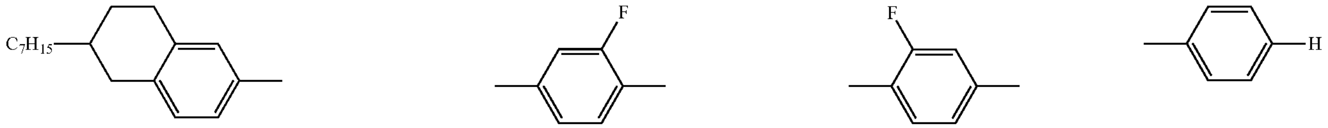

-continued
| | |
|---|---|
| 1065 | 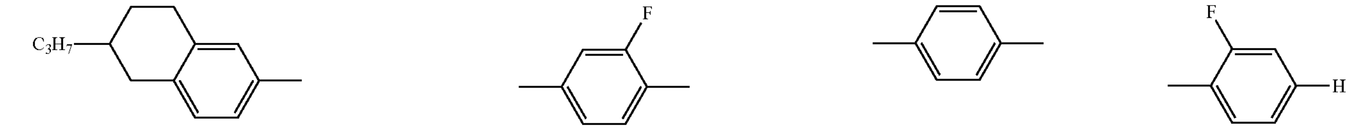 |
| 1066 | 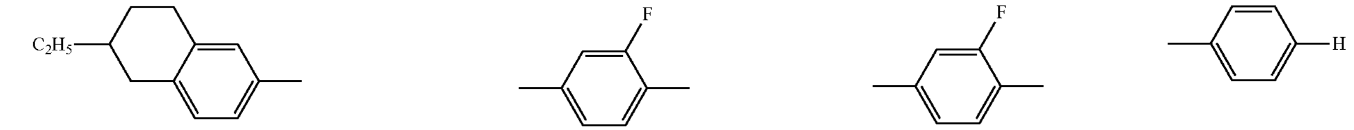 |
| 1067 | 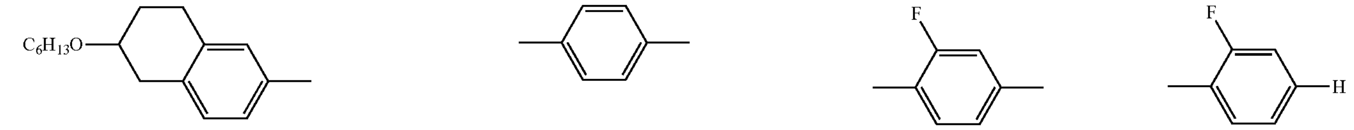 |
| 1068 | 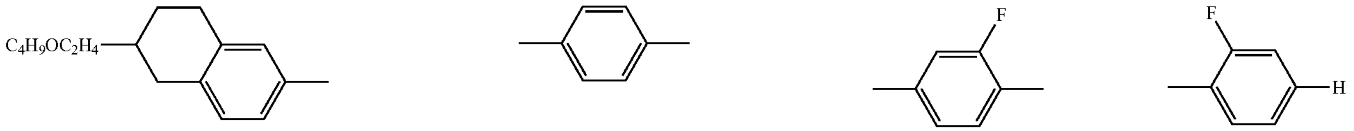 |
| 1069 | 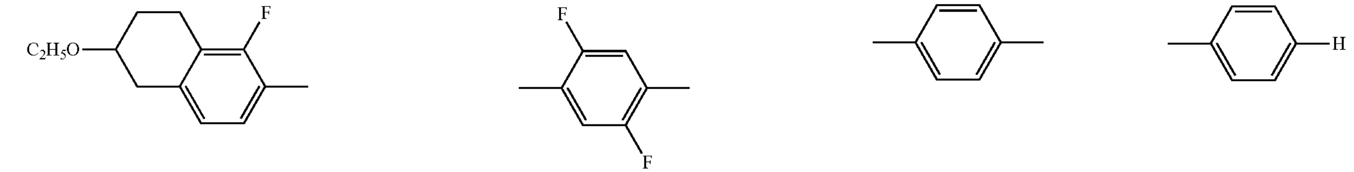 |
| 1070 | 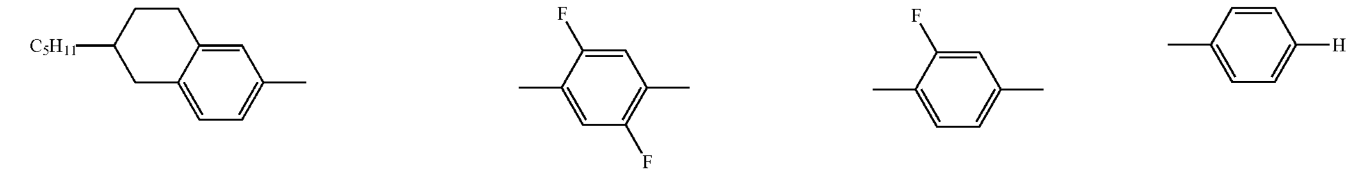 |

-continued
1071 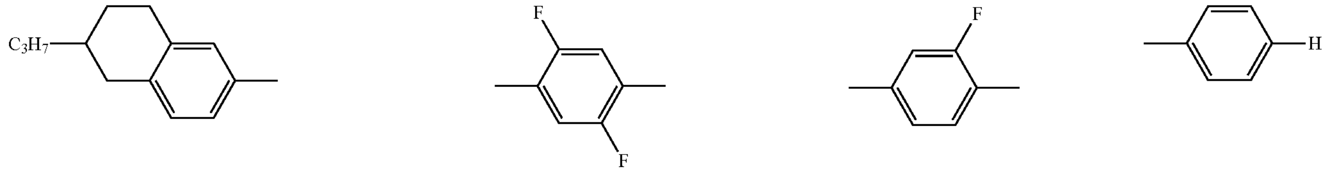
1072 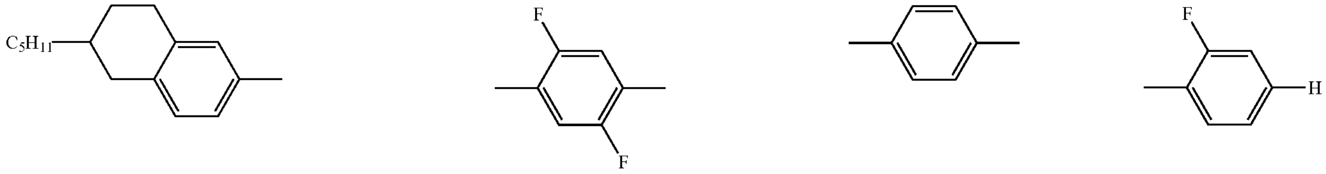
1073 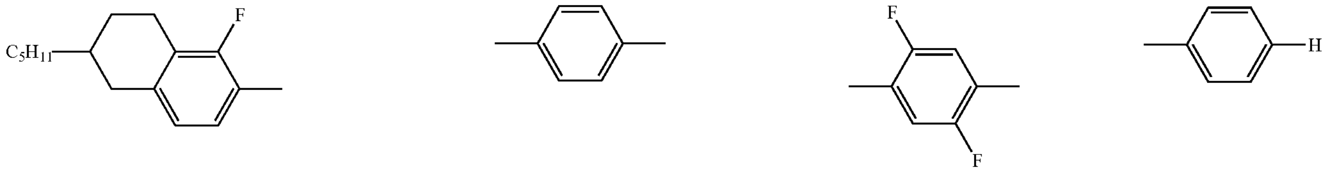
1074 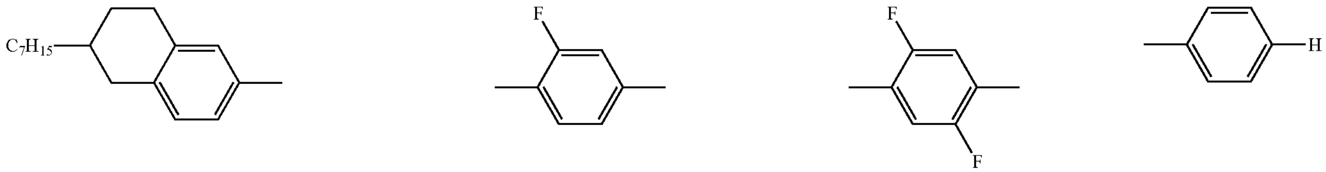
1075 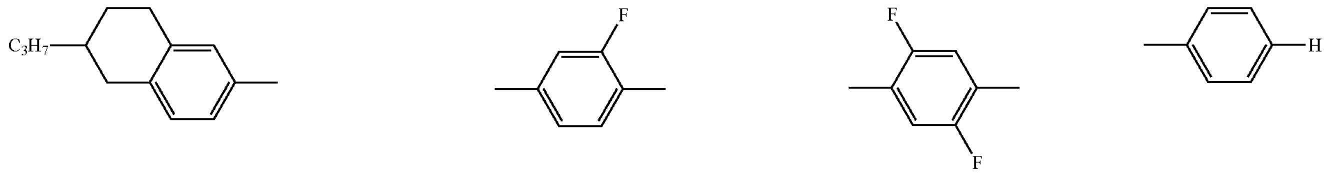

-continued
| | |
|---|---|
| 1076 | 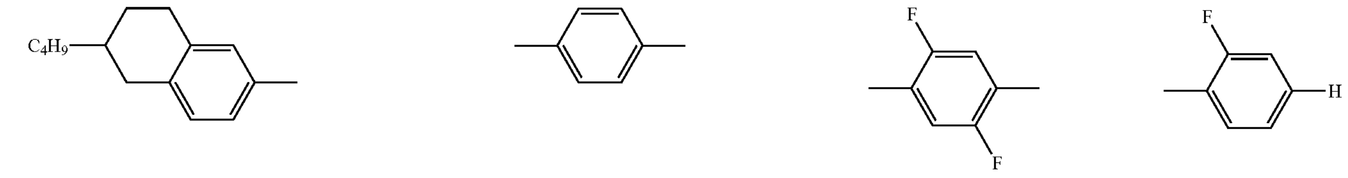 |
| 1077 | 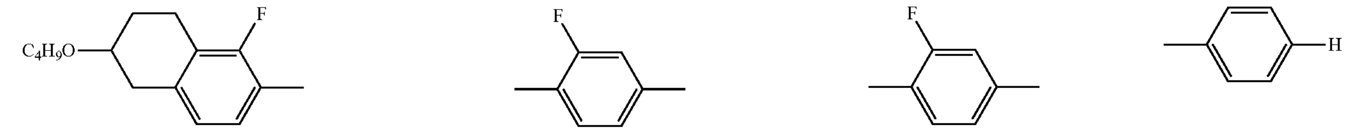 |
| 1078 | 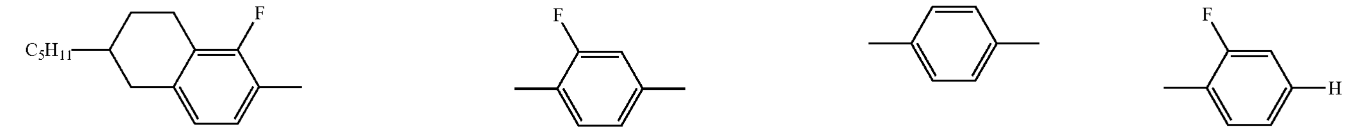 |
| 1079 | 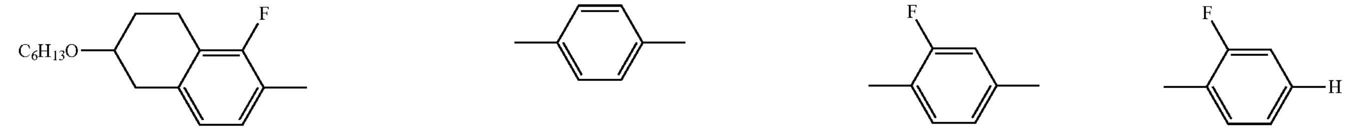 |
| 1080 | 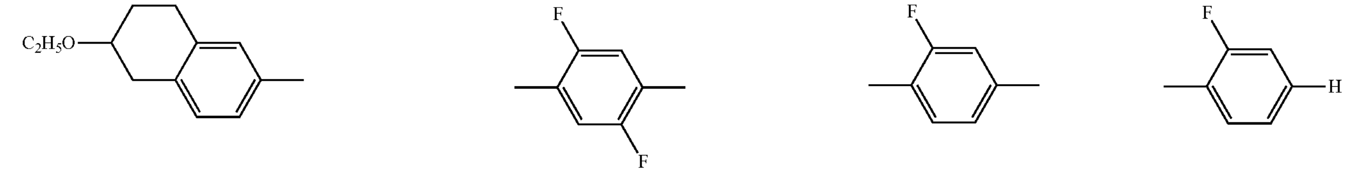 |
| 1081 | 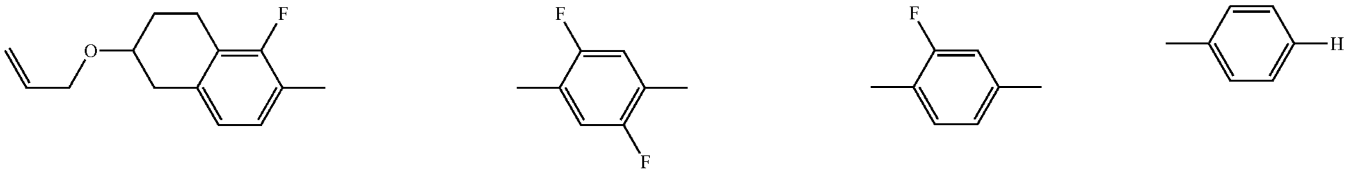 |

-continued
| | |
|---|---|
| 1082 | 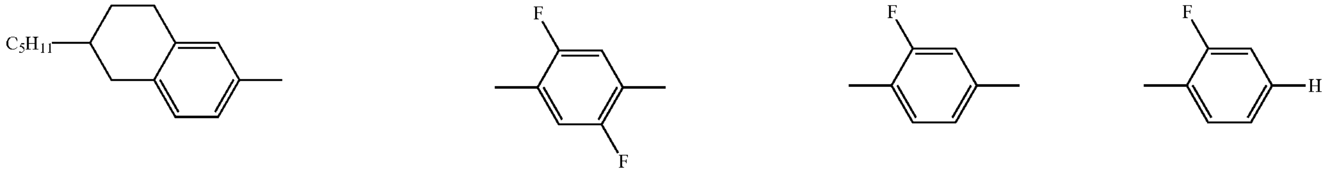 |
| 1083 | 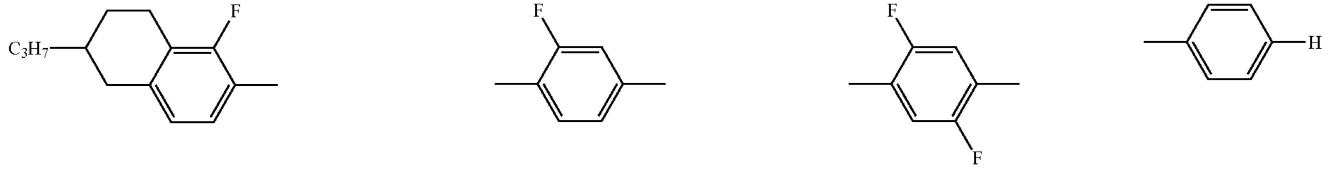 |
| 1084 | 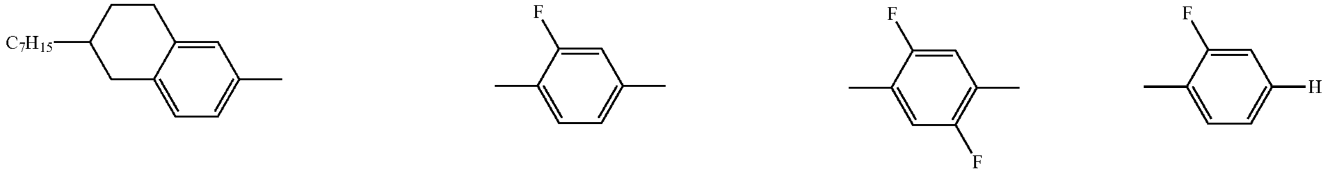 |
| 1085 | 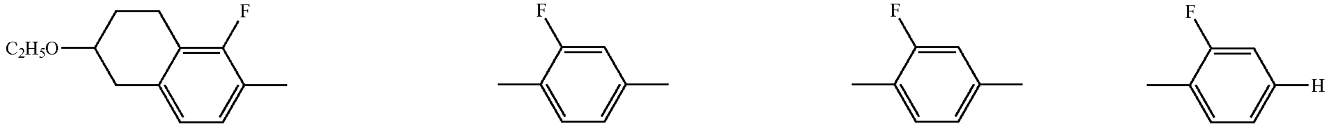 |
| 1086 | 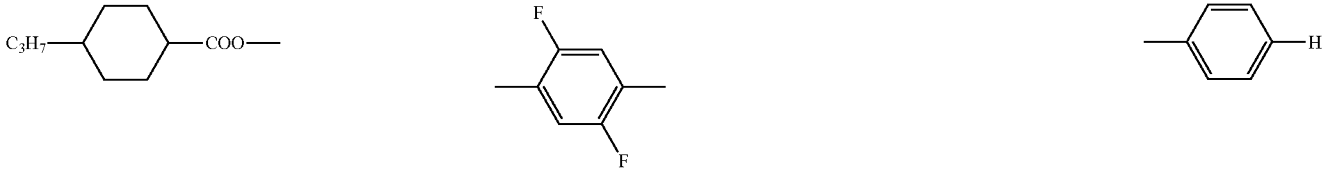 |
| 1087 | 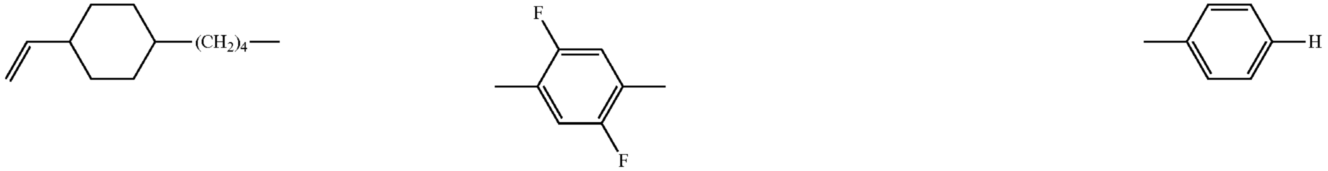 |

-continued
1088 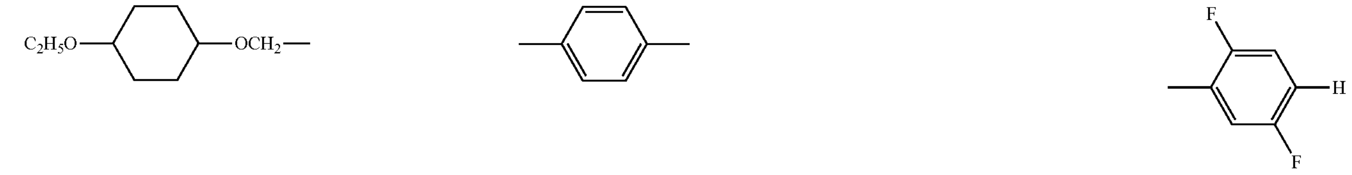
1089 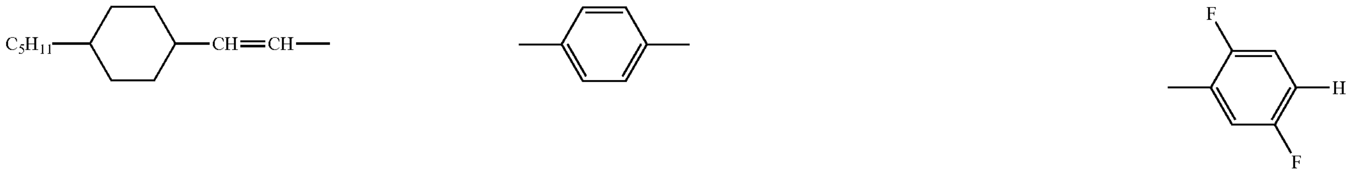
1090 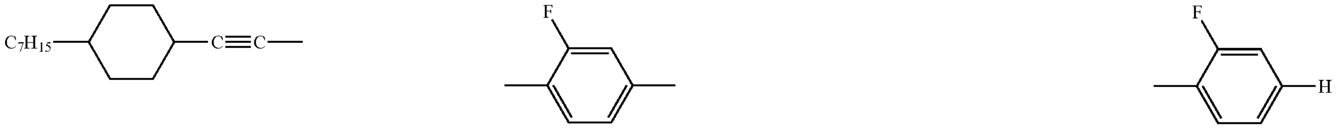
1091 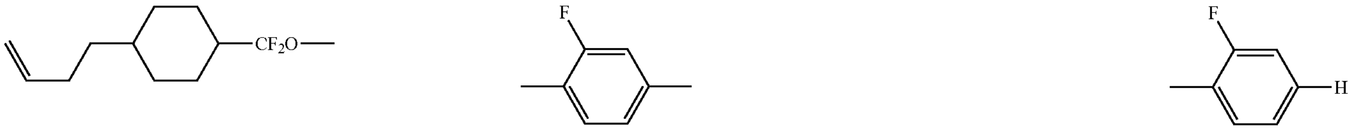
1092 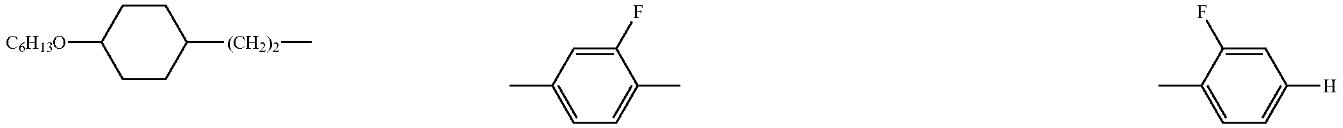
1093 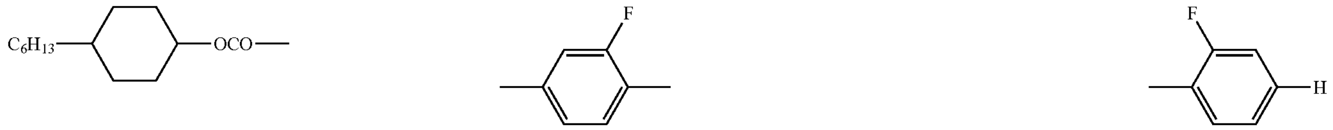

-continued
| | |
|---|---|
| 1094 | 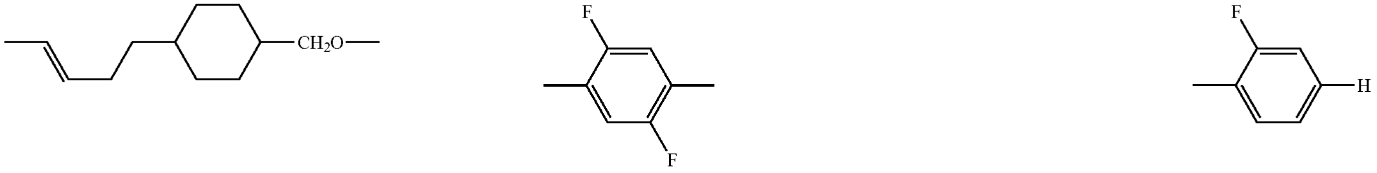 |
| 1095 | 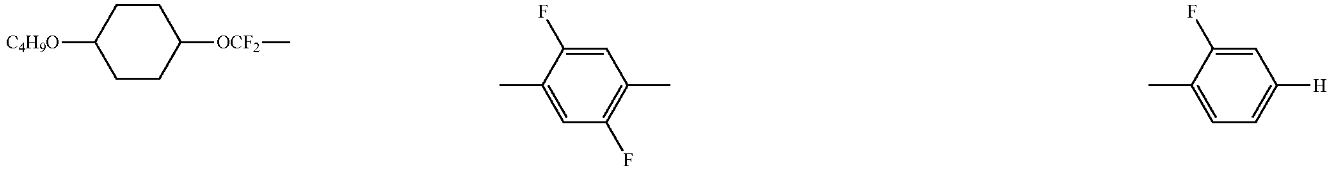 |
| 1096 | 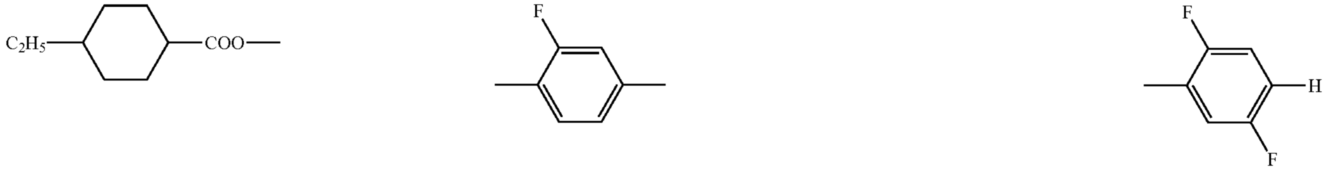 |
| 1097 | 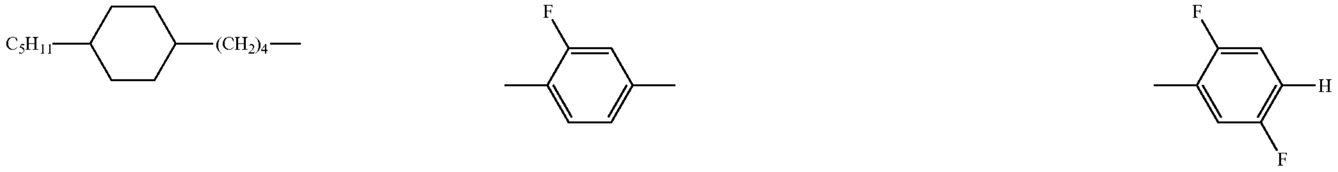 |
| 1098 | 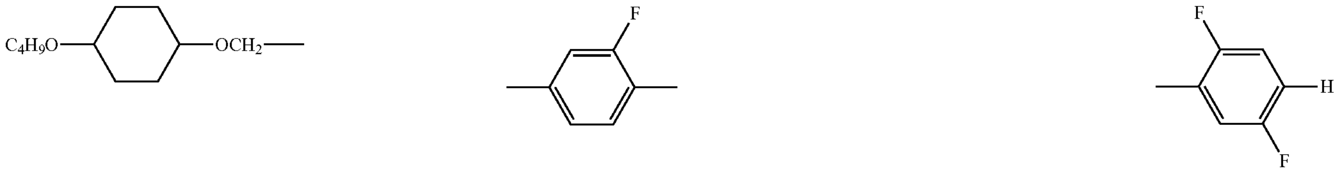 |

-continued
1099 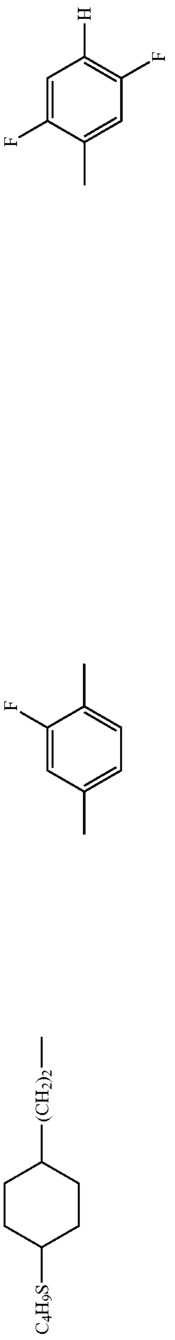
1100 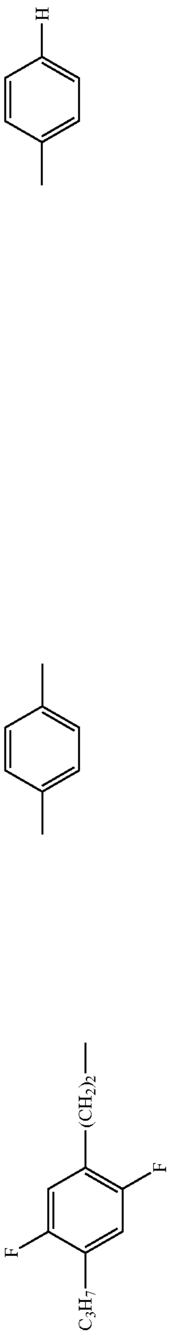
1101 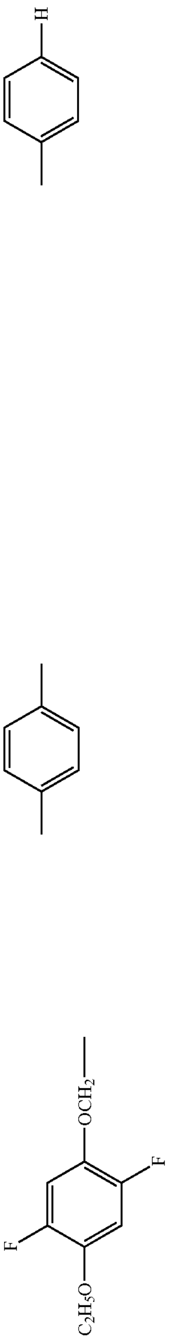
1102 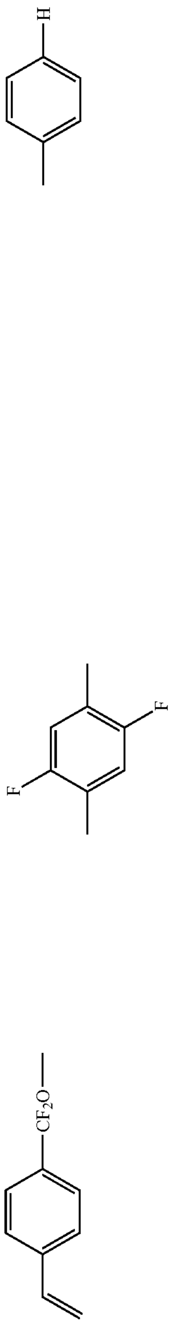
1103 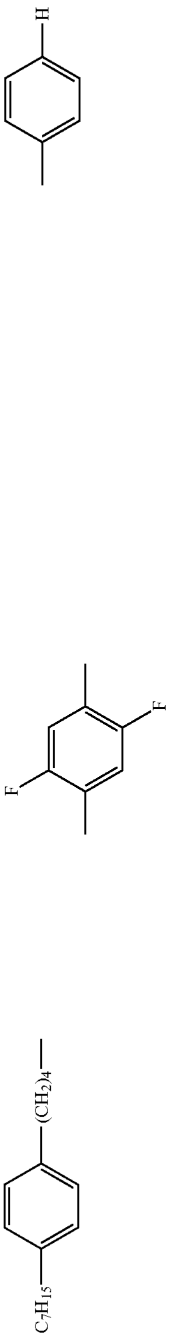

-continued
| | |
|---|---|
| 1104 | 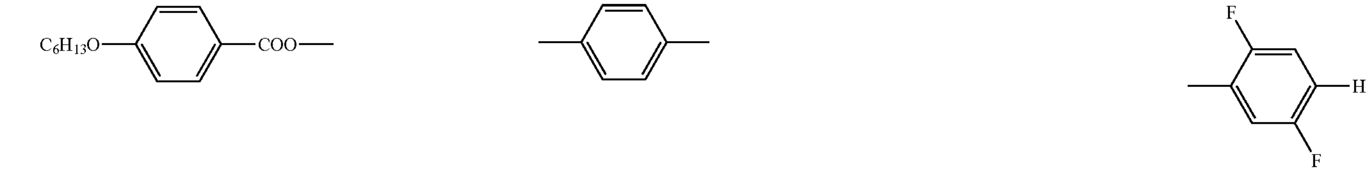 |
| 1105 | 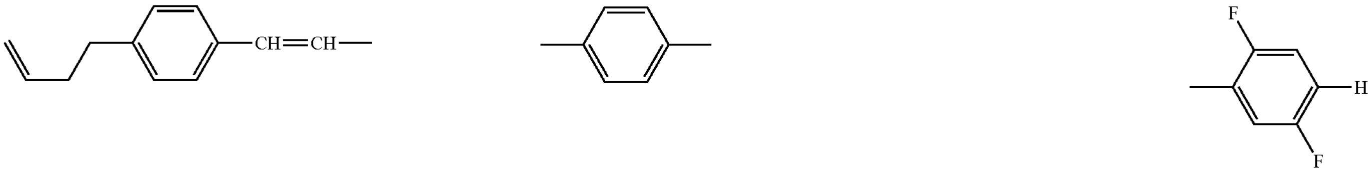 |
| 1106 | 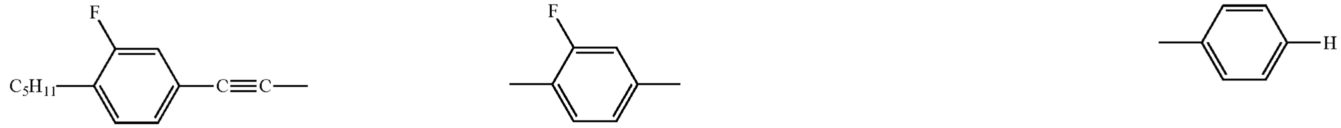 |
| 1107 | 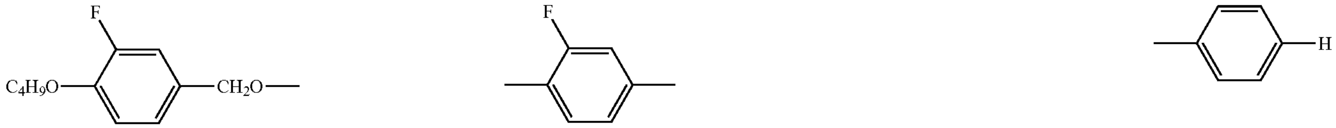 |
| 1108 | 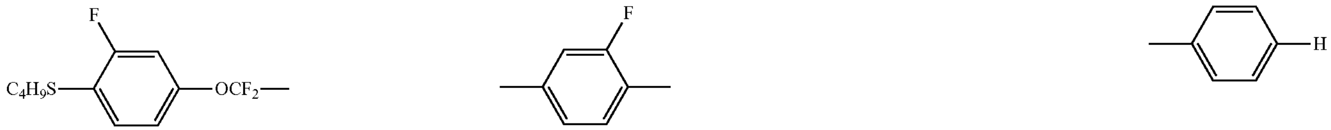 |
| 1109 | 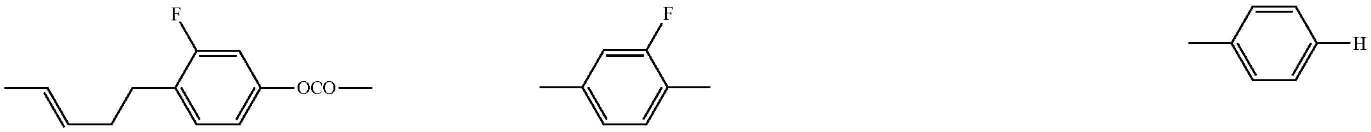 |
| 1110 | 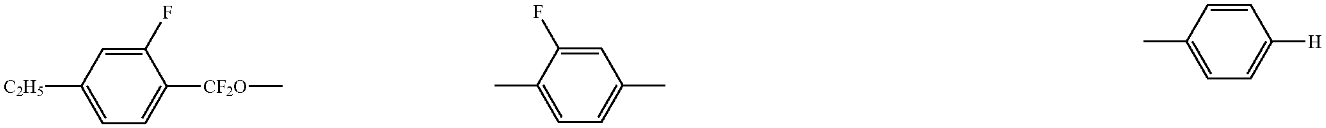 |

-continued
| | | | |
|---|---|---|---|
| 1111 | 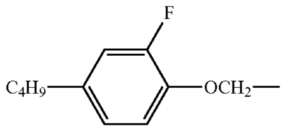 | 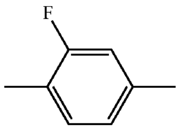 | 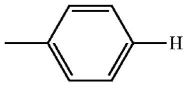 |
| 1113 | 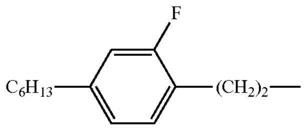 | 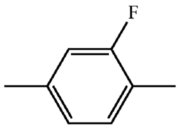 | 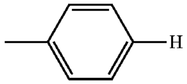 |
| 1113 | 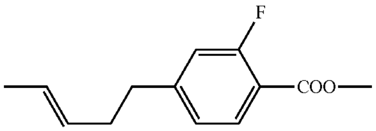 | 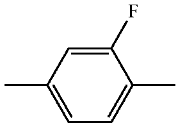 | 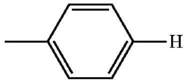 |
| 1114 | 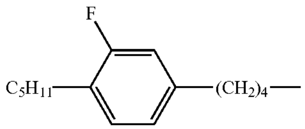 | 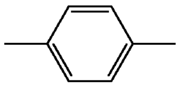 | 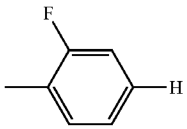 |
| 1115 | 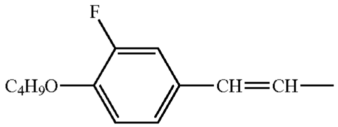 | 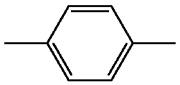 | 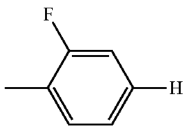 |
| 1116 | 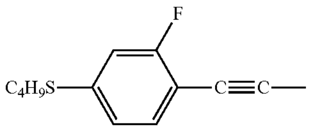 | 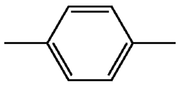 | 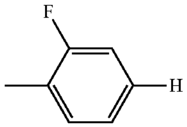 |
| 1117 | 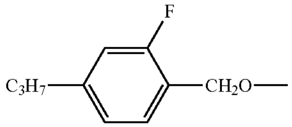 | 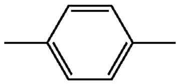 | 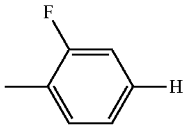 |

-continued
1118 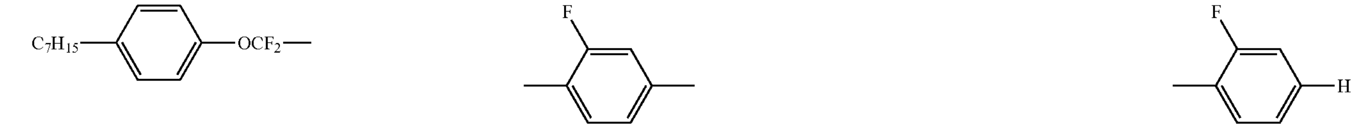
1119 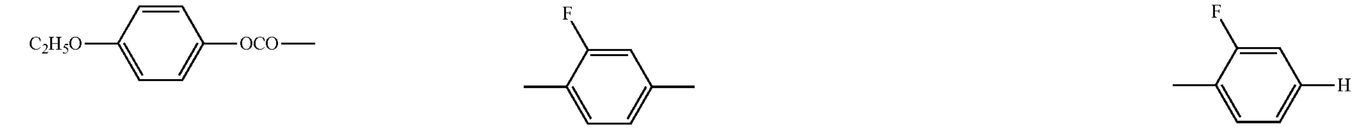
1120 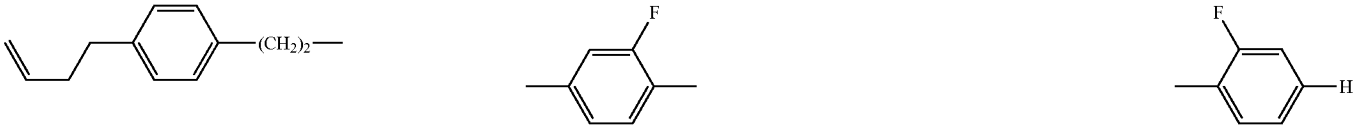
1121 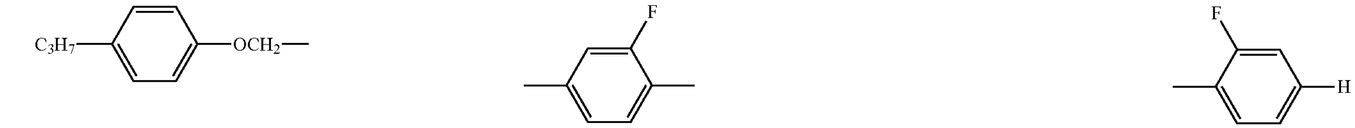
1122 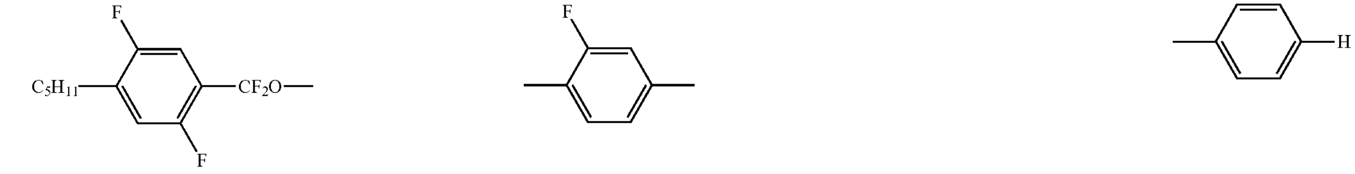
1123 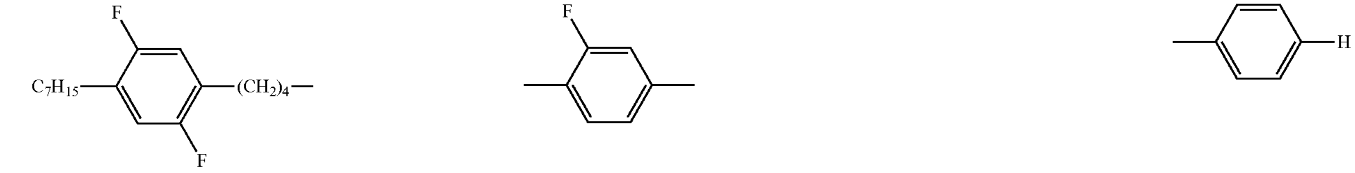

-continued
| | | | |
|---|---|---|---|
| 1124 | 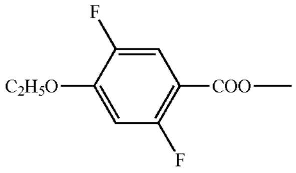 | 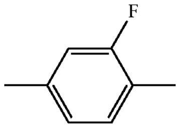 | 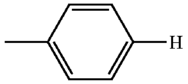 |
| 1125 | 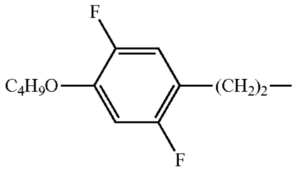 | 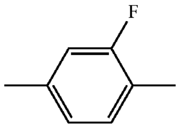 | 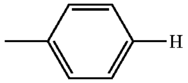 |
| 1126 | 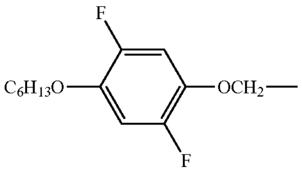 | 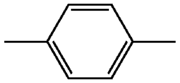 | 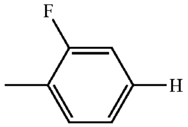 |
| 1127 | 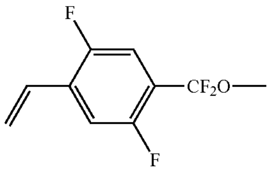 | 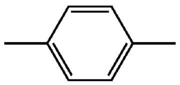 | 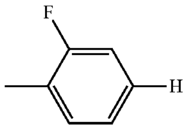 |
| 1128 | 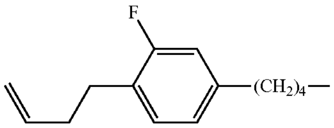 | 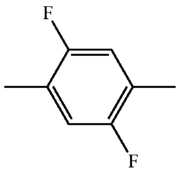 | 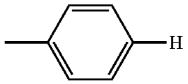 |

-continued
| | | | |
|---|---|---|---|
| 1129 | 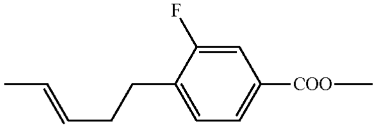 | 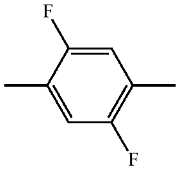 | 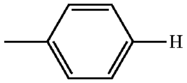 |
| 1130 | 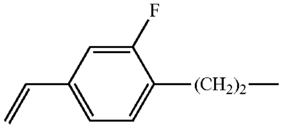 | 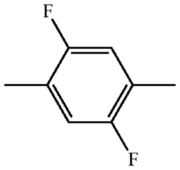 | 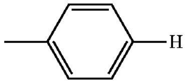 |
| 1131 | 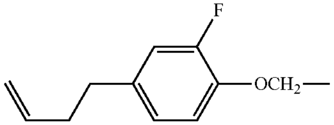 | 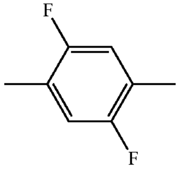 | 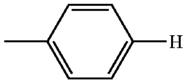 |
| 1132 | 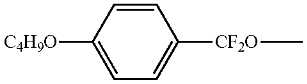 | 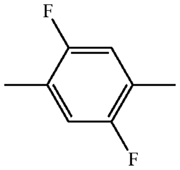 | 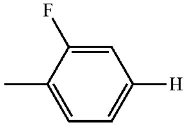 |
| 1133 | 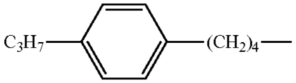 | 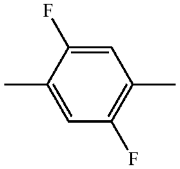 | 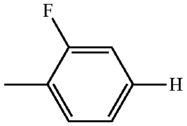 |

-continued
1134 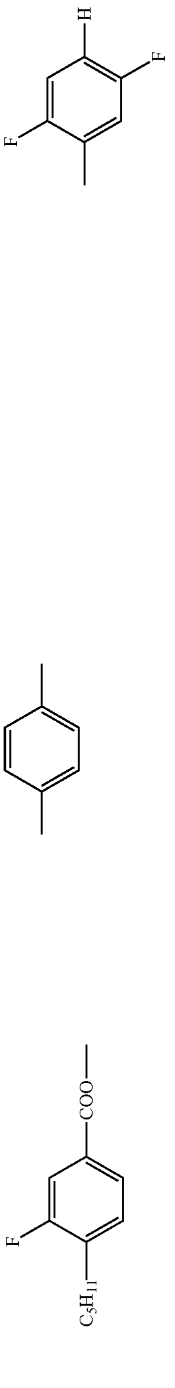
1135 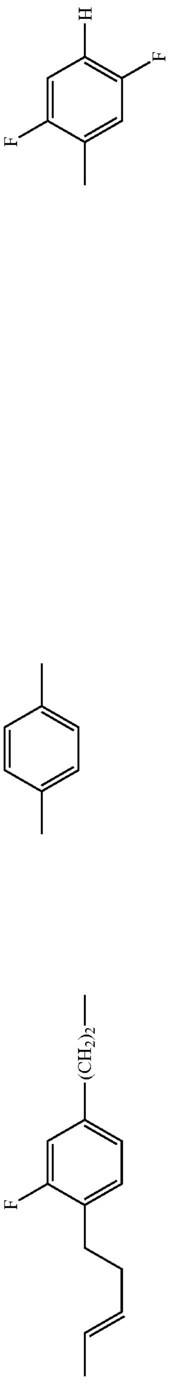
1136 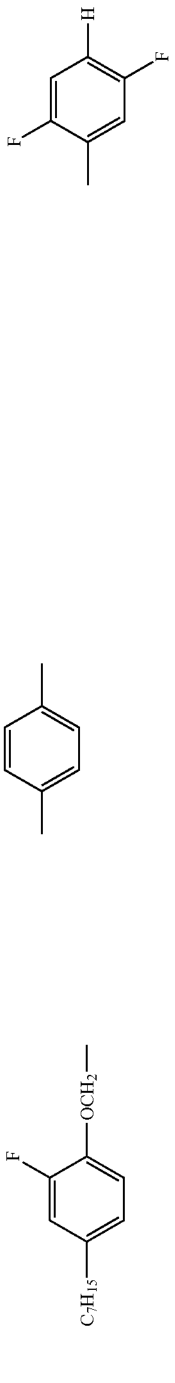
1137 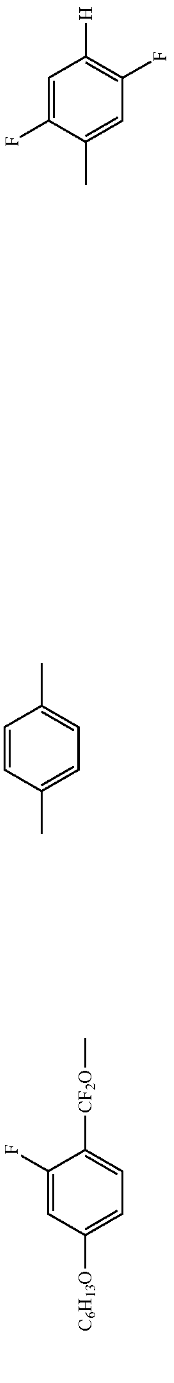
1138 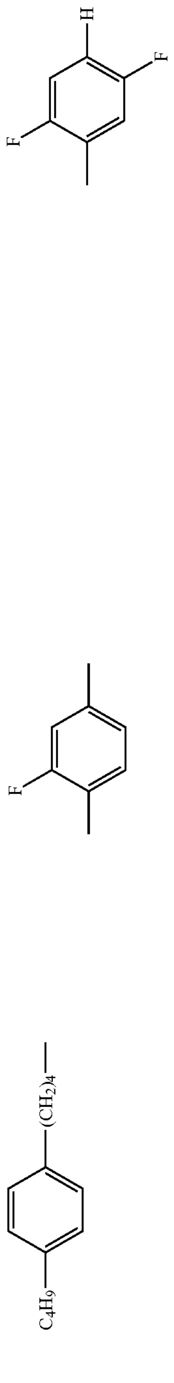

-continued
1139 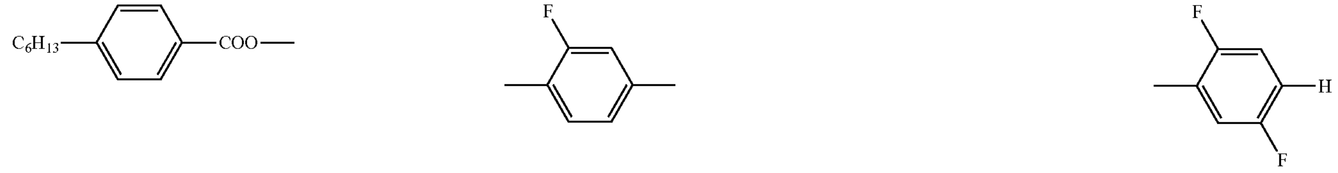
1140 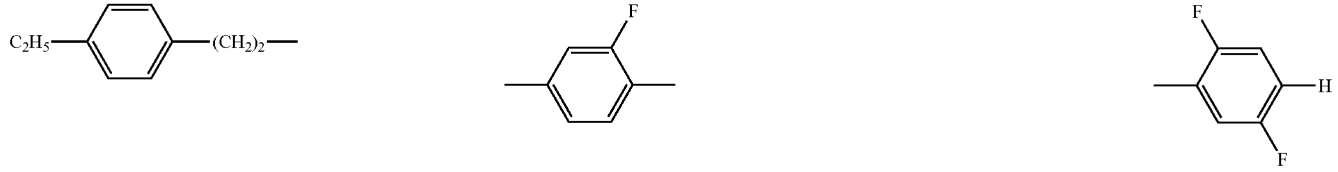
1141 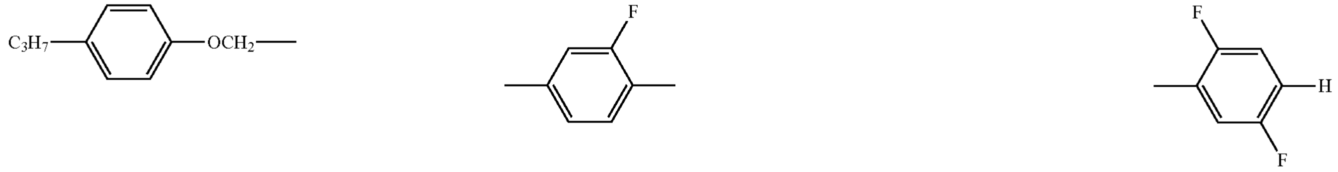
1142 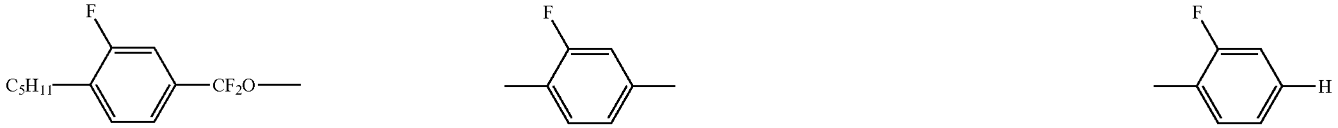
1143 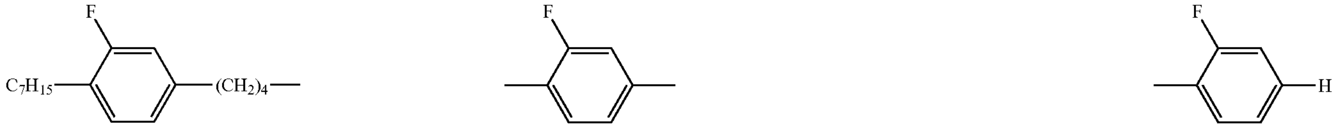
1144 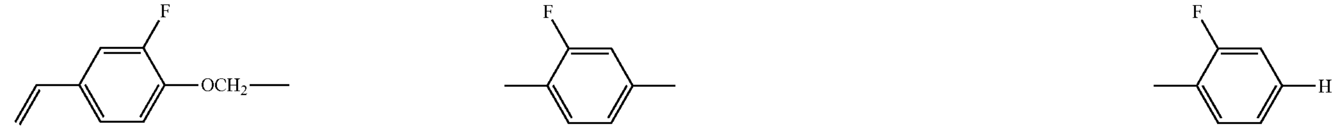

-continued
1145 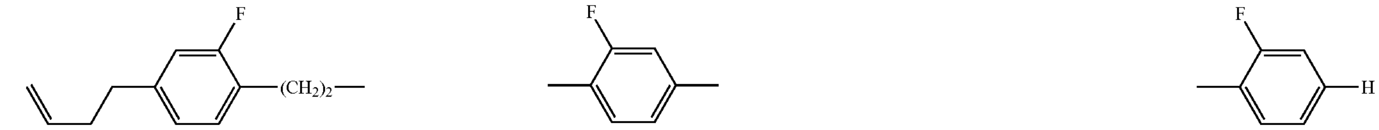
1146 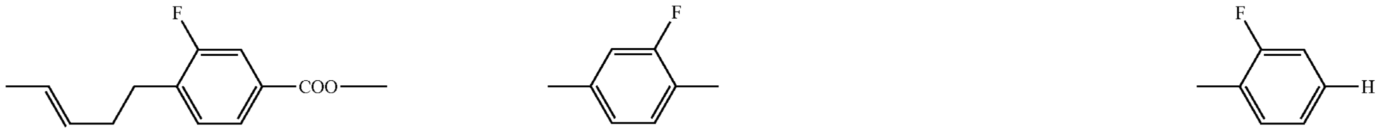
1147 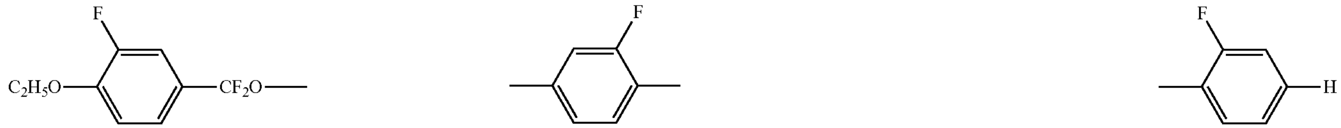
1148 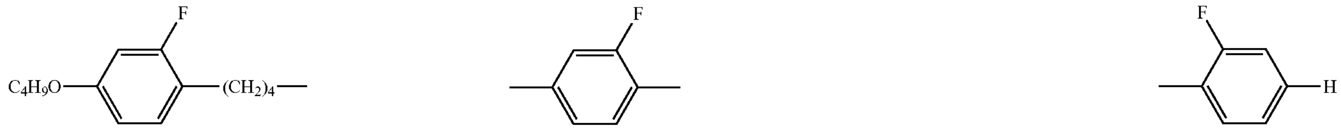
1149 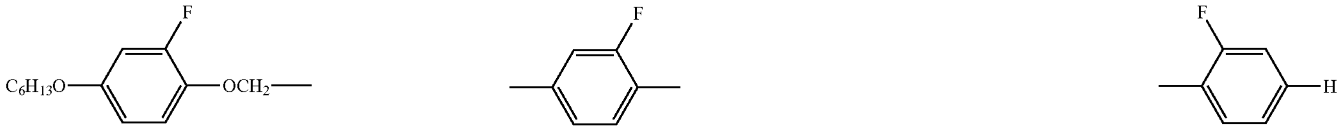
1150 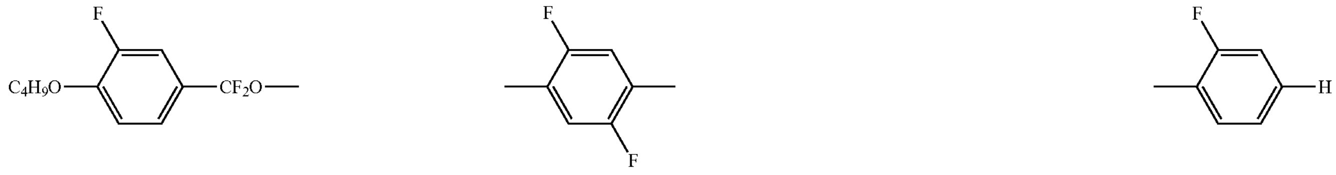
1151 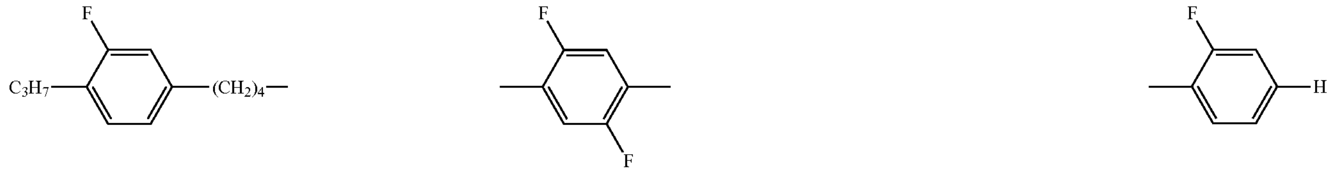

-continued
| | | | |
|---|---|---|---|
| 1152 | 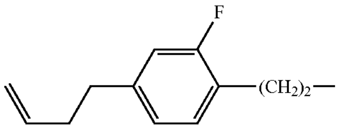 | 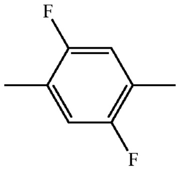 | 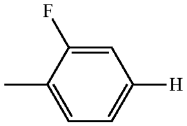 |
| 1153 | 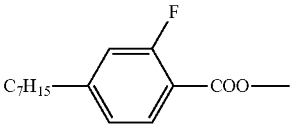 | 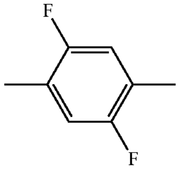 | 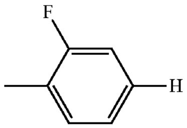 |
| 1154 | 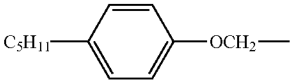 | 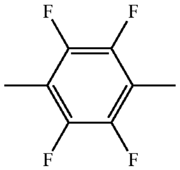 | 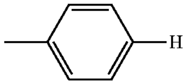 |
| 1155 | 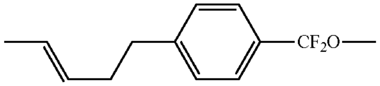 | 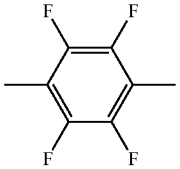 | 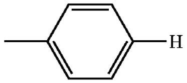 |
| 1156 | 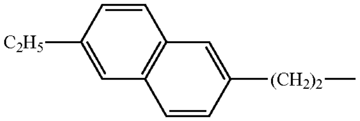 | 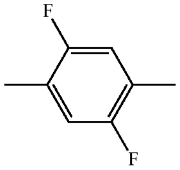 | 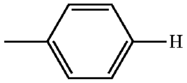 |

-continued
| | | | |
|---|---|---|---|
| 1157 | 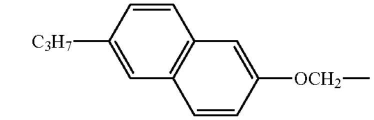 | 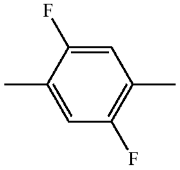 | 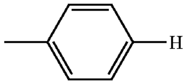 |
| 1158 | 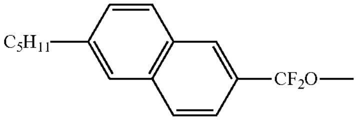 | 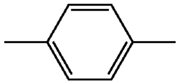 | 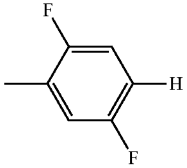 |
| 1159 | 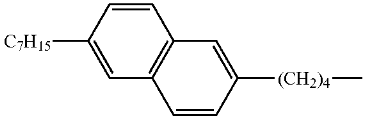 | 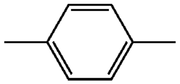 | 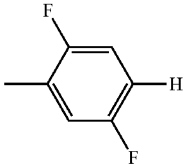 |
| 1160 | 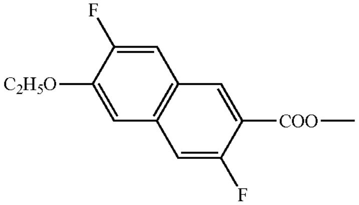 | 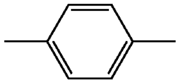 | 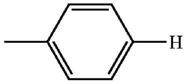 |
| 1161 | 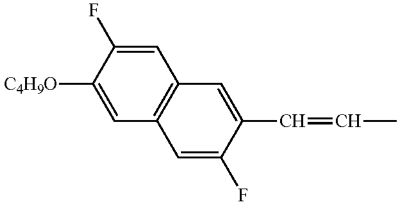 | 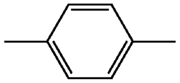 | 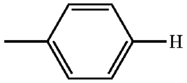 |

-continued
1162 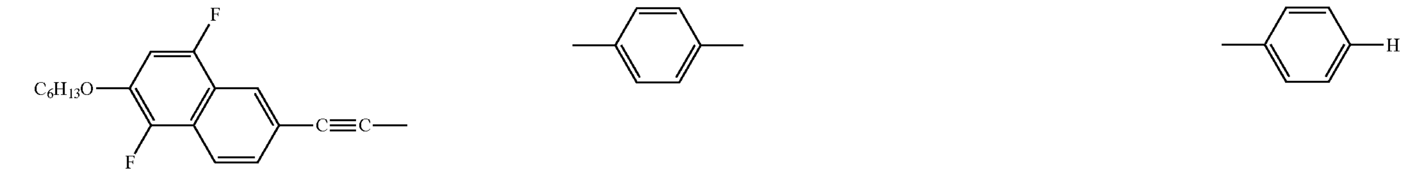
1163 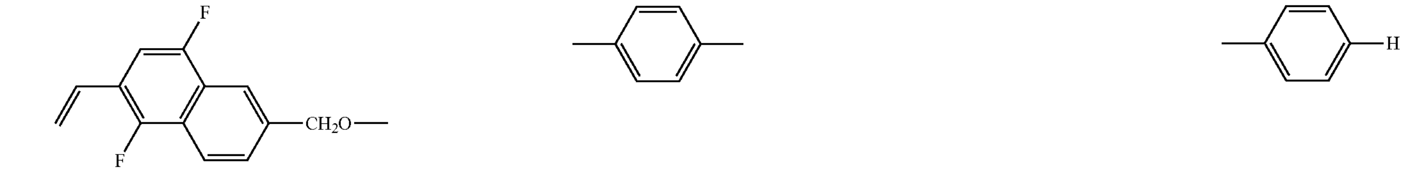
1164 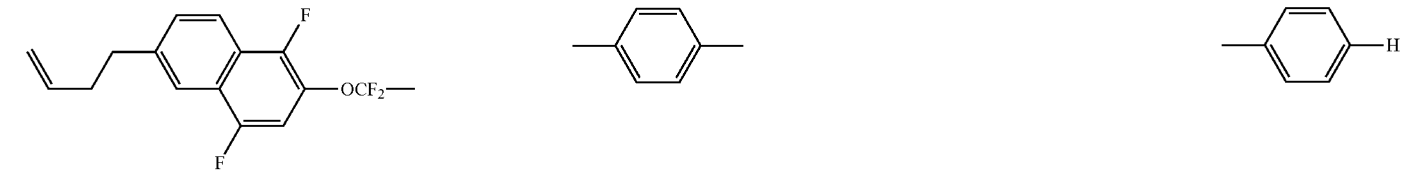
1165 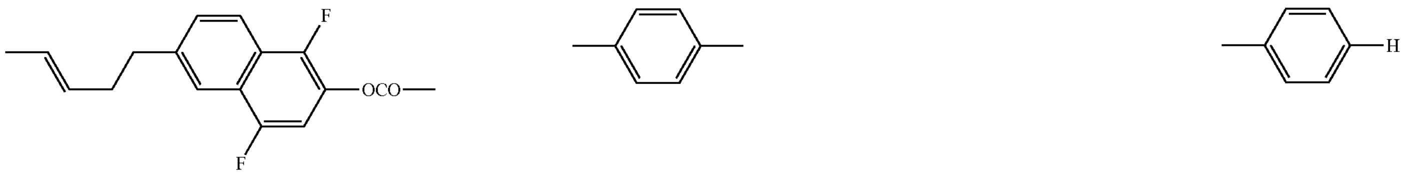
1166 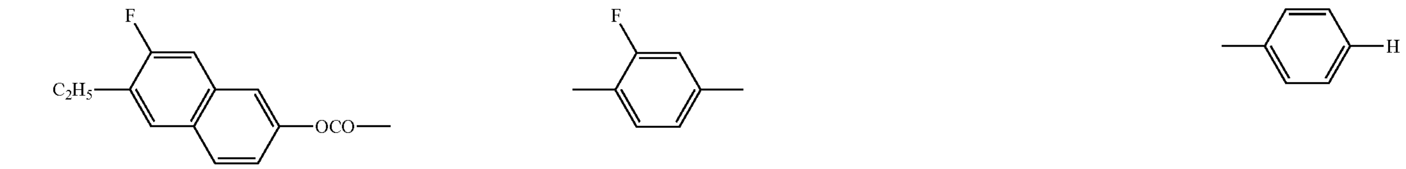
1167 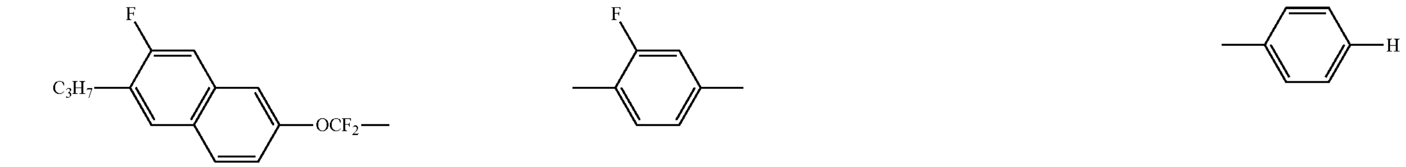

-continued
1168 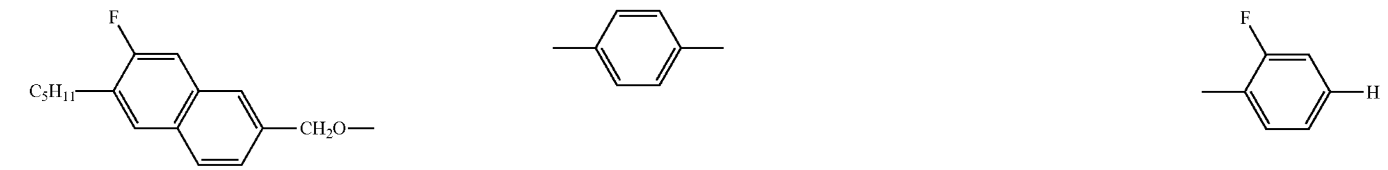
1169 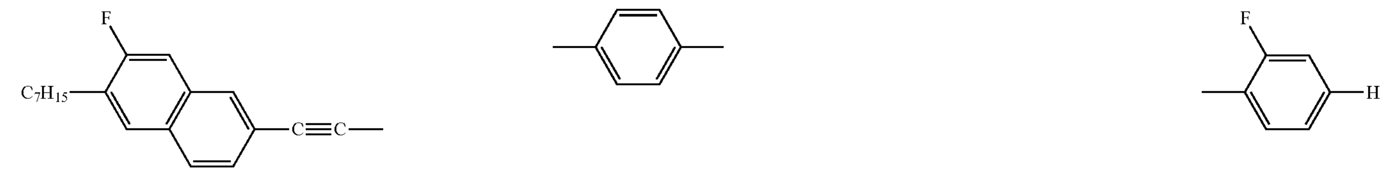
1170 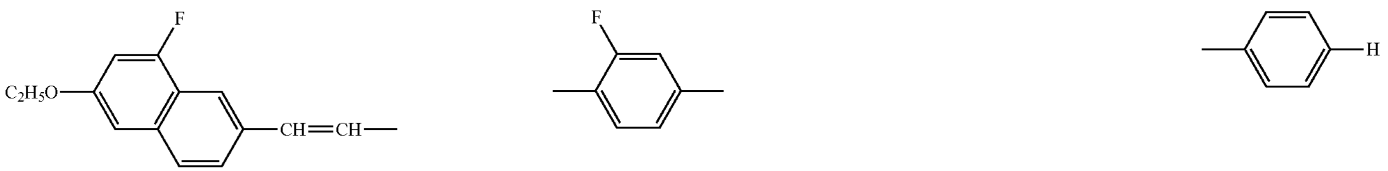
1171 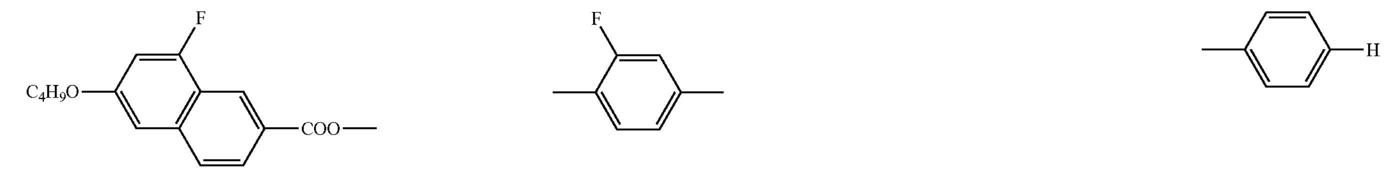
1172 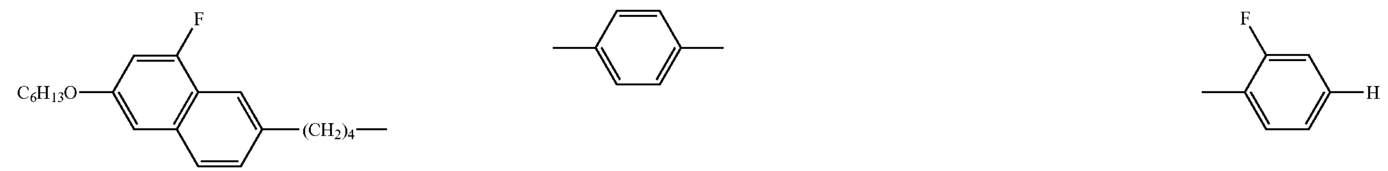
1173 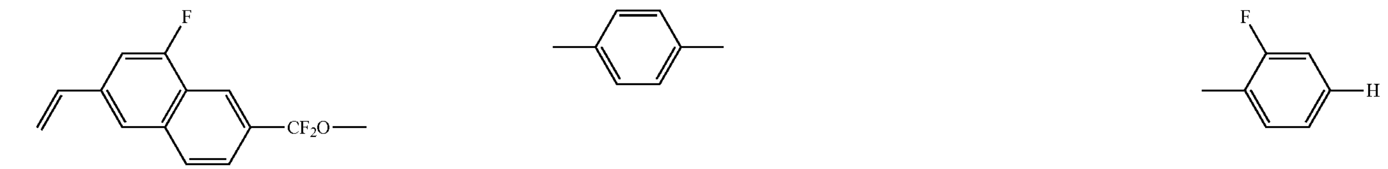

-continued
1174 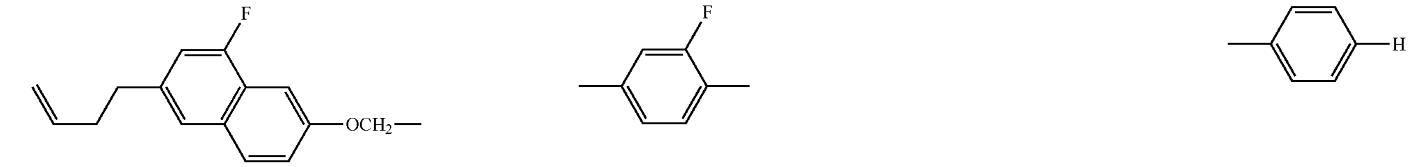
1175 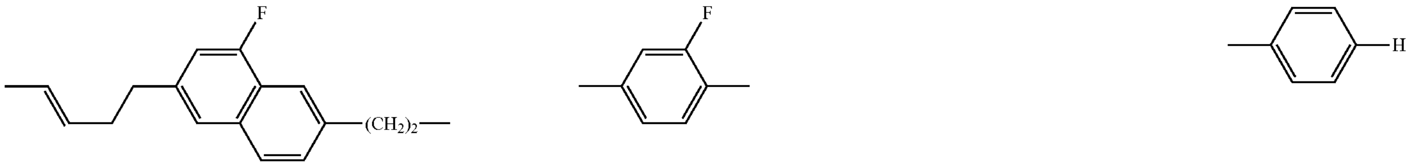
1176 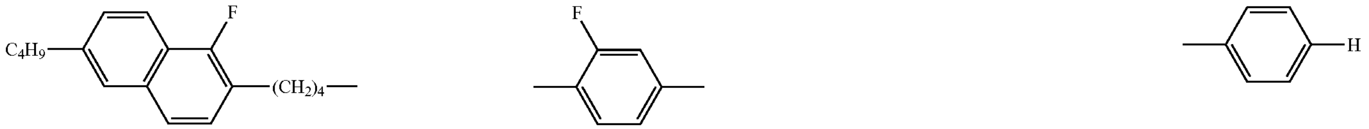
1177 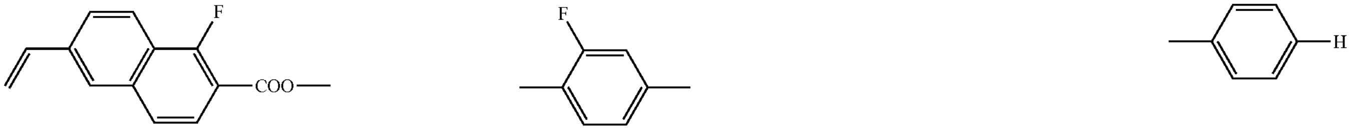
1178 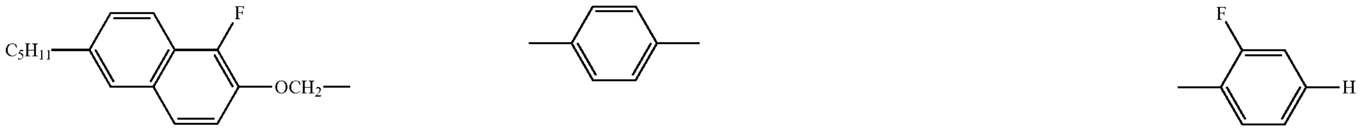
1179 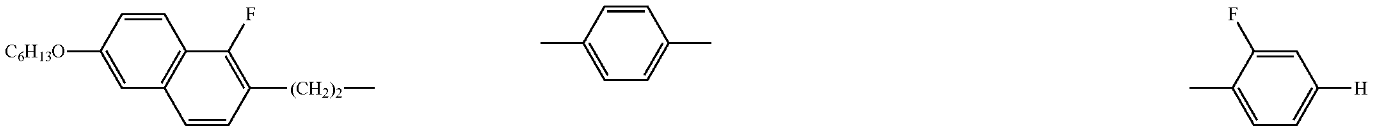
1180 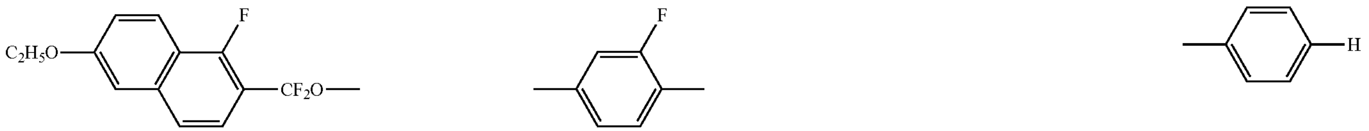

-continued
1181 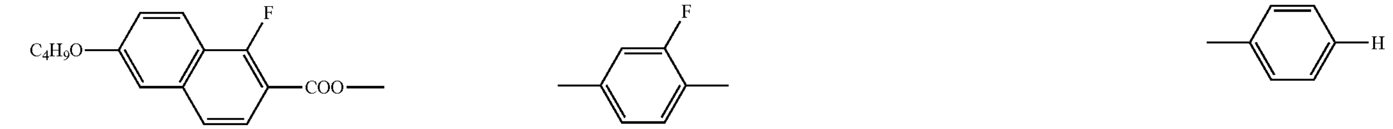
1182 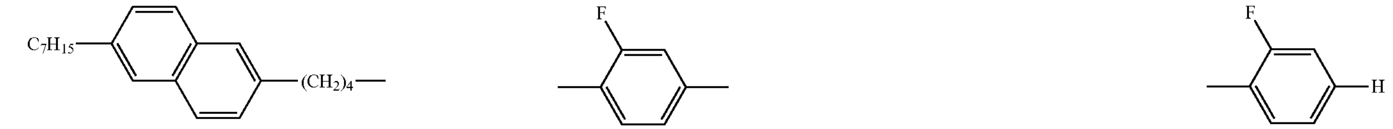
1183 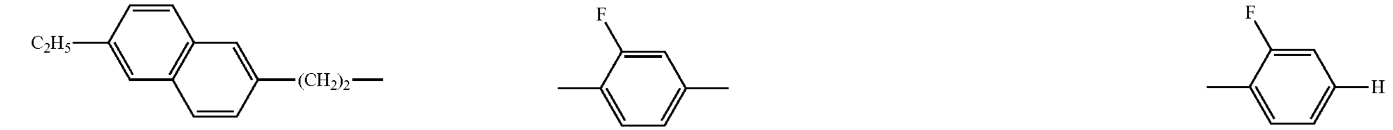
1184 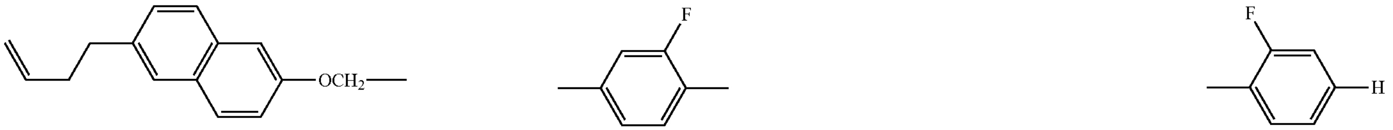
1185 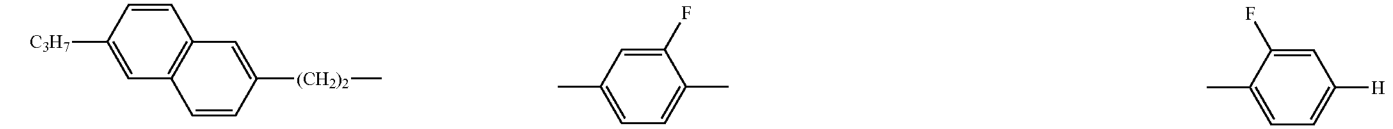
1186 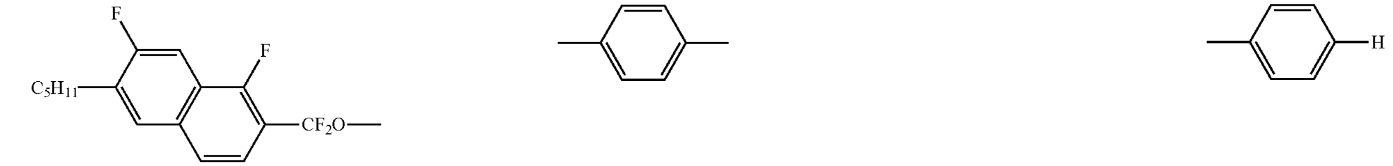

-continued
1187 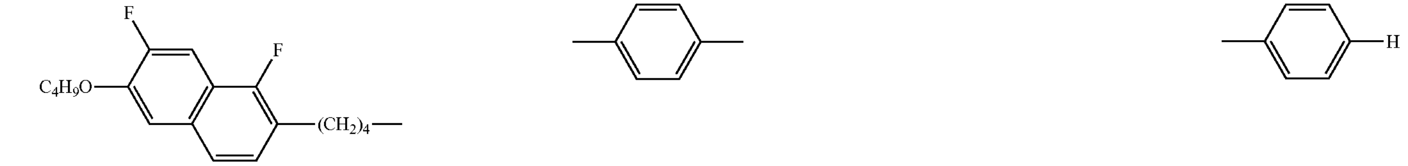
1188 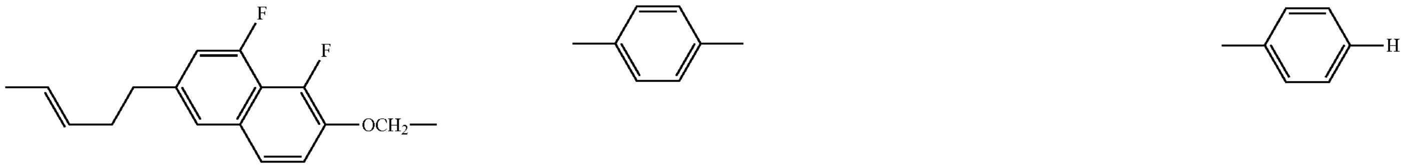
1189 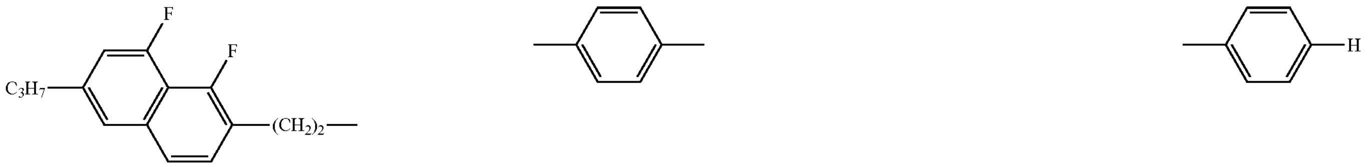
1190 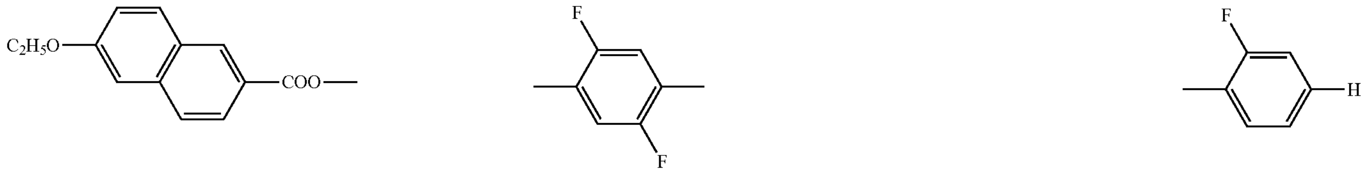
1191 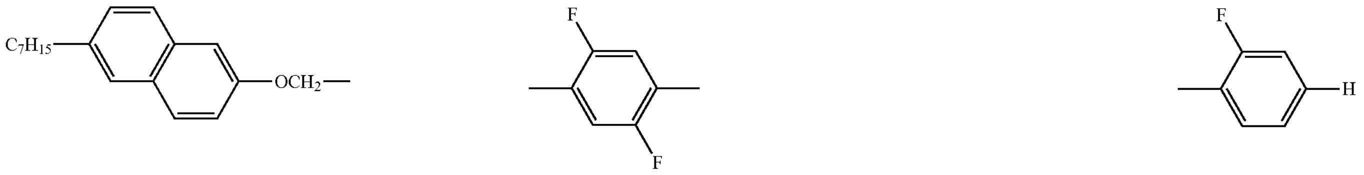
1192 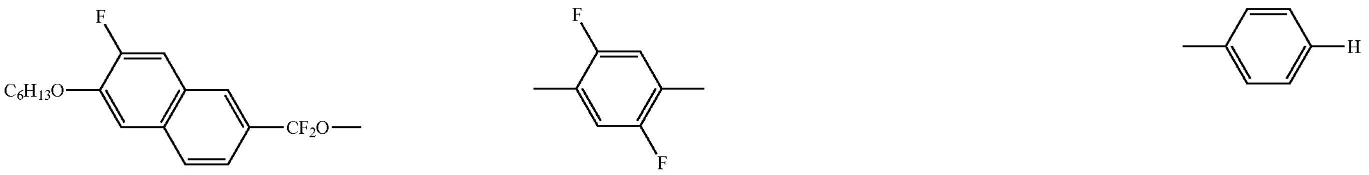

-continued
| | |
|---|---|
| 1193 | 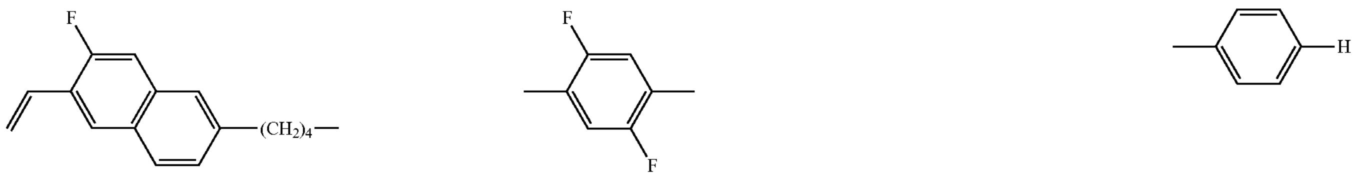 |
| 1194 | 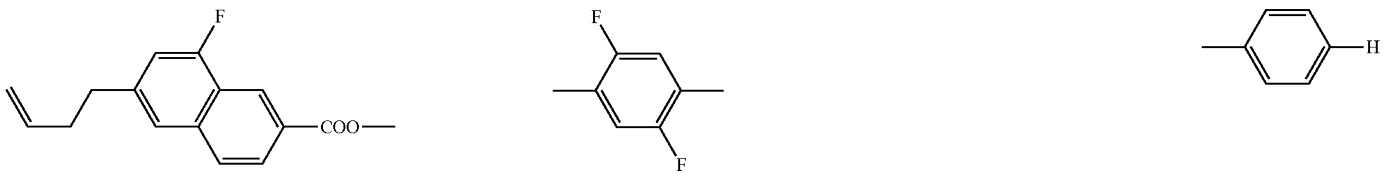 |
| 1195 | 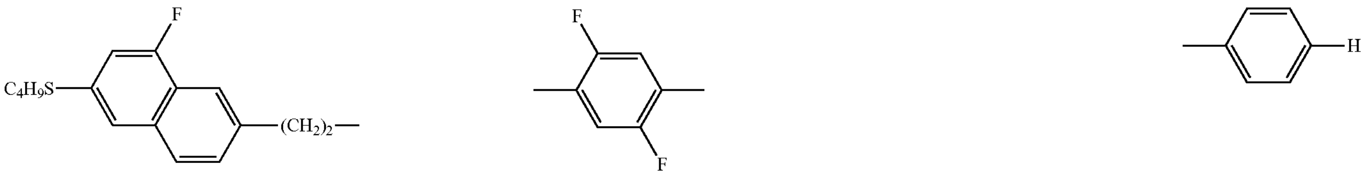 |
| 1196 | 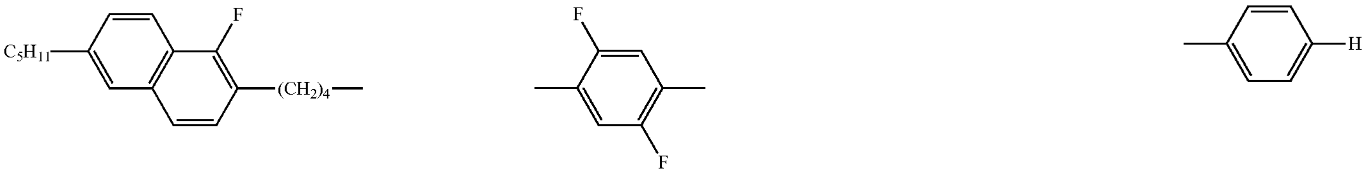 |
| 1197 | 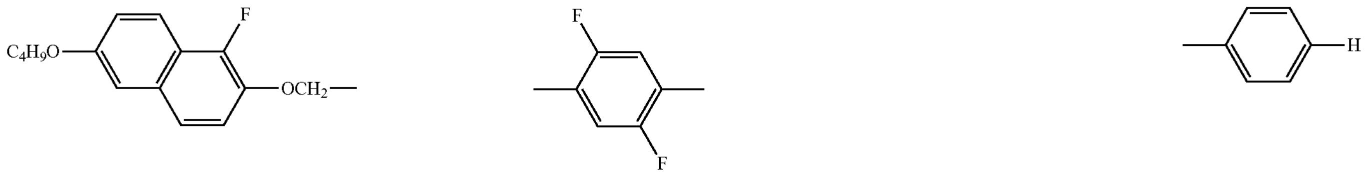 |

-continued
1198 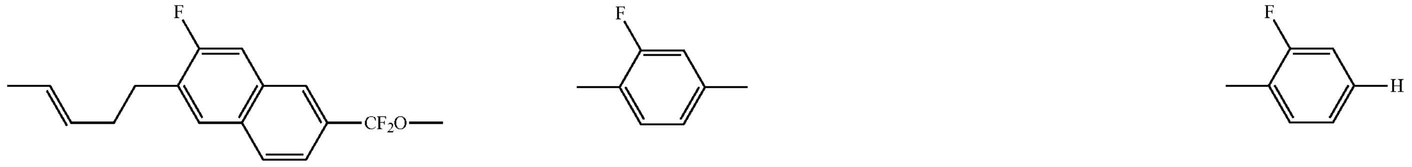
1199 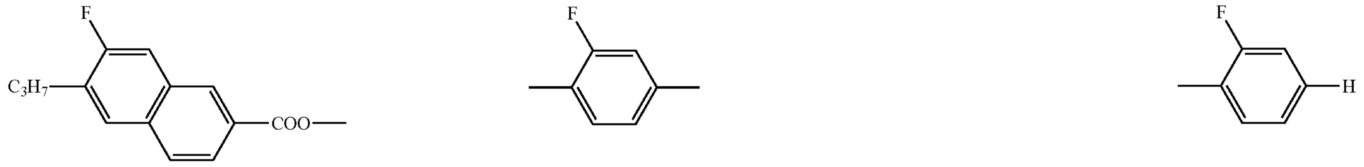
1200 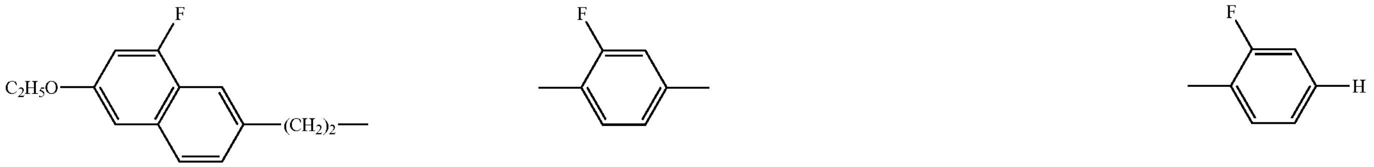
1201 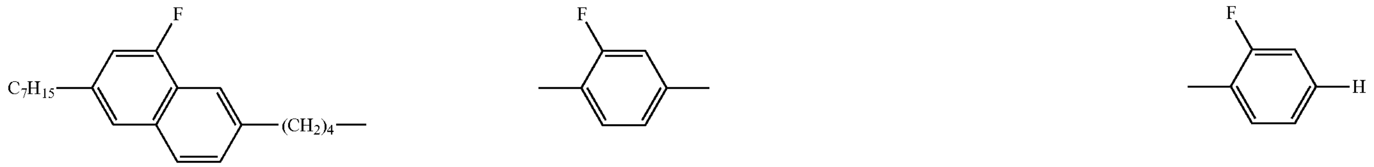
1202 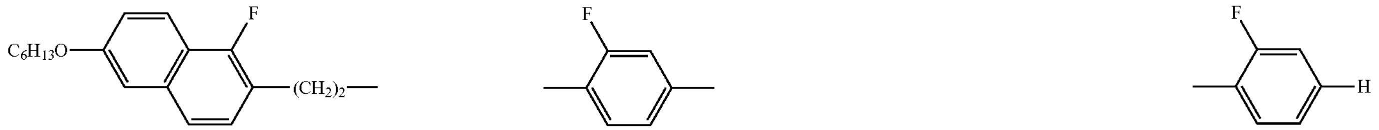
1203 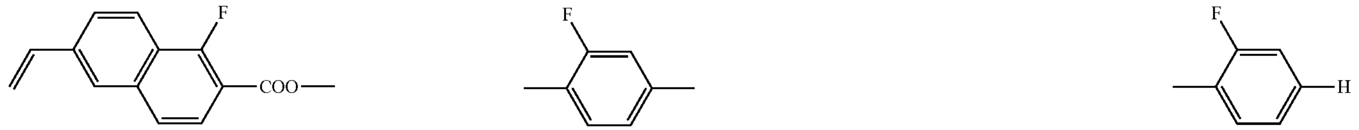

-continued
1204 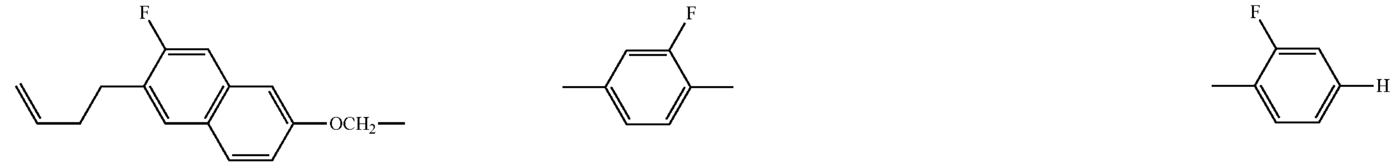
1205 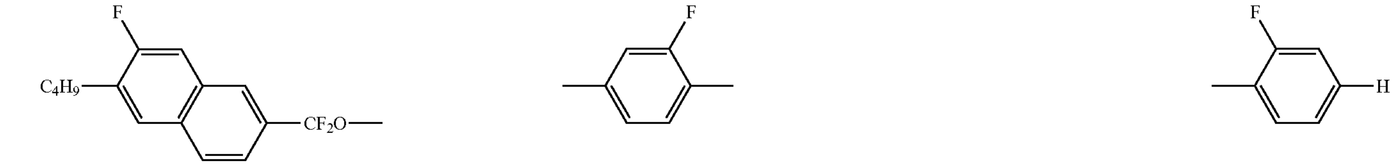
1206 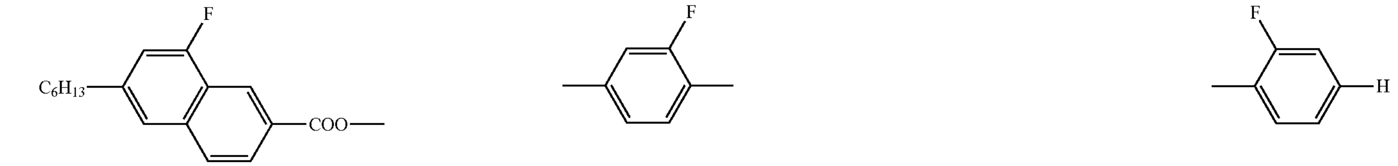
1207 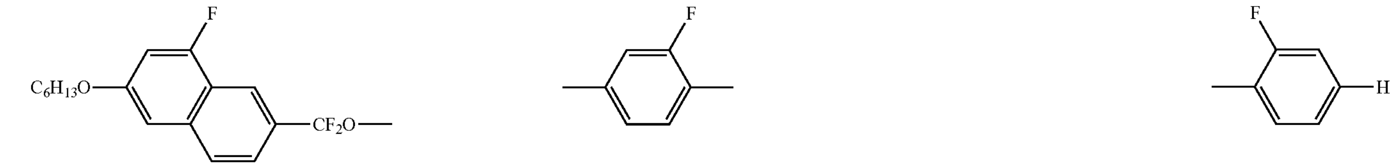
1208 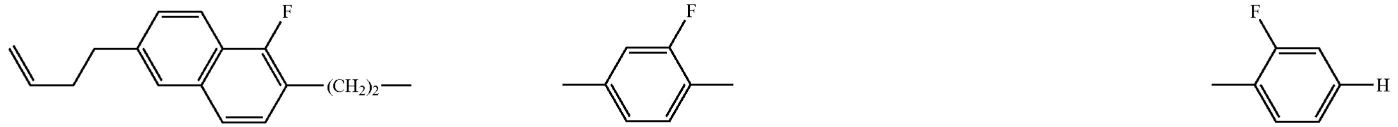
1209 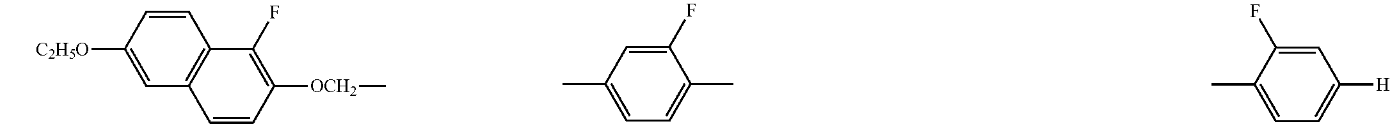

-continued
1210 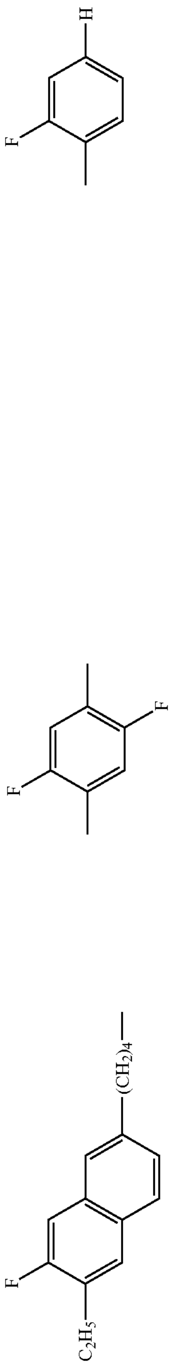
1211 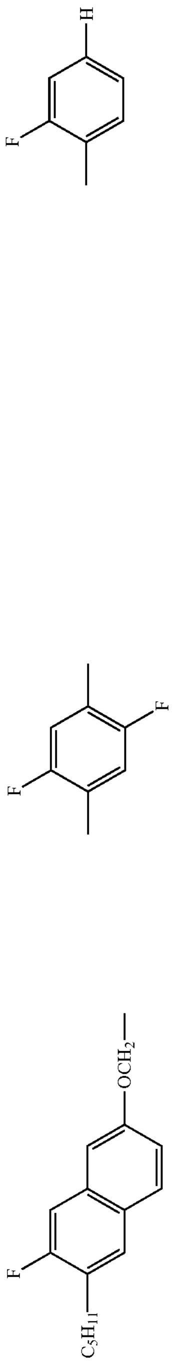
1212 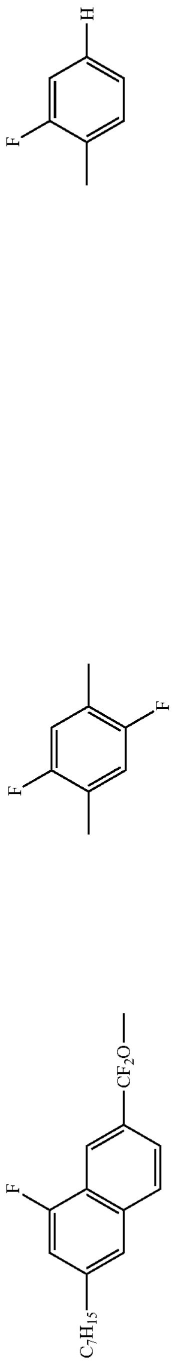
1213 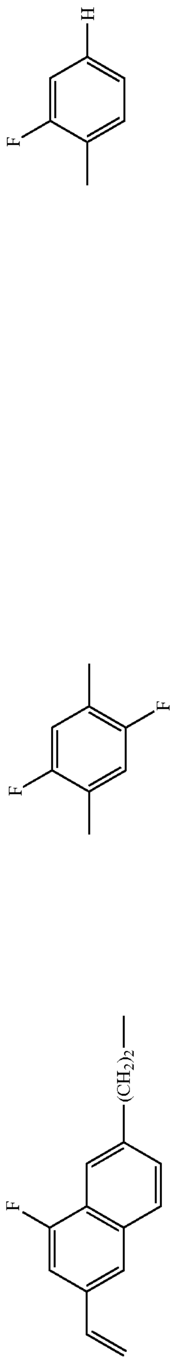
1214 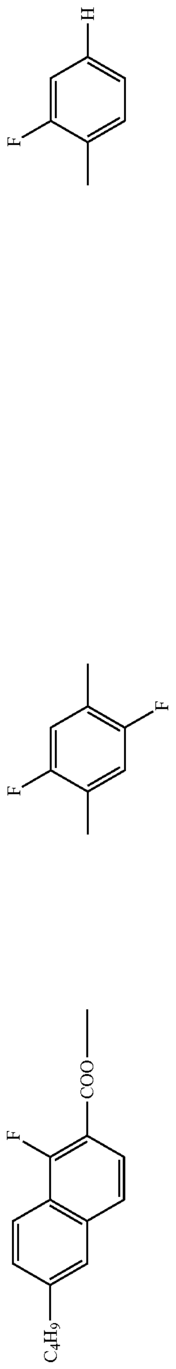

-continued
1215 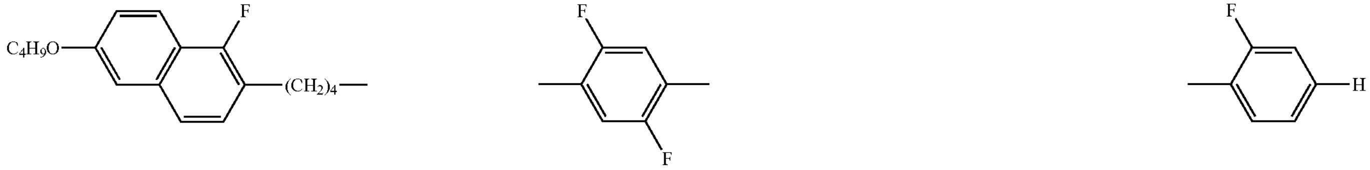
1216 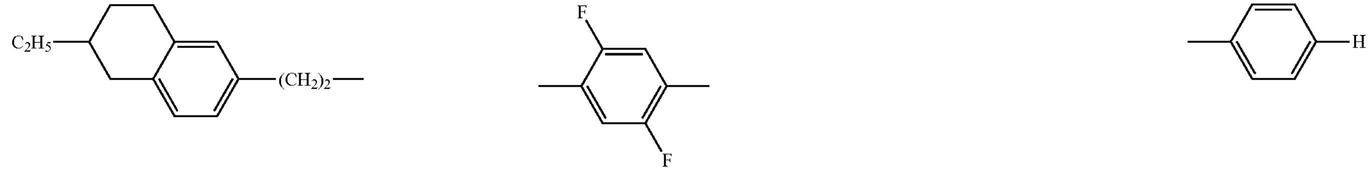
1217 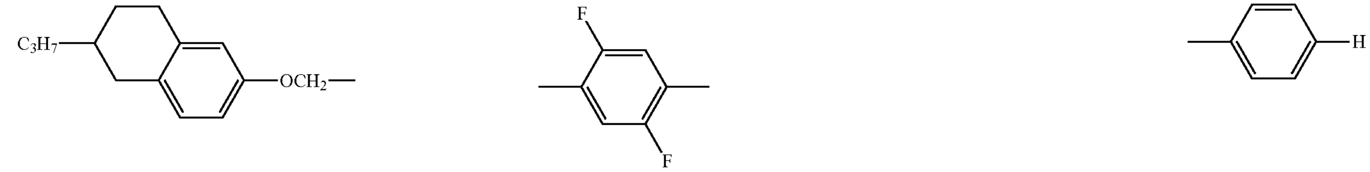
1218 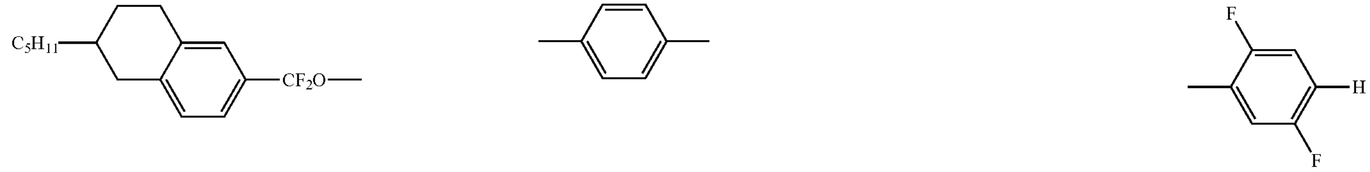
1219 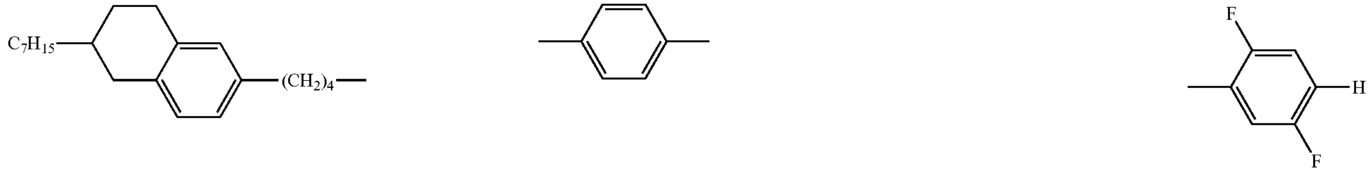

-continued
| | |
|---|---|
| 1220 | 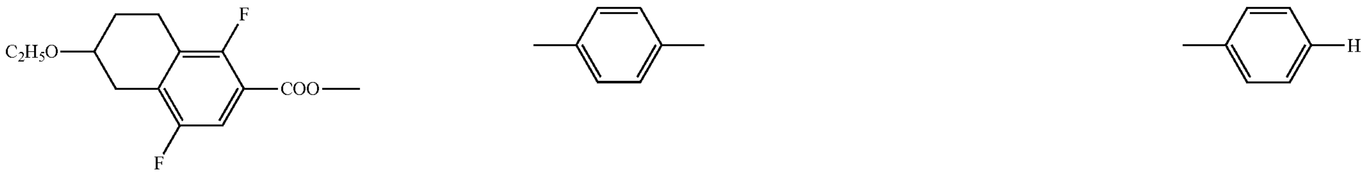 |
| 1221 | 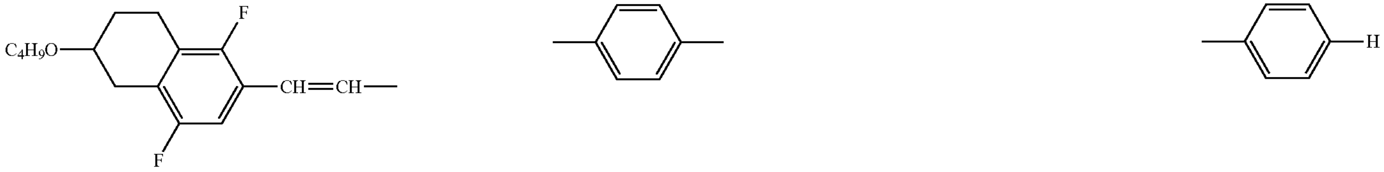 |
| 1222 | 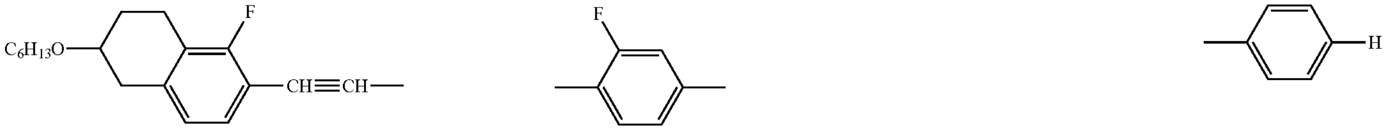 |
| 1223 | 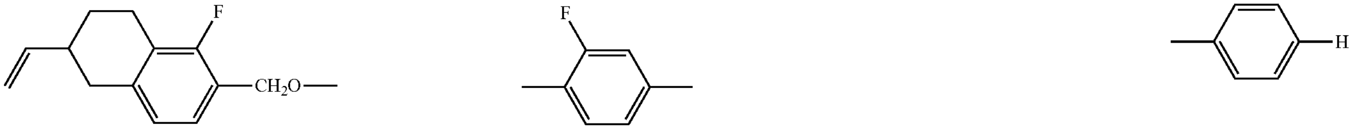 |
| 1224 | 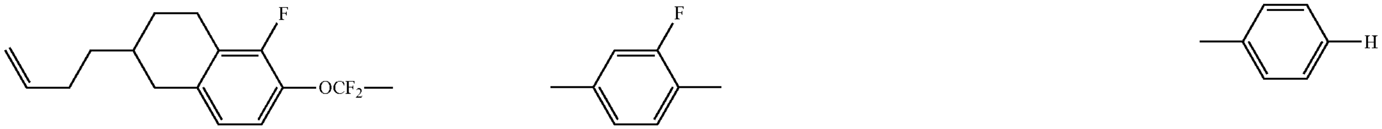 |
| 1225 | 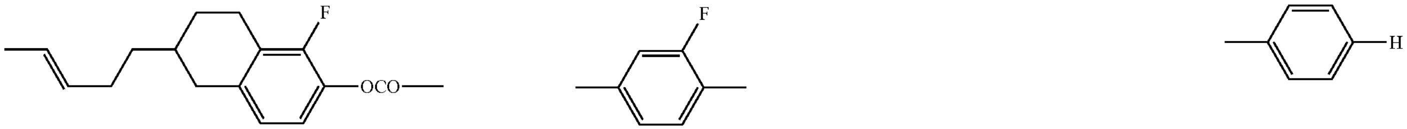 |
| 1226 | 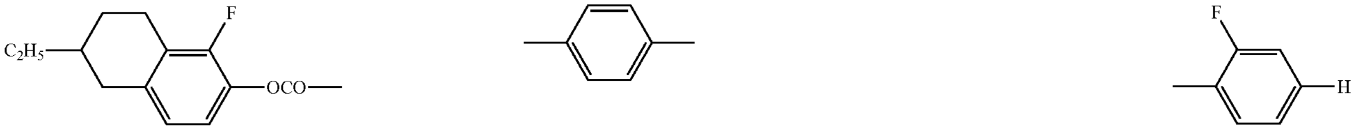 |

-continued
1227 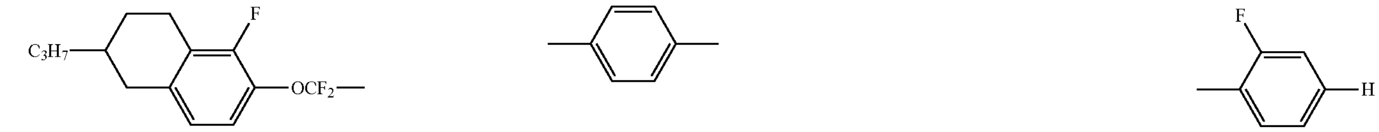
1228 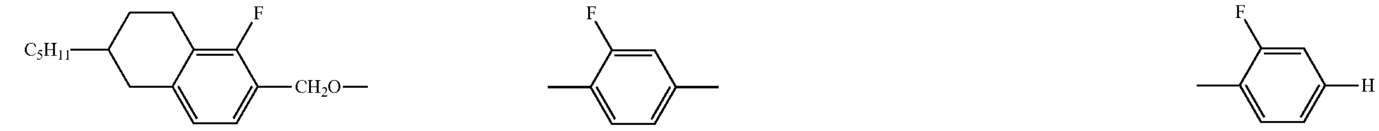
1229 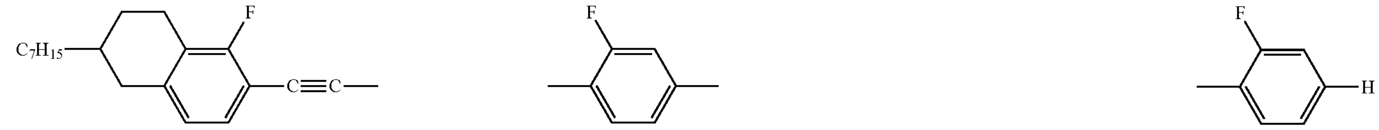
1230 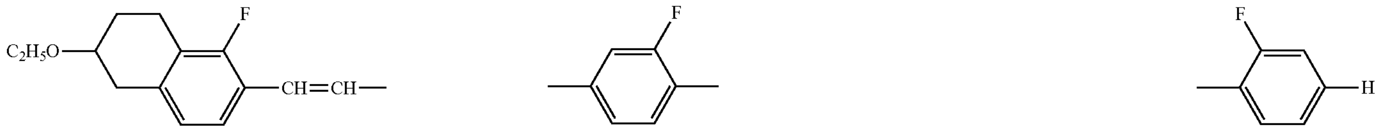
1231 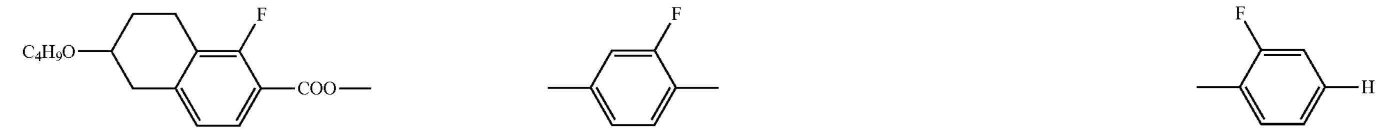
1232 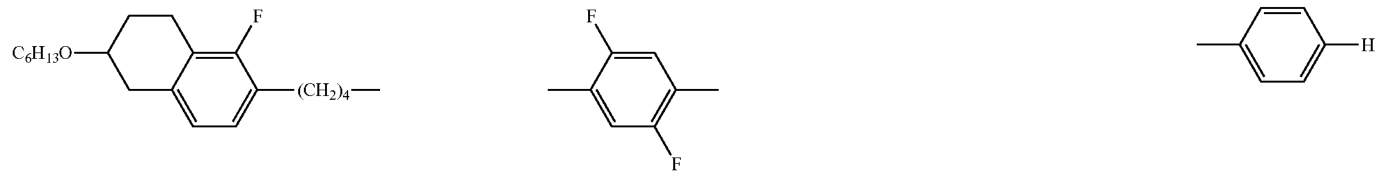

-continued
| | | | |
|---|---|---|---|
| 1233 | 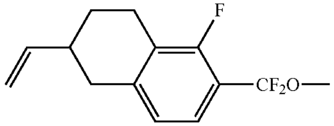 | 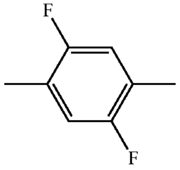 | 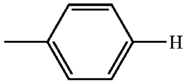 |
| 1234 | 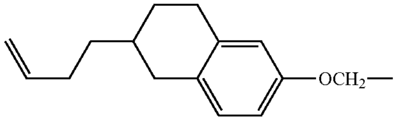 | 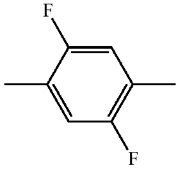 | 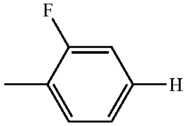 |
| 1235 | 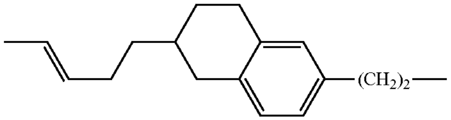 | 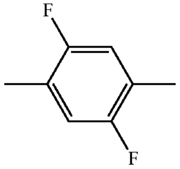 | 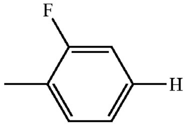 |
| 1236 | 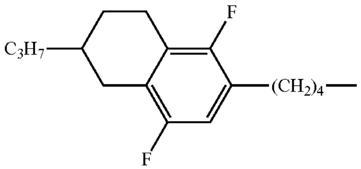 | 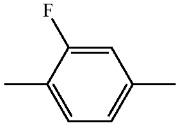 | 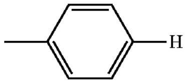 |
| 1237 | 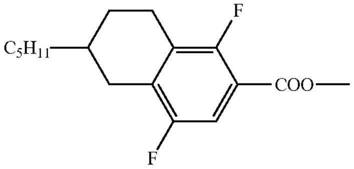 | 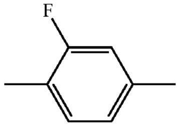 | 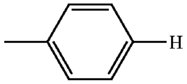 |

-continued
| | |
|---|---|
| 1238 | 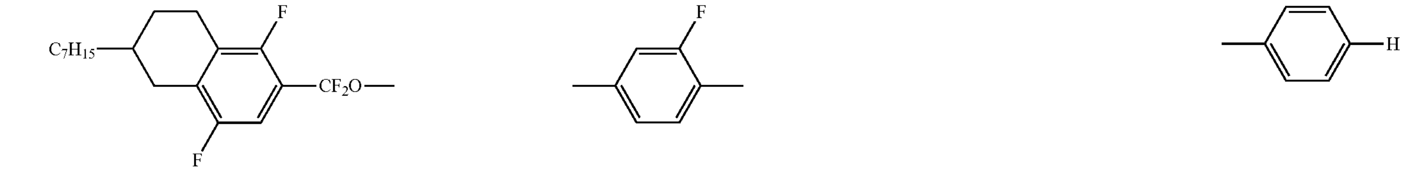 |
| 1239 | 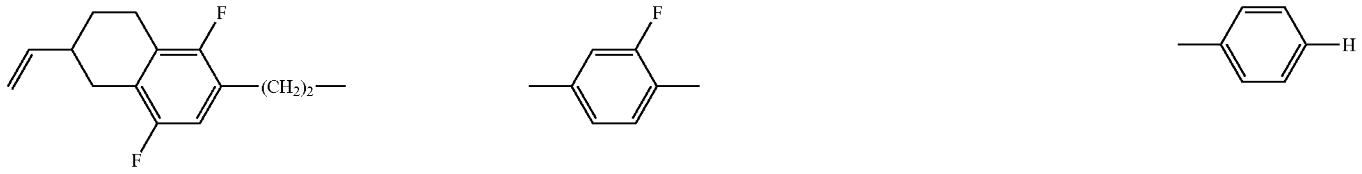 |
| 1240 | 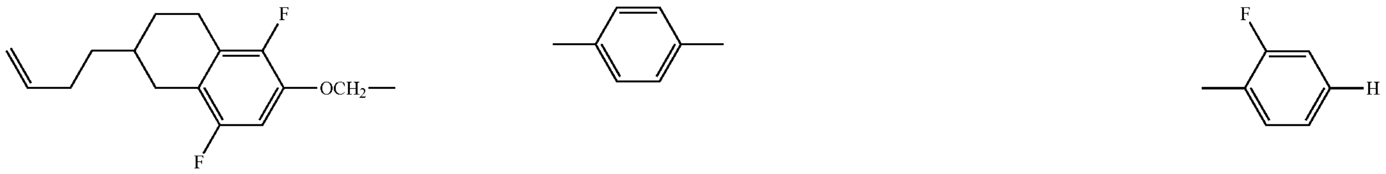 |
| 1241 | 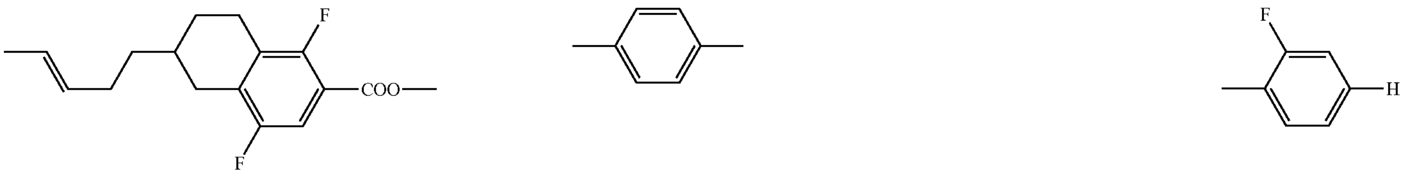 |
| 1242 | 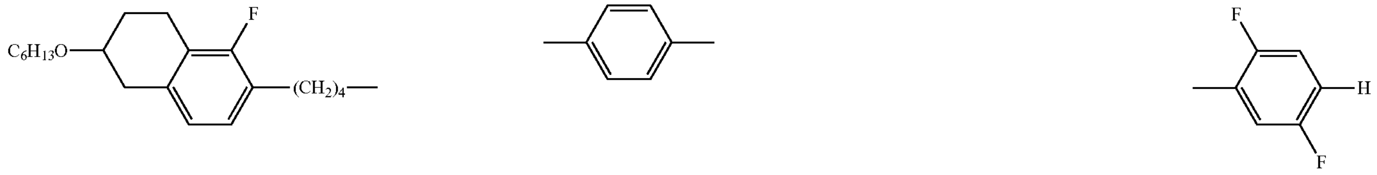 |

-continued
| | |
|---|---|
| 1243 | 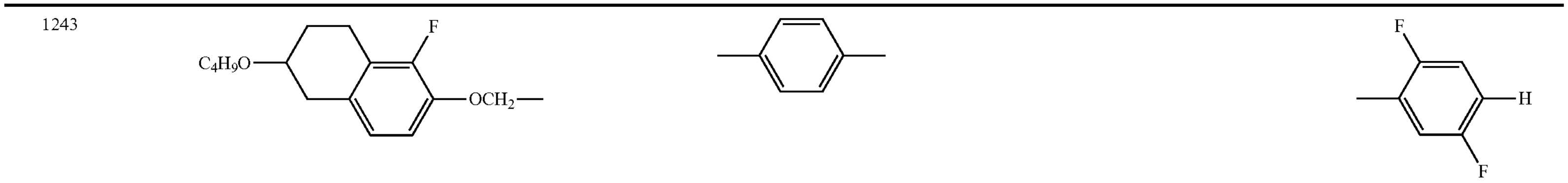 |
| 1244 | 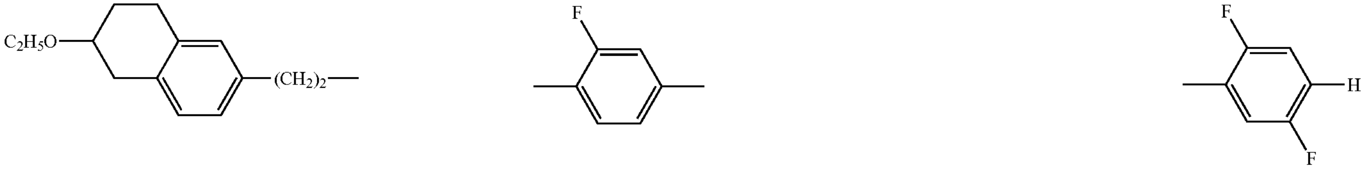 |
| 1245 | 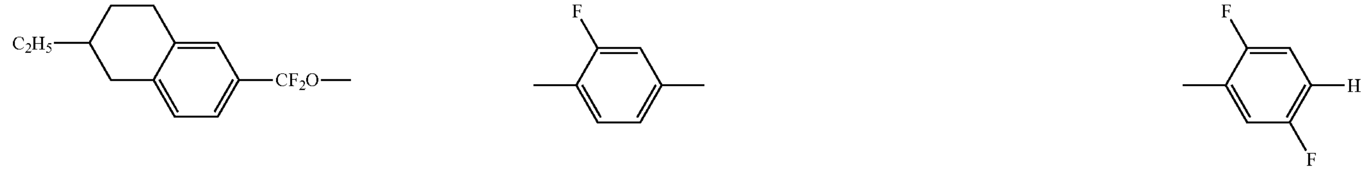 |
| 1246 | 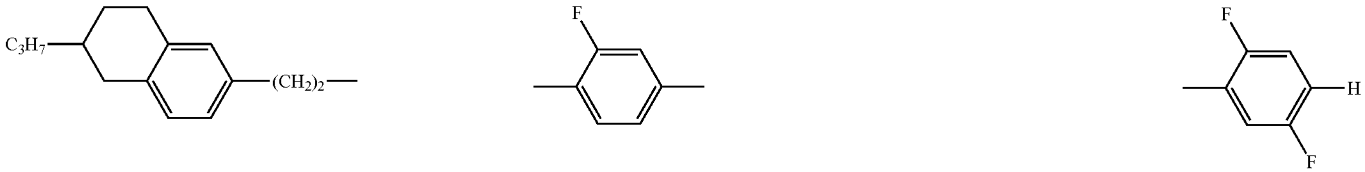 |
| 1247 | 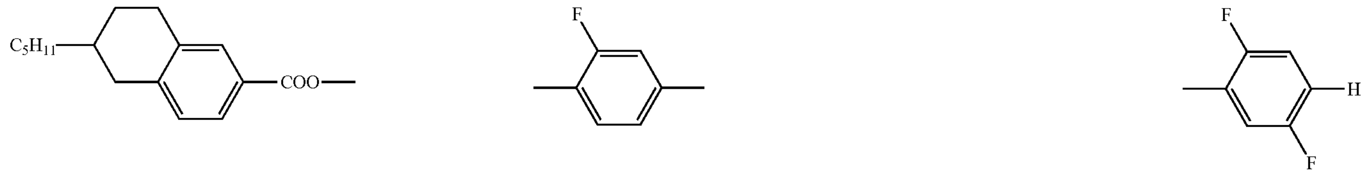 |

-continued
| | | | |
|---|---|---|---|
| 1248 | 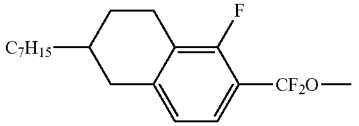 | 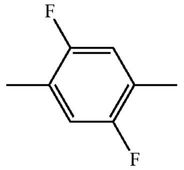 | 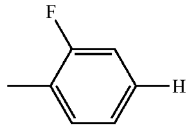 |
| 1249 | 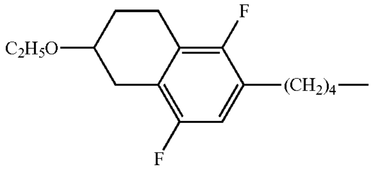 | 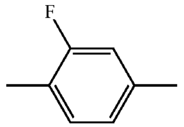 | 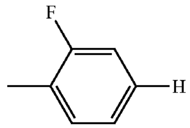 |
| 1250 | 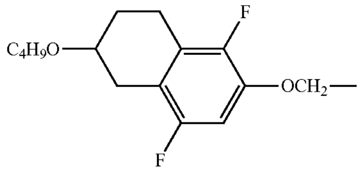 | 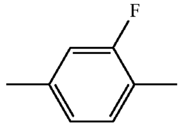 | 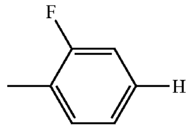 |
| 1251 | 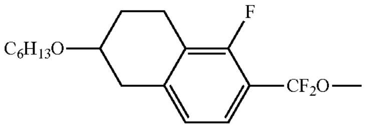 | 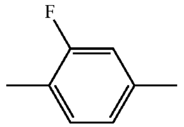 | 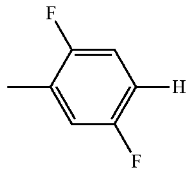 |
| 1252 | 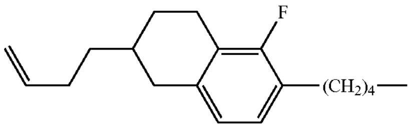 | 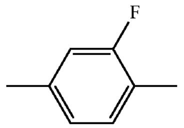 | 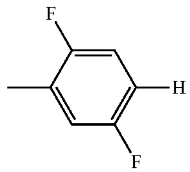 |

-continued
1253 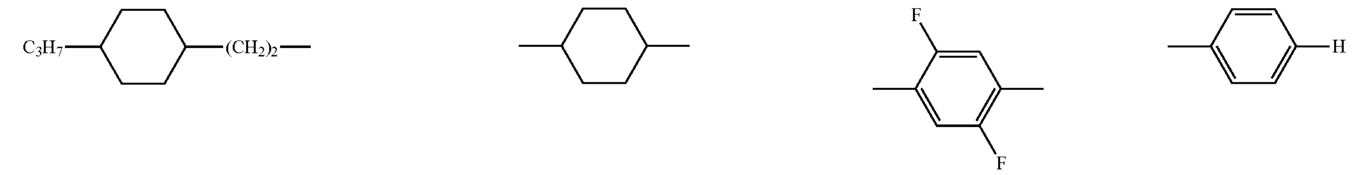
1254 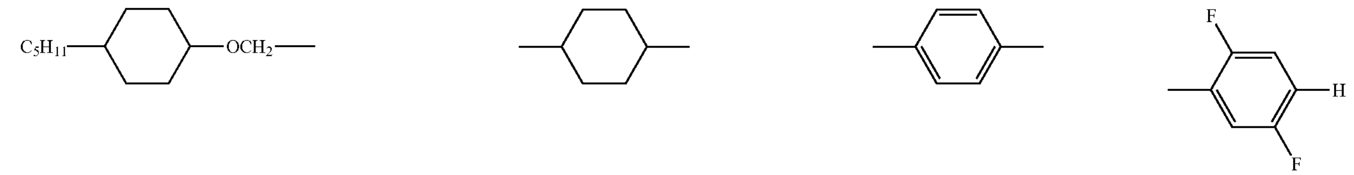
1255 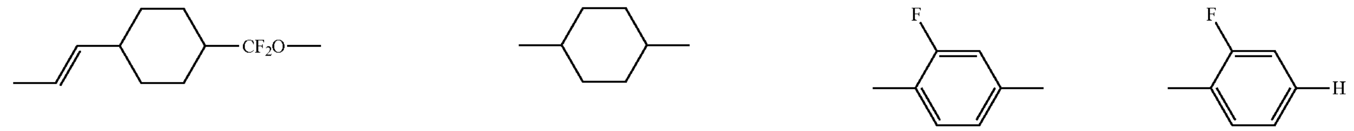
1256 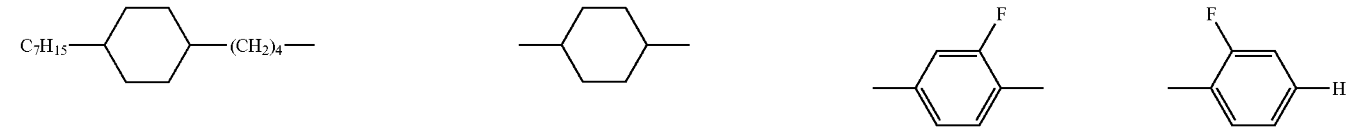
1257 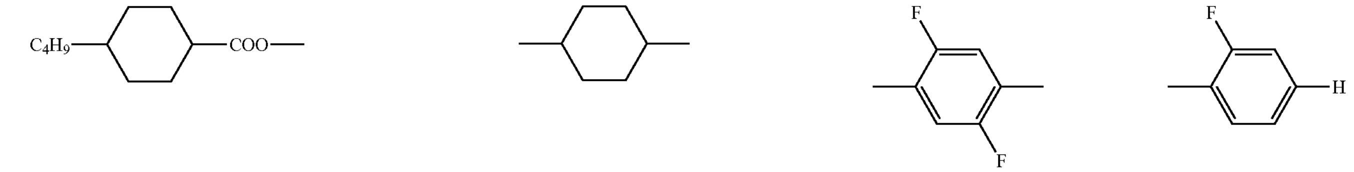
1258 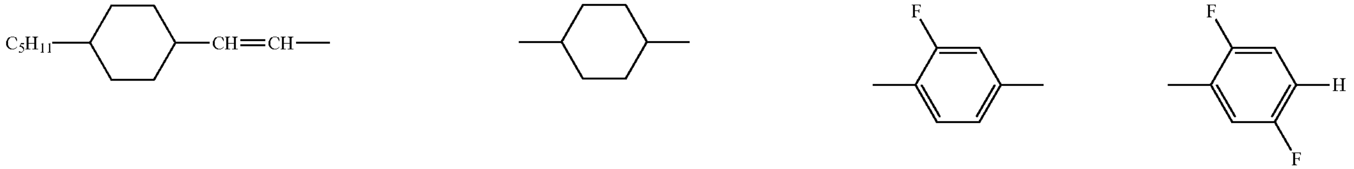

-continued
1259 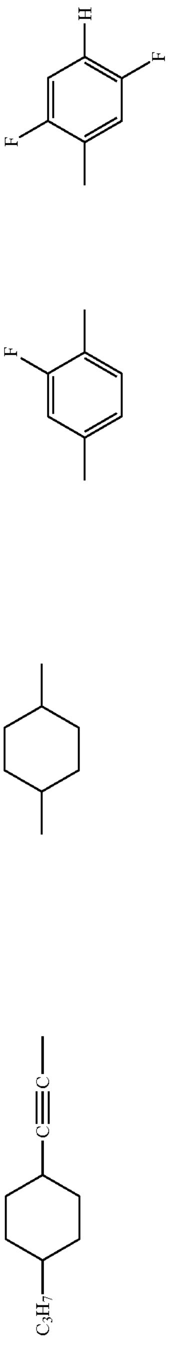
1260 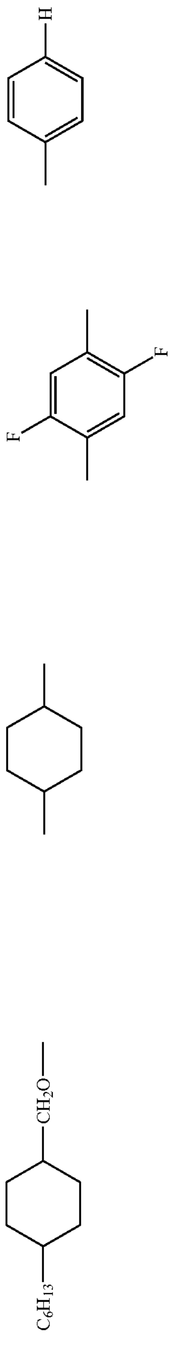
1261 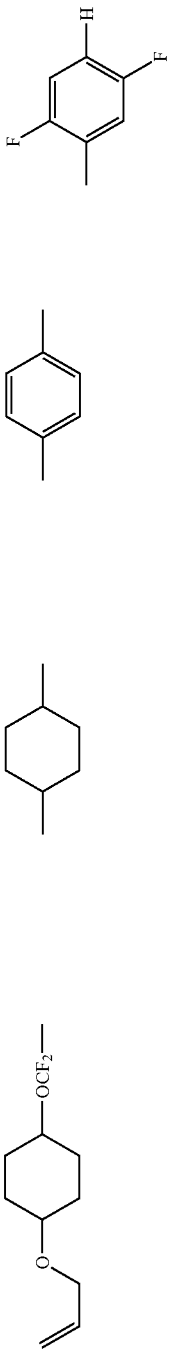
1262 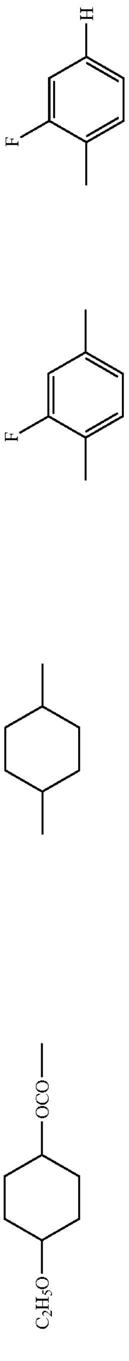
1263 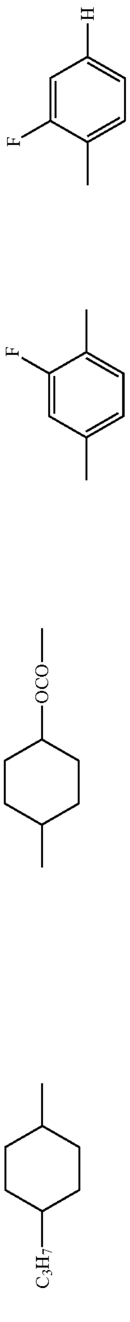
1264 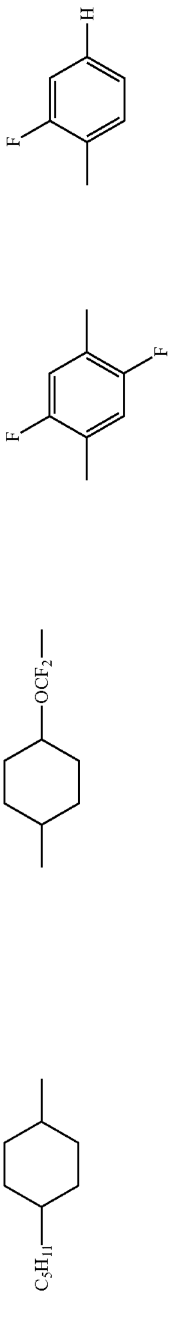

-continued
1265 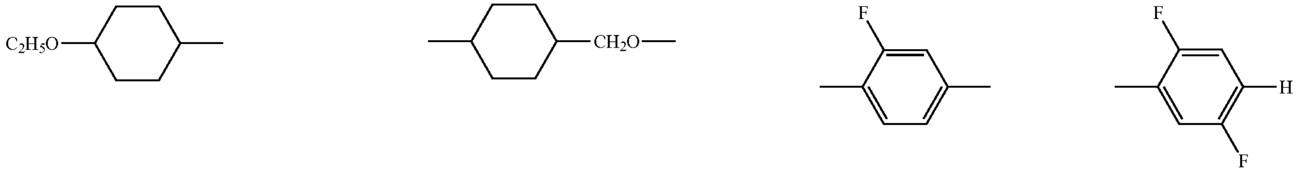
1266 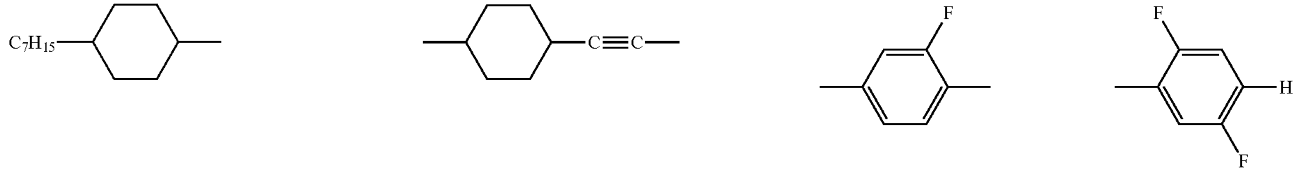
1267 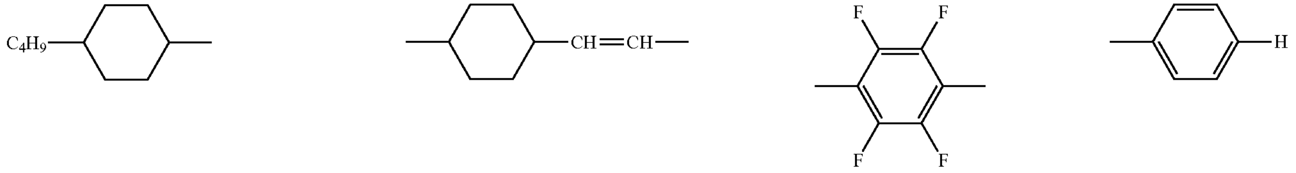
1268 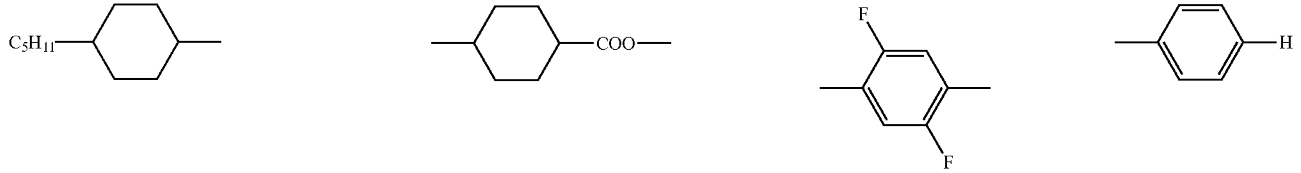
1269 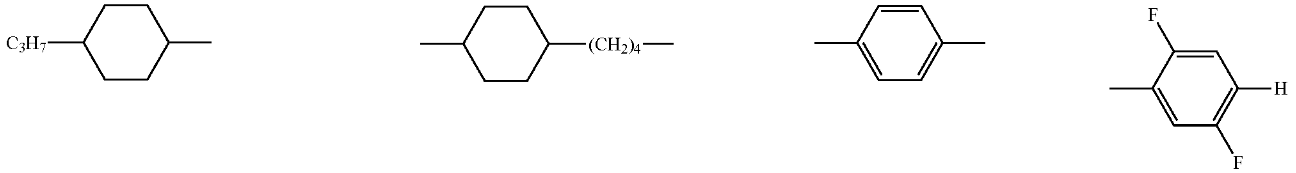
1270 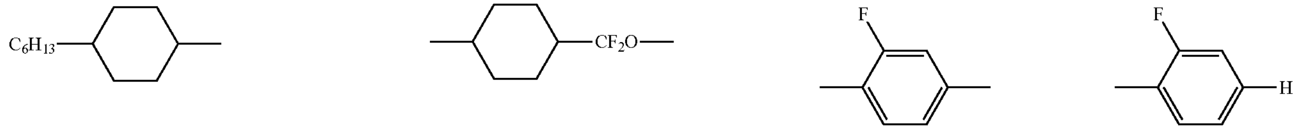

-continued
| | |
|---|---|
| 1271 | 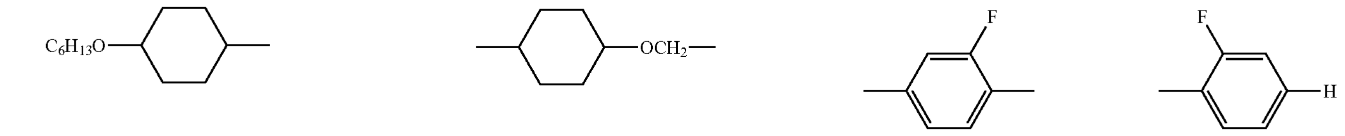 |
| 1272 | 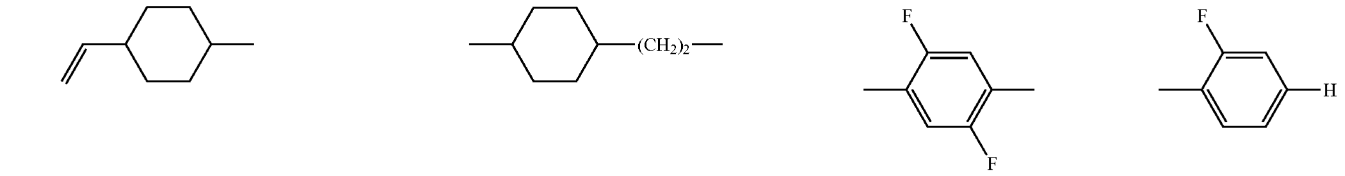 |
| 1273 | 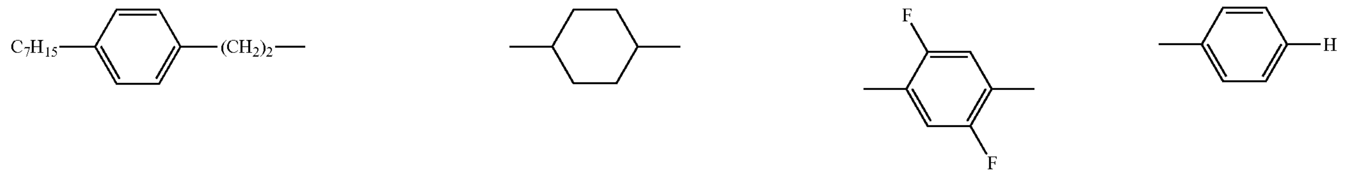 |
| 1274 | 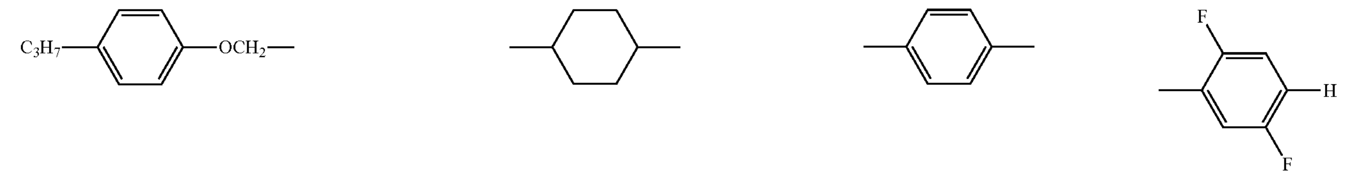 |
| 1275 | 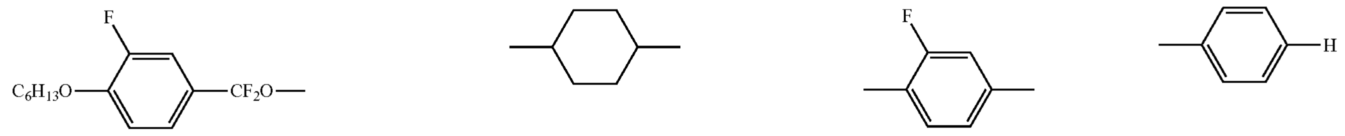 |
| 1276 | 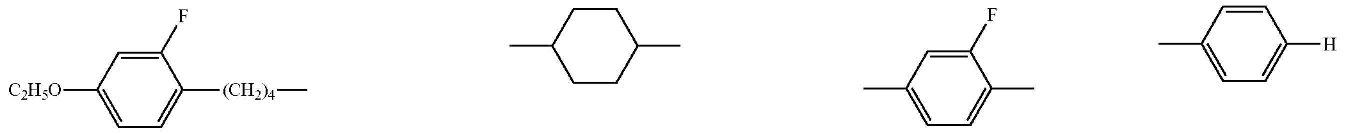 |

-continued
1277
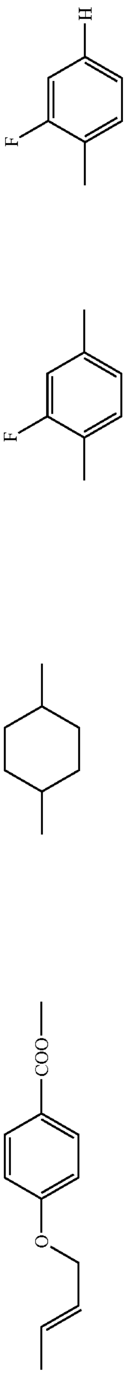
1278
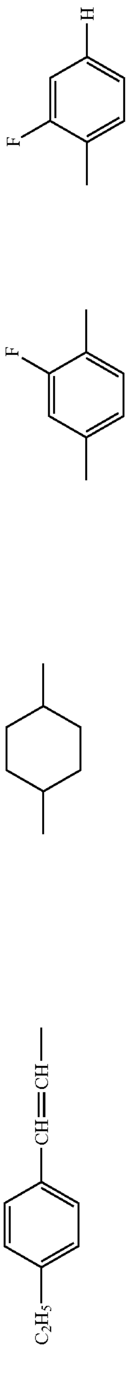
1279
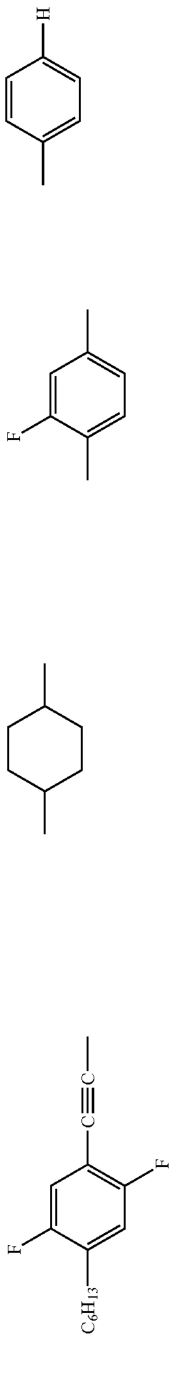
1280
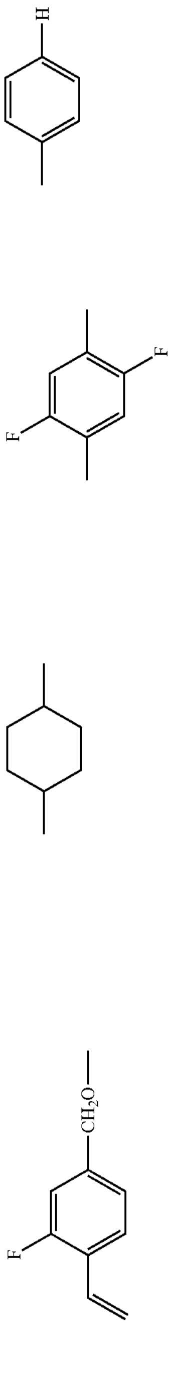
1281
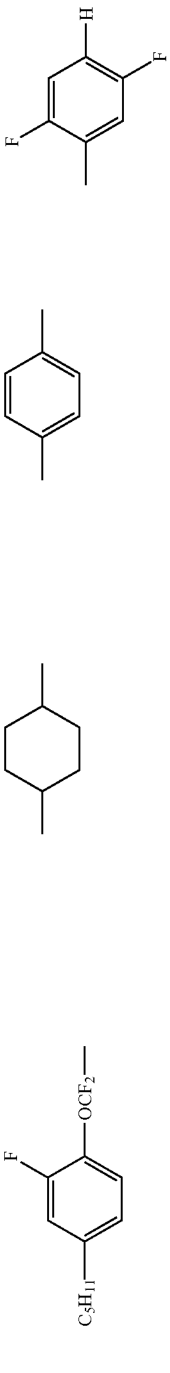
1282
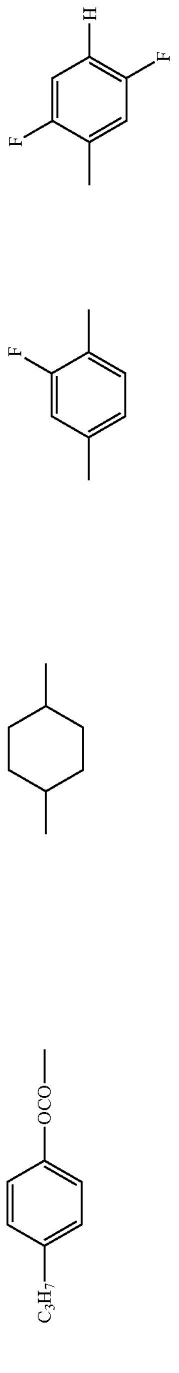

-continued
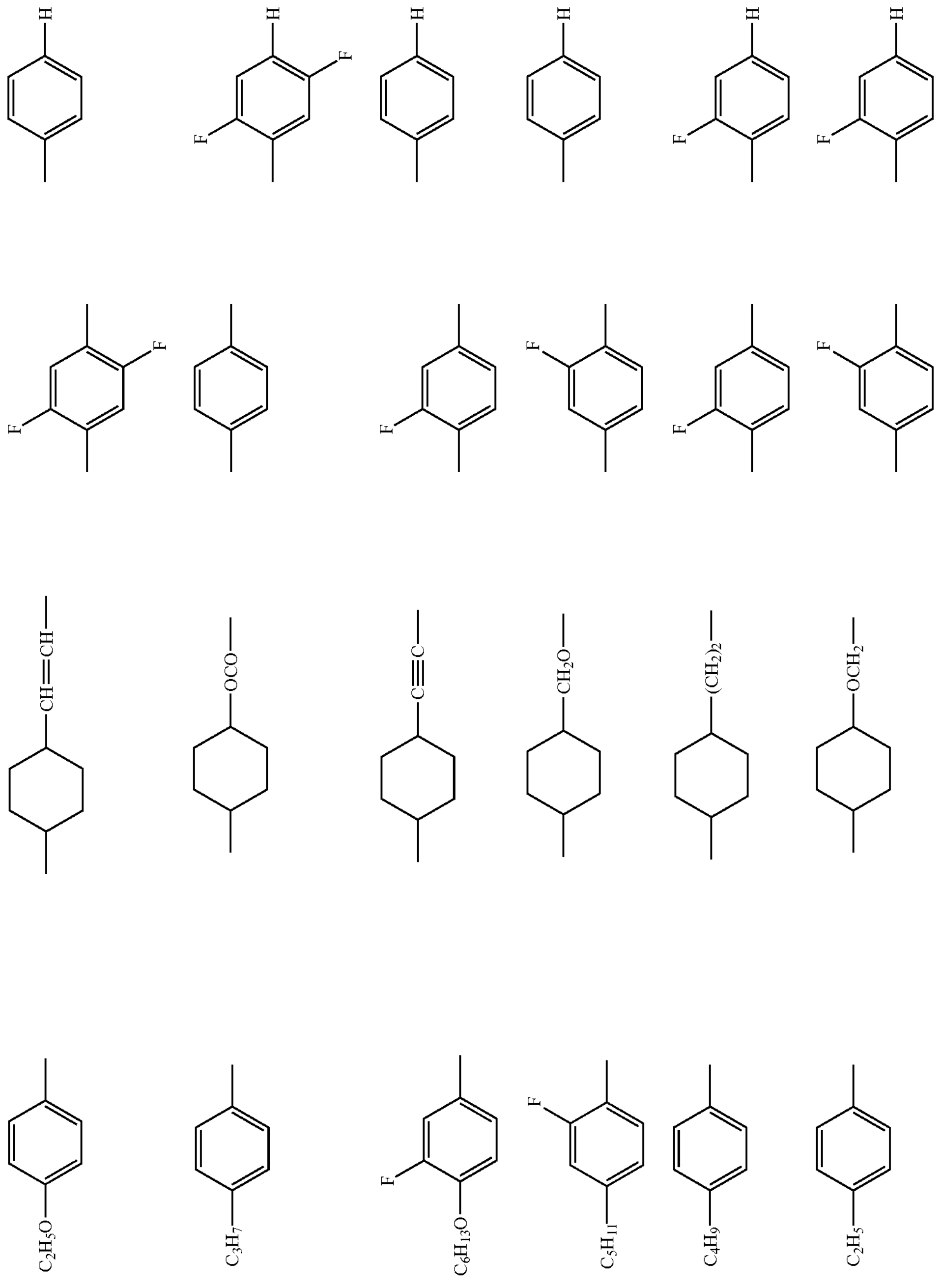
1283
1284
1285
1286
1287
1288
-continued
| | | | |
|---|---|---|---|
| 1283 | C₂H₅O—⬡— | —CH=CH—⬢— | —⬡—H |
| 1284 | C₃H₇—⬡— | —OCO—⬢— | —⬡(F,F)—H |
| 1285 | C₆H₁₃O—⬡(F)— | —C≡C—⬢— | —⬡—H |
| 1286 | C₅H₁₁—⬡(F)— | —CH₂O—⬢— | —⬡—H |
| 1287 | C₄H₉—⬡— | —(CH₂)₂—⬢— | —⬡(F)—H |
| 1288 | C₂H₅—⬡— | —OCH₂—⬢— | —⬡(F)—H |

-continued
1289 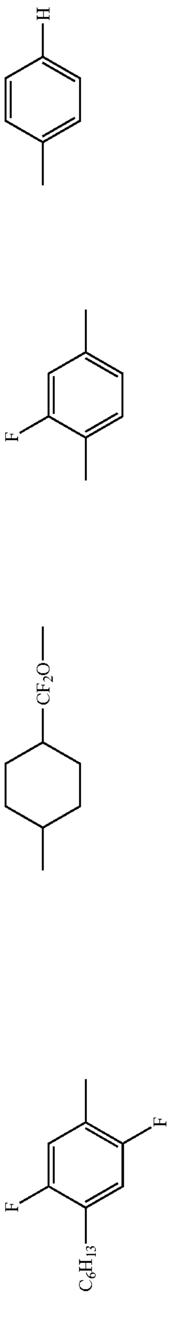
1290 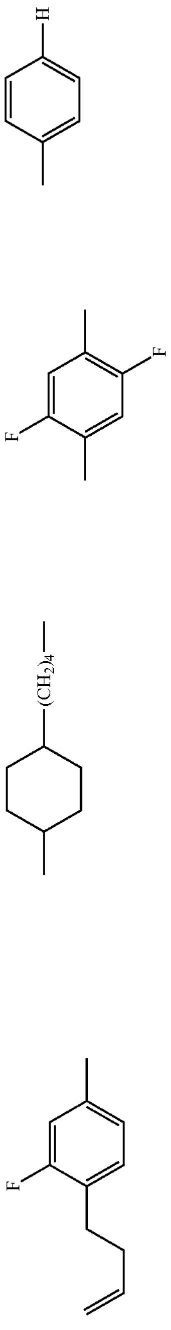
1291 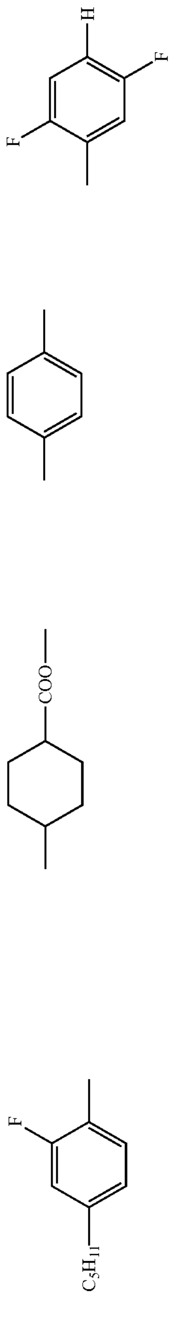
1292 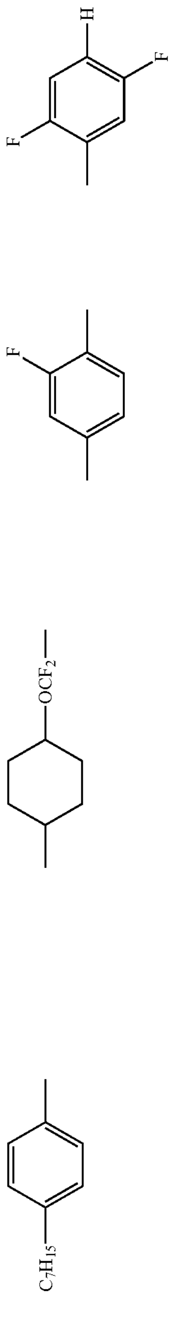
1293 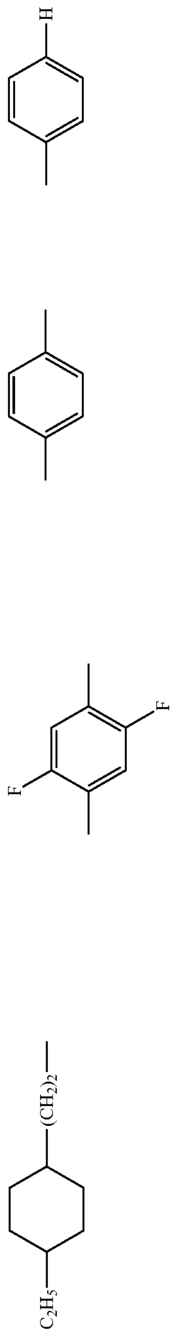
1294 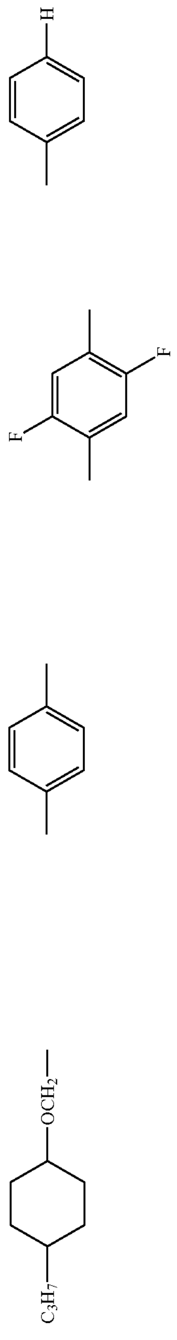

-continued
| | |
|---|---|
| 1295 | 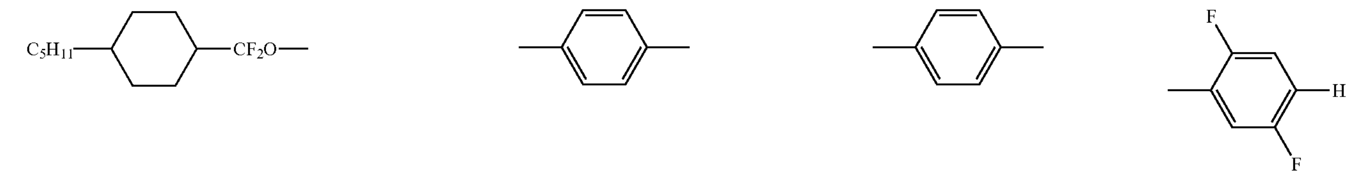 |
| 1296 | 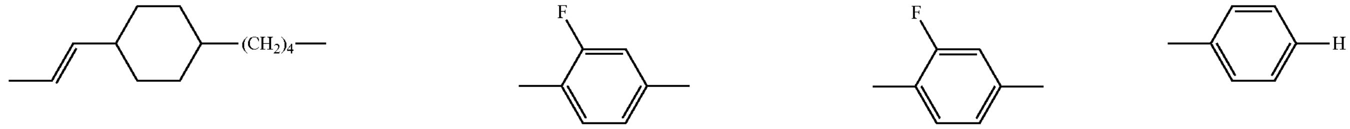 |
| 1297 | 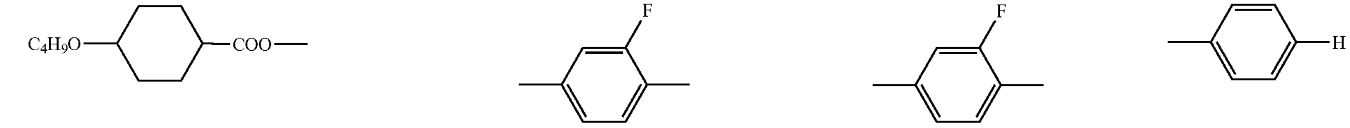 |
| 1298 | 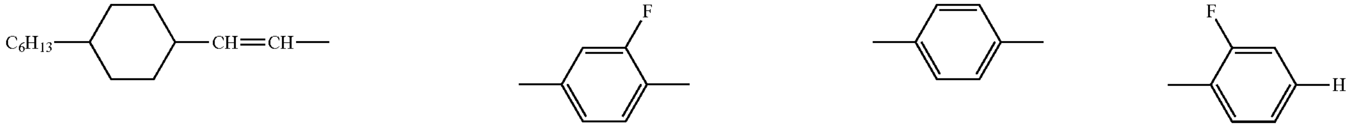 |
| 1299 | 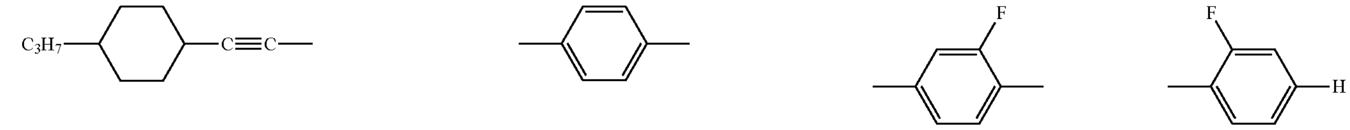 |
| 1300 | 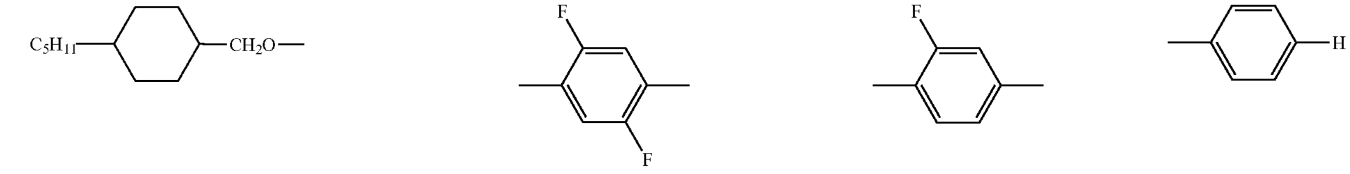 |

-continued
1301
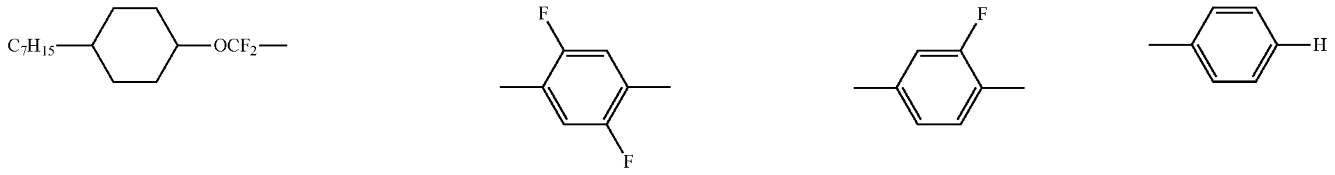
1302
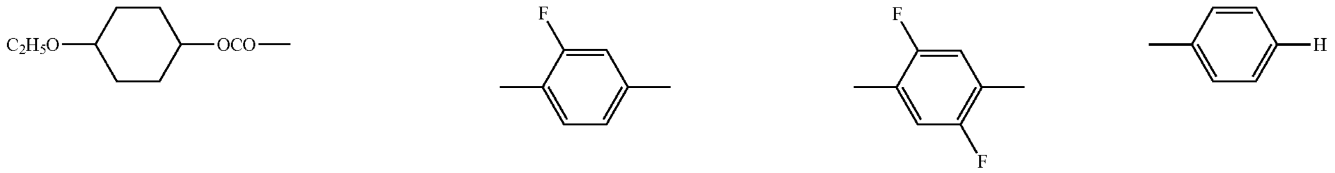
1303
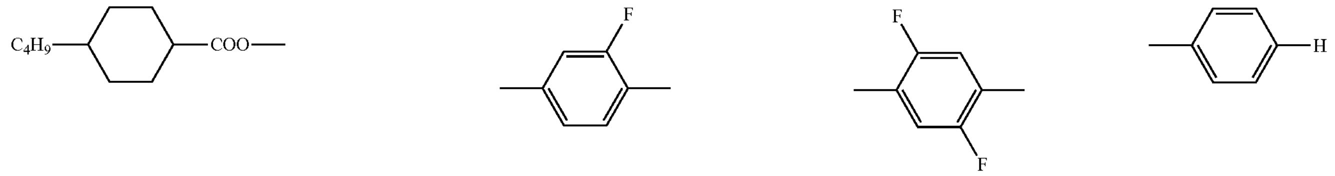
1304
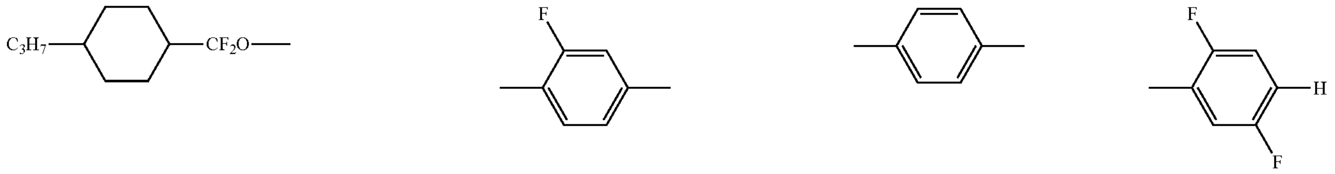
1305
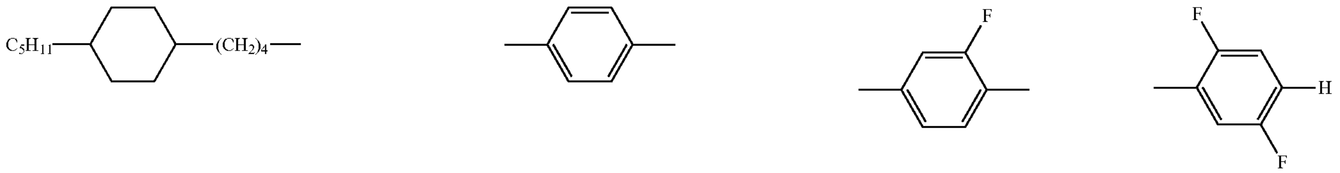
1306
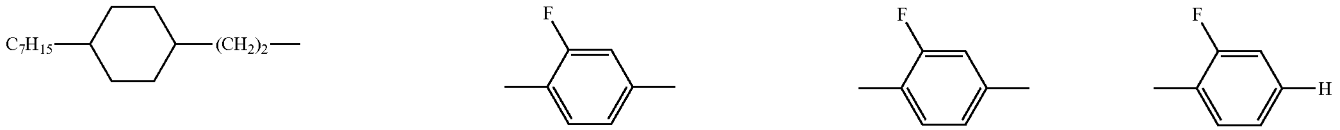

-continued
1307 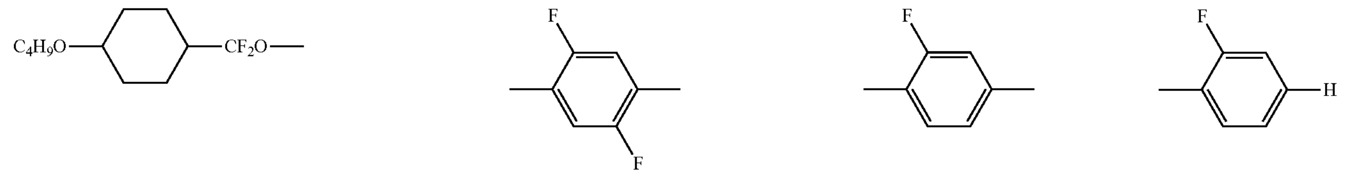
1308 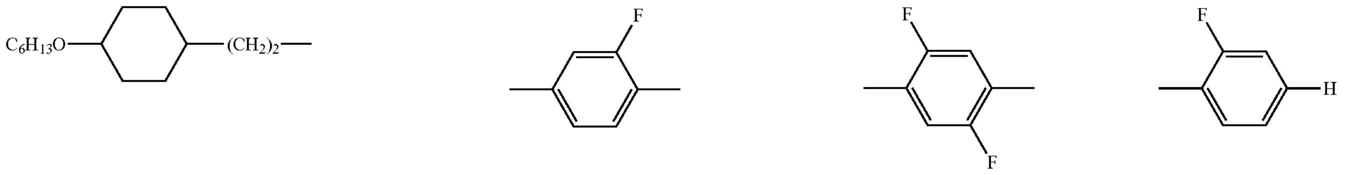
1309 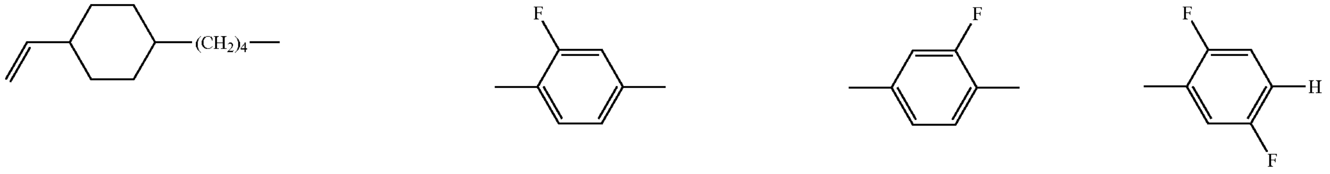
1310 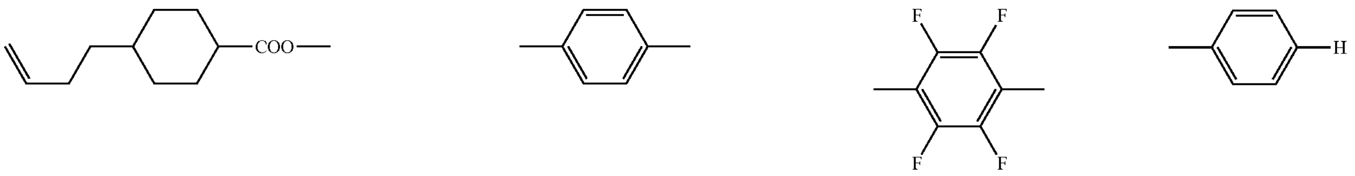
1311 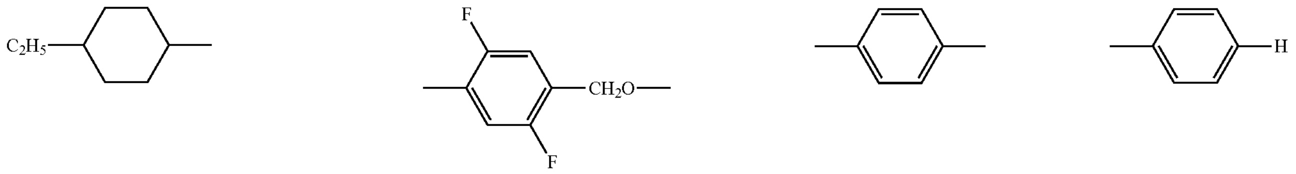

-continued
| | |
|---|---|
| 1312 | 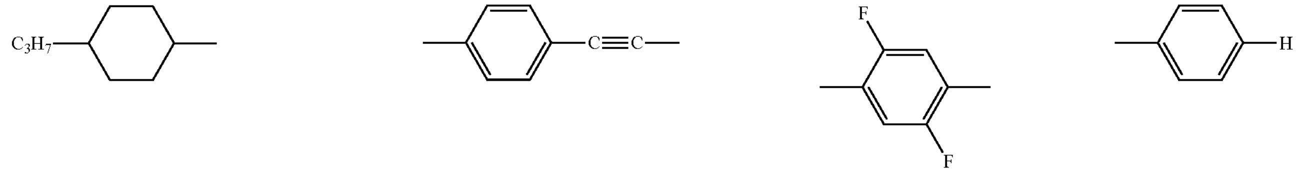 |
| 1313 | 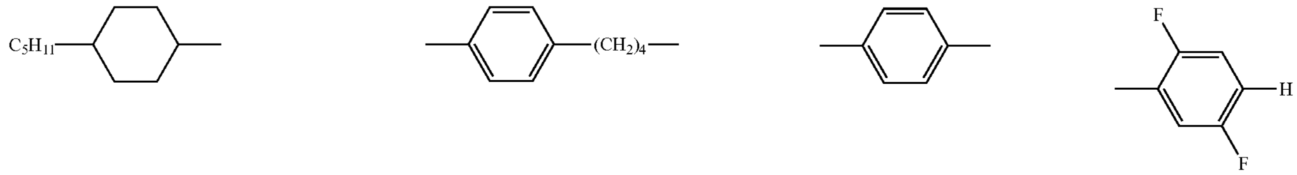 |
| 1314 | 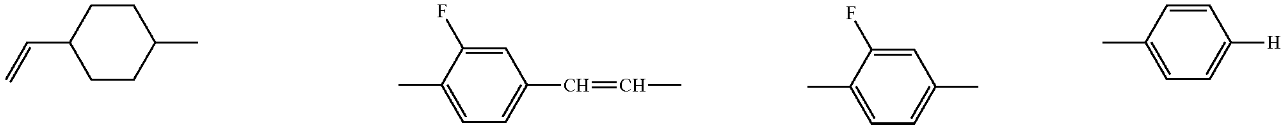 |
| 1315 | 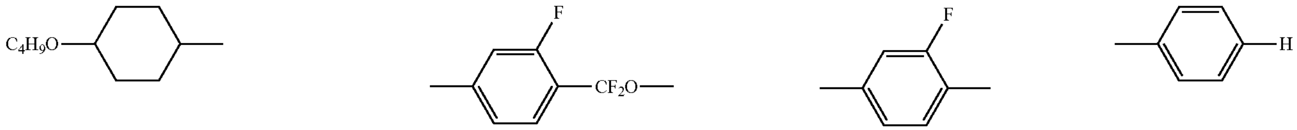 |
| 1316 | 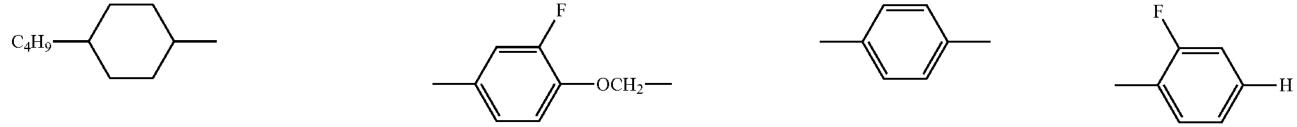 |
| 1317 | 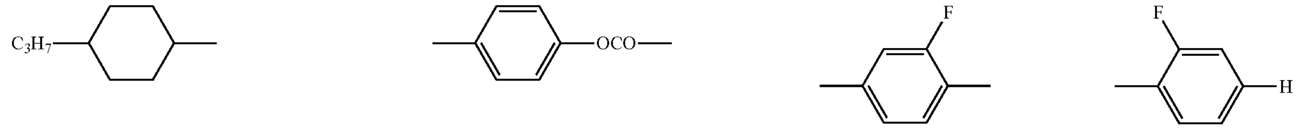 |

-continued
1318 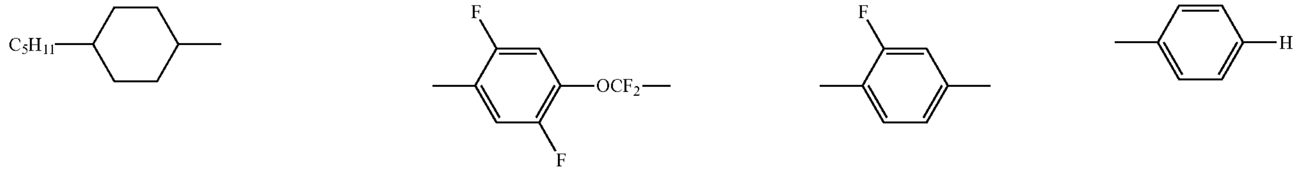
1319 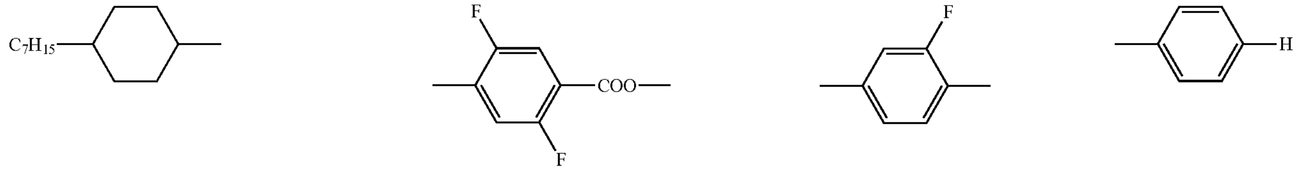
1320 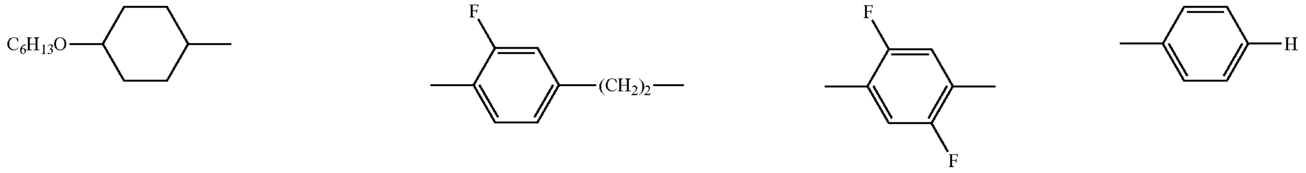
1321 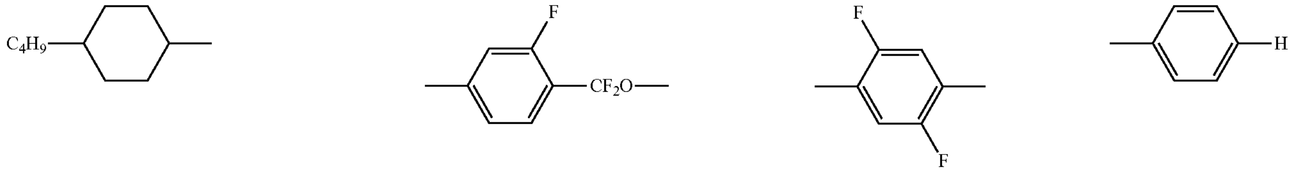
1322 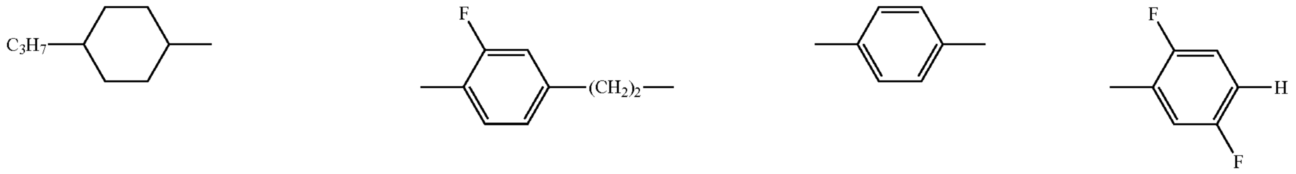

-continued
| | |
|---|---|
| 1323 | 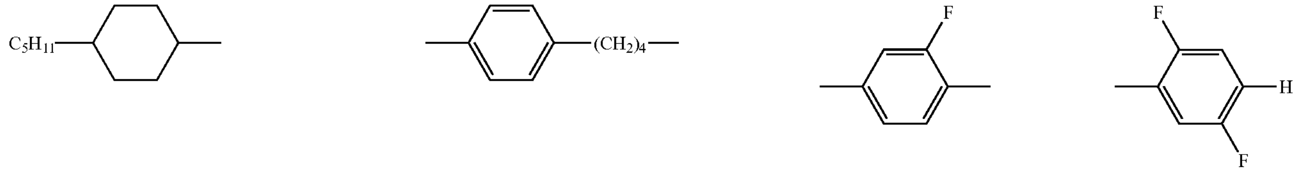 |
| 1324 | 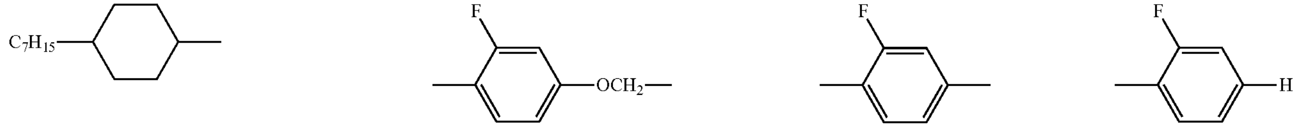 |
| 1325 | 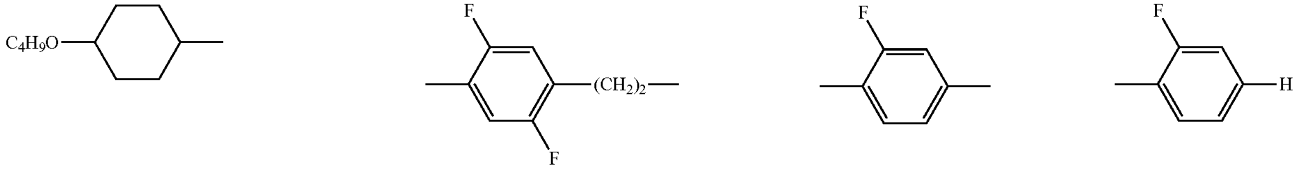 |
| 1326 | 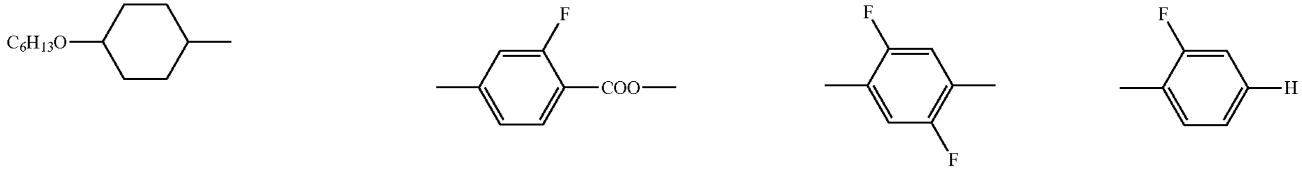 |
| 1327 | 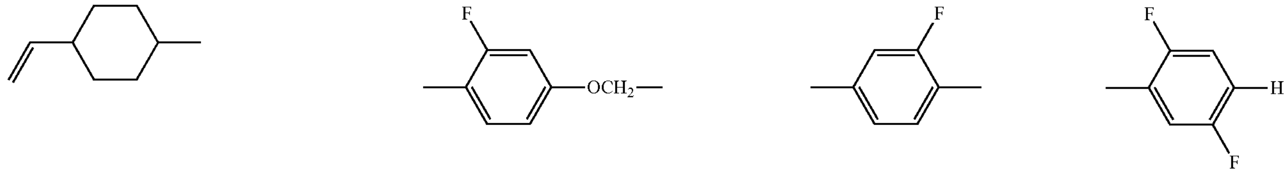 |
| 1328 | 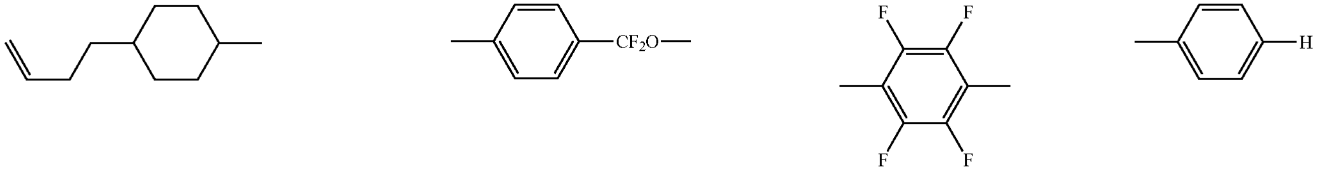 |

-continued
| | |
|---|---|
| 1329 | 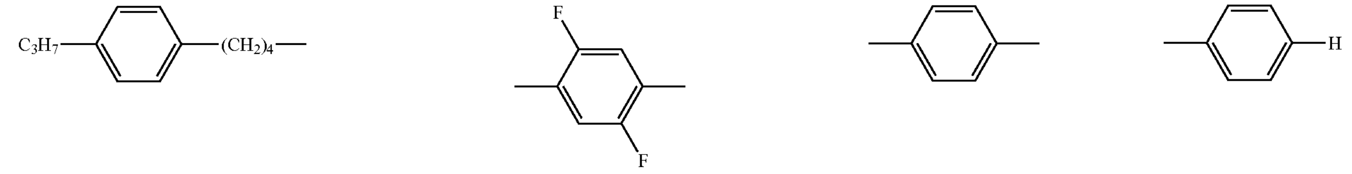 |
| 1330 | 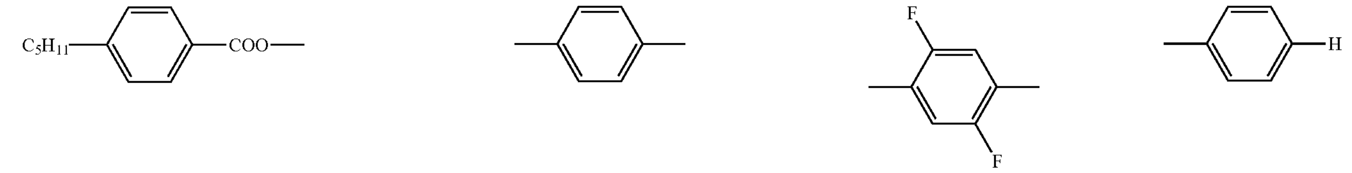 |
| 1331 | 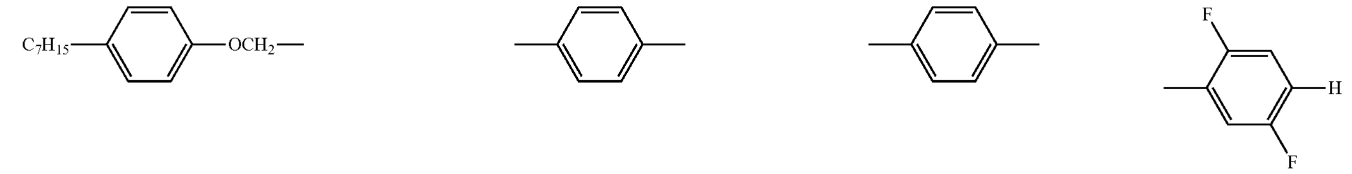 |
| 1332 | 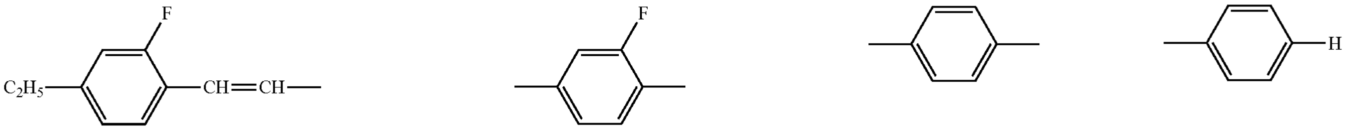 |
| 1333 | 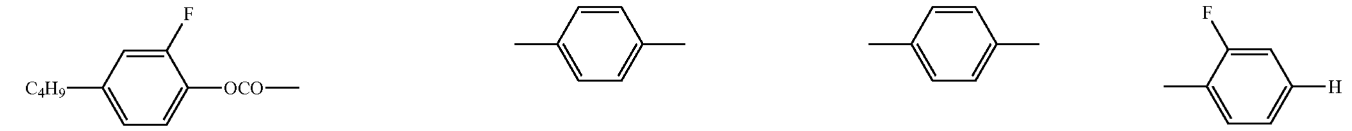 |
| 1334 | 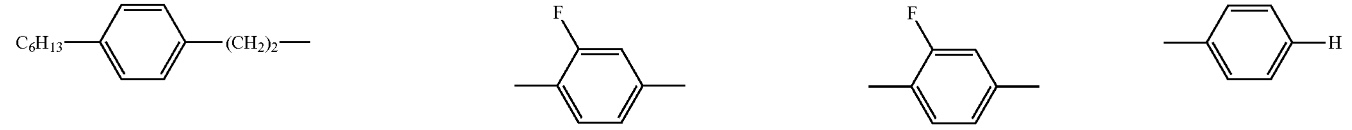 |

-continued
1335 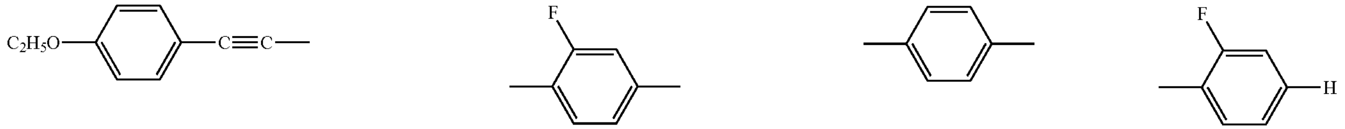
1336 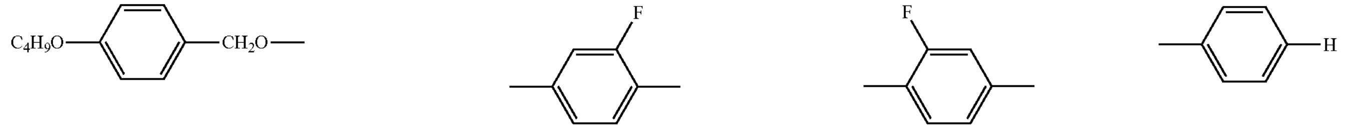
1337 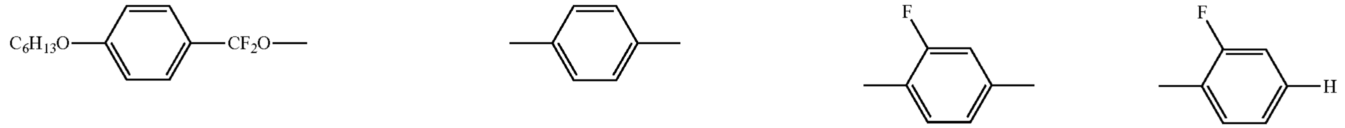
1338 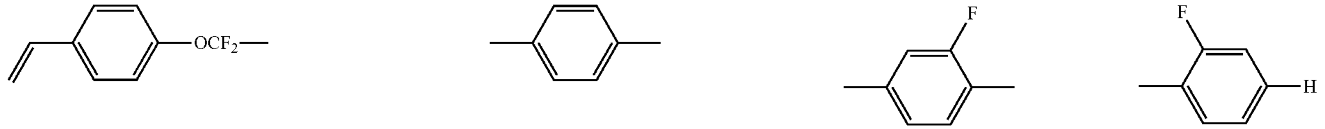
1339 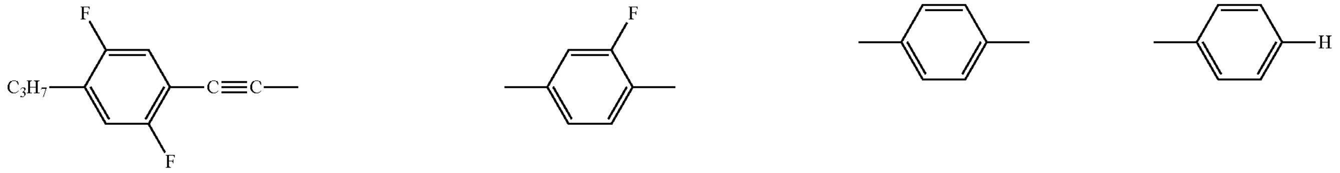
1340 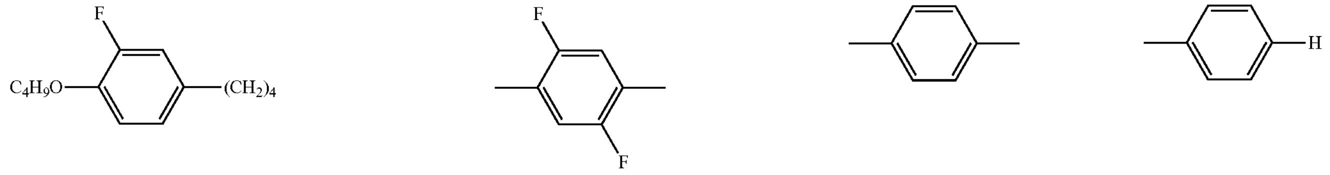

-continued
| | |
|---|---|
| 1341 | 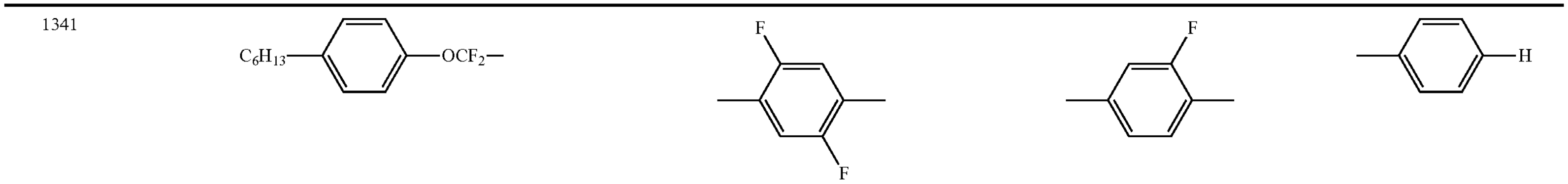 |
| 1342 | 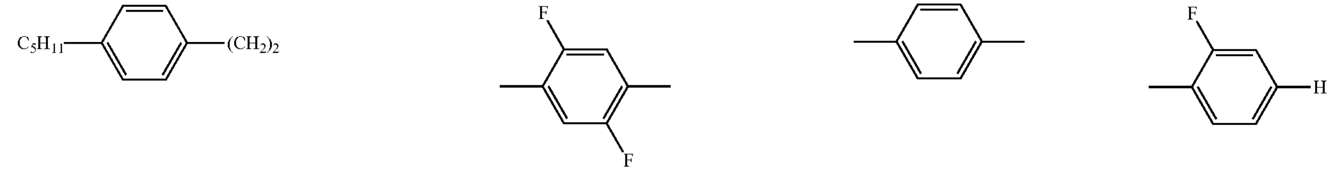 |
| 1343 | 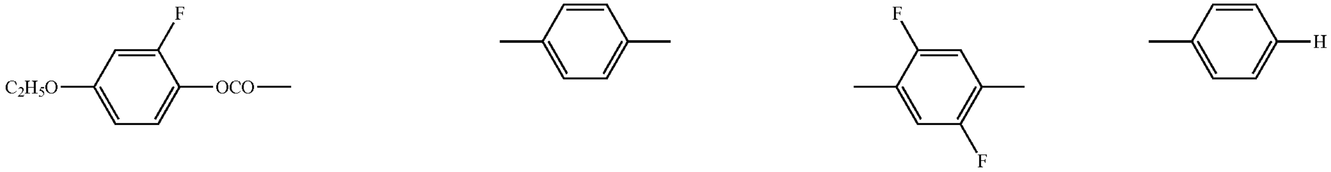 |
| 1344 | 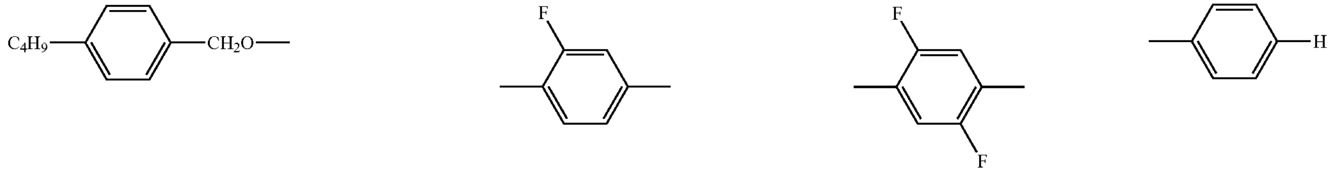 |
| 1345 | 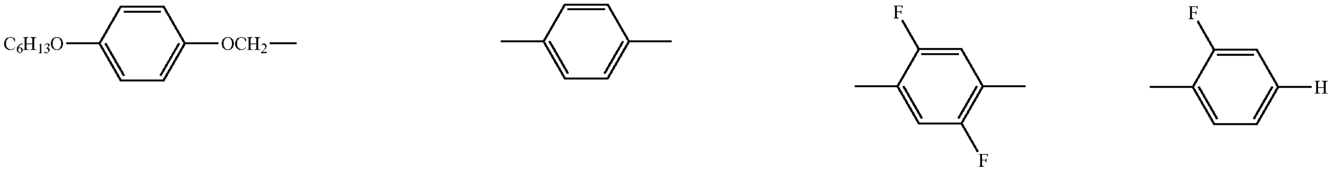 |

-continued
1346 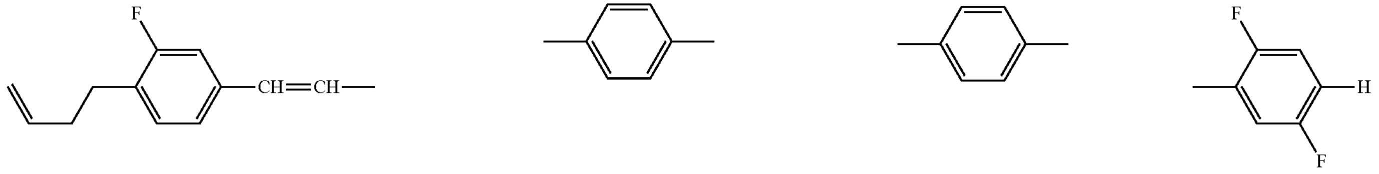
1347 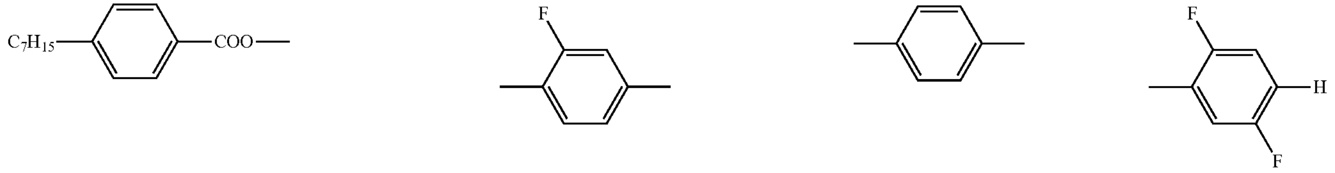
1348 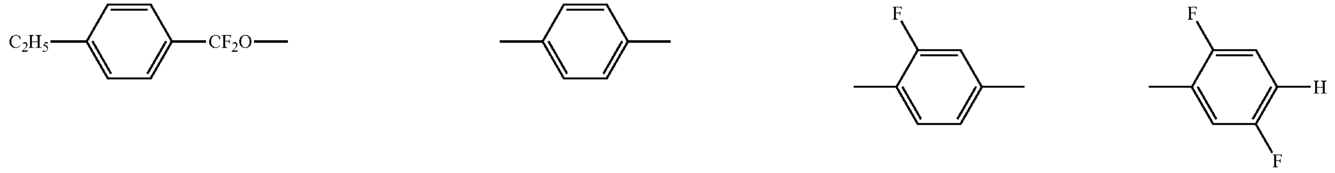
1349 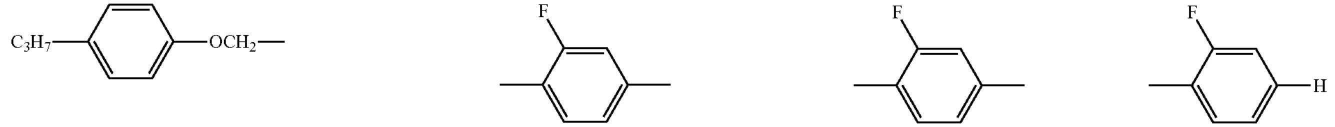
1350 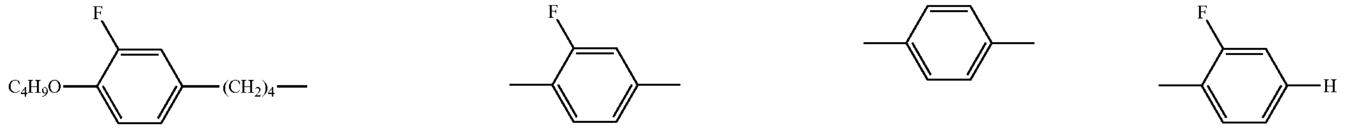
1351 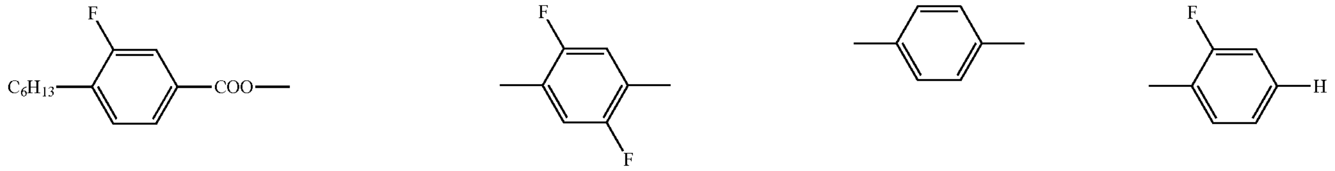

-continued
1352 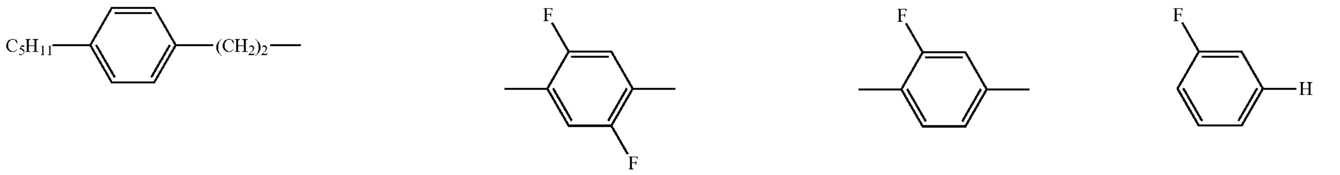
1353 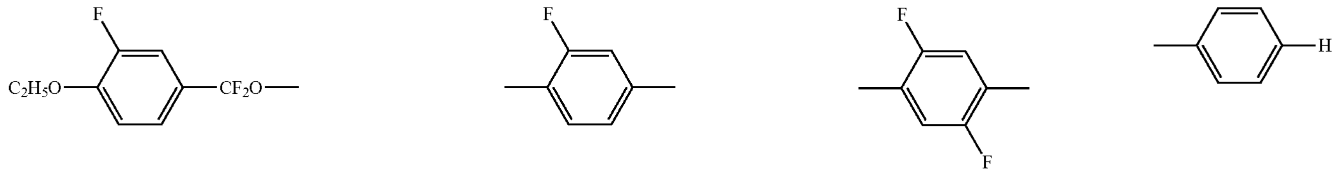
1354 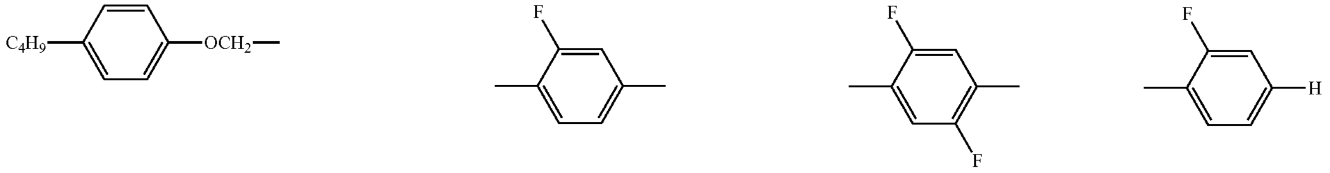
1355 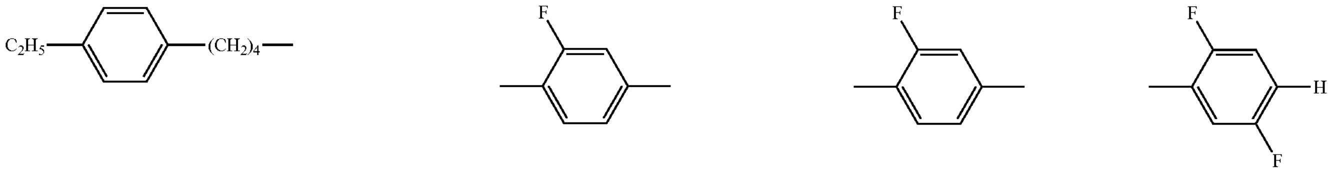
1356 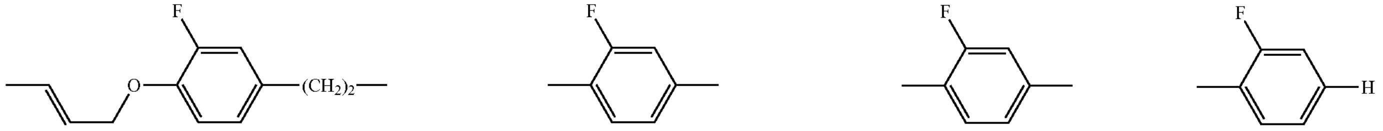
1357 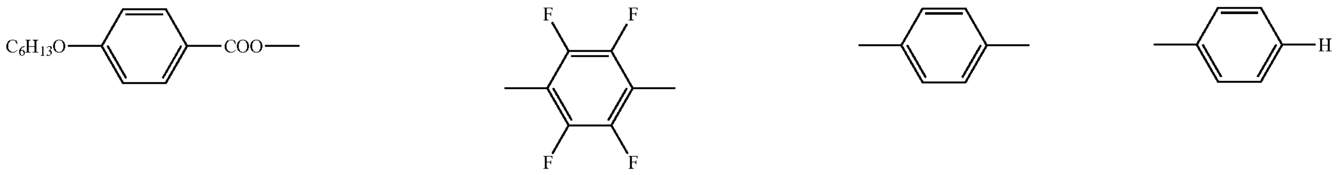

-continued
| | |
|---|---|
| 1358 | 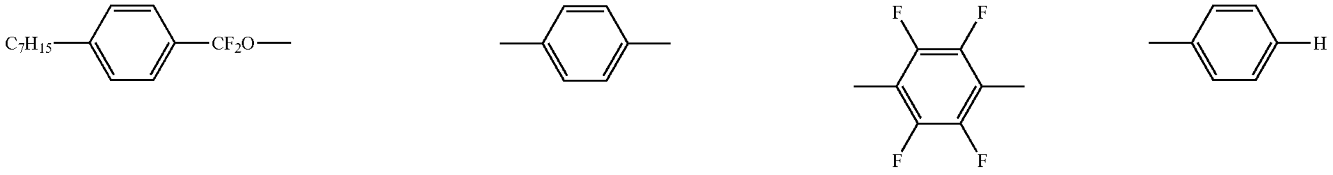 |
| 1359 | 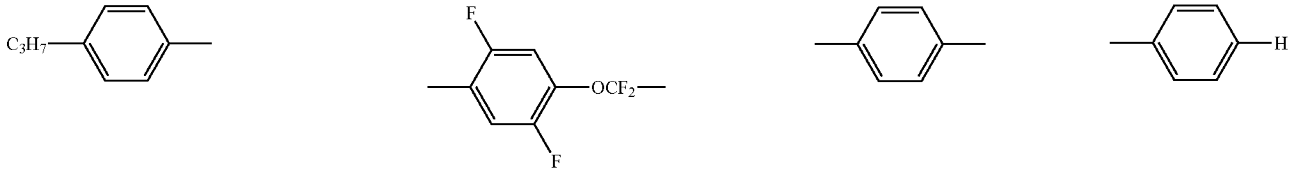 |
| 1360 | 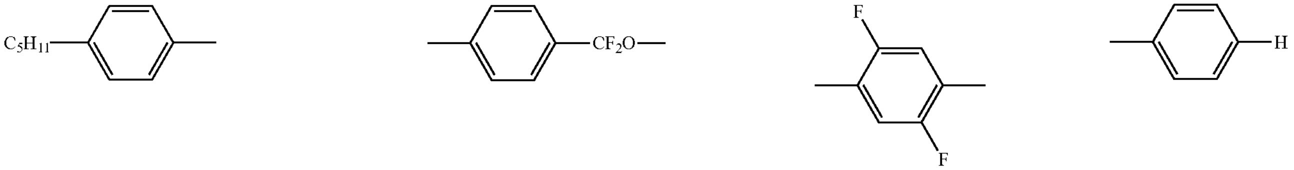 |
| 1361 | 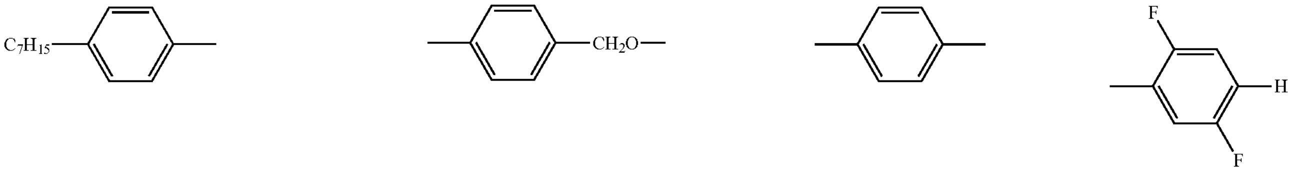 |
| 1362 | 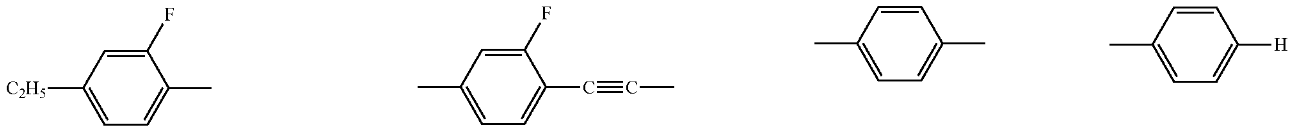 |
| 1363 | 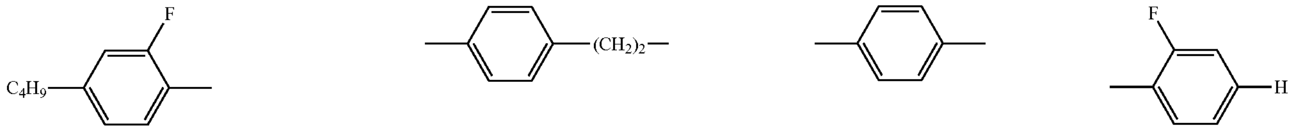 |

-continued
1364 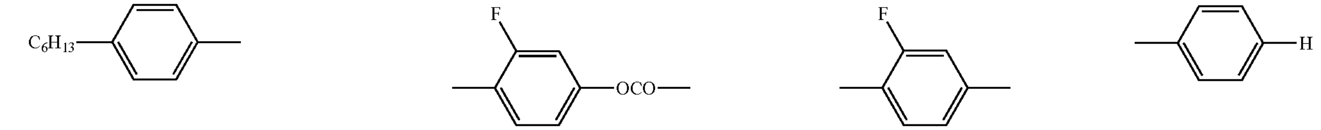
1365 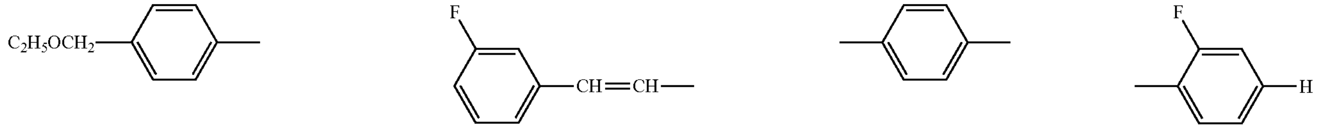
1366 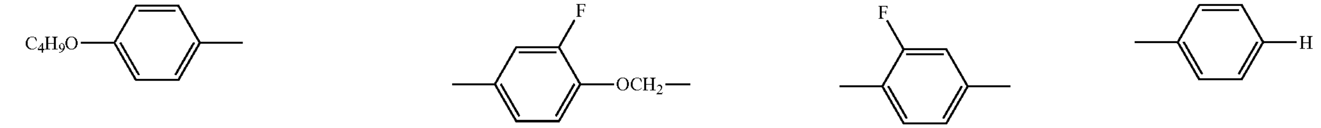
1367 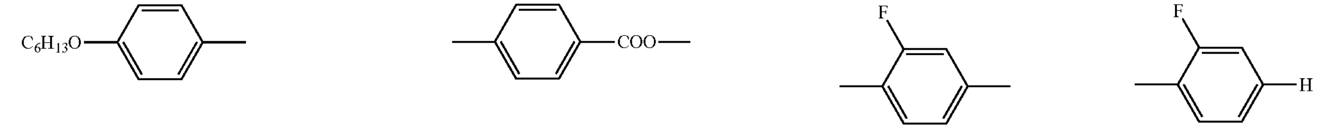
1368 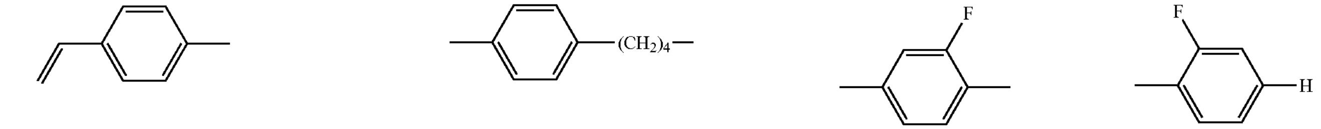
1369 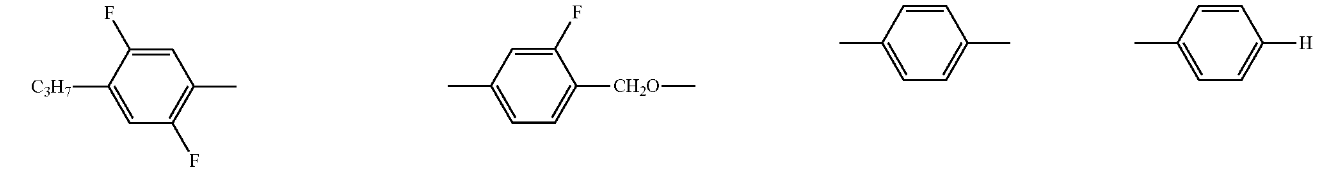
1370 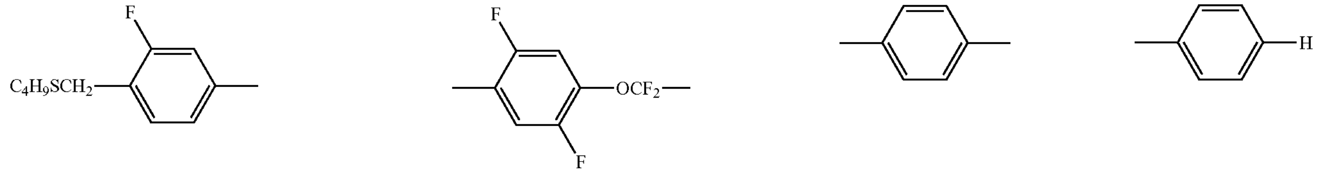

-continued
1371 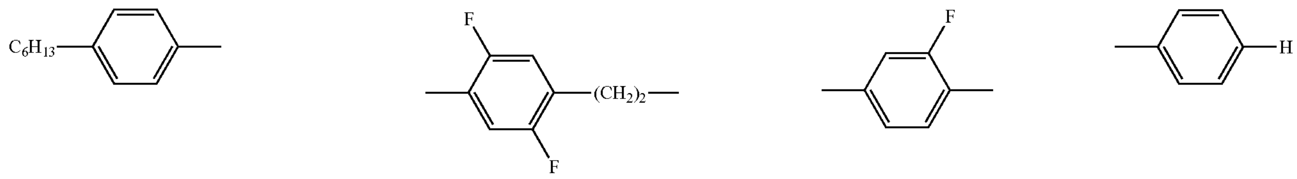
1372 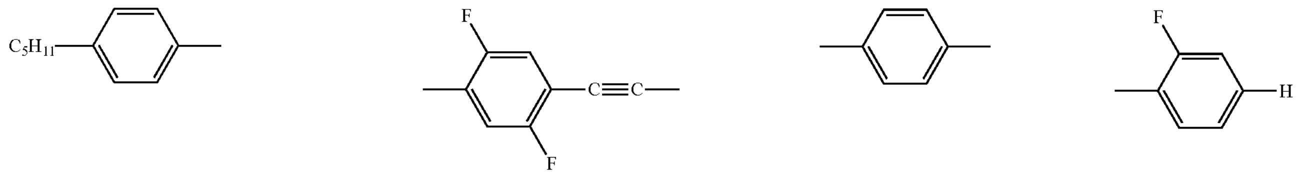
1373 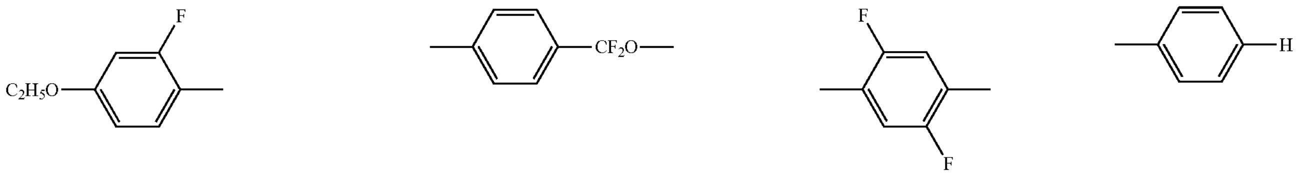
1374 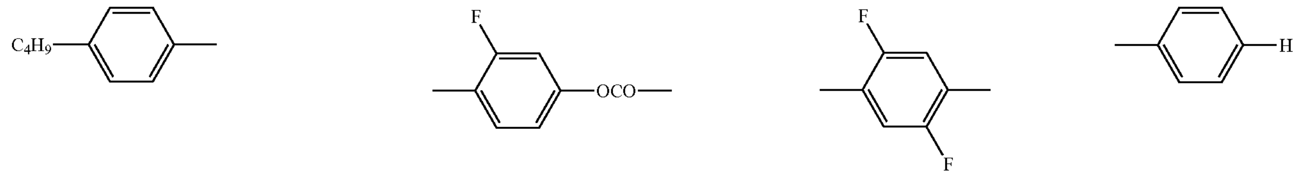
1375 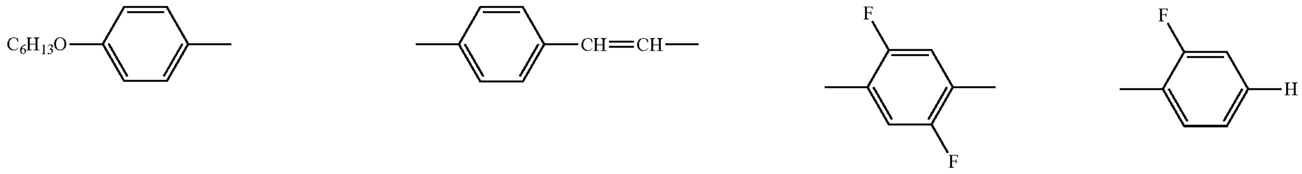

-continued
| | |
|---|---|
| 1376 | 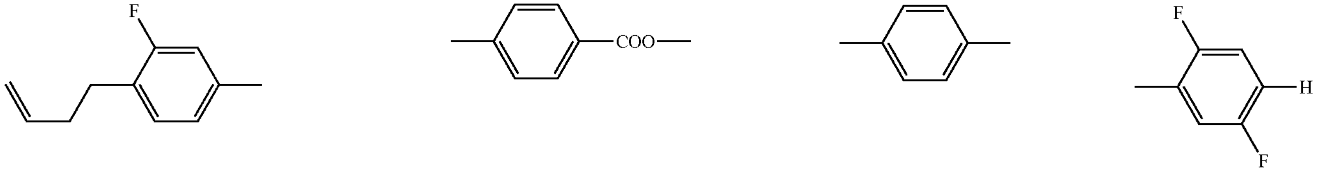 |
| 1377 | 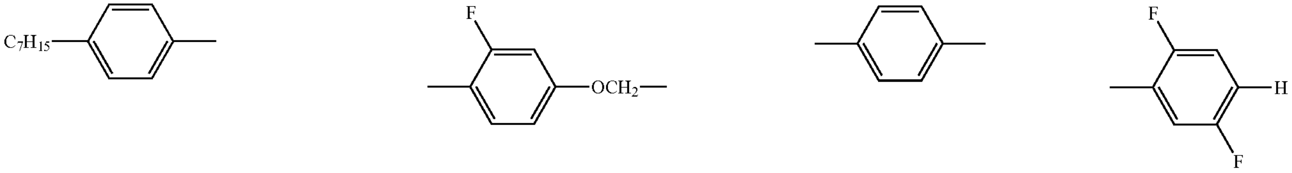 |
| 1378 | 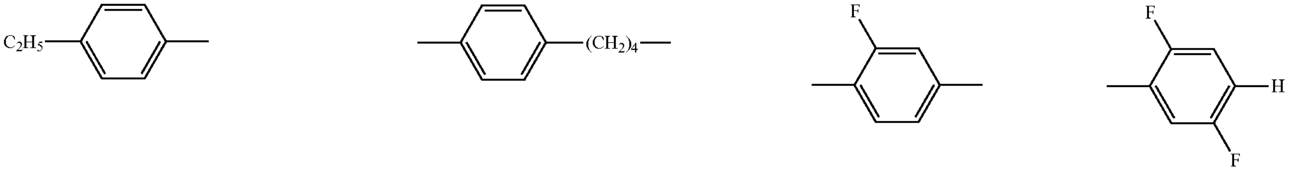 |
| 1379 | 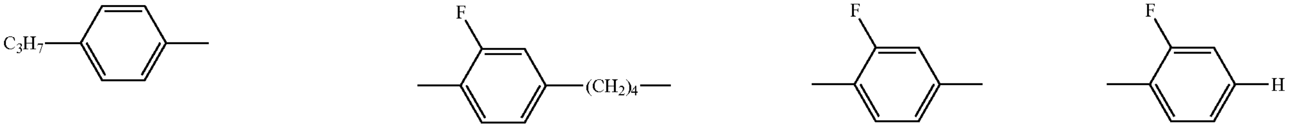 |
| 1380 | 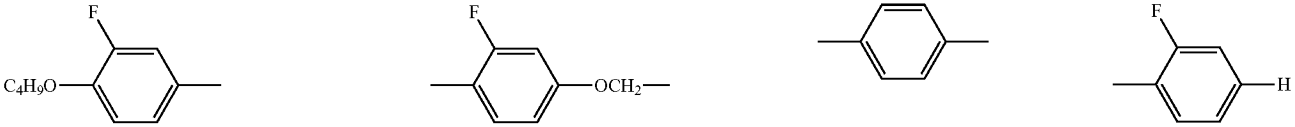 |
| 1381 | 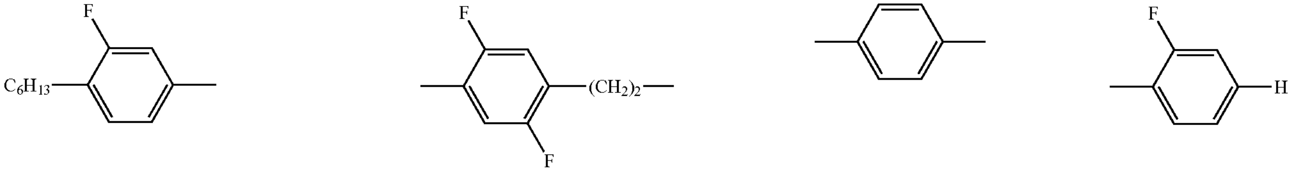 |

-continued
1382
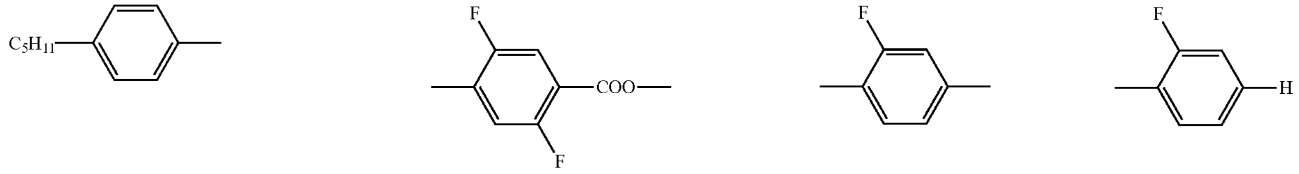
1383
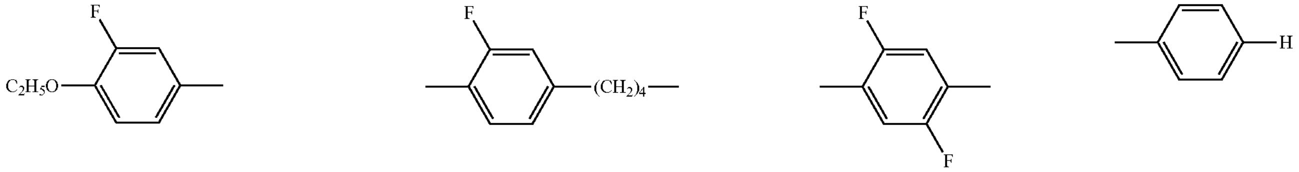
1384
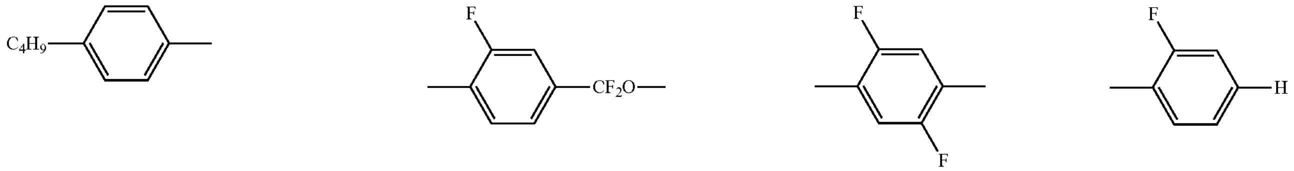
1385
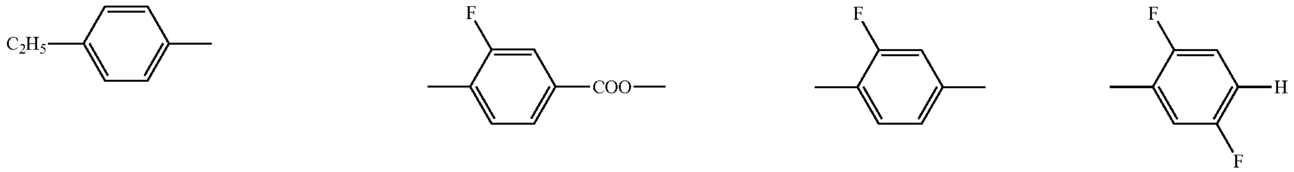
1386
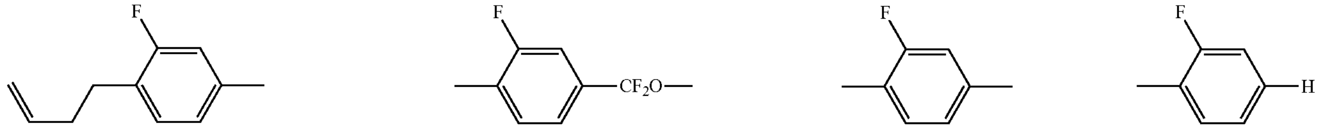
1387
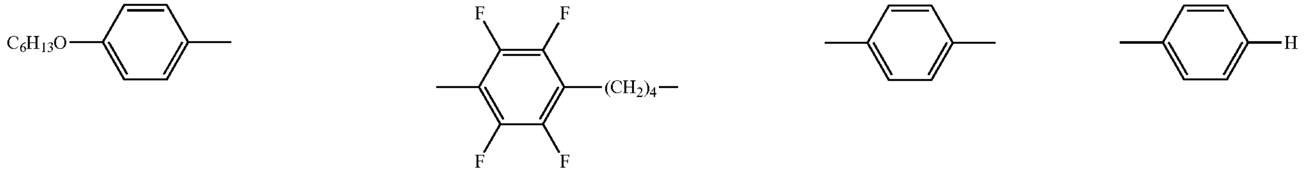

-continued
| | |
|---|---|
| 1388 | 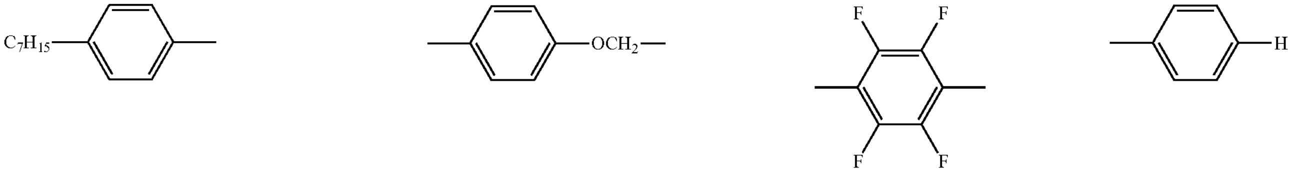 |
| 1389 | 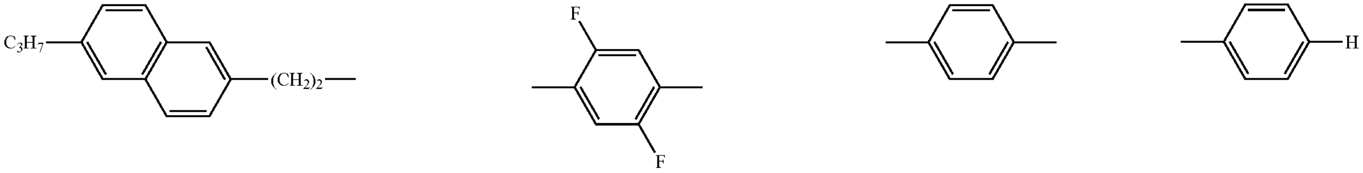 |
| 1390 | 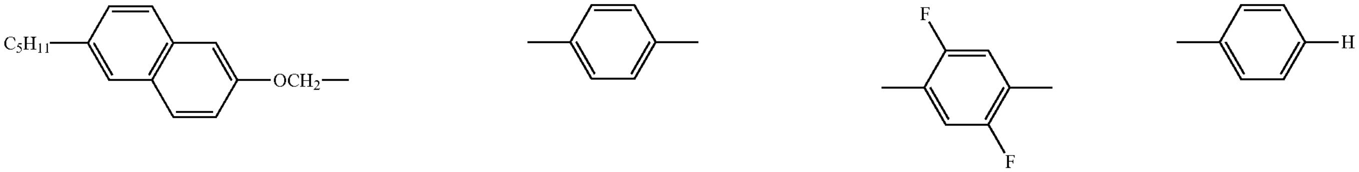 |
| 1391 | 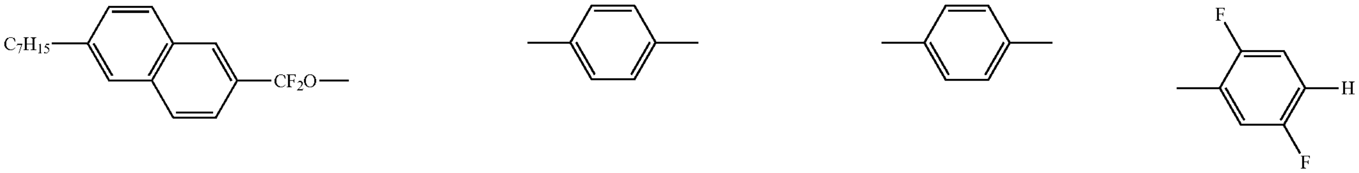 |
| 1392 | 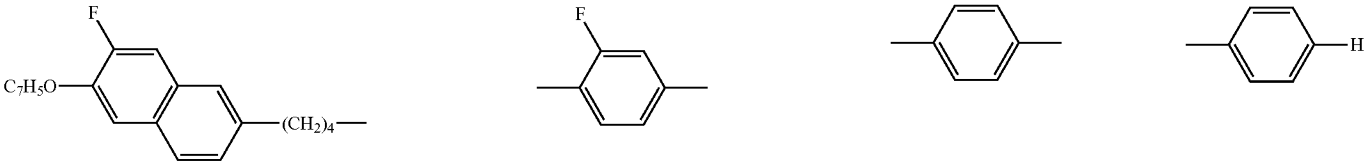 |
| 1393 | 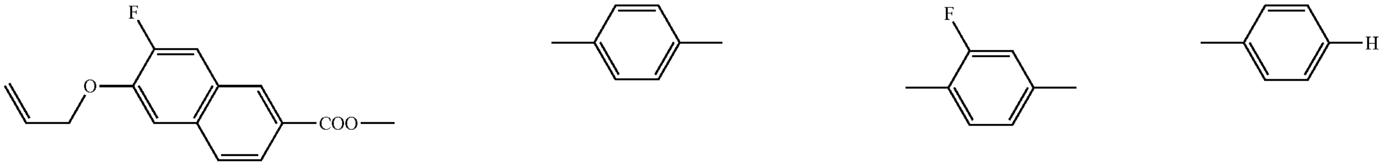 |

-continued
1394
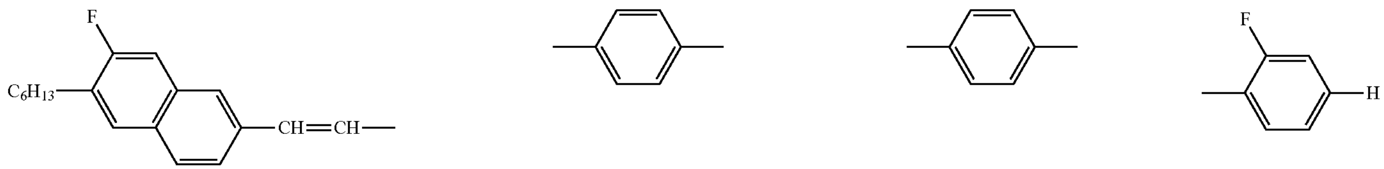
1395
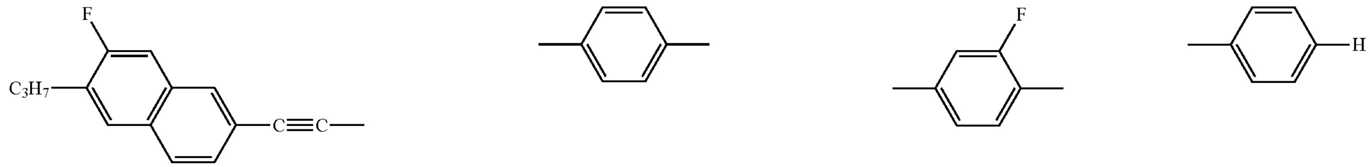
1396
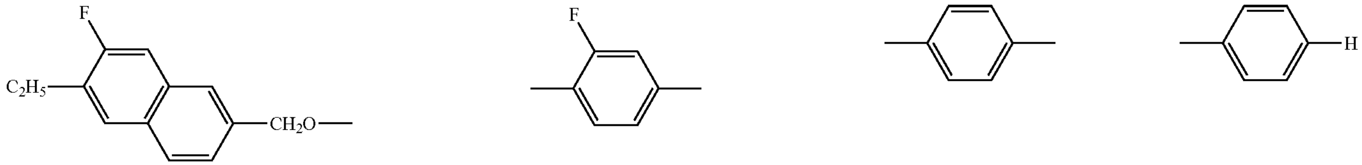
1397
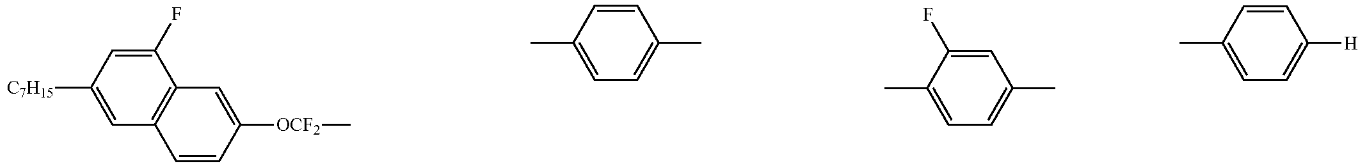
1398
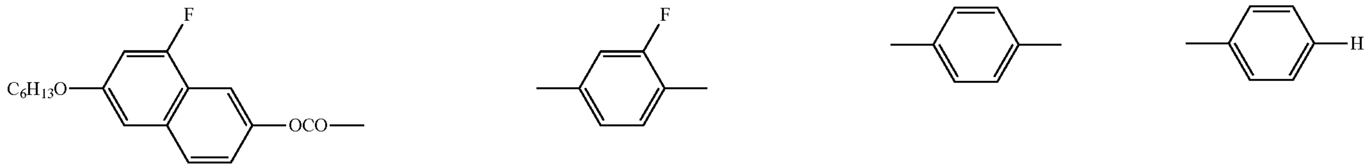
1399
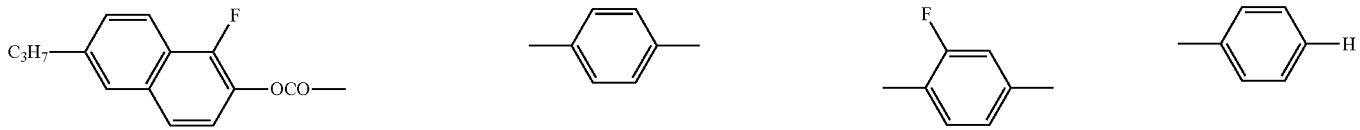

-continued
| | |
|---|---|
| 1400 | 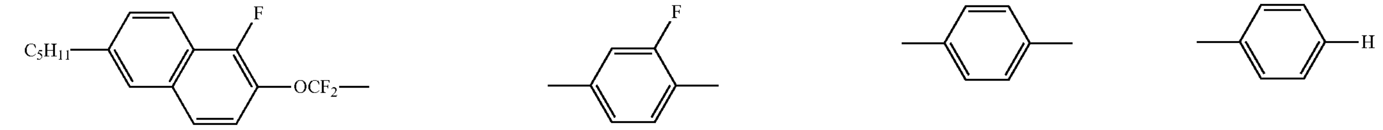 |
| 1401 | 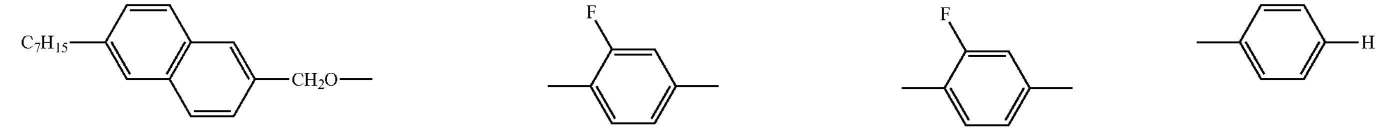 |
| 1402 | 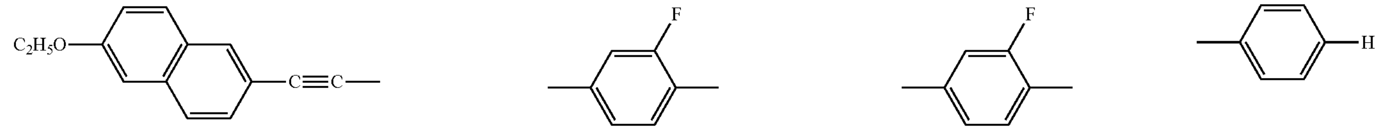 |
| 1403 | 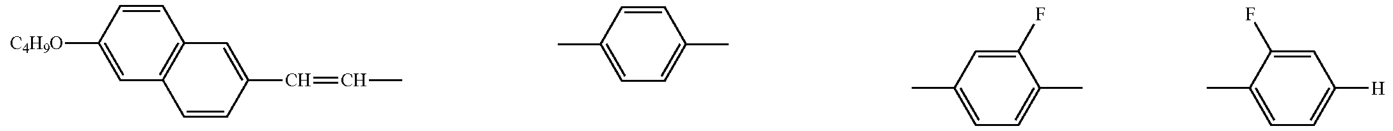 |
| 1404 | 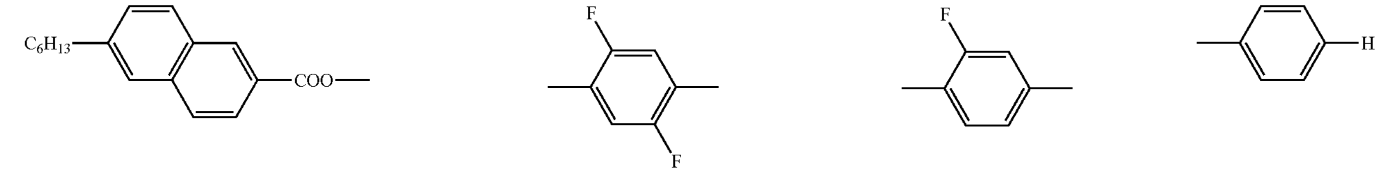 |
| 1405 | 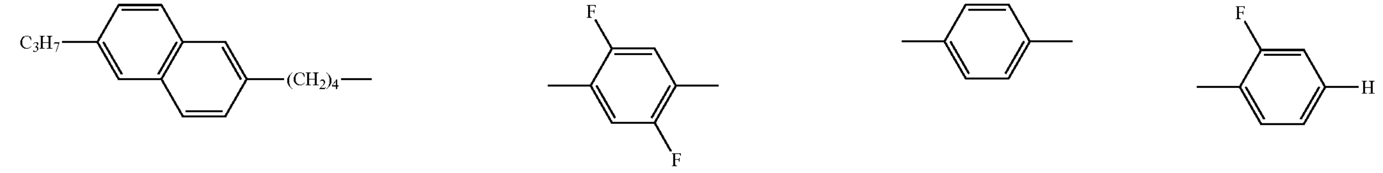 |

-continued
1406 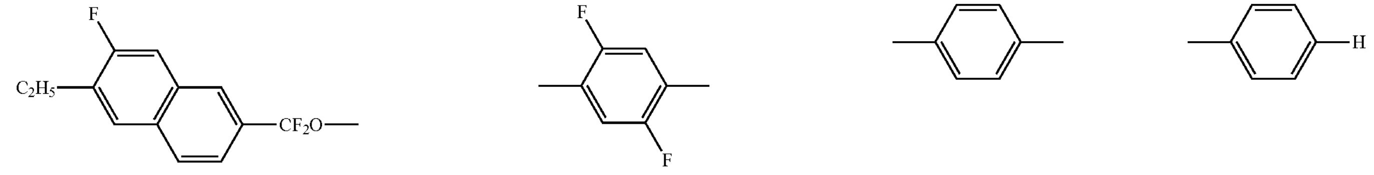
1407 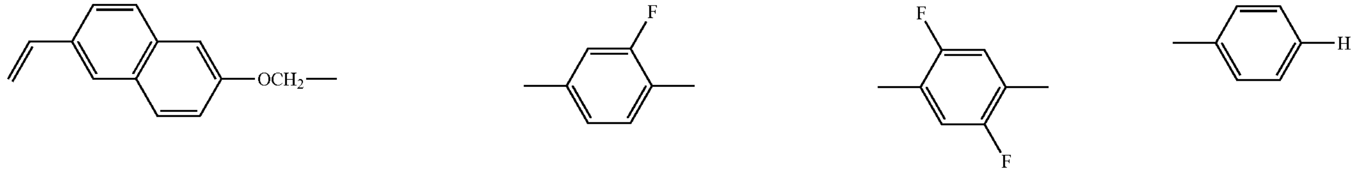
1408 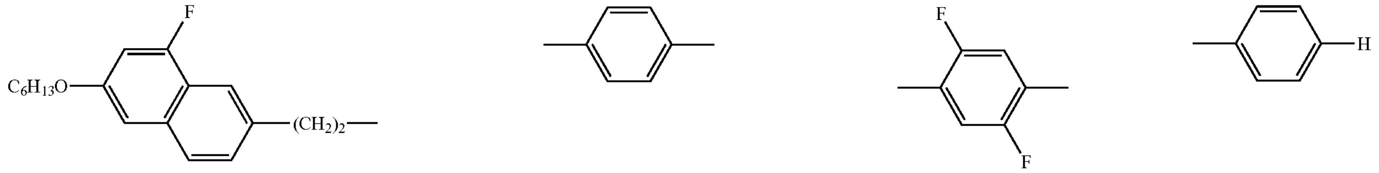
1409 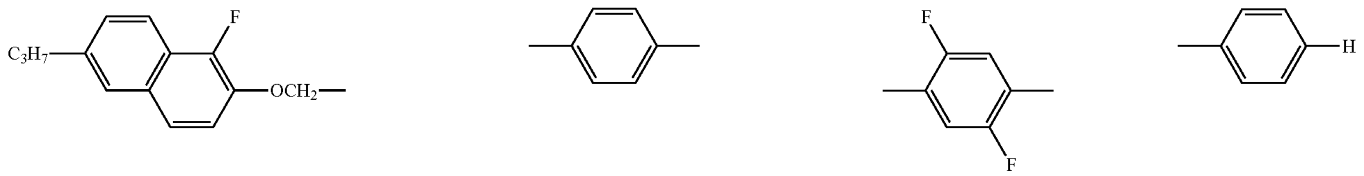
1410 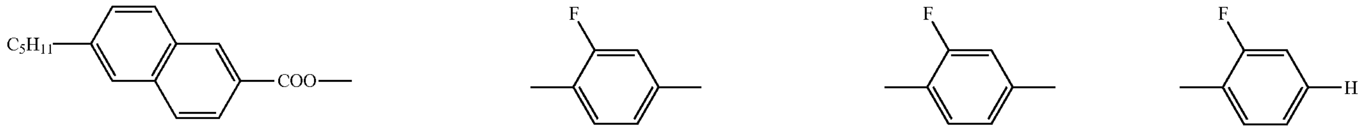
1411 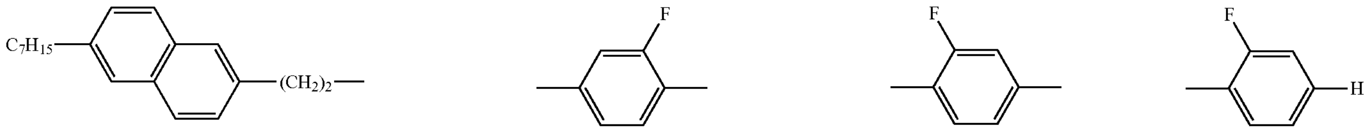

-continued
1412 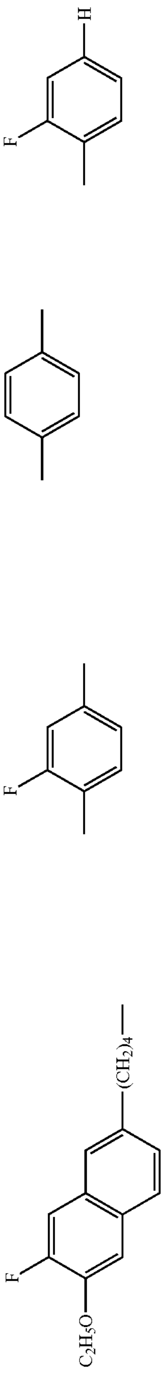
1413 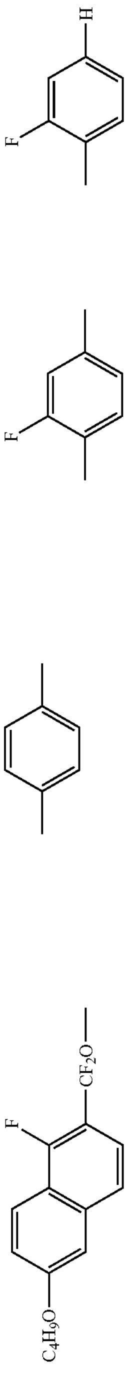
1414 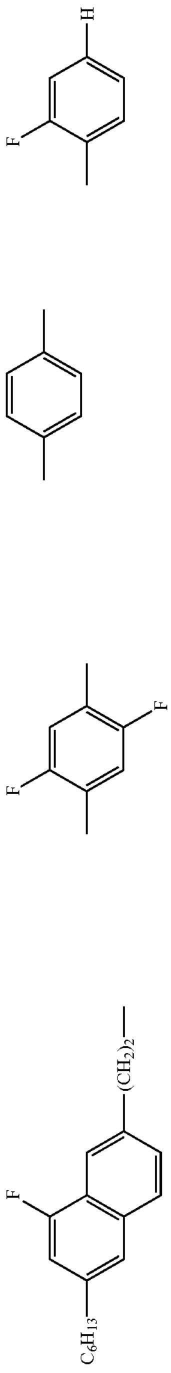
1415 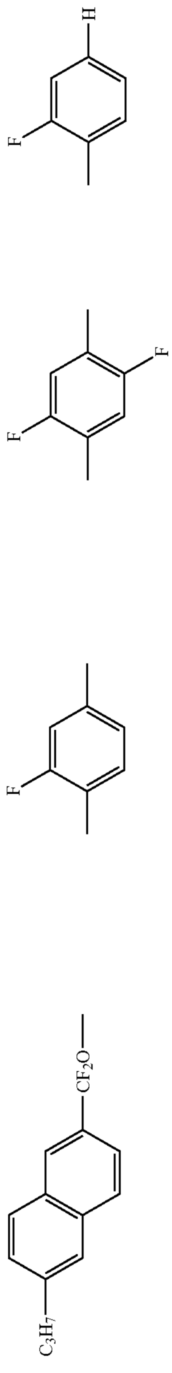
1416 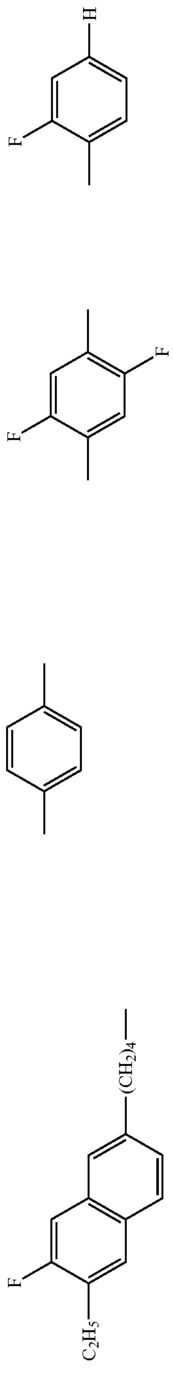
1417 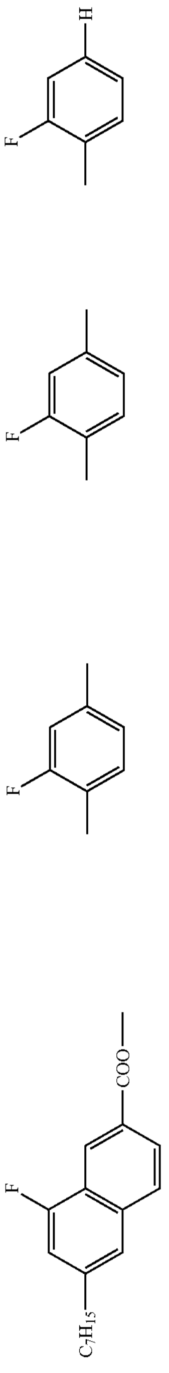

-continued
1418 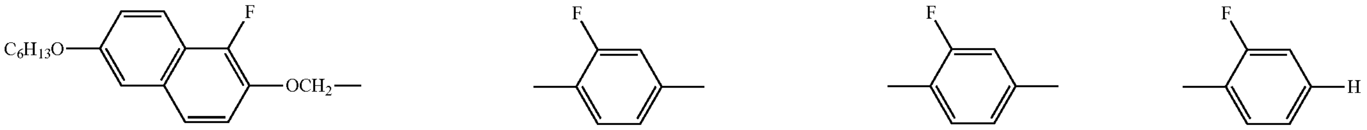
1419 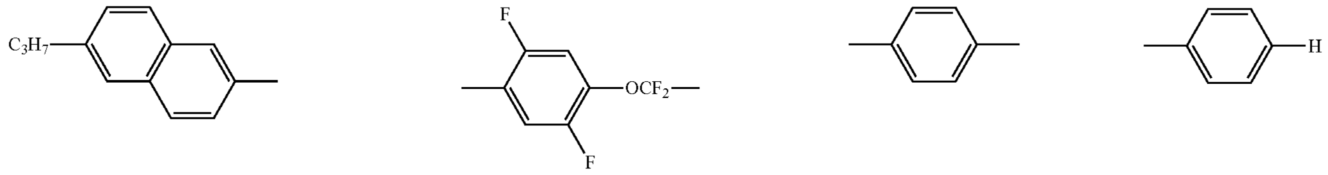
1420 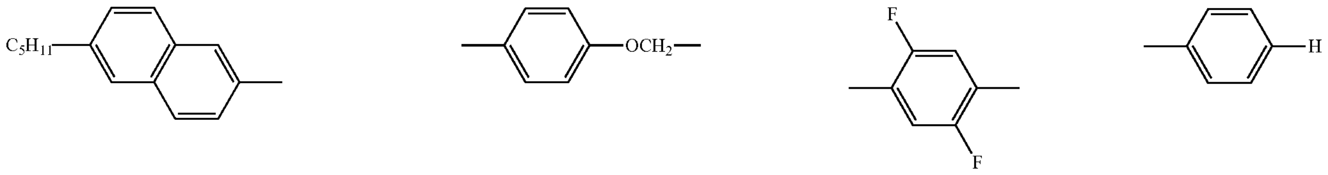
1421 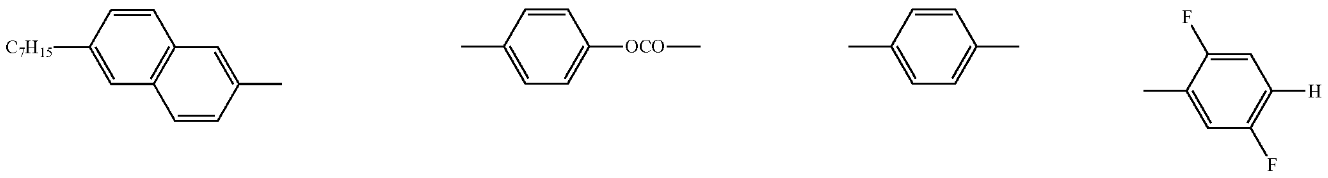
1422 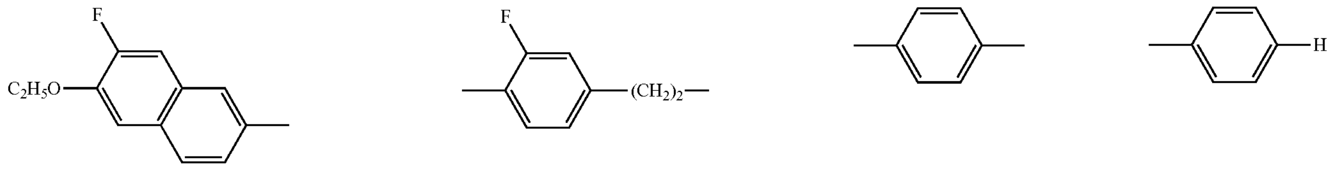
1423 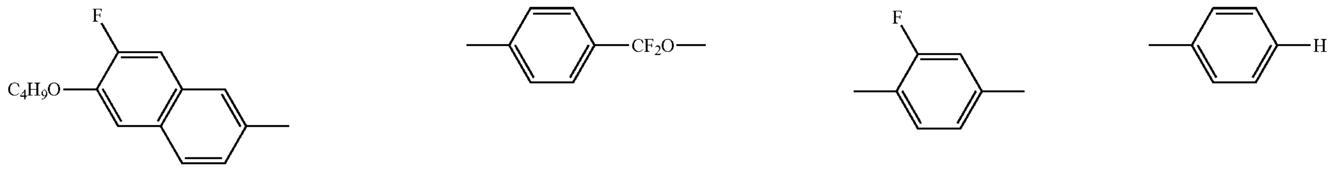

-continued
| | |
|---|---|
| 1424 | 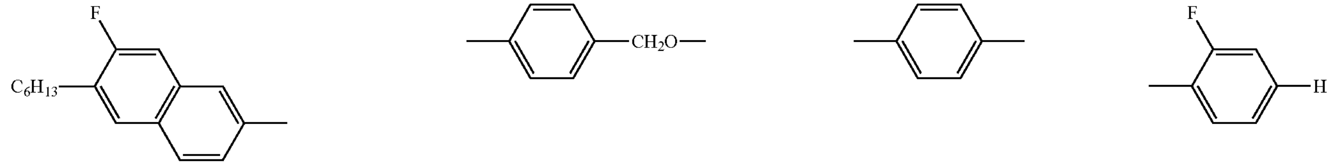 |
| 1425 | 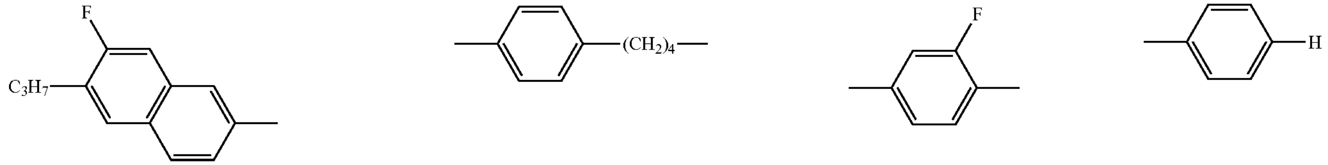 |
| 1426 | 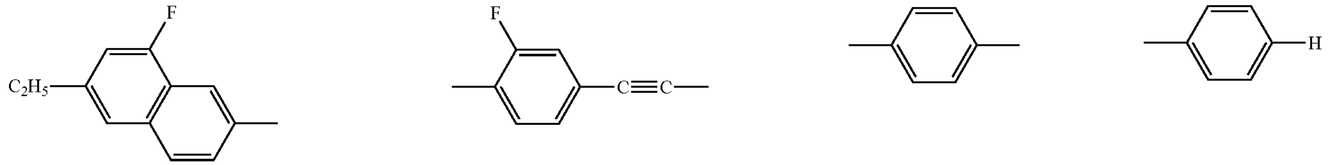 |
| 1427 | 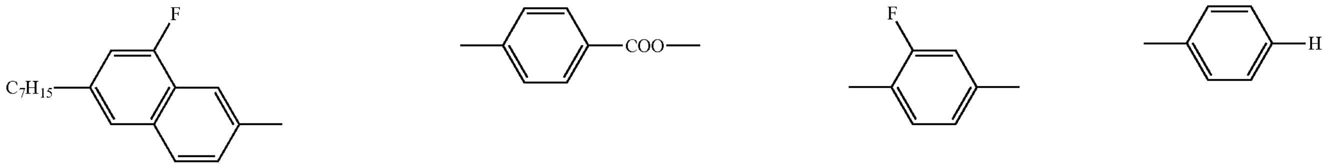 |
| 1428 | 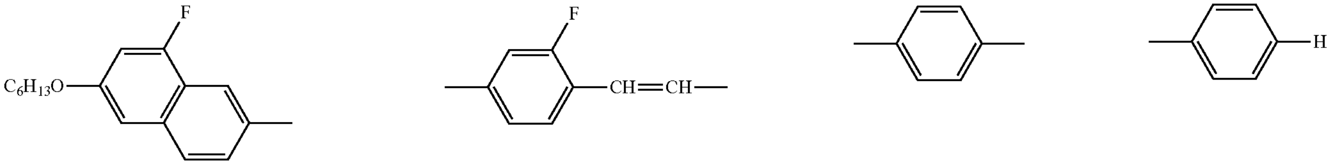 |
| 1429 | 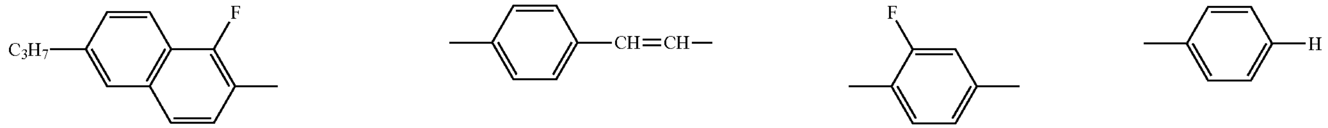 |

-continued
| | |
|---|---|
| 1430 | 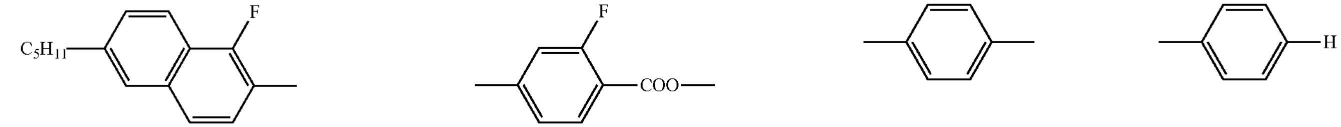 |
| 1431 | 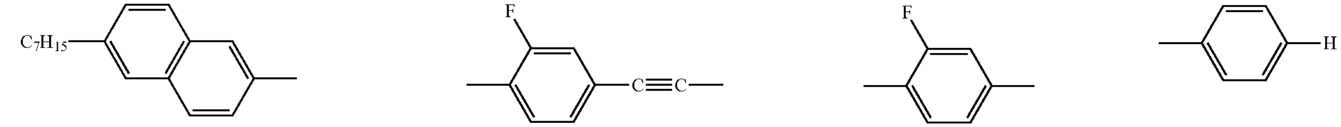 |
| 1432 | 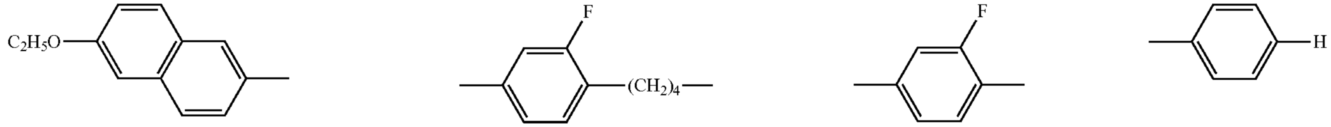 |
| 1433 | 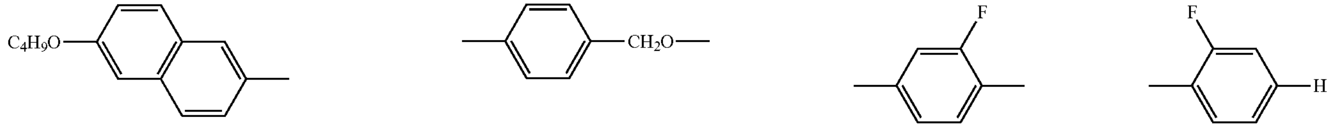 |
| 1434 | 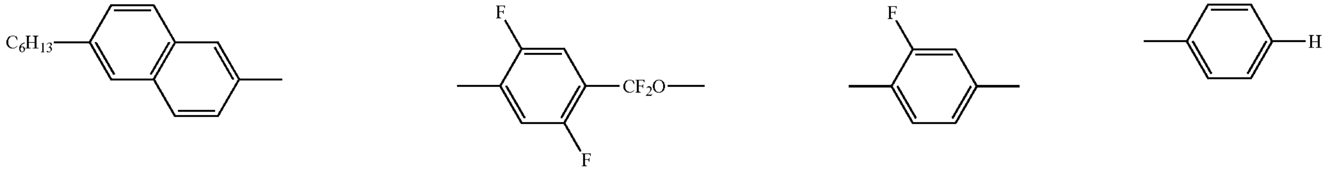 |
| 1435 | 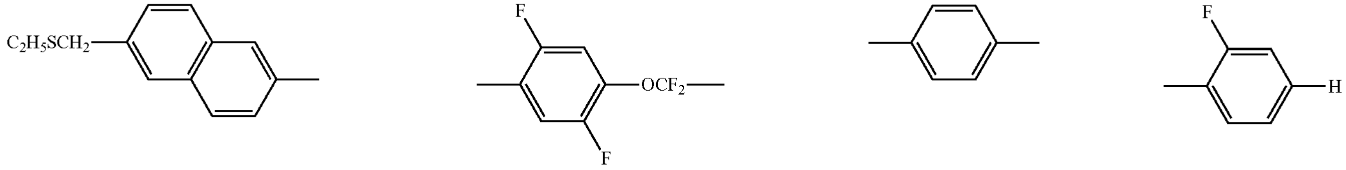 |

-continued
1436 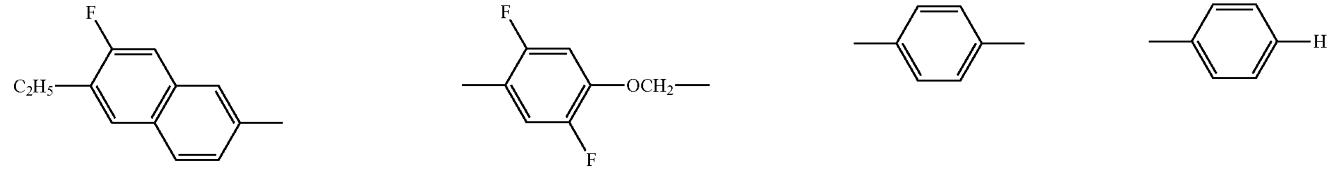
1437 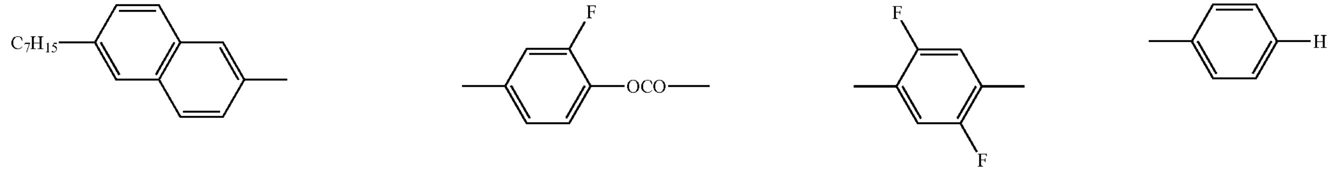
1438 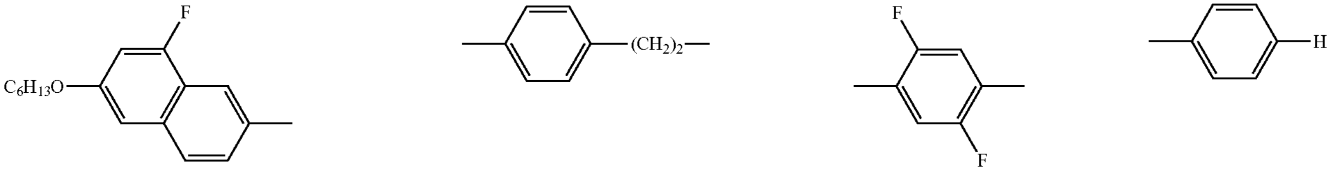
1439 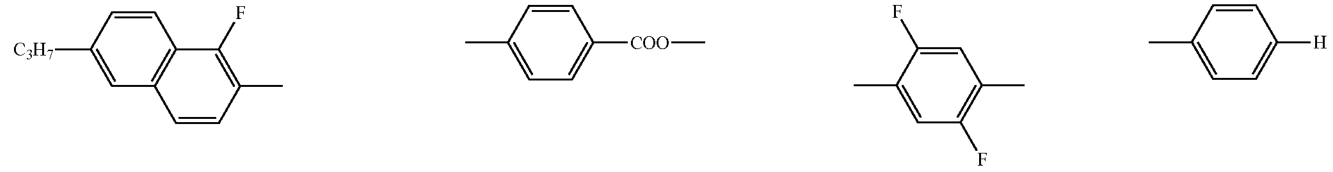
1440 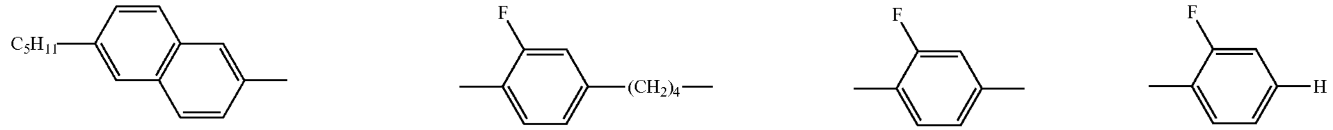
1441 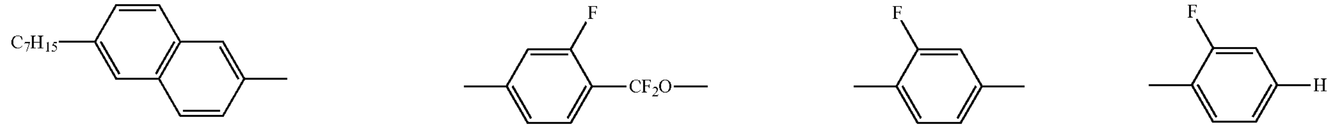

-continued
1442 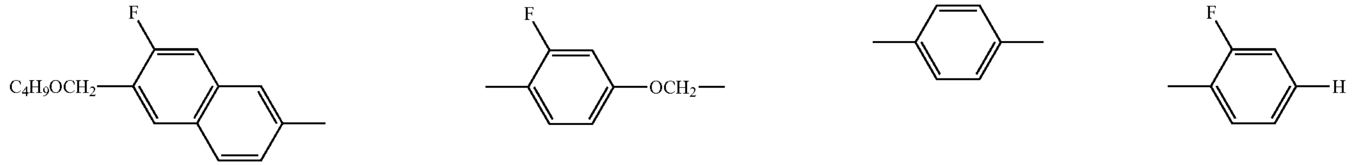
1443 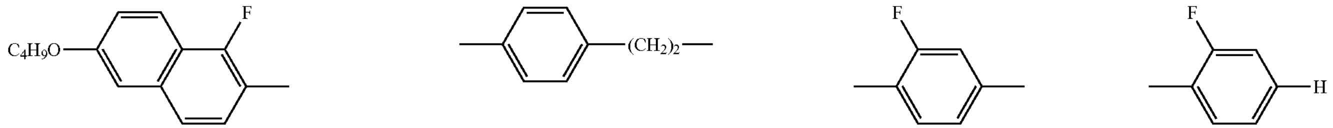
1444 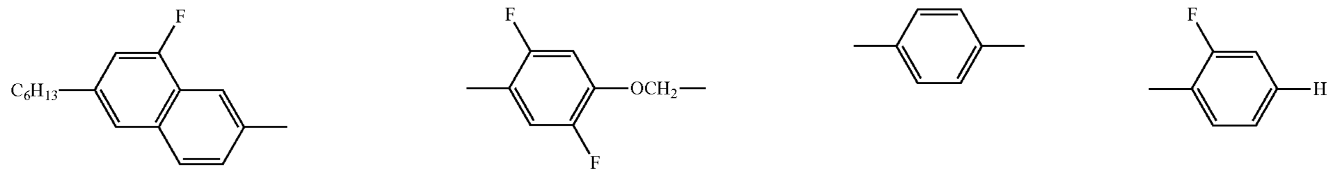
1445 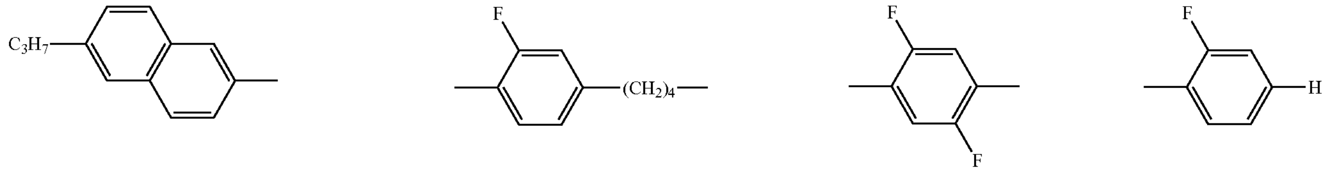
1446 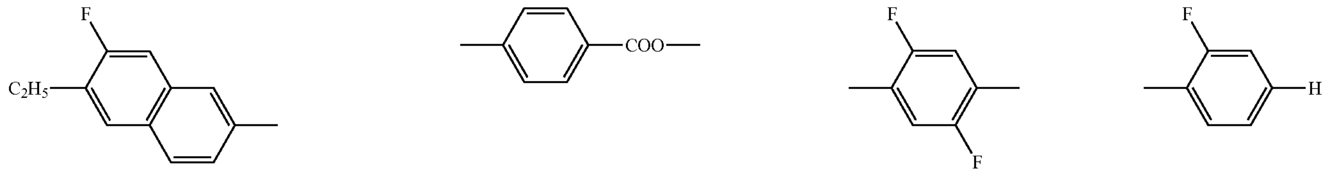
1447 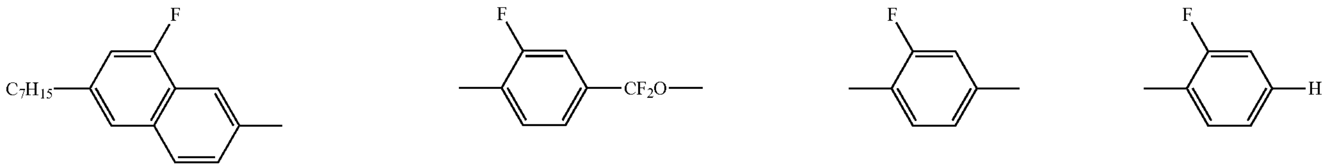

-continued
1448 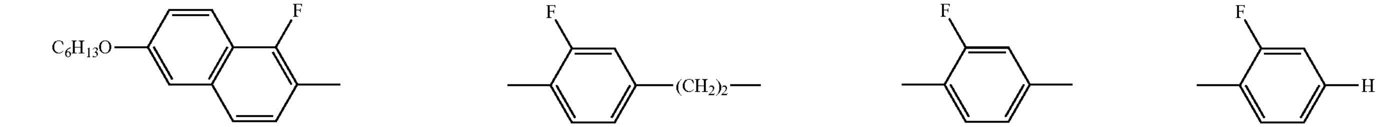
1449 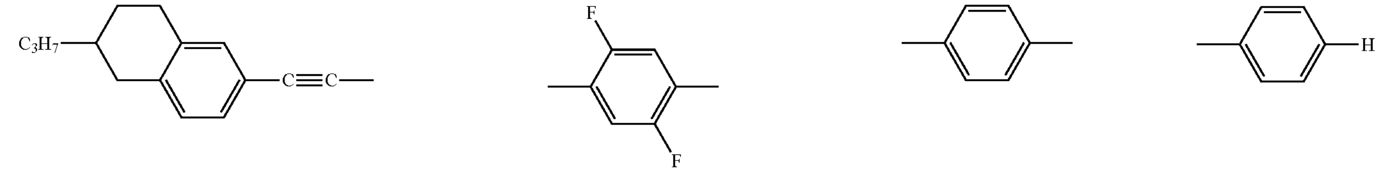
1450 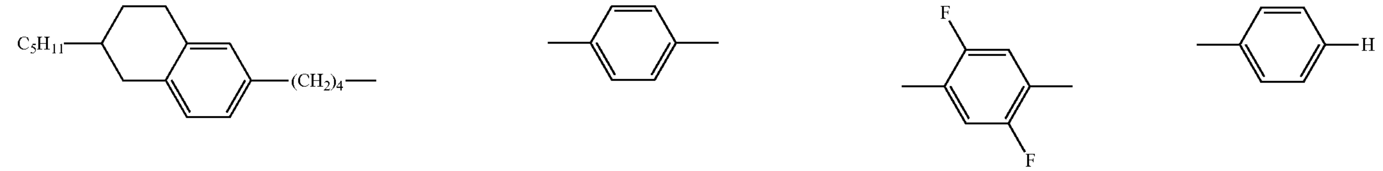
1451 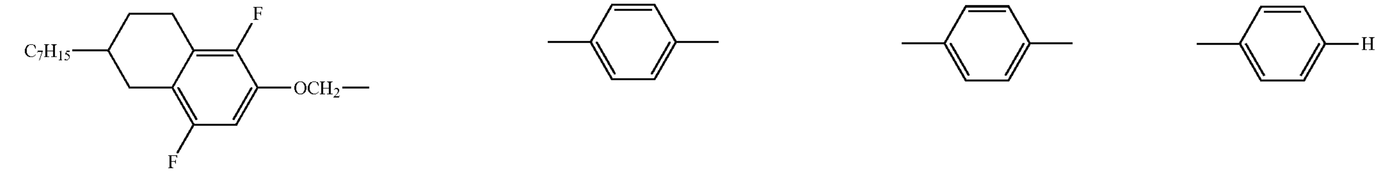
1452 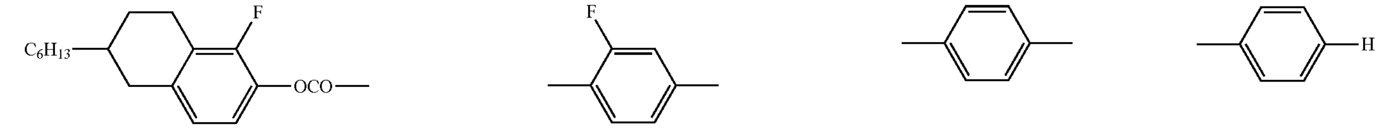
1453 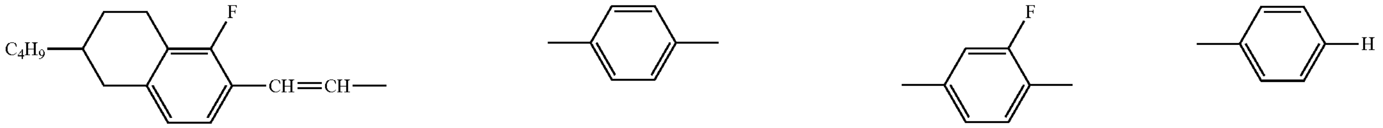

-continued
1454 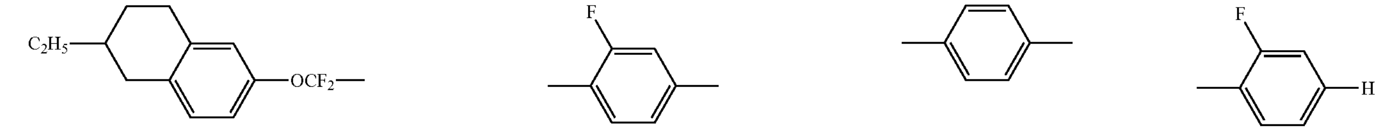
1455 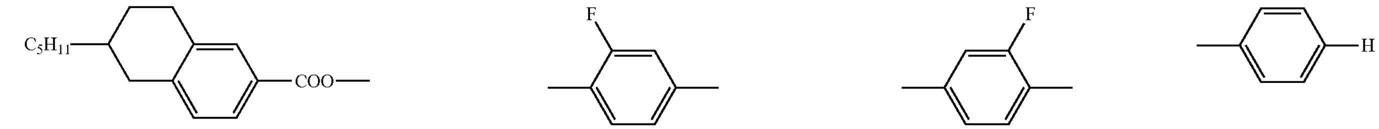
1456 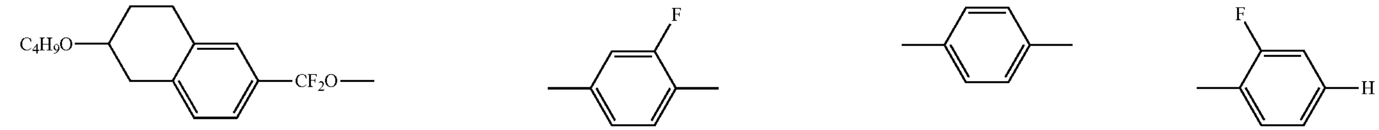
1457 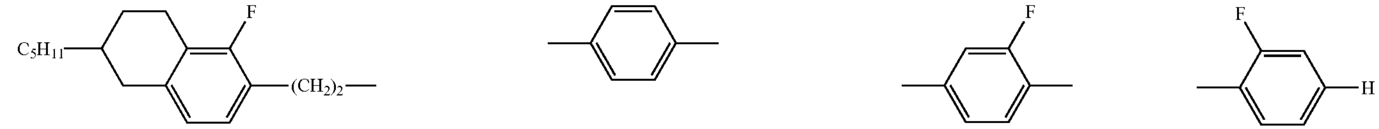
1458 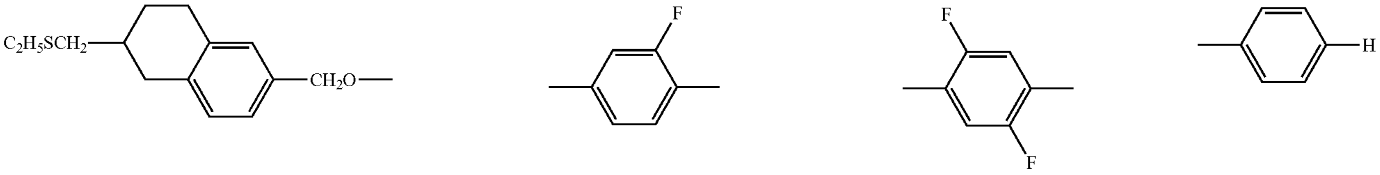
1459 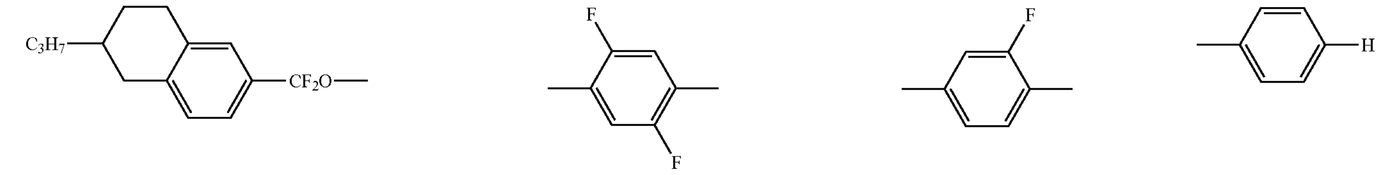

-continued
1460 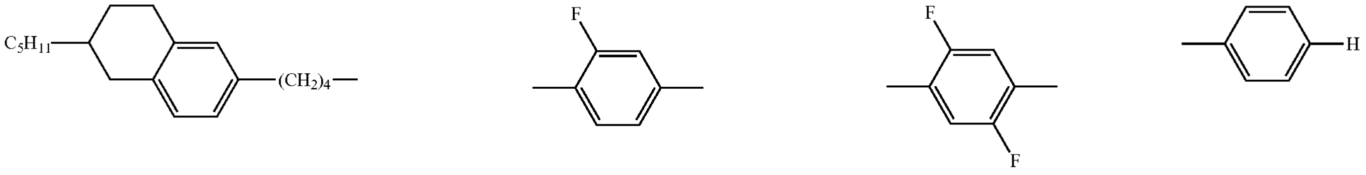
1461 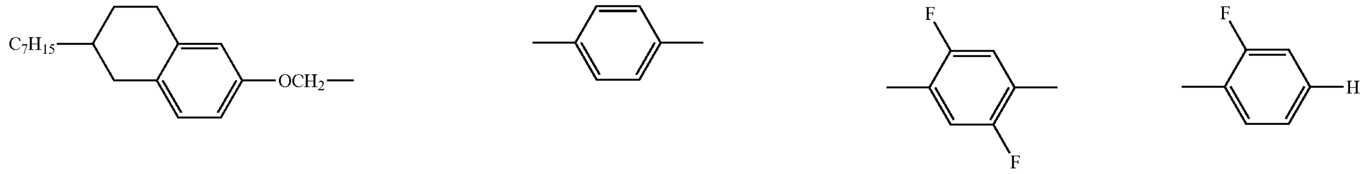
1462 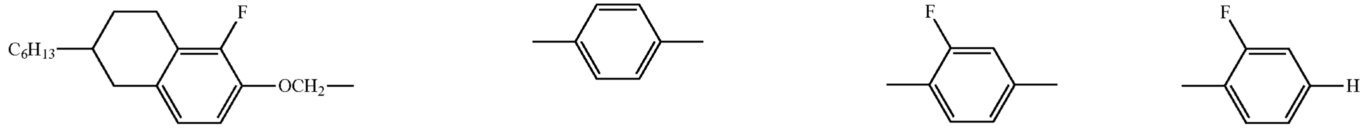
1463 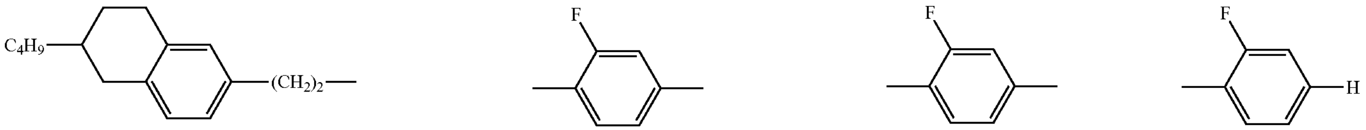
1464 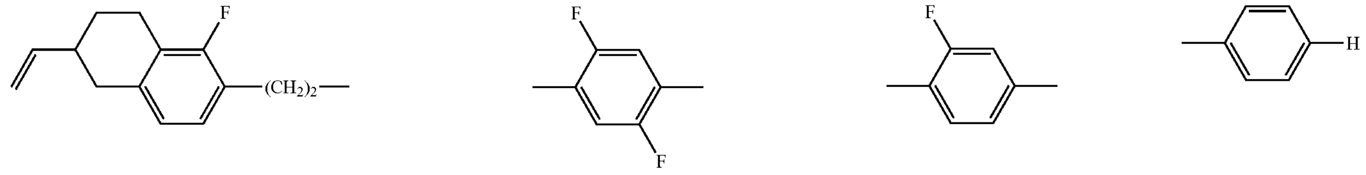
1465 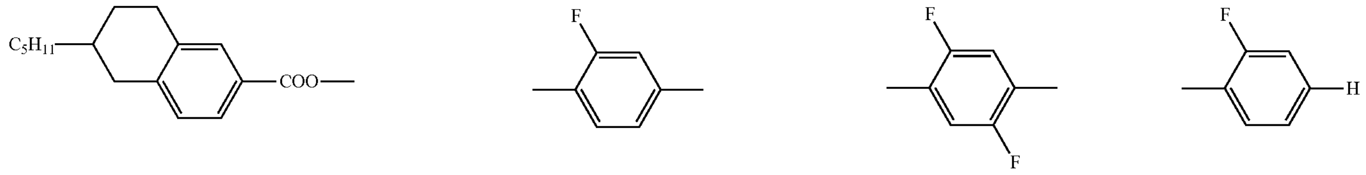

-continued
1466 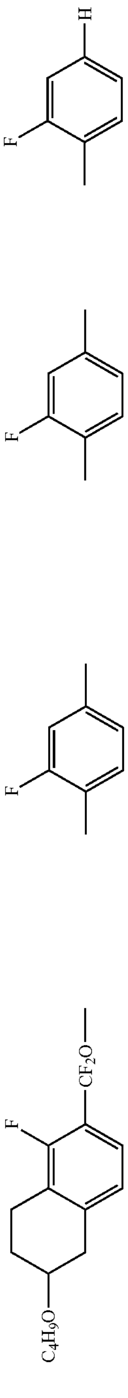
1467 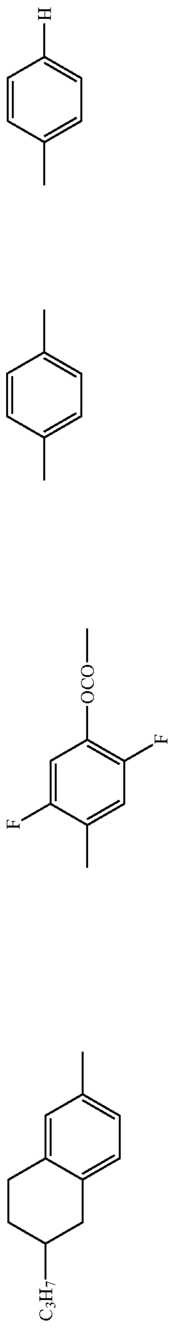
1468 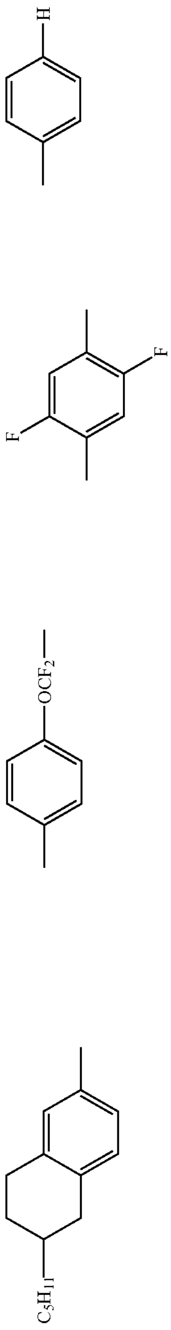
1469 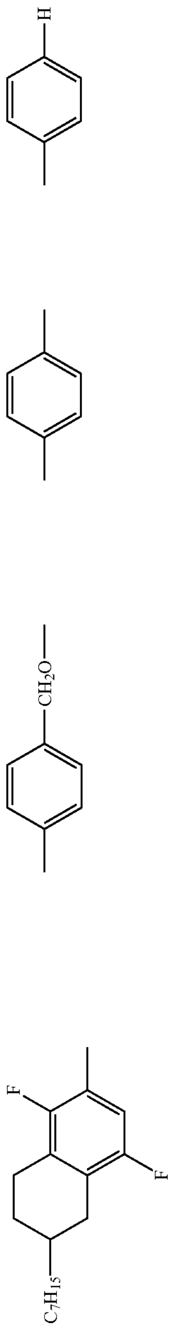
1470 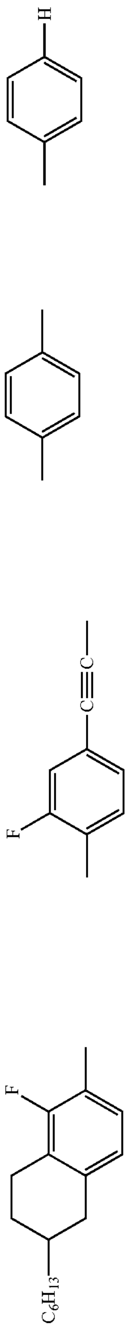
1471 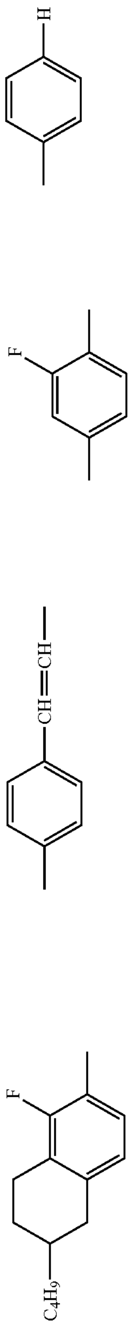

-continued
| | |
|---|---|
| 1472 | 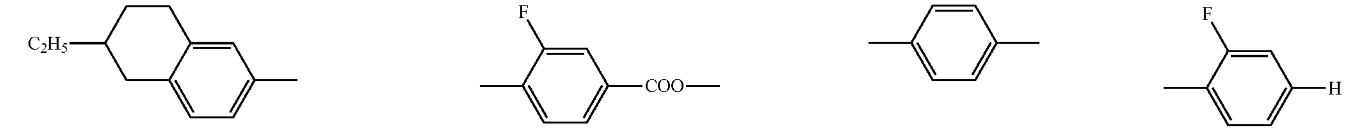 |
| 1473 | 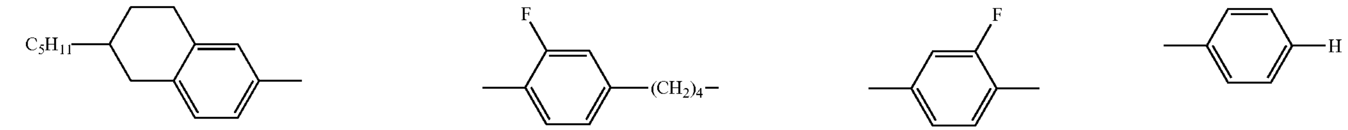 |
| 1474 | 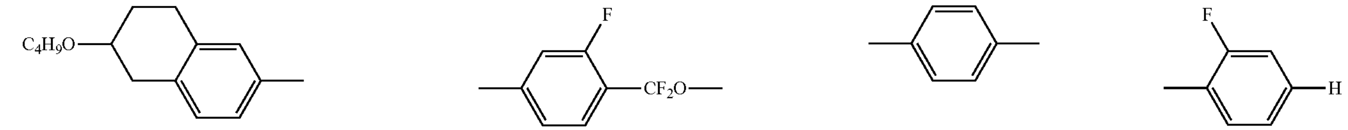 |
| 1475 | 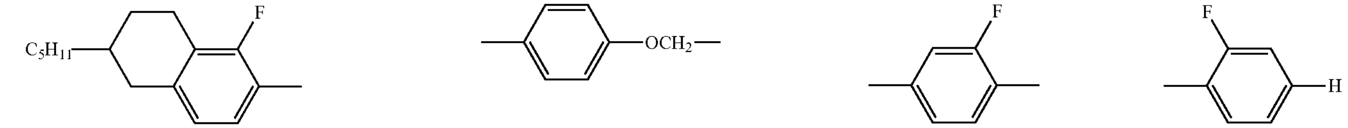 |
| 1476 | 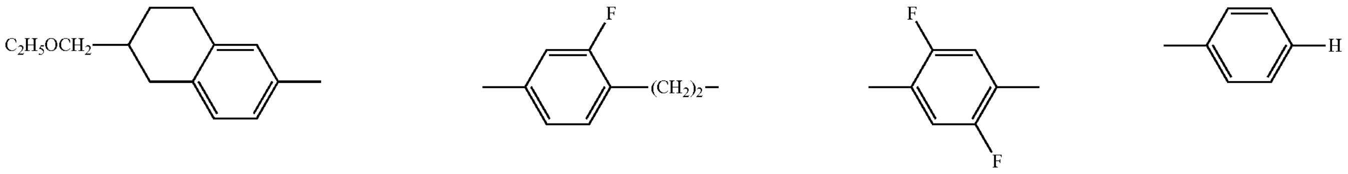 |
| 1477 | 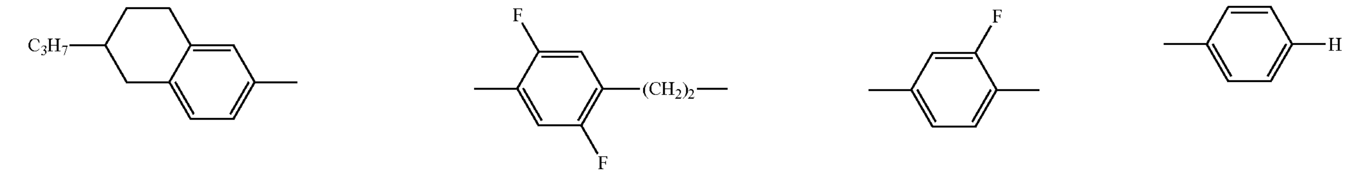 |

-continued
| | |
|---|---|
| 1478 | 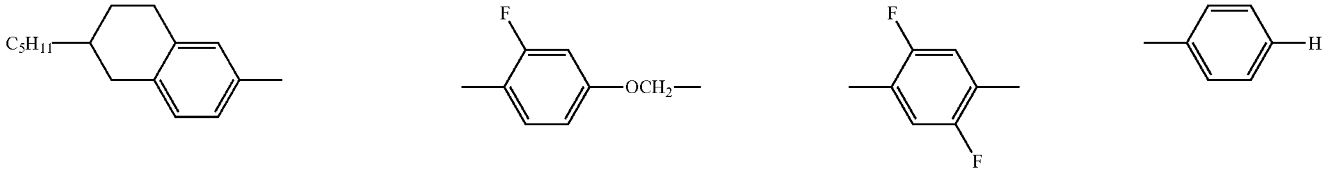 |
| 1479 | 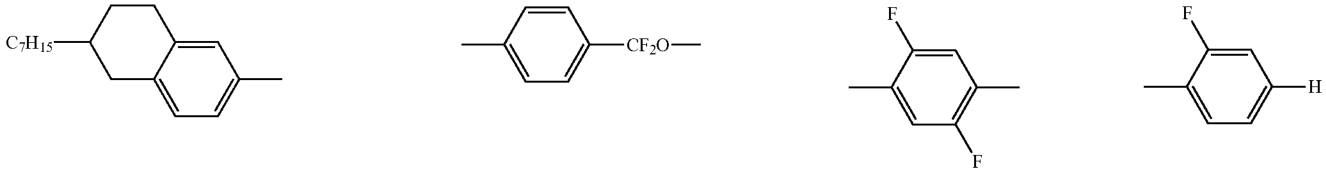 |
| 1480 | 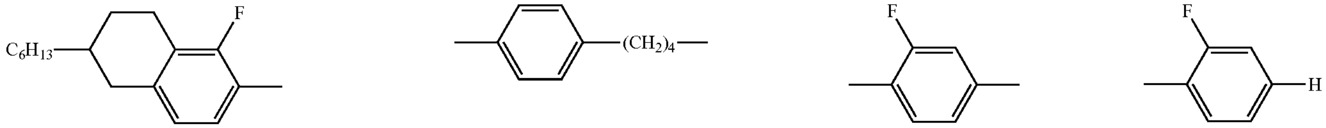 |
| 1481 | 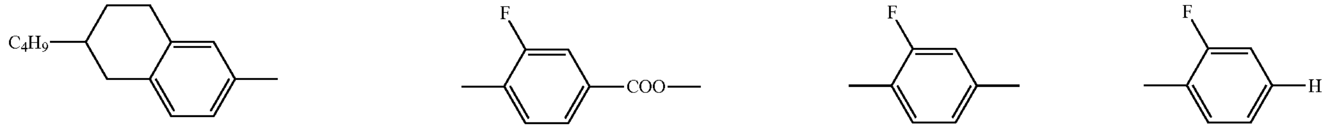 |
| 1482 | 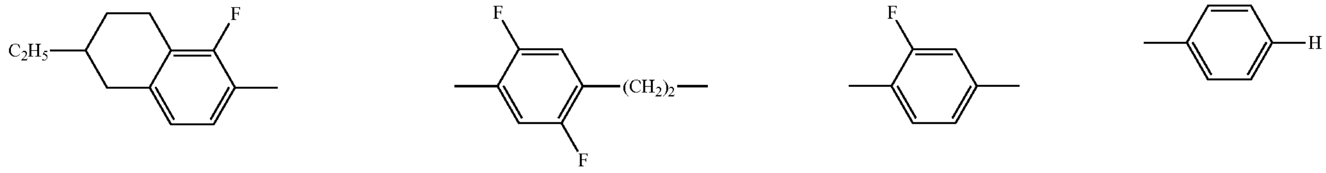 |
| 1483 | 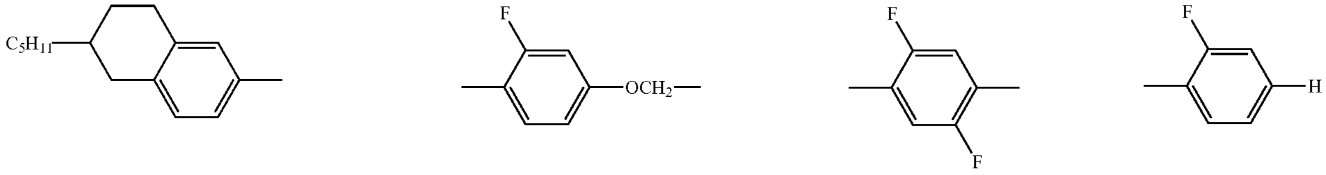 |

-continued
1484
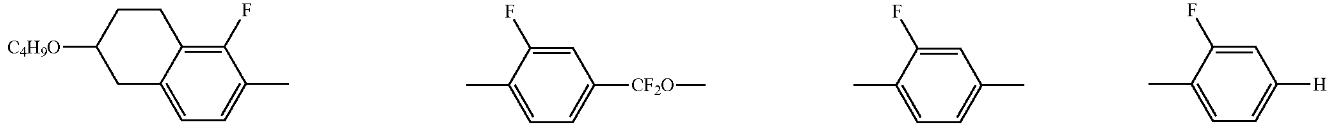
1485
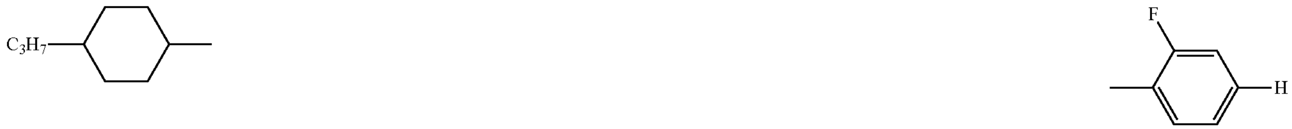
1486
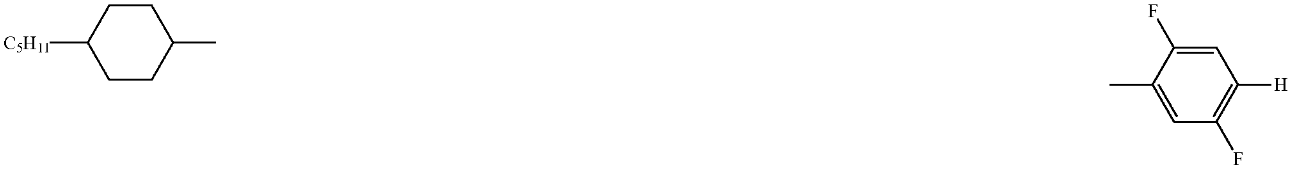
1487
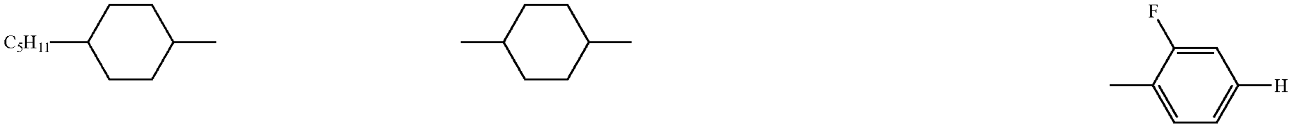
1488
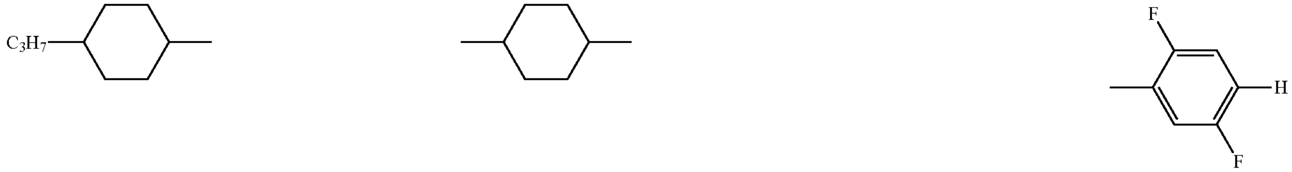
1489
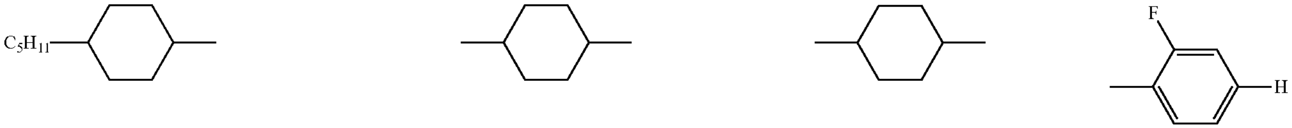

-continued
1490
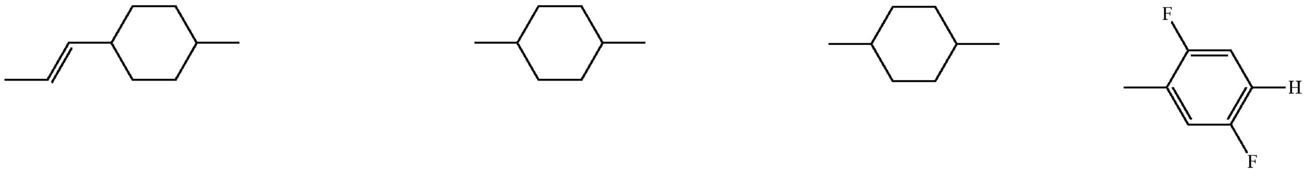
1491
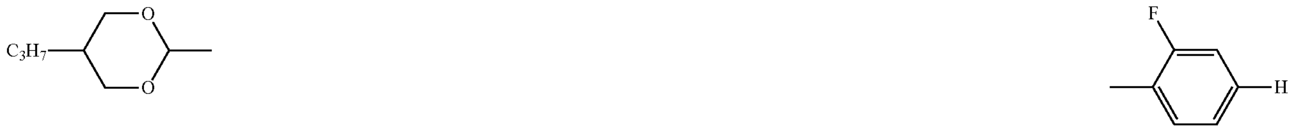
1492
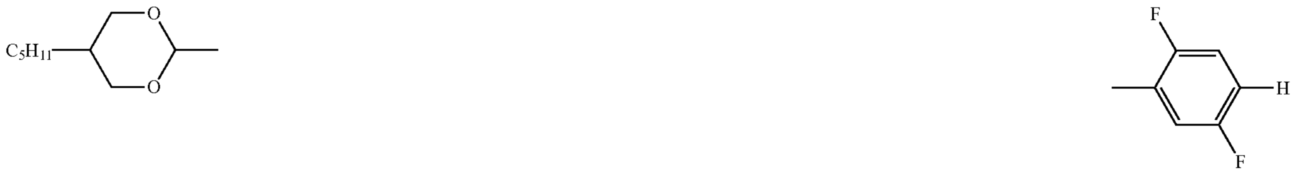
1493
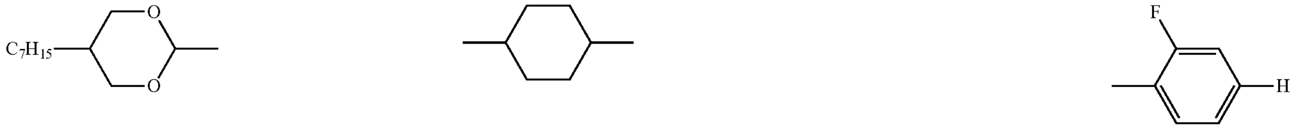
1494
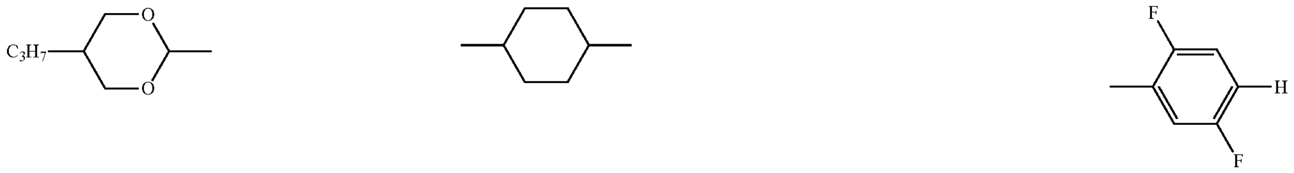
1495
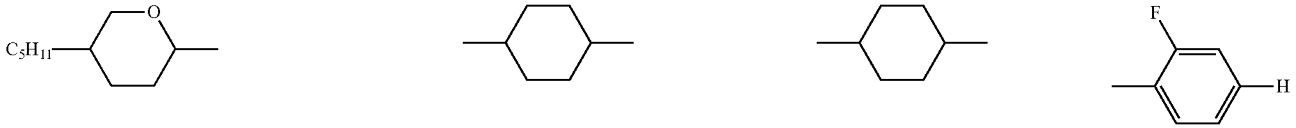

-continued
1496 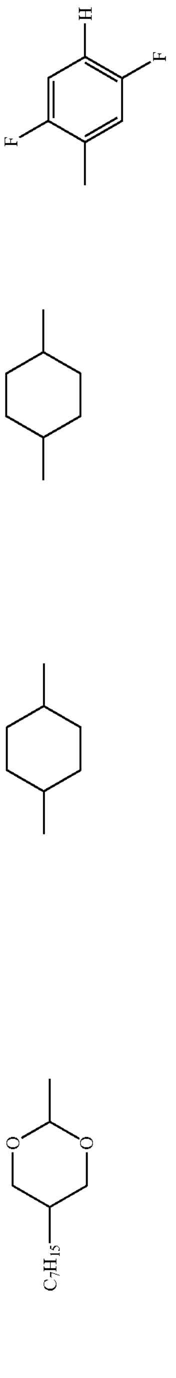
1497 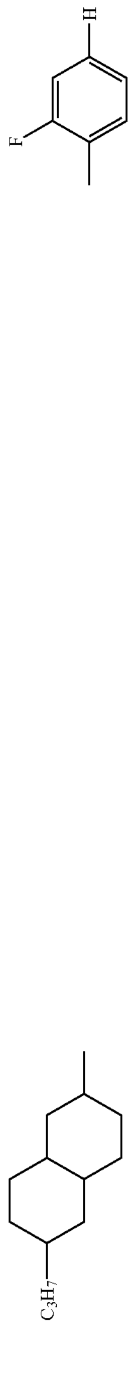
1498 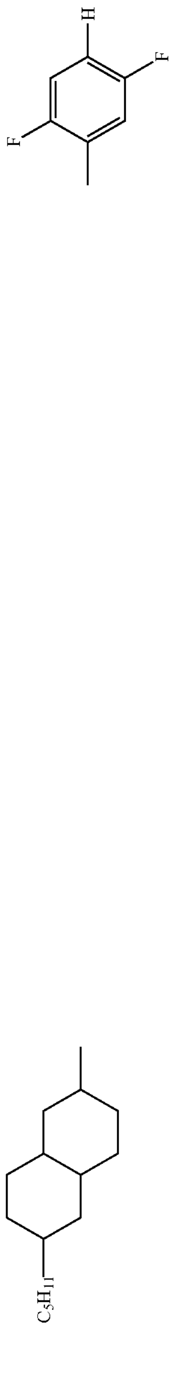
1499 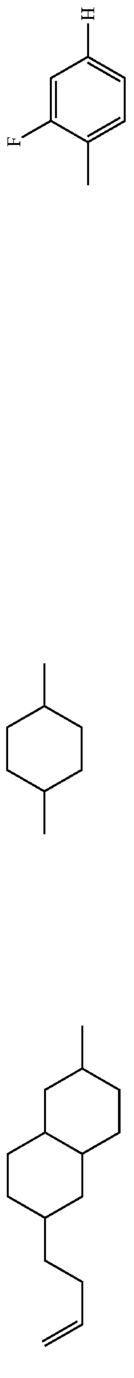
1500 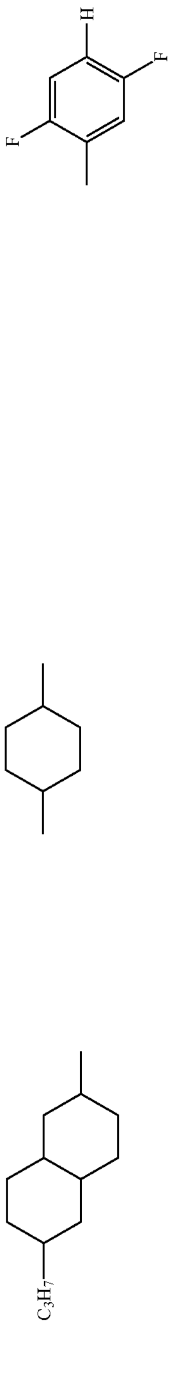
1501 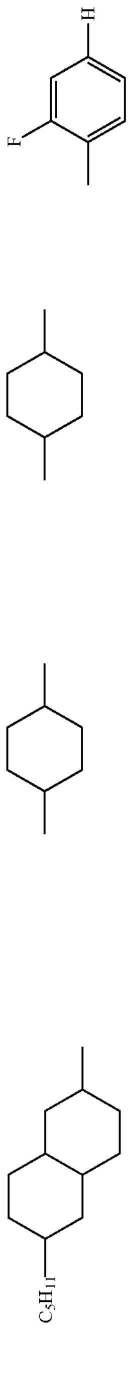

-continued
| | |
|---|---|
| 1502 | 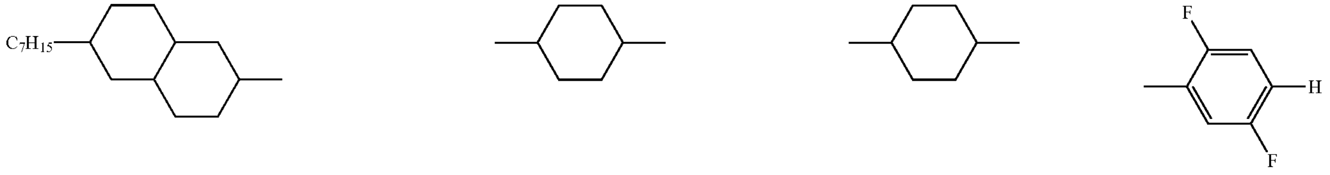 |
| 1503 | 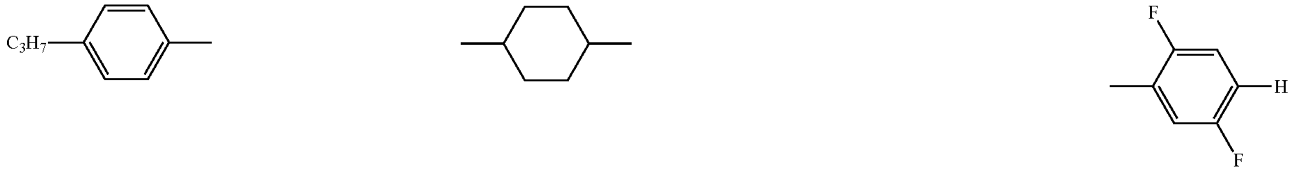 |
| 1504 | 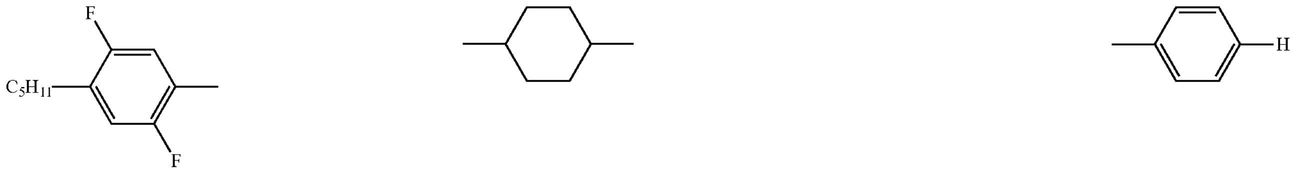 |
| 1505 | 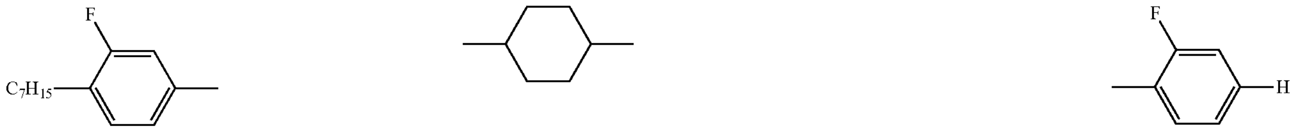 |
| 1506 | 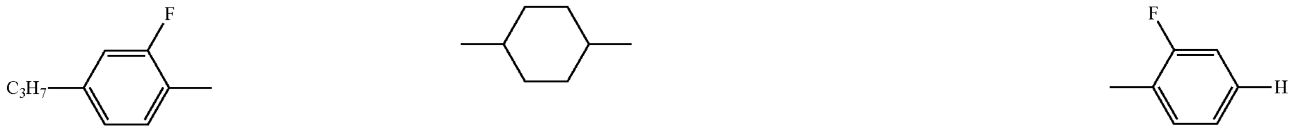 |
| 1507 | 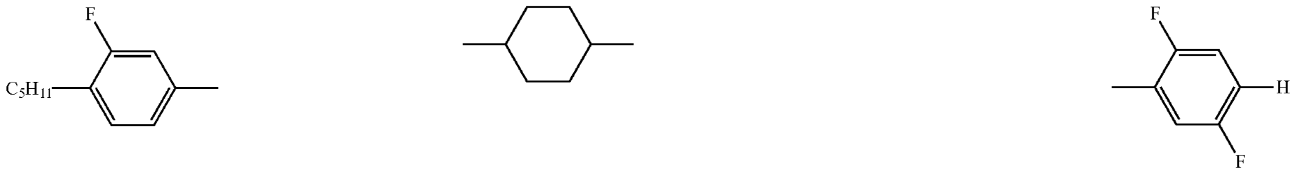 |

-continued
1508 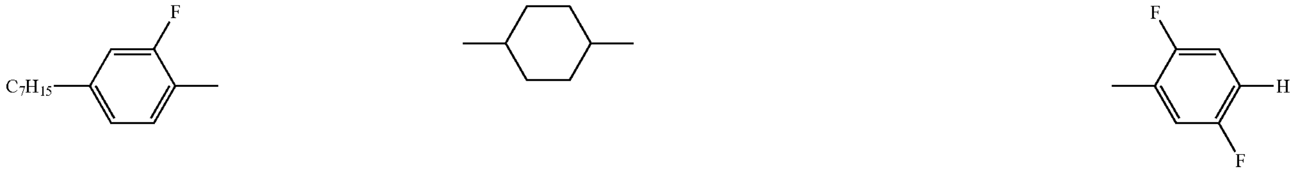
1509 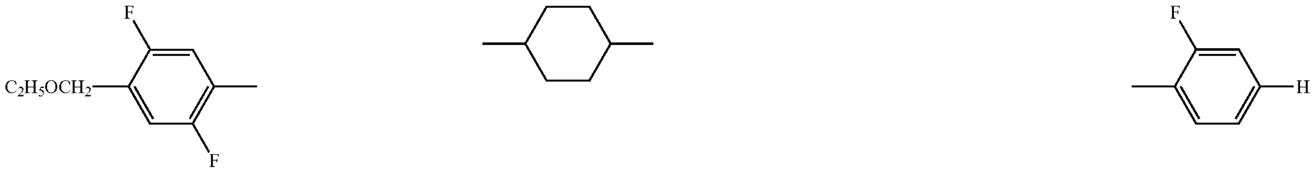
1510 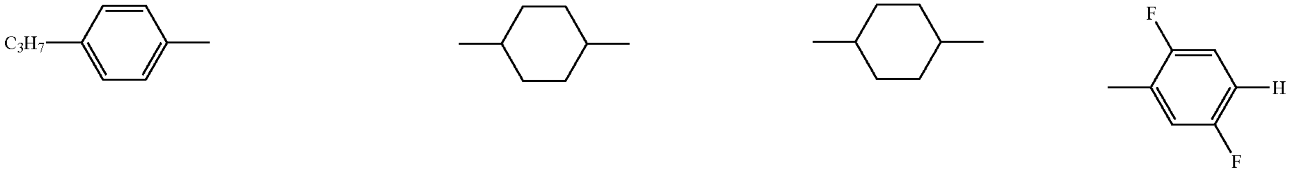
1511 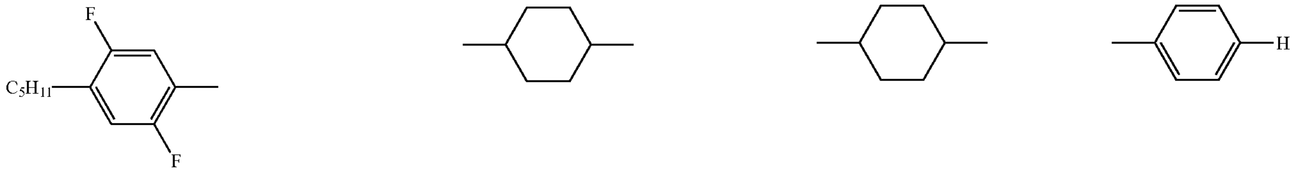
1512 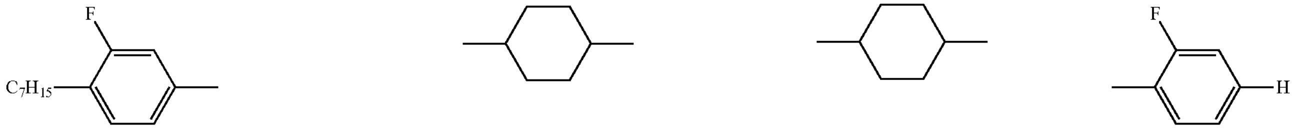
1513 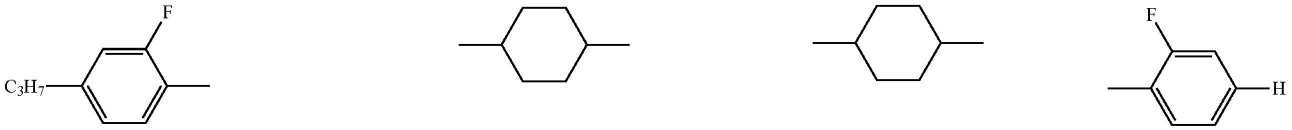

-continued
| | |
|---|---|
| 1514 | 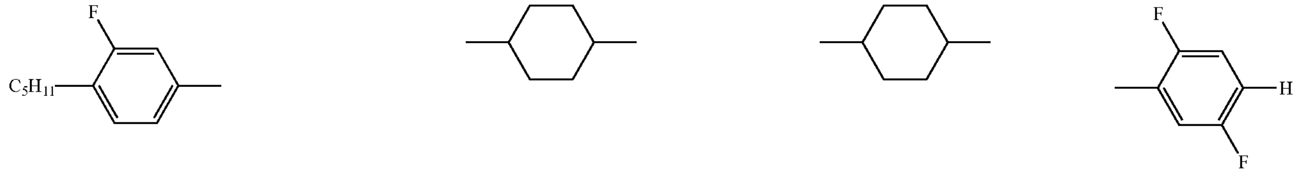 |
| 1515 | 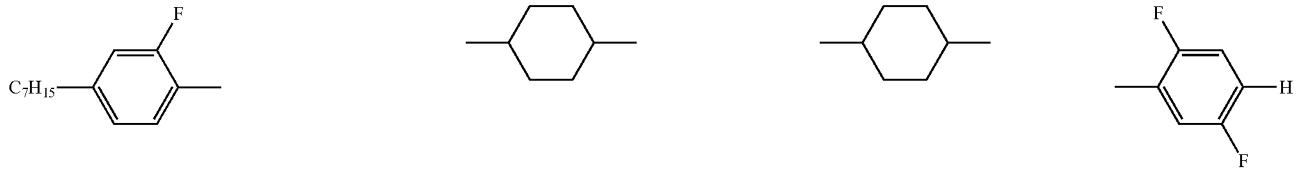 |
| 1516 | 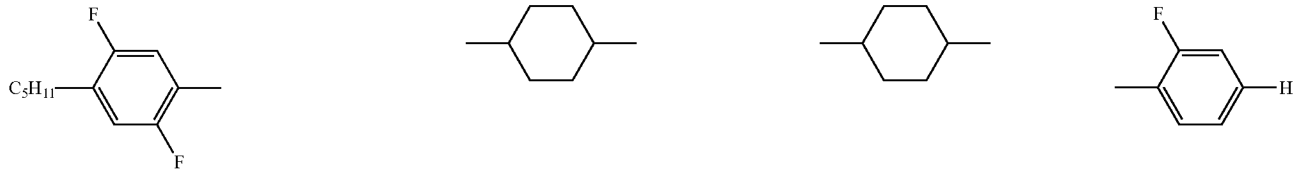 |
| 1517 | 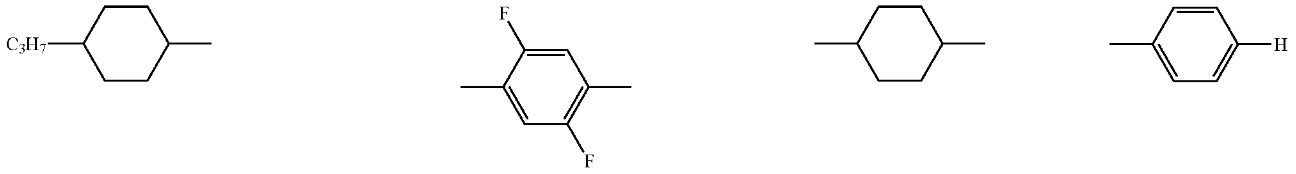 |
| 1518 | 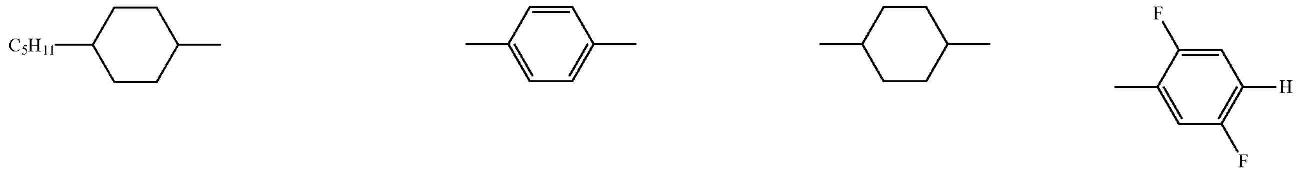 |
| 1519 | 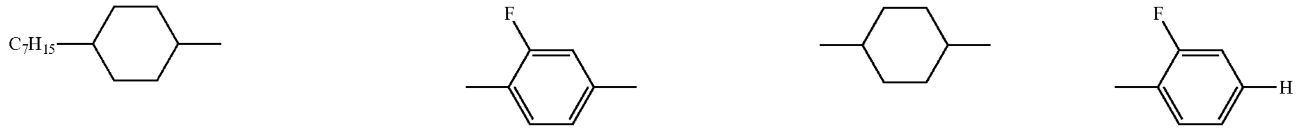 |

-continued
1520
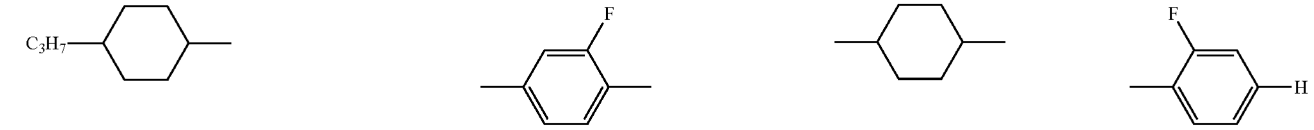
1521
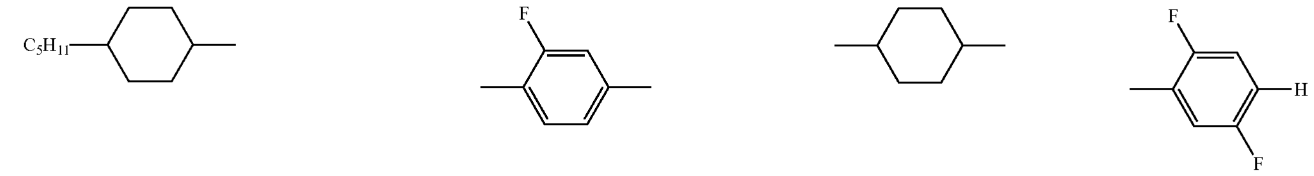
1522
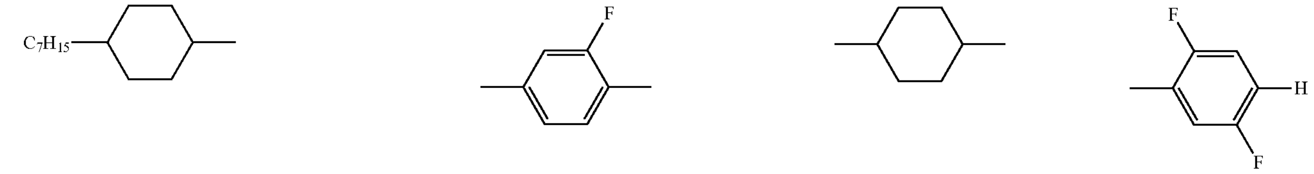
1523
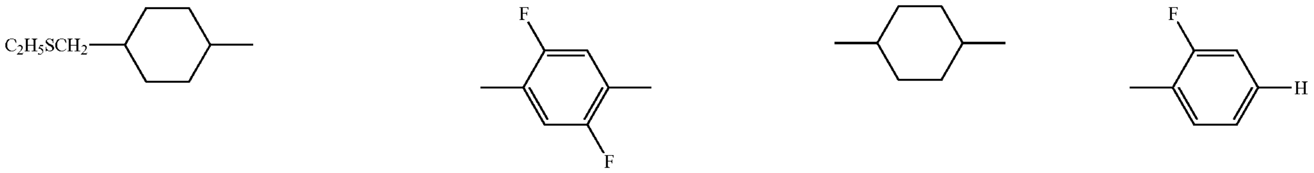
1524
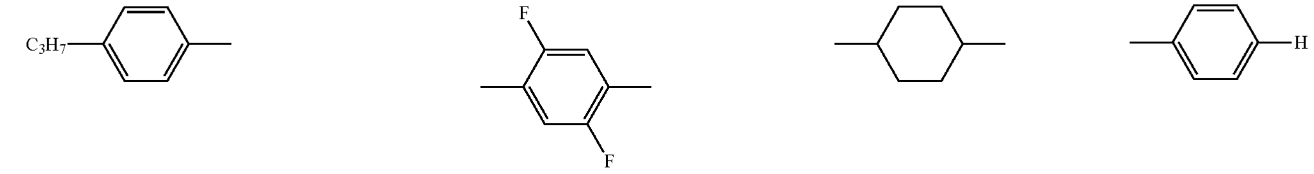
1525
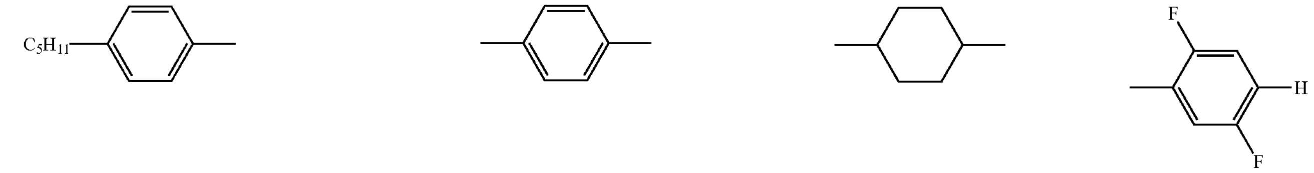

-continued
| | |
|---|---|
| 1526 | 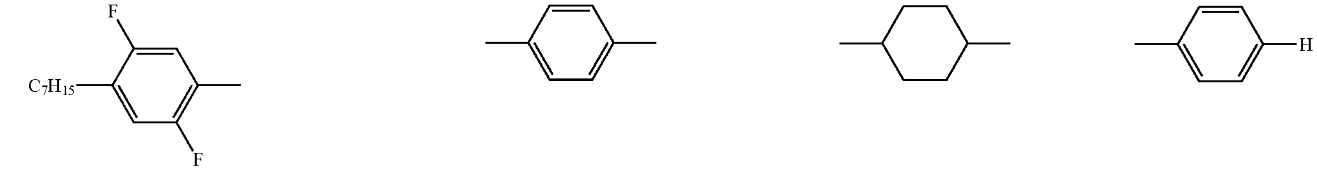 |
| 1527 | 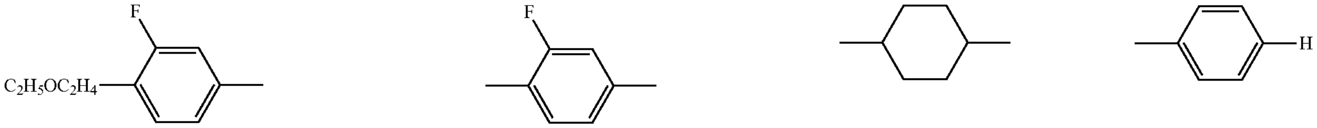 |
| 1528 | 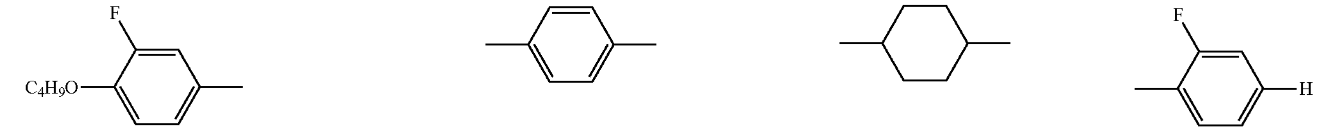 |
| 1529 | 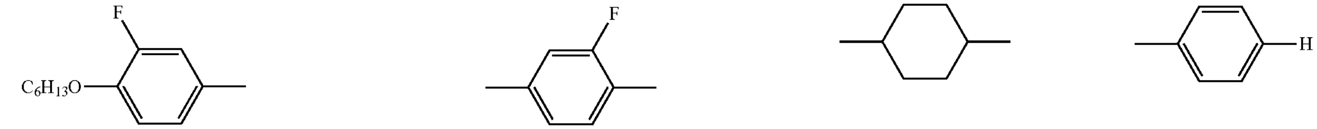 |
| 1530 | 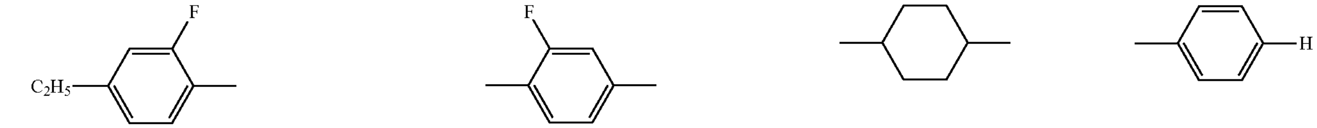 |
| 1531 | 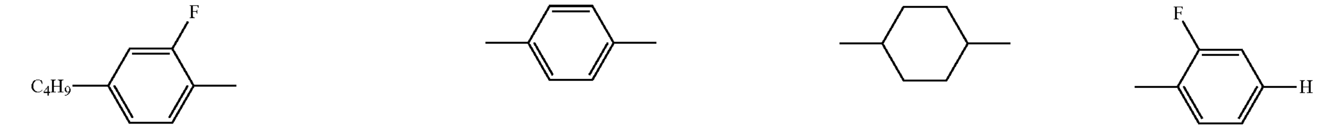 |
| 1532 | 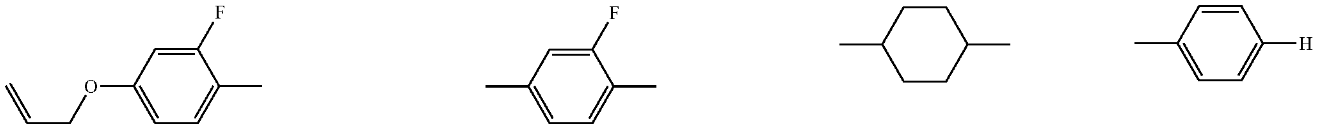 |

-continued
| | |
|---|---|
| 1533 | 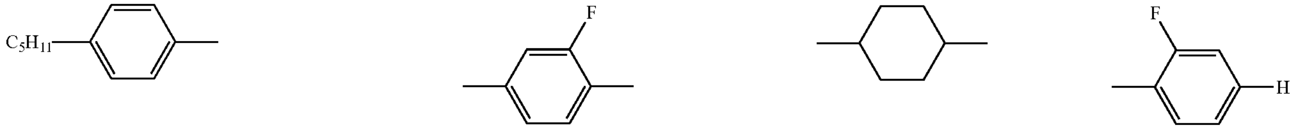 |
| 1534 | 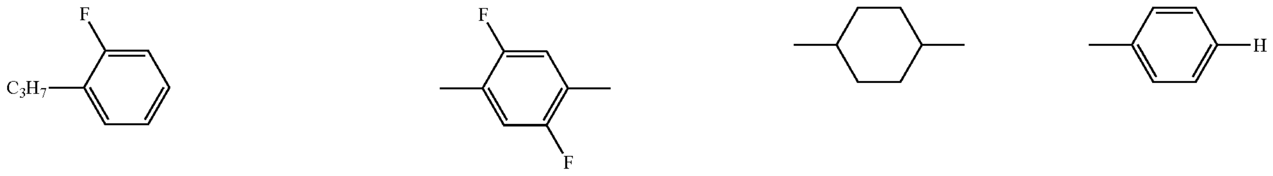 |
| 1535 | 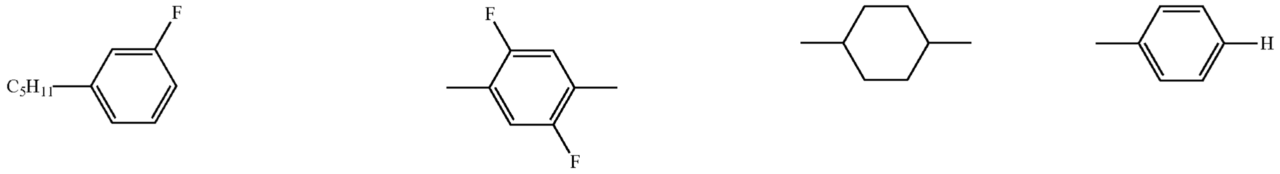 |
| 1536 | 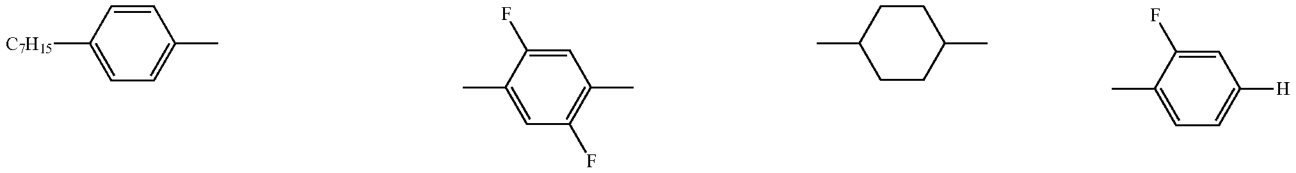 |
| 1537 | 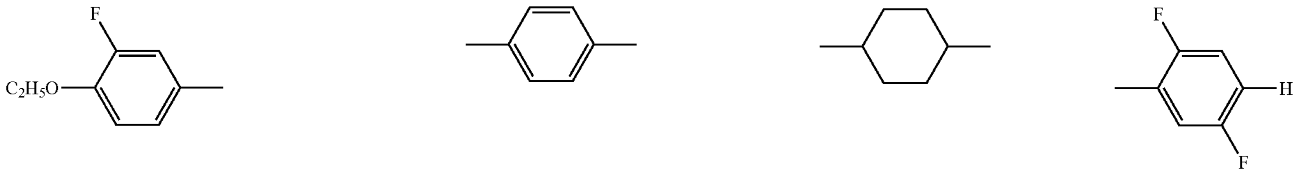 |
| 1538 | 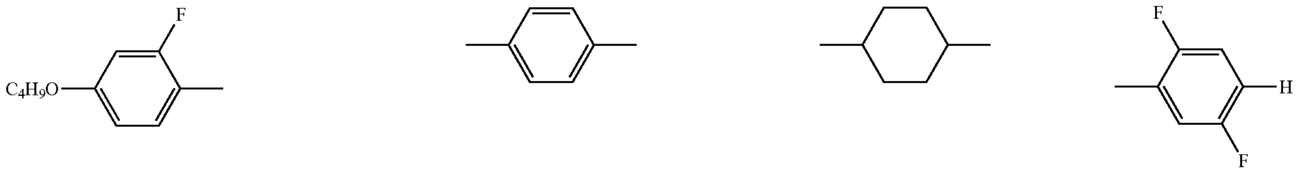 |

-continued
1539 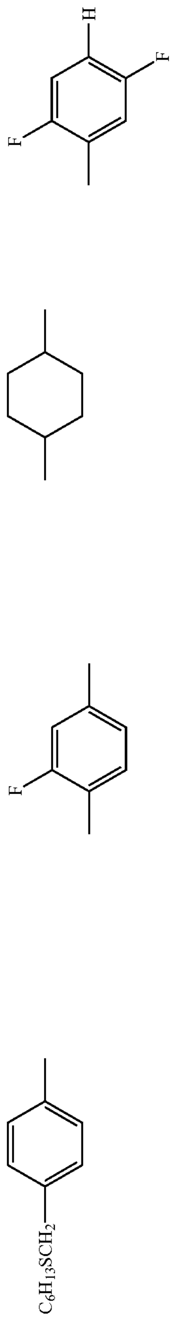
1540 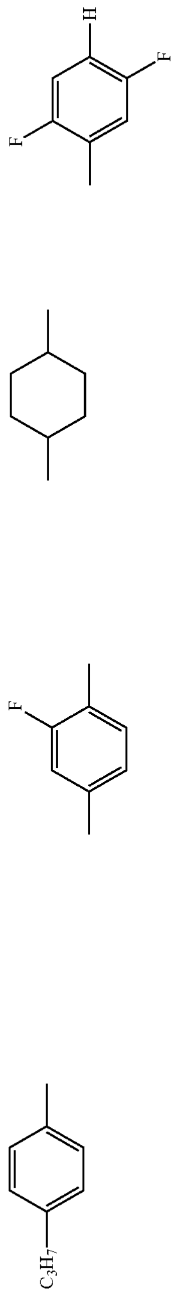
1541 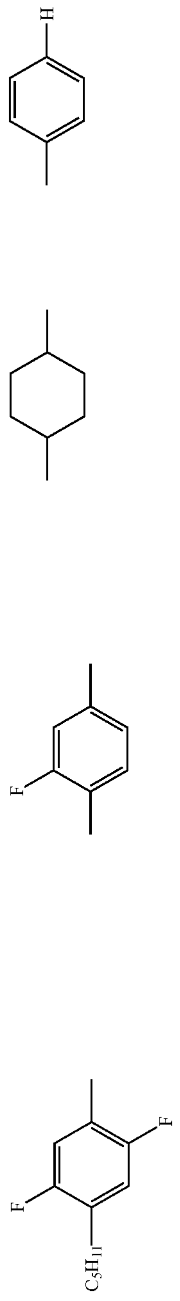
1542 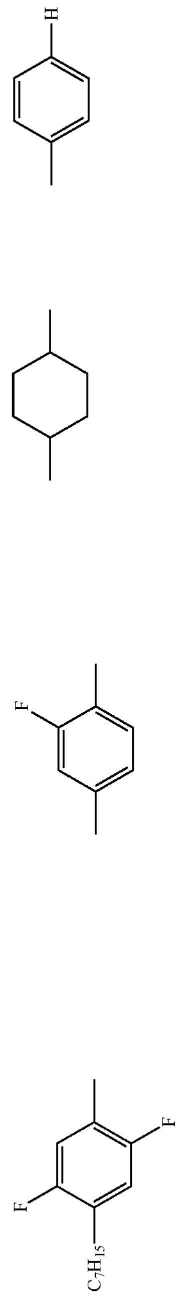
1543 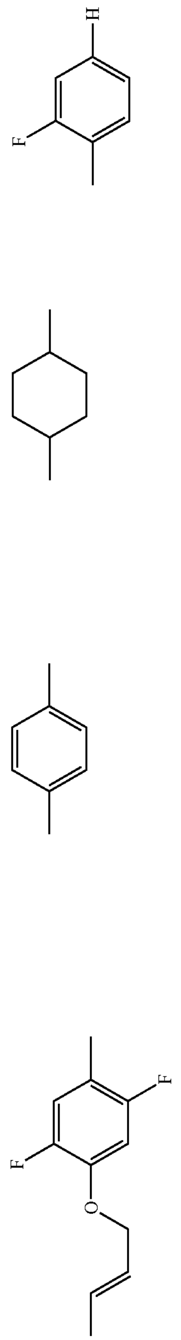
1544 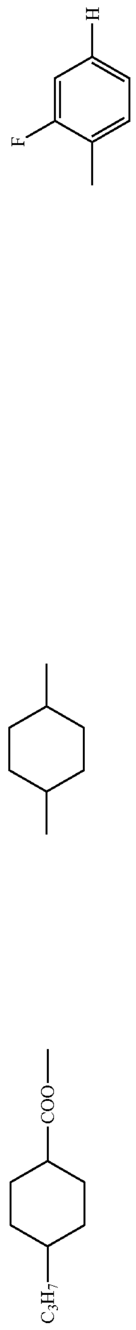

-continued
1545 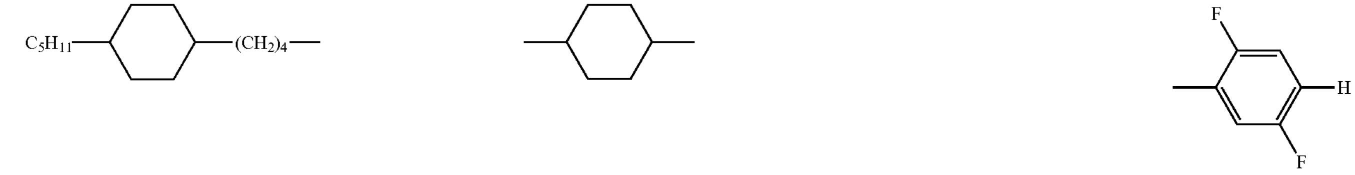
1546 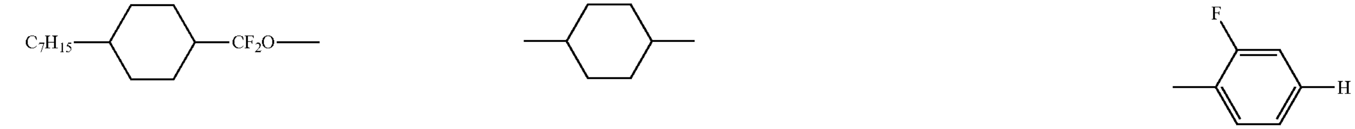
1547 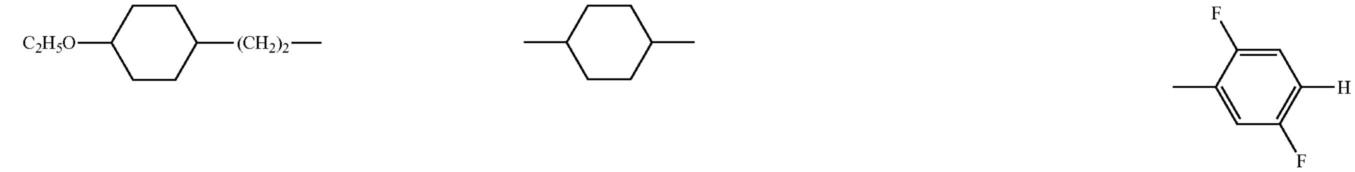
1548 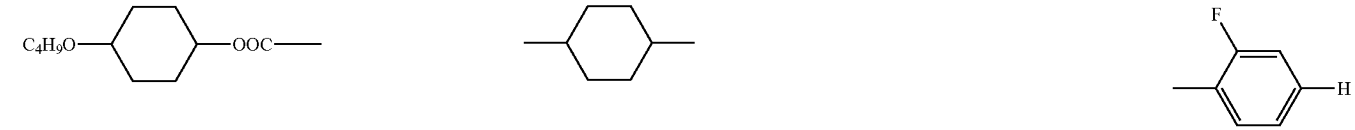
1549 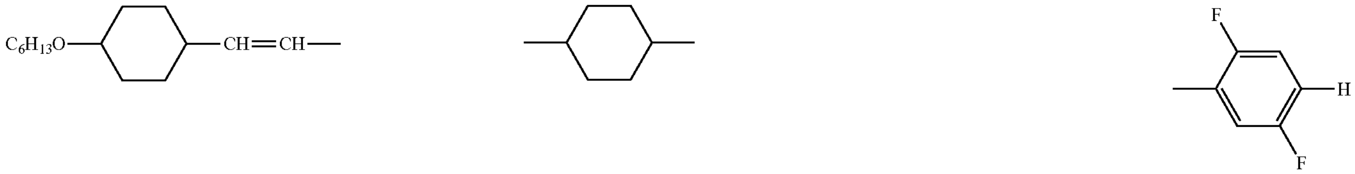
1550 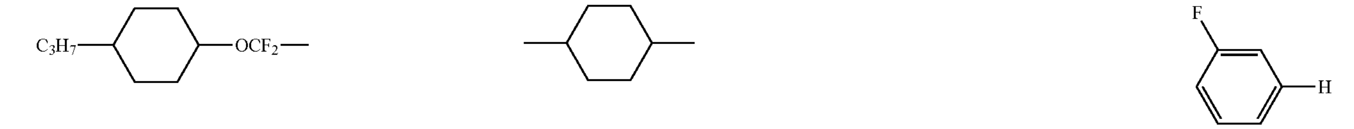

-continued
1551 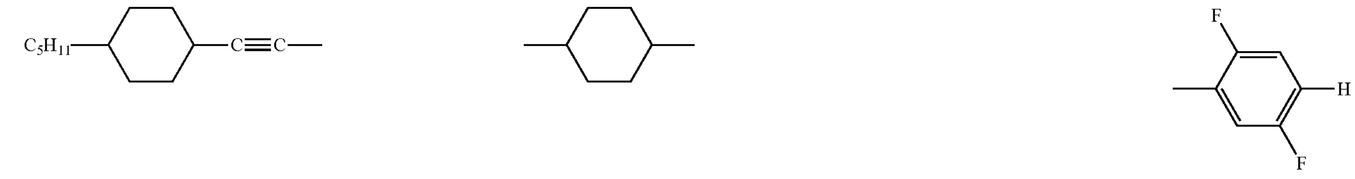
1552 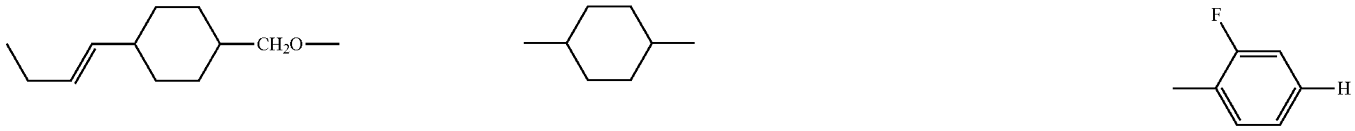
1553 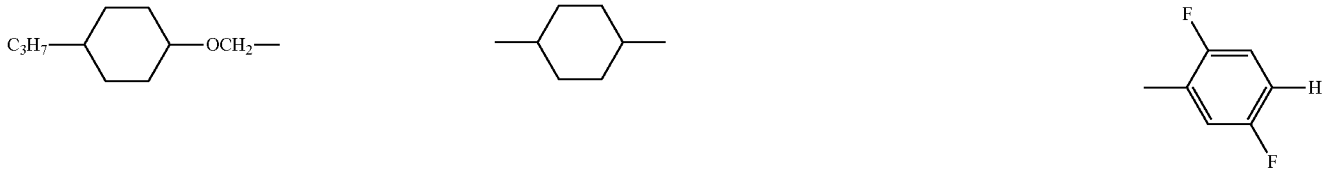
1554 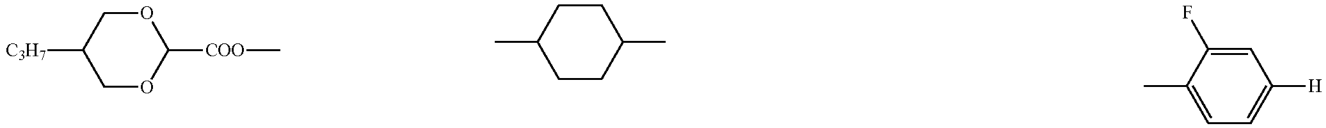
1555 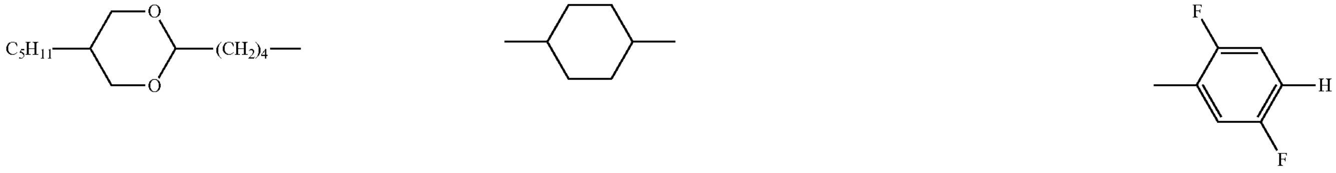
1556 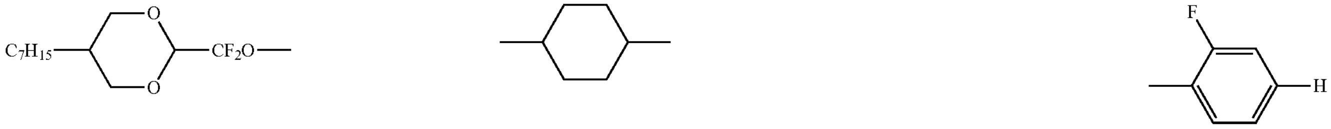

-continued
| | |
|---|---|
| 1557 | 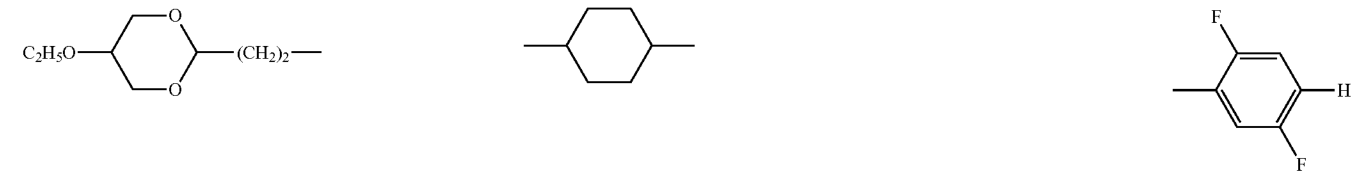 |
| 1558 | 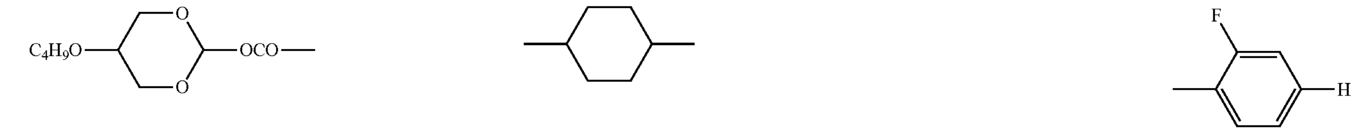 |
| 1559 | 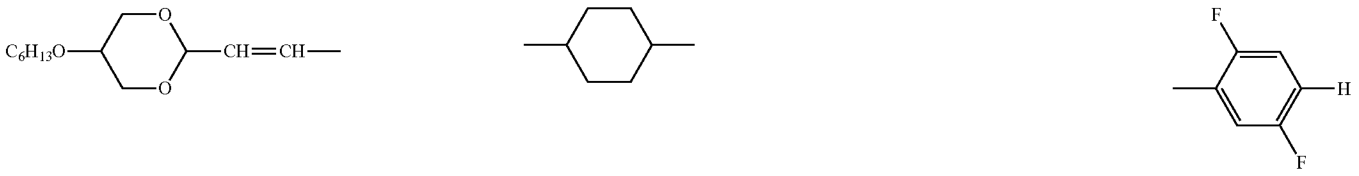 |
| 1560 | 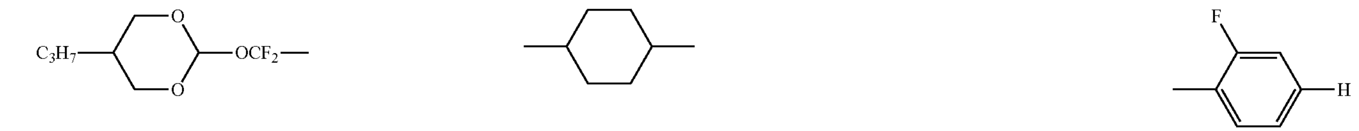 |
| 1561 | 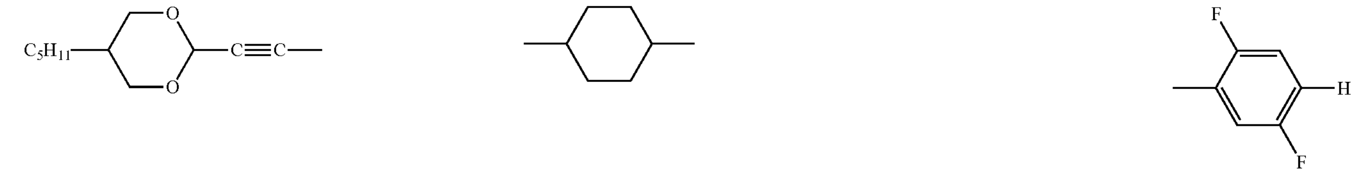 |
| 1562 | 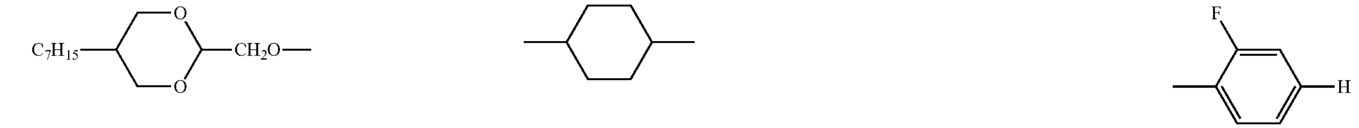 |

-continued
1563
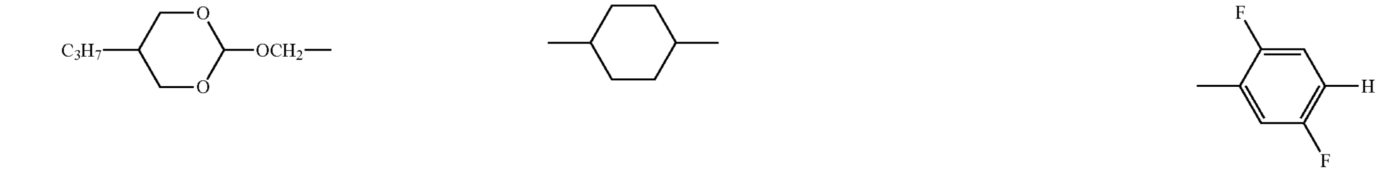
1564
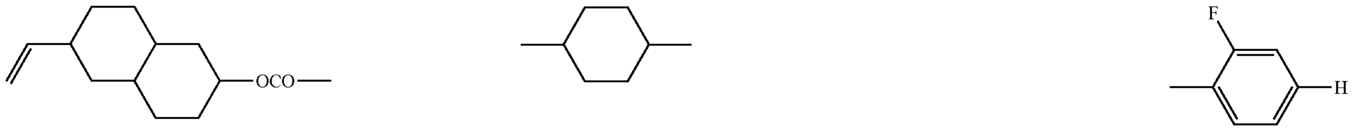
1565
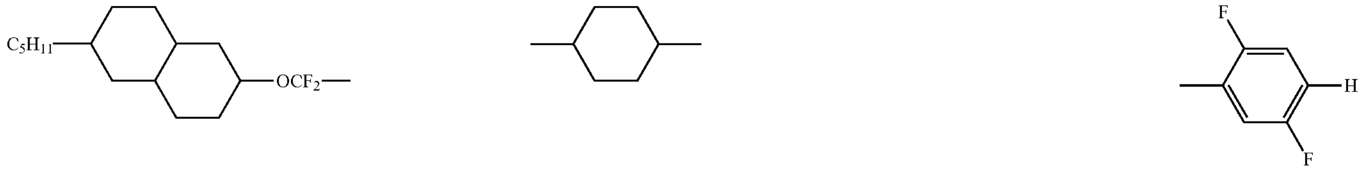
1566
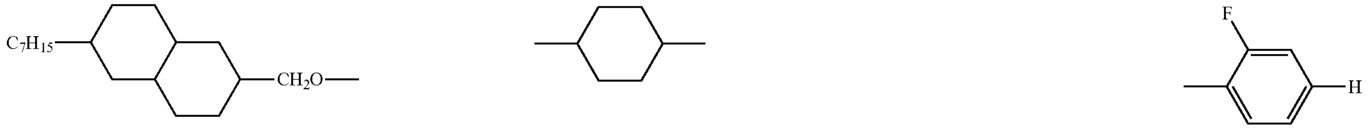
1567
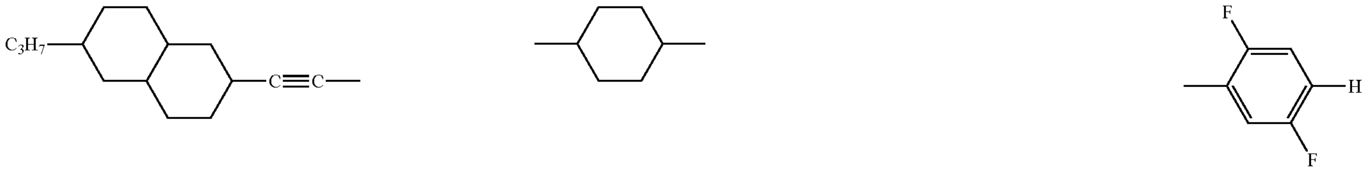
1568
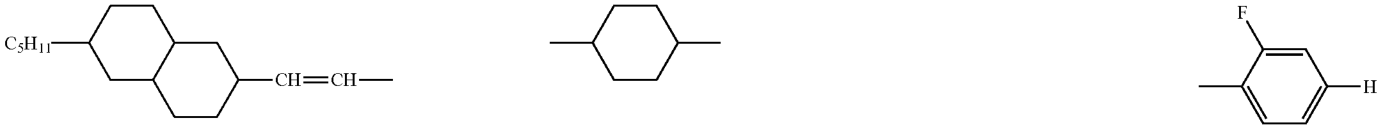

-continued
1569
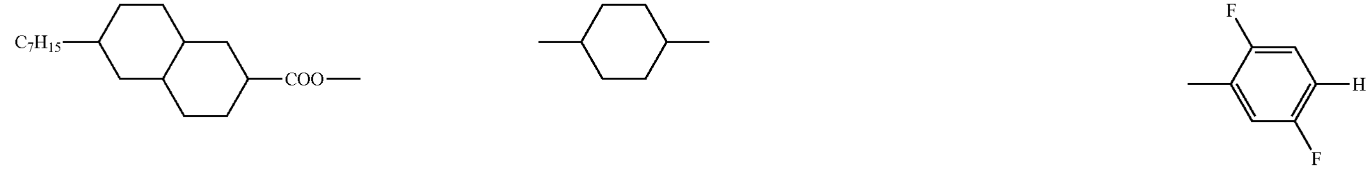
1570
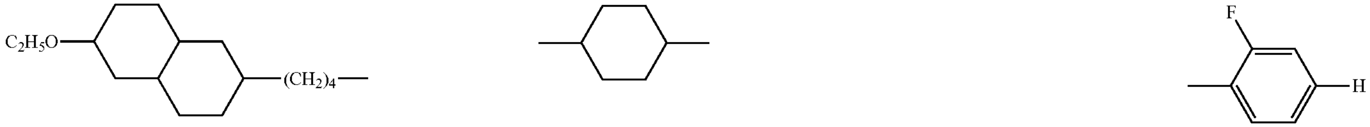
1571
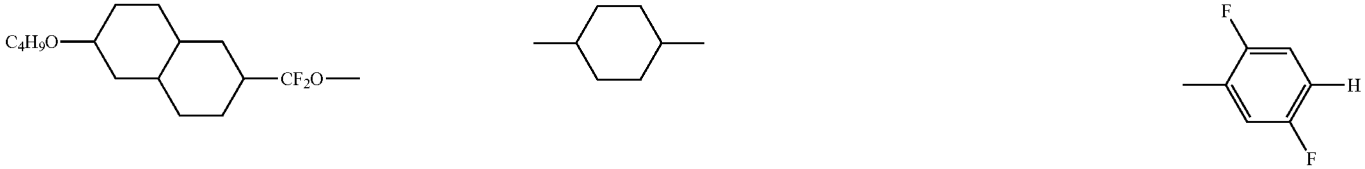
1572
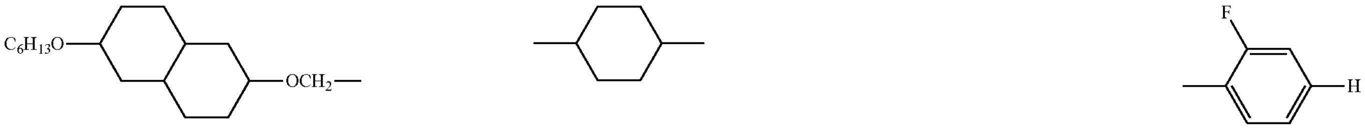
1573
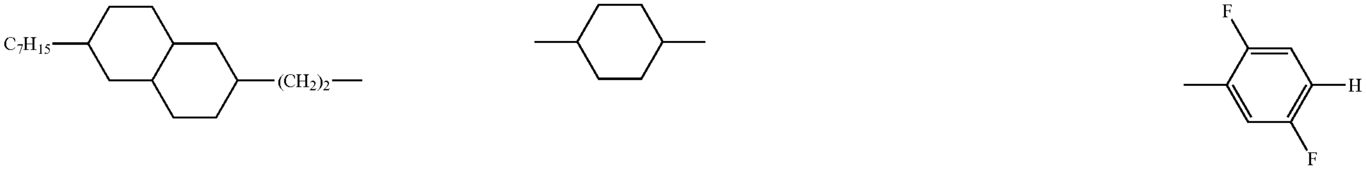
1574
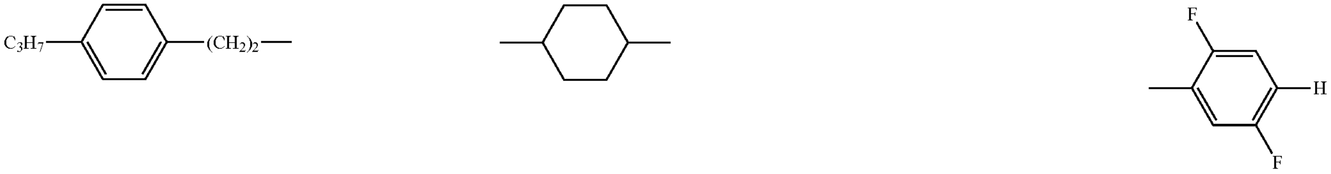

-continued
1575 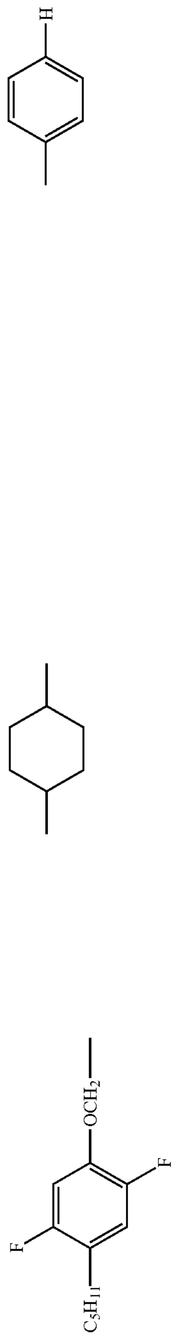
1576 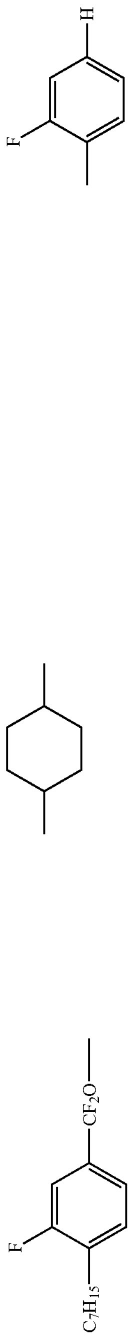
1577 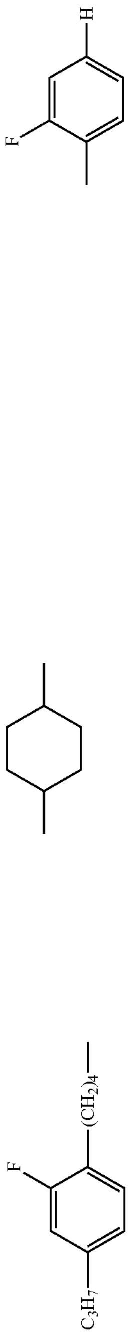
1578 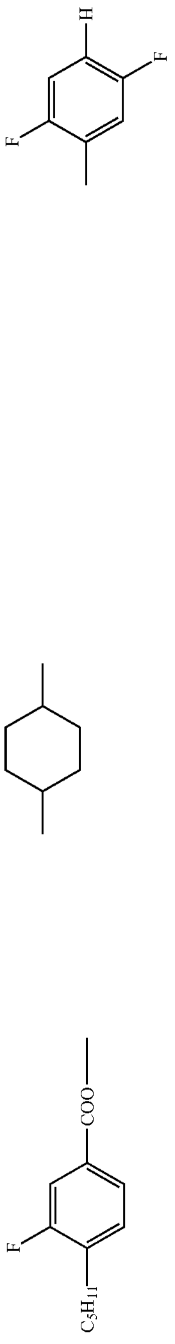
1579 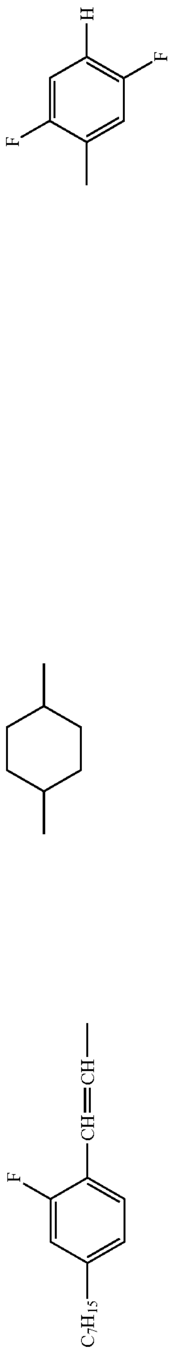
1580 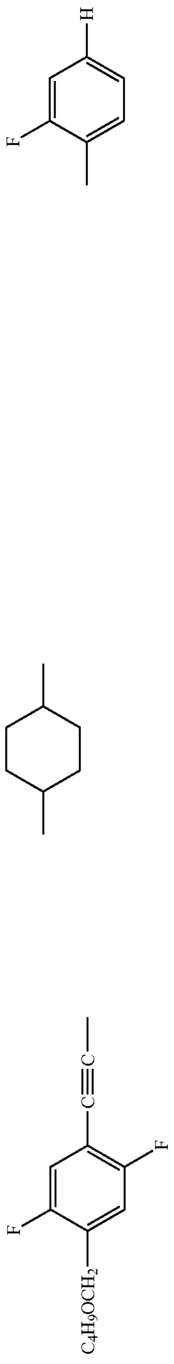

-continued
1581 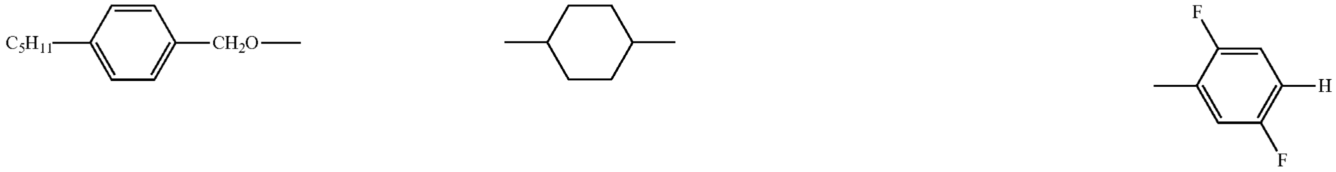
1582 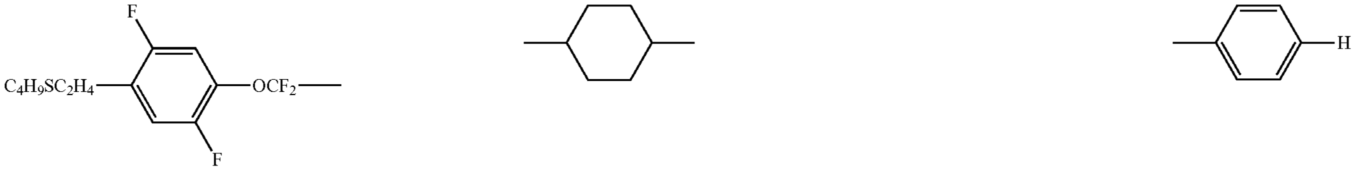
1583 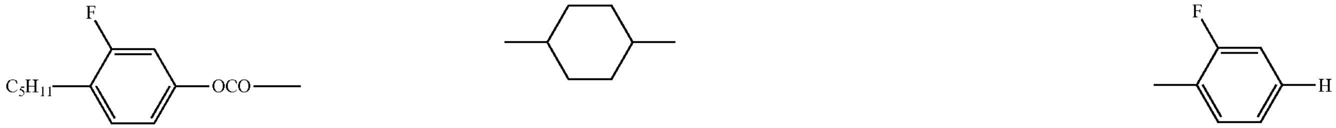
1584 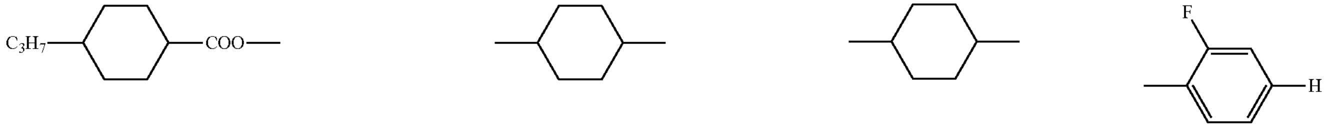
1585 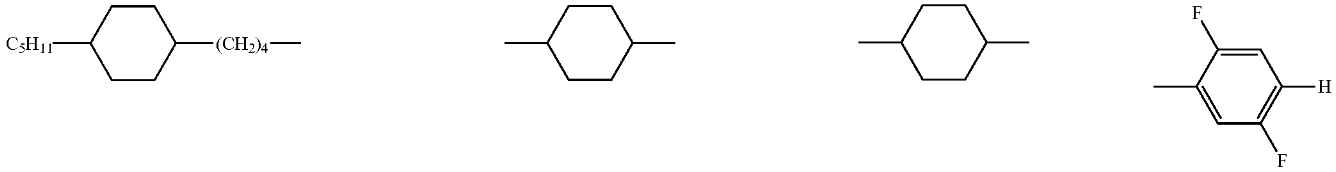
1586 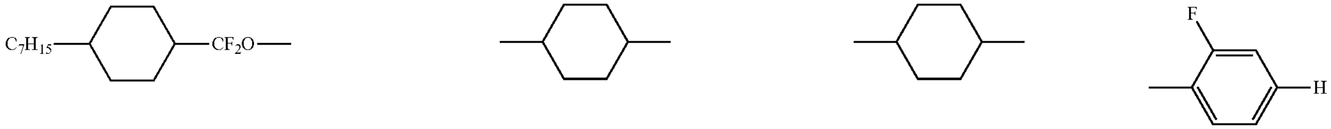

-continued
1587 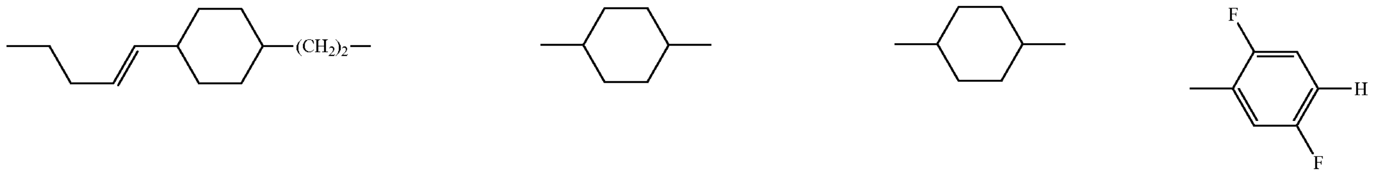
1588 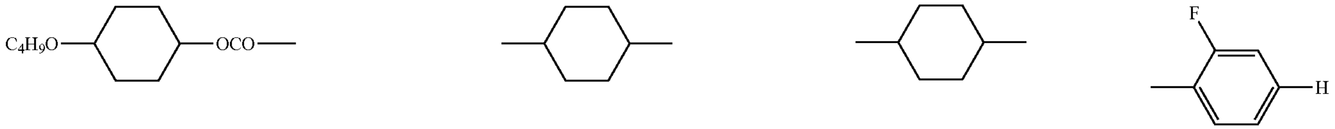
1589 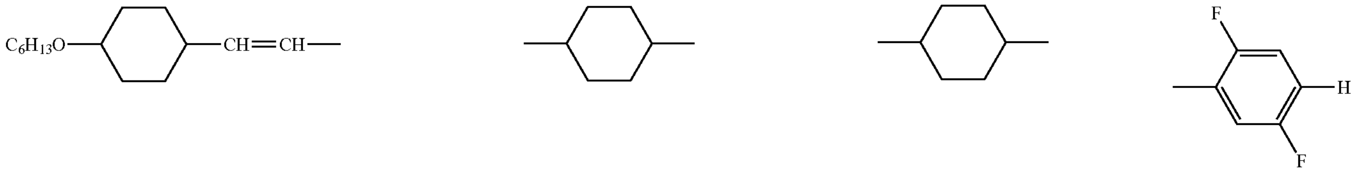
1590 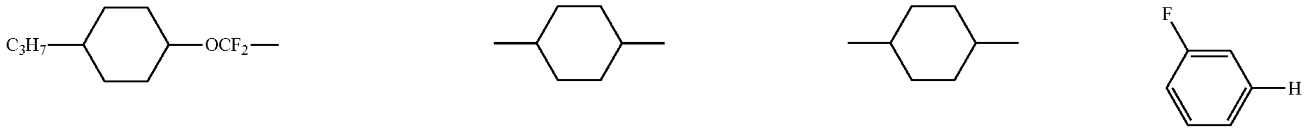
1591 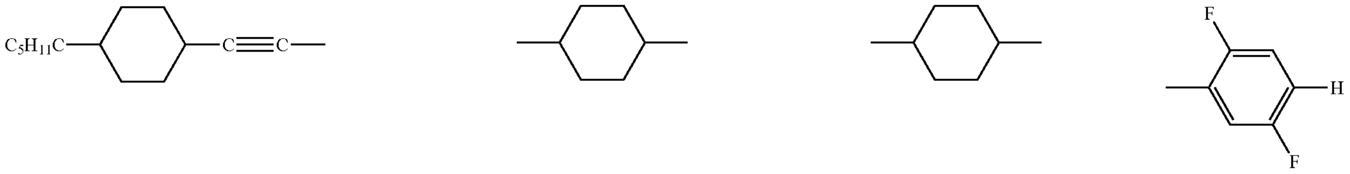
1592 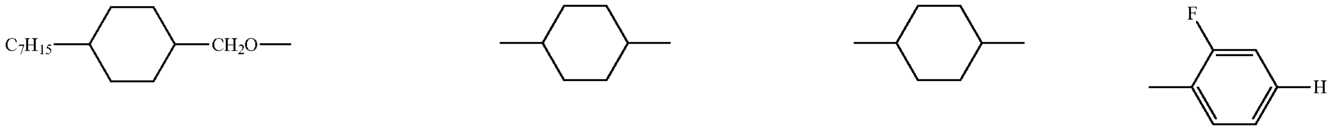

-continued
1593 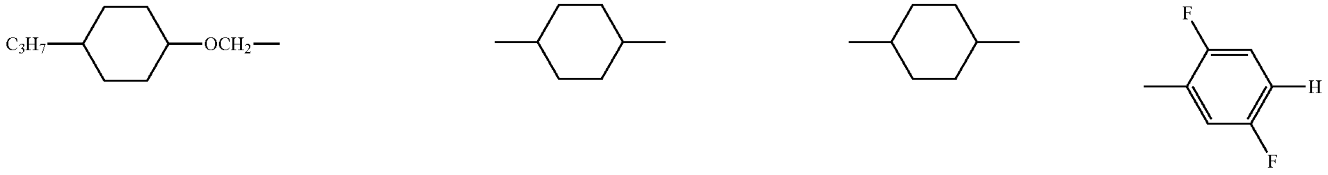
1594 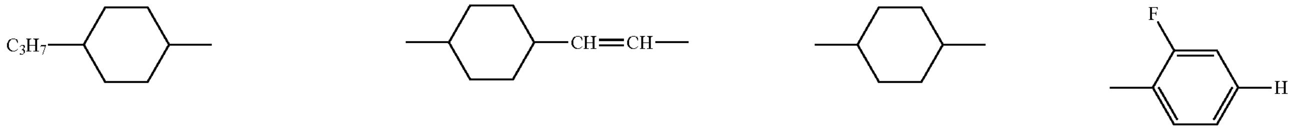
1595 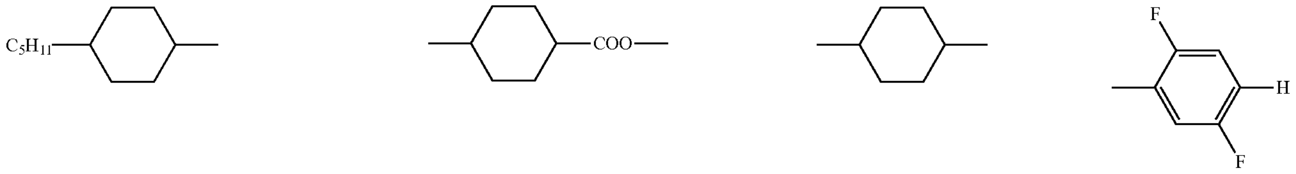
1596 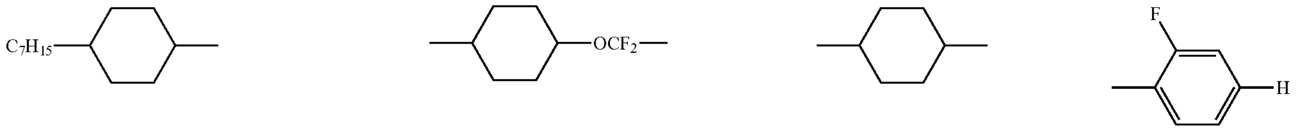
1597 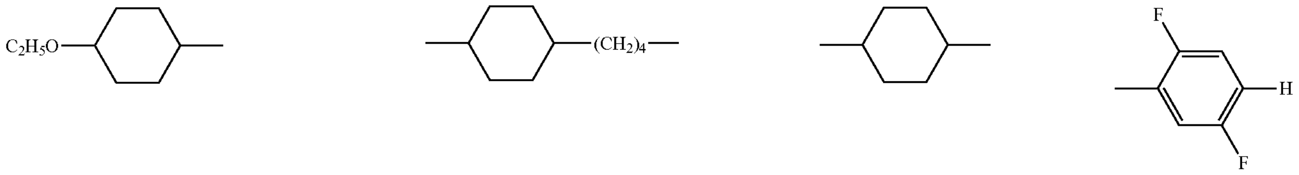
1598 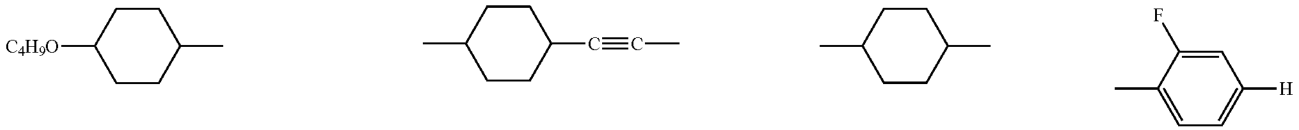

-continued
| | |
|---|---|
| 1599 | 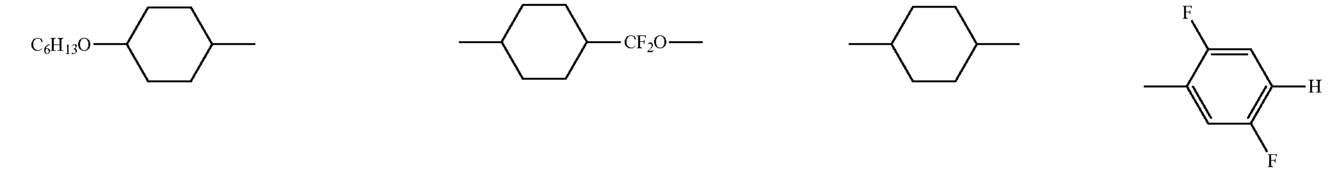 |
| 1600 | 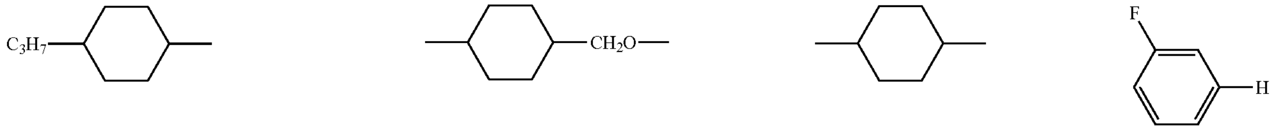 |
| 1601 | 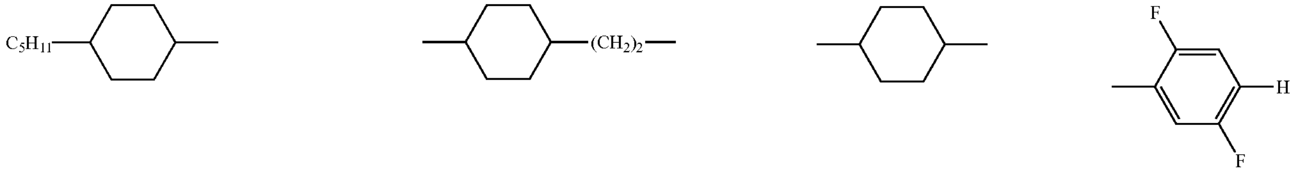 |
| 1602 | 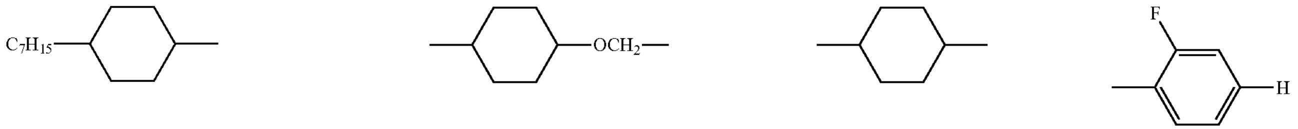 |
| 1603 | 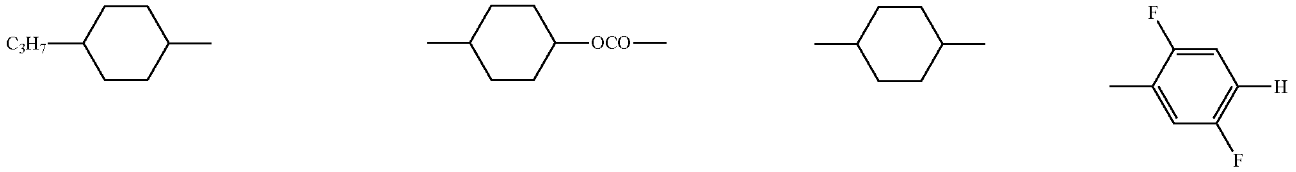 |
| 1604 | 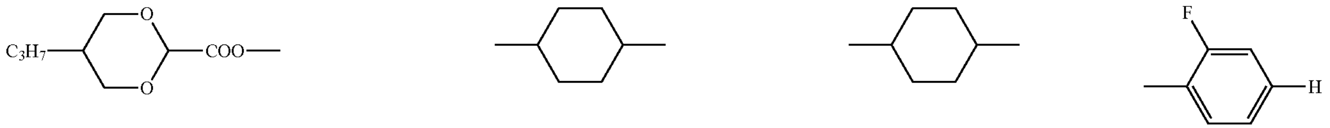 |

-continued
1605 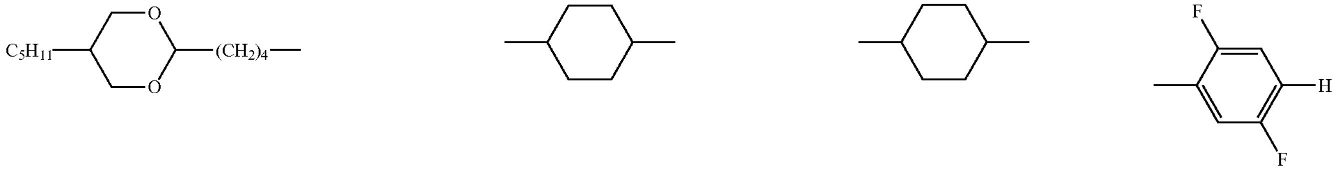
1606 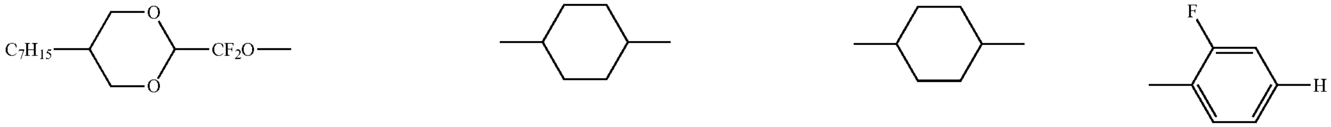
1607 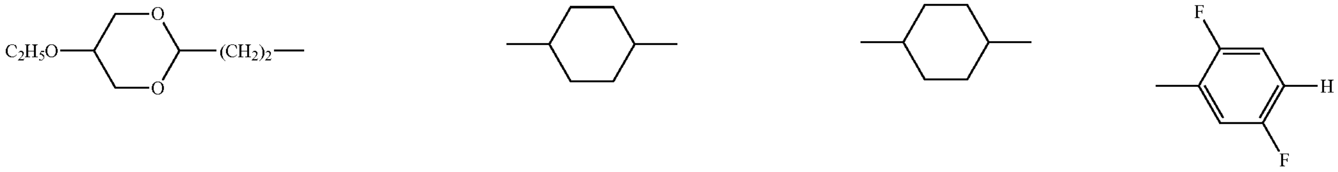
1608 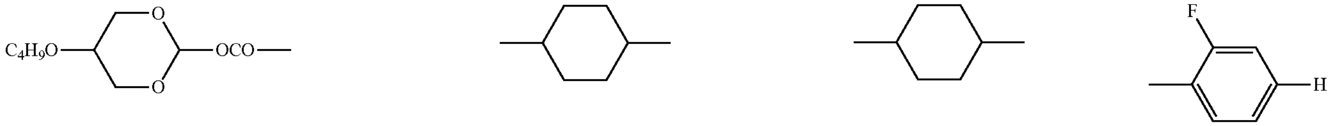
1609 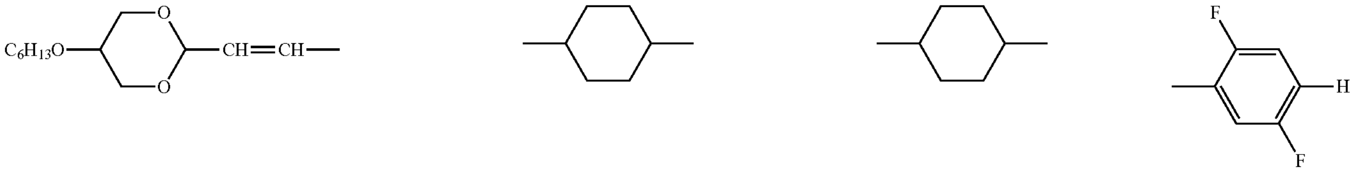
1610 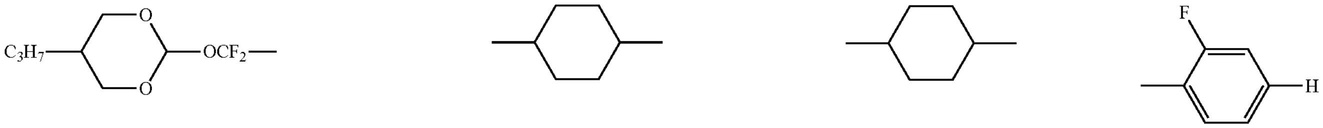

-continued
1611 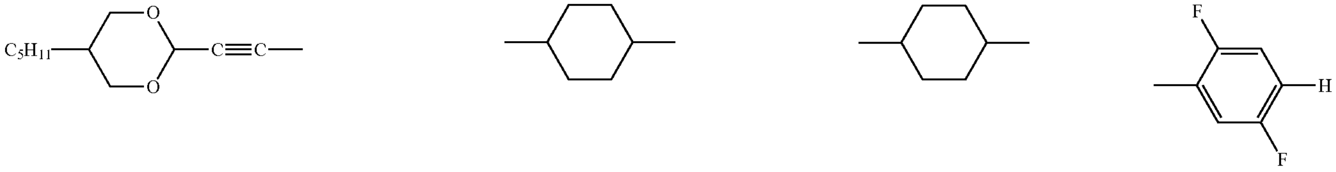
1612 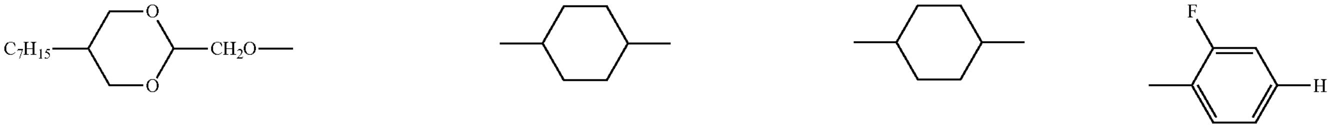
1613 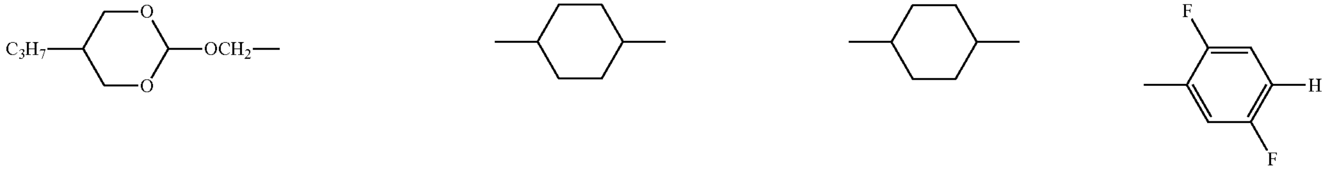
1614 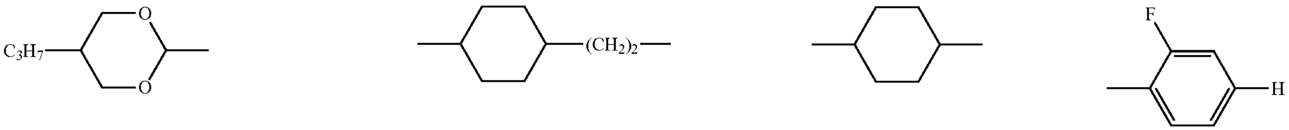
1615 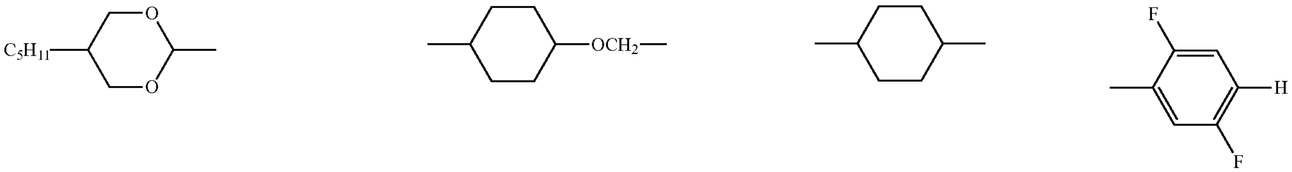
1616 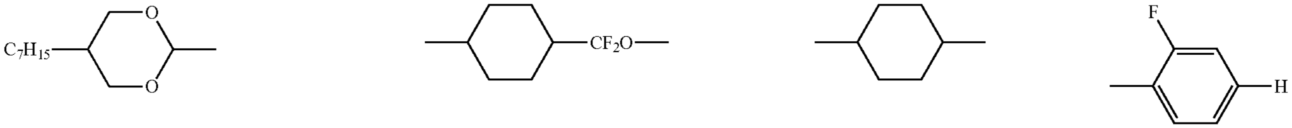

-continued
| | |
|---|---|
| 1617 | 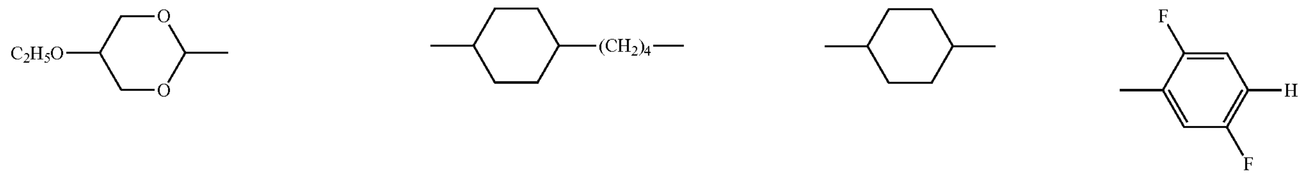 |
| 1618 | 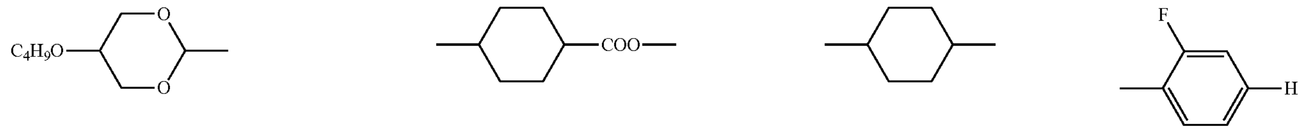 |
| 1619 | 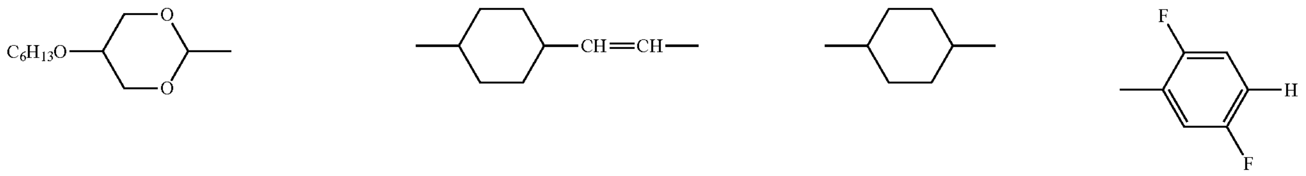 |
| 1620 | 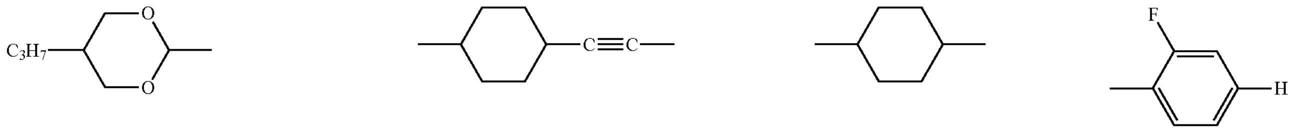 |
| 1621 | 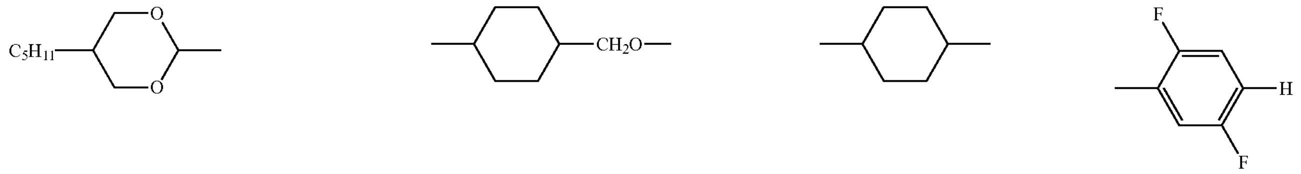 |
| 1622 | 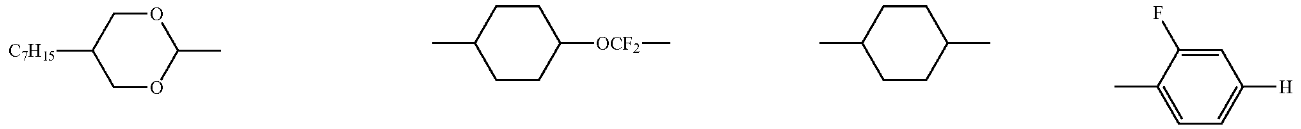 |

-continued
1623 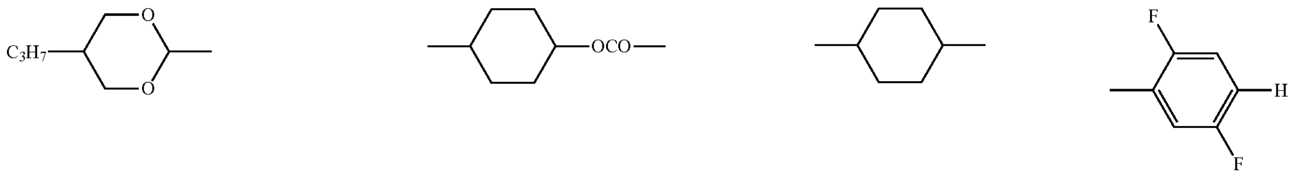
1624 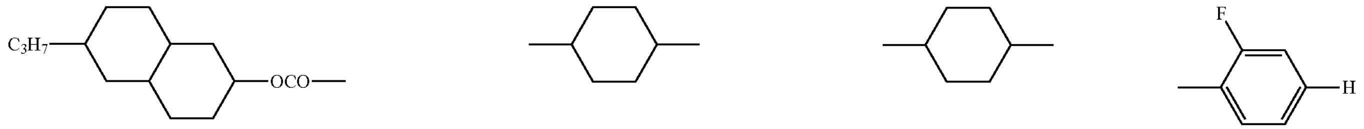
1625 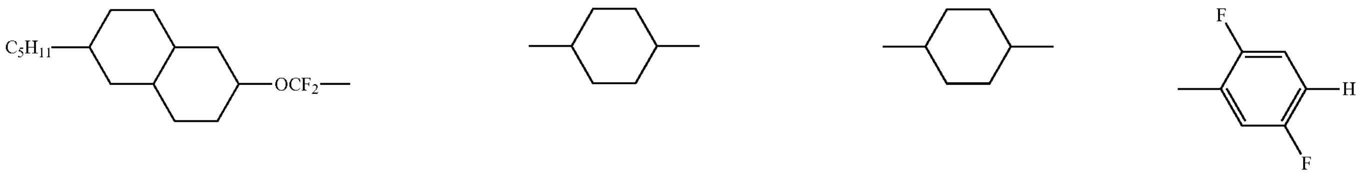
1626 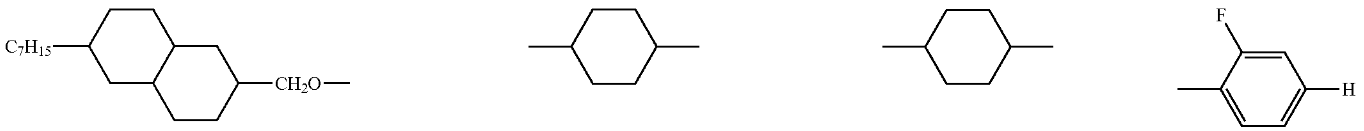
1627 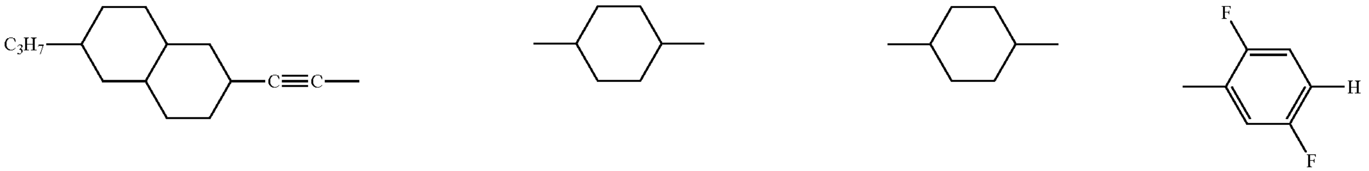
1628 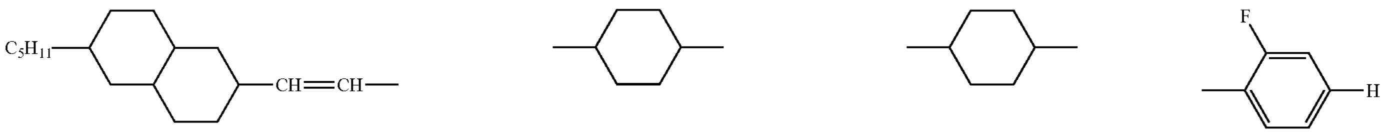

-continued
| | |
|---|---|
| 1629 | 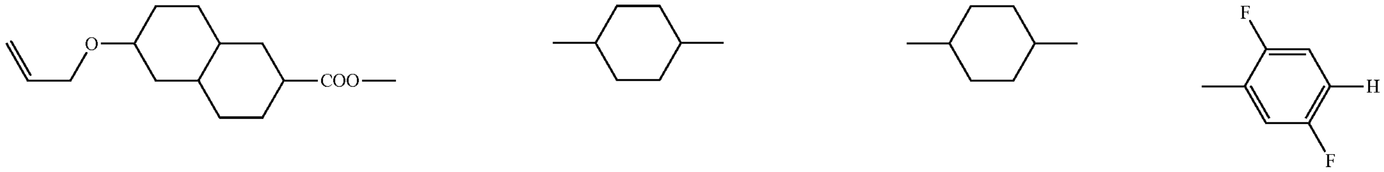 |
| 1630 | 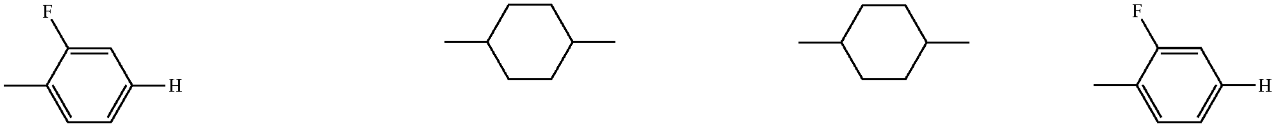 |
| 1631 | 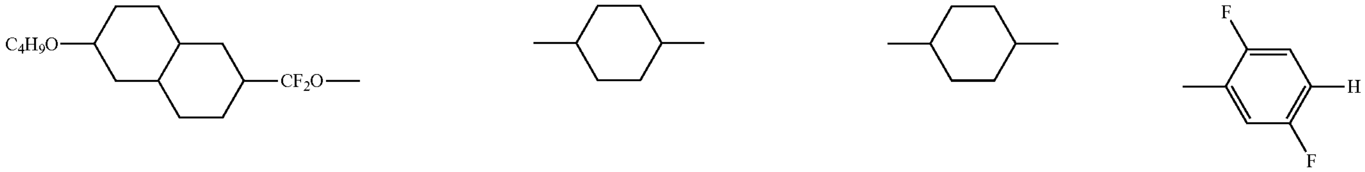 |
| 1632 | 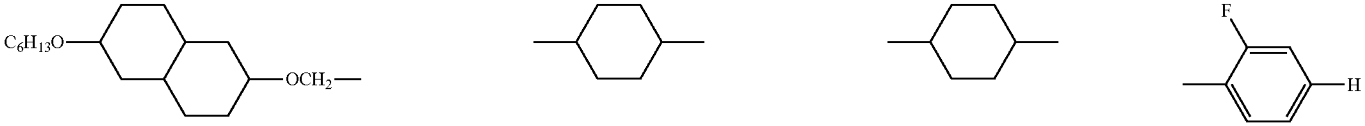 |
| 1633 | 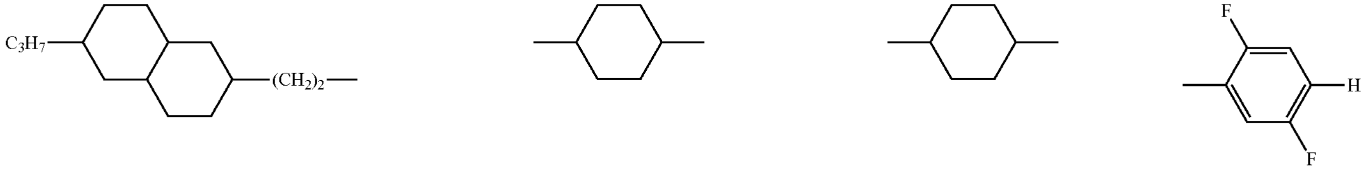 |
| 1634 | 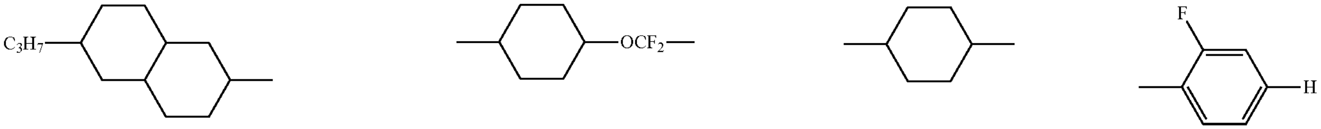 |

-continued
1635 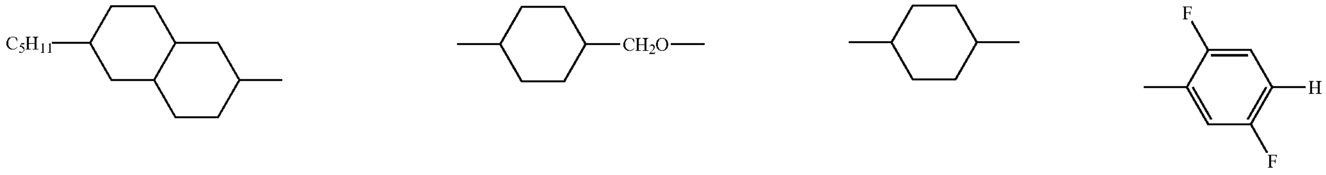
1636 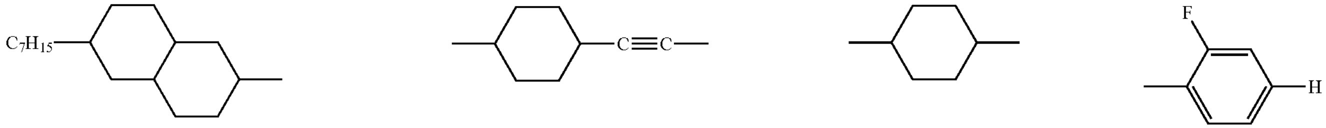
1637 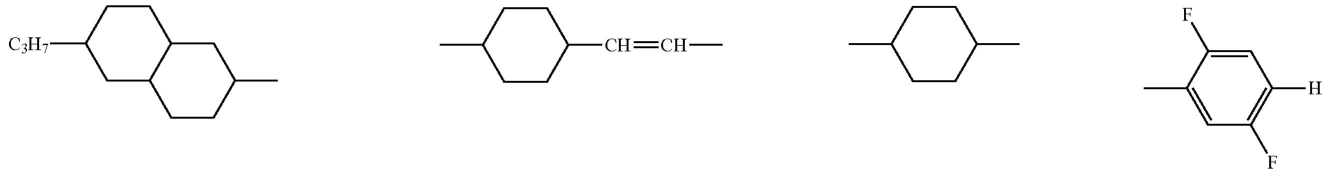
1638 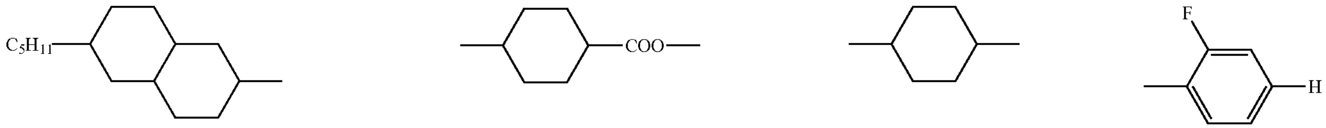
1639 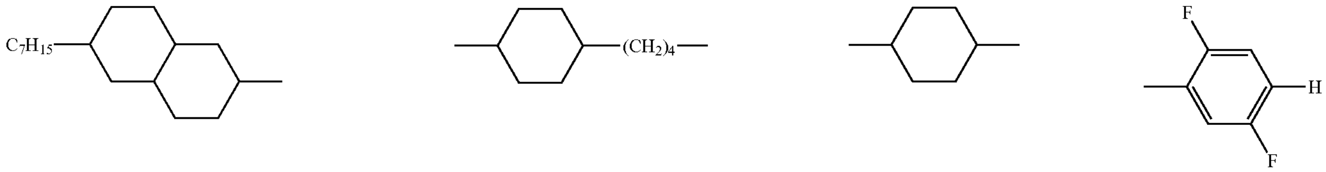
1640 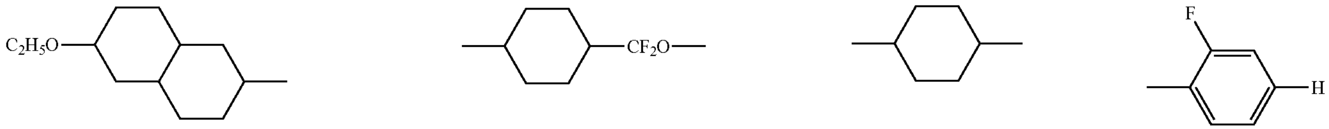

-continued
1641 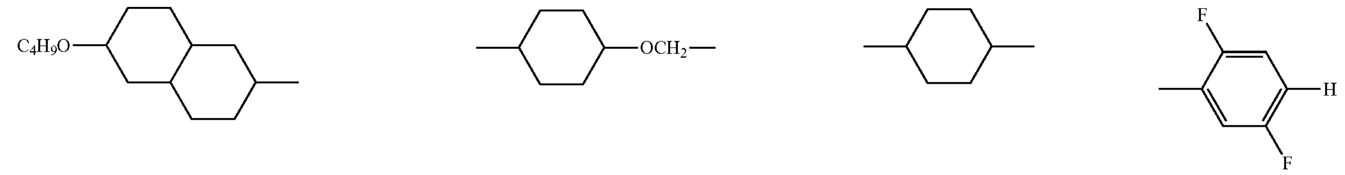
1642 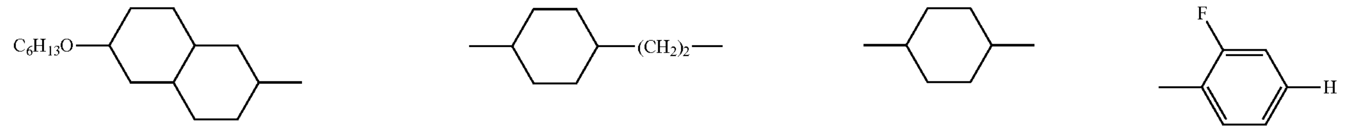
1643 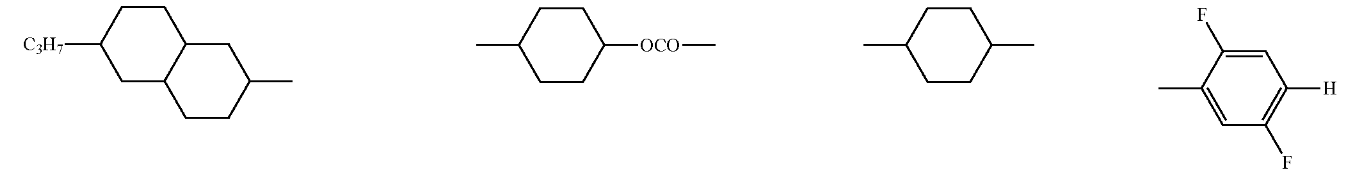
1644 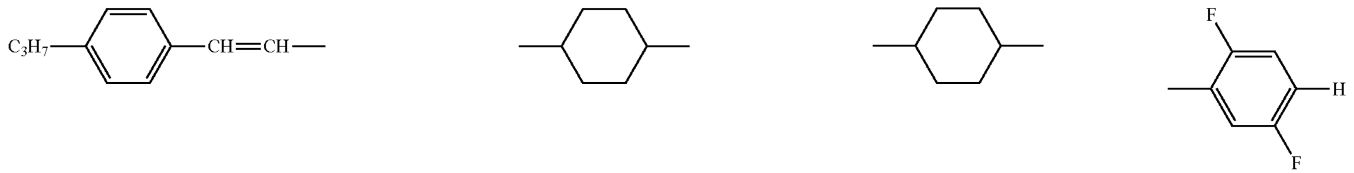
1645 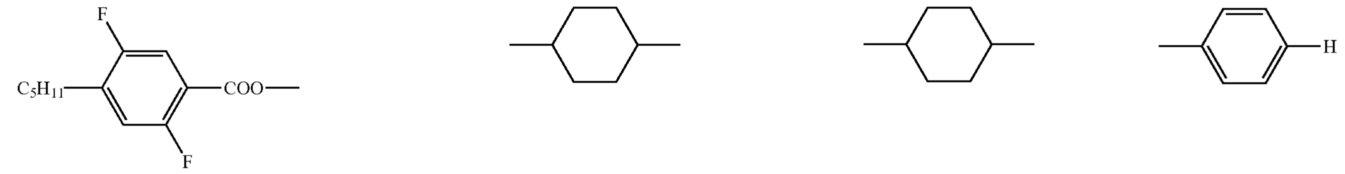
1646 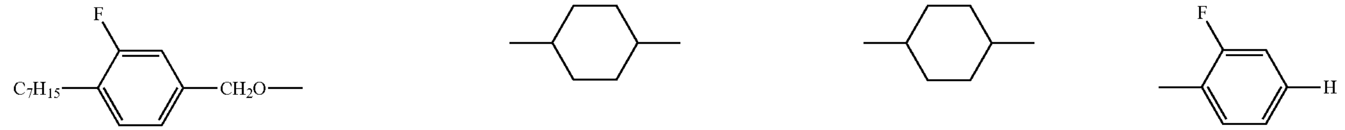

-continued
1647 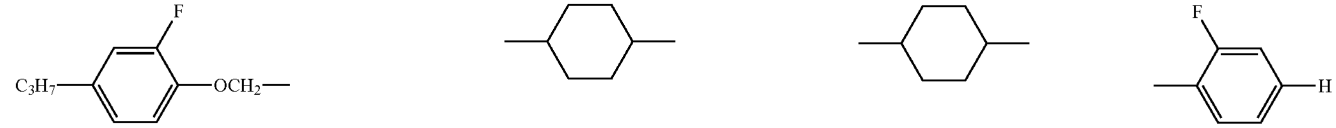
1648 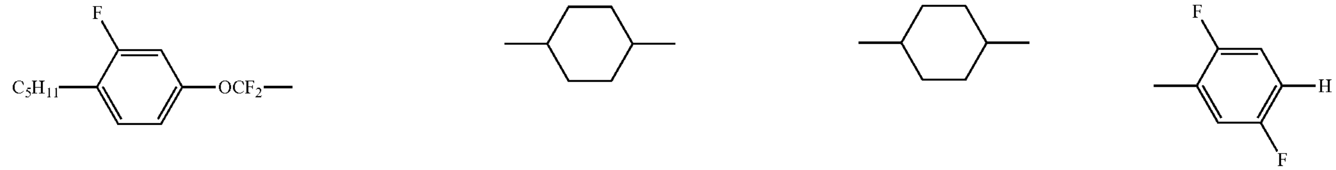
1649 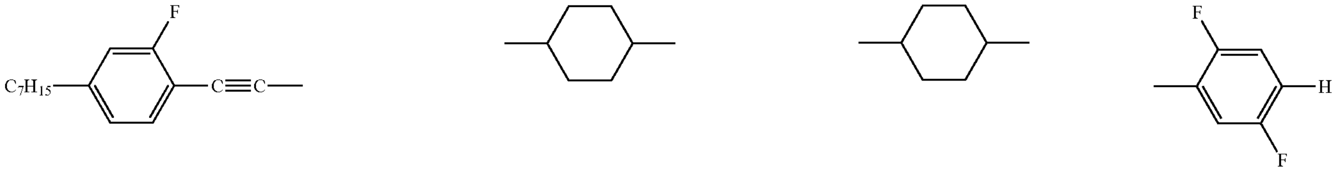
1650 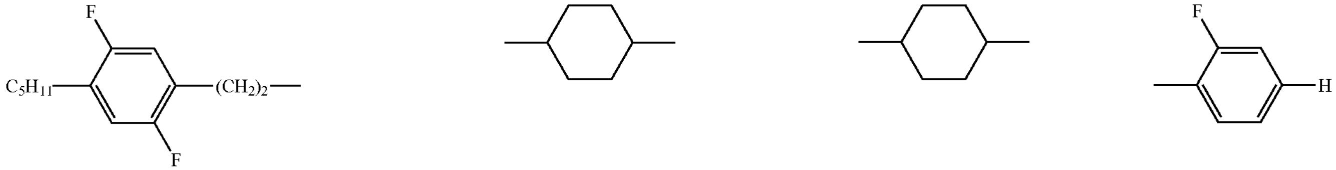
1651 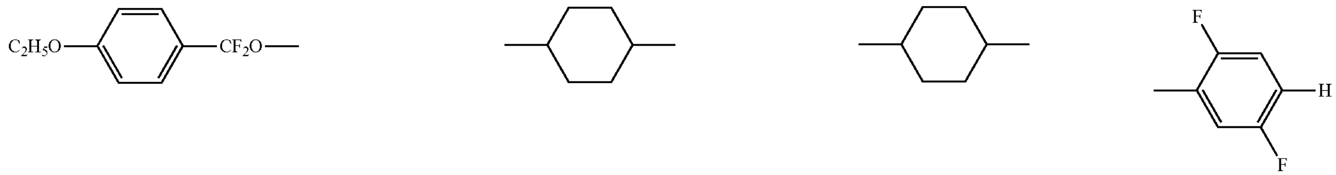
1652 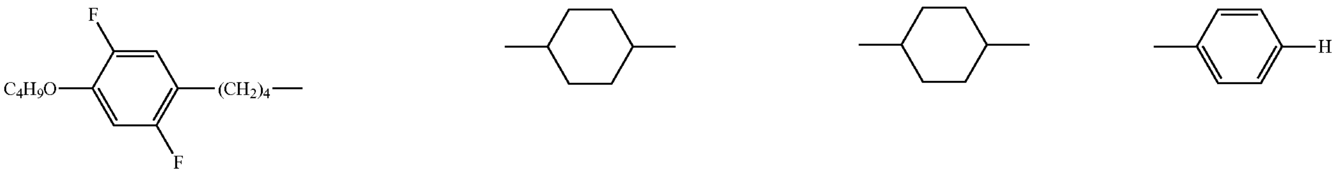

-continued
1653
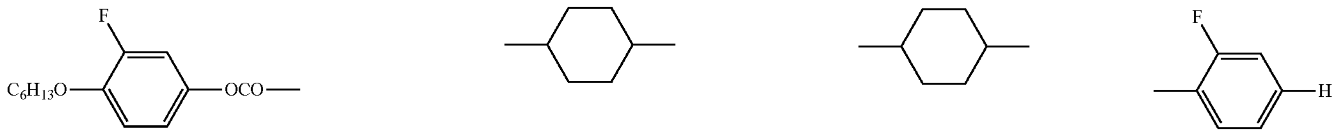
1654
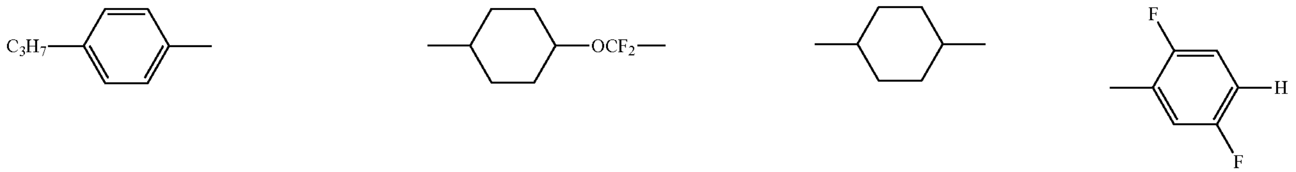
1655
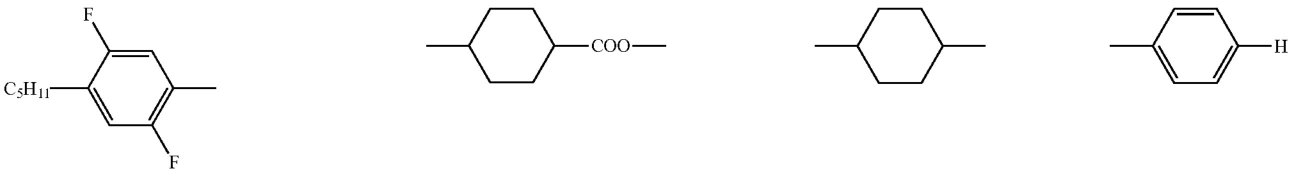
1656
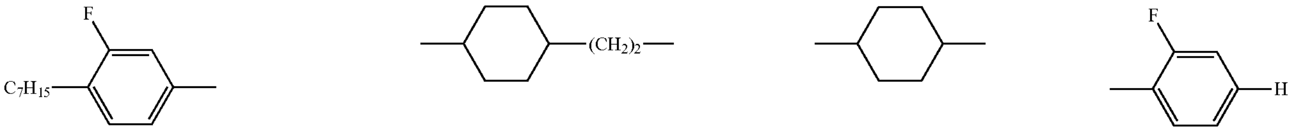
1657
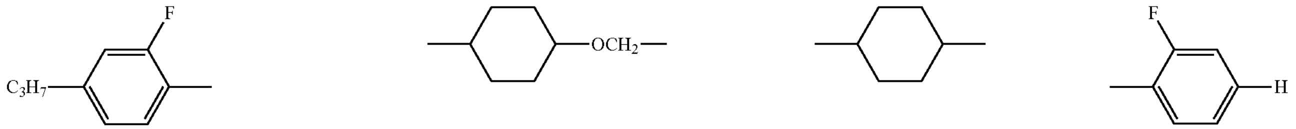
1658
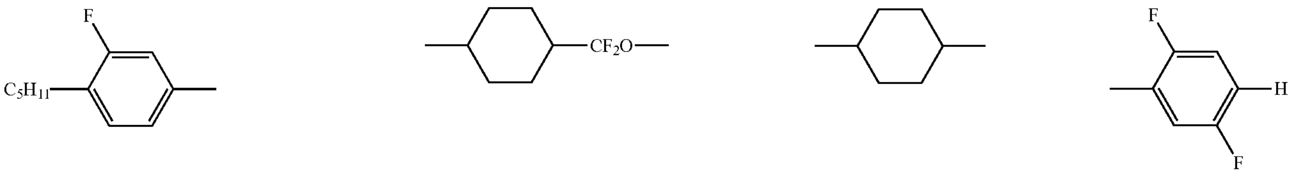

-continued
1659
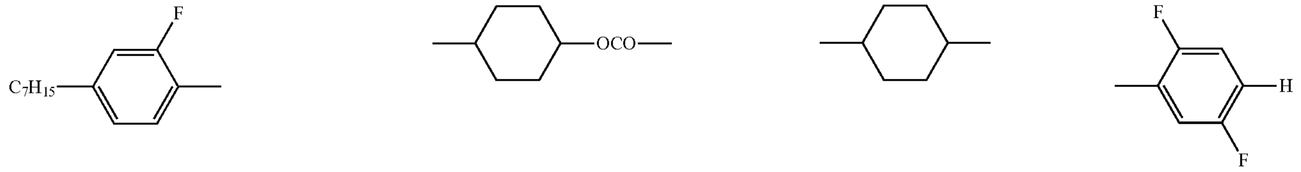
1660
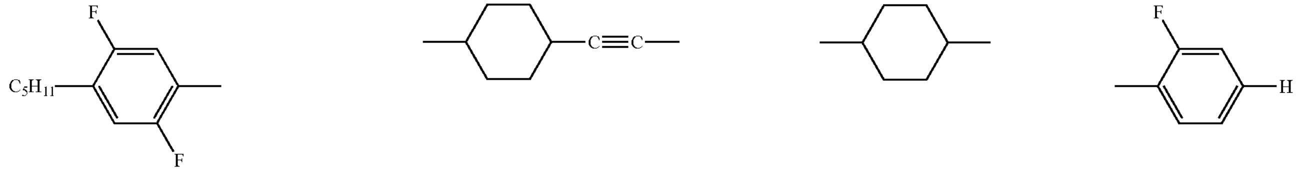
1661
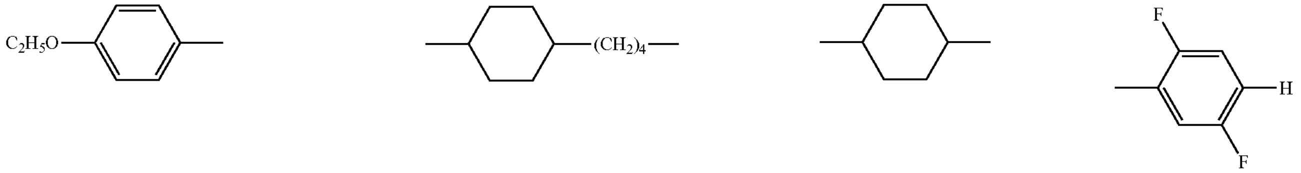
1662
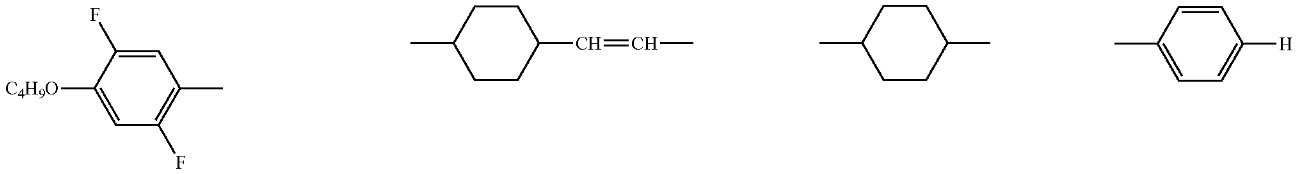
1663
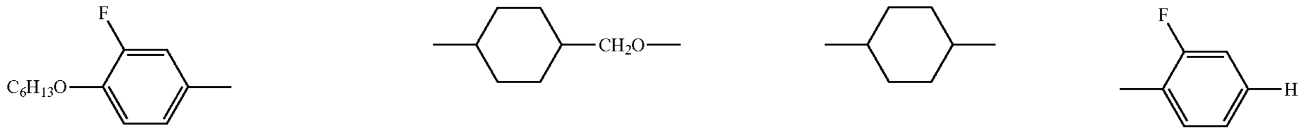
1664
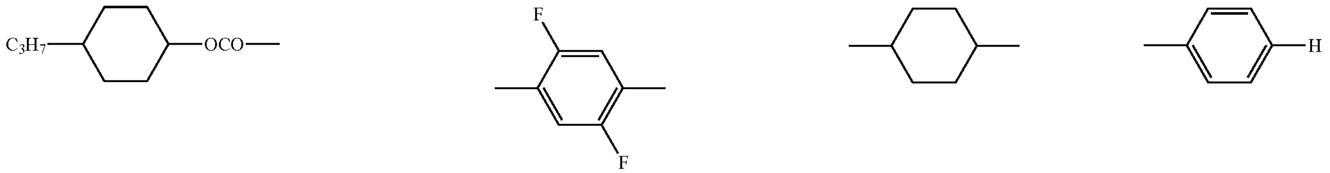

-continued
1665 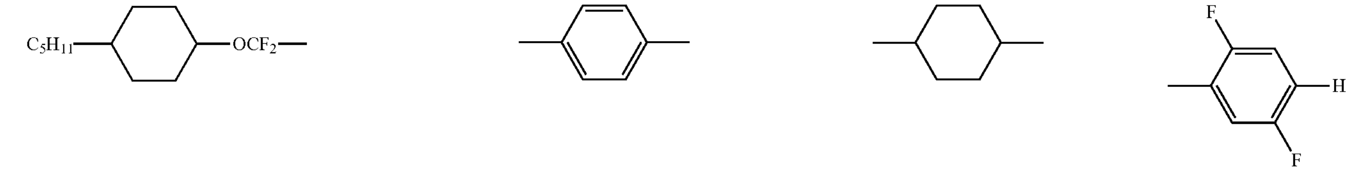
1666 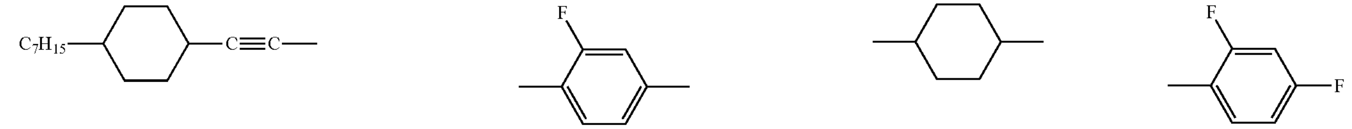
1667 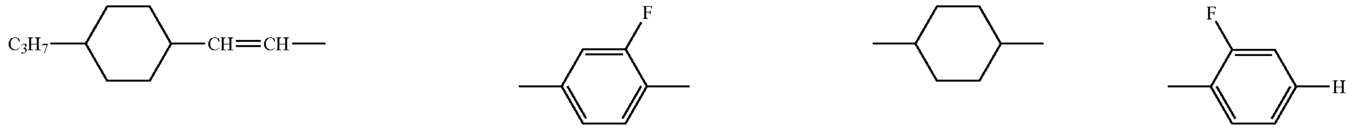
1668 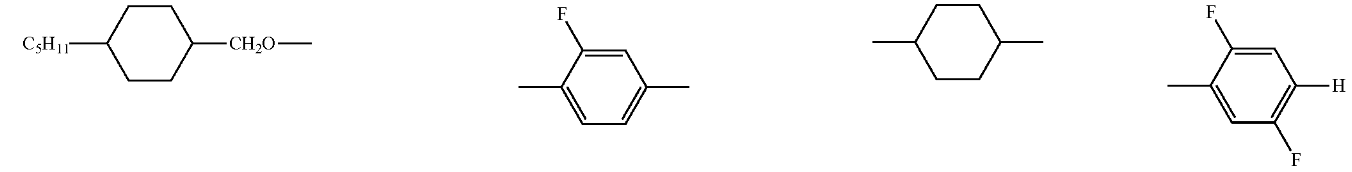
1669 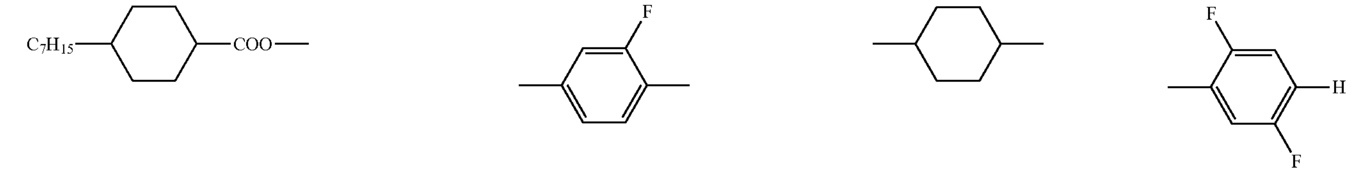
1670 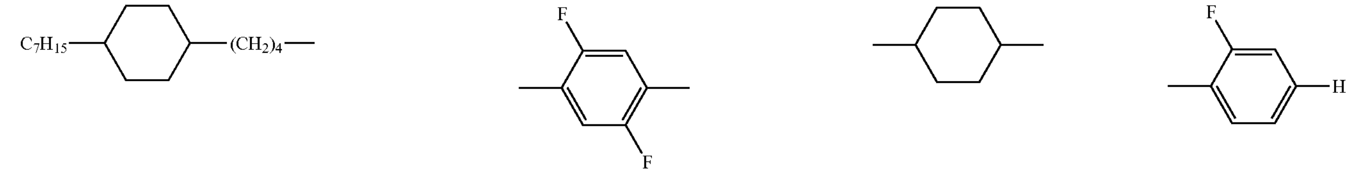

-continued
1671 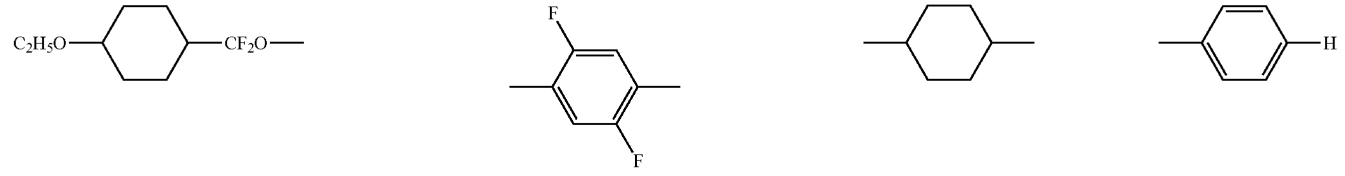
1672 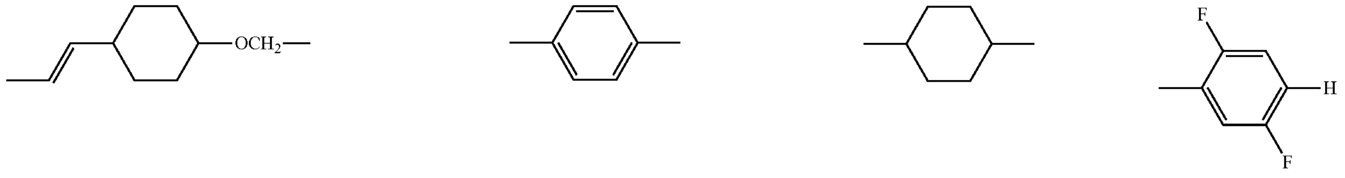
1673 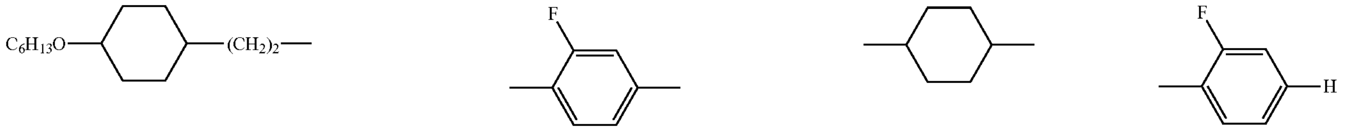
1674 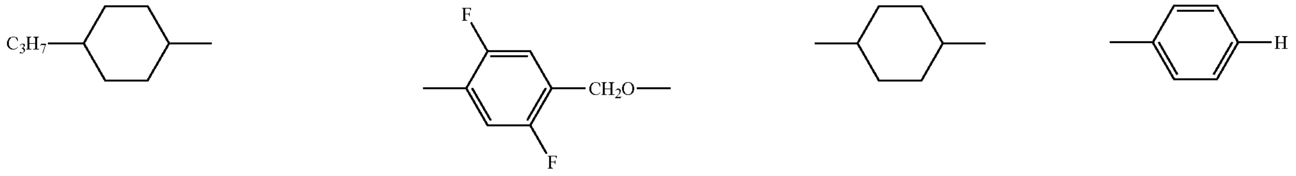
1675 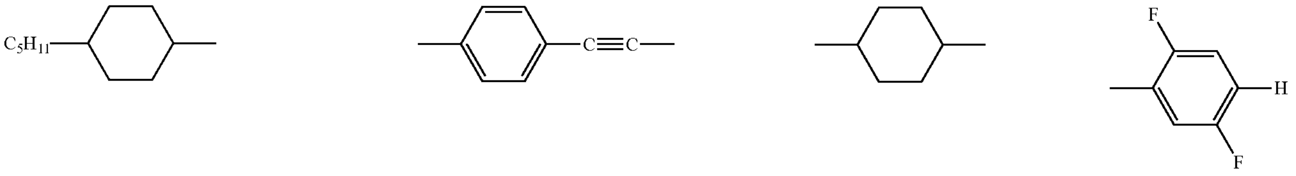
1676 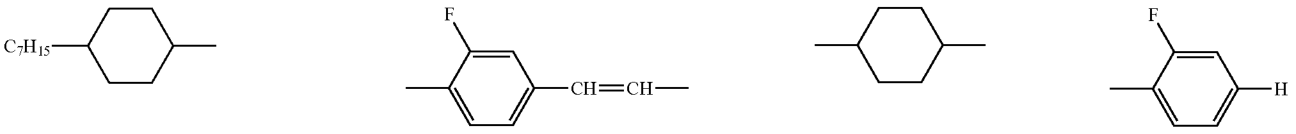

-continued
| | |
|---|---|
| 1677 | 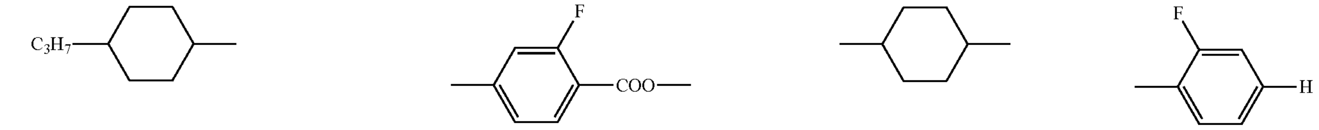 |
| 1678 | 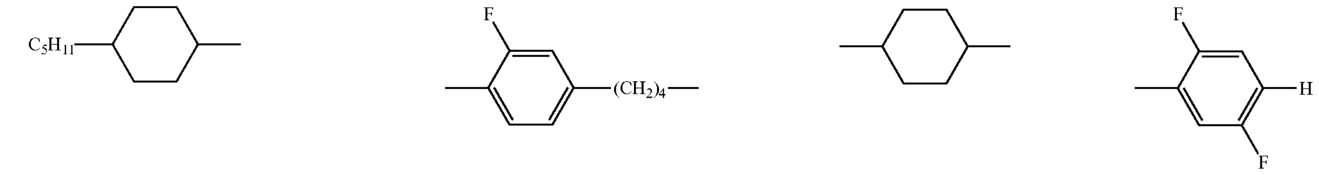 |
| 1679 | 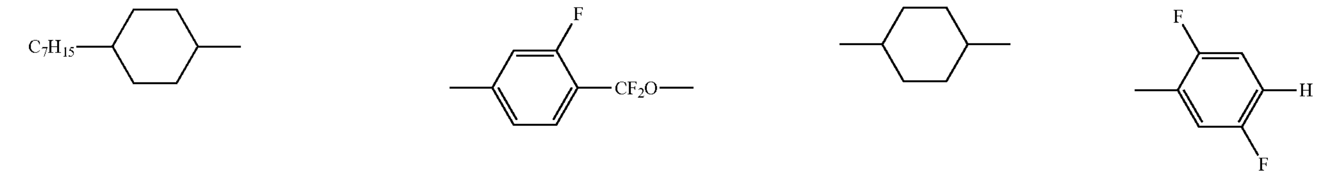 |
| 1680 | 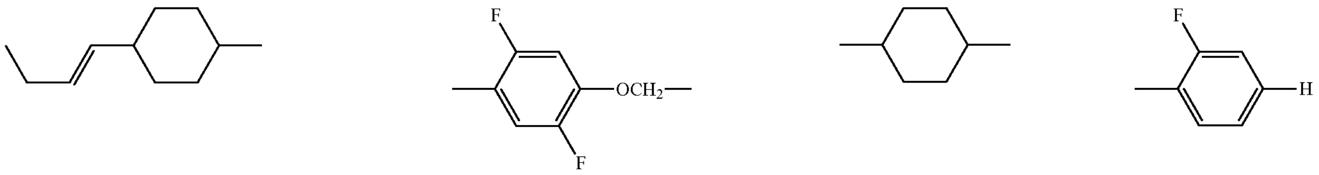 |
| 1681 | 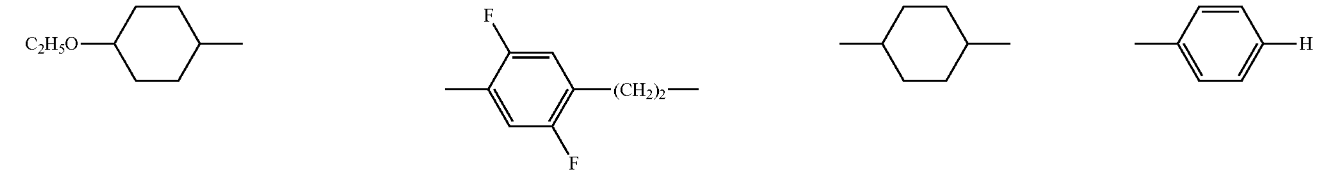 |
| 1682 | 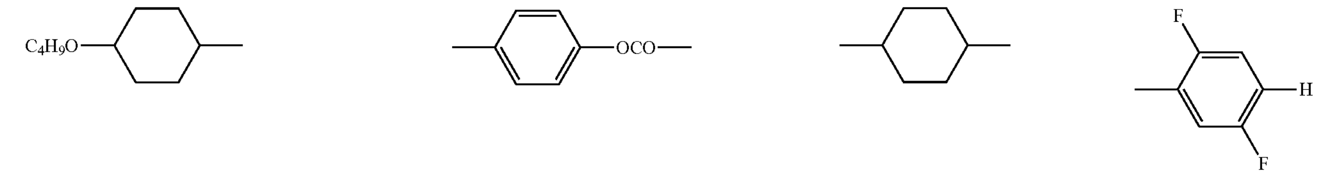 |

-continued
| | |
|---|---|
| 1683 | 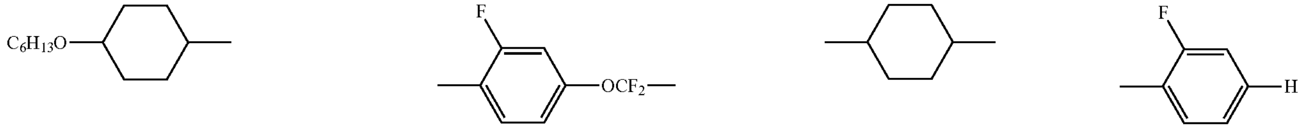 |
| 1684 | 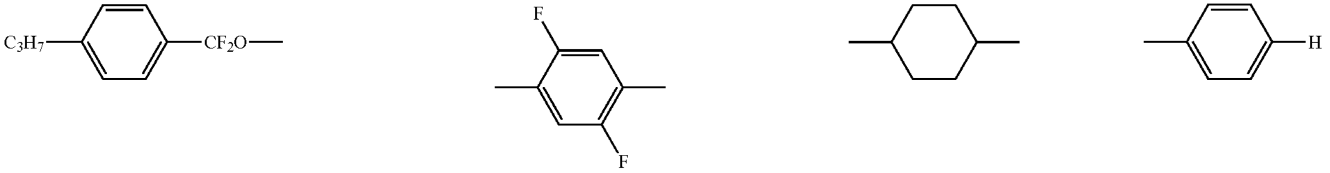 |
| 1685 | 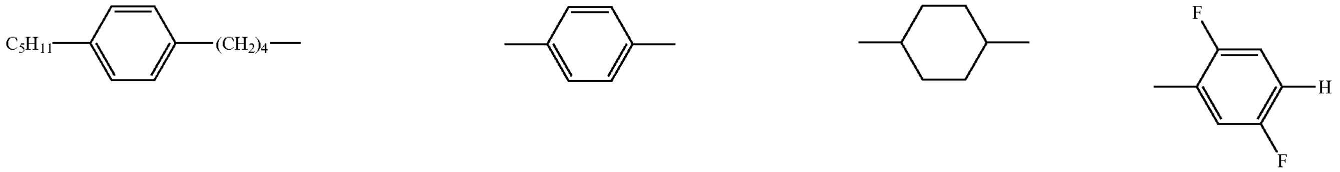 |
| 1686 | 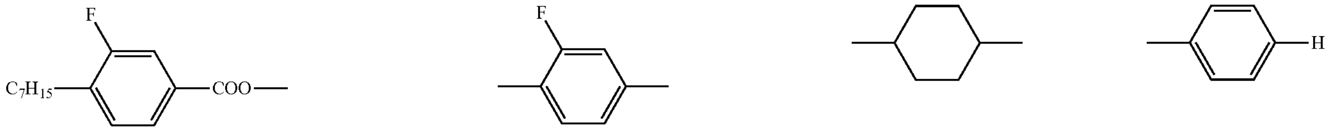 |
| 1687 | 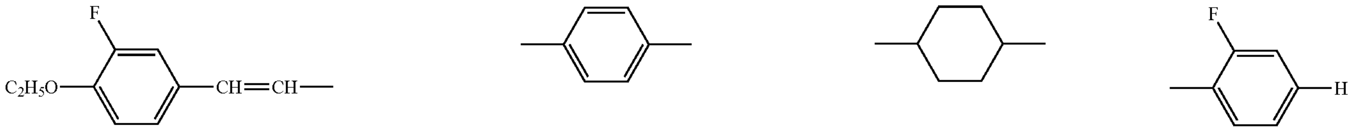 |
| 1688 | 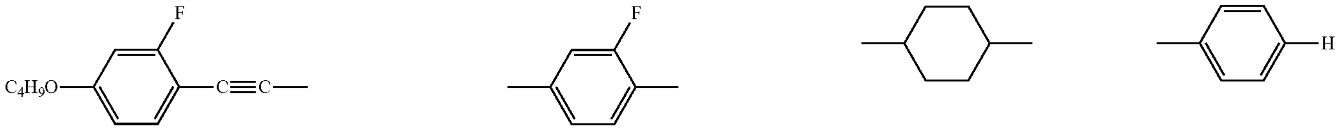 |

-continued
| | |
|---|---|
| 1689 | 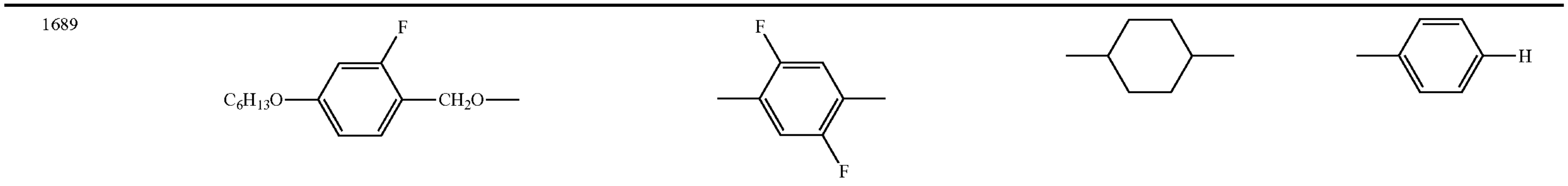 |
| 1690 | 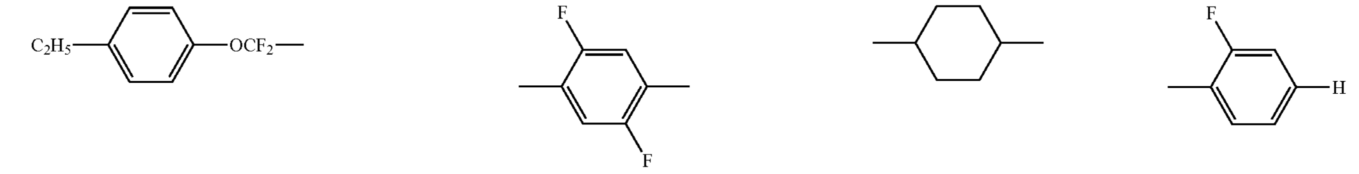 |
| 1691 | 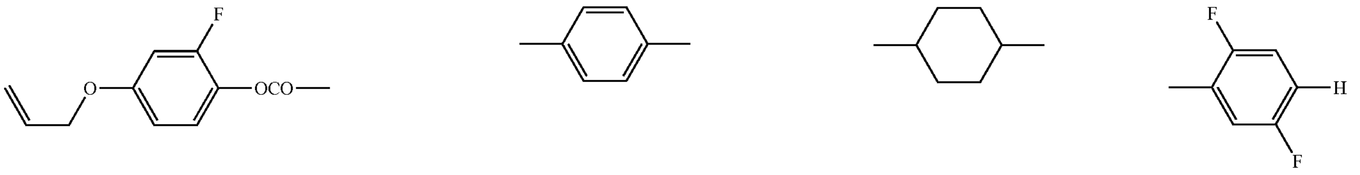 |
| 1692 | 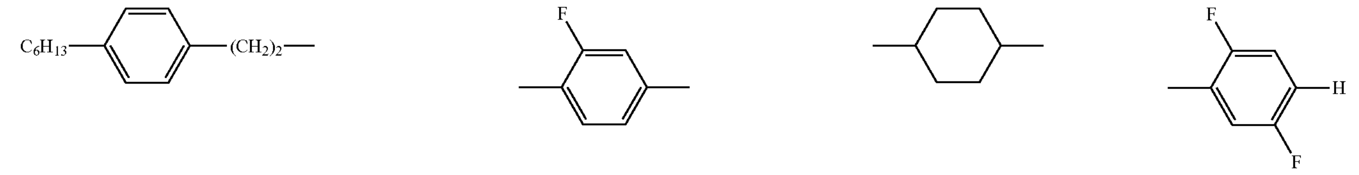 |
| 1693 | 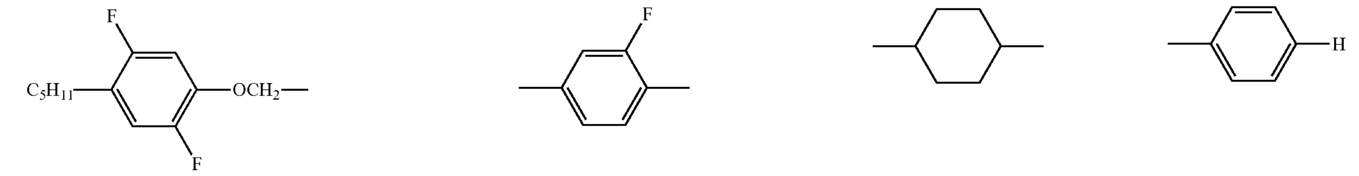 |

-continued
1694
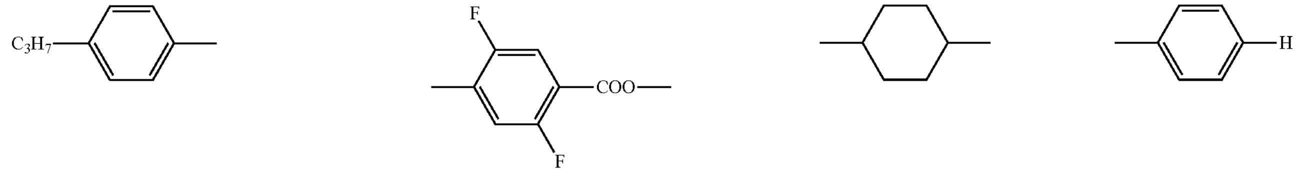
1695
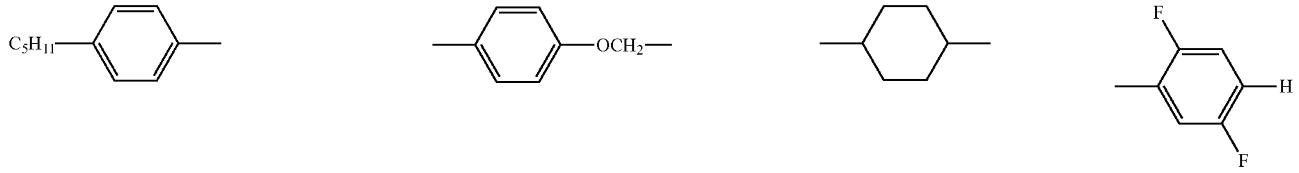
1696
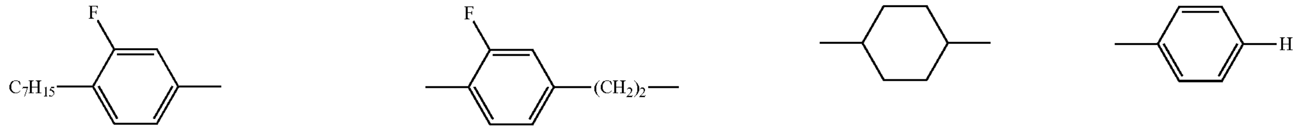
1697
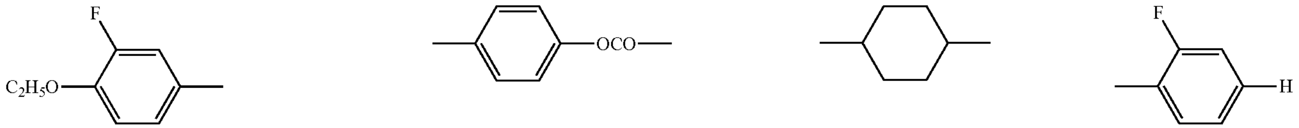
1698
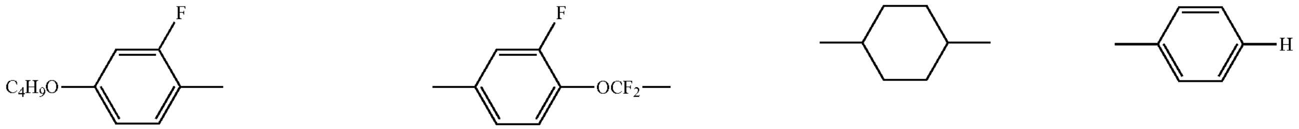
1699
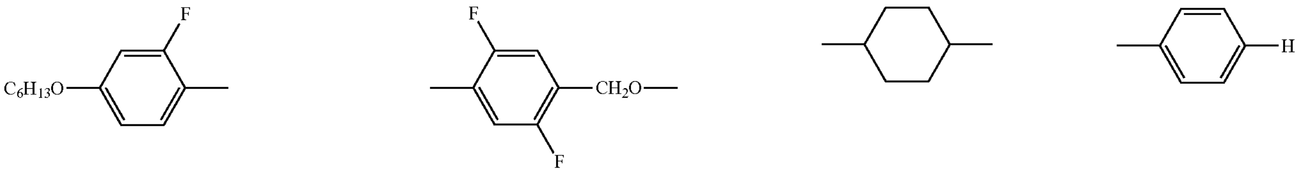

-continued
1700 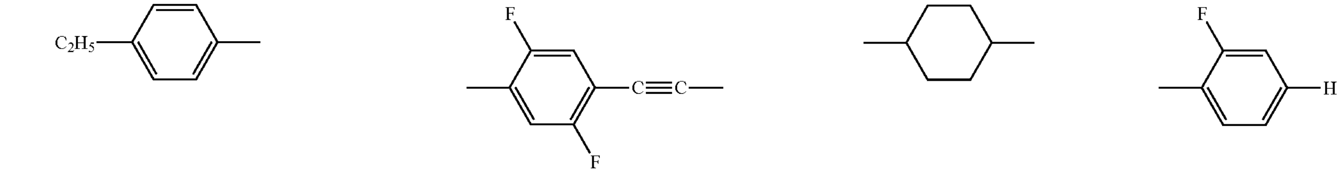
1701 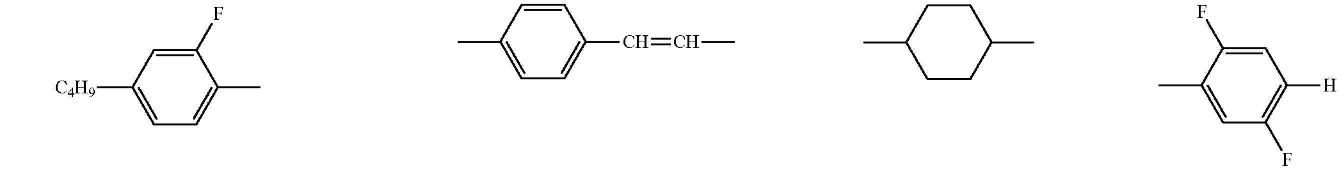
1702 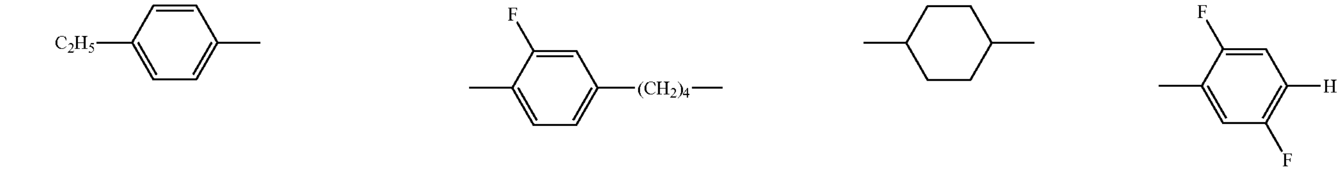
1703 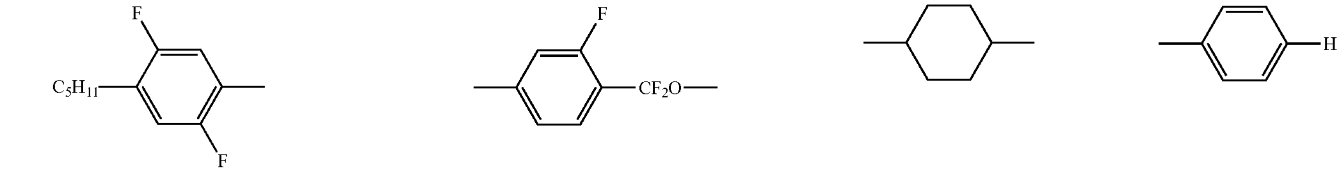
1704 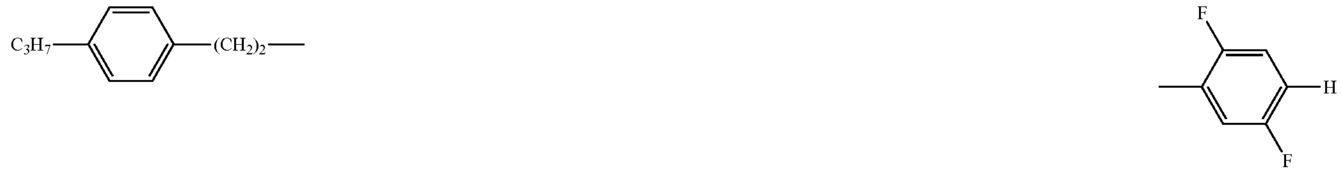
1705 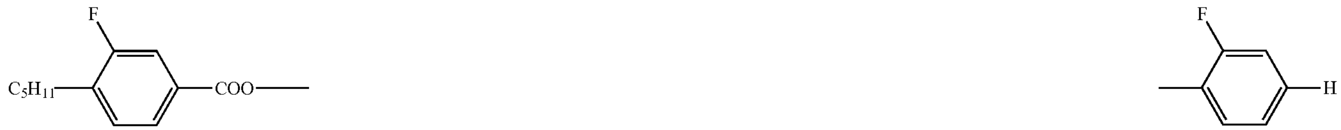

-continued
1706 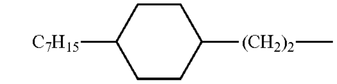 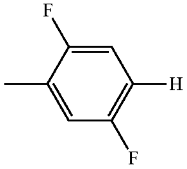
1707 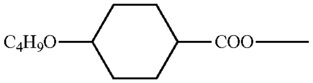 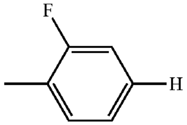
1708 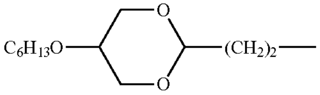 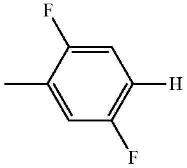
1709 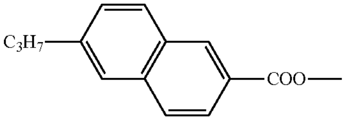 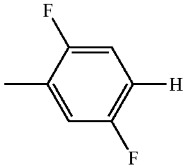
1710 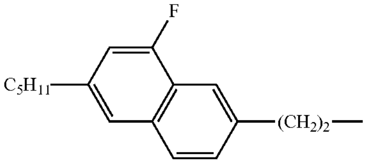 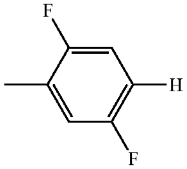
1711 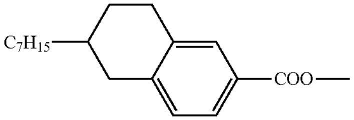 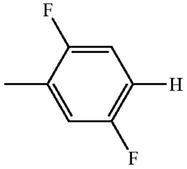

-continued
| | | | |
|---|---|---|---|
| 1712 | 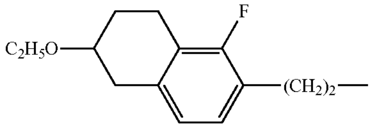 | | 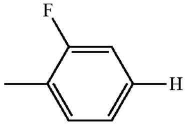 |
| 1713 | 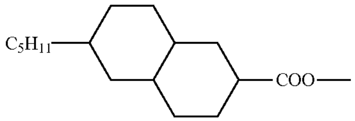 | | 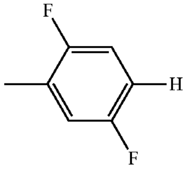 |
| 1714 | 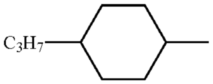 | 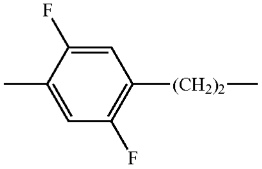 | 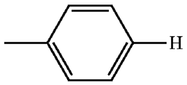 |
| 1715 | 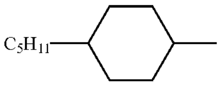 | 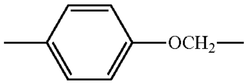 | 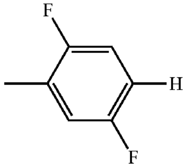 |
| 1716 | 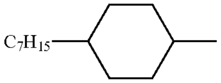 | 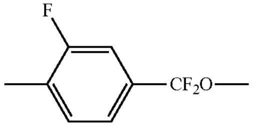 | 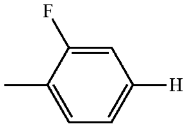 |
| 1717 | 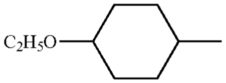 | 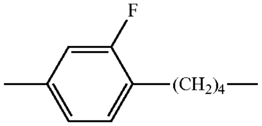 | 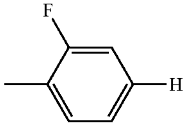 |

-continued
1718 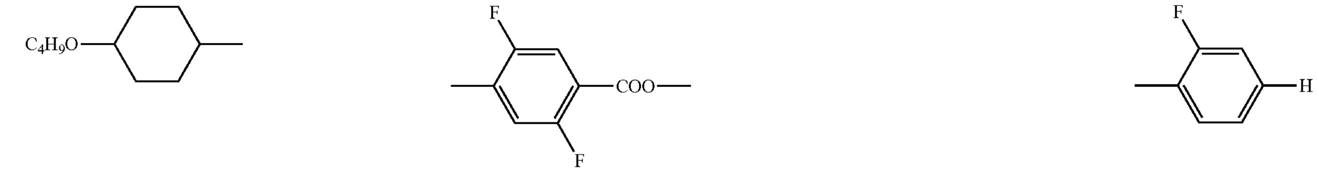
1719 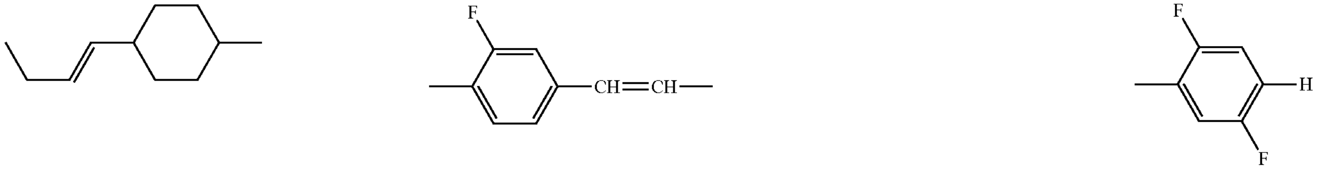
1720 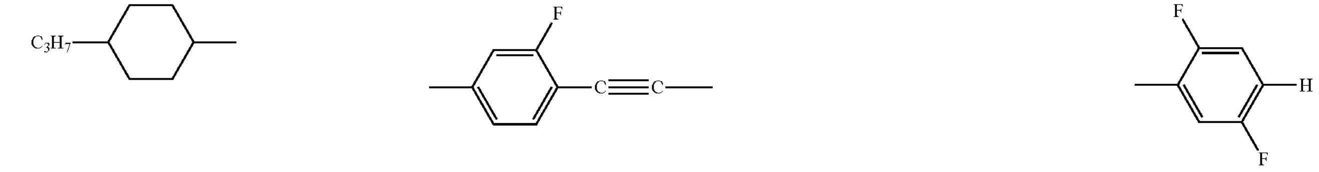
1721 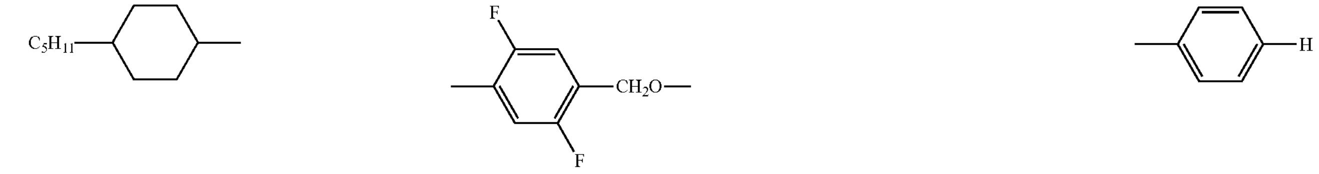
1722 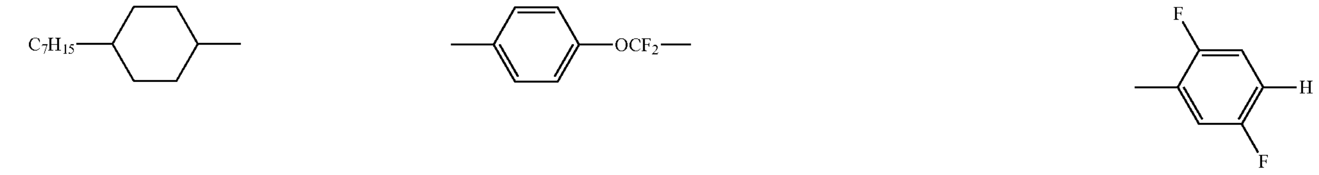
1723 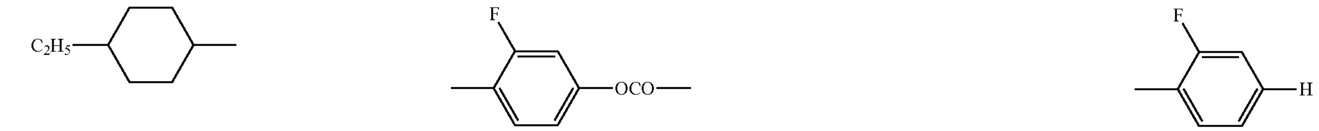

-continued
1724 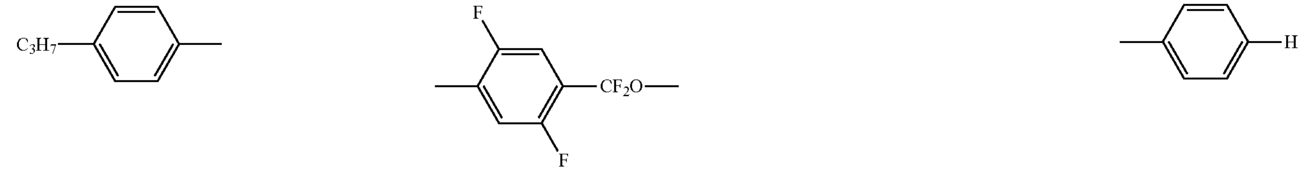
1725 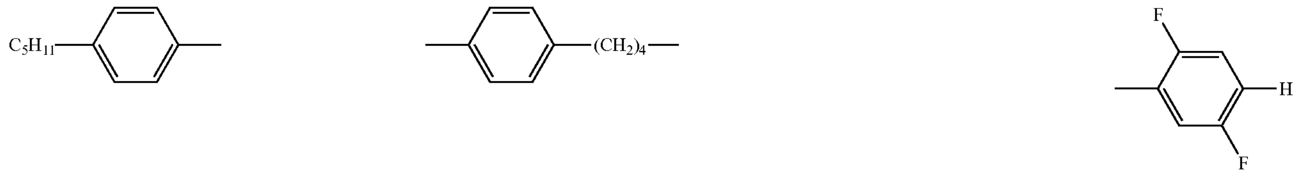
1726 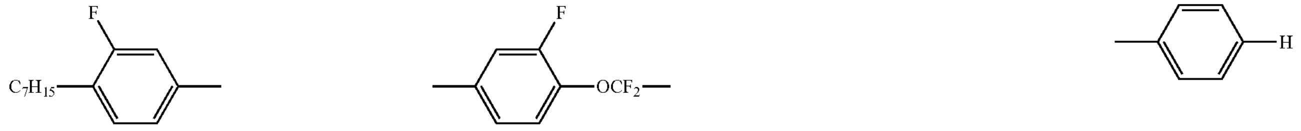
1727 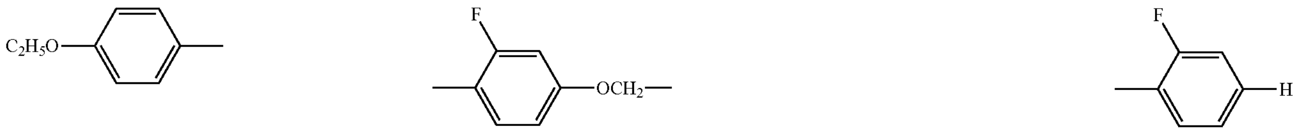
1728 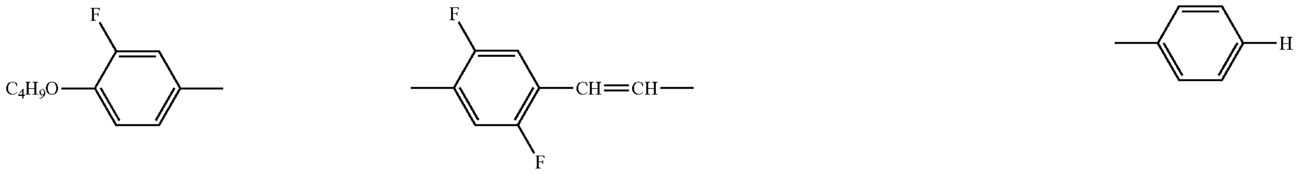
1729 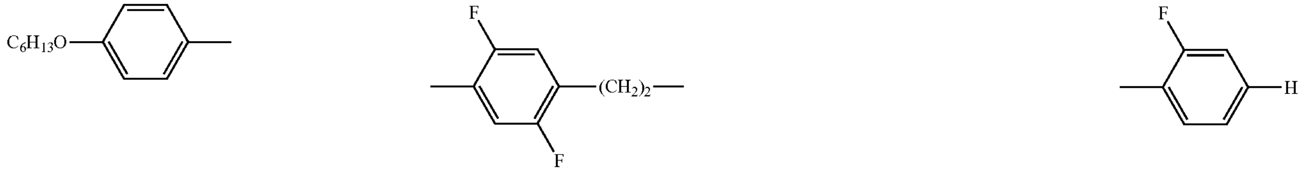

-continued
| | |
|---|---|
| 1730 | 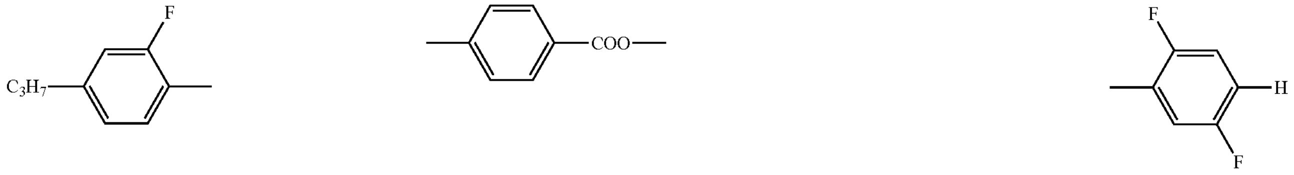 |
| 1731 | 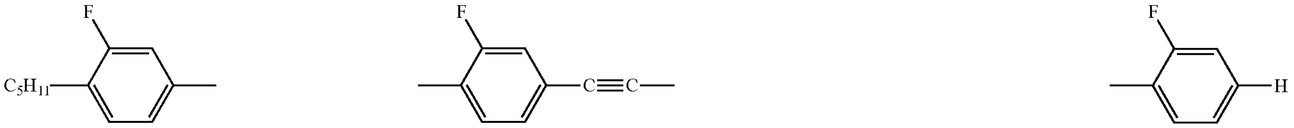 |
| 1732 | 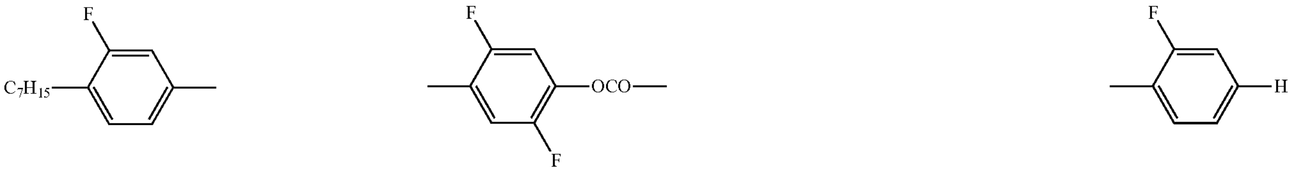 |
| 1733 | 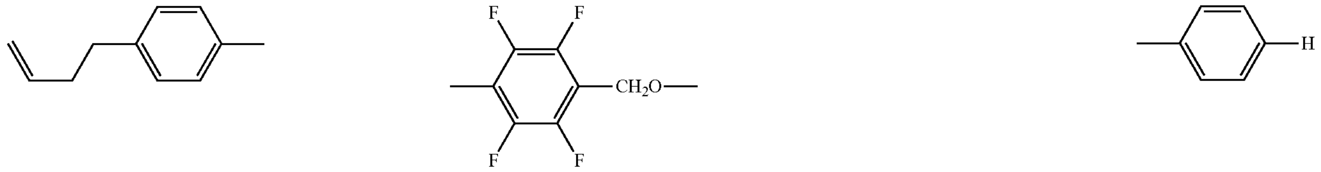 |
| 1734 | 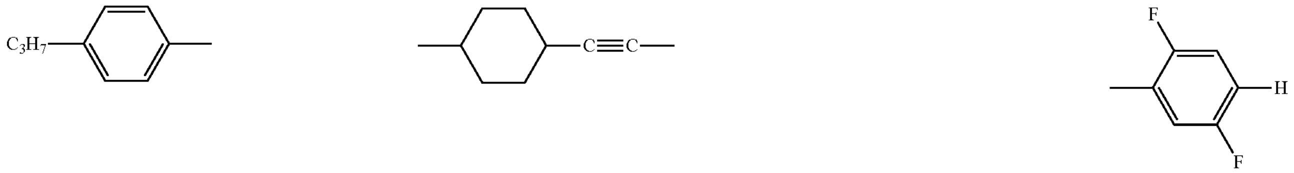 |
| 1735 | 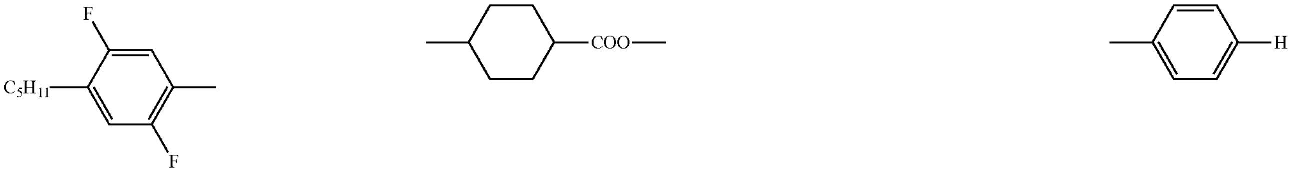 |

-continued
1736 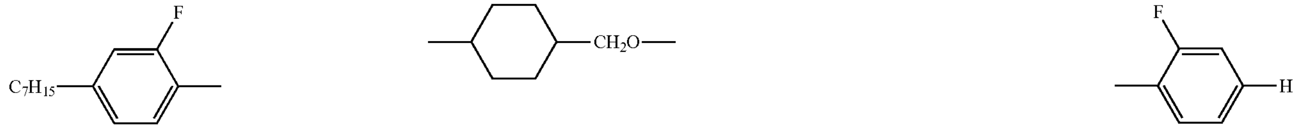
1737 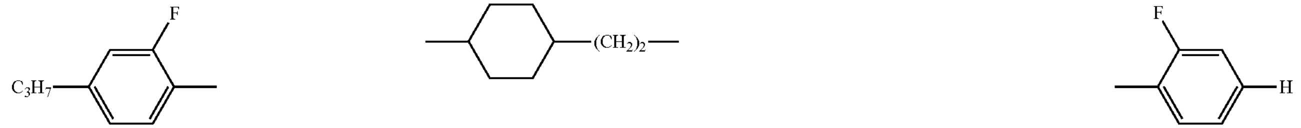
1738 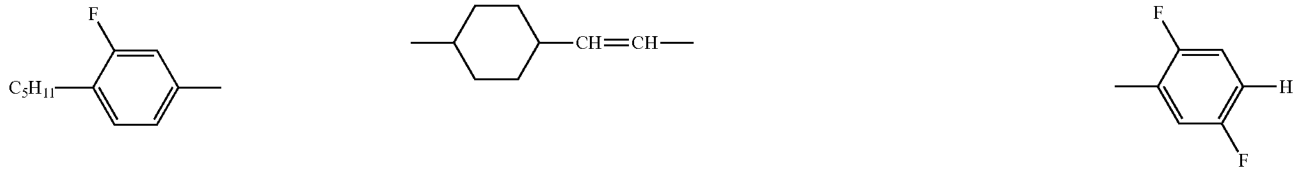
1739 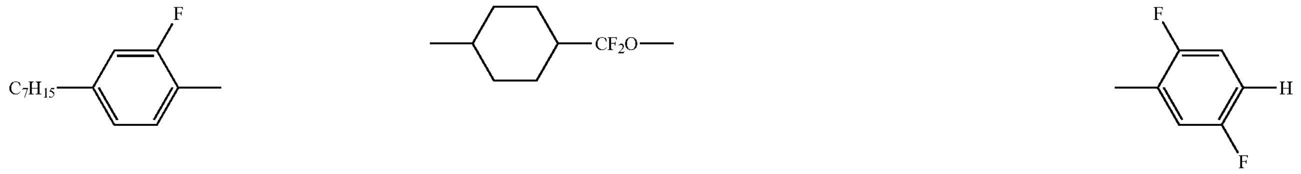
1740 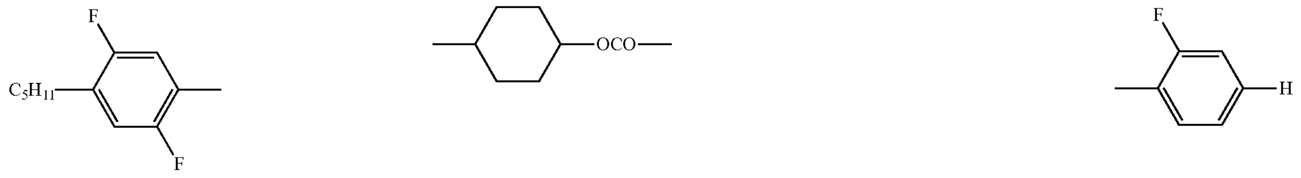
1741 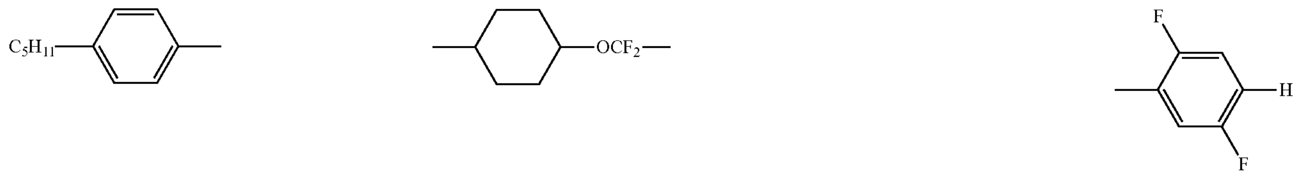

-continued
1742 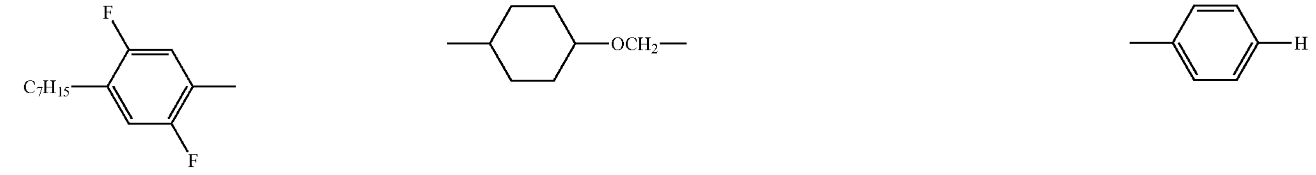
1743 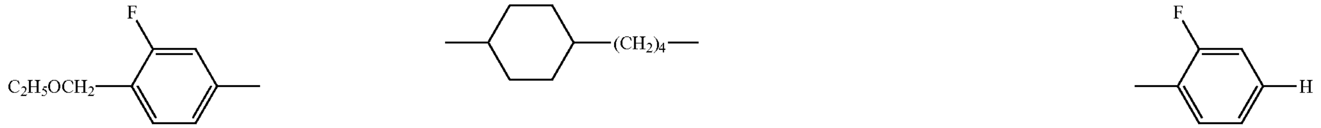
1744 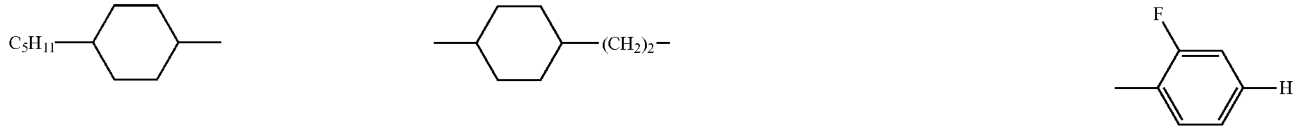
1745 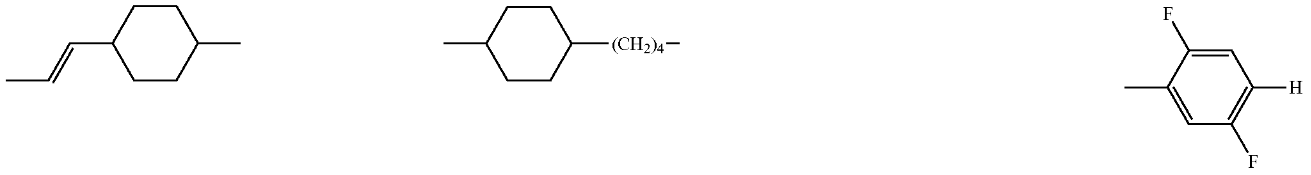
1746 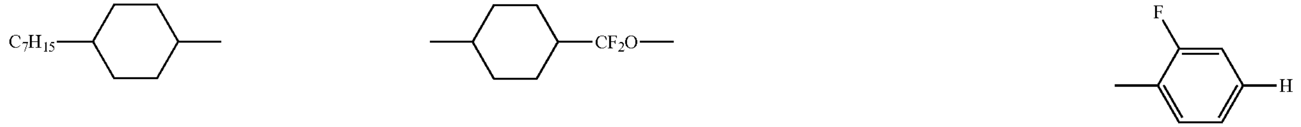
1747 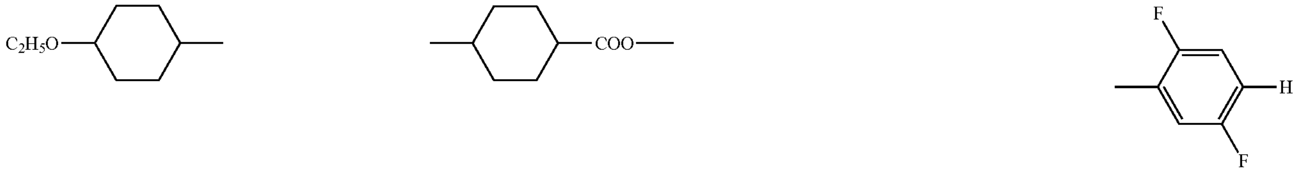

-continued
1748 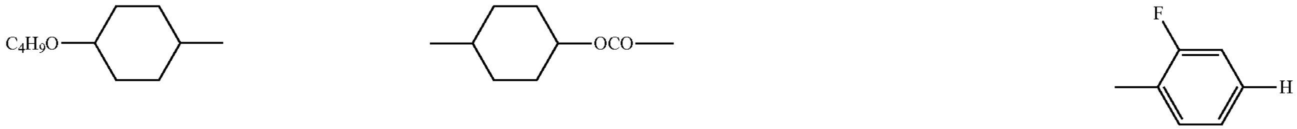
1749 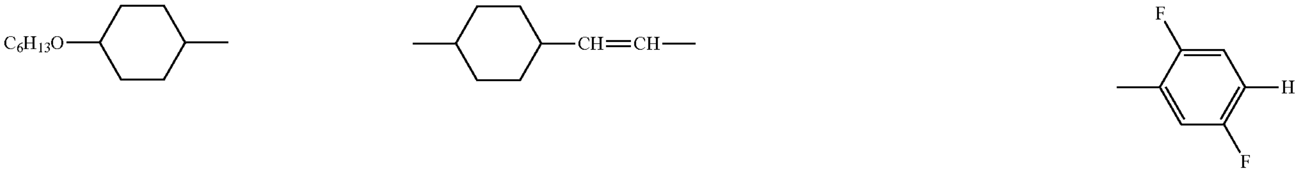
1750 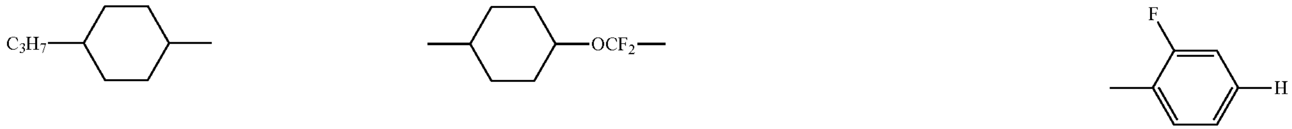
1751 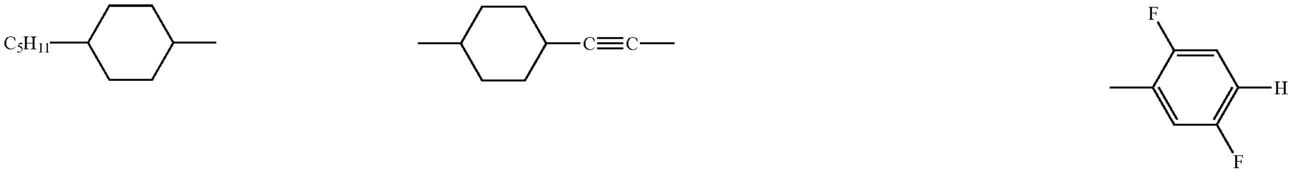
1752 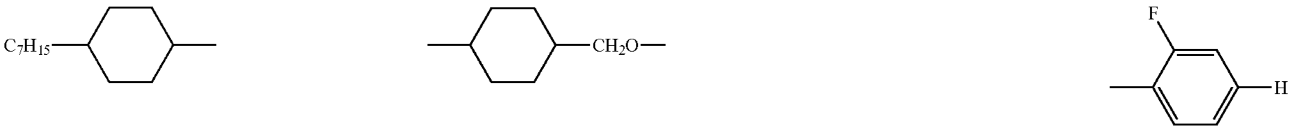
1753 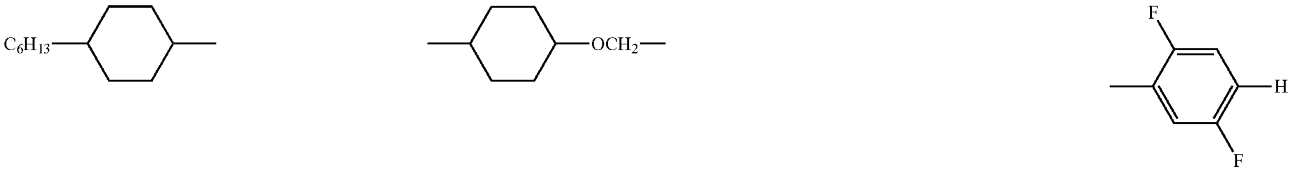

-continued
| | |
|---|---|
| 1754 | 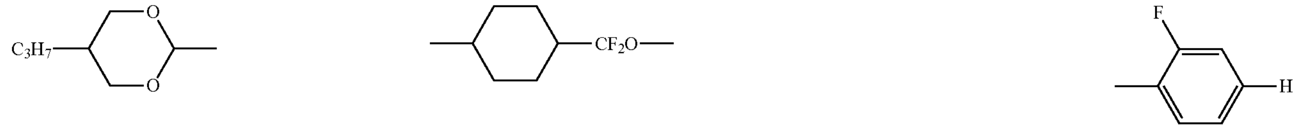 |
| 1755 | 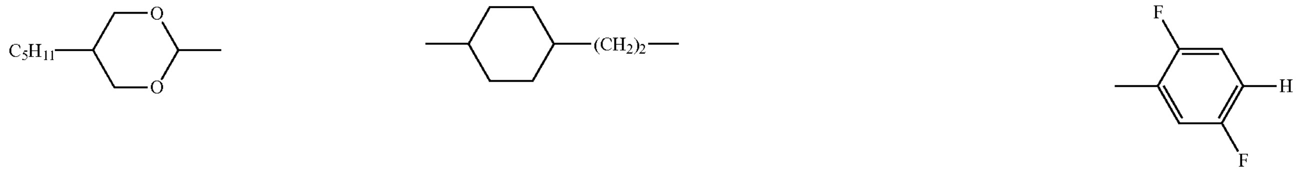 |
| 1756 | 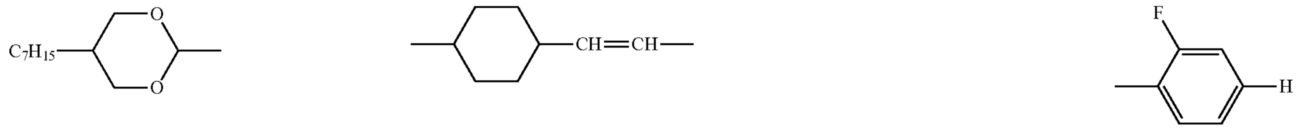 |
| 1757 | 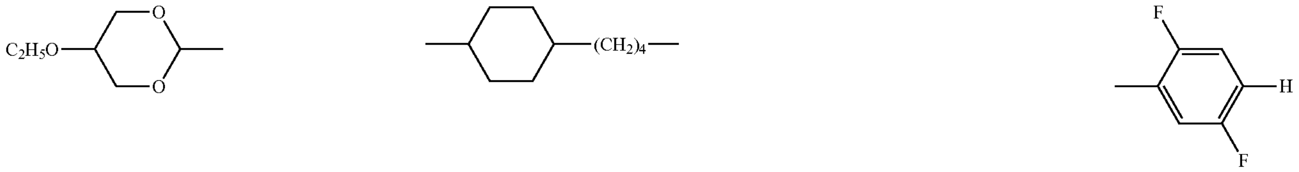 |
| 1758 | 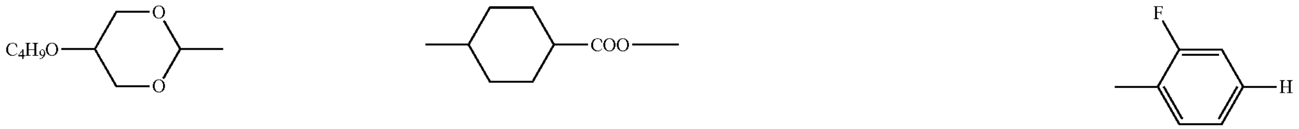 |
| 1759 | 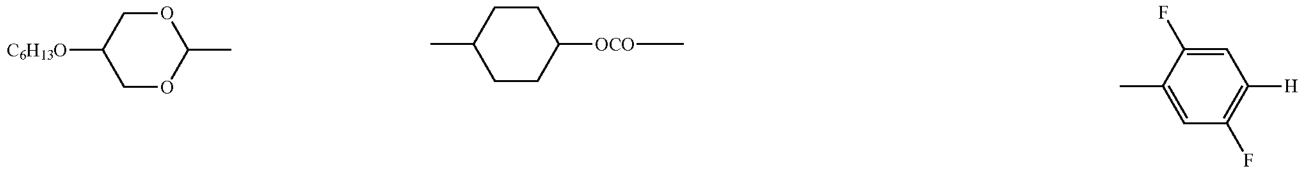 |

-continued
| | |
|---|---|
| 1760 | 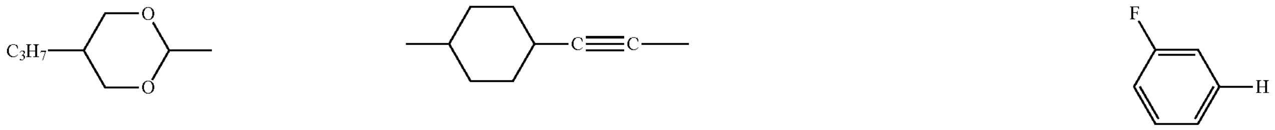 |
| 1761 | 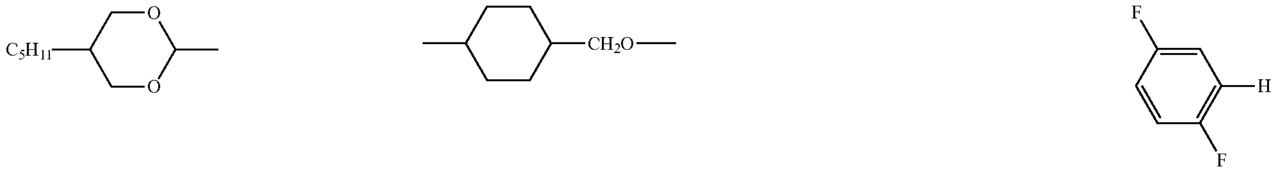 |
| 1762 | 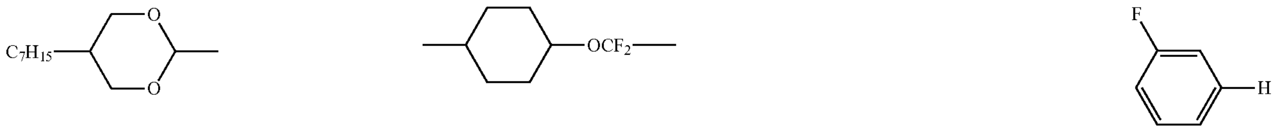 |
| 1763 | 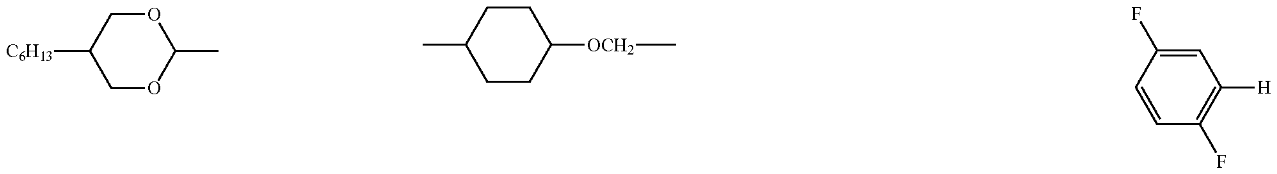 |
| 1764 | 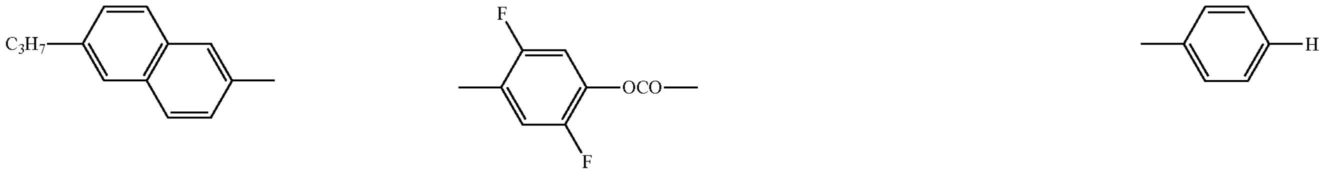 |
| 1765 | 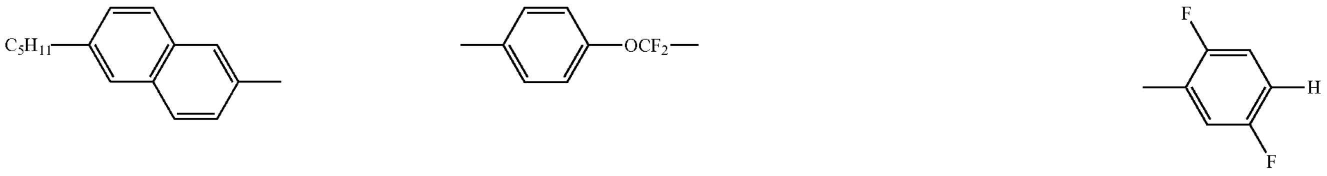 |

-continued
| | |
|---|---|
| 1766 | 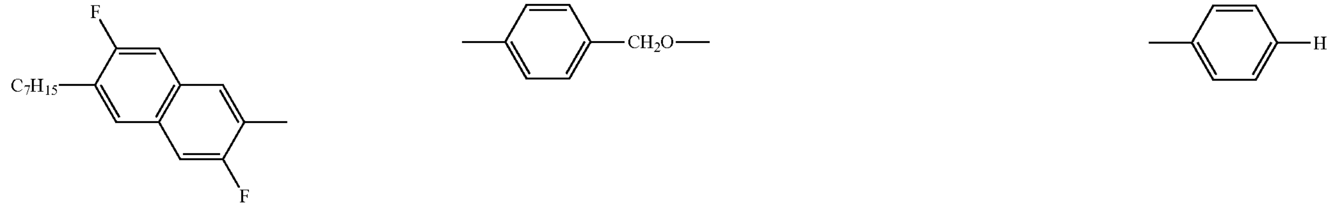 |
| 1767 | 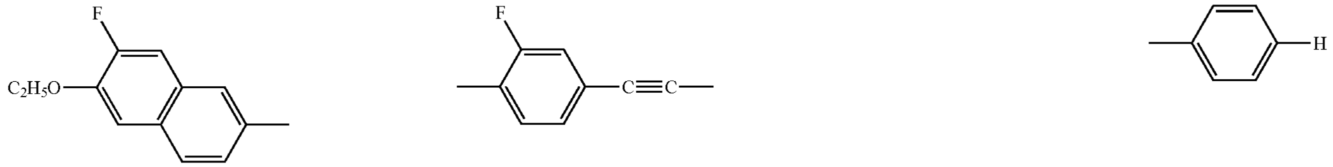 |
| 1768 | 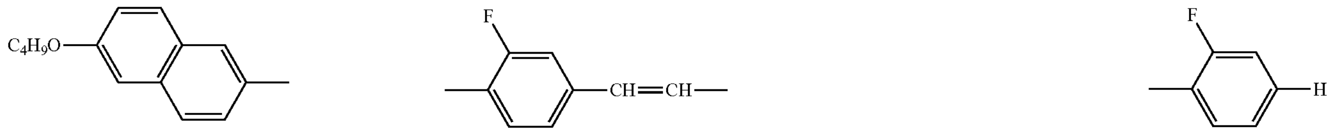 |
| 1769 | 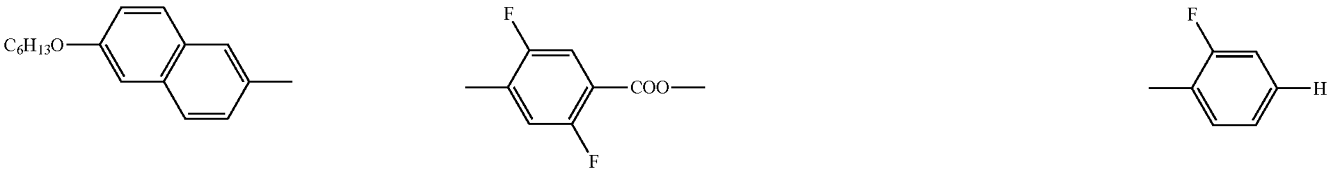 |
| 1770 | 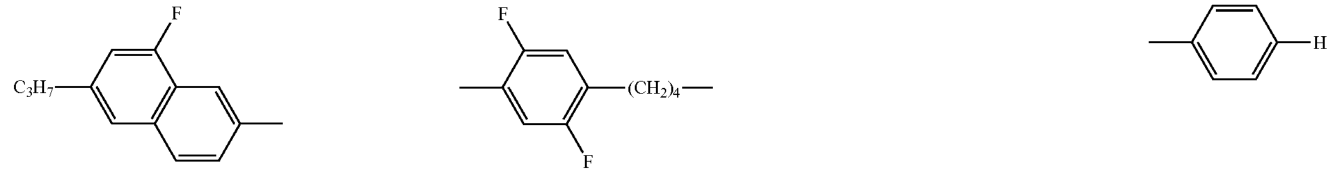 |
| 1771 | 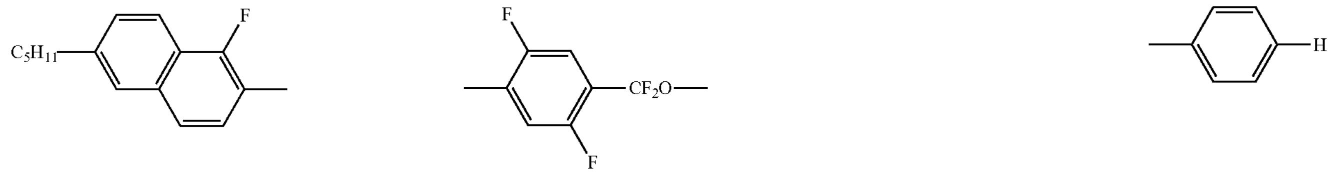 |

-continued
| | | | |
|---|---|---|---|
| 1772 | 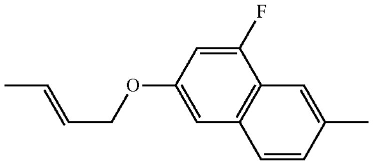 | 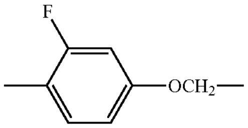 | 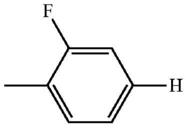 |
| 1773 | 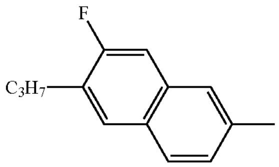 | 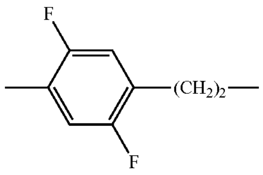 | 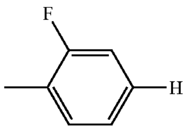 |
| 1774 | 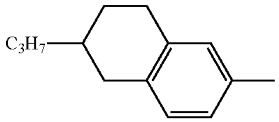 | 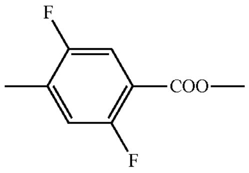 | 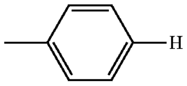 |
| 1775 | 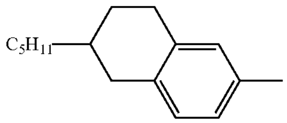 | 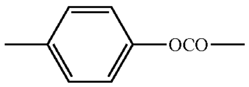 | 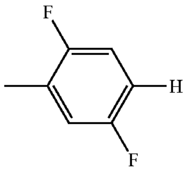 |
| 1776 | 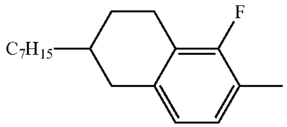 | 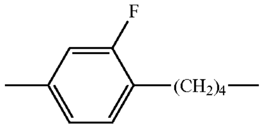 | 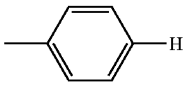 |
| 1777 | 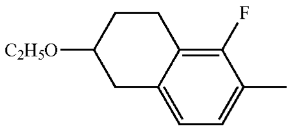 | 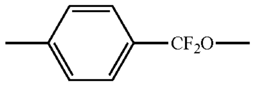 | 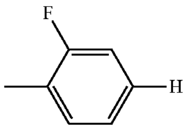 |

-continued
| | |
|---|---|
| 1778 | 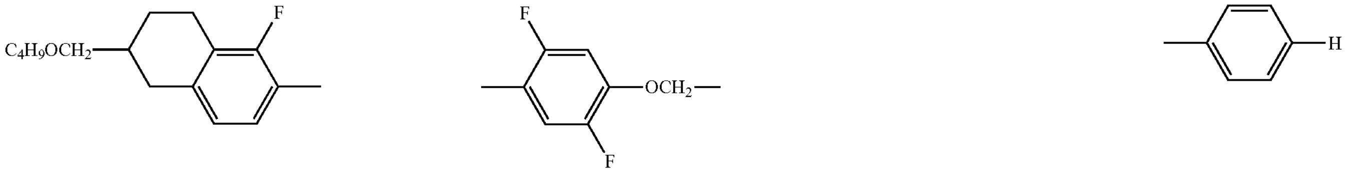 |
| 1779 | 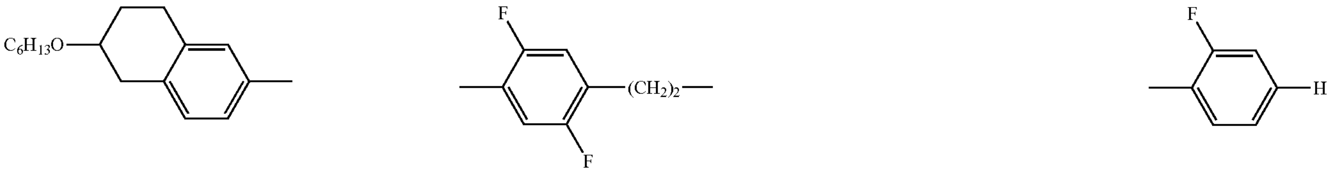 |
| 1780 | 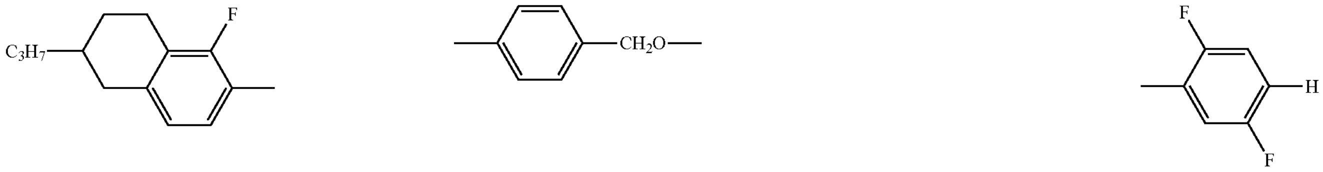 |
| 1781 | 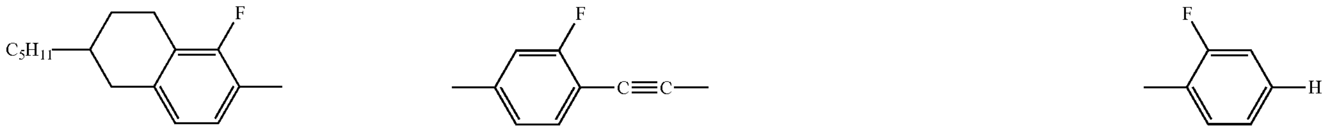 |
| 1782 | 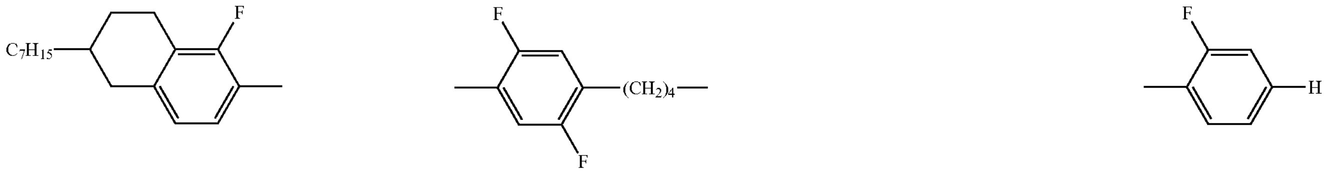 |
| 1783 | 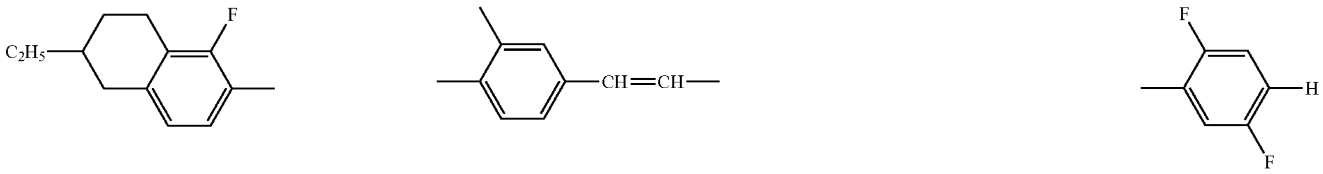 |

-continued
1784
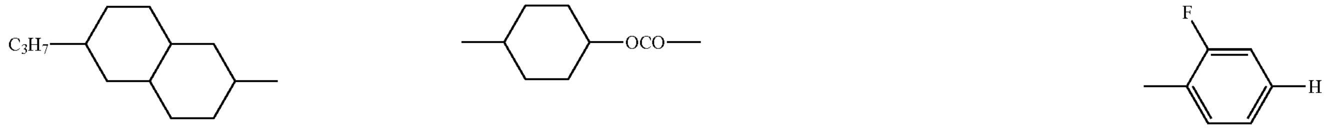
1785
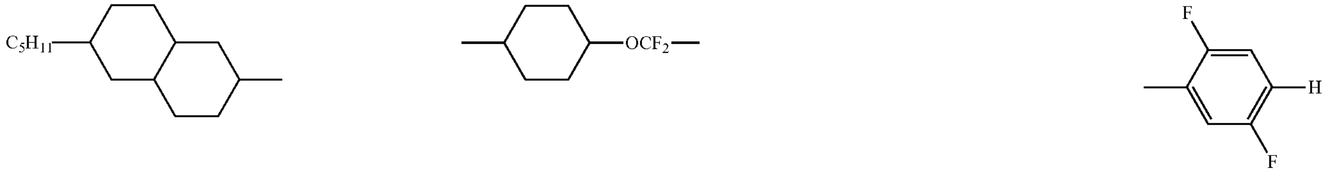
1786
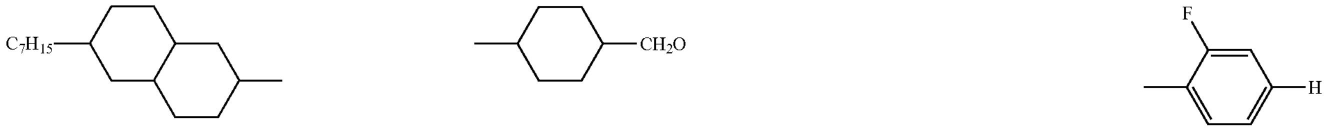
1787
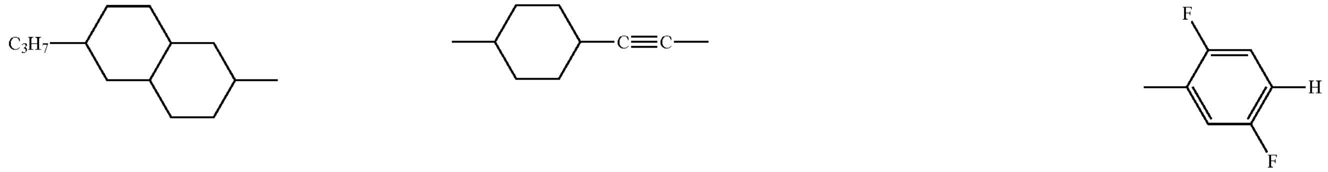
1788
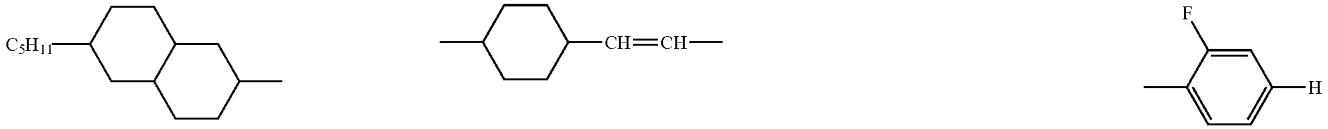
1789
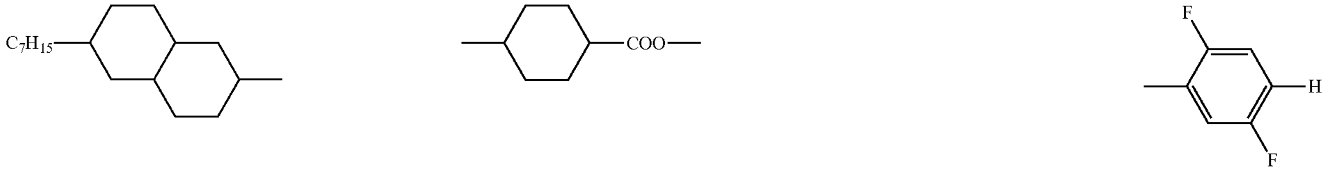

-continued
1790 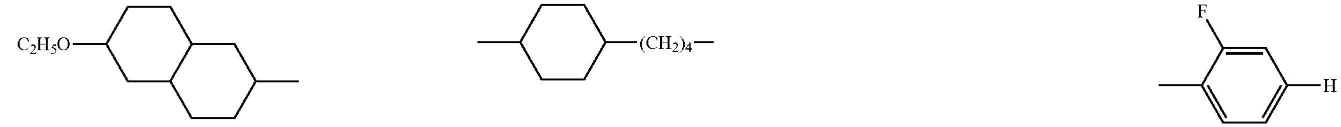
1791 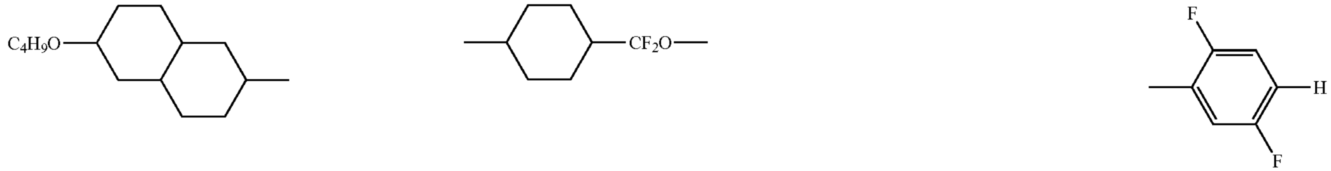
1792 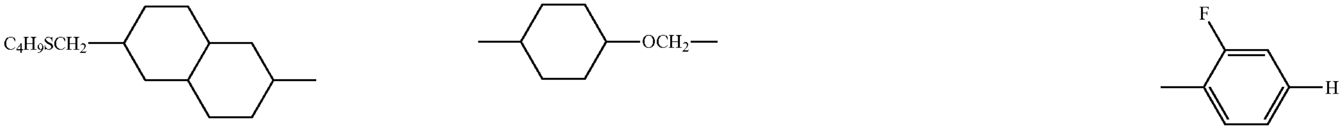
1793 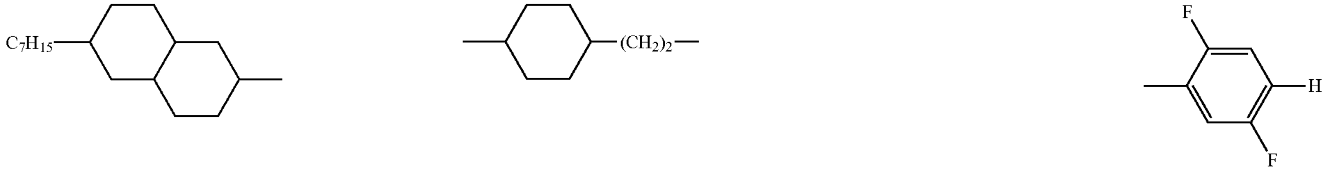
1794 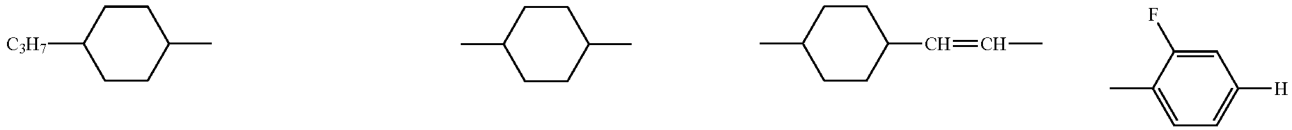
1795 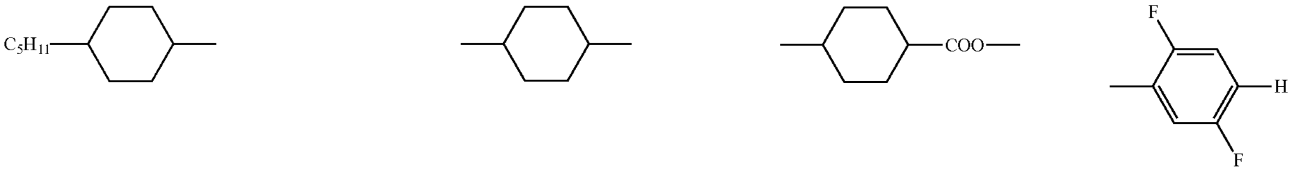

-continued
1796 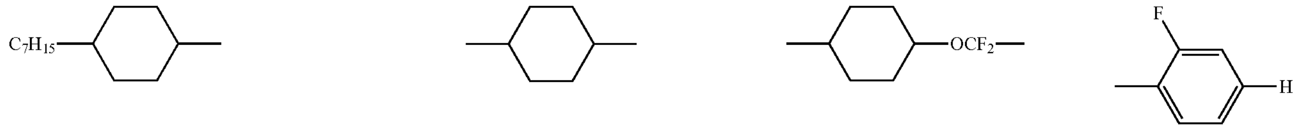
1797 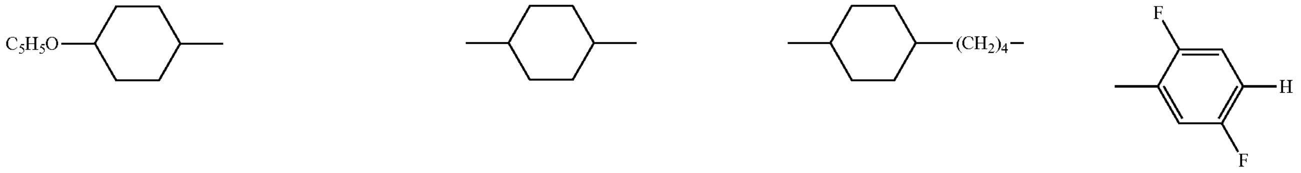
1798 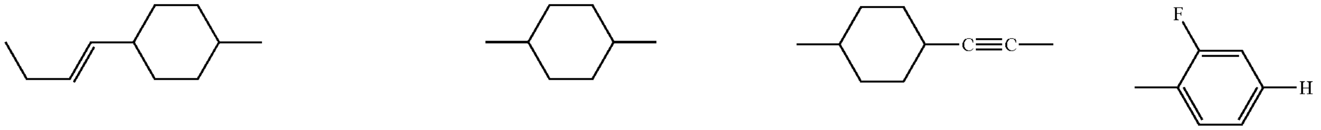
1799 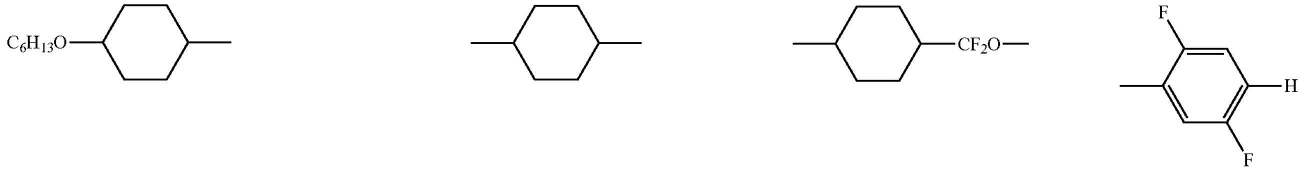
1800 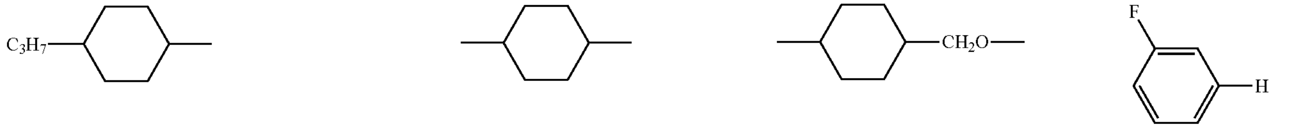
1801 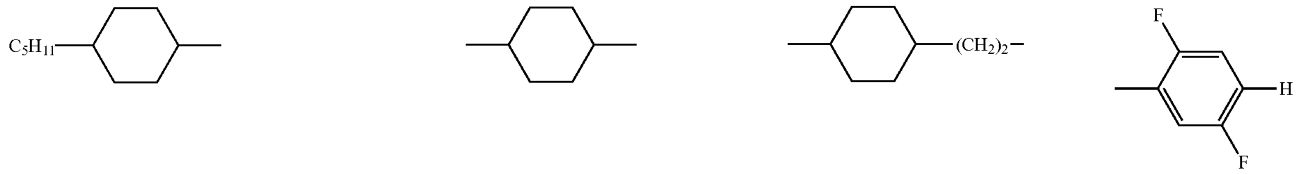

-continued
1802 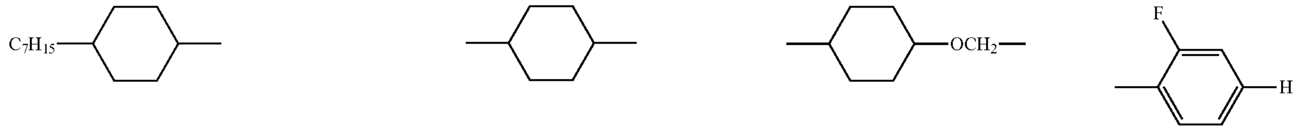
1803 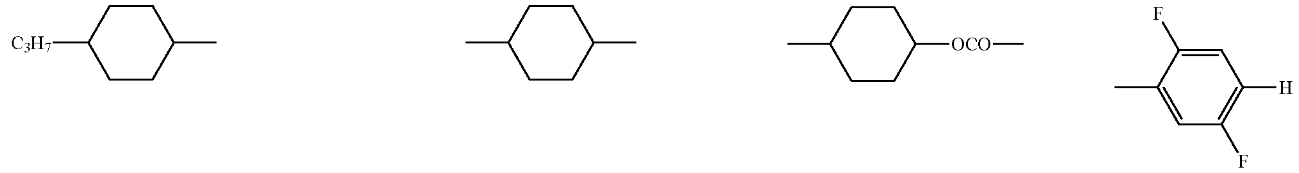
1804 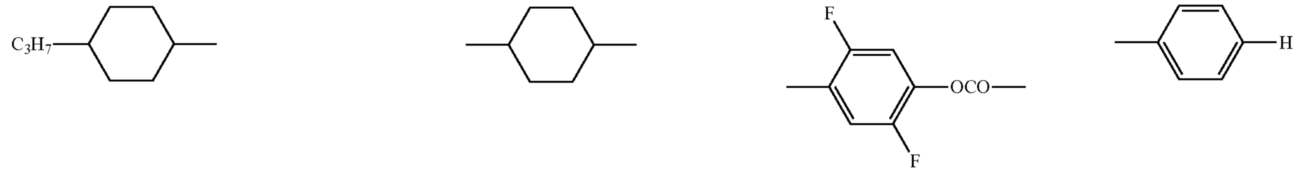
1805 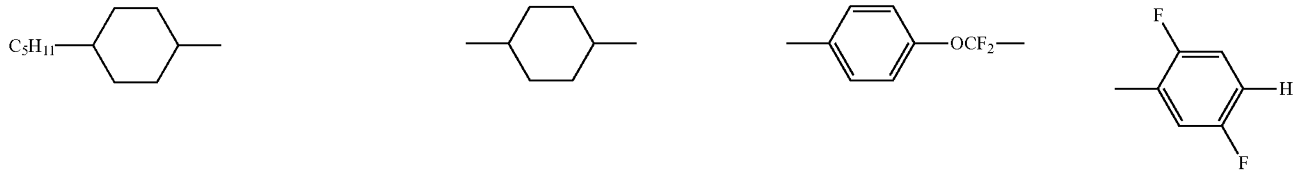
1806 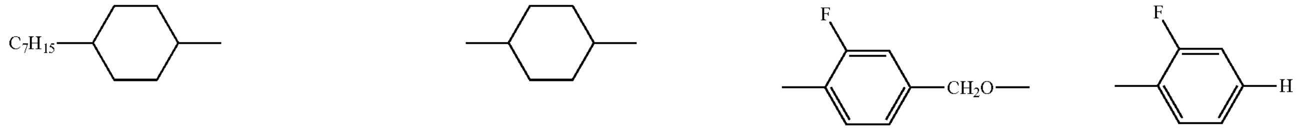
1807 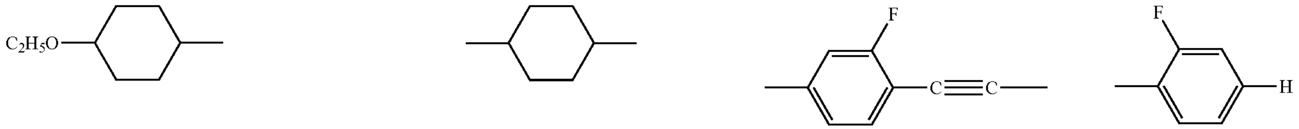

-continued
| | |
|---|---|
| 1808 | 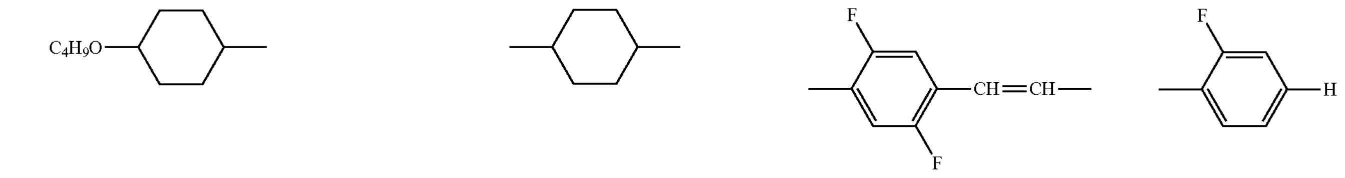 |
| 1809 | 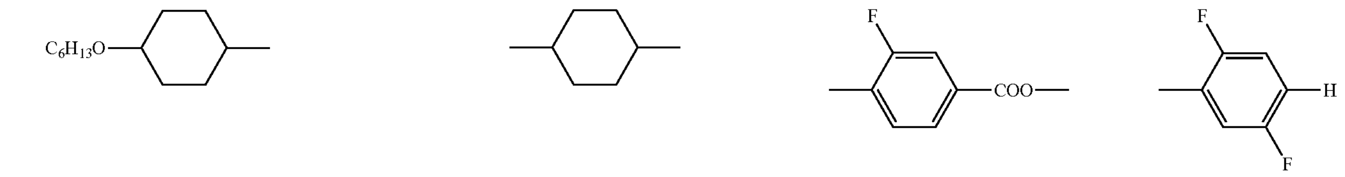 |
| 1810 | 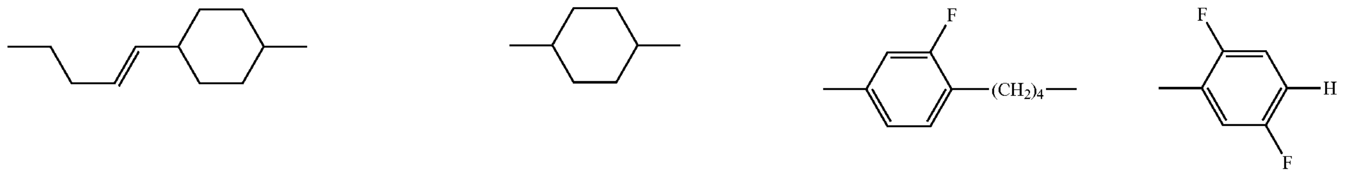 |
| 1811 | 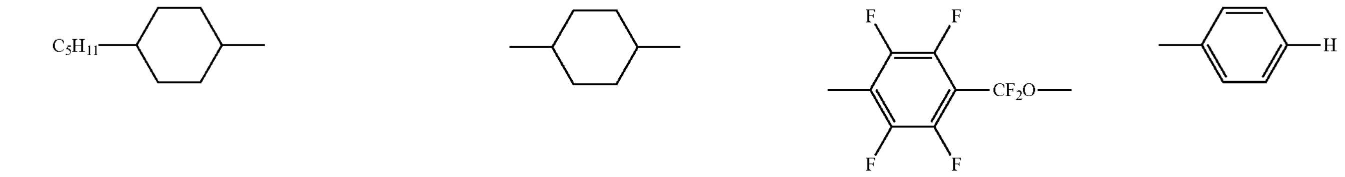 |
| 1812 | 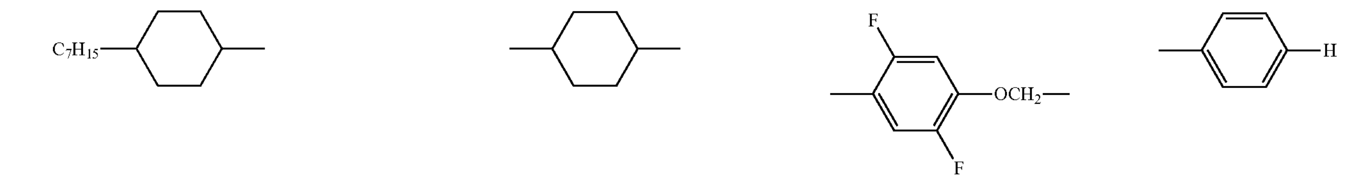 |

-continued
1813 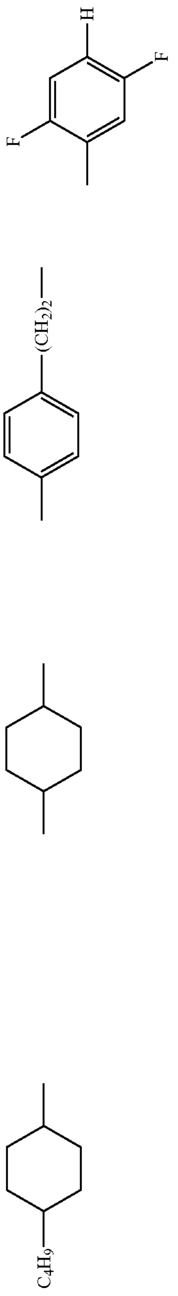
1814 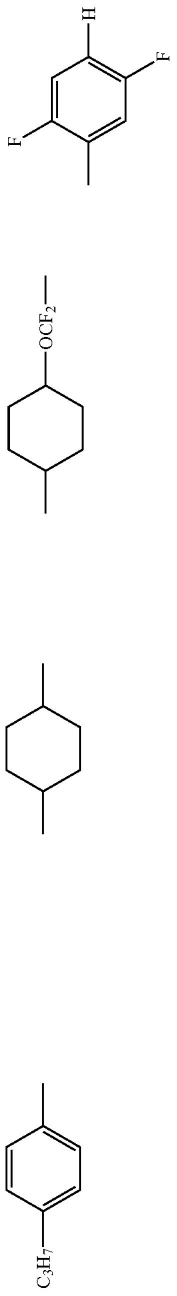
1815 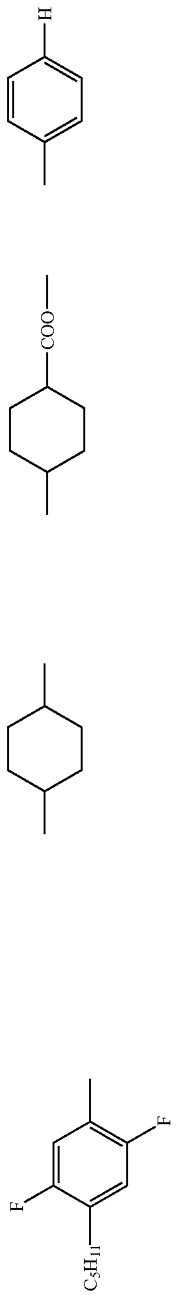
1816 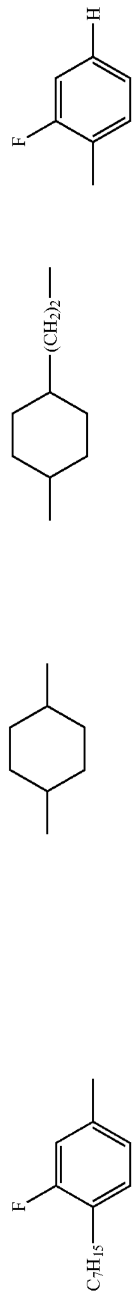
1817 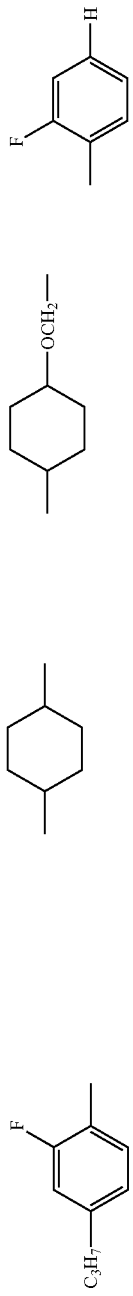
1818 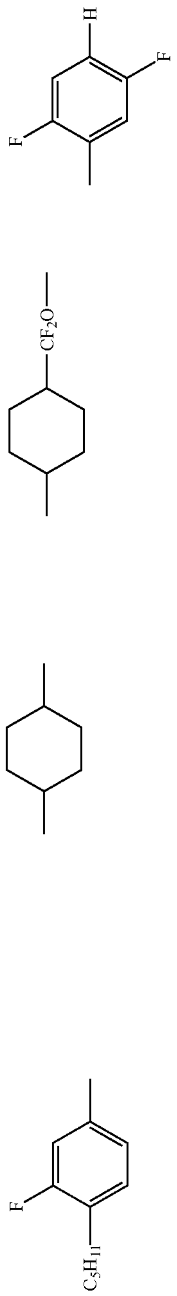

-continued
| | |
|---|---|
| 1819 | 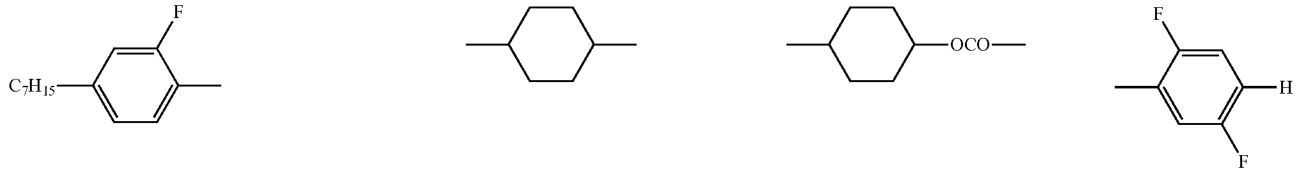 |
| 1820 | 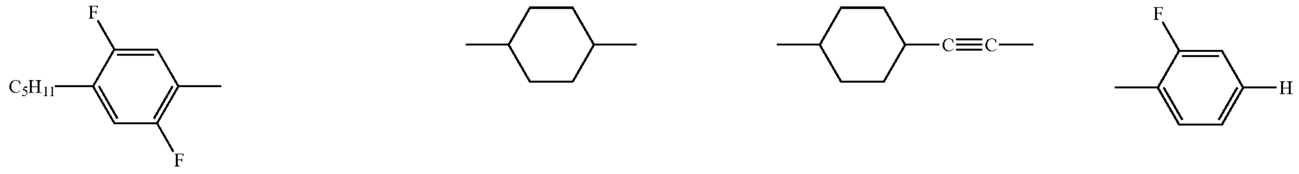 |
| 1821 | 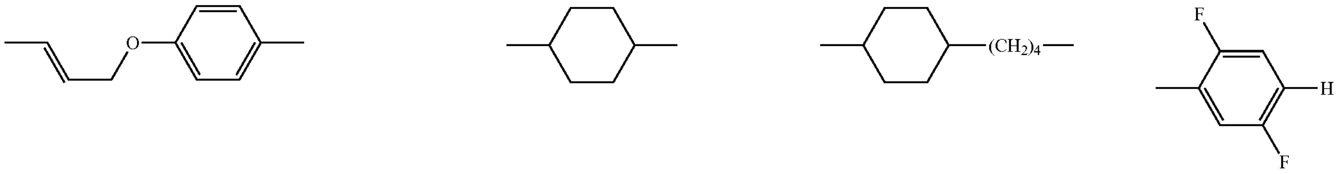 |
| 1822 | 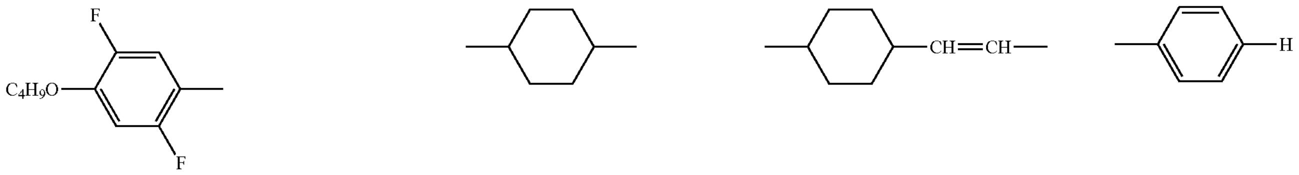 |
| 1823 | 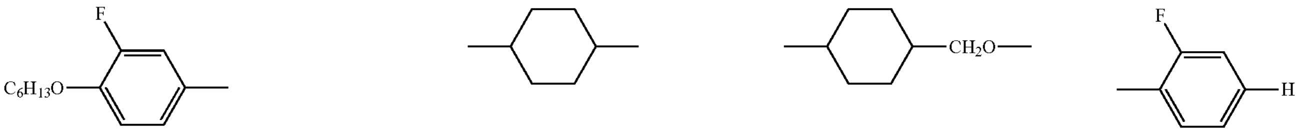 |
| 1824 | 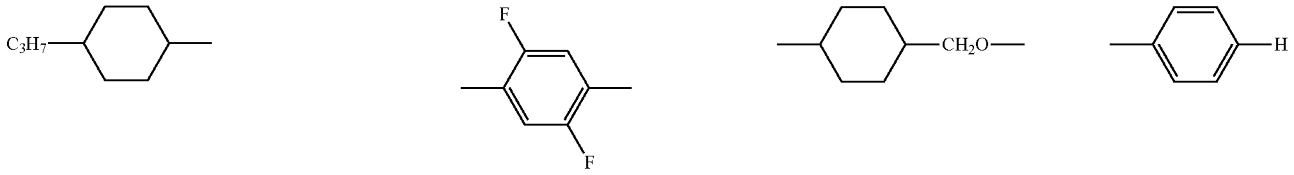 |

-continued
| | |
|---|---|
| 1825 | 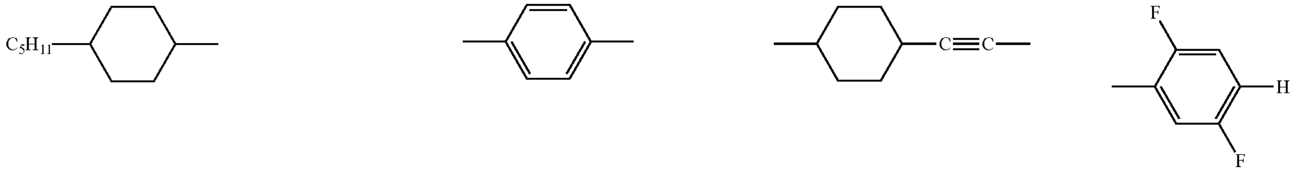 |
| 1826 | 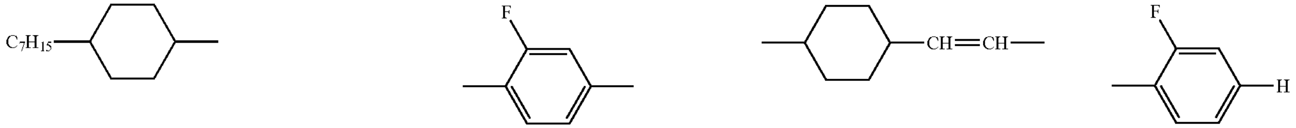 |
| 1827 | 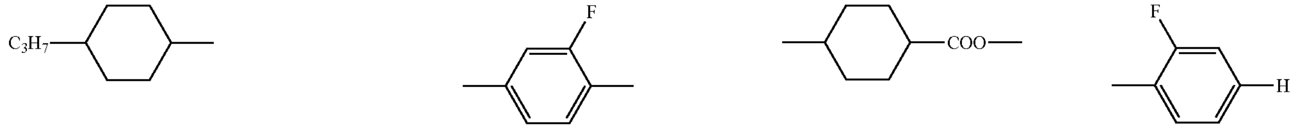 |
| 1828 | 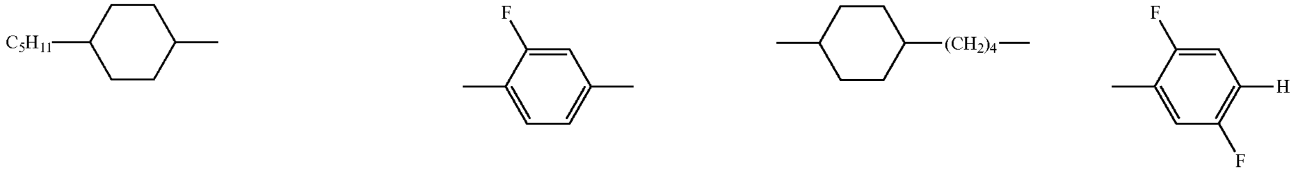 |
| 1829 | 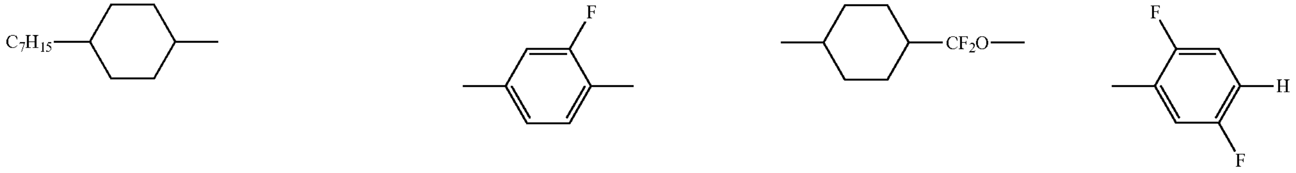 |
| 1830 | 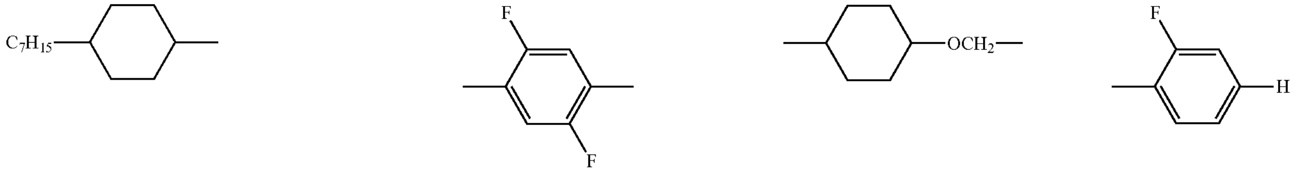 |

-continued
| | |
|---|---|
| 1831 | 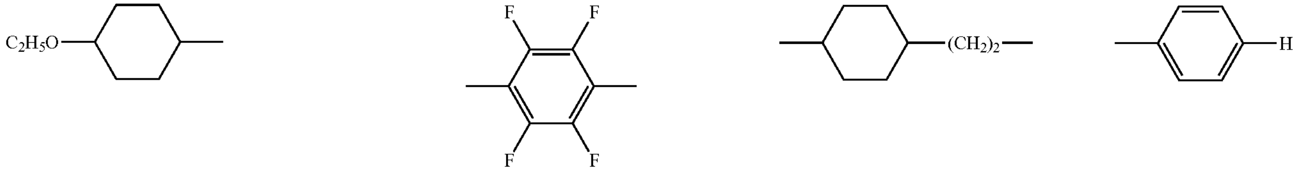 |
| 1832 | 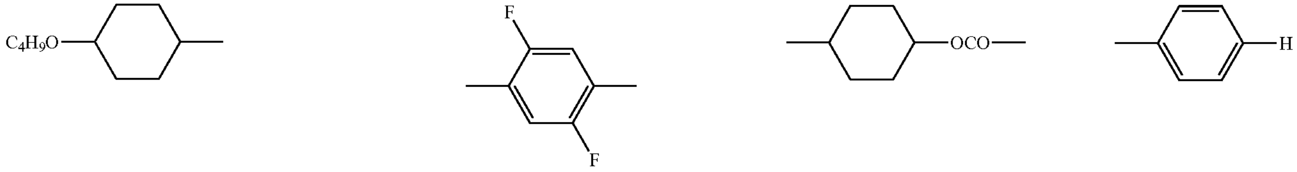 |
| 1833 | 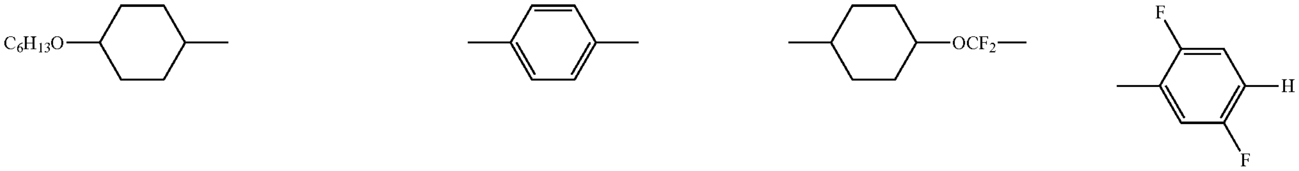 |
| 1834 | 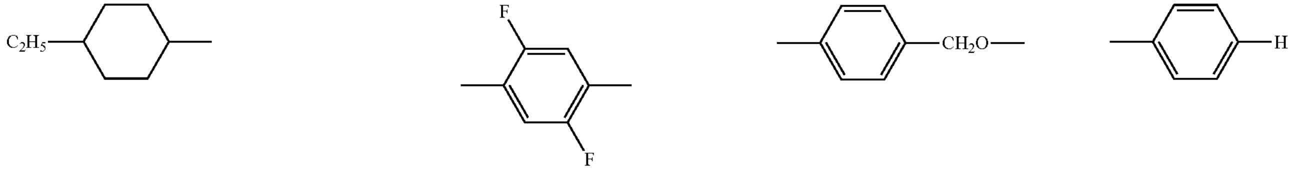 |
| 1835 | 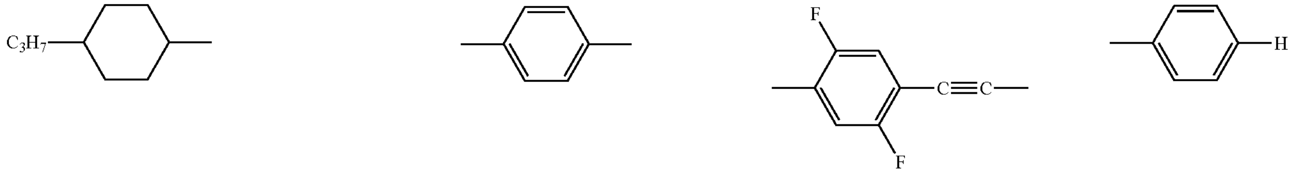 |
| 1836 | 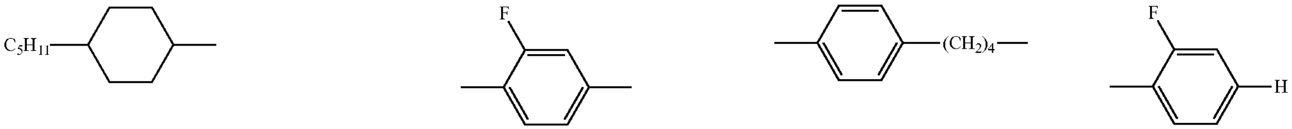 |

-continued
1837 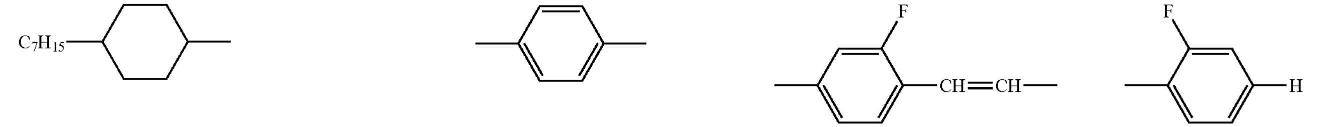
1838 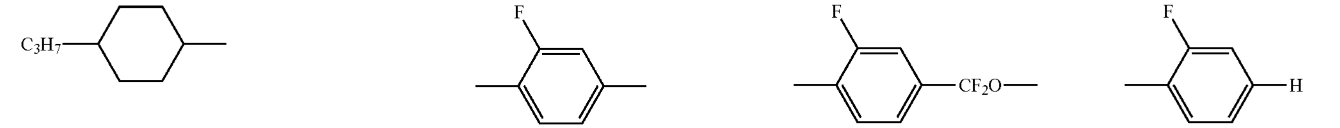
1839 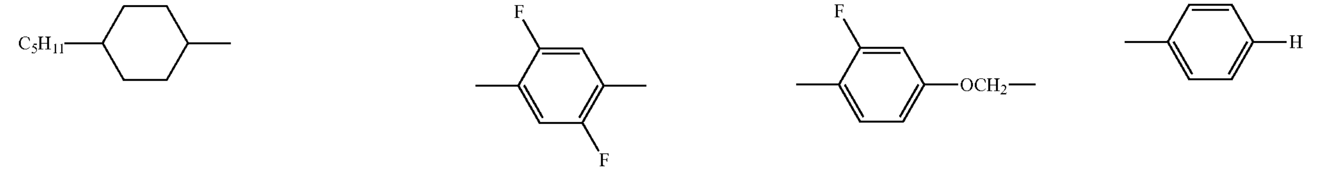
1840 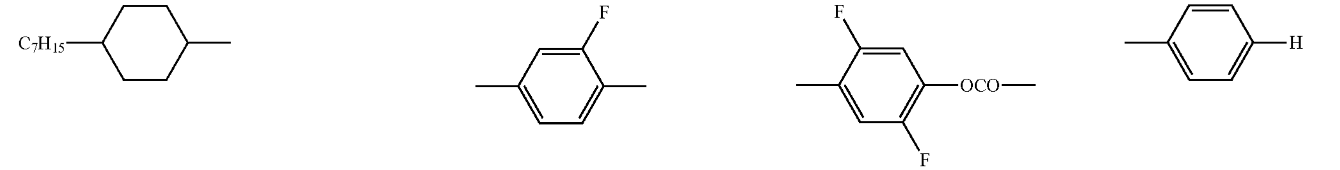
1841 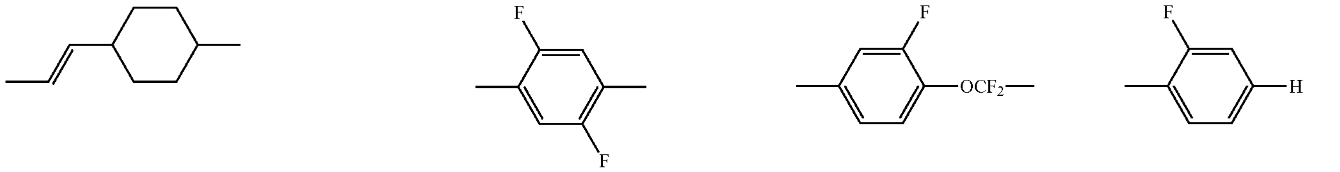
1842 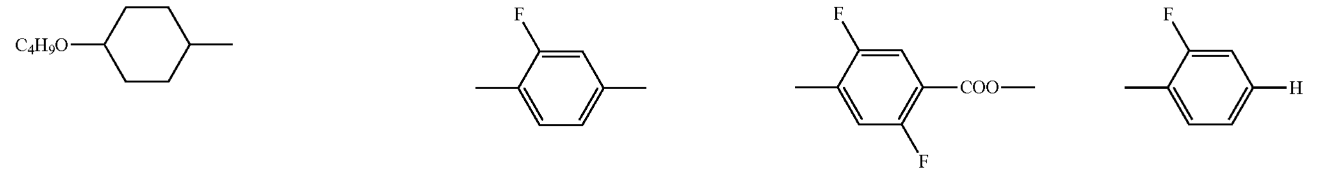

-continued
1843
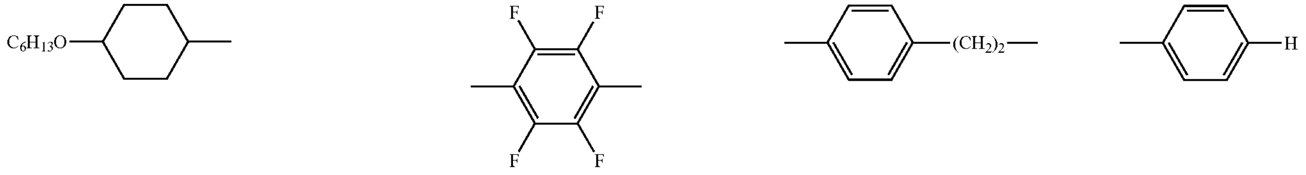
1844
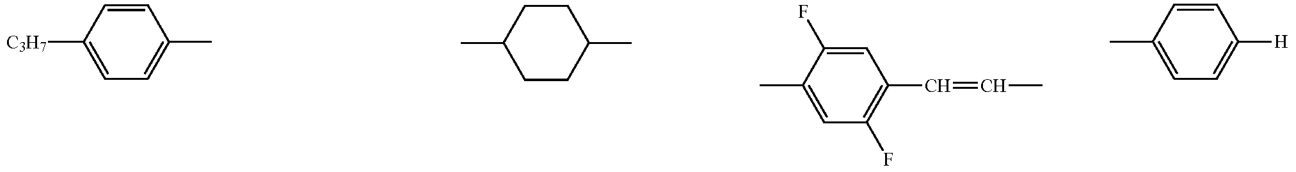
1845
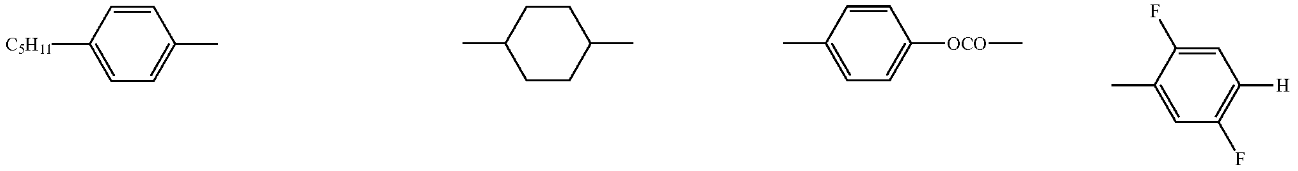
1846
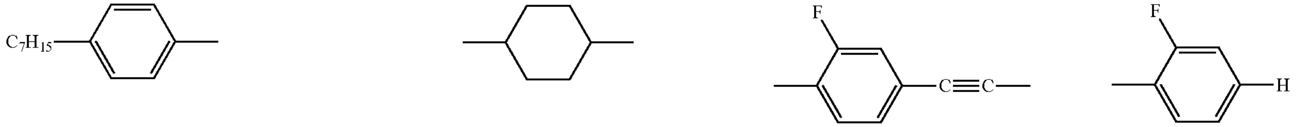
1847
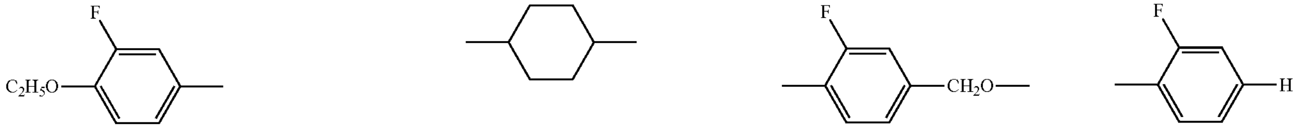
1848
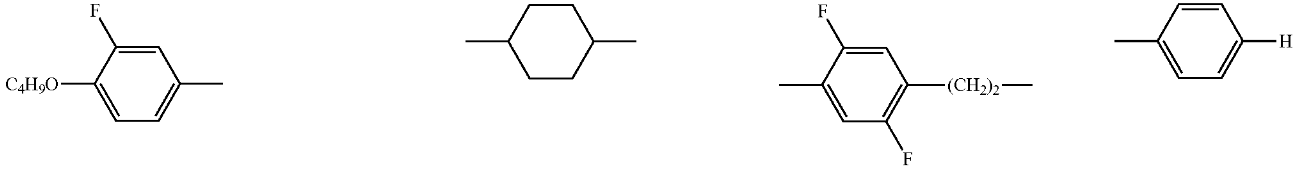

-continued
1849
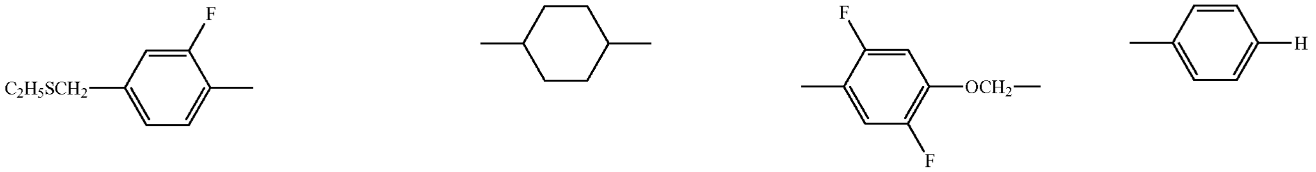
1850
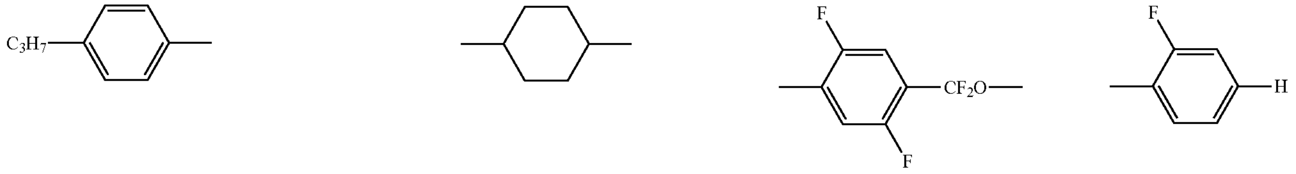
1851
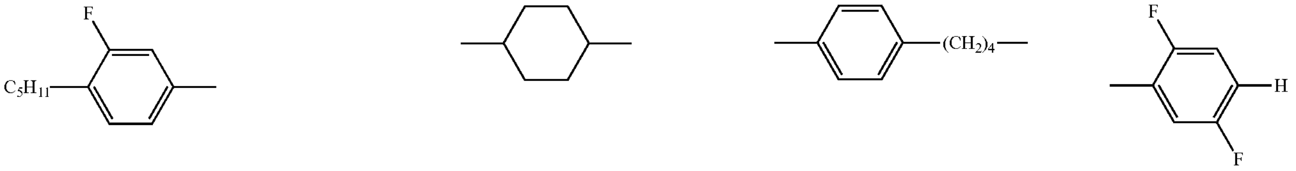
1852
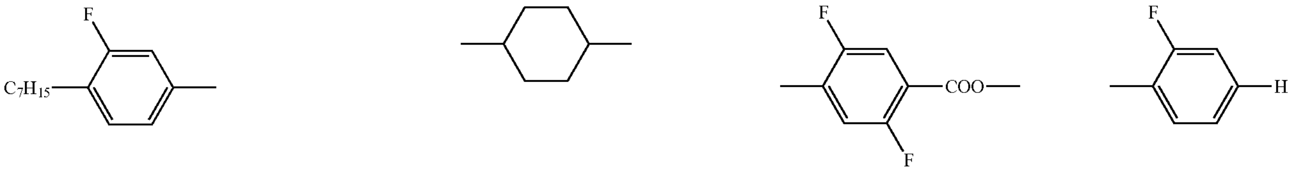
1853
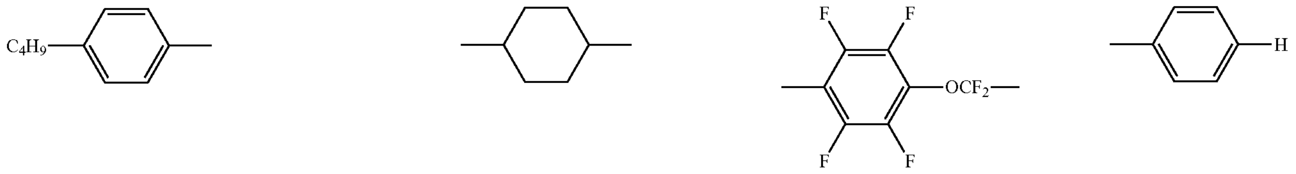

-continued
1854 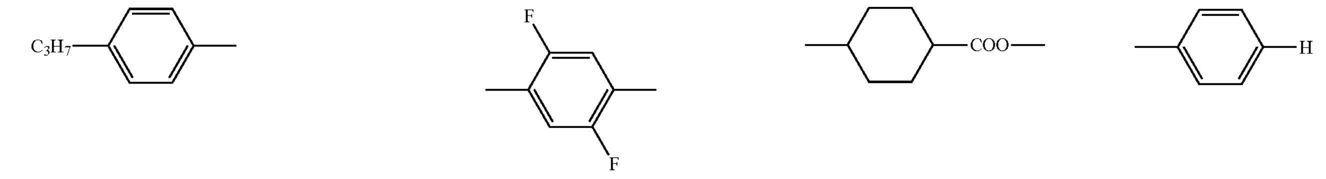
1855 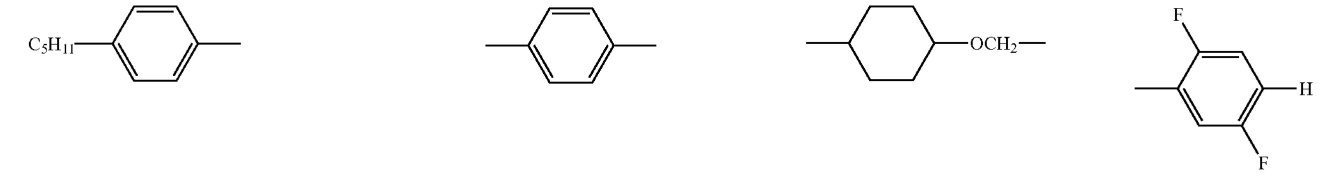
1856 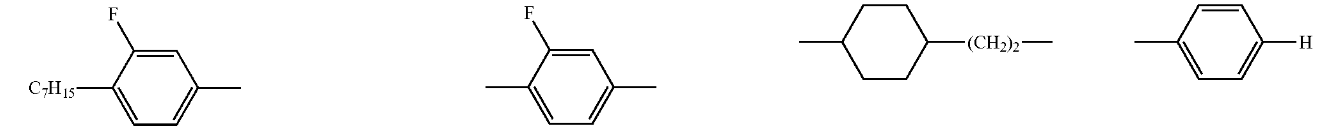
1857 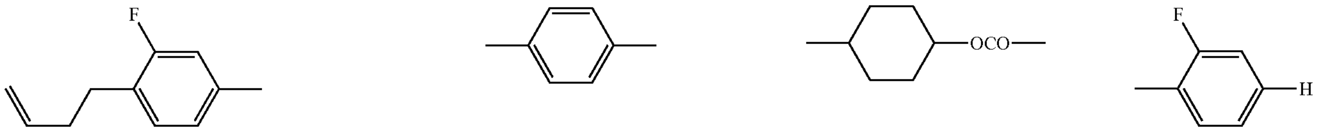
1858 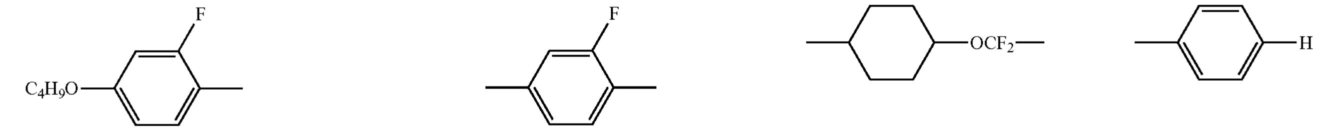
1859 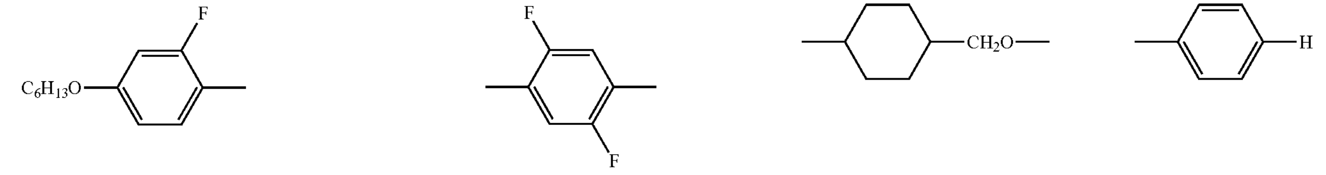

-continued
| | | | | |
|---|---|---|---|---|
| 1860 | 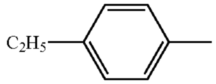 | 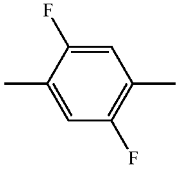 | 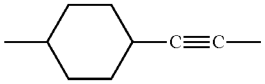 | 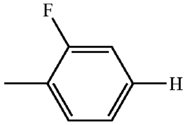 |
| 1861 | 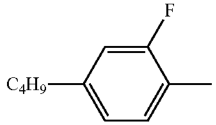 | 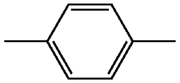 | 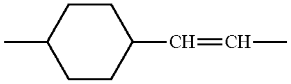 | 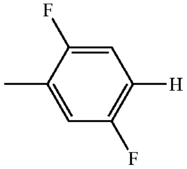 |
| 1862 | 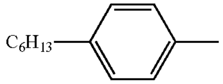 | 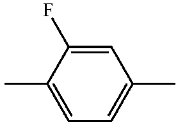 | 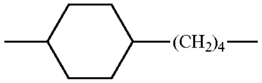 | 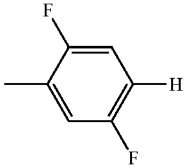 |
| 1863 | 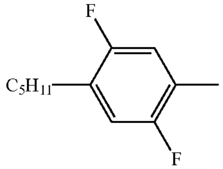 | 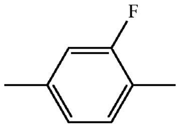 | 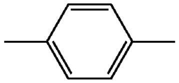 | 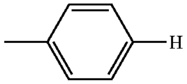 |
| 1864 | 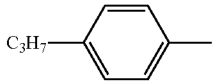 | 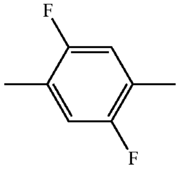 | 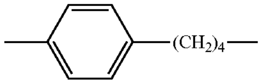 | 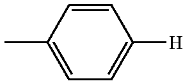 |

-continued
| | |
|---|---|
| 1865 | 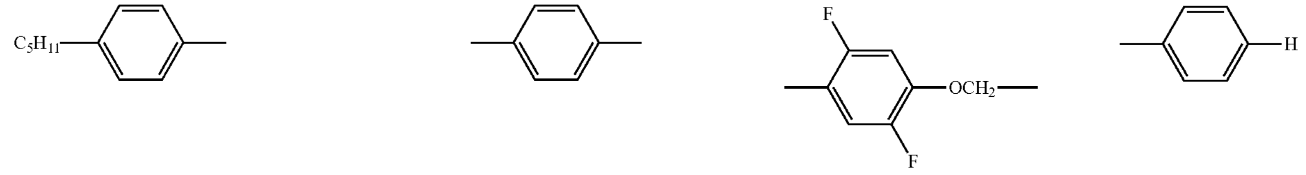 |
| 1866 | 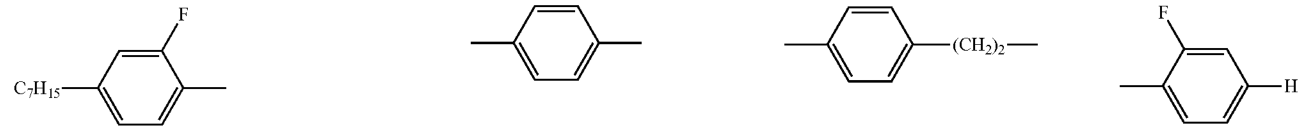 |
| 1867 | 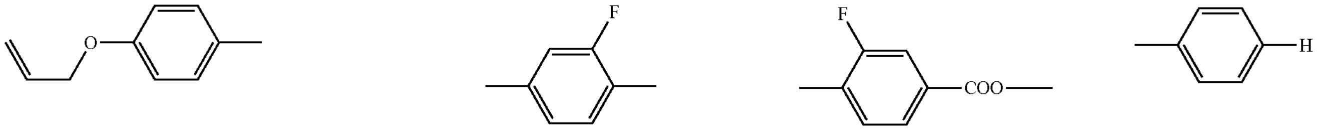 |
| 1868 | 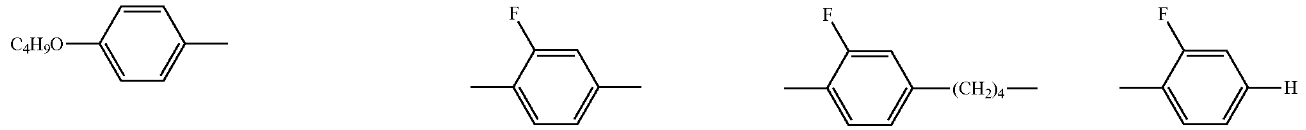 |
| 1869 | 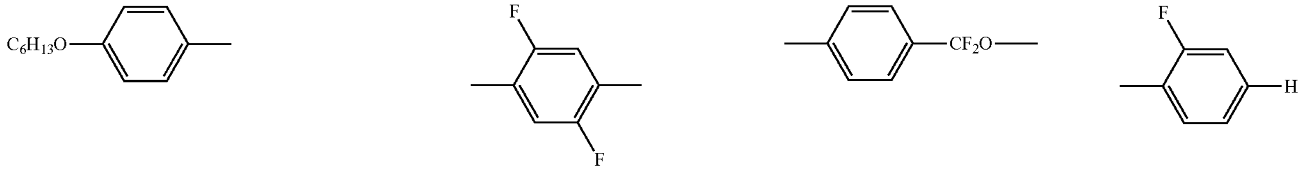 |
| 1870 | 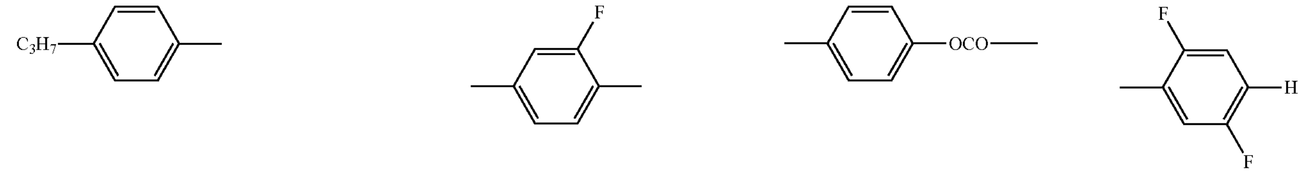 |

-continued
1871 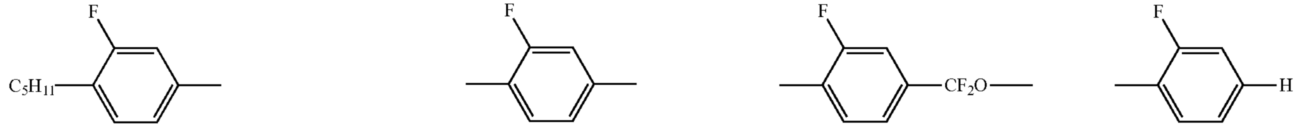
1872 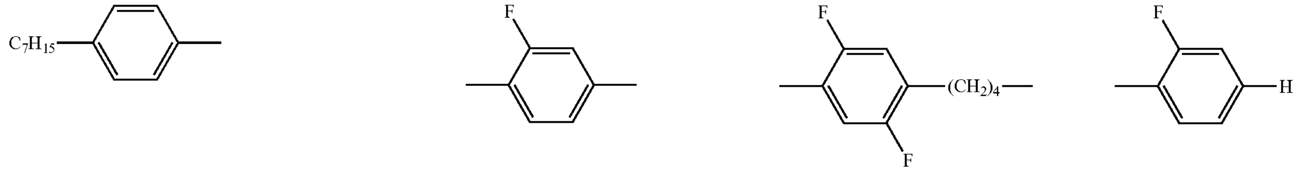
1873 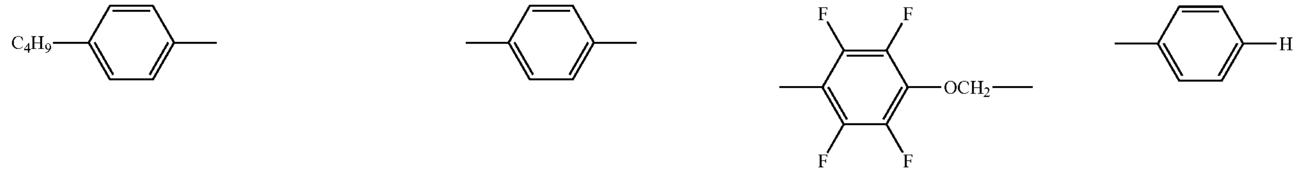
1874 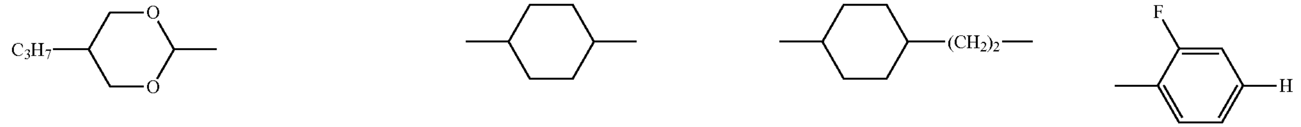
1875 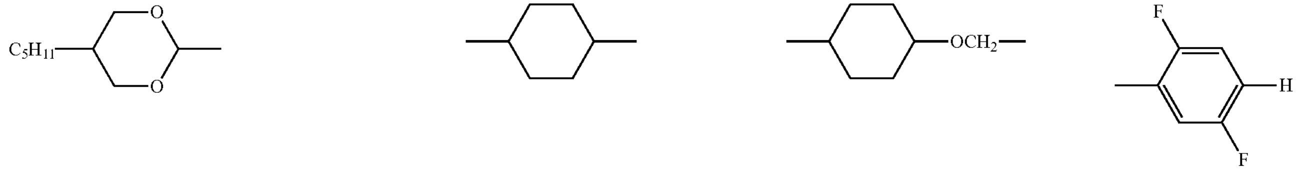
1876 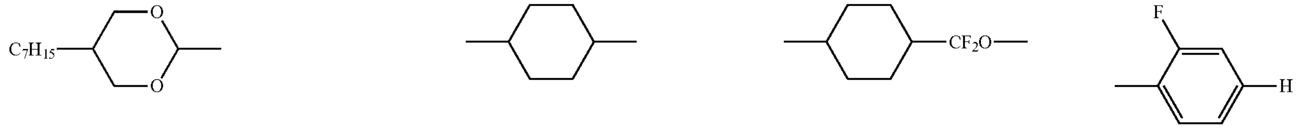

-continued
| | |
|---|---|
| 1877 | 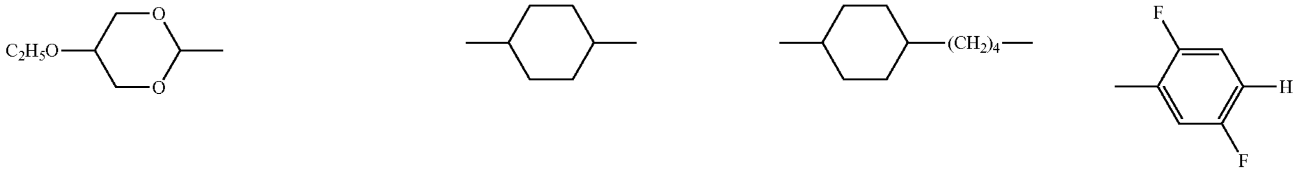 |
| 1878 | 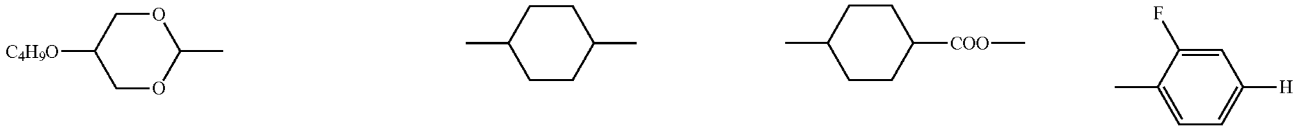 |
| 1879 | 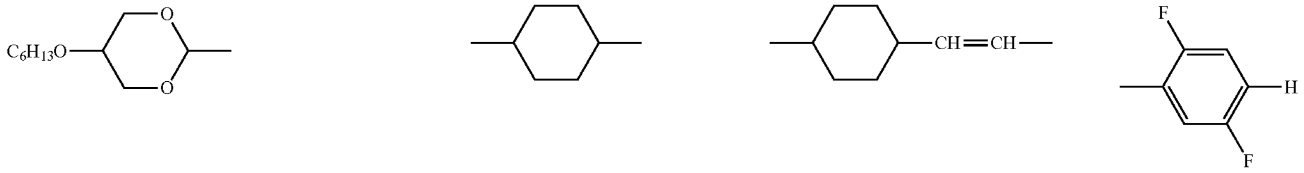 |
| 1880 | 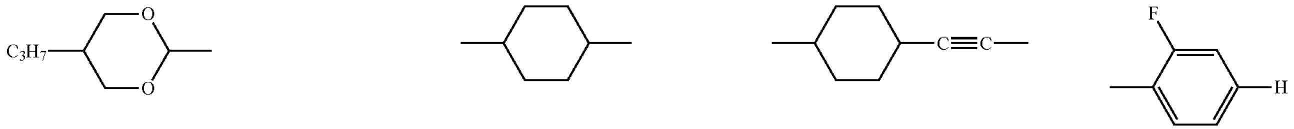 |
| 1881 | 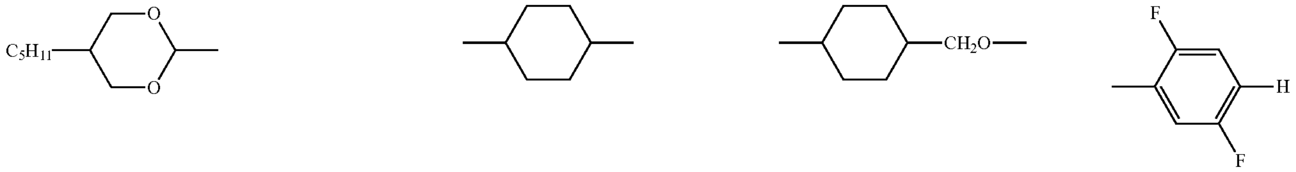 |
| 1882 | 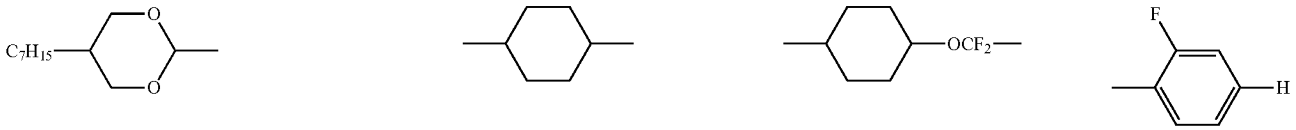 |

-continued
1883
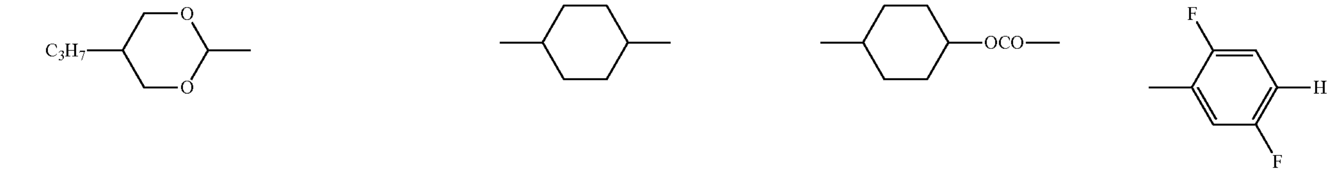
1884
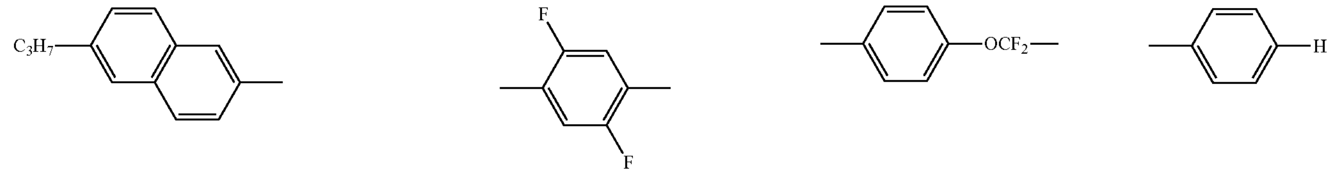
1885
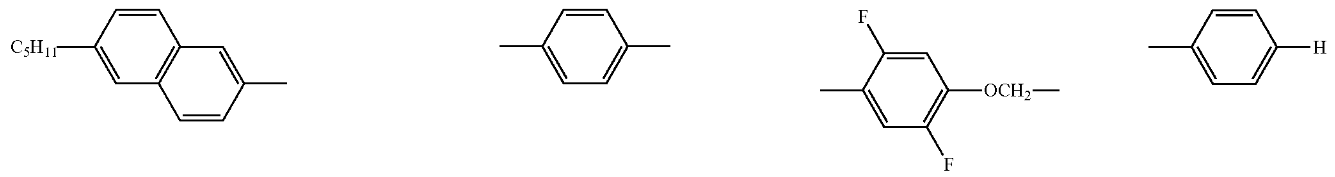
1886
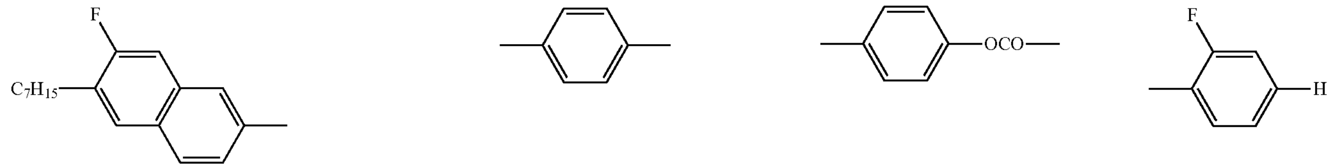
1887
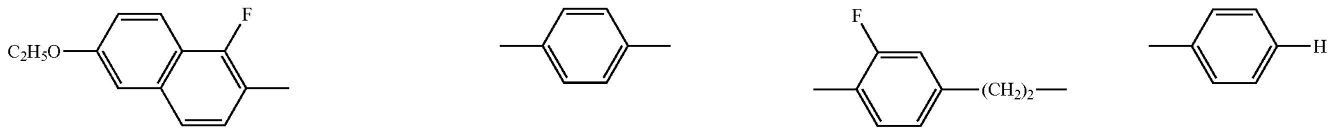
1888
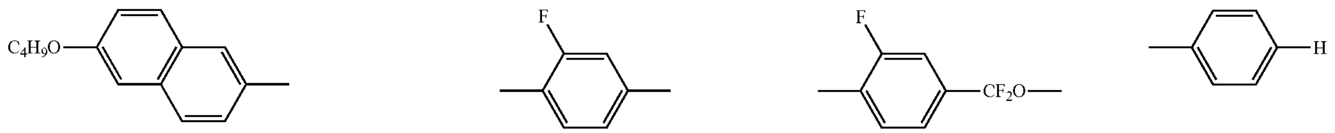

-continued
1889 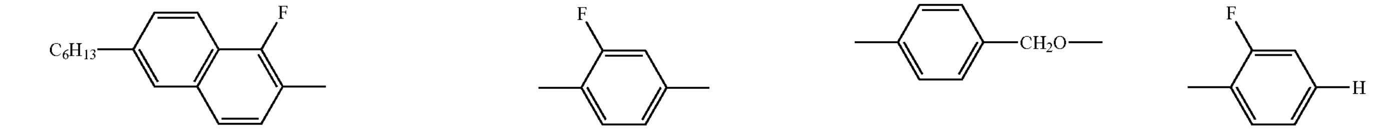
1890 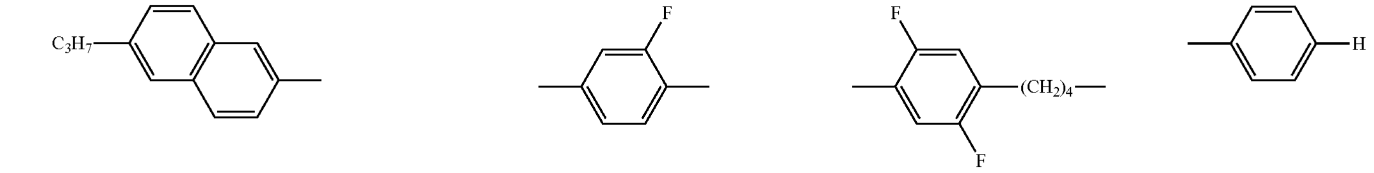
1891 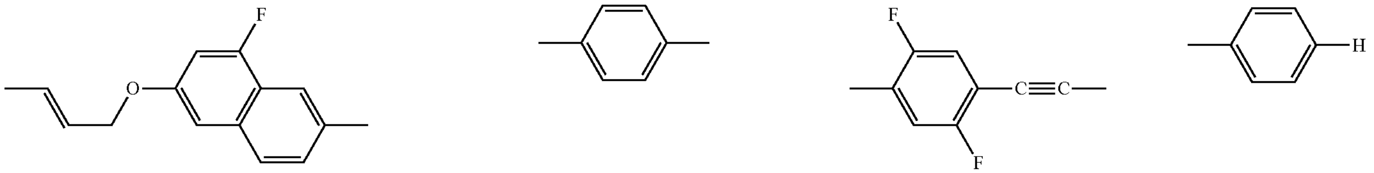
1892 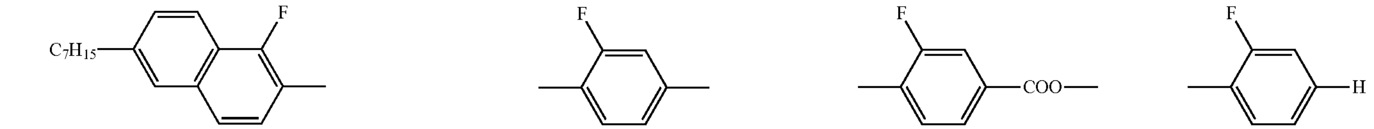
1893 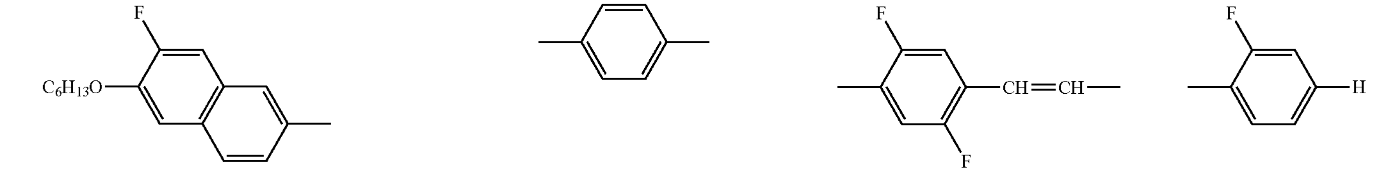
1894 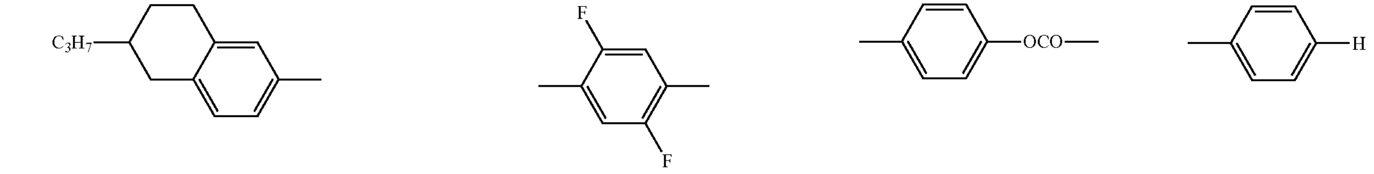

-continued
1895
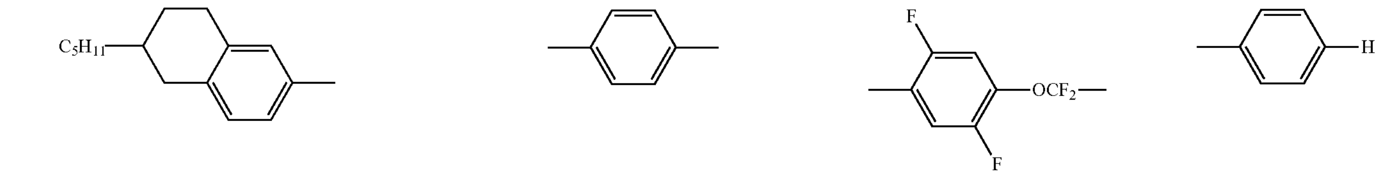
1896
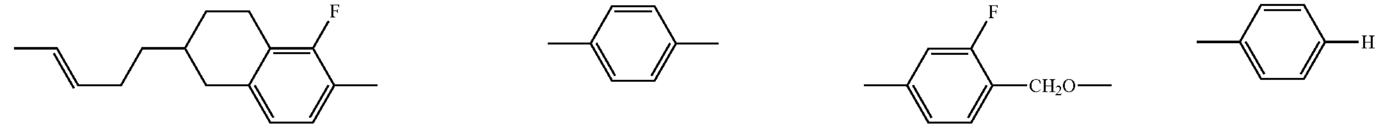
1897
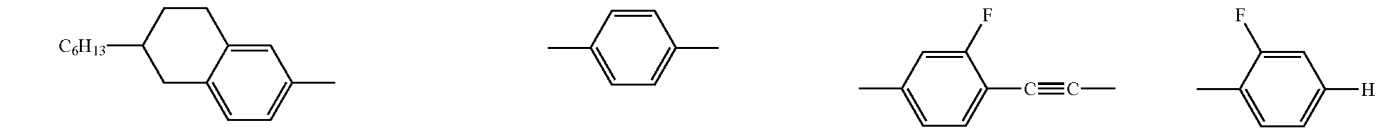
1898
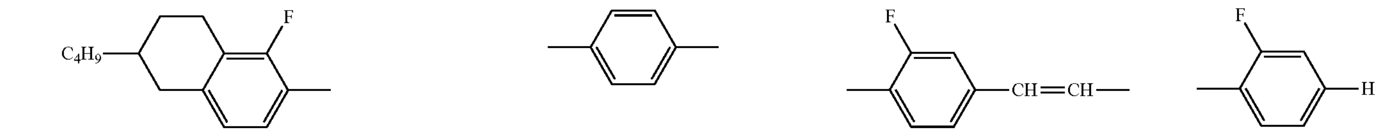
1899
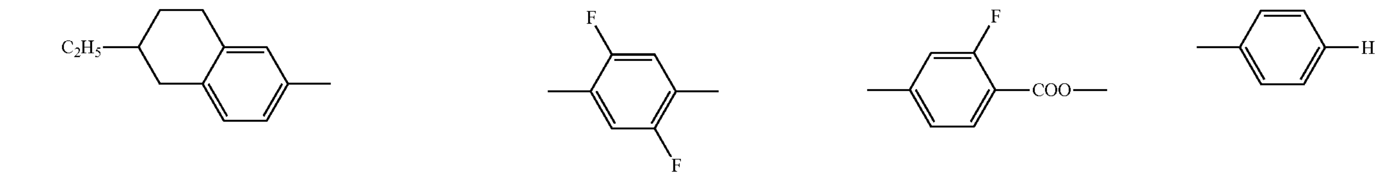

-continued
1900 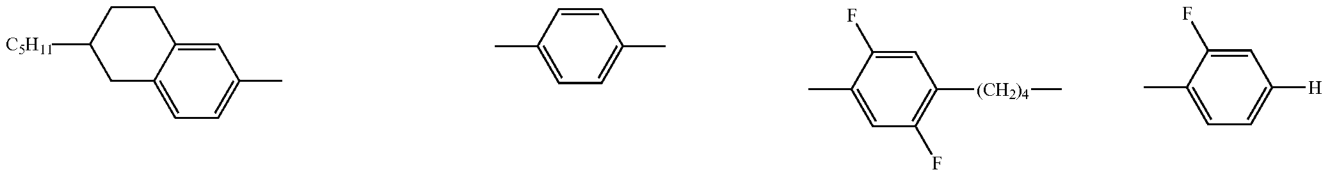
1901 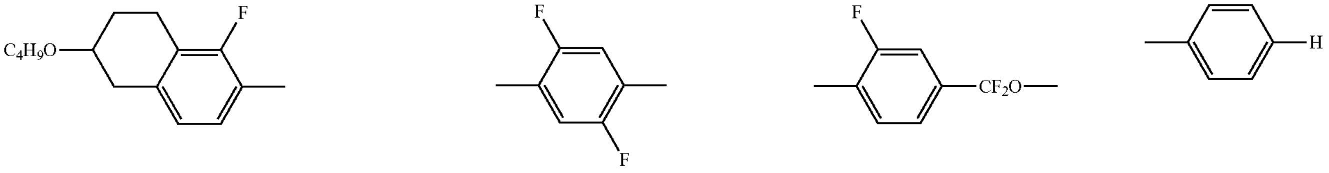
1902 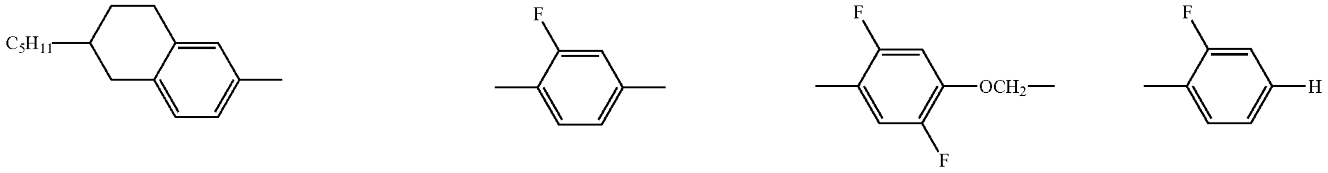
1903 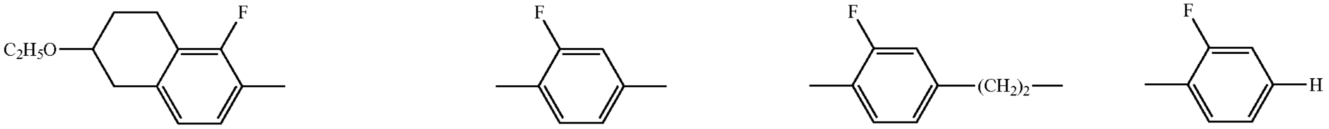
1904 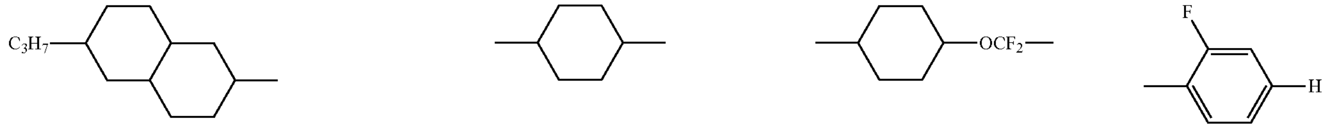

-continued
1905 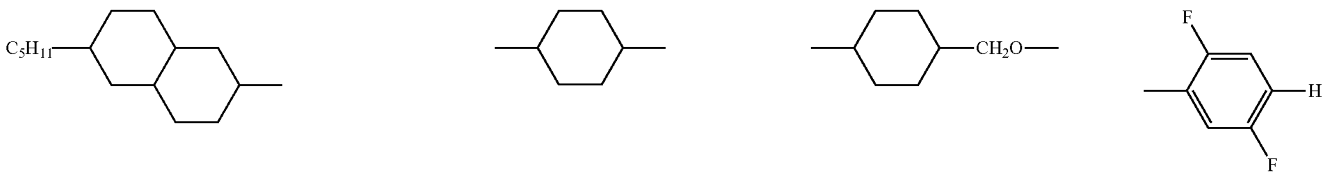
1906 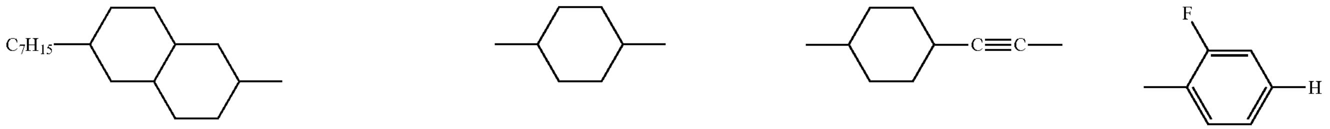
1907 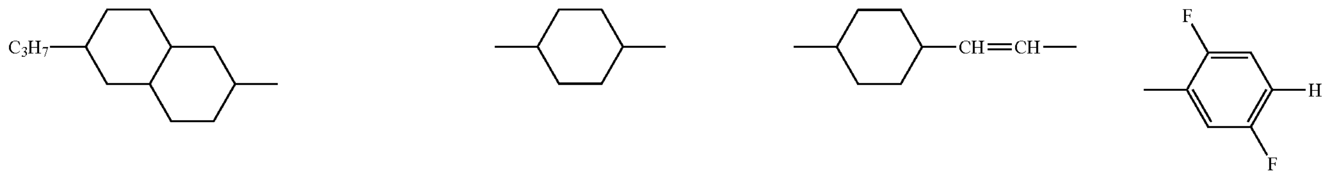
1908 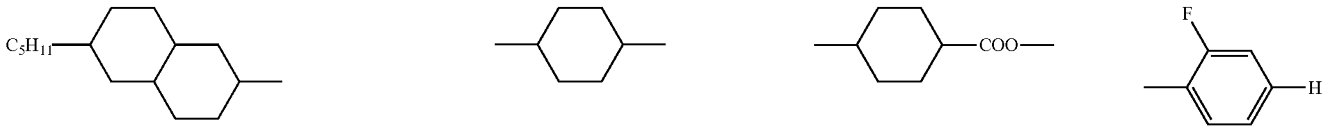
1909 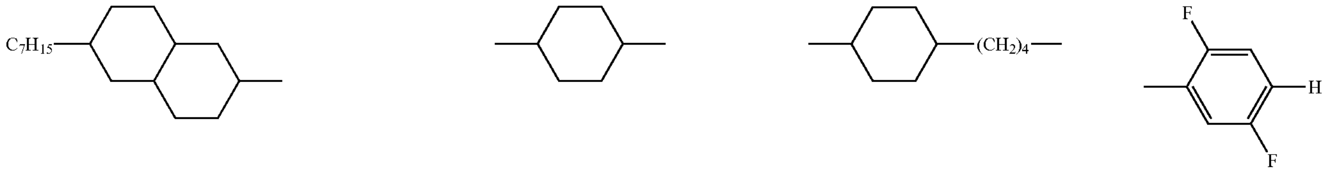

-continued
| | |
|---|---|
| 1910 | 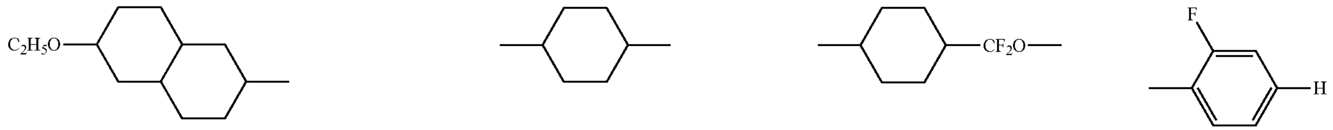 |
| 1911 | 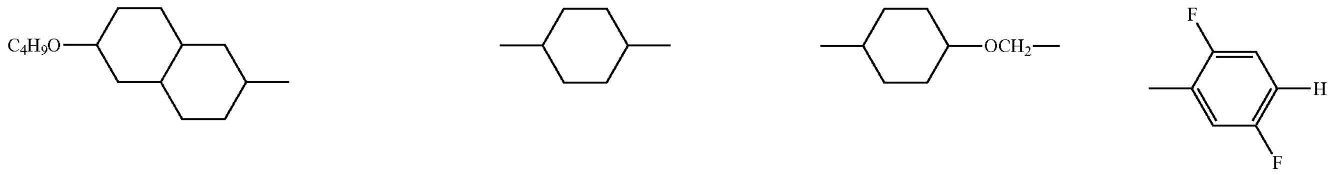 |
| 1912 | 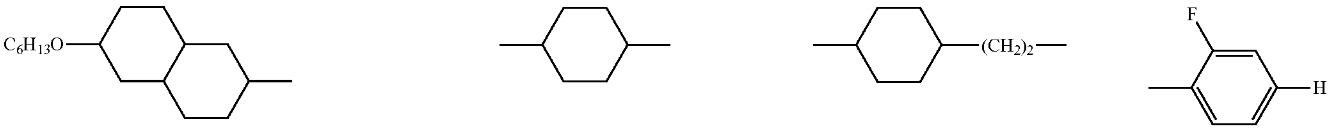 |
| 1913 | 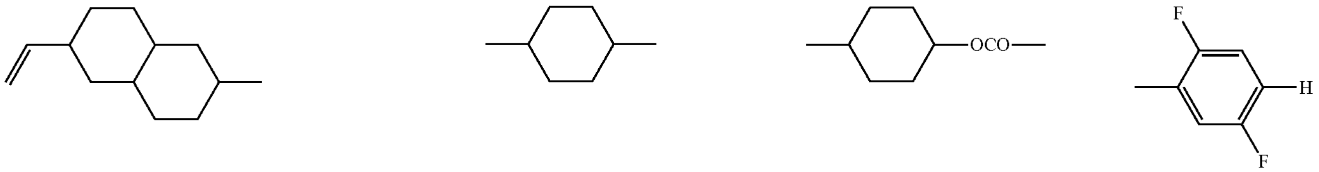 |

| | | |
|---|---|---|
| 1914 | 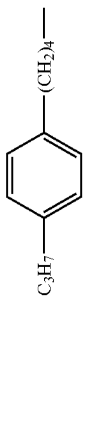 | 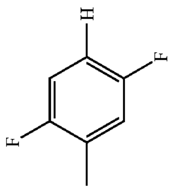 |
| 1915 | 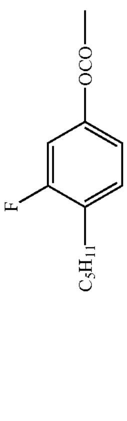 | 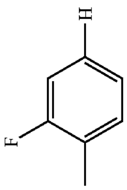 |
| 1916 | 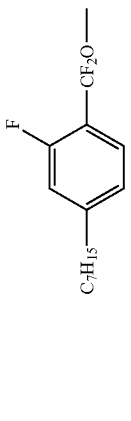 | 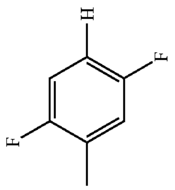 |
| 1917 | 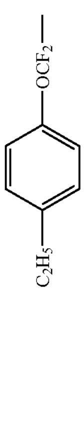 | 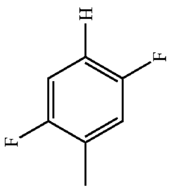 |
| 1918 | 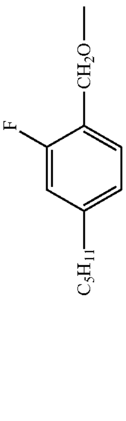 | 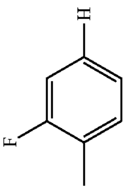 |
| 1919 | 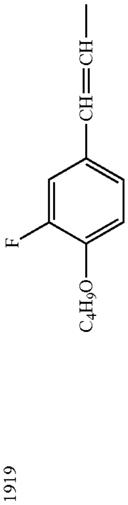 | 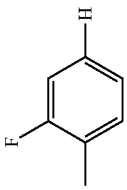 |

-continued
1920 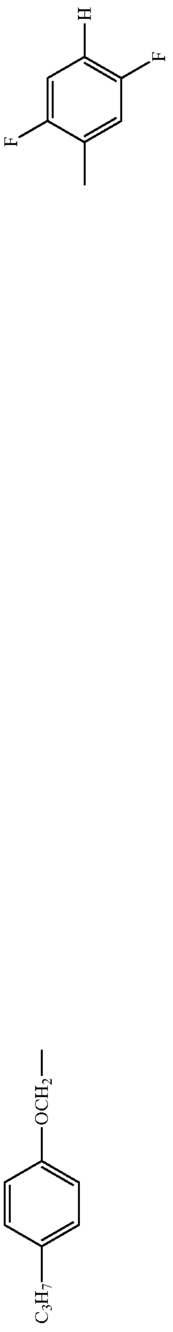
1921 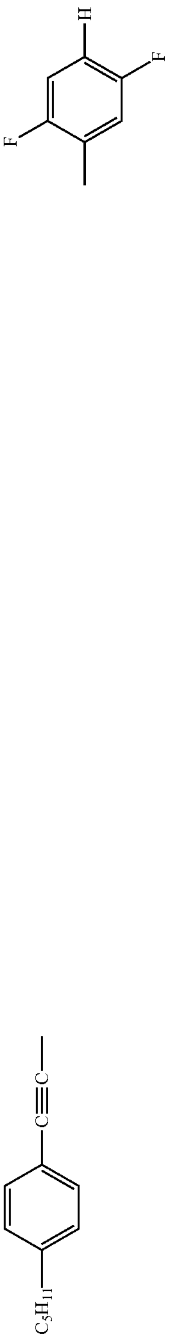
1922 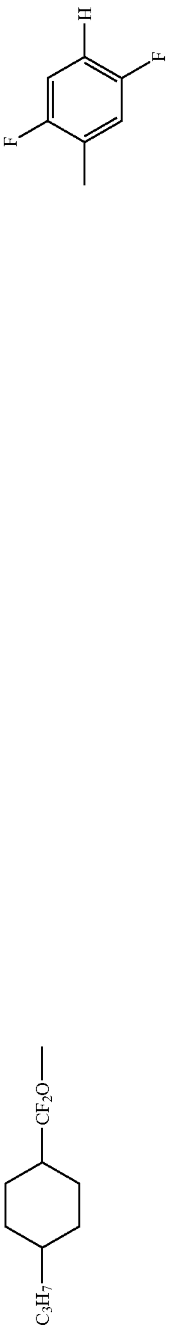
1923 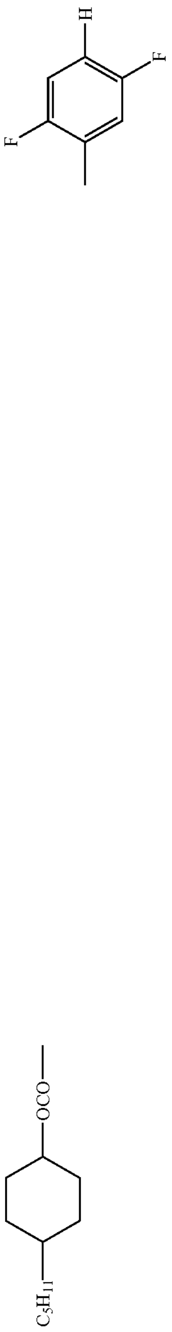
1924 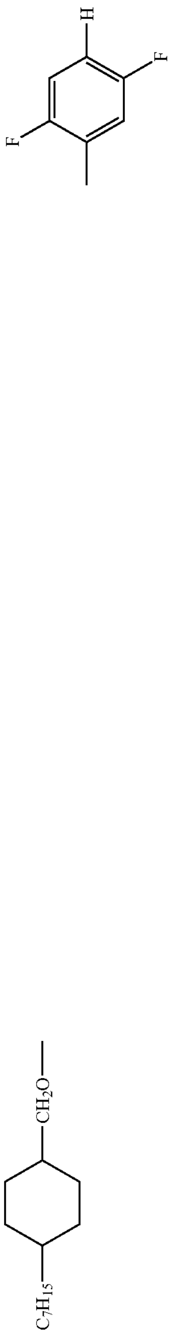

-continued
| | | |
|---|---|---|
| 1925 | 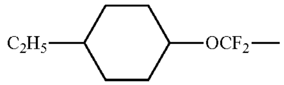 | 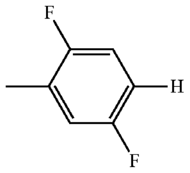 |
| 1926 | 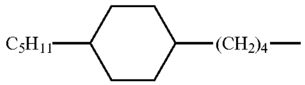 | 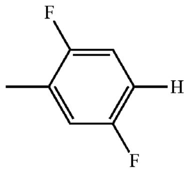 |
| 1927 | 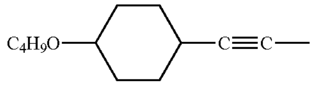 | 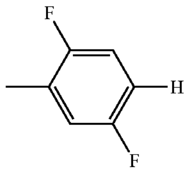 |
| 1928 | 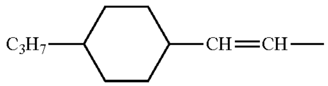 | 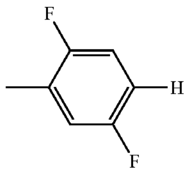 |
| 1929 | 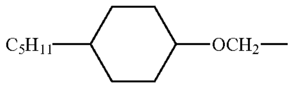 | 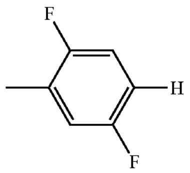 |

1930 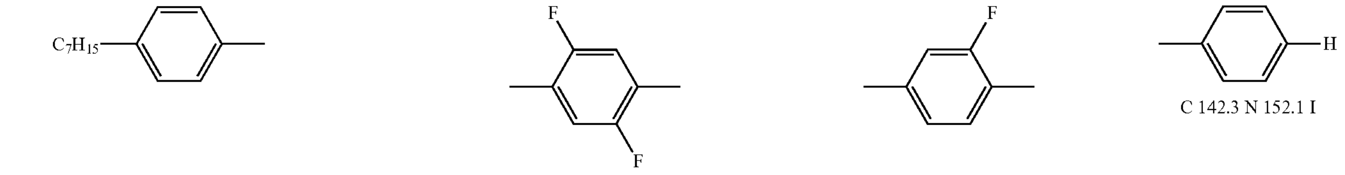
C 142.3 N 152.1 I
1931 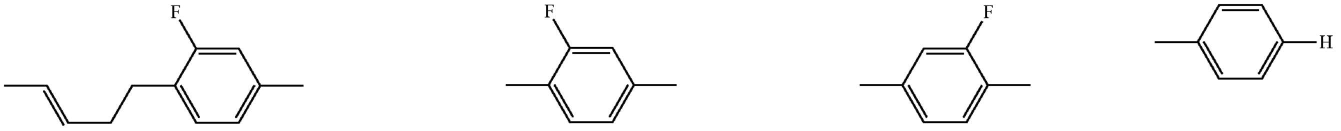
1932 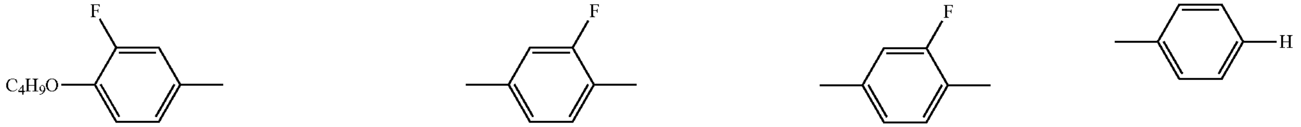
1933 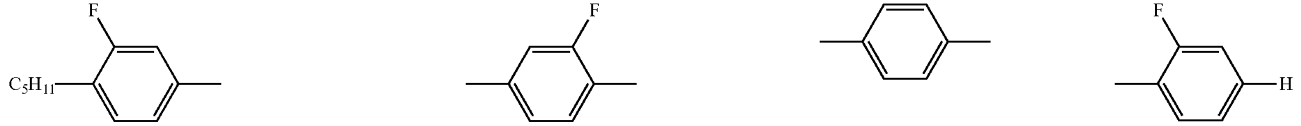
1934 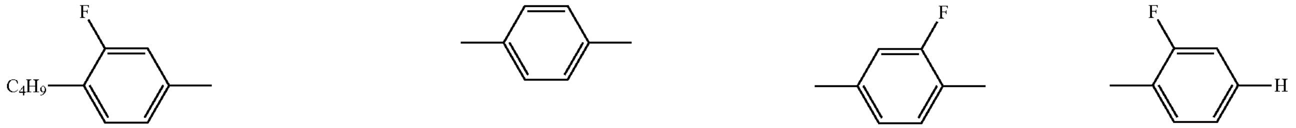
1935 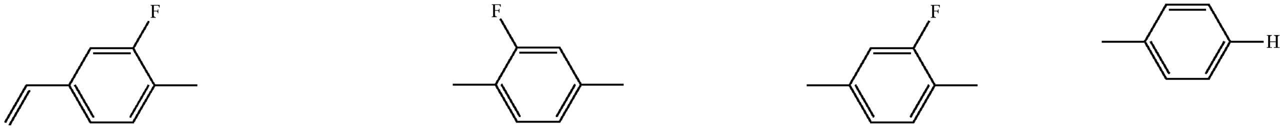
1936 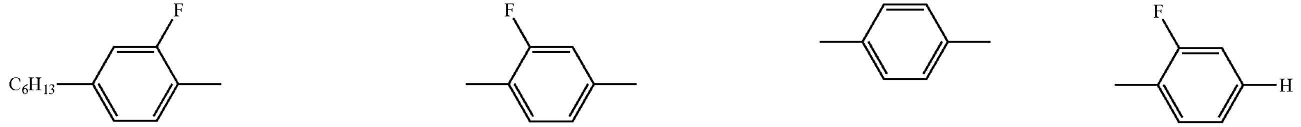

-continued
1937
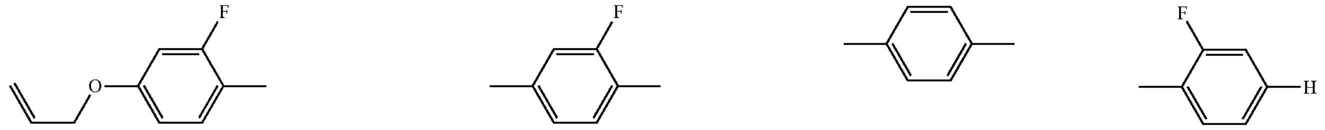
1938
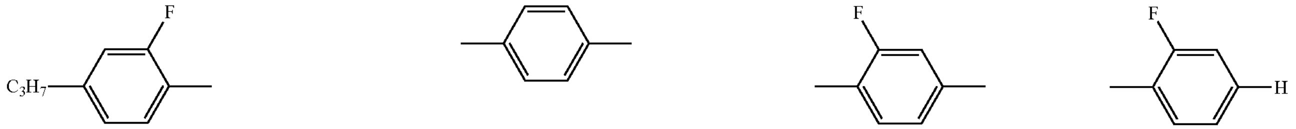
1939
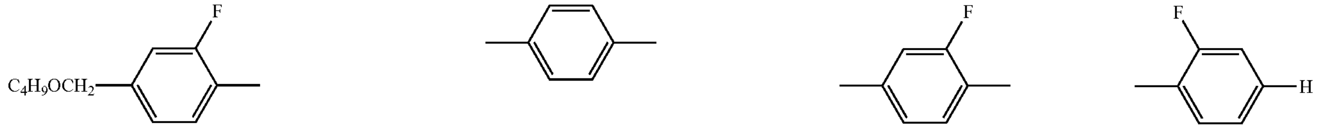
1940
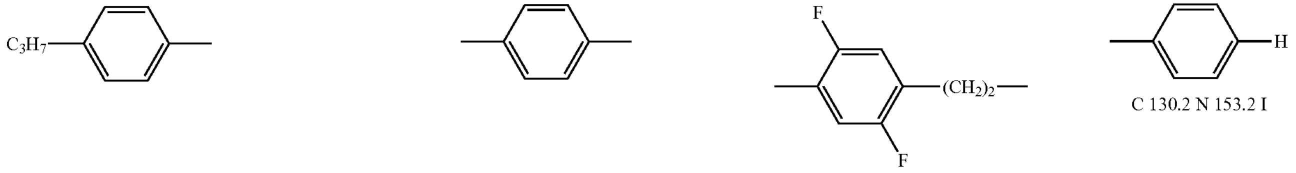
C 130.2 N 153.2 I
1941
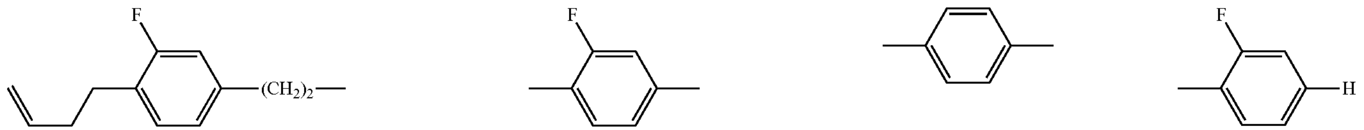
1942
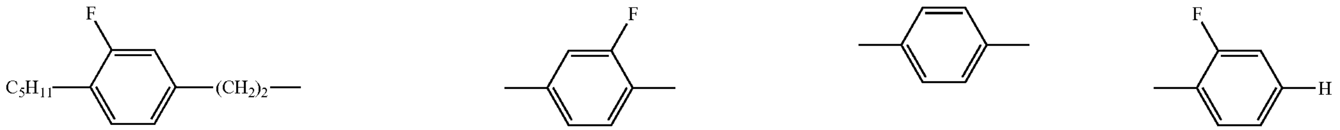
1943
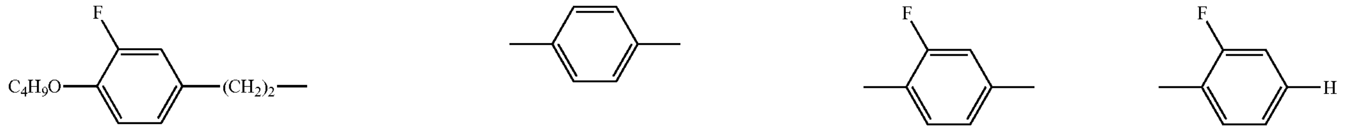

-continued
| | |
|---|---|
| 1944 | 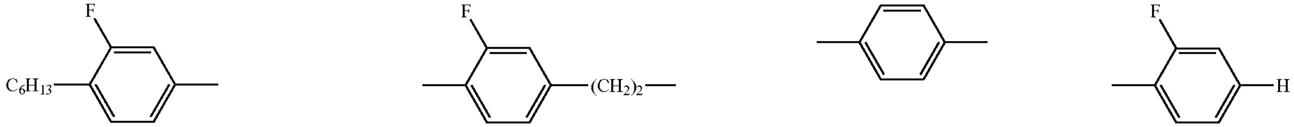 |
| 1945 | 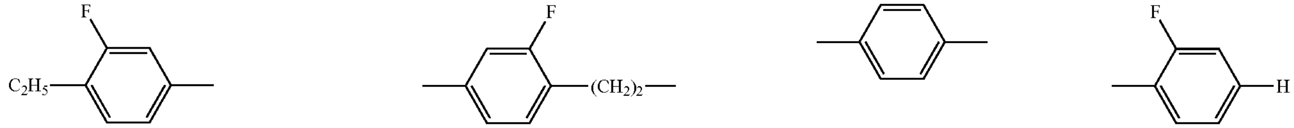 |
| 1946 | 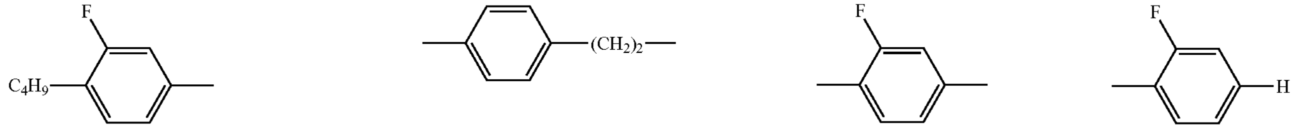 |
| 1947 | 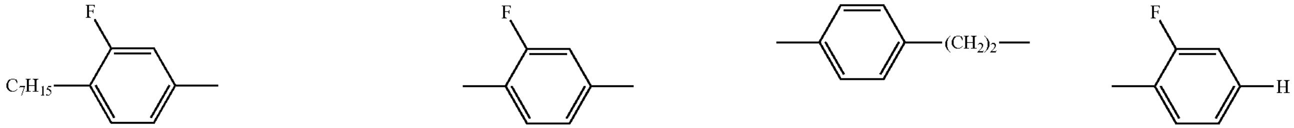 |
| 1948 | 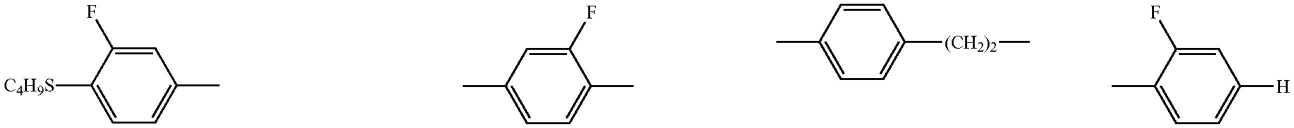 |
| 1949 | 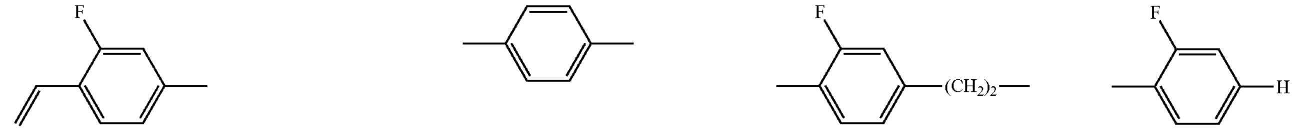 |

Example 10

| | |
|---|---|
| 5-BB(2F, 5F)B(2F) (No. 429) | 5.0% |
| 5-BB(F)B(2F) (No. 369) | 10.0% |
| 1V2-BEB(F, F)—C | 5.0% |
| 3-HB—C | 15.0% |
| 1-BTB-3 | 5.0% |
| 2-BTB-1 | 5.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

NI=92.0 (° C.); η=23.2 (mPa·s); Δn=0.168; Δε=6.9; Vth=2.13 (V).

Example 11

| | |
|---|---|
| 5-HHB(2F, 5F)B (No. 792) | 4.0% |
| 5-HHB(F)B(2F) (No. 796) | 4.0% |
| 201-BEB(F)—C | 5.0% |
| 301-BEB(F)—C | 15.0% |
| 401-BEB(F)—C | 13.0% |
| 501-BEB(F)—C | 13.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HHB-1 | 8.0% |

NI=91.5 (° C.); η=89.9 (mPa·s); Δn=0.149; Δε=31.3; Vth=0.85 (V).

Example 12

| | |
|---|---|
| 5-BB(2F, 5F)B (No. 275) | 3.0% |
| 5-HHB(2F, 5F)B (No. 792) | 5.0% |
| 5-PyB—F | 4.0% |
| 3-PyB(F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 3-H2BTB-2 | 5.0% |
| 3-H2BTB-3 | 5.0% |
| 3-H2BTB-4 | 5.0% |

NI=95.2 (° C.); η=37.7 (mPa·s); Δn=0.201; Δε=6.5; Vth=2.27 (V).

Example 13

| | |
|---|---|
| 5-BB(2F, 5F)B (No. 275) | 5.0% |
| 5-BB(F)B(2F) (No. 369) | 2.0% |
| 3-GB—C | 10.0% |
| 4-GB—C | 10.0% |
| 2-BEB—C | 12.0% |
| 3-BEB—C | 4.0% |
| 3-PyB(F)—F | 6.0% |
| 3-HEB—O4 | 8.0% |
| 4-HEB—O2 | 6.0% |
| 5-HEB—O1 | 6.0% |
| 5-HEB—O2 | 4.0% |
| 5-HEB-5 | 5.0% |
| 4-HEB-5 | 5.0% |
| 10-BEB-2 | 2.0% |
| 3-HHB-1 | 6.0% |
| 3-HHEBB—C | 3.0% |
| 3-HBEBB—C | 3.0% |
| 5-HBEBB—C | 3.0% |

NI=68.6 (° C.); η=41.2 (mPa·s); Δn=0.129; Δε=11.6; Vth=1.28 (V).

Example 14

| | |
|---|---|
| 5-BB(2F, 5F)B (No. 275) | 3.0% |
| 5-BB(F)B(2F) (No. 369) | 9.0% |
| 5-HHB(2F, 5F)B (No. 792) | 3.0% |
| 5-HHB(F)B(2F) (No. 796) | 5.0% |
| 3-HB—C | 9.0% |
| 7-HB—C | 3.0% |
| 101-HB—C | 10.0% |
| 3-HB(F)—C | 10.0% |
| 2-PyB-2 | 2.0% |
| 3-PyB-2 | 2.0% |
| 4-PyB-2 | 2.0% |
| 101-HH-3 | 7.0% |
| 2-BTB—O1 | 4.0% |
| 3-HHB-1 | 7.0% |
| 3-HHB—F | 4.0% |
| 3-HHB—O1 | 2.0% |
| 3-HHB-3 | 8.0% |
| 3-H2BTB-2 | 3.0% |
| 2-PyBH-3 | 4.0% |
| 3-PyBB-2 | 3.0% |

NI=79.1 (° C.); η=24.1 (mPa·s); Δn=0.145; Δε=8.0; Vth=1.75 (V).

Example 15

| | |
|---|---|
| 5-BB(2F, 5F)B(2F) (No. 429) | 9.0% |
| 5-HHB(2F) (No. 1487) | 5.0% |
| 5-HH2B(2F) (No. 1744) | 2.0% |
| 5-HHB(2F, 5F)B (No. 792) | 6.0% |
| 2-BEB(F)—C | 5.0% |
| 3-BEB(F)—C | 4.0% |
| 4-BEB(F)—C | 12.0% |
| 1V2-BEB(F, F)—C | 10.0% |
| 3-HH-EMe | 5.0% |
| 3-HB—O2 | 9.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F, F)—C | 2.0% |
| 3-HHB—F | 2.0% |
| 3-HHB—O1 | 4.0% |
| 3-HHB-3 | 7.0% |
| 3-HEBEB—F | 2.0% |
| 3-HEBEB-1 | 2.0% |

NI=78.9 (° C.); η=48.1 (mPa·s); Δn=0.132; Δε=25.3; Vth=0.87 (V).

Example 16

| | |
|---|---|
| 5-BB(2F, 5F)B(2F) (No 429) | 5.0% |
| 5-HHB(2F, 5F)B (No. 792) | 8.0% |
| 5-HHB(F)B(2F) (No. 796) | 7.0% |
| 2-BEB(F)—C | 5.0% |
| 3-BEB(F)—C | 4.0% |
| 4-BEB(F)—C | 12.0% |
| 1V2-BEB(F, F)—C | 16.0% |
| 3-HB—O2 | 5.0% |
| 3-HH-4 | 3.0% |
| 3-HHB—F | 3.0% |
| 3-HHB-1 | 4.0% |
| 3-HHB—O1 | 4.0% |
| 3-HBEB—F | 4.0% |
| 3-HHEB—F | 7.0% |
| 3-H2BTB-2 | 4.0% |
| 3-H2BTB-3 | 4.0% |
| 3-HB(F)TB-2 | 5.0% |

NI=91.4 (° C.); η=49.9 (mPa·s); Δn=0.154; Δε=28.6; Vth=1.04 (V).

Example 17

| | |
|---|---|
| 5-BB(2F, 5F)B (No. 275) | 5.0% |
| 5-BB(F)B(2F) (No. 369) | 14.0% |
| 5-HHB(2F) (No. 1487) | 4.0% |
| 5-HHB(2F, 5F)B (No. 792) | 3.0% |
| 2-BEB—C | 12.0% |
| 3-BEB—C | 4.0% |
| 4-BEB—C | 6.0% |
| 3-HB—C | 14.0% |
| 3-HEB—O4 | 12.0% |
| 4-HEB—O2 | 8.0% |
| 5-HEB—O1 | 4.0% |
| 3-HEB—O2 | 6.0% |
| 3-HHB-1 | 4.0% |
| 3-HHB—O1 | 4.0% |

NI=63.4 (° C.); η=33.4 (mPa·s); Δn=0.134; Δε=9.8; Vth=1.38 (V).

Example 18

| | |
|---|---|
| 5-BB(2F, 5F)B(2F) (No. 429) | 10.0% |
| 5-BB(F)B(2F) (No. 369) | 7.0% |
| 5-HH2B(2F) (No. 1744) | 6.0% |
| 5-HHB(2F, 5F)B (No. 792) | 4.0% |
| 2-BEB—C | 10.0% |
| 5-BB—C | 12.0% |
| 1-BTB-3 | 7.0% |
| 10-BEB-2 | 10.0% |
| 10-BEB-5 | 12.0% |
| 2-HHB-1 | 4.0% |
| 3-HHB—F | 4.0% |
| 3-HHB-1 | 3.0% |
| 3-HHB—O1 | 4.0% |
| 3-HHB-3 | 7.0% |

NI=65.1 (° C.); η=33.6 (mPa·s); Δn=0.158; Δε=6.7; Vth=1.74 (V).

Example 19

| | |
|---|---|
| 5-BB(2F, 5F)B(2F) (No. 429) | 7.0% |
| 5-BB(F)B(2F) (No. 369) | 6.0% |
| 5-HH2B(2F) (No. 1744) | 4.0% |
| 5-HHB(2F, 5F)B (No. 792) | 7.0% |
| 2-HB—C | 5.0% |
| 3-HB—C | 6.0% |
| 3-HB—O2 | 8.0% |
| 2-BTB-1 | 3.0% |
| 3-HHB-1 | 4.0% |
| 3-HHB—F | 4.0% |
| 3-HHB—O1 | 5.0% |
| 3-HHB-3 | 7.0% |
| 3-HHEB—F | 4.0% |
| 5-HHEB—F | 4.0% |
| 2-HHB(F)—F | 7.0% |
| 3-HHB(F)—F | 7.0% |
| 5-HHB(F)—F | 7.0% |
| 3-HHB(F, F)—F | 5.0% |

NI=99.5 (° C.); η=30.1 (mPa·s); Δn=0.115; Δε=4.9; Vth=2.49 (V).

Example 20

| | |
|---|---|
| 5-BB(F)B(2F) (No. 369) | 4.0% |
| 5-HHB(2F) (No. 1487) | 7.0% |
| 5-HHB(2F, 5F)B (No. 1744) | 7.0% |
| 5-HHB(F)B(2F) (No. 792) | 6.0% |
| 3-BEB(F)—C | 8.0% |
| 3-HB—C | 4.0% |
| V—HB—C | 8.0% |
| 1V—HB—C | 8.0% |
| 3-HB—O2 | 3.0% |
| 3-HH-2V | 7.0% |
| 3-HH-2V1 | 7.0% |
| V2-HHB-1 | 8.0% |
| 3-HHB-1 | 5.0% |
| 3-HHEB—F | 7.0% |
| 3-H2BTB-2 | 6.0% |
| 3-H2BTB-4 | 5.0% |

NI=101.2 (° C.); η=27.3 (mPa·s); Δn=0.136; Δε=8.7; Vth=2.16 (V).

Example 21

| | |
|---|---|
| 5-BB (2F, 5F) B (2F) (No. 429) | 3.0% |
| 5-BB (F) B (2F) (No. 369) | 18.0% |
| 5-HHB (2F, 5F) B (No. 792) | 5.0% |
| 5-HHB (F) B (2F) (No. 796) | 4.0% |
| V2-HB-C | 6.0% |
| 1V2-HB-C | 12.0% |
| 3-HB-C | 12.0% |
| 3-HB (F)-C | 5.0% |
| 2-BTB-1 | 2.0% |
| 3-HH-4 | 8.0% |
| 3-HH-VFF | 3.0% |
| 2-HHB-C | 3.0% |
| 3-HHB-C | 6.0% |
| 3-HB (F) TB-2 | 4.0% |
| 3-H2BTB-3 | 5.0% |
| 3-H2BTB-4 | 4.0% |

NI=88.6 (° C.); η=28.9 (mPa·s); Δn=0.165; Δε=8.4; Vth=2.06 (V).

Example 22

| | |
|---|---|
| 5-BB (F) B (2F) (No. 369) | 5.0% |
| 5-HHB (2F, 5F) B (No. 792) | 8.0% |
| 5-HHB (F) B (2F) (No. 796) | 2.0% |
| 5-BEB (F)-C | 5.0% |
| V-HB-C | 6.0% |
| 5-PyB-C | 6.0% |
| 4-BB-3 | 11.0% |
| 3-HH-2V | 10.0% |
| 5-HH-V | 11.0% |
| V-HHB-1 | 4.0% |
| V2-HHB-1 | 15.0% |
| 3-HHB-1 | 9.0% |
| 1V2-HBB-2 | 5.0% |
| 3-HHEBH-3 | 3.0% |

NI=92.0 (° C.); η=20.4 (mPa·s); Δn=0.120; Δε=4.7; Vth=2.38 (V).

Example 23

| | |
|---|---|
| 5-BB (F) B (2F) (No. 369) | 12.0% |
| 5-HHB (2F, 5F) B (No. 792) | 4.0% |
| 5-HHB (F) B (2F) (No. 796) | 4.0% |
| 1V2-BEB (F, F)-C | 8.0% |
| 3-HB-C | 5.0% |
| V2V-HB-C | 7.0% |
| V2V-HH-3 | 19.0% |
| 3-HB-O2 | 4.0% |
| 3-HHB-1 | 10.0% |
| 3-HHB-3 | 15.0% |
| 3-HB (F) TB-3 | 4.0% |
| 3-H2BTB-2 | 4.0% |
| 3-H2BTB-4 | 4.0% |

NI=101.1 (° C.); η=23.4 (mPa·s); Δn=0.133; Δε=7.7; Vth=2.13 (V).

Example 24

| | |
|---|---|
| 5-BB (F) B (2F) (No. 369) | 5.0% |
| 5-HHB (2F, 5F) B (No. 792) | 3.0% |
| 5-HHB (F) B (2F) (No. 796) | 5.0% |
| V2-HB-TC | 10.0% |
| 3-HB-TC | 10.0% |
| 3-HB-C | 5.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-3 | 3.0% |
| 3-HB (F) TB-2 | 3.0% |
| 5-BTB (F) TB-3 | 5.0% |

NI=101.6 (° C.); η=18.7 (mPa·s); Δn=0.194; Δε=6.6; Vth=2.14 (V).

Example 25

| | |
|---|---|
| 5-BB (F) B (2F) (No. 369) | 9.0% |
| 5-HHB (2F, 5F) B (No. 792) | 4.0% |
| 1V2-BEB (F, F)-C | 6.0% |
| 3-HB-C | 9.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-HHB-1 | 4.0% |

NI=82.3 (° C.); η=16.0 (mPa·s); Δn=0.135; Δε=6.3; Vth=2.11 (V).

Example 26

| | |
|---|---|
| 5-BB (2F, SF) B (2F) (No. 429) | 5.0% |
| 5-BB (F) B (2F) (No. 369) | 9.0% |
| 5-HHB (2F, 5F) B (No. 792) | 5.0% |
| 5-HBCF2OB (F, F)-C | 3.0% |
| 3-HB (F, F) CF2OB (F, F)-C | 3.0% |
| 3-HB-C | 9.0% |
| 2-BTB-1 | 5.0% |
| 5-HH-VFF | 30.0% |
| 1-BHH-VFF | 8.0% |
| 1-BHH-2VFF | 11.0% |
| 3-H2BTB-3 | 4.0% |
| 3-H2BTB-4 | 4.0% |
| 3-HHB-1 | 4.0% |

NI=84.7 (° C.); η=21.1 (mPa·s); Δn=0.129; Δε=4.3; Vth=2.59 (V).

Example 27

| | |
|---|---|
| 5-BB (2F, 5F) B (No. 275) | 5.0% |
| 5-BB (F) B (2F) (No. 369) | 6.0% |
| 5-HH2B (2F) (No. 1744) | 5.0% |
| 2-HHB (F)-F | 17.0% |
| 3-HHB (F)-F | 17.0% |
| 5-HHB (F)-F | 16.0% |
| 2-H2HB (F)-F | 5.0% |
| 3-H2HB (F)-F | 5.0% |
| 5-H2HB (F)-F | 5.0% |
| 3-HBB (F)-F | 6.0% |
| 5-HBB (F)-F | 13.0% |

NI=98.1 (° C.); η=28.3 (mPa·s); Δn=0.105; Δε=5.0; Vth=2.18 (V).

Example 28

| | |
|---|---|
| 5-BB (2F, 5F) B (No. 275) | 3.0% |
| 5-BB (F) B (2F) (No. 369) | 9.0% |
| 5-HHB (2F) (No. 1487) | 4.0% |
| 5-HH2B (2F) (No. 1744) | 10.0% |
| 7-HB (F, F) F | 3.0% |
| 3-HB-O2 | 4.0% |
| 2-HHB (F)-F | 10.0% |
| 3-HHB (F)-F | 10.0% |
| 3-HBB (F)-F | 9.0% |
| 5-HBB (F)-F | 16.0% |
| 3-HBB-F | 4.0% |
| 5-HBB-F | 3.0% |
| 3-HBB (F, F)-F | 5.0% |
| 5-HBB (F, F)-F | 10.0% |

NI=82.9 (° C.); η=30.8 (mPa·s); Δn=0.123; Δε=5.6; Vth=2.01 (V).

Example 29

| | |
|---|---|
| 5-HHB (2F, 5F) B (No. 792) | 3.0% |
| 5-HHB (F) B (2F) (No. 796) | 3.0% |
| 5-HB-CL | 16.0% |
| 3-HH-4 | 12.0% |
| 3-HH-5 | 4.0% |
| 3-HHB-F | 4.0% |
| 4-HHB-CL | 4.0% |
| 3-HHB (F)-F | 10.0% |
| 4-HHB (F)-F | 9.0% |
| 5-HHB (F)-F | 9.0% |
| 7-HHB (F)-F | 8.0% |
| 5-HBB (F)-F | 4.0% |
| 5-HBBH-1O1 | 3.0% |
| 3-HHBB (F, F)-F | 2.0% |
| 4-HHBB (F. F)-F | 3.0% |
| 5-HHBB (F, F)-F | 3.0% |
| 3-HH2BB (F, F)-F | 3.0% |

NI=115.1 (° C.); η=20.4 (mPa·s); Δn=0.092; Δε=3.7; Vth=2.57 (V).

Example 30

| | |
|---|---|
| 5-BB (2F, 5F) B (No. 275) | 10.0% |
| 5-BB (F) B (2F) (No. 369) | 10.0% |
| 5-HHB (2F) (No. 1487) | 4.0% |
| 5-HHB (2F, 5F) B (No. 792) | 4.0% |
| 5-HHB (F) B (2F) (No. 796) | 4.0% |
| 3-HHB (F, F)-F | 9.0% |
| 3-H2HB (F, F)-F | 8.0% |
| 4-H2HB (F, F)-F | 4.0% |
| 5-H2HB (F, F)-F | 4.0% |
| 3-HBB (F, F)-F | 11.0% |
| 5-HBB (F, F)-F | 10.0% |
| 3-H2BB (F, F)-F | 10.0% |
| 5-HHBB (F, F)-F | 3.0% |
| 5-HHEBB-F | 2.0% |
| 3-HH2BB (F, F)-F | 3.0% |
| 4-HBBH-1O1 | 4.0% |

NI=97.6 (° C.); η=38.6 (mPa·s); Δn=0.138; Δε=8.0; Vth=1.85 (V).

Example 31

| | |
|---|---|
| 5-BB (F) B (2F) (No. 369) | 10.0% |
| 5-HHB (2F, 5F) B (No. 792) | 4.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 5-HH2B-OCF3 | 4.0% |
| 3-HHB (F, F)-OCF3 | 5.0% |
| 3-HBB (F)-F | 10.0% |
| 3-HH2B (F)-F | 3.0% |
| 3-HB (F) BH-3 | 3.0% |
| 5-HBBH-3 | 3.0% |
| 3-HHB (F, F)-OCF2H | 4.0% |

NI=83.4 (° C.); η=18.7 (mPa·s); Δn=0.103; Δε=4.5; Vth=2.37 (V).

Example 32

| | |
|---|---|
| 5-BB (F) B (2F) (No. 369) | 11.0% |
| 5-HHB (2F) (No. 1487) | 2.0% |
| 2-HHB (F)-F | 3.0% |
| 2-HBB (F)-F | 7.0% |
| 3-HBB (F)-F | 7.0% |
| 5-HBB (F)-F | 15.0% |
| 2-H2BB (F)-F | 10.0% |
| 3-H2BB (F)-F | 10.0% |
| 3-HBB (F, F)-F | 11.0% |
| 5-HBB (F, F)-F | 6.0% |
| 2-HHBB (F, F)-F | 5.0% |
| 3-HHBB (F, F)-F | 5.0% |
| 4-HHBB (F, F)-F | 5.0% |
| 3-HHB-F | 3.0% |

NI=96.2 (° C.); η=34.7 (mPa·s); Δn=0.146; Δε=7.0; Vth=1.95 (V).

Example 33

| | |
|---|---|
| 5-BB (2F, 5F) B (2F) (No. 429) | 5.0% |
| 5-BB (F) B (2 F) (No. 369) | 10.0% |
| 5-HHB (F) B (2F) (No. 796) | 3.0% |
| 5-HB-CL | 6.0% |
| 3-HH-4 | 8.0% |
| 3-HBB (F, F)-F | 10.0% |
| 5-HBB (F, F)-F | 15.0% |
| 3-HHB (F, F)-F | 8.0% |
| 3-HHEB (F, F)-F | 10.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 5.0% |
| 5-HBEB (F, F)-F | 3.0% |
| 3-HHBB (F, F)-F | 3.0% |
| 3-HHB-1 | 5.0% |

NI=80.9 (° C.); η=26.8 (mPa·s); Δn=0.119; Δε=8.3; Vth=1.58 (V).

Example 34

| | |
|---|---|
| 5-BB (2F, 5F) B (No. 275) | 2.0% |
| 5-BB (F) B (2F) (No. 369) | 11.0% |
| 5-HHB (2F, 5F) B (No. 792) | 4.0% |
| 5-HHB (F) B (2F) (No. 796) | 4.0% |
| 7-HB (F)-F | 6.0% |
| 5-H2B (F)-F | 6.0% |
| 3-HB-O2 | 4.0% |
| 3-HH-4 | 12.0% |
| 3-HHB (F)-F | 11.0% |
| 5-HHB (F)-F | 11.0% |
| 3-HBB (F)-F | 2.0% |
| 5-HBB (F)-F | 4.0% |
| 3-HBB (F, F)-F | 3.0% |
| 3-HHBB (F, F)-F | 5.0% |
| 5-HHEB-F | 4.0% |
| 3-HHB-1 | 7.0% |
| 3-HHB-F | 4.0% |

NI=98.1 (° C.); η=23.1 (mPa·s); Δn=0.107; Δε=4.3; Vth=2.29 (V).

Example 35

| | |
|---|---|
| 3-BB (2F, 5F) B (No. 273) | 10.0% |
| 5-BB (2F, 5F) B (No. 275) | 10.0% |
| 3-BB (F) B (2F) (No. 368) | 10.0% |
| 5-BB (F) B (2F) (No. 369) | 10.0% |
| 3-HH-4 | 4.0% |
| 3-H2HB (F, F)-F | 10.0% |
| 4-H2HB (F, F)-F | 10.0% |
| 5-H2HB (F, F)-F | 8.0% |
| 3-HBB (F, F)-F | 13.0% |
| 5-HBB (F, F)-F | 12.0% |
| 3-HHBB (F, F)-F | 3.0% |

NI=61.4 (° C.); η=33.4 (mPa·s); Δn=0.142; Δϵ=7.0; Vth=1.57 (V).

Example 36

| | |
|---|---|
| 5-BB (2F, 5F) B (No. 275) | 5.0% |
| 5-BB (F) B (2F) (No. 369) | 3.0% |
| 5-HHB (F) B (2F) (No. 796) | 3.0% |
| 7-HB (F, F)—F | 5.0% |
| 3-H2HB (F, F)—F | 12.0% |
| 4-H2HB (F, F)—F | 5.0% |
| 3-HHB (F, F)—F | 10.0% |
| 4-HHB (F, F)—F | 5.0% |
| 3-HBB (F, F)—F | 10.0% |
| 3-HHEB (F, F)—F | 10.0% |
| 5-HHEB (F, F)—F | 3.0% |
| 2-HBEB (F, F)—F | 3.0% |
| 3-HBEB (F, F)—F | 5.0% |
| 5-HBEB (F, F)—F | 3.0% |
| 3-HGB (F, F)—F | 15.0% |
| 3-HHBB (F, F)—F | 3.0% |

NI=72.7 (° C.); η=35.1 (mPa·s); Δn=0.096; Δϵ=12.8; Vth=1.38 (V).

Example 37

| | |
|---|---|
| 5-BB (2F, 5F) B (2F) (No. 429) | 4.0% |
| 5-HHB (2F) (No. 1487) | 5.0% |
| 5-H4HB (F, F)—F | 7.0% |
| 5-H4HB—OCF3 | 15.0% |
| 3-H4HB (F, F)—CF3 | 8.0% |
| 5-H4HB (F, F)—CF3 | 10.0% |
| 3-HB—CL | 6.0% |
| 2-H2BB (F)—F | 5.0% |
| 3-H2BB (F)—F | 5.0% |
| 5-H2HB (F, F)—F | 5.0% |
| 3-HHB—OCF3 | 5.0% |
| 3-H2HB—OCF3 | 5.0% |
| V-HHB (F)—F | 5.0% |
| 3-HHB (F)—F | 5.0% |
| 5-HHB (F)—F | 5.0% |
| 3-HBEB (F, F)—F | 5.0% |

NI=70.7 (° C.); η=29.1 (mPa·s); Δn=0.099; Δϵ=8.0; Vth=1.79 (V).

Example 38

| | |
|---|---|
| 5-BB (F) B (2F) (No. 369) | 5.0% |
| 5-HHB (2F) (No. 1487) | 3.0% |
| 5-HHB (2F, 5F) B (No. 792) | 4.0% |
| 5-HB—CL | 17.0% |
| 7-HB (F, F)—F | 3.0% |
| 3-HH-4 | 10.0% |
| 3-HH-5 | 5.0% |
| 3-HB—O2 | 15.0% |
| 4-H2HB (F, F)—F | 5.0% |
| 3-HHB (F, F)—F | 6.0% |
| 2-HHB (F)—F | 4.0% |
| 3-HHB (F)—F | 7.0% |
| 5-HHB (F)—F | 7.0% |
| 3-HHB-1 | 4.0% |
| 3-HHB—O1 | 5.0% |

NI=70.9 (° C.); η=16.6 (mPa·s); Δn=0.084; Δϵ=2.7; Vth=2.02 (V).

Example 39

| | |
|---|---|
| 5-BB (2F, 5F) B (2F) (No. 429) | 2.0% |
| 5-BB (F) B (2F) (No. 369) | 11.0% |
| 5-HH2B (2F) (No. 1744) | 9.0% |
| 5-HHB (F) B (2F) (No. 796) | 3.0% |
| 5-HB—CL | 2.0% |
| 4-HHB (F)—F | 10.0% |
| 5-HHB (F)—F | 9.0% |
| 3-HHB (F, F)—F | 8.0% |
| 4-HHB (F, F)—F | 3.0% |
| 3-H2HB (F, F)—F | 12.0% |
| 3-HBB (F, F)—F | 11.0% |
| 2-HHBB (F, F)—F | 3.0% |
| 3-GHB (F, F)—F | 3.0% |
| 4-GHB (F, F)—F | 8.0% |
| 5-GHB (F, F)—F | 6.0% |

NI=79.1 (° C.); η=35.1 (mPa·s); Δn=0.103; Δϵ=8.0; Vth=1.28 (V).

Example 40

| | |
|---|---|
| 5-BB (2F, 5F) B (No. 275) | 7.0% |
| 5-BB (F) B (2F) (No. 369) | 11.0% |
| 5-HHB (F) B (2F) (No. 796) | 5.0% |
| 2-HHB (F)—F | 7.0% |
| 3-HHB (F)—F | 8.0% |
| 3-HHB (F, F)—F | 8.0% |
| 3-HBB (F, F)—F | 10.0% |
| 3-H2HB (F, F)—F | 10.0% |
| 3-HHEB (F, F)—F | 5.0% |
| 4-HHEB (F, F)—F | 3.0% |
| 2-HBEB (F, F)—F | 2.0% |
| 3-HBEB (F, F)—F | 3.0% |
| 3-GHB (F, F)—F | 3.0% |
| 4-GHB (F, F)—F | 7.0% |
| 5-GHB (F, F)—F | 7.0% |
| 3-HHBB (F, F)—F | 4.0% |

NI=79.0 (° C.); η=40.7 (mPa·s); Δn=0.114; Δϵ=10.2; Vth=1.13 (V).

Example 41

| | |
|---|---|
| 5-HHB (2F) (No. 1487) | 5.0% |
| 5-HH2B (2F) (No. 1744) | 8.0% |
| 7-HB (F)—F | 7.0% |
| 5-HB—CL | 3.0% |
| 3-HH-4 | 9.0% |
| 3-HH-EMe | 18.0% |
| 3-HHEB (F, F)—F | 10.0% |
| 4-HHEB (F, F)—F | 5.0% |
| 3-HHEB—F | 4.0% |
| 5-HHEB—F | 4.0% |
| 4-HGB (F, F)—F | 5.0% |
| 5-HGB (F, F)—F | 6.0% |
| 2-H2GB (F, F)—F | 4.0% |
| 3-H2GB (F, F)—F | 5.0% |
| 5-GHB (F, F)—F | 7.0% |

NI=74.7 (° C.); η=22.8 (mPa·s); Δn=0.063; Δε=5.6; Vth=1.47 (V).

Example 42

| | |
|---|---|
| 5-BB (F) B (2F) (No. 369) | 15.0% |
| 3-H2HB (F, F)—F | 5.0% |
| 5-H2HB (F, F)—F | 5.0% |
| 3-HBB (F, F)—F | 15.0% |
| 5-HBB (F, F)—F | 30.0% |
| 5-HBB (F) B-2 | 10.0% |
| 5-HBB (F) B-3 | 10.0% |
| 3-BB (F) B (F, F)—F | 5.0% |
| 5-B2B (F, F) B (F)—F | 5.0% |

NI=104.8 (° C.); η=51.5 (mPa·s); Δn=0.166; Δε=9.8; Vth=1.76 (V).

Example 43

| | |
|---|---|
| 5-BB (2F, 5F) B (2F) (No. 429) | 3.0% |
| 5-BB (F) B (2F) (No. 369) | 8.0% |
| 5-HHB (2F) (No. 1487) | 7.0% |
| 5-HHB (2F, 5F) B (No. 792) | 6.0% |
| 3-HB (F, F) CF2OB (F, F)—F | 11.0% |
| 5-HB (F, F) CF2OB (F, F)—F | 11.0% |
| 5-HB—CL | 4.0% |
| 3-HH-4 | 7.0% |
| 2-HH-5 | 4.0% |
| 3-HHB-1 | 4.0% |
| 5-HHEB—F | 6.0% |
| 3-HHB (F, F)—F | 6.0% |
| 4-HHB (F, F)—F | 3.0% |
| 4-HHEB (F, F)—F | 3.0% |
| 5-HHEB (F, F)—F | 2.0% |
| 2-HBEB (F, F)—F | 3.0% |
| 3-HBEB (F, F)—F | 3.0% |
| 5-HBEB (F, F)—F | 3.0% |
| 2-HHBB (F, F)—F | 3.0% |
| 3-HHBB (F, F)—F | 3.0% |

NI=80.3 (° C.); η=29.4 (mPa·s); Δn=0.100; Δε=8.3; Vth=1.24 (V).

Example 44

| | |
|---|---|
| 5-BB (F) B (2F) (No. 369) | 4.0% |
| 5-HHB (F) B (2F) (No. 796) | 3.0% |
| 3-BB (F, F) CF2OB (F, F)—F | 35.0% |
| 3-HH-4 | 8.0% |
| 3-HHB (F, F)—F | 10.0% |
| 3-H2HB (F, F)—F | 5.0% |
| 3-HBB (F, F)—F | 15.0% |
| 2-HHBB (F, F)—F | 3.0% |
| 3-HHBB (F, F)—F | 3.0% |
| 3-HH2BB (F, F)—F | 4.0% |
| 3-HHB-1 | 3.0% |
| 5-HBBH-1O1 | 7.0% |

NI=80.6 (° C.); η=30.5 (mPa·s); Δn=0.123; Δε=12.5; Vth=1.36 (V).

Example 45

| | |
|---|---|
| 5-HHB (2F) (No. 1487) | 9.0% |
| 3-HEB—O4 | 28.0% |
| 4-HEB—O2 | 20.0% |
| 5-HEB—O1 | 20.0% |
| 3-HEB—O2 | 9.0% |
| 5-HEB—O2 | 14.0% |

NI=76.9 (° C.); η=20.6 (mPa·s); Δn=0.087.

Example 46

| | |
|---|---|
| 5-HH2B (2F) (No. 1744) | 12.0% |
| 5-HHB (2F, 5F) B (No. 792) | 7.0% |
| 3-HH-2 | 5.0% |
| 3-HH-4 | 6.0% |
| 3-HH—O1 | 4.0% |
| 3-HH—O3 | 5.0% |
| 5-HH—O1 | 4.0% |
| 3-HB (2F, 3F)—O2 | 12.0% |
| 5-HB (2F, 3F)—O2 | 11.0% |
| 3-HHB (2F, 3F)—O2 | 7.0% |
| 5-HHB (2F, 3F)—O2 | 15.0% |
| 3-HHB (2F, 3F)-2 | 12.0% |

NI=87.6 (° C.); Δn=0.081; Δε=−4.4.

Example 47

| | |
|---|---|
| 5-HHB (2F) (No. 1487) | 2.0% |
| 5-HH2B (2F) (No. 1744) | 5.0% |
| 5-HHB (2F, 5F) B (No. 792) | 6.0% |
| 3-HH-5 | 5.0% |
| 3-HH-4 | 5.0% |
| 3-HH—O1 | 6.0% |
| 3-HH—O3 | 6.0% |
| 3-HB—O1 | 5.0% |
| 3-HB—O2 | 5.0% |
| 3-HB (2F, 3F)—O2 | 10.0% |
| 5-HB (2F, 3F)—O2 | 10.0% |
| 3-HHB (2F, 3F)—O2 | 6.0% |
| 5-HHB (2F, 3F)—O2 | 13.0% |
| 3-HHB (2F, 3F)-2 | 2.0% |
| 2-HHB (2F, 3F)-1 | 4.0% |
| 3-HHEH-3 | 5.0% |
| 4-HHEH-3 | 5.0% |

NI=84.2 (° C.); Δn=0.080; Δε=−3.4.

Example 48

| | |
|---|---|
| 2-HHB (F)—F | 13.3% |
| 3-HHB (F)—F | 13.3% |
| 5-HHB (F)—F | 13.3% |
| 2-H2HB (F)—F | 13.3% |
| 3-H2HB (F)—F | 6.7% |
| 5-H2HB (F)—F | 13.3% |
| 2-HB (F)—F | 6.7% |
| 3-HB (F)—F | 6.7% |
| 5-HB (F)—F | 13.4% |

A composition (F-Mix) consisting of the nine compounds described above is prepared. The composition (F-Mix) was mixed with the compound (No. 275) in the following ratio, and the physical properties of the mixture are as shown below. The composition was kept in a freezer at −20° C. According to the observation after 30 days, the composition still had a nematic phase, and did not changed to a smectic phase or crystals.

| | |
|---|---|
| 5-BB (2F, 5F) B (No. 275) | 10.0% |
| F-Mix | 90.0% |

$\eta$=29.2 (mPa·s); $\Delta n$=0.105; $\Delta\epsilon$=4.2; Vth=2.35 (V).

Comparative Example 1

| | |
|---|---|
| 2-BB (2F, 5F) B-2 | 10.0% |
| F-Mix | 90.0% |

$\eta$=27.8 (mPa·s); $\Delta n$=0.107; $\Delta\epsilon$=4.2; Vth=2.33 (V).

For comparison, 2-BB(2F,5F)B-2 and composition (F-Mix) were mixed. The mixture was kept in a freezer at −20° C., and crystals were separated out after 14 days.

Example 48 is compared with Comparative Example 1. The compound No. 275 and 2-BB(2F,5F)B-2 differ in the terminal group, but they are almost equal in molecular weight. On the other hand, physical properties of the two compositions are similar. Values of viscosity, optical anisotropy, dielectric anisotropy, and threshold voltage are almost equal. However, the two compounds differ considerably in a miscibility at low temperature. The compound of this invention has an excellent miscibility at low temperature.

In Example 10 described above, when 0.8% by weight of the optically active compound (Op-4) based on the composition was added to the composition, a value of the pitch was 11.2 μm. In Example 27 described above, when 0.3% by weight of the optically active compound (Op-8) based on the composition was added to the composition, a value of the pitch was 79.2 μm.

Effect of the Invention

The compound (1) has a good stability for heat and ultraviolet, a large optical anisotropy, a small dielectric anisotropy, and an excellent miscibility with other liquid crystal compounds. The composition comprising the compound has the general characteristics required for a composition, a large optical anisotropy and good miscibility at low temperature. The composition is especially useful for a liquid crystal display element having a small cell gap.

What is claimed is:

1. A compound represented by the following formula (1):

(1)

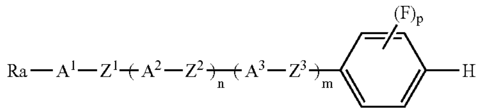

wherein Ra is alkyl having 1 to 15 carbons and any —$CH_2$— in the alkyl may be replaced by —O—, —S—, —CH═CH—, or —C≡C—; $A^1$, $A^2$ and $A^3$ independently are 1,4-cyclohexylene, 1,3-dioxane-2,5-diyl, decahydronaphthalene-2,6-diyl, 1,4-phenylene in which any hydrogen may be replaced by fluorine, naphthalene-2,6-diyl in which any hydrogen may be replaced by fluorine, or 1,2,3,4-tetrahydronaphthalene-2,6-diyl in which any —CH═ may be replaced by —CF═; $Z^1$, $Z^2$ and $Z^3$ independently are a single bond, —$(CH_2)_2$—, —$(CF_2)_2$—, —COO—, —OCO—, —$CH_2O$—, —$OCH_2$—, —$CF_2O$—, —$OCF_2$—, —CH═CH—, —CF═CF—, —C≡C—, —$(CH_2)_4$—, —$(CH_2)_3O$—, or —$O(CH_2)_3$—; n and m independently are 0 or 1; phenyl having $(F)_p$ is phenyl, 2-fluorophenyl, 2,5-difluorophenyl, 2,3,5-trifluorophenyl, or 2,3,6-trifluorophenyl; with the proviso that when $A^1$, $A^2$ and $A^3$ are 1,4-phenylene in which any hydrogen may be replaced by fluorine and $Z^1$, $Z^2$ and $Z^3$ are a single bond, the total number of fluorine in formula (1) is at least two; and with the further proviso that the following compounds are excluded:

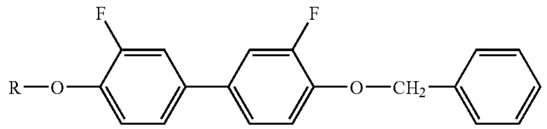

wherein R is alkoxy or alkoxyalkoxy, and

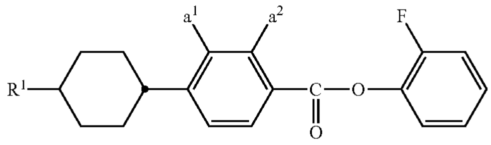

wherein $R^1$ is alkyl, either one of $a^1$ or $a^2$ is fluorine and the other thereof is hydrogen.

2. A compound represented by the following formula (1):

(1)

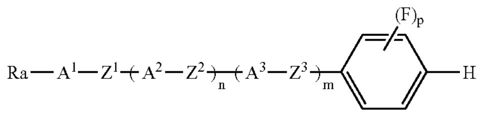

wherein Ra is alkyl having 1 to 15 carbons and any —$CH_2$— in the alkyl may be replaced by —O— or —CH═CH—; $A^1$, $A^2$ and $A^3$ independently are 1,4-cyclohexylene, 1,3-dioxane-2,5-diyl, 1,4-phenylene in which any hydrogen may be replaced by fluorine, or naphthalene-2,6-diyl in which any hydrogen may be replaced by fluorine; $Z^1$, $Z^2$ and $Z^3$ independently are a single bond, —$(CH_2)_2$—, —COO—, —OCO—, —$CH_2O$—, —$OCH_2$—, —$CF_2O$—, —$OCF_2$—, —CH═CH—, —C≡C—, or —$(CH_2)_4$—; n and m independently are 0 or 1; phenyl having $(F)_p$ is phenyl, 2-fluorophenyl, 2,5-difluorophenyl, 2,3,5-trifluorophenyl, or 2,3,6-trifluorophenyl; with the proviso that when $A^1$, $A^2$ and $A^3$ are 1,4-phenylene in which any hydrogen may be replaced by fluorine and $Z^1$, $Z^2$ and $Z^3$ are a single bond, the total number of fluorine in formula (1) is at least two; and with the further proviso that the following compounds are excluded:

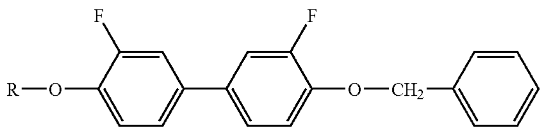

wherein R is alkoxy or alkoxyalkoxy, and

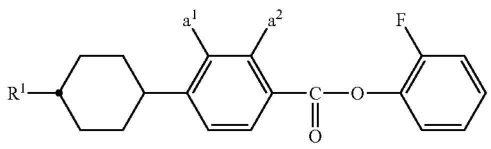

wherein $R^1$ is alkyl, either one of $a^1$ or $a^2$ is fluorine and the other thereof is hydrogen.

3. The compound according to claim 1 or 2, wherein phenyl having $(F)_p$ in formula (1) is phenyl.

4. The compound according to claim 1 or 2, wherein phenyl having $(F)_p$ in formula (1) is 2-fluorophenyl.

5. The compound according to claim 1 or 2, wherein phenyl having $(F)_p$ in formula (1) is 2,5-difluorophenyl.

6. The compound according to claim 1 or 2, wherein phenyl having $(F)_p$ in formula (1) is 2,3,5-trifluorophenyl.

7. The compound according to claim 1 or 2, wherein phenyl having $(F)_p$ in formula (1) is 2,3,6-trifluorophenyl.

8. The compound according to claim 1 or 2, wherein $Z^1$, $Z^2$ and $Z^3$ in formula (1) independently are a single bond, —$(CH_2)_2$—, —COO—, —OCO—, —$CH_2O$—, —$OCH_2$—, —$CF_2O$—, —$OCF_2$—, or —$(CH_2)_4$—.

9. The compound according to claim 1 or 2, wherein in formula (1), $A^1$, $A^2$ and $A^3$ independently are 1,4-phenylene in which any hydrogen may be replaced by fluorine or naphthalene-2,6-diyl in which any hydrogen may be replaced by fluorine; and $Z^1$, $Z^2$ and $Z^3$ independently are a single bond, —$(CH_2)_2$—, —$CH_2O$—, or —$OCH_2$—.

10. The compound according to claim 1 or 2, wherein in formula (1), at least one of $A^1$ and $A^2$ is 1,4-phenylene, 2-fluoro-1,4-phenylene, 3-fluoro-1,4-phenylene, or 2,5-difluoro-1,4-phenylene; $Z^1$ and $Z^2$ independently are a single bond, —$(CH_2)_2$—, —$CH_2O$—, or —$OCH_2$—; n is 1 and m is 0; and phenyl having $(F)_p$ is phenyl, 2-fluorophenyl or 2,5-difluorophenyl.

11. The compound according to claim 1 or 2, wherein in formula (1), at least two of $A^1$, $A^2$ and $A^3$ are 1,4-phenylene, 2-fluoro-1,4-phenylene, 3-fluoro-1,4-phenylene, or 2,5-difluoro-1,4-phenylene; $Z^1$, $Z^2$ and $Z^3$ independently are a single bond, —$(CH_2)_2$— or —$OCH_2$—; n is 1 and m is 1; and phenyl having $(F)_p$ is phenyl, 2-fluorophenyl or 2,5-difluorophenyl.

12. The compound according to claim 1 or 2, wherein in formula (1), $A^1$, $A^2$ and $A^3$ independently are 1,4-phenylene, 2-fluoro-1,4-phenylene, 3-fluoro-1,4-phenylene, or 2,5-difluoro-1,4-phenylene; and phenyl having $(F)_p$ is phenyl, 2-fluorophenyl or 2,5-difluorophenyl.

13. The compound according to claim 12, wherein $Z^1$, $Z^2$ and $Z^3$ in formula (1) are a single bond or —$(CH_2)_2$—.

14. The compound according to claim 13, wherein phenyl having $(F)_p$ in formula (1) is phenyl.

15. The compound according to claim 13, wherein phenyl having $(F)_p$ in formula (1) is 2-fluorophenyl.

16. The compound according to claim 13, wherein phenyl having $(F)_p$ in formula (1) is 2,5-difluorophenyl.

17. A compound represented by any of the following formulas:

(1-1)

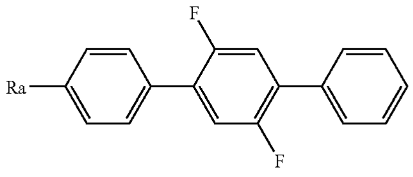

(1-2)

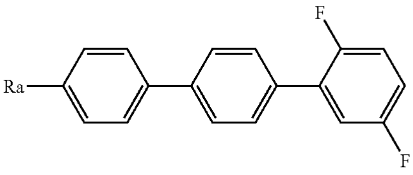

(1-3)

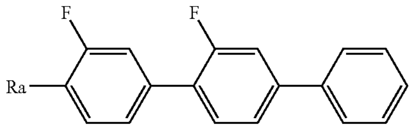

(1-4)

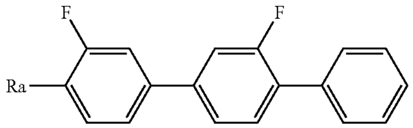

(1-5)

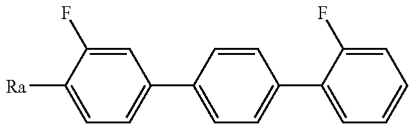

(1-6)

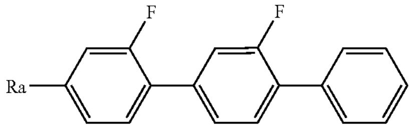

(1-7)

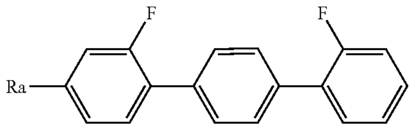

(1-8)

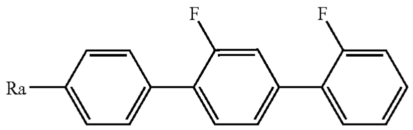

-continued
(1-9)
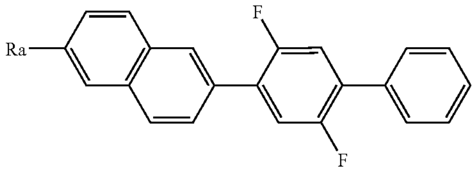
(1-10)
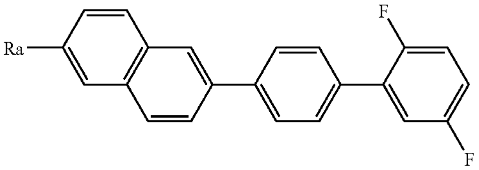
(1-11)
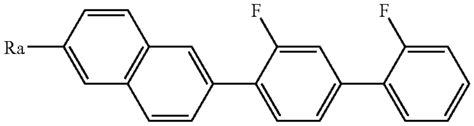
(1-12)
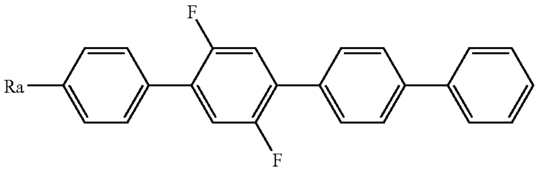
(1-13)
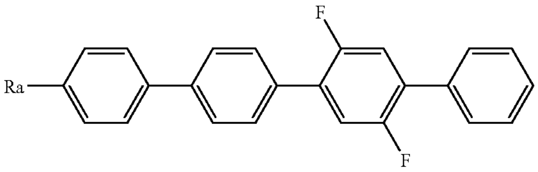
(1-14)
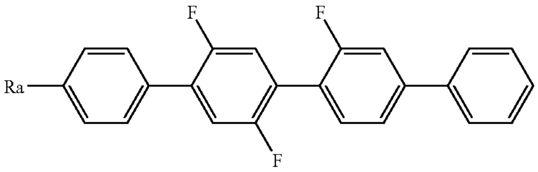
(1-15)
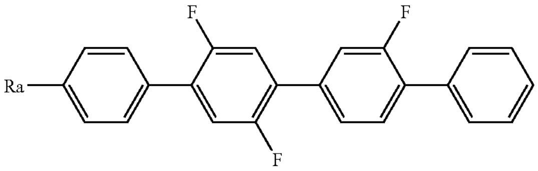
(1-16)
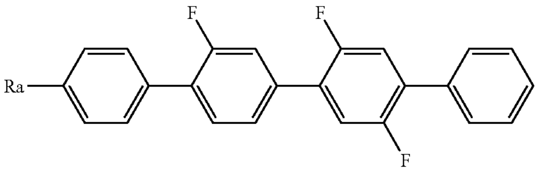
-continued
(1-17)
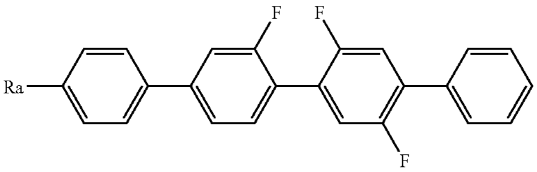
(1-18)
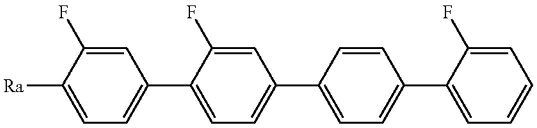
(1-19)
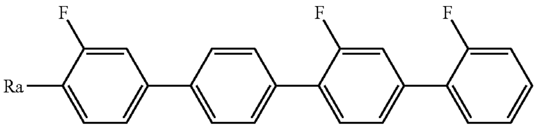
(1-20)
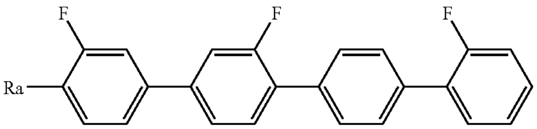
(1-21)
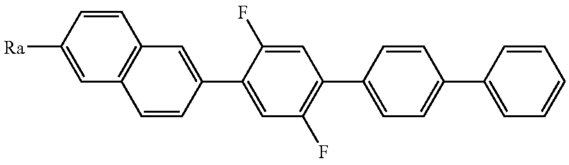
(1-22)
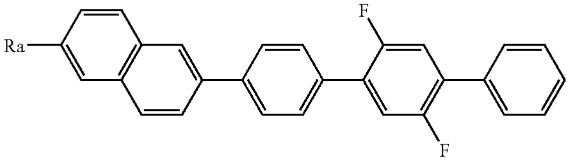
(1-23)
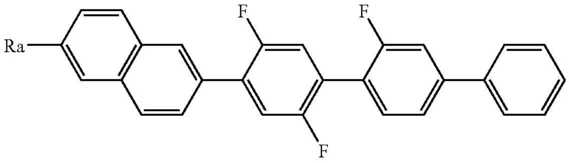
(1-24)
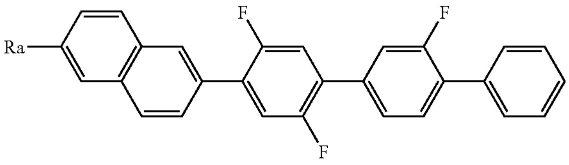
(1-25)
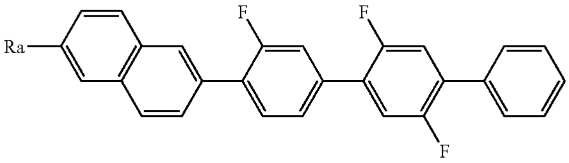

-continued (1-26)

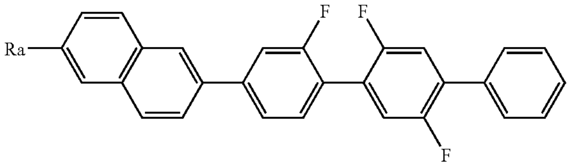

(1-27)

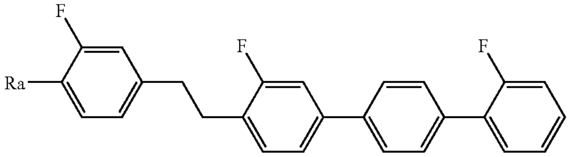

(1-28)

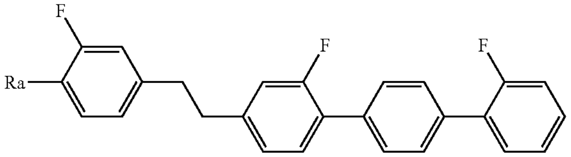

(1-29)

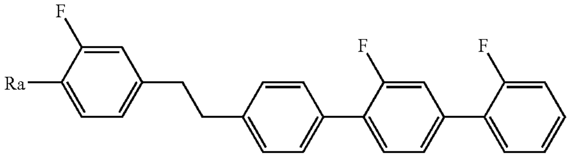

(1-30)

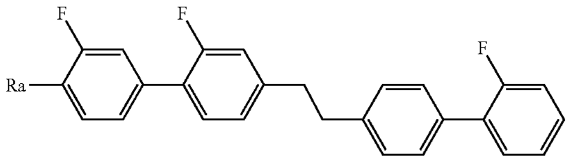

(1-31)

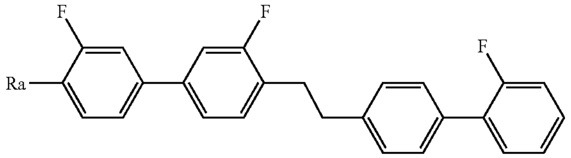

(1-32)

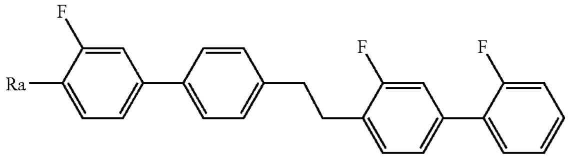

(1-33)

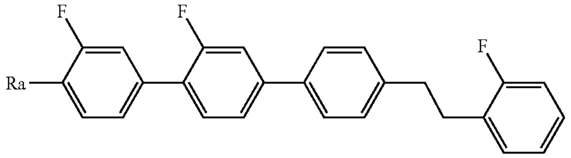

-continued (1-34)

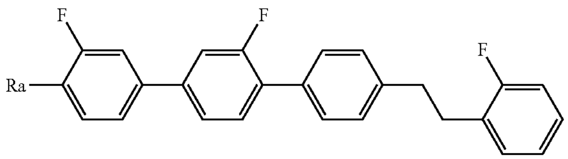

(1-35)

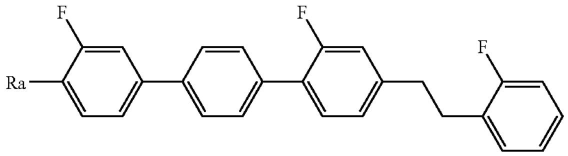

wherein Ra is alkyl having 1 to 15 carbons and any —$CH_2$— in the alkyl may be replaced by —O— or —CH═CH—.

18. A liquid crystal composition comprising at least one compound described in claim 1 or 2.

19. The composition according to claim 18, further comprising at least one compound selected from the group consisting of the compounds represented by formulas (2), (3) and (4):

(2)

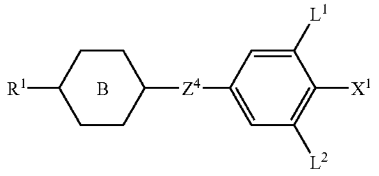

(3)

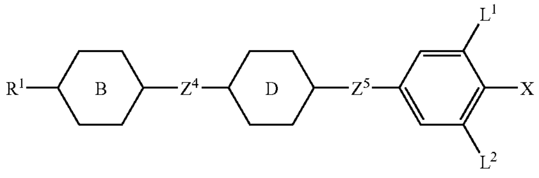

(4)

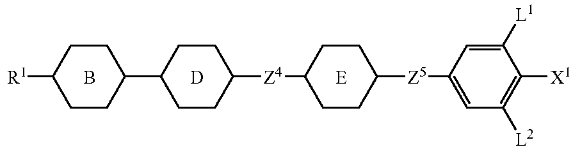

wherein $R^1$ is alkyl having 1 to 10 carbons, any —$CH_2$— in the alkyl may be replaced by —O— or —CH═CH— and any hydrogen in the alkyl may be replaced by fluorine; $X^1$ is fluorine, chlorine, —$OCF_3$, —$OCHF_2$, —$CF_3$, —$CHF_2$, —$CH_2F$, —$OCF_2CHF_2$, or —$OCF_2CHFCF_3$; ring B and ring D independently are 1,4-cyclohexylene, 1,3-dioxane-2, 5-diyl or 1,4-phenylene in which any hydrogen may be replaced by fluorine; ring E is 1,4-cyclohexylene or 1,4-phenylene in which any hydrogen may be replaced by fluorine; $Z^4$ and $Z^5$ independently are —$(CH_2)_2$—, —$(CH_2)_4$—, —COO—, —$CF_2O$—, —$OCF_2$—, —CH═CH—, or a single bond; and $L^1$ and $L^2$ independently are hydrogen or fluorine.

20. The composition according to claim 18, further comprising at least one compound selected from the group consisting of the compounds represented by formulas (5) and (6):

(5)

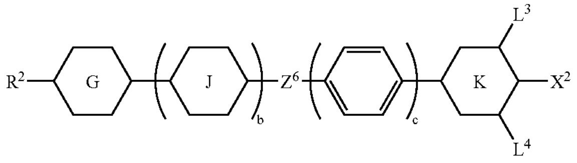

(6)

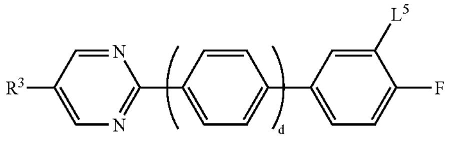

wherein $R^2$ and $R^3$ independently are alkyl having 1 to 10 carbons, any —$CH_2$— in the alkyl may be replaced by —O— or —CH═CH— and any hydrogen in the alkyl may be replaced by fluorine; $X^2$ is —CN or —C≡C—CN; ring G is 1,4-cyclohexylene, 1,4-phenylene, 1,3-dioxane-2,5-diyl, or pyrimidine-2,5-diyl; ring J is 1,4-cyclohexylene, pyrimidine-2,5-diyl or 1,4-phenylene in which any hydrogen may be replaced by fluorine; ring K is 1,4-cyclohexylene or 1,4-phenylene; $Z^6$ is —$(CH_2)_2$—, —COO—, —$CF_2O$—, —$OCF_2$—, or a single bond; $L^3$, $L^4$ and $L^5$ independently are hydrogen or fluorine; and b, c and d independently are 0 or 1.

21. The composition according to claim 18, further comprising at least one compound selected from the group consisting of the compounds represented by formulas (7), (8) and (9):

(7)

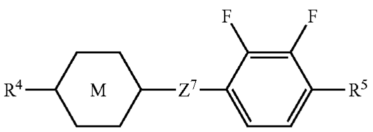

(8)

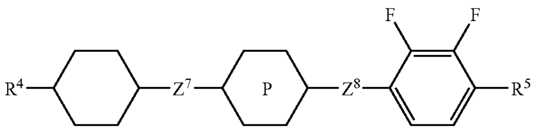

(9)

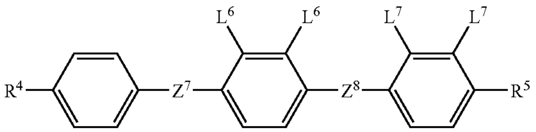

wherein $R^4$ and $R^5$ independently are alkyl having 1 to 10 carbons, any —$CH_2$— in the alkyl may be replaced by —O— or —CH═CH— and any hydrogen in the alkyl may be replaced by fluorine; ring M and ring P independently are 1,4-cyclohexylene or 1,4-phenylene; $Z^7$ and $Z^8$ independently are —$(CH_2)_2$—, —COO— or a single bond; $L^6$ and $L^7$ independently are hydrogen or fluorine, and at least one of $L^6$ and $L^7$ is fluorine.

22. The composition according to claim 19, further comprising at least one compound selected from the group consisting of the compounds represented by formulas (10), (11) and (12):

(10)

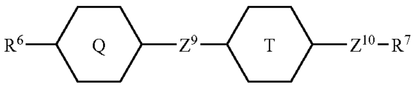

(11)

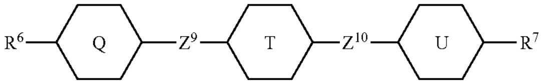

(12)

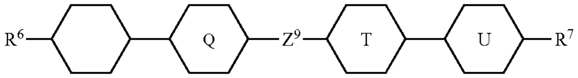

wherein $R^6$ and $R^7$ independently are alkyl having 1 to 10 carbons, any —$CH_2$— in the alkyl may be replaced by —O— or —CH═CH— and any hydrogen in the alkyl may be replaced by fluorine; ring Q, ring T and ring U independently are 1,4-cyclohexylene, pyrimidine-2,5-diyl, or 1,4-phenylene in which any hydrogen may be replaced by fluorine; $Z^9$ and $Z^{10}$ independently are —C≡C—, —COO—, —$(CH_2)_2$—, —CH═CH—, or a single bond.

23. The composition according to claim 20, further comprising at least one compound selected from the group consisting of the compounds represented by formulas (10), (11) and (12):

(10)

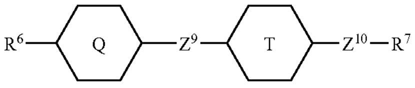

(11)

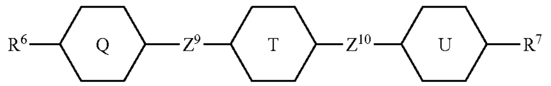

(12)

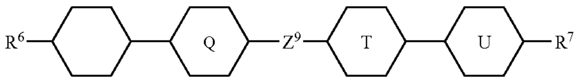

wherein $R^6$ and $R^7$ independently are alkyl having 1 to 10 carbons, any $—CH_2—$ in the alkyl may be replaced by —O— or —CH═CH— and any hydrogen in the alkyl may be replaced by fluorine; ring Q, ring T and ring U independently are 1,4-cyclohexylene, pyrimidine-2,5-diyl, or 1,4-phenylene in which any hydrogen may be replaced by fluorine; $Z^9$ and $Z^{10}$ independently are —C≡C—, —COO—, $—(CH_2)_2—$, —CH═CH—, or a single bond.

24. The composition according to claim 21, further comprising at least one compound selected from the group consisting of the compounds represented by formulas (10), (11) and (12):

(10)

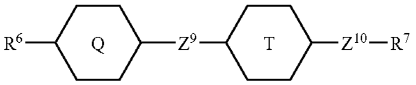

(11)

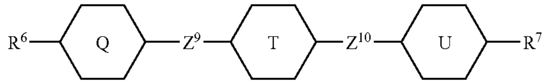

(12)

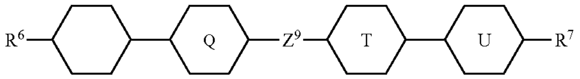

wherein $R^6$ and $R^7$ independently are alkyl having 1 to 10 carbons, any $—CH_2—$ in the alkyl may be replaced by —O— or —CH═CH— and any hydrogen in the alkyl may be replaced by fluorine; ring Q, ring T and ring U independently are 1,4-cyclohexylene, pyrimidine-2,5-diyl, or 1,4-phenylene in which any hydrogen may be replaced by fluorine; $Z^9$ and $Z^{10}$ independently are —C≡C—, —COO—, $—(CH_2)_2—$, —CH═CH—, or a single bond.

25. The composition according to claim 22, further comprising at least one compound selected from the group consisting of the compounds represented by formulas (5) and (6);

(5)

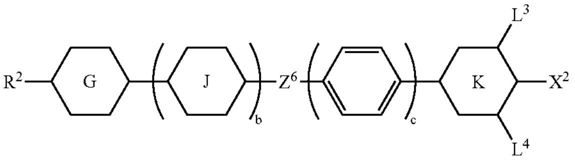

(6)

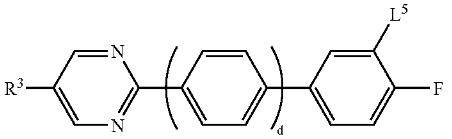

wherein $R^2$ and $R^3$ independently are alkyl having 1 to 10 carbons, any $—CH_2—$ in the alkyl may be replaced by —O— or —CH═CH— and any hydrogen in the alkyl may be replaced by fluorine; $X^2$ is —CN or —C≡C—CN; ring G is 1,4-cyclohexylene, 1,4-phenylene, 1,3-dioxane-2,5-diyl, or pyrimidine-2,5-diyl; ring J is 1,4-cyclohexylene, pyrimidine-2,5-diyl or 1,4-phenylene in which any hydrogen may be replaced by fluorine; ring K is 1,4-cyclohexylene or 1,4-phenylene; $Z^6$ is $—(CH_2)_2—$, —COO—, $—CF_2O—$, $—OCF_2—$, or a single bond; $L^3$, $L^4$ and $L^5$ independently are hydrogen or fluorine; and b, c and d independently are 0 or 1.

26. The composition according to claim 18, further comprising at least one optically active compound.

27. A liquid crystal display element comprising the composition described in claims 18.

* * * * *